(12) United States Patent
Lee et al.

(10) Patent No.: US 10,533,010 B2
(45) Date of Patent: Jan. 14, 2020

(54) SUBSTITUTED INDOLE MCL-1 INHIBITORS

(71) Applicant: Vanderbilt University, Nashville, TN (US)

(72) Inventors: Taekyu Lee, Brentwood, TN (US); Zhiguo Bian, Nashville, TN (US); Johannes Belmar, Nashville, TN (US); Plamen P. Christov, Mount Juliet, TN (US); Nicholas F. Pelz, Nashville, TN (US); Subrata Shaw, Nashville, TN (US); Kwangho Kim, Nashville, TN (US); James C. Tarr, Franklin, TN (US); Edward T. Olejniczak, Nashville, TN (US); Bin Zhao, Brentwood, TN (US); Stephen W. Fesik, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 15/129,042

(22) PCT Filed: Mar. 26, 2015

(86) PCT No.: PCT/US2015/022841
§ 371 (c)(1),
(2) Date: Sep. 26, 2016

(87) PCT Pub. No.: WO2015/148854
PCT Pub. Date: Oct. 1, 2015

(65) Prior Publication Data
US 2017/0174689 A1 Jun. 22, 2017

Related U.S. Application Data

(60) Provisional application No. 61/971,023, filed on Mar. 27, 2014.

(51) Int. Cl.
| | | |
|---|---|---|
| C07D 487/04 | (2006.01) |
| A61K 31/381 | (2006.01) |
| A61K 31/4045 | (2006.01) |
| A61K 31/498 | (2006.01) |
| A61K 31/551 | (2006.01) |
| C07D 401/04 | (2006.01) |
| C07D 401/12 | (2006.01) |
| C07D 403/04 | (2006.01) |
| C07D 403/14 | (2006.01) |
| C07D 409/12 | (2006.01) |
| C07D 409/14 | (2006.01) |
| C07D 471/04 | (2006.01) |
| C07D 209/42 | (2006.01) |
| A61K 31/404 | (2006.01) |
| A61K 31/4155 | (2006.01) |
| A61K 31/4439 | (2006.01) |
| A61K 31/454 | (2006.01) |
| A61K 31/4725 | (2006.01) |
| A61K 31/496 | (2006.01) |
| A61K 31/4985 | (2006.01) |
| A61K 31/5377 | (2006.01) |
| A61K 45/06 | (2006.01) |

(Continued)

(52) U.S. Cl.
CPC .......... *C07D 487/04* (2013.01); *A61K 31/381* (2013.01); *A61K 31/404* (2013.01); *A61K 31/4045* (2013.01); *A61K 31/4155* (2013.01); *A61K 31/4439* (2013.01); *A61K 31/454* (2013.01); *A61K 31/4725* (2013.01); *A61K 31/496* (2013.01); *A61K 31/498* (2013.01); *A61K 31/4985* (2013.01); *A61K 31/5377* (2013.01); *A61K 31/551* (2013.01); *A61K 45/06* (2013.01); *C07D 209/42* (2013.01); *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 405/12* (2013.01); *C07D 405/14* (2013.01); *C07D 409/12* (2013.01); *C07D 409/14* (2013.01); *C07D 471/04* (2013.01)

(58) Field of Classification Search
CPC .................................................. C07D 487/04
See application file for complete search history.

(56) References Cited

U.S. PATENT DOCUMENTS

| 4,703,053 A | 10/1987 | Connor et al. |
| 4,980,368 A | 12/1990 | Thielke et al. |

(Continued)

FOREIGN PATENT DOCUMENTS

| EP | 639573 | 2/1995 |
| EP | 2161266 | 3/2010 |

(Continued)

OTHER PUBLICATIONS

Cancer and Metastasis Reviews (1998), 17(1), 91-106.*

(Continued)

*Primary Examiner* — Shawquia Jackson
(74) *Attorney, Agent, or Firm* — Michael Best & Friedrich LLP

(57) ABSTRACT

The present invention provides for compounds that inhibit the activity of an anti-apoptotic Bcl-2 family member Myeloid cell leukemia-1 (Mcl-1) protein. The present invention also provides for pharmaceutical compositions as well as methods for using compounds for treatment of diseases and conditions (e.g., cancer) characterized by the overexpression or dysregulation of Mcl-1 protein.

15 Claims, No Drawings

(51) Int. Cl.
*C07D 401/14* (2006.01)
*C07D 403/12* (2006.01)
*C07D 405/12* (2006.01)
*C07D 405/14* (2006.01)

(56) References Cited

U.S. PATENT DOCUMENTS

| | | | |
|---|---|---|---|
| 4,994,477 | A | 2/1991 | Kempf et al. |
| 5,324,725 | A | 6/1994 | Jasserand et al. |
| 5,436,264 | A | 7/1995 | Pfister et al. |
| 6,787,651 | B2 | 9/2004 | Stolle et al. |
| 2003/0109533 | A1 | 6/2003 | Lavielle et al. |
| 2005/0124675 | A1 | 6/2005 | Hsich et al. |
| 2009/0054402 | A1 | 2/2009 | Wang et al. |
| 2009/0270497 | A1 | 10/2009 | Buggy |
| 2010/0009986 | A1 | 1/2010 | Zemolka et al. |
| 2010/0009991 | A1 | 1/2010 | Terasaka et al. |
| 2011/0263599 | A1 | 10/2011 | Song et al. |
| 2012/0172285 | A1 | 7/2012 | Walensky et al. |
| 2014/0005386 | A1 | 1/2014 | Doemling |
| 2015/0336925 | A1 | 11/2015 | Lee et al. |
| 2016/0106731 | A1 | 4/2016 | Lee et al. |

FOREIGN PATENT DOCUMENTS

| | | |
|---|---|---|
| FR | 2761070 | 9/1998 |
| JP | S62181252 A | 8/1987 |
| JP | 3739432 | 1/2006 |
| JP | 2013537191 A | 9/2013 |
| WO | 9742188 | 11/1997 |
| WO | 9810778 | 3/1998 |
| WO | 2006034391 A2 | 3/2006 |
| WO | 2007112322 | 10/2007 |
| WO | 2010123507 | 10/2010 |
| WO | 2011157668 | 12/2011 |
| WO | 2013112878 | 8/2013 |
| WO | 2014047427 | 3/2014 |
| WO | 2015031608 | 3/2015 |
| WO | 2015148854 | 10/2015 |
| WO | 20170152076 | 9/2017 |

OTHER PUBLICATIONS

Science (1999), vol. 286, 531-537.*
Cancer [online], [retrieved on Jul. 6, 2007]. Retrieved from the internet, URL http://www.nlm.nih.gov/medlineplus/cancer.html>.*
Wahyuningsih, et al. Document No. 147:235137, retrieved from STN; entered in STN on Jun. 11, 2007.
PCT/US2017/020699 International Search Report and Written Opinion dated May 23, 2017 (9 pages).
EP14839887.8 Extended European Search Report dated May 30, 2017 (13 pages).
EP15768818.5 Extended European Search Report dated Jul. 28, 2107 (16 pages).
Tanaka et al., "Discovery of Potewnt Mcl-1/Bcl-xL dual Inhibitors by Using a Hybridization Strategy Based n Structura Analysis of Target Proteins," article (2013) ACS Publicatons, J. Met Chem 56, pp. 9635-9645.
Zhao et al., "Structure of a Myeloid cell leukemia-1 (Mcl-1) inhibitor bound to drug site 3 of Human Serum Albumin," article (2017) Bio-Organic & Medicinal Chemistry, vol. 25, No. 12, pp. 3087-3092.
Lee et al., "Discovery and biological characterizaton of potent myeloid cell leukemia-1 inhibitors," article (2016) Febs Letters, vol. 591, No. 1, pp. 240-251.
PCT/US2013/060881 International Search Report and Written Opinion dated May 5, 2014 (11 pages).
PCT/US2014/053148 International Search Report and Written Opinion dated Jan. 27, 2015 (12 pages).
PCT/US2014/053148 International Preliminary Report on Patentability dated Mar. 1, 2016 (2 pages).
PCT/US2015/022841 International Search Report and Written Opinion dated Jun. 29, 2015 (12 pages).
Friberg, "Discovery of Potent Myeloid Cell Leukemia 1 (Mcl 1) Inhibitors Using Fragment Based Methods and Structure Based Design," manuscript (2014) pp. 1-38, National Institutes of Health.
Hung et al, "Document No. 152:66468, Caplus," retrieved from STN; Oct. 28, 2009.
Jansen et al., "Document No. 140:111233, Caplus," retrieved from STN; Oct. 22, 2009.
Chan et al., "Document No. 150:563639," retrieved from STN; May 22, 2009.
Shultz et al. "Optimization of the in vitro cardiac safety of hydroxamate-based histone deacetylase inhibitors." Journal of medicinal chemistry. Jun. 17, 2011;54(13):4752-72.
Tabatabaeian et al., "Solvent-free, ruthenium-catalyzed, regioselective ring-opening of epoxides, an efficient route various 3-alkylated indoles." Tetrahedron Letters. Feb. 25, 2008;49(9):1450-4.
Kalaus et al., "Synthesis of vinca alkaloids and related compounds. 63. A new synthetic pathway for preparing alkaloids and related compounds with the aspidosperma skeleton. Total syntheses of (.+-31 .)-vincadifformine,(.+-31 .)-tabersonine, and (.+-31 .)-oxotabersonine." the Journal of Organic Chemistry. Mar. 1993;58(6):1434-42.
Vago et al., "Synthesis of vinca alkaloids and related compounds 95. Attempted build-up of the aspidospermidine skeleton by [4+ 2] cycloaddition. Some unexpected reactions, and formation of a new ring system." Heterocycles. 2001 May 1;55(5):873-80.
Shaw et al., "Optimization of potent and selective tricyclic indole diazepinone myeloid cell leukemia-1 inhibitors using design." Journal of medicinal chemistry. Jan. 11, 2018;61(6):2410-21.
Japanese Patent Office Action for Application No. 2017502932 dated Dec. 6, 2018, with translation, 15 pages.
Lee et al., "Discovery of Potent Myeloid Cell Leukemia-1 (Mcl-1) Inhibitors That Demonstrate in Vivo Activity in Mouse Xenograft Models of Human Cancer." Journal of medicinal chemistry. Mar. 30 2019;62(8):3971-88.
Australian Patent Office Action for Application No. 2015235944, dated Aug. 28, 2019, 6 pages.

* cited by examiner

SUBSTITUTED INDOLE MCL-1 INHIBITORS

CROSS REFERENCE TO RELATED APPLICATIONS

This application is a U.S. national stage filing under 35 U.S.C. 371 of International Application No. PCT/US2015/022841, filed Mar. 26, 2015, which application claims the benefit of and priority to U.S. Provisional Patent Application Ser. No. 61/971,023, filed Mar. 27, 2014, the entire contents of each of which are hereby incorporated by reference.

STATEMENT REGARDING FEDERALLY SPONSORED RESEARCH OR DEVELOPMENT

This invention was made with government support under grants CA098131 and CA174419 awarded by the National Institutes of Health. The government has certain rights in the invention.

FIELD OF THE INVENTION

The present invention pertains to compounds that inhibit the activity of an anti-apoptotic Bcl-2 family member Myeloid cell leukemia-1 (Mcl-1) protein, compositions containing the compounds, and methods of treating cancer involving over-expressed or dysregulated Mcl-1 protein.

BACKGROUND OF THE INVENTION

Abnormal regulation of apoptosis is now recognized to play an important role in the development of cancer. The apoptosis pathway can be initiated by various extracellular and intracellular stresses, including growth factor deprivation, DNA damage, oncogene induction, and cytotoxic drugs (Danial, N. N. and Korsmeyer, S J. *Cell* (2004) 116, 205-219). The death signal leads to the oligomerization of the pro-apoptotic proteins Bax and Bak. Upon activation, they permeabilize the mitochondrial outer membrane and release apoptogenic factors into the cytoplasm. This process is tightly regulated by both pro-apoptotic (Bax, Bak, Bad, Bid, Bim, Bmf, NOXA, PUMA) and anti-apoptotic (Bcl-2, Bcl-xL, Bcl-w, Bcl2-A1, Mcl-1) members of the Bcl-2 family of proteins. Recent data suggests that the anti-apoptotic Bcl-2 proteins function to protect the cell from apoptotic insults, primarily by preventing disruption of mitochondrial outer membrane integrity by binding to the pro-apoptotic proteins as described in Adams, J. M. and Cory S. *Oncogene* (2007) 26, 1324-1337; Willis, S. N. et al. *Science* (2007) 315, 856-859. Because tumor cells are under stress, alterations in their apoptotic signaling pathways are believed to be crucial for survival. Recent data implicates down-regulated apoptosis in the onset of cancer. Research has shown, for example, that anti-apoptotic proteins, are over-expressed in many cancer cell types as described in Beroukhim, R. et al. *Nature* (2010) 463, 899-905; Zhang J. Y., *Nature Reviews Drug Discovery*, (2002) 1, 101; Kirkin, V. et al. *Biochimica et Biophysica Acta* (2004) 1644, 229-249; and Amundson, S. A. et al. *Cancer Research* (2000) 60, 6101-6110. This dysregulation results in the survival of cells that would otherwise have undergone apoptosis such as cancer cells. This suggests that neutralizing the function of anti-apoptotic Bcl-2 proteins may offer an effective strategy for the elimination of cancer cells. In addition, resistance to chemotherapy which is a major cause of treatment failure and poor prognosis in many cancers can be caused by the upregulation of anti-apoptotic Bcl-2 family proteins.

An important anti-apoptotic member of the Bcl-2 family is Myeloid cell leukemia-1 (Mcl-1). Mcl-1 is one of the most frequently amplified anti-apoptotic genes in human cancers including prostate, lung, pancreatic, breast, ovarian, and cervical cancers, as well as melanoma, B-cell chronic lymphocytic leukemia (B-CLL), acute myeloid leukemia (AML) and acute lymphoblastic leukemia (ALL) (Beroukhim et al. *Nature* (2010) 463, 899-905). Moreover, its overexpression is implicated as a resistance factor for multiple therapies including widely prescribed microtubule-targeted agents for breast cancers, such as paclitaxel and vincristine as well as Gemcitabine, a first-line treatment option for pancreatic cancer (Wei et al. *Cancer Chemother Pharmacol* (2008) 62, 1055-1064 and Wertz et al. *Nature* (2011) 471, 110-114). These data suggest that Mcl-1 is an important target for a wide variety of cancers.

In many cancer cell types, the cancer cell's survival is attributed to the dysregulation of the apoptotic pathway caused by the over-expression of one or more anti-apoptotic Bcl-2 protein family members. Because of the important role for Bcl-2 family of proteins in regulating apoptosis in both cancerous and non-cancerous cells, and the inter-cell variability of Bcl-2 family protein expression, it could be advantageous to have a small molecule inhibitor that selectively targets and preferably binds to one type or a subset of anti-apoptotic Bcl-2 protein(s). A selective compound also may confer certain advantages in the clinical setting, by providing flexibility to select a dosing regimen to reduce on-target toxic effects in normal cells.

Because Mcl-1 protein is an important Bcl-2 family member associated with a number of diseases, there is a need for compounds which bind to and inhibit the activity of Mcl-1 protein.

SUMMARY OF THE INVENTION

In some embodiments, the present invention provides compounds, and pharmaceutically acceptable compositions thereof, that are effective as inhibitors of Mcl-1. Such compounds have the general formula I or II:

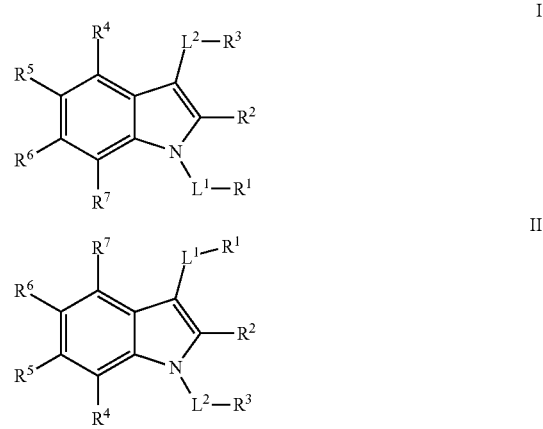

or a pharmaceutically acceptable salt thereof, wherein each of $L^1$, $L^2$, $R^1$, $R^2$, $R^3$, $R^4$, $R^5$, $R^6$, and $R^7$ is as defined and described in embodiments herein.

Compounds of the present invention, and pharmaceutically acceptable compositions thereof, are useful for treating a variety of diseases, disorders or conditions, associated with MCl-1. Such diseases, disorders, or conditions include those described herein.

Compounds provided by this invention are also useful for the study of Mcl-1 in biological and pathological phenomena and the comparative evaluation of new Mcl-1 inhibitors in vitro or in vivo.

DETAILED DESCRIPTION OF CERTAIN EMBODIMENTS OF THE INVENTION

1. General Description of Compounds of the Invention

In certain embodiments, the present invention provides inhibitors of Mcl-1. In some embodiments, such compounds include those of formula I:

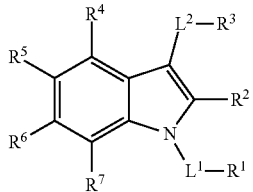

or a pharmaceutically acceptable salt thereof, wherein:
$L^1$ is selected from a covalent bond or an optionally substituted bivalent straight or branched $C_{1-6}$ hydrocarbon chain wherein one or more methylene units are optionally and independently replaced with -Cy-;
-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;
$L^2$ is an optionally substituted bivalent straight or branched $C_{3-6}$ hydrocarbon chain wherein one or two methylene units of $L^2$ are optionally and independently replaced with —O—, —S—, or —N(R')—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;
each R' is independently selected from hydrogen or optionally substituted $C_{1-4}$ alkyl;
$R^1$ is selected from hydrogen, halogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, —S(O)R$^y$, or —S(O)$_2$R$^y$;
$R^2$ is selected from —C(O)-L$^3$-R$^z$, —C(O)N(R)-L$^3$-R$^z$, —C(O)N(R)—C(R)$_2$-L$^3$-R$^z$, —C(O)O-L$^3$-R$^z$ or —C(O)S-L$^3$-R$^z$;
$L^3$ is selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;
$R^z$ is selected from hydrogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^y$, or is selected from:

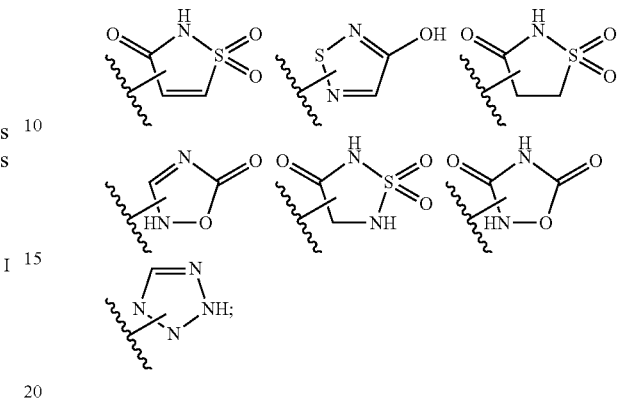

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R;
$R^y$ is selected from —N(R)C(O)CF$_3$, —N(R)C(O)R, or —N(R)C(O)N(R)$_2$;
each R is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur;
$R^3$ is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
each of $R^4$, $R^5$, and $R^6$ is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';
$R^7$ is selected from hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally $R^1$ and $R^2$, $R^1$ and $R^7$, $R^4$ and $R^5$, $R^5$ and $R^6$ and/or $R^6$ and $R^7$ are taken together with their intervening atoms to form an optionally substituted ring selected from a 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In certain embodiments, the present invention provides a compound of formula II:

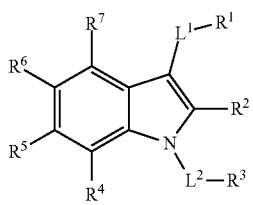

II or a pharmaceutically acceptable salt thereof, wherein:

$L^1$ is selected from a covalent bond or an optionally substituted bivalent straight or branched $C_{1-6}$ hydrocarbon chain wherein one or more methylene units are optionally and independently replaced with -Cy-;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

$L^2$ is an optionally substituted bivalent straight or branched $C_{3-6}$ hydrocarbon chain wherein one or two methylene units of $L^2$ are optionally and independently replaced with —O—, —S—, or —N(R')—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;

each R' is independently selected from hydrogen or optionally substituted $C_{1-4}$ alkyl;

$R^1$ is selected from hydrogen, halogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, —S(O)R$^y$, or —S(O)$_2$R$^y$;

$R^2$ is selected from —C(O)-L$^3$-R$^z$, —C(O)N(R)-L$^3$-R$^z$, —C(O)N(R)—C(R)$_2$-L$^3$-R$^z$, —C(O)O-L$^3$-R$^z$ or —C(O)S-L$^3$-R$^z$;

L$^3$ is selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;

R$^z$ is selected from hydrogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R, or is selected from:

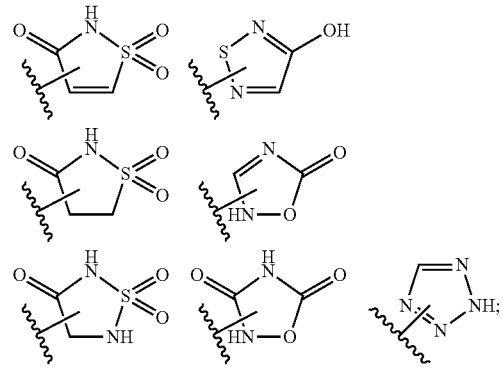

R$^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R;

R$^y$ is selected from —N(R)C(O)CF$_3$, —N(R)C(O)R, or —N(R)C(O)N(R)$_2$;

each R is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur;

$R^3$ is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each of R⁴, R⁵, and R⁶ is independently selected from R, halogen, —CN, —NO₂, —C(O)OR', —OR', —SR', —C(O)N(R')₂—N(R')₂, —S(O)₂N(R)₂, —N(R')S(O)₂CF₃, —C(O)R', —N(R')C(O)R', —S(O)R', —S(O)₂R', —N(R')C(O)OR', and —N(R')S(O)₂R';

R⁷ is selected from hydrogen, halogen, —CN, —NO₂, —C(O)OR, —OCF₃, —OR, —SR, —S(O)₂OR, —P(O)(OH)₂, —C(O)N(R)₂, —N(R)₂, —S(O)₂N(R)₂, —N(R)S(O)₂CF₃, —C(O)N(R)S(O)₂R, —S(O)₂N(R)C(O)OR, —S(O)₂N(R)C(O)N(R)₂, —C(O)R, —C(O)N(R)S(O)₂CF₃, —N(R)C(O)R, —OC(O)R, —OC(O)N(R)₂, —C(NR)N(R)₂, —N(R)C(NR)N(R)₂, —S(O)R, —S(O)₂R, —N(R)C(O)OR, or —N(R)S(O)₂R, or an optionally substituted group selected from C₁₋₆ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally R¹ and R², R¹ and R⁷, R⁴ and R⁵, R⁵ and R⁶ and/or R⁶ and R⁷ are taken together with their intervening atoms to form an optionally substituted ring selected from a 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In certain embodiments, the present invention provides a compound of formula III:

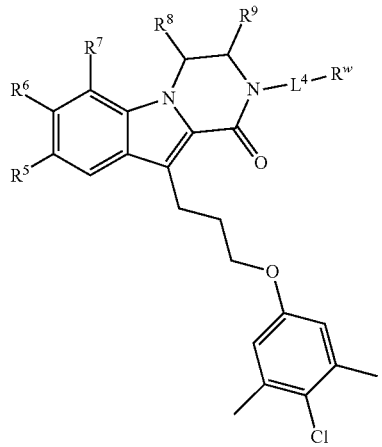

III or a pharmaceutically acceptable salt thereof, wherein:
each of R⁵, R⁶, R⁸, and R⁹ is independently selected from R, halogen, —CN, —NO₂, —C(O)OR', —OR', —SR', —C(O)N(R')₂—N(R')₂, —S(O)₂N(R)₂, —N(R')S(O)₂CF₃, —C(O)R', —N(R')C(O)R', —S(O)R', —S(O)₂R', —N(R')C(O)OR', and —N(R')S(O)₂R';

each R' is independently selected from hydrogen or optionally substituted C₁₋₄ alkyl;

L⁴ is independently selected from a covalent bond or an optionally substituted bivalent straight or branched C₁₋₈ hydrocarbon chain wherein one or more methylene units are optionally and independently replaced with -Cy'-, —O—, —S—, —N(R)—, —N(R)C(O)—, —N(R)S(O)₂—, —C(O)—, —C(O)N(R)—, —S(O)—, —S(O)₂—, or —S(O)₂N(R)—;

-Cy'- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, 3-8 membered saturated or partially unsaturated heterocylylene having 1-4 heteroatoms independently selected from nitrogen, oxygen, or sulfur, an 8-10 membered bicyclic arylene or heteroarylene having 1-4 heteroatoms independently selected from nitrogen, oxygen, or sulfur, or an 8-10 membered saturated or partially unsaturated heterocyclylene having 1-4 heteroatoms independently selected from nitrogen, oxygen, or sulfur;

Rʷ is selected from hydrogen, R, —OR, —SR, —S(O)R, —S(O)₂R, —S(O)₂N(R)₂, —N(R)₂, —C(O)N(R)₂, —C(O)R, —N(R)C(O)R, —N(R)C(O)OR, —N(R)C(O)N(R)₂, —N(R)S(O)₂R, —N(R)S(O)₂N(R)₂, —C(O)OH, —C(O)OR, —C(O)Rˣ, —S(O)₂OH, or —S(O)₂Rʸ, or is selected from:

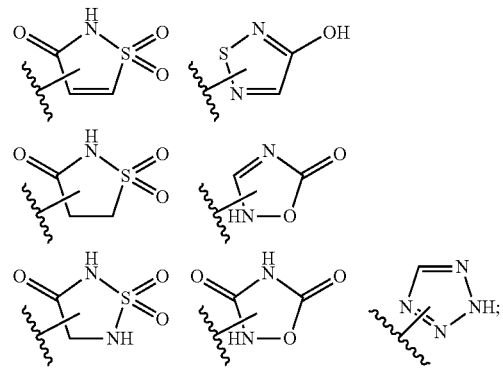

Rˣ is selected from —C(O)OR, —N(R)S(O)₂CF₃, —N(R)C(O)R, —N(R)C(O)OR, —N(R)C(O)N(R)₂, or —N(R)S(O)₂R; and Rʸ is selected from —N(R)C(O)CF₃, —N(R)C(O)R, or —N(R)C(O)N(R)₂;

each R is independently selected from hydrogen or an optionally substituted group selected from C₁₋₁₂ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; and $R^7$ is selected from hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from C$_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In certain embodiments, the present invention provides a compound of formula IV:

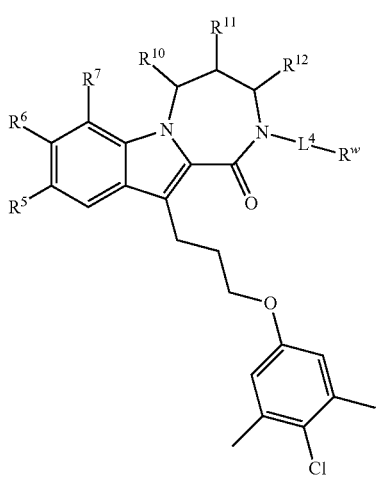

IV or a pharmaceutically acceptable salt thereof, wherein:
each of $R^5$, $R^6$, $R^{10}$, $R^{11}$, and $R^{12}$ is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';
each R' is independently hydrogen or optionally substituted C$_{1-4}$ alkyl;
$L^4$ is independently selected from a covalent bond or an optionally substituted bivalent straight or branched C$_{1-8}$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;
-Cy'- is an optionally substituted bivalent ring independently selected from phenylene, 3-8 membered saturated or partially unsaturated carbocylylene, 5-6 membered heteroarylene having 1-4 heteroatoms independently selected from nitrogen, oxygen, or sulfur, 3-8 membered saturated or partially unsaturated heterocyclylene having 1-4 heteroatoms independently selected from nitrogen, oxygen, or sulfur, an 8-10 membered bicyclic arylene or heteroarylene having 1-4 heteroatoms independently selected from nitrogen, oxygen, or sulfur, or an 8-10 membered saturated or partially unsaturated heterocyclylene having 1-4 heteroatoms independently selected from nitrogen, oxygen, or sulfur;

$R^w$ is selected from hydrogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)OR, —C(O)R$^x$, —S(O)$_2$OH, or —S(O)$_2$R$^y$, or is selected from:

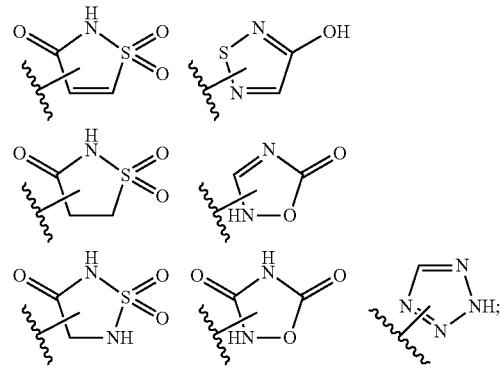

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R;
$R^y$ is selected from —N(R)C(O)CF$_3$, —N(R)C(O)R, or —N(R)C(O)N(R)$_2$;
each R is independently selected from hydrogen or an optionally substituted group selected from C$_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; and
$R^7$ is selected from hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from C$_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In certain embodiments, the present invention provides a compound of formula V:

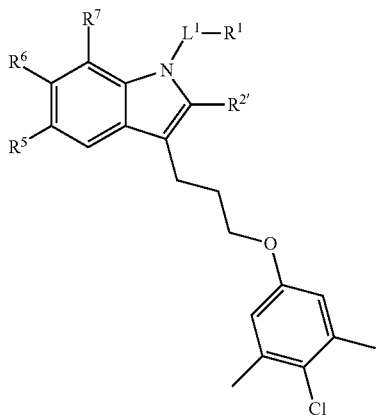

or a pharmaceutically acceptable salt thereof, wherein:

$L^1$ is selected from a covalent bond or an optionally substituted bivalent straight or branched $C_{1-6}$ hydrocarbon chain wherein one or more methylene units are optionally and independently replaced with -Cy-;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

$R^1$ is selected from hydrogen, halogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, —S(O)R$^y$, or —S(O)$_2$R$^y$;

each of $R^5$ and $R^6$ is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';

each R' is independently hydrogen or optionally substituted $C_{1-4}$ alkyl;

$R^{2'}$ is selected from —C(O)-L$^4$-R$^w$, —C(O)N(R)-L$^4$-R$^w$, —C(O)N(R)—C(R)$_2$-L$^4$-R$^w$, —C(O)O-L$^4$-R$^w$ or —C(O)S-L$^4$-R$^w$ L$^4$ is independently selected from a covalent bond or an optionally substituted bivalent straight or branched $C_{1-8}$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;

-Cy'- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, 3-8 membered saturated or partially unsaturated heterocyclylene having 1-4 heteroatoms independently selected from nitrogen, oxygen, or sulfur, or an 8-10 membered bicyclic arylene or heteroarylene having 1-4 heteroatoms independently selected from nitrogen, oxygen, or sulfur, or an 8-10 membered saturated or partially unsaturated heterocyclylene having 1-4 heteroatoms independently selected from nitrogen, oxygen, or sulfur;

$R^w$ is selected from hydrogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)OR, —C(O)R$^x$, —S(O)$_2$OH, or —S(O)$_2$R$^y$, or is selected from:

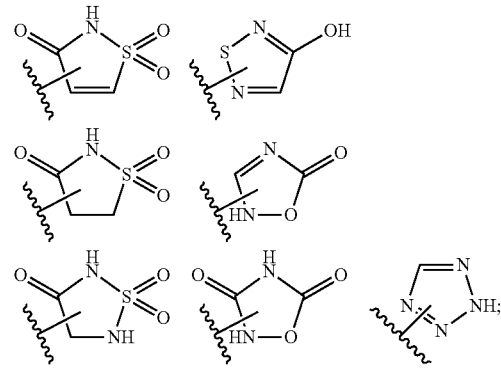

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R;

$R^y$ is selected from —N(R)C(O)CF$_3$, —N(R)C(O)R, or —N(R)C(O)N(R)$_2$;

each R is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur;

$R^7$ is selected from hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally $R^1$ and $R^{2'}$ are taken together with their intervening atoms to form an optionally substituted ring selected from a 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In certain embodiments, the present invention provides a compound of formula VI:

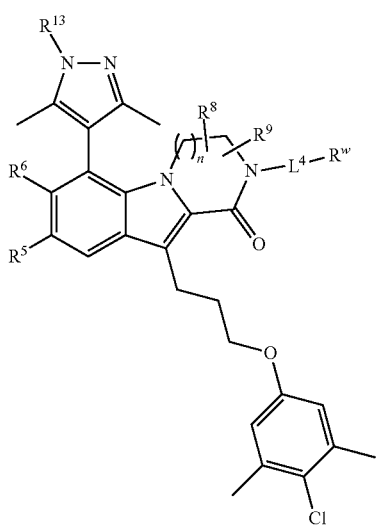

VI or a pharmaceutically acceptable salt thereof, wherein:
each of $R^5$, $R^6$, $R^8$, $R^9$, and $R^{13}$ is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';
each R' is independently selected from hydrogen or optionally substituted C$_{1-4}$ alkyl;
n is selected from 1 or 2;
$L^4$ is independently selected from a covalent bond or an optionally substituted bivalent straight or branched C$_{1-8}$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;
-Cy'- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, 3-8 membered saturated or partially unsaturated heterocyclylene having 1-4 heteroatoms independently selected from nitrogen, oxygen, or sulfur, an 8-10 membered bicyclic arylene or heteroarylene having 1-4 heteroatoms independently selected from nitrogen, oxygen, or sulfur, or an 8-10 membered saturated or partially unsaturated heterocyclylene having 1-4 heteroatoms independently selected from nitrogen, oxygen, or sulfur;

$R^w$ is selected from hydrogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)OR, —C(O)R$^x$, —S(O)$_2$OH, or —S(O)$_2$R$^y$, or is selected from:

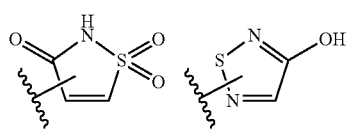

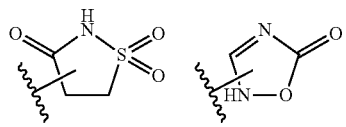

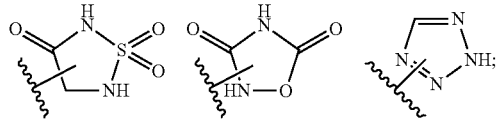

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R;

$R^y$ is selected from —N(R)C(O)CF$_3$, —N(R)C(O)R, or —N(R)C(O)N(R)$_2$; and each R is independently selected from hydrogen or an optionally substituted group selected from C$_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur In certain embodiments, the present invention provides a compound of formula VII:

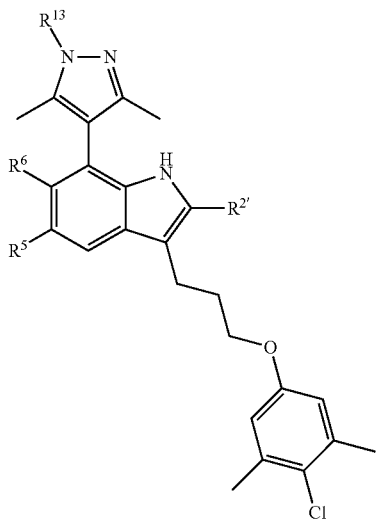

or a pharmaceutically acceptable salt thereof, wherein:

each of $R^5$, $R^6$, and $R^{13}$ is independently selected from R, halogen, —CN, —$NO_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';

each R' is independently hydrogen or optionally substituted $C_{1-4}$ alkyl;

$R^{2'}$ is selected from —C(O)-$L^4$-$R^w$, —C(O)N(R)-$L^4$-$R^w$, —C(O)N(R)—C(R)$_2$-$L^4$-$R^w$, —C(O)O-$L^4$-$R^w$ or —C(O)S-$L^4$-$R^w$ $L^4$ is independently selected from a covalent bond or an optionally substituted bivalent straight or branched $C_{1-8}$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;

-Cy'- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, 3-8 membered saturated or partially unsaturated heterocyclylene having 1-4 heteroatoms independently selected from nitrogen, oxygen, or sulfur, an 8-10 membered bicyclic arylene or heteroarylene having 1-4 heteroatoms independently selected from nitrogen, oxygen, or sulfur, or an 8-10 membered saturated or partially unsaturated heterocyclylene having 1-4 heteroatoms independently selected from nitrogen, oxygen, or sulfur;

$R^w$ is selected from hydrogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)OR, —C(O)$R^x$, —S(O)$_2$OH, or —S(O)$_2R^y$, or is selected from:

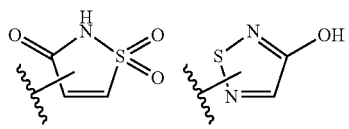

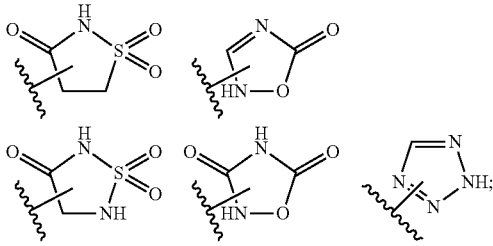

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R; and $R^y$ is selected from —N(R)C(O)CF$_3$, —N(R)C(O)R, or —N(R)C(O)N(R)$_2$; and each R is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic or polycyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C3-C6 hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a C1-4 straight or branched alkyl group. Exemplary lower alkyl groups are methyl, ethyl, propyl, isopropyl, butyl, isobutyl, and tert-butyl.

The term "lower haloalkyl" refers to a C1-4 straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen; or a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

As used herein, the term "bivalent C1-8 (or C1-6) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)n-, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, naphthyl, anthracyl and the like, which may be optionally substituted. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $-(CH_2)_{0-4}SC(O)R^\circ$; $-(CH_2)_{0-4}C(O)NR^\circ_2$; $-(CH_2)_{0-4}C(O)N(R^\circ)S(O)_2R^\circ$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)R^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-S(O)_2N(R^\circ)C(O)R^\circ$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $-SiR^\circ_3$; $-(C1-4$ straight or branched alkylene)$O-N(R^\circ)_2$; or $-(C1-4$ straight or branched alkylene)$C(O)O-N(R^\circ)_2$, wherein each $R^\circ$ may be substituted as defined below and is independently hydrogen, C1-6 aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}S(O)R^\bullet$, $-(CH_2)_{0-2}S(O)_2R^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a suitable carbon atom of an "optionally substituted" group include the following: $=O$, $=S$, $=NNR*_2$, $=NNHC(O)R*$, $=NNHC(O)OR*$, $=NNHS(O)_2R*$, $=NR*$, $=NOR*$, $-O(C(R*_2))_{2-3}O-$, or $-S(C(R*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, -(halo$R^\bullet$), $-OH$, $-OR^\bullet$, $-O(haloR^\bullet)$, $-CN$, $-C(O)R^\bullet$, $-C(O)OH$, $-C(O)OR^\bullet$, $-C(O)NR^\bullet_2$, $-SR^\bullet$, $-S(O)R^\bullet$, $-S(O)_2R^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, $-C(NR^\dagger)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(halo$R^\bullet$), $-OH$, $-OR^\bullet$, $-O(haloR^\bullet)$, $-CN$, $-C(O)OH$, $-C(O)OR^\bullet$, $-C(O)NR^\bullet_2$, $-SR^\bullet$, $-S(O)R^\bullet$, $-S(O)_2R^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention.

3. Description of Exemplary Embodiments:

In some embodiments, the present invention provides a compound of formula I:

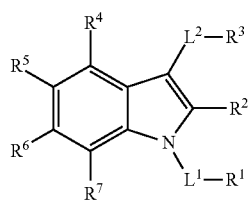

or a pharmaceutically acceptable salt thereof, wherein:
$L^1$ is selected from a covalent bond or an optionally substituted bivalent straight or branched $C_{1-6}$ hydrocarbon chain wherein one or more methylene units are optionally and independently replaced with -Cy-;
-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;
$R^1$ is selected from hydrogen, halogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, —S(O)R$^y$, or —S(O)$_2$R$^y$;
$R^2$ is selected from —C(O)-L$^3$-R$^z$, —C(O)N(R)-L$^3$-R$^z$, —C(O)N(R)—C(R)$_2$-L$^3$-R$^z$, —C(O)O-L$^3$-R$^z$ or —C(O)S-L$^3$-R$^z$;
$L^3$ is independently selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;
$R^z$ is selected from hydrogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^y$, or is selected from:

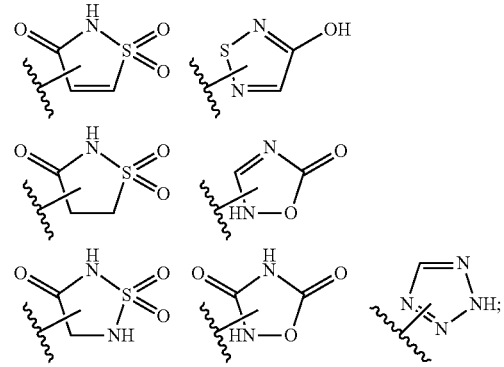

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R;
$R^y$ is selected from —N(R)C(O)CF$_3$, —N(R)C(O)R, or —N(R)C(O)N(R)$_2$; each R is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur;
$L^2$ is an optionally substituted bivalent straight or branched $C_{3-6}$ hydrocarbon chain wherein one or two methylene units of $L^2$ are optionally and independently replaced with —O—, —S—, or —N(R')—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;

each R' is independently selected from hydrogen or optionally substituted $C_{1-4}$ alkyl;

$R^3$ is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each of $R^4$, $R^5$, and $R^6$ is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';

$R^7$ is selected from hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally $R^1$ and $R^2$, $R^1$ and $R^7$, $R^4$ and $R^5$, $R^5$ and $R^6$ and/or $R^6$ and $R^7$ are taken together with their intervening atoms to form an optionally substituted ring selected from a 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, the present invention provides a compound of formula II:

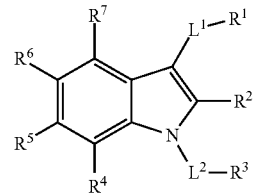

or a pharmaceutically acceptable salt thereof, wherein:

$L^1$ is selected from a covalent bond or an optionally substituted bivalent straight or branched $C_{1-6}$ hydrocarbon chain wherein one or more methylene units are optionally and independently replaced with -Cy-;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

$R^1$ is selected from hydrogen, halogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, —S(O)R$^y$, or —S(O)$_2$R$^y$;

$R^2$ is selected from —C(O)-L$^3$-R$^z$, —C(O)N(R)-L$^3$-R$^z$, —C(O)N(R)—C(R)$_2$-L$^3$-R$^z$, —C(O)O-L$^3$-R$^z$ or —C(O)S-L$^3$-R$^z$;

$L^3$ is independently selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—; R$^z$ is selected from hydrogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^y$, or is selected from:

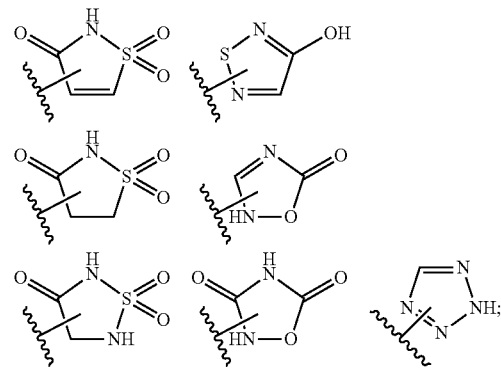

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R;

$R^y$ is selected from —N(R)C(O)CF$_3$, —N(R)C(O)R, or —N(R)C(O)N(R)$_2$;

each R is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur;

$L^2$ is an optionally substituted bivalent straight or branched $C_{3-6}$ hydrocarbon chain wherein one or two methylene units of $L^2$ are optionally and independently replaced with —O—, —S—, or —N(R')—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;

each R' is independently selected from hydrogen or optionally substituted $C_{1-4}$ alkyl;

$R^3$ is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each of $R^4$, $R^5$, and $R^6$ is independently selected from R, halogen, —CN, —NO$_2$, —C(O)OR', —OR', —SR', —C(O)N(R')$_2$, —N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';

$R^7$ is selected from hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally $R^1$ and $R^2$, $R^1$ and $R^7$, $R^4$ and $R^5$, $R^5$ and $R^6$ and/or $R^6$ and $R^7$ are taken together with their intervening atoms to form an optionally substituted ring selected from a 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, the present invention provides a compound of any one of formulae III, IV, V, VI, and VII, or a pharmaceutically acceptable salt thereof, wherein each variable is as defined above and described herein.

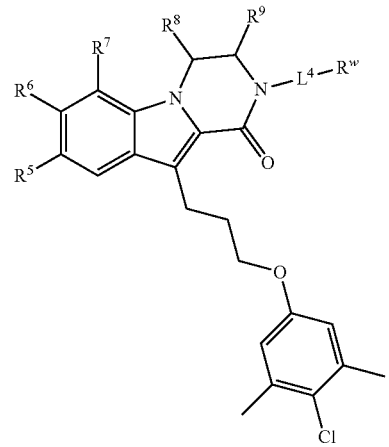

III

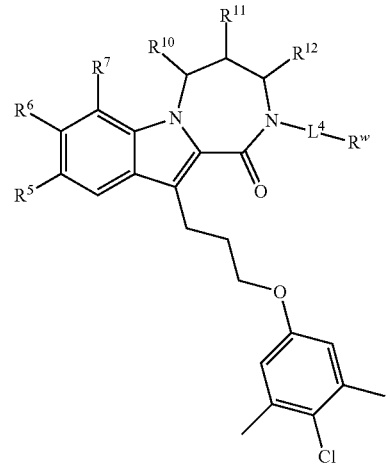

IV

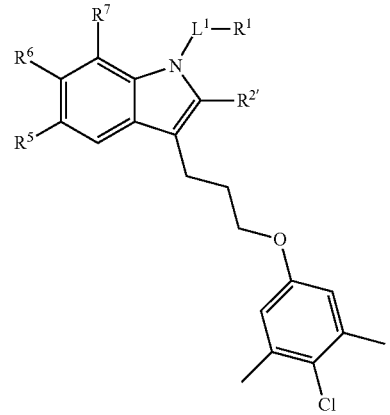

V

-continued

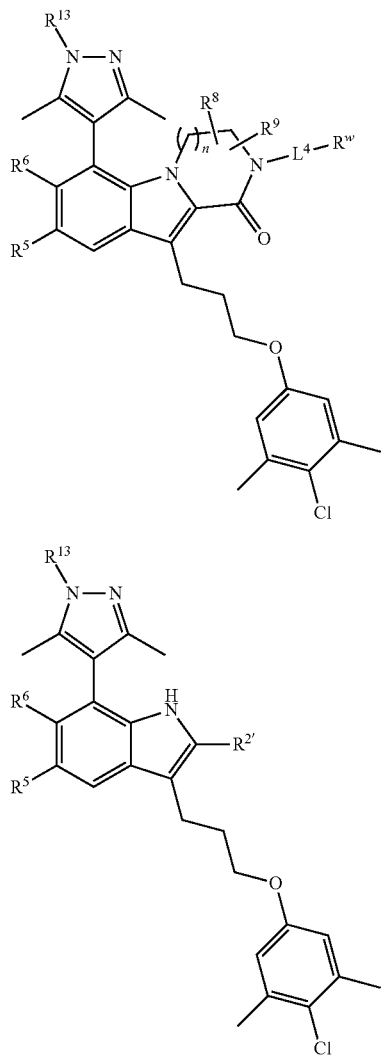

VI

VII

As generally defined above, $L^1$ of formula I, II, or V is selected from a covalent bond or an optionally substituted bivalent straight or branched $C_{1-6}$ hydrocarbon chain wherein one or more methylene units are optionally and independently replaced with -Cy-. In some embodiments, $L^1$ is a covalent bond. In some embodiments, $L^1$ is an optionally substituted bivalent straight or branched $C_{1-6}$ hydrocarbon chain wherein one or more methylene units are optionally and independently replaced with -Cy-. In some embodiments, $L^1$ is an optionally substituted bivalent straight or branched $C_{1-6}$ hydrocarbon chain. In some embodiments, $L^1$ is an optionally substituted bivalent straight or branched $C_{1-6}$ hydrocarbon chain wherein one or more methylene units are independently replaced with -Cy-.

In some embodiments, $L^1$ is an optionally substituted bivalent straight or branched $C_{1-6}$ hydrocarbon chain. In some embodiments, $L^1$ is an optionally substituted bivalent straight or branched $C_{2-6}$ hydrocarbon chain. In some embodiments, $L^1$ is an optionally substituted bivalent straight or branched $C_{3-6}$ hydrocarbon chain. In some embodiments, $L^1$ is an optionally substituted bivalent straight or branched $C_{4-6}$ hydrocarbon chain. In some embodiments, $L^1$ is an optionally substituted bivalent straight or branched $C_{5-6}$ hydrocarbon chain. In some embodiments, $L^1$ is an optionally substituted methylene group. In some embodiments, $L^1$ is an optionally substituted bivalent $C_2$ hydrocarbon chain. In some embodiments, $L^1$ is an optionally substituted bivalent straight or branched $C_3$ hydrocarbon chain. In some embodiments, $L^1$ is an optionally substituted bivalent straight or branched $C_4$ hydrocarbon chain. In some embodiments, $L^1$ is an optionally substituted bivalent straight or branched $C_5$ hydrocarbon chain. In some embodiments, $L^1$ is an optionally substituted bivalent straight or branched $C_6$ hydrocarbon chain.

In some embodiments, $L^1$ is an unsubstituted bivalent $C_{1-6}$ hydrocarbon chain. In some embodiments, $L^1$ is an unsubstituted bivalent $C_{2-6}$ hydrocarbon chain. In some embodiments, $L^1$ is an unsubstituted bivalent $C_{3-6}$ hydrocarbon chain. In some embodiments, $L^1$ is an unsubstituted bivalent $C_{4-6}$ hydrocarbon chain. In some embodiments, $L^1$ is an unsubstituted bivalent $C_{5-6}$ hydrocarbon chain. In some embodiments, $L^1$ is an unsubstituted methylene group. In some embodiments, $L^1$ is an unsubstituted bivalent $C_2$ hydrocarbon chain. In some embodiments, $L^1$ is an unsubstituted bivalent $C_3$ hydrocarbon chain. In some embodiments, $L^1$ is an unsubstituted bivalent $C_4$ hydrocarbon chain. In some embodiments, $L^1$ is an unsubstituted bivalent $C_5$ hydrocarbon chain. In some embodiments, $L^1$ is an unsubstituted bivalent $C_6$ hydrocarbon chain.

In some embodiments, $L^1$ is a substituted bivalent $C_{1-6}$ hydrocarbon chain. In some embodiments, $L^1$ is a substituted bivalent $C_{2-6}$ hydrocarbon chain. In some embodiments, $L^1$ is a substituted bivalent $C_{3-6}$ hydrocarbon chain. In some embodiments, $L^1$ is a substituted bivalent $C_{4-6}$ hydrocarbon chain. In some embodiments, $L^1$ is a substituted bivalent $C_{5-6}$ hydrocarbon chain. In some embodiments, $L^1$ is a substituted methylene group. In some embodiments, $L^1$ is a substituted bivalent $C_2$ hydrocarbon chain. In some embodiments, $L^1$ is a substituted bivalent $C_3$ hydrocarbon chain. In some embodiments, $L^1$ is a substituted bivalent $C_4$ hydrocarbon chain. In some embodiments, $L^1$ is a substituted bivalent $C_5$ hydrocarbon chain. In some embodiments, $L^1$ is a substituted bivalent $C_6$ hydrocarbon chain.

In some embodiments, $L^1$ is a substituted bivalent $C_{1-6}$ hydrocarbon chain wherein none of the substituents are —N(R)$_2$ or —N(R)C(O)R. In some embodiments, $L^1$ is a substituted bivalent $C_{1-6}$ hydrocarbon chain wherein none of the substituents are —N(R)$_2$ or —NHC(O)R.

In some embodiments, $L^1$ is optionally substituted methylene. In some embodiments, $L^1$ is —CH$_2$—. In some embodiments, $L^1$ is optionally substituted —CH$_2$CH$_2$—. In some embodiments, $L^1$ is —CH$_2$CH$_2$—. In some embodiments, $L^1$ is —CH(CH$_3$)—. In some embodiments, $L^1$ is —CH(CH$_2$CH$_3$)—. In some embodiments, $L^1$ is —CH(Ph)-. In some embodiments, $L^1$ is —CH(CH$_3$)CH$_2$—. In some embodiments, $L^1$ is —CH(Ph)CH$_2$—.

In some embodiments, $L^1$ is partially unsaturated. In some embodiments, $L^1$ comprises one or more double bonds. In some embodiments, $L^1$ is —CH=CH—. In some embodiments, $L^1$ comprises one or more triple bonds.

As defined generally above, -Cy- of formula I, II, or V is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur.

In some embodiments, -Cy- is optionally substituted phenylene. In some embodiments, -Cy- is substituted phenylene. In some embodiments, -Cy- is unsubstituted phenylene. In some embodiments, -Cy- is

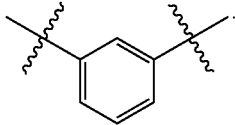 [SMILES: *c1cccc(*)c1]

In some embodiments, -Cy- is

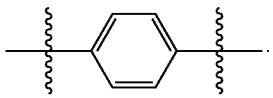

In some embodiments, -Cy- is optionally substituted bivalent 3-8 membered saturated or partially unsaturated carbocyclylene. In certain embodiments, -Cy- is optionally substituted bivalent 3-8 membered saturated carbocyclylene. In certain embodiments, -Cy- is optionally substituted bivalent 3-6 membered saturated carbocyclylene. In certain embodiments, -Cy- is optionally substituted bivalent 3-membered saturated carbocyclylene. In certain embodiments, -Cy- is optionally substituted bivalent 4-membered saturated carbocyclylene. In certain embodiments, -Cy- is optionally substituted bivalent 5-membered saturated carbocyclylene. In certain embodiments, -Cy- is optionally substituted bivalent 6-membered saturated carbocyclylene.

In some embodiments, -Cy- is optionally substituted bivalent 5-6 membered heteroarylene having 1-4 heteroatoms independently selected from nitrogen, oxygen, or sulfur. In certain embodiments, -Cy- is optionally substituted bivalent 5-membered heteroarylene having 1-4 heteroatoms independently selected from nitrogen, oxygen, or sulfur. In certain embodiments, -Cy- is optionally substituted bivalent 5-membered heteroarylene having 1-2 heteroatoms independently selected from nitrogen, oxygen, or sulfur. In certain embodiments, -Cy- is optionally substituted bivalent 5-membered heteroarylene having one heteroatom independently selected from nitrogen, oxygen, or sulfur. In some embodiments, -Cy- is

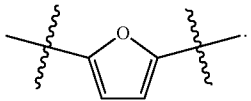

In certain embodiments, -Cy- is optionally substituted bivalent 6-membered heteroarylene having 1-4 heteroatoms independently selected from nitrogen, oxygen, or sulfur. In certain embodiments, -Cy- is optionally substituted bivalent 6-membered heteroarylene having 1-2 heteroatoms independently selected from nitrogen, oxygen, or sulfur.

In some embodiments, -Cy- is optionally substituted bivalent 3-8 membered saturated or partially unsaturated heterocyclylene having 1-4 heteroatoms independently selected from nitrogen, oxygen, or sulfur. In certain embodiments, -Cy- is optionally substituted bivalent 3-8 membered saturated heterocyclylene having 1-4 heteroatoms independently selected from nitrogen, oxygen, or sulfur. In certain embodiments, -Cy- is optionally substituted bivalent 3-8 membered saturated heterocyclylene having 1-2 heteroatoms independently selected from nitrogen, oxygen, or sulfur. In certain embodiments, -Cy- is optionally substituted bivalent 5-6 membered saturated heterocyclylene having 1-4 heteroatoms independently selected from nitrogen, oxygen, or sulfur. In certain embodiments, -Cy- is optionally substituted bivalent 5-6 membered saturated heterocyclylene having 1-2 heteroatoms independently selected from nitrogen, oxygen, or sulfur. In certain embodiments, -Cy- is optionally substituted bivalent 5-membered saturated heterocyclylene having 1-2 heteroatoms independently selected from nitrogen, oxygen, or sulfur. In certain embodiments, -Cy- is optionally substituted bivalent 6-membered saturated heterocyclylene having 1-2 heteroatoms independently selected from nitrogen, oxygen, or sulfur.

As defined generally above, $R^1$ of formula I, II, or V is hydrogen, halogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, —S(O)R$^y$, or —S(O)$_2$R$^y$. In some embodiments, $R^1$ is hydrogen. In some embodiments, $R^1$ is not hydrogen. In some embodiments, $R^1$ is halogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, —S(O)R$^y$, or —S(O)$_2$R$^y$.

In some embodiments, $R^1$ is halogen. In some embodiments, $R^1$ is —F. In some embodiments, $R^1$ is —Cl. In some embodiments, $R^1$ is —Br. In some embodiments, $R^1$ is —I.

In some embodiments, $R^1$ is R. In some embodiments, $R^1$ is R, wherein R is not hydrogen. In some embodiments, $R^1$ is optionally substituted $C_{1-12}$ aliphatic. In some embodiments, $R^1$ is optionally substituted $C_{1-6}$ alkyl. In some embodiments, $R^1$ is methyl.

In some embodiments, $R^1$ is —OR. In some embodiments, $R^1$ —SR. In some embodiments, $R^1$ is —S(O)R. In some embodiments, $R^1$ is —S(O)$_2$R. In some embodiments, $R^1$ is —S(O)$_2$N(R)$_2$. In some embodiments, $R^1$ is —N(R)$_2$. In some embodiments, $R^1$ is —C(O)N(R)$_2$. In some embodiments, $R^1$ is —C(O)R. In some embodiments, $R^1$ is —N(R)C(O)R. In some embodiments, $R^1$ is —N(R)C(O)OR. In some embodiments, $R^1$ is —N(R)C(O)N(R)$_2$. In some embodiments, $R^1$ is —N(R)S(O)$_2$R. In some embodiments, $R^1$ is —N(R)S(O)$_2$N(R)$_2$. In some embodiments, $R^1$ is —C(O)OH. In some embodiments, $R^1$ is —C(O)R$^x$. In some embodiments, $R^1$ is —C(O)N(R)S(O)$_2$R. In some embodiments, $R^1$ is —C(O)NHS(O)$_2$R. In some embodiments, $R^1$ is —C(O)NHS(O)$_2$Me. In some embodiments, $R^1$ is —S(O)$_2$OH. In some embodiments, $R^1$ is —S(O)R$^y$. In some embodiments, $R^1$ is —S(O)$_2$R$^y$. In some embodiments, $R^1$ is —S(O)$_2$N(R)C(O)$_R$. In some embodiments, $R^1$ is —S(O)$_2$NHC(O)R. In some embodiments, $R^1$ is —S(O)$_2$NHC(O)Me.

In some embodiments, $R^1$ is R. In some embodiments, $R^1$ is phenyl. In some embodiments, $R^1$ is pyridinyl. In some embodiments, $R^1$ is 2-pyridinyl. In some embodiments, $R^1$ is 3-pyridinyl. In some embodiments, $R^1$ is 4-pyridinyl. In some embodiments, $R^1$ is morpholino.

As defined generally above, $R^x$ of formula I, II, III, IV, V, VI, or VII is selected from —C(O)OR, —N(R)S(O)$_2$CF$_3$, —N(R)C(O)R, —N(R)C(O)OR, —N(R)C(O)N(R)$_2$, or —N(R)S(O)$_2$R. In some embodiments, $R^x$ is —C(O)OR. In some embodiments, $R^x$ is —N(R)S(O)$_2$CF$_3$. In some embodiments, $R^x$ is —N(R)C(O)R. In some embodiments, $R^x$ is —NHC(O)R. In some embodiments, $R^x$ is —NHC(O)

R, wherein R is not hydrogen. In some embodiments, $R^x$ is —N(R)C(O)OR. In some embodiments, $R^x$ is —NHC(O)OR. In some embodiments, $R^x$ is —NHC(O)OR, wherein R is not hydrogen. In some embodiments, $R^x$ is —N(R)C(O)N(R)$_2$. In some embodiments, $R^x$ is —NHC(O)N(R)$_2$. In some embodiments, $R^x$ is —NHC(O)N(R)$_2$, wherein at least one R is not hydrogen. In some embodiments, $R^x$ is —N(R)S(O)$_2$R. In some embodiments, $R^x$ is —NHS(O)$_2$R. In some embodiments, $R^x$ is —NHS(O)$_2$R, wherein R is not hydrogen.

As defined generally above, $R^y$ of formula I, II, III, IV, V, VI, or VII is selected from —N(R)C(O)CF$_3$, —N(R)C(O)R, or —N(R)C(O)N(R)$_2$. In some embodiments, $R^y$ is —N(R)C(O)CF$_3$. In some embodiments, $R^y$ is —NHC(O)CF$_3$. In some embodiments, $R^y$ is —N(R)C(O)R. In some embodiments, $R^y$ is —NHC(O)R. In some embodiments, $R^y$ is —NHC(O)R, wherein R is not hydrogen. In some embodiments, $R^y$ is —N(R)C(O)N(R)$_2$. In some embodiments, $R^y$ is —NHC(O)N(R)$_2$. In some embodiments, $R^y$ is —NHC(O)N(R)$_2$, wherein at least one R is not hydrogen.

As defined generally above, each R of formula I, II, III, IV, V, VI, or VII is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur. In some embodiments, each R is independently selected from hydrogen or an optionally substituted group selected from $C_{1-6}$ aliphatic or a ring selected from a 3-10 membered saturated or partially unsaturated carbocyclic ring, phenyl, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur.

In some embodiments, R is hydrogen.

In some embodiments, R is an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur. In some embodiments, R is an optionally substituted group selected from $C_{1-6}$ aliphatic or a ring selected from a 3-10 membered saturated or partially unsaturated carbocyclic ring, phenyl, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur.

In some embodiments, R is substituted. In some embodiments, R is unsubstituted.

In some embodiments, R is optionally substituted $C_{1-12}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is optionally substituted adamantyl. In some embodiments, R is

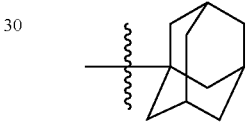

In some embodiments, R is

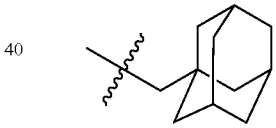

In some embodiments, R is an optionally substituted 3-10 membered saturated or partially unsaturated carbocyclic ring. In some embodiments, R is an optionally substituted 3-10 membered saturated or partially unsaturated monocyclic, bicyclic or polycyclic carbocyclic ring. In some embodiments, R is an optionally substituted 3-10 membered saturated or partially unsaturated monocyclic, bicyclic or tricyclic carbocyclic ring. In some embodiments, R is an optionally substituted 3-10 membered saturated or partially unsaturated monocyclic or bicyclic carbocyclic ring. In some embodiments, R is an optionally substituted 3-10 membered saturated or partially unsaturated monocyclic carbocyclic ring. In some embodiments, R is an optionally substituted 4-10 membered saturated or partially unsaturated bicyclic carbocyclic ring. In some embodiments, R is an optionally substituted 4-10 membered saturated or partially unsaturated polycyclic carbocyclic ring. In some embodiments, R is an optionally substituted 3-10 membered saturated or partially unsaturated tricyclic carbocyclic ring. In some embodiments, R is an optionally substituted 3-membered saturated or partially unsaturated monocyclic carbocyclic ring. In some embodiments, R is an optionally substituted 4-membered saturated or partially unsaturated monocyclic carbocyclic ring. In some embodiments, R is an optionally substituted 5-membered saturated or partially unsaturated monocyclic carbocyclic ring. In some embodiments, R is an optionally substituted 6-membered saturated or partially unsaturated monocyclic carbocyclic ring. In some embodiments, R is an optionally substituted 6-membered saturated or partially unsaturated bicyclic carbocyclic ring. In some embodiments, R is an optionally substituted 7-membered saturated or partially unsaturated monocyclic carbocyclic ring. In some embodiments, R is an optionally substituted 7-membered saturated or partially unsaturated bicyclic carbocyclic ring. In some embodiments, R is an optionally substituted 8-membered saturated or partially unsaturated monocyclic carbocyclic ring. In some embodiments, R is an optionally substituted 8-membered saturated or partially unsaturated bicyclic carbocyclic ring. In some embodiments, R is an optionally substituted 9-membered saturated or partially unsaturated monocyclic carbocyclic ring. In some embodiments, R is an optionally substituted 9-membered saturated or partially unsaturated bicyclic carbocyclic ring. In some embodiments, R is an optionally substituted 9-membered saturated or partially unsaturated tricyclic carbocyclic ring. In some embodiments, R is

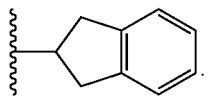

In some embodiments, R is an optionally substituted 10-membered saturated or partially unsaturated monocyclic carbocyclic ring. In some embodiments, R is an optionally substituted 10-membered saturated or partially unsaturated bicyclic carbocyclic ring. In some embodiments, R is an optionally substituted 10-membered saturated or partially unsaturated tricyclic carbocyclic ring.

In some embodiments, R is an optionally substituted 3-8 membered saturated monocyclic carbocyclic ring. In some embodiments, R is an optionally substituted cycloheptyl. In some embodiments, R is an optionally substituted cyclohexyl. In some embodiments, R is an optionally substituted cyclopentyl. In some embodiments, R is an optionally substituted cyclobutyl. In some embodiments, R is an optionally substituted cyclopropyl.

In some embodiments, R is an optionally substituted 3-8 membered unsaturated monocyclic carbocyclic ring. In some embodiments, R is an optionally substituted cycloheptenyl. In some embodiments, R is an optionally substituted cyclohexenyl. In some embodiments, R is an optionally substituted cyclopentenyl. In some embodiments, R is an optionally substituted cyclobutenyl. In some embodiments, R is an optionally substituted cyclopropyl.

In some embodiments, R is

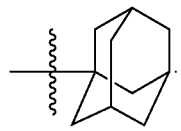

In some embodiments, R is optionally substituted phenyl. In some embodiments, R is unsubstituted phenyl. In some embodiments, R is substituted phenyl. In some embodiments, R is 4-bromophenyl. In some embodiments, R is 2-trifluoromethylphenyl. In some embodiments, R is 4-trifluoromethylphenyl. In some embodiments, R is 2-cyanophenyl. In some embodiments, R is 3-cyanophenyl. In some embodiments, R is 4-cyanophenyl. In some embodiments, R is 2-nitrophenyl. In some embodiments, R is 3-nitrophenyl. In some embodiments, R is 4-nitrophenyl.

In some embodiments, R is a 6-10 membered bicyclic saturated, partially unsaturated or aryl ring. In some embodiments, R is a 6-10 membered bicyclic saturated ring. In some embodiments, R is an 8-10 membered bicyclic partially unsaturated ring. In some embodiments, R is an 8-10 membered bicyclic aryl ring. In some embodiments, R is optionally substituted naphthyl. In some embodiments, R is

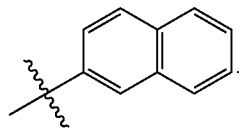 [SMILES: *c1ccc2ccccc2c1]

In some embodiments, R is an optionally substituted 3-8 membered saturated or partially unsaturated heterocyclic ring having 1-2 heteroatoms independently selected from nitrogen, oxygen or sulfur. In some embodiments, R is a substituted 3-8 membered saturated or partially unsaturated heterocyclic ring having 1-2 heteroatoms independently selected from nitrogen, oxygen or sulfur. In some embodiments, R is an unsubstituted 3-8 membered saturated or partially unsaturated heterocyclic ring having 1-2 heteroatoms independently selected from nitrogen, oxygen or sulfur.

In some embodiments, R is an optionally substituted 3-8 membered saturated heterocyclic ring having 1-2 heteroatoms independently selected from nitrogen, oxygen or sulfur. In some embodiments, R is a substituted 3-8 membered saturated heterocyclic ring having 1-2 heteroatoms independently selected from nitrogen, oxygen or sulfur. In some embodiments, R is an unsubstituted 3-8 membered saturated heterocyclic ring having 1-2 heteroatoms independently selected from nitrogen, oxygen or sulfur.

In some embodiments, R is an optionally substituted 3-membered saturated heterocyclic ring having one heteroatom selected from nitrogen, oxygen or sulfur. Exemplary R groups include but are not limited to optionally substituted aziridinyl, thiiranyl or oxiranyl. In some embodiments, R is a substituted 3-membered saturated heterocyclic ring having one heteroatom selected from nitrogen, oxygen or sulfur. In some embodiments, R is an unsubstituted saturated 3-membered heterocyclic ring having one heteroatom selected from nitrogen, oxygen or sulfur.

In some embodiments, R is an optionally substituted 4-membered saturated heterocyclic ring having 1-2 heteroatoms independently selected from nitrogen, oxygen, or sulfur. Exemplary R groups include but are not limited to optionally substituted azetidinyl, oxetanyl, thietanyl, oxazetidinyl, thiazetidinyl, or diazetidinyl. In some embodiments, R is a substituted 4-membered saturated heterocyclic ring having 1-2 heteroatoms independently selected from nitrogen, oxygen, or sulfur. In some embodiments, R is an unsubstituted 4-membered saturated heterocyclic ring having 1-2 heteroatoms independently selected from nitrogen, oxygen, or sulfur.

In some embodiments, R is an optionally substituted 5-membered saturated heterocyclic ring having 1-2 heteroatoms independently selected from nitrogen, oxygen, or sulfur. Exemplary R groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, or thiazolidinyl. In some embodiments, R is a substituted 5-membered saturated heterocyclic ring having 1-2 heteroatoms independently selected from nitrogen, oxygen, or sulfur. In some embodiments, R is an unsubstituted 5-membered saturated heterocyclic ring having 1-2 heteroatoms independently selected from nitrogen, oxygen, or sulfur.

In some embodiments, R is an optionally substituted 6-membered saturated heterocyclic ring having 1-2 heteroatoms independently selected from nitrogen, oxygen, or sulfur. Exemplary R groups include but are not limited to optionally substituted piperidinyl, tetrahydropyranyl, tetrahydrothiopyranyl, piperazinyl, morpholinyl, thiomorpholinyl, dithianyl, dioxanyl, and oxathianyl. In some embodiments, R is a substituted 6-membered saturated heterocyclic ring having 1-2 heteroatoms independently selected from nitrogen, oxygen, or sulfur. In some embodiments, R is an unsubstituted 6-membered saturated heterocyclic ring having 1-2 heteroatoms independently selected from nitrogen, oxygen, or sulfur.

In some embodiments, R is optionally substituted 7-membered saturated heterocyclic ring having 1-2 heteroatoms independently selected from nitrogen, oxygen, or sulfur. Exemplary R groups include but are not limited to optionally substituted azepanyl, oxepanyl, thiepanyl, diazepanyl, oxazepanyl, thiazepanyl, dioxepanyl, oxathiepanyl, or dithiepanyl. In some embodiments, R is a substituted 7-membered saturated heterocyclic ring having 1-2 heteroatoms independently selected from nitrogen, oxygen, or sulfur. In some embodiments, R is an unsubstituted 7-membered saturated heterocyclic ring having 1-2 heteroatoms independently selected from nitrogen, oxygen, or sulfur.

In some embodiments, R is optionally substituted 8-membered saturated heterocyclic ring having 1-2 heteroatoms independently selected from nitrogen, oxygen, or sulfur. In some embodiments, R is a substituted 8-membered saturated heterocyclic ring having 1-2 heteroatoms independently selected from nitrogen, oxygen, or sulfur. In some embodiments, R is an unsubstituted 8-membered saturated heterocyclic ring having 1-2 heteroatoms independently selected from nitrogen, oxygen, or sulfur.

In some embodiments, R is an optionally substituted 3-8 membered partially unsaturated heterocyclic ring having 1-2 heteroatoms independently selected from nitrogen, oxygen or sulfur. In certain embodiments, R is an optionally substituted 5-7 membered partially unsaturated ring having 1-2 heteroatoms independently selected from nitrogen, oxygen, or sulfur. In certain embodiments, R is an optionally substituted 5-6 membered partially unsaturated ring having 1-2 heteroatoms independently selected from nitrogen, oxygen, or sulfur.

In certain embodiments, R is an optionally substituted 5-membered partially unsaturated ring having 1-2 heteroatoms independently selected from nitrogen, oxygen, or sulfur. Exemplary R groups include but are not limited to optionally substituted dihydroimidazolyl, dihydrothiazolyl, dihydrooxazolyl, or oxazolinyl.

In certain embodiments, R is an optionally substituted 6-membered partially unsaturated ring having 1-2 heteroatoms independently selected from nitrogen, oxygen, or sulfur. Exemplary R groups include but are not limited to optionally substituted dihydropyridinyl, tetrahydropyridinyl, dihydropyrimidinyl, tetrahydropyrimidinyl, dihydropyrazinyl, tetrahydropyrazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl.

In certain embodiments, R is an optionally substituted 7-membered partially unsaturated ring having 1-2 heteroatoms independently selected from nitrogen, oxygen, or sulfur. Exemplary R groups include but are not limited to optionally substituted azepinyl, oxepinyl, thiepinyl, diazepinyl, oxazepinyl, thiazepinyl, triazepinyl, oxadiazepinyl, thiadiazepinyl, dihydroazepinyl, dihydrooxepinyl, dihydrothiepinyl, dihydrodiazepinyl, dihydrooxazepinyl, dihydrothiazepinyl, tetrahydroazepinyl, tetrahydrooxepinyl, tetrahydrothiepinyl, tetrahydrodiazepinyl, tetrahydrooxazepinyl or tetrahydrothiazepinyl.

In some embodiments, R is an optionally substituted 8-membered partially unsaturated ring having 1-2 heteroatoms independently selected from nitrogen, oxygen or sulfur.

In some embodiments, R is an optionally substituted 5-6 membered heteroaryl ring having 1-4 heteroatoms independently selected from nitrogen, oxygen, or sulfur. In some embodiments, R is a substituted 5-6 membered heteroaryl ring having 1-4 heteroatoms independently selected from nitrogen, oxygen, or sulfur. In some embodiments, R is an unsubstituted 5-6 membered heteroaryl ring having 1-4 heteroatoms independently selected from nitrogen, oxygen, or sulfur.

In some embodiments, R is an optionally substituted 5-membered heteroaryl ring having 1-4 heteroatoms independently selected from nitrogen, oxygen or sulfur. In some embodiments, R is a substituted 5-membered heteroaryl ring having 1-4 heteroatoms independently selected from nitrogen, oxygen or sulfur. In some embodiments, R is an unsubstituted 5-membered heteroaryl ring having 1-4 heteroatoms independently selected from nitrogen, oxygen or sulfur. In some embodiments, R is an optionally substituted 6-membered heteroaryl ring having 1-4 heteroatoms independently selected from nitrogen, oxygen, or sulfur. In some embodiments, R is a substituted 6-membered heteroaryl ring having 1-4 heteroatoms independently selected from nitrogen, oxygen, or sulfur. In some embodiments, R is an unsubstituted 6-membered heteroaryl ring having 1-4 heteroatoms independently selected from nitrogen, oxygen, or sulfur.

In some embodiments, R is an optionally substituted 5-membered heteroaryl ring having one heteroatom selected from nitrogen, oxygen, or sulfur. In some embodiments, R is selected from optionally substituted pyrrolyl, furanyl, or thienyl. In some embodiments, R is optionally substituted pyrrolyl. In some embodiments, R is optionally substituted furanyl. In some embodiments, R is optionally substituted thienyl.

In some embodiments, R is an optionally substituted 5-membered heteroaryl ring having two heteroatoms independently selected from nitrogen, oxygen, or sulfur. In certain embodiments, R is an optionally substituted 5-membered heteroaryl ring having one nitrogen atom, and an additional heteroatom selected from sulfur or oxygen. Exemplary R groups include but are not limited to optionally substituted pyrazolyl, imidazolyl, thiazolyl, isothiazolyl, oxazolyl or isoxazolyl. In some embodiments, R is optionally substituted pyrazolyl. In some embodiments, R is In some embodiments, R is

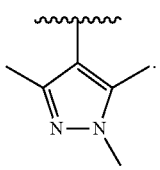

In some embodiments, R is

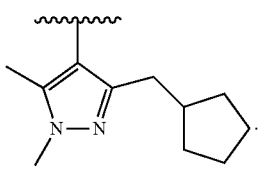 [SMILES: *c1c(CC2CCCC2)nn(C)c1C]

In some embodiments, R is an optionally substituted 5-membered heteroaryl ring having three heteroatoms independently selected from nitrogen, oxygen, or sulfur. Exemplary R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, or sulfur. Exemplary R groups include but are not limited to optionally substituted tetrazolyl, oxatriazolyl and thiatriazolyl.

In some embodiments, R is a 6-membered heteroaryl ring having 1-4 nitrogen atoms. In some embodiments, R is a 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Exemplary R groups include but are not limited to optionally substituted pyridinyl, pyrimidinyl, pyrazinyl, pyridazinyl, triazinyl, or tetrazinyl. In some embodiments, R is optionally substituted pyridinyl. In some embodiments, R is pyridinyl. In some embodiments, R is

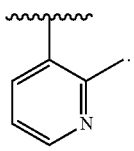 [SMILES: *c1cccnc1C]

In some embodiments, R is a 7-10 membered bicyclic saturated or partially unsaturated heterocyclic ring having 1-5 heteroatoms independently selected from nitrogen, oxygen or sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an 8-10 membered bicyclic heteroaryl ring having 1-5 heteroatoms independently selected from nitrogen, oxygen or sulfur.

In some embodiments, R is an optionally substituted 5,6-fused heteroaryl ring having 1-5 heteroatoms independently selected from nitrogen, oxygen or sulfur. In some embodiments, R is an optionally substituted 5,6-fused heteroaryl ring having 1-4 heteroatoms independently selected from nitrogen, oxygen or sulfur. In some embodiments, R is an optionally substituted 5,6-fused heteroaryl ring having 1-3 heteroatoms independently selected from nitrogen, oxygen or sulfur. In some embodiments, R is an optionally substituted 5,6-fused heteroaryl ring having two heteroatoms independently selected from nitrogen, oxygen or sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen or sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen or sulfur. In some embodiments, R is an optionally substituted 5,6-fused heteroaryl ring having five heteroatoms independently selected from nitrogen, oxygen or sulfur.

In some embodiments, R is an optionally substituted 5,6-fused heteroaryl ring having 1-5 heteroatoms independently selected from nitrogen, oxygen or sulfur. In other embodiments, R is an optionally substituted 5,6-fused heteroaryl ring having 1-2 heteroatoms independently selected from nitrogen, oxygen or sulfur. In certain embodiments, R is an optionally substituted 5,6-fused heteroaryl ring having one heteroatom independently selected from nitrogen, oxygen or sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen or sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen or sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen or sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen or sulfur. In some embodiments, R is

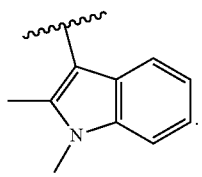 [SMILES: *c1c(C)n(C)c2ccccc12]

In certain embodiments, R is an optionally substituted 6,6-fused heteroaryl ring having 1-5 heteroatoms independently selected from nitrogen, oxygen or sulfur. In some embodiments, R is an optionally substituted 6,6-fused heteroaryl ring having 1-2 heteroatoms independently selected from nitrogen, oxygen or sulfur. In other embodiments, R is an optionally substituted 6,6-fused heteroaryl ring having one heteroatom selected from nitrogen, oxygen or sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen or sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen or sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen or sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen or sulfur.

As defined generally above, $R^2$ of formula I or II is —C(O)-$L^3$-$R^z$, —C(O)N(R)-$L^3$-$R^z$, —C(O)N(R)—C(R)$_2$-$L^3$-$R^z$, —C(O)O-$L^3$-$R^z$ or —C(O)S-$L^3$-$R^z$.

In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are optionally taken together with their intervening atoms to form an optionally substituted 4-8 membered saturated, partially unsaturated or aryl ring having 2-4 heteroatoms independently selected from nitrogen, oxygen, or sulfur. In some embodiments, $R^2$ is —C(O)N(R)-$L^3$-$R^z$, wherein the R group attached to the nitrogen atom and $R^1$ are optionally taken together with their intervening atoms to form an optionally substituted 4-8 membered saturated, partially unsaturated or aryl ring having 2-4 heteroatoms independently selected from nitrogen, oxygen, or sulfur. In some embodiments, $R^2$ is —C(O)N(R)—C(R)$_2$-$L^3$-$R^z$, wherein the R group attached to the nitrogen atom and $R^1$ are optionally taken together with their intervening atoms to form an optionally substituted 4-8 membered saturated, partially unsaturated or aryl ring having 2-4 heteroatoms independently selected from nitrogen, oxygen, or sulfur.

In some embodiments, $R^2$ is —C(O)-$L^3$-$R^z$. In some embodiments, $R^2$ is —C(O)N(R)-$L^3$-$R^z$. In some embodiments, $R^2$ is —C(O)N(R)—C(R)$_2$-$L^3$-$R^z$. In some embodiments, $R^2$ is —C(O)O-$L^3$-$R^z$. In some embodiments, $R^2$ is —C(O)S-$L^3$-$R^z$.

As generally defined above, $L^3$ of formula I or II is selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —C(O)—, —C(O)N(R)—, or —S(O)—. In some embodiments, $L^3$ is selected from a covalent bond or an optionally substituted bivalent straight or branched $C_{1-8}$ hydrocarbon chain wherein one or more methylene units are optionally and independently replaced with -Cy-, —O—, —N(R)—, —N(R)C(O)—, —C(O)—, or —C(O)N(R)—. $L^3$ is selected from a covalent bond or an optionally substituted bivalent straight or branched $C_{1-8}$ hydrocarbon chain wherein one or more methylene units are optionally and independently replaced with -Cy- or —O—.

In some embodiments, $L^3$ is a covalent bond. In some embodiments, $L^3$ is an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted methylene group or -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_2$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_3$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_4$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_5$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_6$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_7$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_8$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—.

In some embodiments, L$^3$ is an optionally substituted bivalent straight or branched C$_{1-8}$ hydrocarbon chain wherein one or more methylene units are independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, L$^3$ is an optionally substituted bivalent straight or branched C$_{1-8}$ hydrocarbon chain wherein one or more methylene units are independently replaced with -Cy-, —O—, —S—, —N(R)—, —N(R)C(O)—, —C(O)—, —C(O)N(R)—, or —S(O)—. In some embodiments, L$^3$ is an optionally substituted bivalent straight or branched C$_{1-8}$ hydrocarbon chain wherein one or more methylene units are independently replaced with -Cy-, —O—, —N(R)—, —N(R)C(O)—, —C(O)—, or —C(O)N(R)—. In some embodiments, L$^3$ is an optionally substituted bivalent straight or branched C$_{1-8}$ hydrocarbon chain wherein one or more methylene units are independently replaced with -Cy- or —O—.

In some embodiments, L$^3$ is an optionally substituted bivalent straight or branched C$_{1-8}$ hydrocarbon chain. In some embodiments, L$^3$ is a bivalent straight or branched C$_{1-8}$ hydrocarbon chain. In some embodiments, L$^3$ is a bivalent straight C$_{1-8}$ hydrocarbon chain.

In some embodiments, one or more methylene units of L$^3$ are optionally and independently replaced with -Cy-, —O—, —S—, —N(R)—, —N(R)C(O)—, —C(O)—, —C(O)N(R)—, or —S(O)—. In some embodiments, R$^2$ is —C(O)-L$^3$-R$^z$, —C(O)N(R)-L$^3$-R$^z$, —C(O)N(R)—C(R)$_2$-L$^3$-R$^z$, —C(O)O-L$^3$-R$^z$ or —C(O)S-L$^3$-R$^z$, wherein the methylene unit of L$^3$ that is directly bonded to said —C(O)—, —C(O)N(R)—, —C(O)N(R)—C(R)$_2$—, —C(O)O— or —C(O)S— moiety is optionally and independently replaced by -Cy-, —O—, —S—, —N(R)—, —N(R)C(O)—, —C(O)—, —C(O)N(R)—, or —S(O)—. In some embodiments, one or more methylene units of L$^3$ are optionally and independently replaced with -Cy-, —O—, —N(R)—, —N(R)C(O)—, —C(O)—, or —C(O)N(R)—. In some embodiments, R$^2$ is —C(O)-L$^3$-R$^z$, —C(O)N(R)-L$^3$-R$^z$, —C(O)N(R)—C(R)$_2$-L$^3$-R$^z$, —C(O)O-L$^3$-R$^z$ or —C(O)S-L$^3$-R$^z$, wherein the methylene unit of L$^3$ that is directly bonded to said —C(O)—, —C(O)N(R)—, —C(O)N(R)—C(R)$_2$—, —C(O)O— or —C(O)S— moiety is optionally and independently replaced by -Cy-, —O—, —N(R)—, —N(R)C(O)—, —C(O)—, or —C(O)N(R)—. In some embodiments, one or more methylene units of L$^3$ are optionally and independently replaced with -Cy- or —O—. In some embodiments, R$^2$ is —C(O)-L$^3$-R$^z$, —C(O)N(R)-L$^3$-R$^z$, —C(O)N(R)—C(R)$_2$-L$^3$-R$^z$, —C(O)O-L$^3$-R$^z$ or —C(O)S-L$^3$-R$^z$, wherein the methylene unit of L$^3$ that is directly bonded to said —C(O)—, —C(O)N(R)—, —C(O)N(R)—C(R)$_2$—, —C(O)O— or —C(O)S— moiety is optionally and independently replaced by -Cy- or —O—.

In some embodiments, one or more methylene units are independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, one or more methylene units are replaced with -Cy-. In some embodiments, one or more methylene units are replaced with —O—. In some embodiments, one or more methylene units are replaced with —S—. In some embodiments, one or more methylene units are replaced with —N(R)—. In some embodiments, one or more methylene units are replaced with —N(R)C(O)—. In some embodiments, one or more methylene units are replaced with —N(R)S(O)$_2$—. In some embodiments, one or more methylene units are replaced with —C(O)—. In some embodiments, one or more methylene units are replaced with —C(O)N(R)—. In some embodiments, one or more methylene units are replaced with —S(O)—. In some embodiments, one or more methylene units are replaced with —S(O)$_2$—. In some embodiments, one or more methylene units are replaced with —S(O)$_2$N(R)—.

In some embodiments, the methylene unit of L$^3$ that is directly bonded to R$^z$ is optionally replaced with -Cy-. In some embodiments, the methylene unit of L$^3$ that is directly bonded to R$^z$ is replaced with -Cy-. In some embodiments, the methylene unit of L$^3$ that is directly bonded to R$^z$ is replaced with an optionally substituted phenylene. In some embodiments, the methylene unit of L$^3$ that is directly bonded to R$^z$ is replaced with an optionally substituted 5-6 membered heteroarylene having 1-4 heteroatoms independently selected from nitrogen, oxygen, or sulfur.

In some embodiments, L$^3$ is —NRS(O)$_2$(CH$_2$)$_2$N(R)C(O)—.

As generally defined above, R$^z$ of formula I or II is hydrogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^y$, or is selected from:

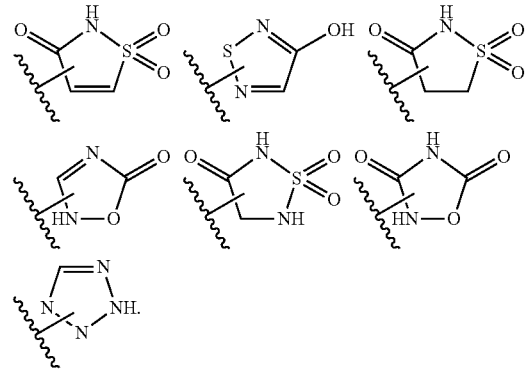

In some embodiments, R$^z$ is —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^y$, or is selected from:

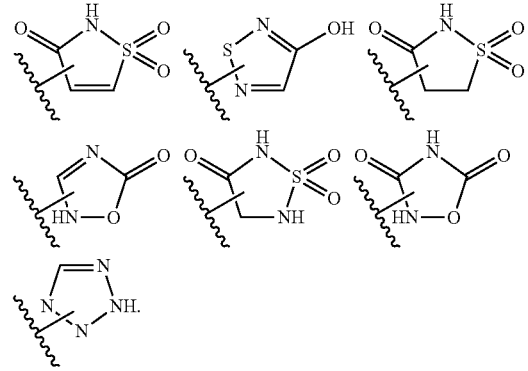

In some embodiments, $R^z$ is —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^y$, or is selected from:

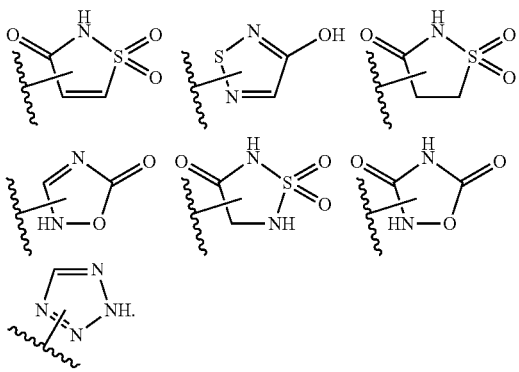

In some embodiments, $R^z$ is —S(O)$_2$N(R)$_2$, —C(O)N(R)$_2$, —C(O)OH, —C(O)R$^x$, —S(O)$_2$OH, or —S(O)$_2$R$^y$, or is selected from:

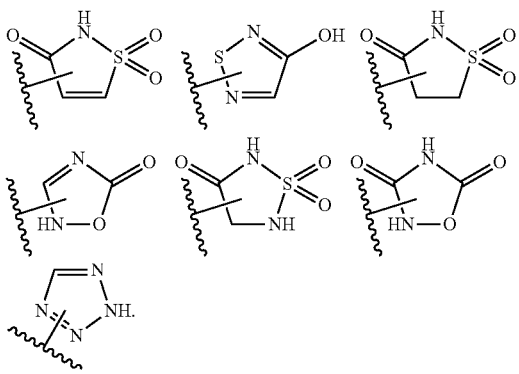

In some embodiments, $R^z$ is —S(O)$_2$N(R)$_2$, —C(O)N(R)$_2$, —C(O)OH, —C(O)R$^x$, —S(O)$_2$OH, or —S(O)$_2$R. In some embodiments, $R^z$ is —COOH, —C(O)N(R)SO$_2$R or —SO$_2$N(R)C(O)R. In some embodiments, $R^z$ is —COOH, —C(O)NHSO$_2$R or —SO$_2$NHC(O)R.

In some embodiments, $R^z$ is hydrogen. In some embodiments, $R^z$ is not hydrogen.

In some embodiments, $R^z$ is R. In some embodiments, $R^z$ is R, wherein R is not hydrogen.

In some embodiments, $R^z$ is —OR. In some embodiments, $R^z$ —SR. In some embodiments, $R^z$ is —S(O)R. In some embodiments, $R^z$ is —S(O)$_2$R. In some embodiments, $R^z$ is —S(O)$_2$N(R)$_2$. In some embodiments, $R^z$ is —N(R)$_2$. In some embodiments, $R^z$ is —C(O)N(R)$_2$. In some embodiments, $R^z$ is —C(O)R. In some embodiments, $R^z$ is —N(R)C(O)R. In some embodiments, $R^z$ is —N(R)C(O)OR. In some embodiments, $R^z$ is —N(R)C(O)N(R)$_2$. In some embodiments, $R^z$ is —N(R)S(O)$_2$R. In some embodiments, $R^z$ is —N(R)S(O)$_2$N(R)$_2$.

In some embodiments, $R^z$ is —C(O)OH.

In some embodiments, $R^z$ is —C(O)R$^x$. In some embodiments, $R^z$ is —C(O)N(R)S(O)$_2$R. In some embodiments, $R^z$ is —C(O)NHS(O)$_2$R. In some embodiments, $R^z$ is —C(O)N(R)S(O)$_2$R, wherein R is not hydrogen. In some embodiments, $R^z$ is —C(O)NHS(O)$_2$R, wherein R is not hydrogen. In some embodiments, $R^z$ is —C(O)N(R)S(O)$_2$R, wherein R is optionally substituted C$_{1-6}$ aliphatic. In some embodiments, $R^z$ is —C(O)NHS(O)$_2$R, wherein R is optionally substituted C$_{1-6}$ aliphatic. In some embodiments, $R^z$ is —C(O)N(R)S(O)$_2$Me. In some embodiments, $R^z$ is —C(O)NHS(O)$_2$Me. In some embodiments, $R^z$ is

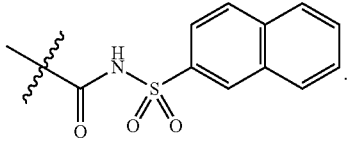 [SMILES: *C(=O)NS(=O)(=O)c1ccc2ccccc2c1]

In some embodiments, $R^z$ is

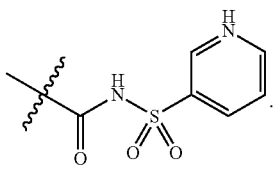

In some embodiments, $R^z$ is

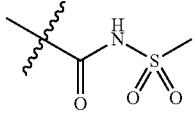

In some embodiments, $R^z$ is

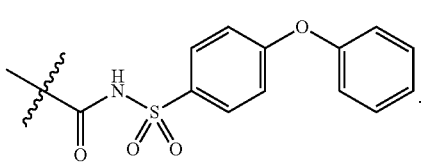 [SMILES: *C(=O)NS(=O)(=O)c1ccc(Oc2ccccc2)cc1]

In some embodiments, $R^z$ is

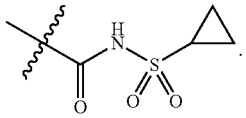 [SMILES: *C(=O)NS(=O)(=O)C1CC1]

In some embodiments, $R^z$ is

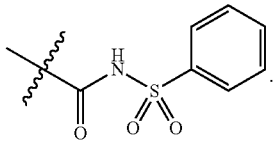 [SMILES: *C(=O)NS(=O)(=O)c1ccccc1]

In some embodiments, $R^z$ is

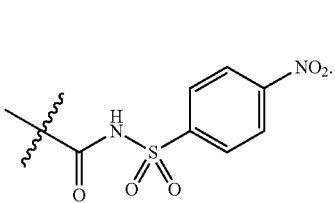 [SMILES: *C(=O)NS(=O)(=O)c1ccc([N+](=O)[O-])cc1]

In some embodiments, $R^z$ is

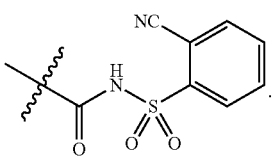 [SMILES: *C(=O)NS(=O)(=O)c1ccccc1C#N]

In some embodiments, $R^z$ is

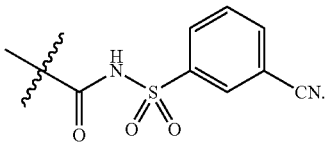 [SMILES: *C(=O)NS(=O)(=O)c1cccc(C#N)c1]

In some embodiments, $R^z$ is

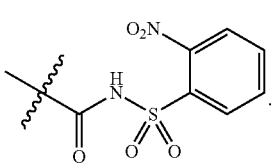 [SMILES: *C(=O)NS(=O)(=O)c1ccccc1[N+](=O)[O-]]

In some embodiments, $R^z$ is

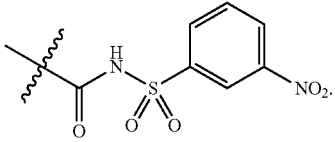 [SMILES: *C(=O)NS(=O)(=O)c1cccc([N+](=O)[O-])c1]

In some embodiments, $R^z$ is —S(O)$_2$OH.

In some embodiments, $R^z$ is —S(O)$_2$R$^y$. In some embodiments, $R^z$ is —S(O)$_2$N(R)C(O)R. In some embodiments, $R^z$ is —S(O)$_2$NHC(O)R. In some embodiments, $R^z$ is —S(O)$_2$N(R)C(O)R, wherein R is not hydrogen. In some embodiments, $R^z$ is —S(O)$_2$NHC(O)R, wherein R is not hydrogen. In some embodiments, $R^z$ is —S(O)$_2$N(R)C(O)R, wherein R is optionally substituted C$_{1-6}$ aliphatic. In some embodiments, $R^z$ is —S(O)$_2$NHC(O)R, wherein R is optionally substituted C$_{1-6}$ aliphatic. In some embodiments, $R^z$ is —S(O)$_2$N(R)C(O)Me. In some embodiments, $R^z$ is —S(O)$_2$NHC(O)Me. In some embodiments, $R^z$ is —S(O)$_2$NHC(O)Me. In some embodiments, $R^z$ is

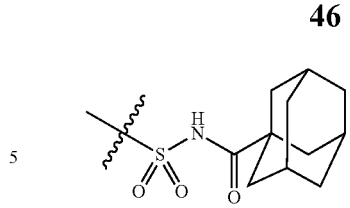

In some embodiments, $R^z$ is

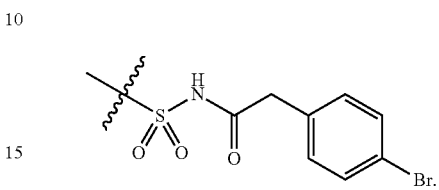

In some embodiments, $R^z$ is

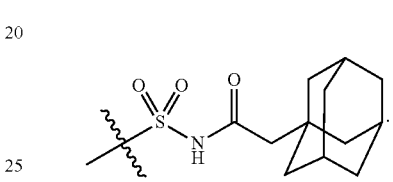

In some embodiments, $R^z$ is selected from:

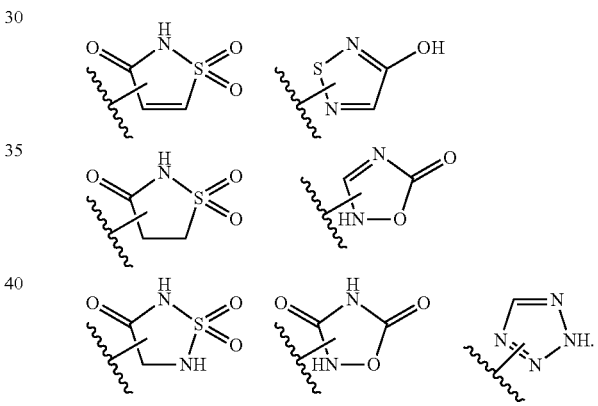

As defined generally above, $R^{2'}$ of formula V or VII is —C(O)-L$^4$-R$^w$, —C(O)N(R)-L$^4$-R$^w$, —C(O)N(R)—C(R)$_2$-L$^4$-R$^w$, —C(O)O-L$^4$-R$^w$ or —C(O)S-L$^4$-R$^w$.

In some embodiments, $R^{2'}$ is —C(O)N(R)-L$^4$-R$^w$ or —C(O)N(R)—C(R)$_2$-L$^4$-R$^w$, wherein the R group attached to the nitrogen atom and R$^1$ are optionally taken together with their intervening atoms to form an optionally substituted 4-8 membered saturated, partially unsaturated or aryl ring having 2-4 heteroatoms independently selected from nitrogen, oxygen, or sulfur. In some embodiments, $R^{2'}$ is —C(O)N(R)-L$^4$-R$^w$, wherein the R group attached to the nitrogen atom and R$^1$ are optionally taken together with their intervening atoms to form an optionally substituted 4-8 membered saturated, partially unsaturated or aryl ring having 2-4 heteroatoms independently selected from nitrogen, oxygen, or sulfur. In some embodiments, $R^{2'}$ is —C(O)N(R)—C(R)$_2$-L$^4$-R$^w$, wherein the R group attached to the nitrogen atom and R$^1$ are optionally taken together with their intervening atoms to form an optionally substituted 4-8 membered saturated, partially unsaturated or aryl ring having 2-4 heteroatoms independently selected from nitrogen, oxygen, or sulfur.

In some embodiments, $R^{2'}$ is —C(O)-$L^4$-$R^w$. In some embodiments, $R^{2'}$ is —C(O)N(R)-$L^4$-$R^w$. In some embodiments, $R^{2'}$ is —C(O)N(R)—C(R)$_2$-$L^4$-$R^w$. In some embodiments, $R^{2'}$ is —C(O)O-$L^4$-$R^w$. In some embodiments, $R^{2'}$ is —C(O)S-$L^4$-$R^w$.

As defined generally above, $L^4$ of formula III, IV, V, VI, or VII is independently selected from a covalent bond or an optionally substituted bivalent straight or branched $C_{1-8}$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—.

In some embodiments, $L^4$ is selected from a covalent bond or an optionally substituted bivalent straight or branched $C_{1-8}$ hydrocarbon chain wherein one or more methylene units are optionally and independently replaced with -Cy'-, —O—, —S—, —N(R)—, —N(R)C(O)—, —C(O)—, —C(O)N(R)—, or —S(O)—. In some embodiments, $L^4$ is selected from a covalent bond or an optionally substituted bivalent straight or branched $C_{1-8}$ hydrocarbon chain wherein one or more methylene units are optionally and independently replaced with -Cy'-, —O—, —N(R)—, —N(R)C(O)—, —C(O)—, or —C(O)N(R)—. $L^4$ is selected from a covalent bond or an optionally substituted bivalent straight or branched $C_{1-8}$ hydrocarbon chain wherein one or more methylene units are optionally and independently replaced with -Cy'- or —O—.

In some embodiments, $L^4$ is a covalent bond. In some embodiments, $L^4$ is an optionally substituted bivalent straight or branched $C_{1-8}$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^4$ is an optionally substituted methylene group or -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^4$ is an optionally substituted bivalent straight or branched $C_2$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^4$ is an optionally substituted bivalent straight or branched $C_3$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^4$ is an optionally substituted bivalent straight or branched $C_4$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^4$ is an optionally substituted bivalent straight or branched $C_5$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^4$ is an optionally substituted bivalent straight or branched $C_6$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^4$ is an optionally substituted bivalent straight or branched $C_7$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^4$ is an optionally substituted bivalent straight or branched $C_8$ hydrocarbon chain wherein one or more methylene units are optionally and independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—.

In some embodiments, $L^4$ is an optionally substituted bivalent straight or branched $C_{1-8}$ hydrocarbon chain wherein one or more methylene units are independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^4$ is an optionally substituted bivalent straight or branched $C_{1-8}$ hydrocarbon chain wherein one or more methylene units are independently replaced with -Cy'-, —O—, —S—, —N(R)—, —N(R)C(O)—, —C(O)—, —C(O)N(R)—, or —S(O)—. In some embodiments, $L^4$ is an optionally substituted bivalent straight or branched $C_{1-8}$ hydrocarbon chain wherein one or more methylene units are independently replaced with -Cy'-, —O—, —N(R)—, —N(R)C(O)—, —C(O)—, or —C(O)N(R)—. In some embodiments, $L^4$ is an optionally substituted bivalent straight or branched $C_{1-8}$ hydrocarbon chain wherein one or more methylene units are independently replaced with -Cy'- or —O—.

In some embodiments, $L^4$ is an optionally substituted bivalent straight or branched $C_{1-8}$ hydrocarbon chain. In some embodiments, $L^4$ is a bivalent straight or branched CI-s hydrocarbon chain. In some embodiments, $L^4$ is a bivalent straight $C_{1-8}$ hydrocarbon chain.

In some embodiments, one or more methylene units of $L^4$ are optionally and independently replaced with -Cy'-, —O—, —S—, —N(R)—, —N(R)C(O)—, —C(O)—, —C(O)N(R)—, or —S(O)—. In some embodiments, $R^{2'}$ is —C(O)-$L^4$-$R^w$, —C(O)N(R)-$L^4$-$R^w$, —C(O)N(R)—C(R)$_2$-$L^4$-$R^w$, —C(O)O-$L^4$-$R^w$ or —C(O)S-$L^4$-$R^w$, wherein the methylene unit of $L^4$ that is directly bonded to said —C(O)—, —C(O)N(R)—, —C(O)N(R)—C(R)$_2$—, —C(O)O— or —C(O)S— moiety is optionally and independently replaced by -Cy'-, —O—, —S—, —N(R)—, —N(R)C(O)—, —C(O)—, —C(O)N(R)—, or —S(O)—. In some embodiments, one or more methylene units of $L^4$ are optionally and independently replaced with -Cy'-, —O—, —N(R)—, —N(R)C(O)—, —C(O)—, or —C(O)N(R)—. In some embodiments, $R^{2'}$ is —C(O)-$L^4$-$R^w$, —C(O)N(R)-$L^4$-$R^w$, —C(O)N(R)—C(R)$_2$-$L^4$-$R^w$, —C(O)O-$L^4$-$R^w$ or —C(O)S-$L^4$-$R^w$, wherein the methylene unit of $L^4$ that is directly bonded to said —C(O)—, —C(O)N(R)—, —C(O)N(R)—C(R)$_2$—, —C(O)O— or —C(O)S— moiety is optionally and independently replaced by -Cy'-, —O—, —N(R)—, —N(R)C(O)—, —C(O)—, or —C(O)N(R)—. In some embodiments, one or more methylene units of $L^4$ are optionally and independently replaced with -Cy'- or —O—. In some embodiments, $R^{2'}$ is —C(O)-$L^4$-$R^w$, —C(O)N(R)-$L^4$-$R^w$, —C(O)N(R)—C(R)$_2$-$L^4$-$R^w$, —C(O)O-$L^4$-$R^w$ or —C(O)S-$L^4$-$R^w$, wherein the methylene unit of $L^4$ that is directly bonded to said —C(O)—, —C(O)N(R)—, —C(O)N(R)—C(R)$_2$—, —C(O)O— or —C(O)S— moiety is optionally and independently replaced by -Cy'- or —O—.

In some embodiments, one or more methylene units are independently replaced with -Cy'-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, one or more methylene units are replaced with -Cy'-. In some embodiments, one or more methylene units are replaced with —O—. In some embodiments, one or more methylene units are replaced with —S—. In some embodiments, one or more methylene units are replaced with —N(R)—. In some embodiments, one or more methylene units are replaced with —N(R)C(O)—. In some embodiments, one or more methylene units are replaced with —N(R)S(O)$_2$—. In some embodiments, one or more methylene units are replaced with —C(O)—. In some embodiments, one or more methylene units are replaced with —C(O)N(R)—. In some embodiments, one or more methylene units are replaced with —S(O)—. In some embodiments, one or more methylene units are replaced with —S(O)$_2$—. In some embodiments, one or more methylene units are replaced with —S(O)$_2$N(R)—.

In some embodiments, the methylene unit of L$^4$ that is directly bonded to R$^w$ is optionally replaced with -Cy'-. In some embodiments, the methylene unit of L$^4$ that is directly bonded to R$^w$ is replaced with -Cy'-. In some embodiments, the methylene unit of L$^4$ that is directly bonded to R$^w$ is replaced with an optionally substituted phenylene. In some embodiments, the methylene unit of L$^4$ that is directly bonded to R$^w$ is replaced with an optionally substituted 5-6 membered heteroarylene having 1-4 heteroatoms independently selected from nitrogen, oxygen, or sulfur. In some embodiments, the methylene unit of L$^4$ that is directly bonded to R$^w$ is replaced with an optionally substituted 3-8 membered saturated or partially unsaturated heterocyclylene having 1-4 heteroatoms independently selected from nitrogen, oxygen, or sulfur. In some embodiments, the methylene unit of L$^4$ that is directly bonded to R$^w$ is replaced with an optionally substituted 8-10 membered bicyclic arylene or heteroarylene having 1-4 heteroatoms independently selected from nitrogen, oxygen, or sulfur. In some embodiments, the methylene unit of L$^4$ that is directly bonded to R$^w$ is replaced with an optionally substituted 8-10 membered saturated or partially unsaturated heterocyclylene having 1-4 heteroatoms independently selected from nitrogen, oxygen, or sulfur.

In some embodiments, L$^4$ is —NRS(O)$_2$(CH$_2$)$_2$N(R)C(O)—.

As defined generally above, -Cy'- of formula III, IV, V, VI, or VII is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, 3-8 membered saturated or partially unsaturated heterocyclylene having 1-4 heteroatoms independently selected from nitrogen, oxygen, or sulfur, an 8-10 membered bicyclic arylene or heteroarylene having 1-4 heteroatoms independently selected from nitrogen, oxygen, or sulfur, or an 8-10 membered saturated or partially unsaturated heterocyclylene having 1-4 heteroatoms independently selected from nitrogen, oxygen, or sulfur.

In some embodiments, -Cy'- is optionally substituted phenylene. In some embodiments, -Cy'- is substituted phenylene. In some embodiments, -Cy'- is unsubstituted phenylene. In some embodiments, -Cy'- is optionally substituted

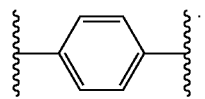

In some embodiments, -Cy'- is optionally substituted

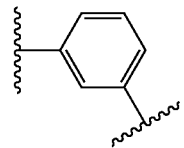

In some embodiments, -Cy'- is optionally substituted

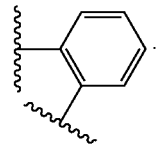

In some embodiments, -Cy'- is

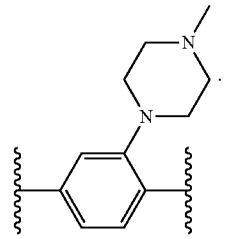 [SMILES: *c1ccc(*)c(N2CCN(C)CC2)c1]

In some embodiments, -Cy'- is

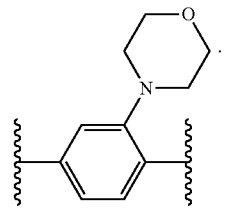 [SMILES: *c1ccc(*)c(N2CCOCC2)c1]

In some embodiments, -Cy'- is

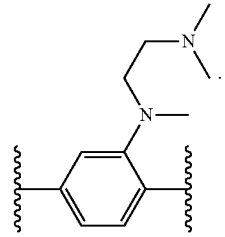 [SMILES: *c1ccc(*)c(N(C)CCN(C)C)c1]

In some embodiments, -Cy'- is

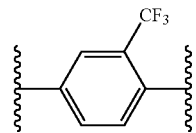

In some embodiments, -Cy'- is
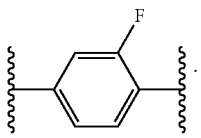 [SMILES: *c1ccc(*)c(F)c1]
In some embodiments, -Cy'- is
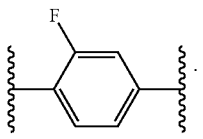
In some embodiments, -Cy'- is
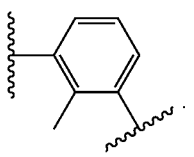 [SMILES: *c1cccc(*)c1C]
In some embodiments, -Cy'- is
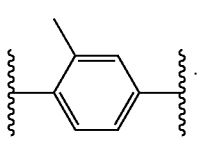 [SMILES: *c1ccc(*)c(C)c1]
In some embodiments, -Cy'- is
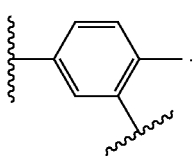 [SMILES: *c1ccc(C)c(*)c1]
In some embodiments, -Cy'- is
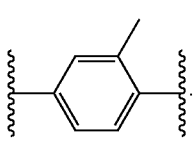
In some embodiments, -Cy'- is
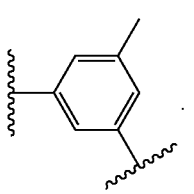 [SMILES: *c1cc(*)cc(C)c1]
In some embodiments, -Cy'- is
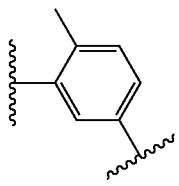
In some embodiments, -Cy'- is
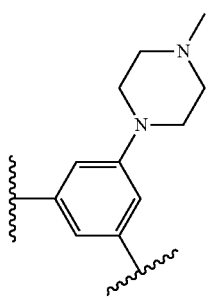
In some embodiments, -Cy'- is
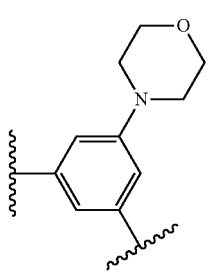
In some embodiments, -Cy'- is
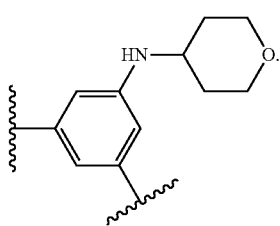 [SMILES: *c1cc(*)cc(NC2CCOCC2)c1]
In some embodiments, -Cy'- is
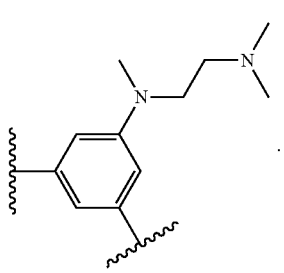 [SMILES: *c1cc(*)cc(N(C)CCN(C)C)c1]

In some embodiments, -Cy'- is
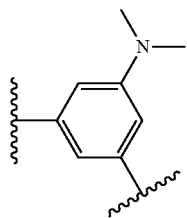
In some embodiments, -Cy'- is
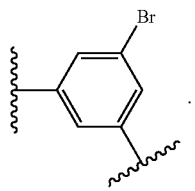 [SMILES: *c1cc(*)cc(Br)c1]
In some embodiments, -Cy'- is
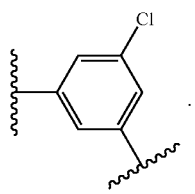 [SMILES: *c1cc(*)cc(Cl)c1]
In some embodiments, -Cy'- is
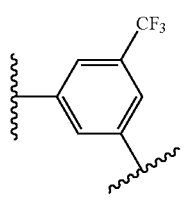
In some embodiments, -Cy'- is
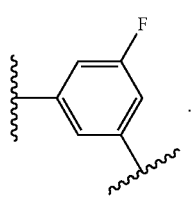 [SMILES: *c1cc(*)cc(F)c1]
In some embodiments, -Cy'- is
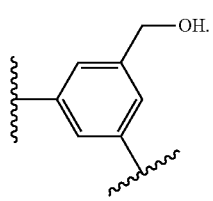 [SMILES: *c1cc(*)cc(CO)c1]
In some embodiments, -Cy'- is
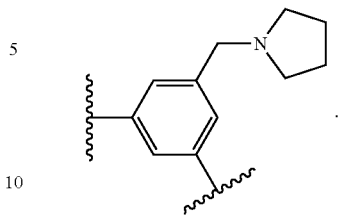
In some embodiments, -Cy'- is
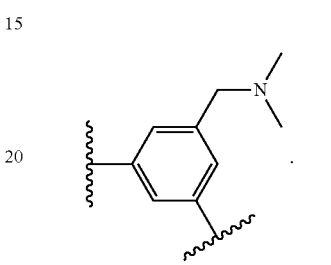
In some embodiments, -Cy'- is
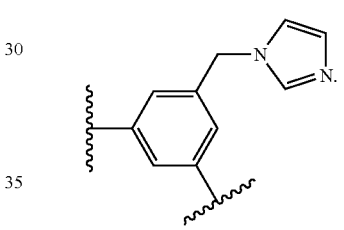
In some embodiments, -Cy'- is
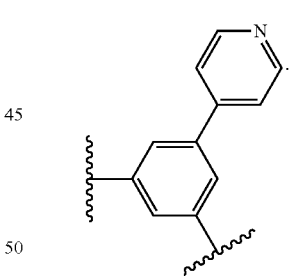
In some embodiments, -Cy'- is
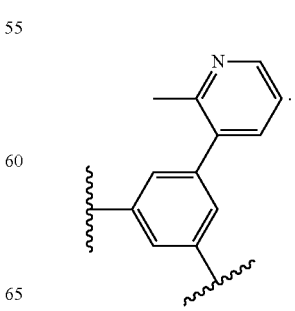

In some embodiments, -Cy'- is

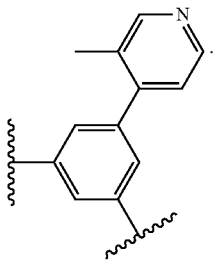 [SMILES: *c1cc(*)cc(-c2ccncc2C)c1]

In some embodiments, -Cy'- is

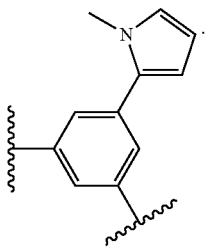 [SMILES: *c1cc(*)cc(-c2cccn2C)c1]

In some embodiments, -Cy'- is

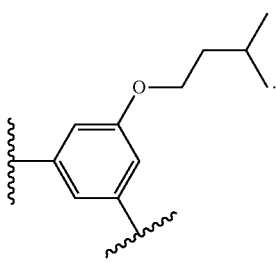 [SMILES: *c1cc(*)cc(OCCC(C)C)c1]

In some embodiments, -Cy'- is

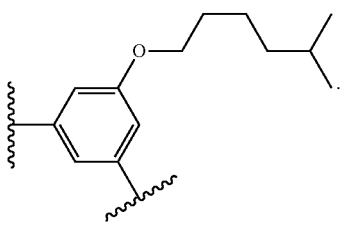 [SMILES: *c1cc(*)cc(OCCCCC(C)C)c1]

In some embodiments, -Cy'- is

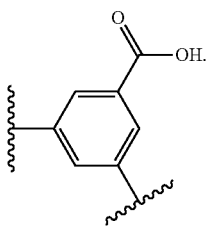 [SMILES: *c1cc(*)cc(C(=O)O)c1]

In some embodiments, -Cy'- is optionally substituted bivalent 3-8 membered saturated or partially unsaturated carbocyclylene. In certain embodiments, -Cy'- is optionally substituted bivalent 3-8 membered saturated carbocyclylene. In certain embodiments, -Cy'- is optionally substituted bivalent 3-6 membered saturated carbocyclylene. In certain embodiments, -Cy'- is optionally substituted bivalent 3-membered saturated carbocyclylene. In certain embodiments, -Cy'- is optionally substituted bivalent 4-membered saturated carbocyclylene. In certain embodiments, -Cy'- is optionally substituted bivalent 5-membered saturated carbocyclylene. In some embodiments -Cy'- is optionally substituted

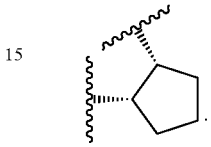

In some embodiments -Cy'- is optionally substituted

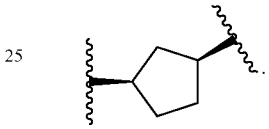

In certain embodiments, -Cy'- is optionally substituted bivalent 6-membered saturated carbocyclylene. In some embodiments -Cy'- is optionally substituted

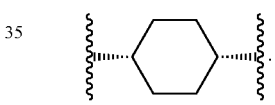

In some embodiments -Cy'- is optionally substituted

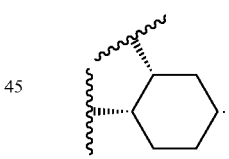

In some embodiments -Cy'- is optionally substituted

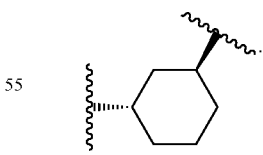

In some embodiments -Cy'- is optionally substituted

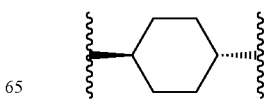

In some embodiments -Cy'- is optionally substituted

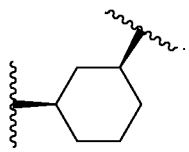 [SMILES: *[C@@H]1CCC[C@H](*)C1]

In some embodiments -Cy'- is optionally substituted

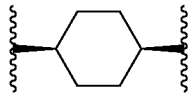

In some embodiments, -Cy'- is optionally substituted bivalent 5-6 membered heteroarylene having 1-4 heteroatoms independently selected from nitrogen, oxygen, or sulfur. In certain embodiments, -Cy'- is optionally substituted bivalent 5-membered heteroarylene having 1-4 heteroatoms independently selected from nitrogen, oxygen, or sulfur. In certain embodiments, -Cy'- is optionally substituted bivalent 5-membered heteroarylene having 1-2 heteroatoms independently selected from nitrogen, oxygen, or sulfur. In certain embodiments, -Cy'- is optionally substituted bivalent 5-membered heteroarylene having one heteroatom independently selected from nitrogen, oxygen, or sulfur. In some embodiments, -Cy'- is optionally substituted

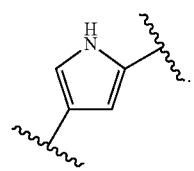 [SMILES: *c1c[nH]c(*)c1]

In some embodiments, -Cy'- is

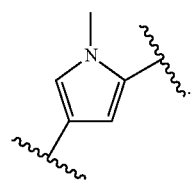 [SMILES: *c1cc(*)n(C)c1]

In some embodiments, -Cy'- is

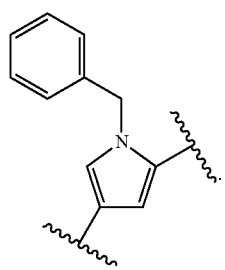 [SMILES: *c1cc(*)n(Cc2ccccc2)c1]

In some embodiments, -Cy'- is optionally substituted

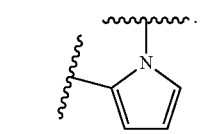

In some embodiments, -Cy'- is optionally substituted

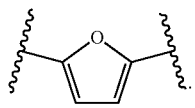 [SMILES: *c1ccc(*)o1]

In some embodiments, -Cy'- is optionally substituted

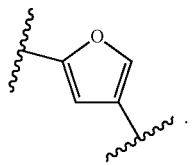 [SMILES: *c1coc(*)c1]

In some embodiments, -Cy'- is optionally substituted

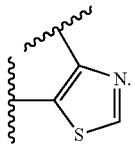

In some embodiments, -Cy'- is optionally substituted

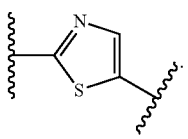

In some embodiments, -Cy'- is optionally substituted.

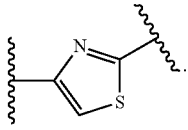 [SMILES: *c1csc(*)n1]

In certain embodiments, -Cy'- is optionally substituted bivalent 6-membered heteroarylene having 1-4 heteroatoms independently selected from nitrogen, oxygen, or sulfur. In certain embodiments, -Cy'- is optionally substituted bivalent 6-membered heteroarylene having 1-2 heteroatoms independently selected from nitrogen, oxygen, or sulfur. In some embodiments, -Cy'- is optionally substituted

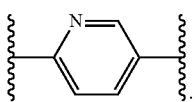 [SMILES: *c1ccc(*)nc1]

In some embodiments, -Cy'- is optionally substituted

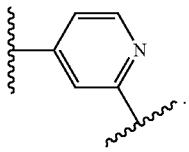 [SMILES: *c1ccnc(*)c1]

In some embodiments, -Cy'- is optionally substituted

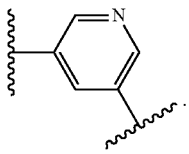 [SMILES: *c1cncc(*)c1]

In some embodiments, -Cy'- is optionally substituted

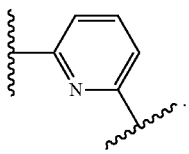 [SMILES: *c1cccc(*)n1]

In some embodiments, -Cy'- is optionally substituted

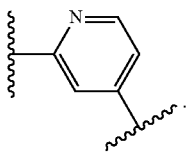 [SMILES: *c1ccnc(*)c1]

In some embodiments, -Cy'- is optionally substituted

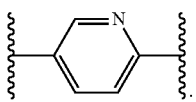

In some embodiments, -Cy'- is

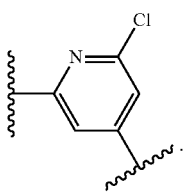 [SMILES: *c1cc(*)nc(Cl)c1]

In some embodiments, -Cy'- is

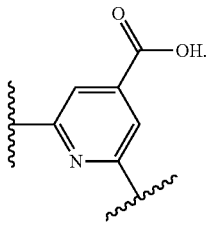 [SMILES: *c1cc(C(=O)O)cc(*)n1]

In some embodiments, -Cy'- is

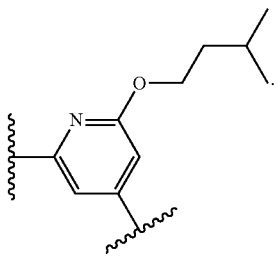 [SMILES: *c1cc(*)nc(OCCC(C)C)c1]

In some embodiments, -Cy'- is optionally substituted

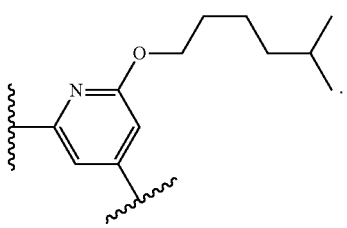 [SMILES: *c1cc(*)nc(OCCCCC(C)C)c1]

In some embodiments, -Cy'- is optionally substituted bivalent 3-8 membered saturated or partially unsaturated heterocyclylene having 1-4 heteroatoms independently selected from nitrogen, oxygen, or sulfur. In certain embodiments, -Cy'- is optionally substituted bivalent 3-8 membered saturated heterocyclylene having 1-4 heteroatoms independently selected from nitrogen, oxygen, or sulfur. In certain embodiments, -Cy'- is optionally substituted bivalent 3-8 membered saturated heterocyclylene having 1-2 heteroatoms independently selected from nitrogen, oxygen, or sulfur. In certain embodiments, -Cy'- is optionally substituted bivalent 5-6 membered saturated heterocyclylene having 1-4 heteroatoms independently selected from nitrogen, oxygen, or sulfur. In certain embodiments, -Cy'- is optionally substituted bivalent 5-6 membered saturated heterocyclylene having 1-2 heteroatoms independently selected from nitrogen, oxygen, or sulfur. In certain embodiments, -Cy'- is optionally substituted bivalent 5-membered saturated heterocyclylene having 1-2 heteroatoms independently selected from nitrogen, oxygen, or sulfur. In certain embodiments, -Cy'- is optionally substituted

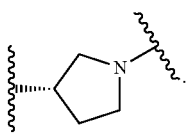 [SMILES: *[C@H]1CCN(*)C1]

In certain embodiments, -Cy'- is optionally substituted

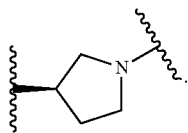 [SMILES: *[C@@H]1CCN(*)C1]

In certain embodiments, -Cy'- is optionally substituted

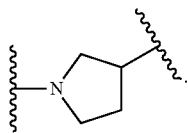 [SMILES: *C1CCN(*)C1]

In certain embodiments, -Cy'- is optionally substituted

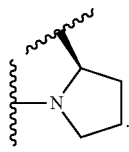

In certain embodiments, -Cy'- is optionally substituted

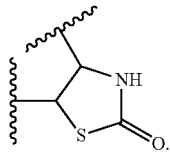 [SMILES: *C1NC(=O)SC1*]

In certain embodiments, -Cy'- is optionally substituted bivalent 6-membered saturated heterocyclylene having 1-2 heteroatoms independently selected from nitrogen, oxygen, or sulfur. In certain embodiments, -Cy'- is optionally substituted

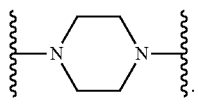

In certain embodiments, -Cy'- is optionally substituted

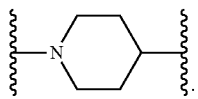

In certain embodiments, -Cy'- is optionally substituted

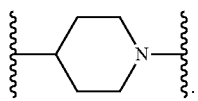

In certain embodiments, -Cy'- is optionally substituted

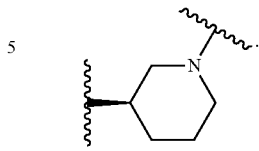

In some embodiments, -Cy'- is an optionally substituted bivalent 8-10 membered bicyclic arylene or heteroarylene having 1-4 heteroatoms independently selected from nitrogen, oxygen, or sulfur. In certain embodiments, -Cy'- is an optionally substituted bivalent 8-10 membered bicyclic arylene or heteroarylene having 1-4 heteroatoms independently selected from nitrogen, oxygen, or sulfur. In certain embodiments, -Cy'- is an optionally substituted bivalent 8 membered bicyclic arylene or heteroarylene having 1-4 heteroatoms independently selected from nitrogen, oxygen, or sulfur. In certain embodiments, -Cy'- is an optionally substituted bivalent 9 membered bicyclic arylene or heteroarylene having 1-4 heteroatoms independently selected from nitrogen, oxygen, or sulfur. In certain embodiments, -Cy'- is an optionally substituted

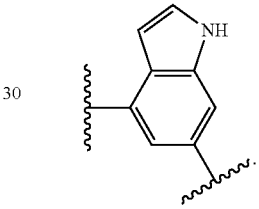

In certain embodiments, -Cy'- is an optionally substituted

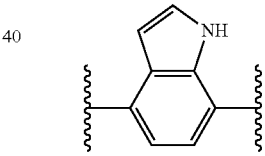

In certain embodiments, -Cy'- is an optionally substituted

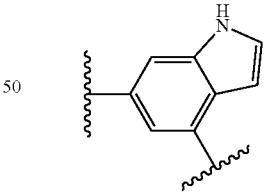

In certain embodiments, -Cy'- is an optionally substituted

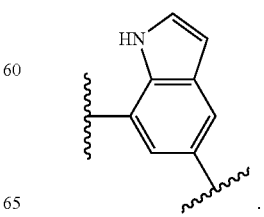

In certain embodiments, -Cy'- is an optionally substituted

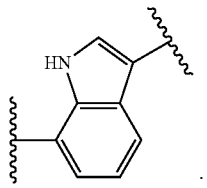 [SMILES: *c1c[nH]c2c(*)cccc12]

In certain embodiments, -Cy'- is an optionally substituted

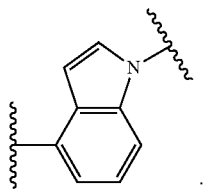 [SMILES: *c1cccc2c1ccn2*]

In certain embodiments, -Cy'- is an optionally substituted

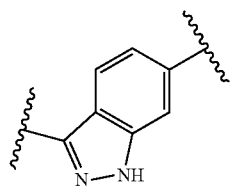

In certain embodiments, -Cy'- is an optionally substituted

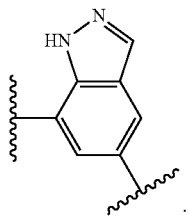 [SMILES: *c1cc(*)c2[nH]ncc2c1]

In certain embodiments, -Cy'- is an optionally substituted

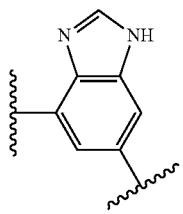

In certain embodiments, -Cy'- is an optionally substituted

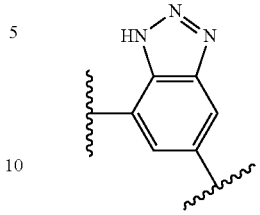

In certain embodiments, -Cy'- is

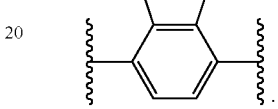

In certain embodiments, -Cy'- is

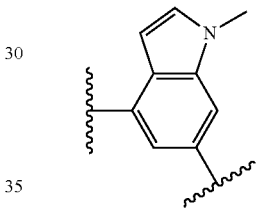

In certain embodiments, -Cy'- is

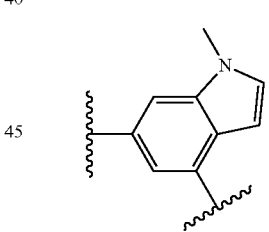

In certain embodiments, -Cy'- is

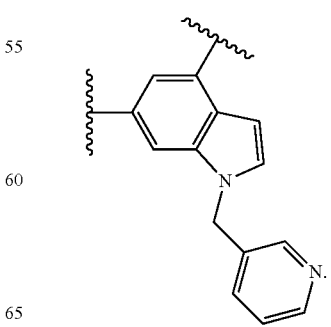

In certain embodiments, -Cy'- is
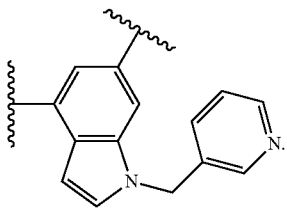 [SMILES: *c1cc(*)c2ccn(Cc3cccnc3)c2c1]
In certain embodiments, -Cy'- is
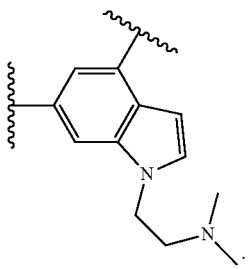 [SMILES: *c1cc(*)c2ccn(CCN(C)C)c2c1]
In certain embodiments, -Cy'- is
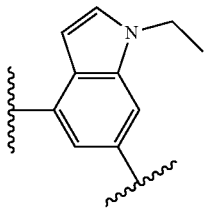
In certain embodiments, -Cy'- is
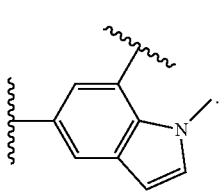 [SMILES: *c1cc(*)c2c(ccn2C)c1]
In certain embodiments, -Cy'- is
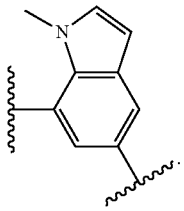 [SMILES: *c1cc(*)c2c(ccn2C)c1]
In certain embodiments, -Cy'- is
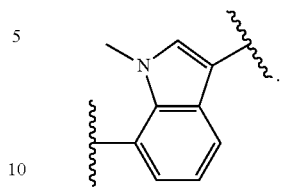
In certain embodiments, -Cy'- is
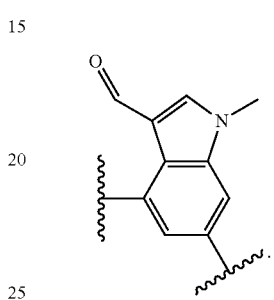
In certain embodiments, -Cy'- is
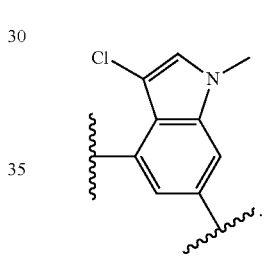
In certain embodiments, -Cy'- is
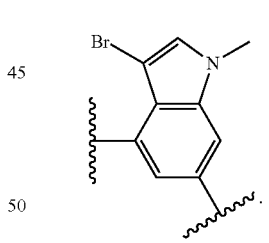
In certain embodiments, -Cy'- is
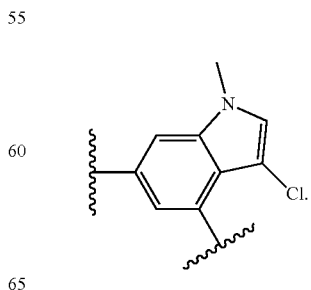

In certain embodiments, -Cy'- is

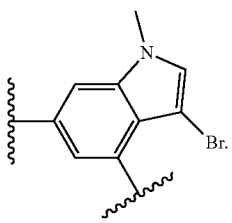 [SMILES: *c1cc(*)c2c(Br)cn(C)c2c1]

In certain embodiments, -Cy'- is

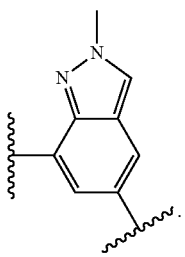 [SMILES: *c1cc(*)c2nn(C)cc2c1]

In certain embodiments, -Cy'- is an optionally substituted. In certain embodiments, -Cy'- is

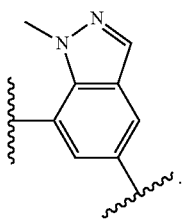 [SMILES: *c1cc(*)c2c(cnn2C)c1]

In certain embodiments, -Cy'- is

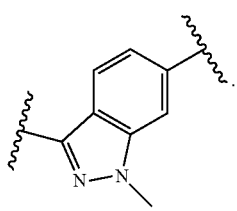 [SMILES: *c1ccc2c(*)nn(C)c2c1]

In certain embodiments, -Cy'- is

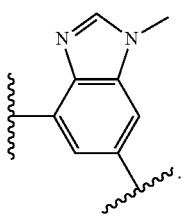 [SMILES: *c1cc(*)c2ncn(C)c2c1]

In certain embodiments, -Cy'- is

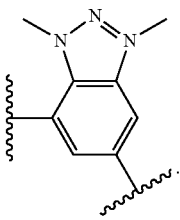

In certain embodiments, -Cy'- is an optionally substituted bivalent 10 membered bicyclic arylene or heteroarylene having 1-4 heteroatoms independently selected from nitrogen, oxygen, or sulfur. In certain embodiments, -Cy'- is an optionally substituted

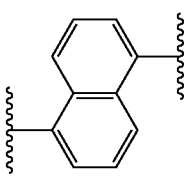

In certain embodiments, -Cy'- is an optionally substituted

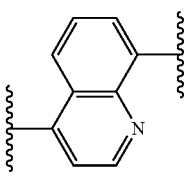

In certain embodiments, -Cy'- is an optionally substituted

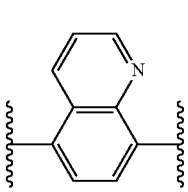

In certain embodiments, -Cy'- is an optionally substituted

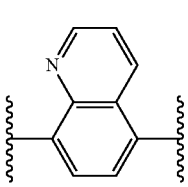

In some embodiments, -Cy'- is optionally substituted bivalent 8-10 membered saturated or partially unsaturated heterocyclylene having 1-4 heteroatoms independently selected from nitrogen, oxygen, or sulfur. In certain embodiments, -Cy'- is optionally substituted bivalent 9 membered saturated or partially unsaturated heterocyclylene having 1-4 heteroatoms independently selected from nitrogen, oxygen, or sulfur. In certain embodiments, -Cy'- is optionally substituted

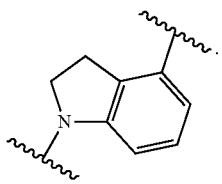 [SMILES: *c1cccc2c1CCN2*]

In certain embodiments, -Cy'- is optionally substituted

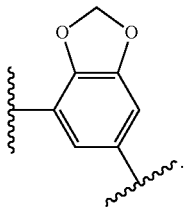 [SMILES: *c1cc(*)c2c(c1)OCO2]

In certain embodiments, -Cy'- is optionally substituted bivalent 10 membered saturated or partially unsaturated heterocyclylene having 1-4 heteroatoms independently selected from nitrogen, oxygen, or sulfur. In certain embodiments, -Cy'- is optionally substituted

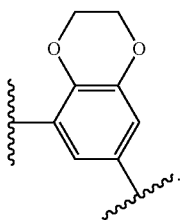 [SMILES: *c1cc(*)c2c(c1)OCCO2]

As generally defined above, $R^w$ of formula III, IV, V, VI, or VII is hydrogen, R, —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)OR, —C(O)R$^x$, —S(O)$_2$OH, or —S(O)$_2$R$^y$, or is selected from:

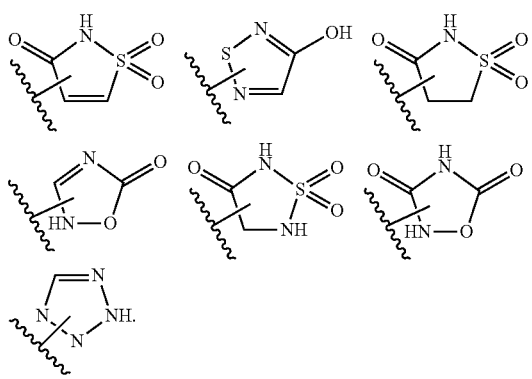

In some embodiments, $R^w$ is —OR, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)OR, —C(O)R$^x$, —S(O)$_2$OH, or —S(O)$_2$R$^y$, or is selected from:

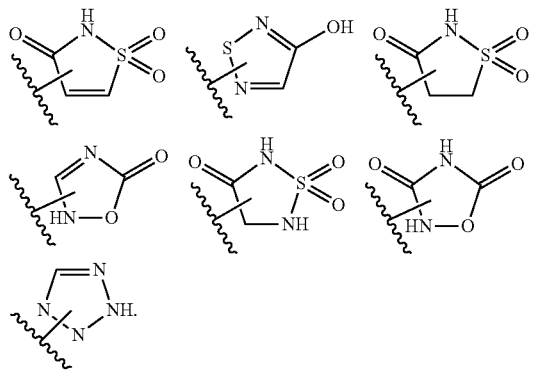

In some embodiments, $R^w$ is —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)OR, —C(O)R$^x$, —S(O)$_2$OH, or —S(O)$_2$R$^y$, or is selected from:

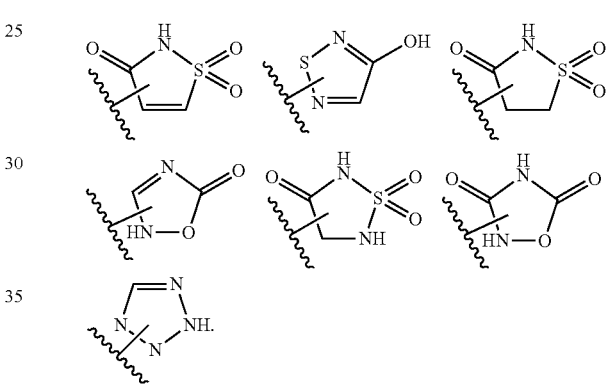

In some embodiments, $R^w$ is —S(O)$_2$N(R)$_2$, —C(O)N(R)$_2$, —C(O)OH, —C(O)OR, —C(O)R$^x$, —S(O)$_2$OH, or —S(O)$_2$R$^y$, or is selected from:

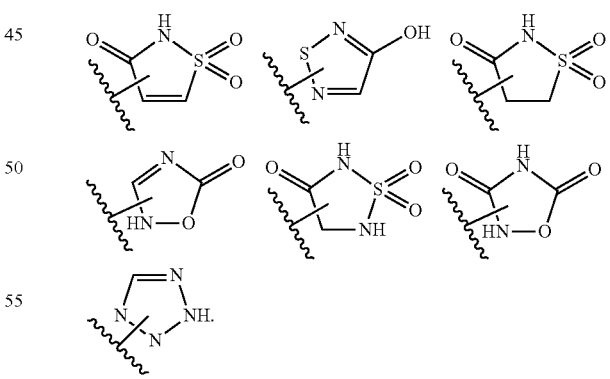

In some embodiments, $R^w$ is —S(O)$_2$N(R)$_2$, —C(O)N(R)$_2$, —C(O)OH, —C(O)OR, —C(O)R$^x$, —S(O)$_2$OH, or —S(O)$_2$R$^y$. In some embodiments, $R^w$ is —COOH, —C(O)OR, —C(O)N(R)SO$_2$R or —SO$_2$N(R)C(O)R. In some embodiments, $R^w$ is —COOH, —C(O)OR, —C(O)NHSO$_2$R or —SO$_2$NHC(O)R.

In some embodiments, $R^w$ is hydrogen. In some embodiments, $R^w$ is not hydrogen.

In some embodiments, $R^w$ is R. In some embodiments, $R^w$ is R, wherein R is not hydrogen.

In some embodiments, $R^w$ is —OR. In some embodiments, R—C(O)OH, —SR. In some embodiments, $R^w$ is —S(O)R. In some embodiments, $R^w$ is —S(O)$_2$R. In some embodiments, $R^w$ is —S(O)$_2$N(R)$_2$. In some embodiments, $R^w$ is —N(R)$_2$. In some embodiments, $R^w$ is —C(O)N(R)$_2$. In some embodiments, $R^w$ is —C(O)R. In some embodiments, $R^w$ is —N(R)C(O)R. In some embodiments, $R^w$ is —N(R)C(O)OR. In some embodiments, $R^w$ is —N(R)C(O)N(R)$_2$. In some embodiments, $R^w$ is —N(R)S(O)$_2$R. In some embodiments, $R^w$ is —N(R)S(O)$_2$N(R)$_2$.

In some embodiments, $R^w$ is —C(O)OH. In some embodiments, $R^w$ is —C(O)OR. In some embodiments, $R^w$ is —C(O)OR, wherein R is $C_{1-6}$ aliphatic. In some embodiments, $R^w$ is —C(O)OR, wherein R is methyl. In some embodiments, $R^w$ is —C(O)OR, wherein R is ethyl.

In some embodiments, $R^w$ is —C(O)$R^x$. In some embodiments, $R^w$ is —C(O)N(R)S(O)$_2$R. In some embodiments, $R^w$ is —C(O)NHS(O)$_2$R. In some embodiments, $R^w$ is —C(O)N(R)S(O)$_2$R, wherein R is not hydrogen. In some embodiments, $R^w$ is —C(O)NHS(O)$_2$R, wherein R is not hydrogen. In some embodiments, $R^w$ is —C(O)N(R)S(O)$_2$R, wherein R is optionally substituted $C_{1-6}$ aliphatic. In some embodiments, $R^w$ is —C(O)NHS(O)$_2$R, wherein R is optionally substituted $C_{1-6}$ aliphatic. In some embodiments, $R^w$ is —C(O)N(R)S(O)$_2$Me. In some embodiments, $R^w$ is —C(O)NHS(O)$_2$Me. In some embodiments, $R^w$ is

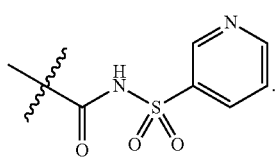 [SMILES: *C(=O)NS(=O)(=O)c1cccnc1]

In some embodiments, $R^w$ is

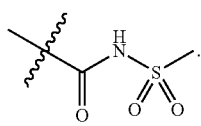 [SMILES: *C(=O)NS(C)(=O)=O]

In some embodiments, $R^w$ is

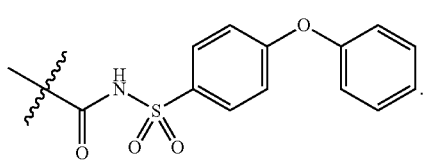 [SMILES: *C(=O)NS(=O)(=O)c1ccc(Oc2ccccc2)cc1]

In some embodiments, $R^w$ is

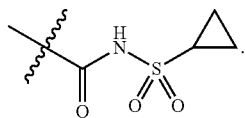 [SMILES: *C(=O)NS(=O)(=O)C1CC1]

In some embodiments, $R^w$ is

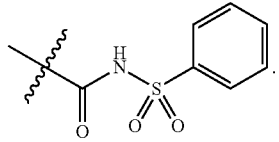 [SMILES: *C(=O)NS(=O)(=O)c1ccccc1]

In some embodiments, $R^w$ is

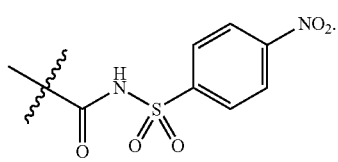 [SMILES: *C(=O)NS(=O)(=O)c1ccc([N+](=O)[O-])cc1]

In some embodiments, $R^w$ is

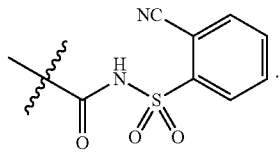 [SMILES: *C(=O)NS(=O)(=O)c1ccccc1C#N]

In some embodiments, $R^w$ is

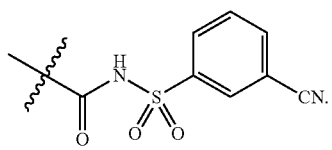 [SMILES: *C(=O)NS(=O)(=O)c1cccc(C#N)c1]

In some embodiments, $R^w$ is

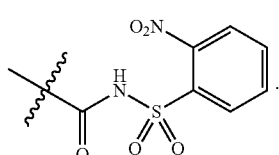

In some embodiments, $R^w$ is

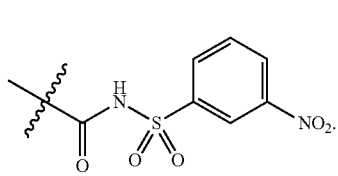 [SMILES: *C(=O)NS(=O)(=O)c1cccc([N+](=O)[O-])c1]

In some embodiments, $R^w$ is —S(O)$_2$OH.

In some embodiments, $R^w$ is —S(O)$_2$R$^y$. In some embodiments, $R^w$ is —S(O)$_2$N(R)C(O)R. In some embodiments, $R^w$ is —S(O)$_2$NHC(O)R. In some embodiments, $R^w$ is —S(O)$_2$N(R)C(O)R, wherein R is not hydrogen. In some embodiments, $R^w$ is —S(O)$_2$NHC(O)R, wherein R is not hydrogen. In some embodiments, $R^w$ is —S(O)$_2$N(R)C(O)R, wherein R is optionally substituted $C_{1-6}$ aliphatic. In some embodiments, $R^w$ is —S(O)$_2$NHC(O)R, wherein R is optionally substituted $C_{1-6}$ aliphatic. In some embodiments, $R^w$ is —S(O)$_2$N(R)C(O)Me. In some embodiments, $R^w$ is —S(O)$_2$NHC(O)Me. In some embodiments, $R^w$ is —S(O)$_2$NHC(O)Me. In some embodiments, $R^w$ is

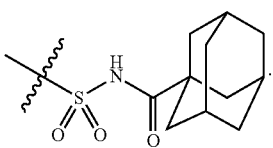 [SMILES: *S(=O)(=O)NC(=O)C12CC3CC(CC(C3)C1)C2]

In some embodiments, $R^w$ is

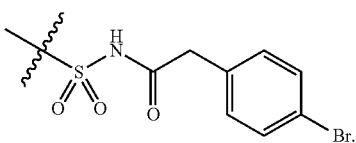 [SMILES: *S(=O)(=O)NC(=O)Cc1ccc(Br)cc1]

In some embodiments, $R^w$ is

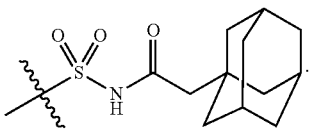 [SMILES: *S(=O)(=O)NC(=O)CC12CC3CC(CC(C3)C1)C2]

In some embodiments, $R^w$ is selected from:

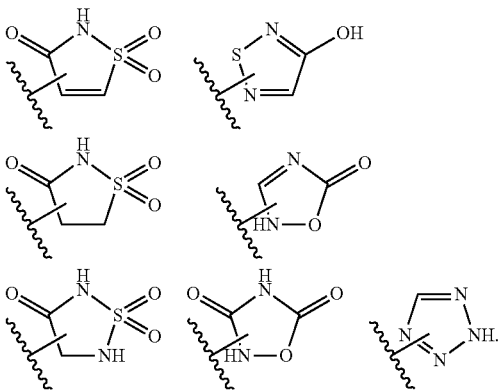

As defined generally above, $L^2$ of formula I or II is an optionally substituted bivalent straight or branched $C_{3-6}$ hydrocarbon chain wherein one or two methylene units of $L^2$ are optionally and independently replaced with —O—, —S—, or —N(R')—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur. In some embodiments, $L^2$ is an optionally substituted bivalent straight or branched $C_{3-6}$ hydrocarbon chain wherein one or two methylene units of $L^2$ are optionally and independently replaced with —O—, —S—, or —N(R')—. In some embodiments, two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur. In some embodiments, two substituents of $L^2$ are optionally taken together to form optionally substituted bivalent 3-8 membered saturated or partially unsaturated carbocyclylene. In some embodiments, two substituents of $L^2$ are optionally taken together to form optionally substituted bivalent 3-8 membered saturated or partially unsaturated heterocyclylene having 1-4 heteroatoms independently selected from nitrogen, oxygen, or sulfur.

In some embodiments, $L^2$ is a substituted bivalent $C_{3-6}$ hydrocarbon chain wherein one or two methylene units of $L^2$ are optionally and independently replaced with —O—, —S—, or —N(R')—. In some embodiments, $L^2$ is an unsubstituted bivalent $C_{3-6}$ hydrocarbon chain wherein one or two methylene units of $L^2$ are optionally and independently replaced with —O—, —S—, or —N(R')—. In some embodiments, $L^2$ is a substituted bivalent $C_{3-6}$ hydrocarbon. In some embodiments, $L^2$ is an unsubstituted bivalent $C_{3-6}$ hydrocarbon. In some embodiments, $L^2$ is an optionally substituted bivalent $C_{4-6}$ hydrocarbon chain wherein one or two methylene units of $L^2$ are optionally and independently replaced with —O—, —S—, or —N(R')—. In some embodiments, $L^2$ is a substituted bivalent $C_{4-6}$ hydrocarbon chain wherein one or two methylene units of $L^2$ are optionally and independently replaced with —O—, —S—, or —N(R')—. In some embodiments, $L^2$ is an unsubstituted bivalent $C_{4-6}$ hydrocarbon chain wherein one or two methylene units of $L^2$ are optionally and independently replaced with —O—, —S—, or —N(R')—. In some embodiments, $L^2$ is a substituted bivalent $C_{4-6}$ hydrocarbon. In some embodiments, $L^2$ is an unsubstituted bivalent $C_{4-6}$ hydrocarbon. In some embodiments, $L^2$ is an optionally substituted bivalent $C_{5-6}$ hydrocarbon chain wherein one or two methylene units of $L^2$ are optionally and independently replaced with —O—, —S—, or —N(R')—. In some embodiments, $L^2$ is a substituted bivalent $C_{5-6}$ hydrocarbon chain wherein one or two methylene units of $L^2$ are optionally and independently replaced with —O—, —S—, or —N(R')—. In some embodiments, $L^2$ is an unsubstituted bivalent $C_{5-6}$ hydrocarbon chain wherein one or two methylene units of $L^2$ are optionally and independently replaced with —O—, —S—, or —N(R')—. In some embodiments, $L^2$ is a substituted bivalent $C_{5-6}$ hydrocarbon. In some embodiments, $L^2$ is an unsubstituted bivalent $C_{5-6}$ hydrocarbon.

In some embodiments, $L^2$ is an optionally substituted bivalent $C_3$ hydrocarbon chain wherein one or two methylene units of $L^2$ are optionally and independently replaced with —O—, —S—, or —N(R')—. In some embodiments, $L^2$ is a substituted bivalent $C_3$ hydrocarbon chain wherein one or two methylene units of $L^2$ are optionally and independently replaced with —O—, —S—, or —N(R')—. In some embodiments, $L^2$ is an unsubstituted bivalent $C_3$ hydrocarbon chain wherein one or two methylene units of $L^2$ are optionally and independently replaced with —O—, —S—, or —N(R')—. In some embodiments, $L^2$ is a substituted bivalent $C_3$ hydrocarbon chain. In some embodiments, $L^2$ is an unsubstituted bivalent $C_3$ hydrocarbon chain.

In some embodiments, $L^2$ is an optionally substituted bivalent $C_4$ hydrocarbon chain wherein one or two methylene units of $L^2$ are optionally and independently replaced with —O—, —S—, or —N(R')—. In some embodiments, $L^2$ is a substituted bivalent $C_4$ hydrocarbon chain wherein one or two methylene units of $L^2$ are optionally and independently replaced with —O—, —S—, or —N(R')—. In some embodiments, $L^2$ is an unsubstituted bivalent $C_4$ hydrocarbon chain wherein one or two methylene units of $L^2$ are optionally and independently replaced with —O—, —S—, or —N(R')—. In some embodiments, $L^2$ is a substituted bivalent $C_4$ hydrocarbon chain. In some embodiments, $L^2$ is an unsubstituted bivalent $C_4$ hydrocarbon chain.

In some embodiments, $L^2$ is an optionally substituted bivalent $C_5$ hydrocarbon chain wherein one or two methylene units of $L^2$ are optionally and independently replaced with —O—, —S—, or —N(R')—. In some embodiments, $L^2$ is a substituted bivalent $C_5$ hydrocarbon chain wherein one or two methylene units of $L^2$ are optionally and independently replaced with —O—, —S—, or —N(R')—. In some embodiments, $L^2$ is an unsubstituted bivalent $C_5$ hydrocarbon chain wherein one or two methylene units of $L^2$ are optionally and independently replaced with —O—, —S—, or —N(R')—. In some embodiments, $L^2$ is a substituted bivalent $C_5$ hydrocarbon chain. In some embodiments, $L^2$ is an unsubstituted bivalent $C_5$ hydrocarbon chain.

In some embodiments, $L^2$ is an optionally substituted bivalent $C_6$ hydrocarbon chain wherein one or two methylene units of $L^2$ are optionally and independently replaced with —O—, —S—, or —N(R')—. In some embodiments, $L^2$ is a substituted bivalent $C_6$ hydrocarbon chain wherein one or two methylene units of $L^2$ are optionally and independently replaced with —O—, —S—, or —N(R')—. In some embodiments, $L^2$ is an unsubstituted bivalent $C_6$ hydrocarbon chain wherein one or two methylene units of $L^2$ are optionally and independently replaced with —O—, —S—, or —N(R')—. In some embodiments, $L^2$ is a substituted bivalent $C_6$ hydrocarbon chain. In some embodiments, $L^2$ is an unsubstituted bivalent $C_6$ hydrocarbon chain.

In some embodiments, two substituents of $L^2$ are optionally taken together to form optionally substituted bivalent 3-8 membered saturated or partially unsaturated carbocyclylene. In some embodiments, two substituents of $L^2$ are taken together to form optionally substituted bivalent 3-8 membered saturated or partially unsaturated carbocyclylene. In some embodiments, two substituents of $L^2$ are optionally taken together to form optionally substituted bivalent 3-8 membered saturated carbocyclylene. In some embodiments, two substituents of $L^2$ are taken together to form optionally substituted bivalent 3-8 membered saturated carbocyclylene. In some embodiments, two substituents of $L^2$ are optionally taken together to form optionally substituted bivalent 3-8 membered partially unsaturated carbocyclylene. In some embodiments, two substituents of $L^2$ are taken together to form optionally substituted bivalent 3-8 membered partially unsaturated carbocyclylene.

In some embodiments, two substituents of $L^2$ are taken together to form optionally substituted bivalent 3-membered saturated or partially unsaturated carbocyclylene. In some embodiments, two substituents of $L^2$ are taken together to form optionally substituted bivalent 3-membered saturated carbocyclylene. In some embodiments, two substituents of $L^2$ are taken together to form optionally substituted bivalent 3-membered partially unsaturated carbocyclylene. In some embodiments, two substituents of $L^2$ are taken together to form optionally substituted bivalent 4-membered saturated or partially unsaturated carbocyclylene. In some embodiments, two substituents of $L^2$ are taken together to form optionally substituted bivalent 4-membered saturated carbocyclylene. In some embodiments, two substituents of $L^2$ are taken together to form optionally substituted bivalent 4-membered partially unsaturated carbocyclylene. In some embodiments, two substituents of $L^2$ are taken together to form optionally substituted bivalent 5-membered saturated or partially unsaturated carbocyclylene. In some embodiments, two substituents of $L^2$ are taken together to form optionally substituted bivalent 5-membered saturated carbocyclylene. In some embodiments, two substituents of $L^2$ are taken together to form optionally substituted bivalent 5-membered partially unsaturated carbocyclylene. In some embodiments, two substituents of $L^2$ are taken together to form optionally substituted bivalent 6-membered saturated or partially unsaturated carbocyclylene. In some embodiments, two substituents of $L^2$ are taken together to form optionally substituted bivalent 6-membered saturated carbocyclylene. In some embodiments, two substituents of $L^2$ are taken together to form optionally substituted bivalent 6-membered partially unsaturated carbocyclylene. In some embodiments, two substituents of $L^2$ are taken together to form optionally substituted bivalent 7-membered saturated or partially unsaturated carbocyclylene. In some embodiments, two substituents of $L^2$ are taken together to form optionally substituted bivalent 7-membered saturated carbocyclylene. In some embodiments, two substituents of $L^2$ are taken together to form optionally substituted bivalent 7-membered partially unsaturated carbocyclylene. In some embodiments, two substituents of $L^2$ are taken together to form optionally substituted bivalent 8-membered saturated or partially unsaturated carbocyclylene. In some embodiments, two substituents of $L^2$ are taken together to form optionally substituted bivalent 8-membered saturated carbocyclylene. In some embodiments, two substituents of $L^2$ are taken together to form optionally substituted bivalent 8-membered partially unsaturated carbocyclylene.

In some embodiments, two substituents of $L^2$ are optionally taken together to form optionally substituted bivalent 3-8 membered saturated or partially unsaturated heterocyclylene having 1-4 heteroatoms independently selected from nitrogen, oxygen, or sulfur. In some embodiments, two substituents of $L^2$ are taken together to form optionally substituted bivalent 3-8 membered saturated or partially unsaturated heterocyclylene having 1-4 heteroatoms independently selected from nitrogen, oxygen, or sulfur. In some embodiments, two substituents of $L^2$ are taken together to form optionally substituted bivalent 3-8 membered saturated heterocyclylene having 1-4 heteroatoms independently selected from nitrogen, oxygen, or sulfur. In some embodiments, two substituents of $L^2$ are taken together to form optionally substituted bivalent 3-8 membered partially unsaturated heterocyclylene having 1-4 heteroatoms independently selected from nitrogen, oxygen, or sulfur.

In some embodiments, two substituents of $L^2$ are taken together to form optionally substituted bivalent 3-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 3-membered saturated heterocyclylene having 1-4 heteroatoms independently selected from nitrogen, oxygen, or sulfur. In some embodiments, two substituents of $L^2$ are taken together to form optionally substituted bivalent 3-membered partially unsaturated heterocyclylene having 1-4 heteroatoms independently selected from nitrogen, oxygen, or sulfur. In some embodiments, two substituents of $L^2$ are taken together to form optionally substituted bivalent 4-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 4-membered saturated heterocyclylene having 1-4 heteroatoms independently selected from nitrogen, oxygen, or sulfur. In some embodiments, two substituents of $L^2$ are taken together to form optionally substituted bivalent 4-membered partially unsaturated heterocyclylene having 1-4 heteroatoms independently selected from nitrogen, oxygen, or sulfur. In some embodiments, two substituents of $L^2$ are taken together to form optionally substituted bivalent 5-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 5-membered saturated heterocyclylene having 1-4 heteroatoms independently selected from nitrogen, oxygen, or sulfur. In some embodiments, two substituents of $L^2$ are taken together to form optionally substituted bivalent 5-membered partially unsaturated heterocyclylene having 1-4 heteroatoms independently selected from nitrogen, oxygen, or sulfur. In some embodiments, two substituents of $L^2$ are taken together to form optionally substituted bivalent 6-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 6-membered saturated heterocyclylene having 1-4 heteroatoms independently selected from nitrogen, oxygen, or sulfur. In some embodiments, two substituents of $L^2$ are taken together to form optionally substituted bivalent 6-membered partially unsaturated heterocyclylene having 1-4 heteroatoms independently selected from nitrogen, oxygen, or sulfur. In some embodiments, two substituents of $L^2$ are taken together to form optionally substituted bivalent 7-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 7-membered saturated heterocyclylene having 1-4 heteroatoms independently selected from nitrogen, oxygen, or sulfur. In some embodiments, two substituents of $L^2$ are taken together to form optionally substituted bivalent 7-membered partially unsaturated heterocyclylene having 1-4 heteroatoms independently selected from nitrogen, oxygen, or sulfur. In some embodiments, two substituents of $L^2$ are taken together to form optionally substituted bivalent 8-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 8-membered saturated heterocyclylene having 1-4 heteroatoms independently selected from nitrogen, oxygen, or sulfur. In some embodiments, two substituents of $L^2$ are taken together to form optionally substituted bivalent 8-membered partially unsaturated heterocyclylene having 1-4 heteroatoms independently selected from nitrogen, oxygen, or sulfur.

In some embodiments, two substituents of $L^2$ are taken together to form optionally substituted bivalent 3-8 membered saturated or partially unsaturated heterocyclylene having one heteroatom selected from nitrogen, oxygen, or sulfur. In some embodiments, two substituents of $L^2$ are taken together to form optionally substituted bivalent 3-8 membered saturated or partially unsaturated heterocyclylene having two heteroatoms independently selected from nitrogen, oxygen, or sulfur. In some embodiments, two substituents of $L^2$ are taken together to form optionally substituted bivalent 3-8 membered saturated or partially unsaturated heterocyclylene having three heteroatoms independently selected from nitrogen, oxygen, or sulfur. In some embodiments, two substituents of $L^2$ are taken together to form optionally substituted bivalent 3-8 membered saturated or partially unsaturated heterocyclylene having four heteroatoms independently selected from nitrogen, oxygen, or sulfur.

In some embodiments, one or two methylene units of $L^2$ are replaced with —O—. In some embodiments, one methylene unit of $L^2$ is replaced with —O—. In some embodiments, $L^2$ is an optionally substituted bivalent $C_3$ hydrocarbon chain wherein one methylene unit of $L^2$ is replaced with —O—. In some embodiments, $L^2$ is a substituted bivalent $C_3$ hydrocarbon chain wherein one methylene unit of $L^2$ is replaced with —O—. In some embodiments, $L^2$ is an unsubstituted bivalent $C_3$ hydrocarbon chain wherein one methylene unit of $L^2$ is replaced with —O—. In some embodiments, $L^2$ is an optionally substituted bivalent $C_4$ hydrocarbon chain wherein one methylene unit of $L^2$ is replaced with —O—. In some embodiments, $L^2$ is a substituted bivalent $C_4$ hydrocarbon chain wherein one methylene unit of $L^2$ is replaced with —O—. In some embodiments, $L^2$ is an unsubstituted bivalent $C_4$ hydrocarbon chain wherein one methylene unit of $L^2$ is replaced with —O—. In some embodiments, $L^2$ is an optionally substituted bivalent $C_5$ hydrocarbon chain wherein one methylene unit of $L^2$ is replaced with —O—. In some embodiments, $L^2$ is a substituted bivalent $C_5$ hydrocarbon chain wherein one methylene unit of $L^2$ is replaced with —O—. In some embodiments, $L^2$ is an unsubstituted bivalent $C_5$ hydrocarbon chain wherein one methylene unit of $L^2$ is replaced with —O—. In some embodiments, $L^2$ is an optionally substituted bivalent $C_6$ hydrocarbon chain wherein one methylene unit of $L^2$ is replaced with —O—. In some embodiments, $L^2$ is a substituted bivalent $C_6$ hydrocarbon chain wherein one methylene unit of $L^2$ is replaced with —O—. In some embodiments, $L^2$ is an unsubstituted bivalent $C_6$ hydrocarbon chain wherein one methylene unit of $L^2$ is replaced with —O—.

In some embodiments, one or two methylene units of $L^2$ are replaced with —S—. In some embodiments, one methylene unit of $L^2$ is replaced with —S—. In some embodiments, $L^2$ is an optionally substituted bivalent $C_3$ hydrocarbon chain wherein one methylene unit of $L^2$ is replaced with —S—. In some embodiments, $L^2$ is a substituted bivalent $C_3$ hydrocarbon chain wherein one methylene unit of $L^2$ is replaced with —S—. In some embodiments, $L^2$ is an unsubstituted bivalent $C_3$ hydrocarbon chain wherein one methylene unit of $L^2$ is replaced with —S—. In some embodiments, $L^2$ is an optionally substituted bivalent $C_4$ hydrocarbon chain wherein one methylene unit of $L^2$ is replaced with —S—. In some embodiments, $L^2$ is a substituted bivalent $C_4$ hydrocarbon chain wherein one methylene unit of $L^2$ is replaced with —S—. In some embodiments, $L^2$ is an unsubstituted bivalent $C_4$ hydrocarbon chain wherein one methylene unit of $L^2$ is replaced with —S—. In some embodiments, $L^2$ is an optionally substituted bivalent $C_5$ hydrocarbon chain wherein one methylene unit of $L^2$ is replaced with —S—. In some embodiments, $L^2$ is a substituted bivalent $C_5$ hydrocarbon chain wherein one methylene unit of $L^2$ is replaced with —S—. In some embodiments, $L^2$ is an unsubstituted bivalent $C_5$ hydrocarbon chain wherein one methylene unit of $L^2$ is replaced with —S—. In some embodiments, $L^2$ is an optionally substituted bivalent $C_6$ hydrocarbon chain wherein one methylene unit of $L^2$ is replaced with —S—. In some embodiments, $L^2$ is a substituted bivalent $C_6$ hydrocarbon chain wherein one methylene unit of $L^2$ is replaced with —S—. In some embodiments, $L^2$ is an unsubstituted bivalent $C_6$ hydrocarbon chain wherein one methylene unit of $L^2$ is replaced with —S—.

In some embodiments, one or two methylene units of $L^2$ are replaced with —N(R')—. In some embodiments, one methylene unit of $L^2$ is replaced with —N(R')—. In some embodiments, $L^2$ is an optionally substituted bivalent $C_3$ hydrocarbon chain wherein one methylene unit of $L^2$ is replaced with —N(R')—. In some embodiments, $L^2$ is a substituted bivalent $C_3$ hydrocarbon chain wherein one methylene unit of $L^2$ is replaced with —N(R')—. In some embodiments, $L^2$ is an unsubstituted bivalent $C_3$ hydrocarbon chain wherein one methylene unit of $L^2$ is replaced with —N(R')—. In some embodiments, $L^2$ is an optionally substituted bivalent $C_4$ hydrocarbon chain wherein one methylene unit of $L^2$ is replaced with —N(R')—. In some embodiments, $L^2$ is a substituted bivalent $C_4$ hydrocarbon chain wherein one methylene unit of $L^2$ is replaced with —N(R')—. In some embodiments, $L^2$ is an unsubstituted bivalent $C_4$ hydrocarbon chain wherein one methylene unit of $L^2$ is replaced with —N(R')—. In some embodiments, $L^2$ is an optionally substituted bivalent $C_5$ hydrocarbon chain wherein one methylene unit of $L^2$ is replaced with —N(R')—. In some embodiments, $L^2$ is a substituted bivalent $C_5$ hydrocarbon chain wherein one methylene unit of $L^2$ is replaced with —N(R')—. In some embodiments, $L^2$ is an unsubstituted bivalent $C_5$ hydrocarbon chain wherein one methylene unit of $L^2$ is replaced with —N(R')—. In some embodiments, $L^2$ is an optionally substituted bivalent $C_6$ hydrocarbon chain wherein one methylene unit of $L^2$ is replaced with —N(R')—. In some embodiments, $L^2$ is a substituted bivalent $C_6$ hydrocarbon chain wherein one methylene unit of $L^2$ is replaced with —N(R')—. In some embodiments, $L^2$ is an unsubstituted bivalent $C_6$ hydrocarbon chain wherein one methylene unit of $L^2$ is replaced with —N(R')—.

In some embodiments, each substituent of $L^2$ is $C_{1-6}$ aliphatic. In some embodiments, each substituent of $L^2$ is $C_{1-6}$ alkyl. In some embodiments, each substituent of $L^2$ is methyl.

In some embodiments, $L^2$ is —$CH_2CH_2O$—. In some embodiments, -$L^2$-$R^3$ is —$CH_2CH_2O$—$R^3$. In some embodiments, $L^2$ is —$CH_2CH_2CH_2O$—. In some embodiments, -L-$R^3$ is —$CH_2CH_2CH_2O$—$R^3$. In some embodiments, -$L^2$-$R^3$ is

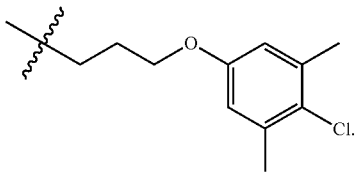 [SMILES: *CCCOc1cc(C)c(Cl)c(C)c1]

In some embodiments, $L^2$ is —$CH_2CH(CH_3)CH_2O$—. In some embodiments, -$L^2$-$R^3$ is —$CH_2CH(CH_3)CH_2O$—$R^3$.

As defined generally above, each R' of formula I, II, III, IV, V, VI, or VII is independently hydrogen or optionally substituted $C_{1-4}$ alkyl. In some embodiments, R' is hydrogen. In some embodiments, R' is optionally substituted $C_{1-4}$ alkyl. In some embodiments, R' is substituted $C_{1-4}$ alkyl. In some embodiments, R' is unsubstituted $C_{1-4}$ alkyl. In some embodiments, R' is optionally substituted methyl. In some embodiments, R' is substituted methyl. In some embodiments, R' is methyl. In some embodiments, R' is optionally substituted ethyl. In some embodiments, R' is substituted ethyl. In some embodiments, R' is ethyl. In some embodiments, R' is optionally substituted propyl. In some embodiments, R' is optionally substituted n-propyl. In some embodiments, R' is optionally substituted isopropyl. In some embodiments, R' is substituted propyl. In some embodiments, R' is substituted n-propyl. In some embodiments, R' is substituted isopropyl. In some embodiments, R' is propyl. In some embodiments, R' is n-propyl. In some embodiments, R' is isopropyl. In some embodiments, R' is optionally substituted butyl. In some embodiments, R' is substituted butyl. In some embodiments, R' is butyl. In some embodiments, R' is optionally substituted n-butyl. In some embodiments, R' is substituted n-butyl. In some embodiments, R' is n-butyl. In some embodiments, R' is optionally substituted isobutyl. In some embodiments, R' is substituted isobutyl. In some embodiments, R' is isobutyl. In some embodiments, R' is optionally substituted sec-butyl. In some embodiments, R' is substituted sec-butyl. In some embodiments, R' is sec-butyl. In some embodiments, R' is optionally substituted t-butyl. In some embodiments, R' is substituted t-butyl. In some embodiments, R' is t-butyl.

As defined generally above, $R^3$ of formula I or II is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^3$ is substituted. In some embodiments, $R^3$ is unsubstituted.

In some embodiments, $R^3$ is an optionally substituted 3-8 membered saturated or partially unsaturated monocyclic carbocyclic ring. In some embodiments, $R^3$ is an optionally substituted 3-membered saturated or partially unsaturated monocyclic carbocyclic ring. In some embodiments, $R^3$ is an optionally substituted 4-membered saturated or partially unsaturated monocyclic carbocyclic ring. In some embodiments, $R^3$ is an optionally substituted 5-membered saturated or partially unsaturated monocyclic carbocyclic ring. In some embodiments, $R^3$ is an optionally substituted 6-membered saturated or partially unsaturated monocyclic carbocyclic ring. In some embodiments, $R^3$ is an optionally substituted 7-membered saturated or partially unsaturated monocyclic carbocyclic ring. In some embodiments, $R^3$ is an optionally substituted 8-membered saturated or partially unsaturated monocyclic carbocyclic ring.

In some embodiments, $R^3$ is an optionally substituted 3-8 membered saturated monocyclic carbocyclic ring. In some embodiments, $R^3$ is an optionally substituted cycloheptyl. In some embodiments, $R^3$ is an optionally substituted cyclohexyl. In some embodiments, $R^3$ is an optionally substituted cyclopentyl. In some embodiments, $R^3$ is an optionally substituted cyclobutyl. In some embodiments, $R^3$ is an optionally substituted cyclopropyl.

In some embodiments, $R^3$ is an optionally substituted 3-8 membered unsaturated monocyclic carbocyclic ring. In some embodiments, $R^3$ is an optionally substituted cycloheptenyl. In some embodiments, $R^3$ is an optionally substituted cyclohexenyl. In some embodiments, $R^3$ is an optionally substituted cyclopentenyl. In some embodiments, $R^3$ is an optionally substituted cyclobutenyl.

In some embodiments, $R^3$ is optionally substituted phenyl. In some embodiments, $R^3$ is substituted phenyl. In some embodiments, $R^3$ is unsubstituted phenyl. In some embodiments, $R^3$ is 3,5-dimethyl-4-chlorophenyl.

In some embodiments, $R^3$ is an optionally substituted 8-10 membered bicyclic aromatic carbocyclic ring. In some embodiments, $R^3$ is a substituted 8-10 membered bicyclic aromatic carbocyclic ring. In some embodiments, $R^3$ is an unsubstituted 8-10 membered bicyclic aromatic carbocyclic ring. In some embodiments, $R^3$ is an optionally substituted 10-membered bicyclic aromatic carbocyclic ring. In some embodiments, $R^3$ is a substituted 10-membered bicyclic aromatic carbocyclic ring. In some embodiments, $R^3$ is an unsubstituted 10-membered bicyclic aromatic carbocyclic ring. In some embodiments, $R^3$ is optionally substituted naphthyl. In some embodiments, $R^3$ is substituted naphthyl. In some embodiments, $R^3$ is unsubstituted naphthyl. In some embodiments, $R^3$ is optionally substituted 1-naphthyl. In some embodiments, $R^3$ is 1-naphthyl. In some embodiments, $R^3$ is optionally substituted 2-naphthyl. In some embodiments, $R^3$ is 2-naphthyl.

In some embodiments, $R^3$ is an optionally substituted 3-8 membered saturated or partially unsaturated monocyclic heterocyclic ring having 1-2 heteroatoms independently selected from nitrogen, oxygen or sulfur. In some embodiments, $R^3$ is an optionally substituted 4-8 membered saturated or partially unsaturated monocyclic heterocyclic ring having 1-2 heteroatoms independently selected from nitrogen, oxygen or sulfur. In some embodiments, $R^3$ is a substituted 4-8 membered saturated or partially unsaturated monocyclic heterocyclic ring having 1-2 heteroatoms independently selected from nitrogen, oxygen or sulfur. In some embodiments, $R^3$ is an unsubstituted 4-8 membered saturated or partially unsaturated monocyclic heterocyclic ring having 1-2 heteroatoms independently selected from nitrogen, oxygen or sulfur.

In some embodiments, $R^3$ is an optionally substituted 3-8 membered saturated heterocyclic ring having 1-2 heteroatoms independently selected from nitrogen, oxygen or sulfur. In some embodiments, $R^3$ is an optionally substituted 4-8 membered saturated heterocyclic ring having 1-2 heteroatoms independently selected from nitrogen, oxygen or sulfur. In some embodiments, $R^3$ is a substituted 4-8 membered saturated heterocyclic ring having 1-2 heteroatoms independently selected from nitrogen, oxygen or sulfur. In some embodiments, $R^3$ is an unsubstituted 4-8 membered saturated heterocyclic ring having 1-2 heteroatoms independently selected from nitrogen, oxygen or sulfur.

In some embodiments, $R^3$ is an optionally substituted 3-membered saturated heterocyclic ring having one heteroatom selected from nitrogen, oxygen or sulfur. Exemplary $R^3$ groups include but are not limited to optionally substituted aziridinyl, thiiranyl or oxiranyl. In some embodiments, $R^3$ is a substituted 3-membered saturated heterocyclic ring having one heteroatom selected from nitrogen, oxygen or sulfur. In some embodiments, $R^3$ is an unsubstituted 3-membered saturated heterocyclic ring having one heteroatom selected from nitrogen, oxygen or sulfur.

In some embodiments, $R^3$ is an optionally substituted 4-membered saturated heterocyclic ring having 1-2 heteroatoms independently selected from nitrogen, oxygen, or sulfur. Exemplary $R^3$ groups include but are not limited to optionally substituted azetidinyl, oxetanyl, thietanyl, oxazetidinyl, thiazetidinyl, or diazetidinyl.

In some embodiments, $R^3$ is an optionally substituted 5-membered saturated heterocyclic ring having 1-2 heteroatoms independently selected from nitrogen, oxygen, or sulfur. Exemplary $R^3$ groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, or thiazolidinyl.

In some embodiments, $R^3$ is an optionally substituted 6-membered saturated heterocyclic ring having 1-2 heteroatoms independently selected from nitrogen, oxygen, or sulfur. Exemplary $R^3$ groups include but are not limited to optionally substituted piperidinyl, tetrahydropyranyl, tetrahydrothiopyranyl, piperazinyl, morpholinyl, thiomorpholinyl, dithianyl, dioxanyl, and oxathianyl.

In some embodiments, $R^3$ is optionally substituted 7-membered saturated heterocyclic ring having 1-2 heteroatoms independently selected from nitrogen, oxygen, or sulfur. Exemplary $R^3$ groups include but are not limited to optionally substituted azepanyl, oxepanyl, thiepanyl, diazepanyl, oxazepanyl, thiazepanyl, dioxepanyl, oxathiepanyl, or dithiepanyl.

In some embodiments, $R^3$ is optionally substituted 8-membered saturated heterocyclic ring having 1-2 heteroatoms independently selected from nitrogen, oxygen, or sulfur.

In some embodiments, $R^3$ is an optionally substituted 4-8 membered partially unsaturated heterocyclic ring having 1-2 heteroatoms independently selected from nitrogen, oxygen or sulfur. In certain embodiments, $R^3$ is an optionally substituted 5-7 membered partially unsaturated ring having 1-2 heteroatoms independently selected from nitrogen, oxygen, or sulfur. In certain embodiments, $R^3$ is an optionally substituted 5-6 membered partially unsaturated ring having 1-2 heteroatoms independently selected from nitrogen, oxygen, or sulfur. In certain embodiments, $R^3$ is an optionally substituted 5-membered partially unsaturated ring having 1-2 heteroatoms independently selected from nitrogen, oxygen, or sulfur. Exemplary $R^3$ groups include but are not limited to optionally substituted dihydroimidazolyl, dihydrothiazolyl, dihydrooxazolyl, or oxazolinyl. In certain embodiments, $R^3$ is an optionally substituted 6-membered partially unsaturated ring having 1-2 heteroatoms independently selected from nitrogen, oxygen, or sulfur. Exemplary $R^3$ groups include but are not limited to optionally substituted dihydropyridinyl, tetrahydropyridinyl, dihydropyrimidinyl, tetrahydropyrimidinyl, dihydropyrazinyl, tetrahydropyrazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, $R^3$ is an optionally substituted 7-membered partially unsaturated ring having 1-2 heteroatoms independently selected from nitrogen, oxygen, or sulfur. Exemplary $R^3$ groups include but are not limited to optionally substituted azepinyl, oxepinyl, thiepinyl, diazepinyl, oxazepinyl, thiazepinyl, triazepinyl, oxadiazepinyl, thiadiazepinyl, dihydroazepinyl, dihydrooxepinyl, dihydrothiepinyl, dihydrodiazepinyl, dihydrooxazepinyl, dihydrothiazepinyl, tetrahydroazepinyl, tetrahydrooxepinyl, tetrahydrothiepinyl, tetrahydrodiazepinyl, tetrahydrooxazepinyl or tetrahydrothiazepinyl. In some embodiments, $R^3$ is an optionally substituted 8-membered partially unsaturated ring having 1-2 heteroatoms independently selected from nitrogen, oxygen or sulfur.

In some embodiments, $R^3$ is an optionally substituted 5-6 membered monocyclic heteroaromatic ring having 1-4 heteroatoms independently selected from nitrogen, oxygen, or sulfur. In some embodiments, $R^3$ is a substituted 5-6 membered monocyclic heteroaromatic ring having 1-4 heteroatoms independently selected from nitrogen, oxygen, or sulfur. In some embodiments, $R^3$ is an unsubstituted 5-6 membered monocyclic heteroaromatic ring having 1-4 heteroatoms independently selected from nitrogen, oxygen, or sulfur.

In some embodiments, $R^3$ is an optionally substituted 5-membered monocyclic heteroaromatic ring having 1-4 heteroatoms independently selected from nitrogen, oxygen or sulfur. In some embodiments, $R^3$ is a substituted 5-membered monocyclic heteroaromatic ring having 1-4 heteroatoms independently selected from nitrogen, oxygen or sulfur. In some embodiments, $R^3$ is an unsubstituted 5-membered monocyclic heteroaromatic ring having 1-4 heteroatoms independently selected from nitrogen, oxygen or sulfur. In some embodiments, $R^3$ is an optionally substituted 6-membered monocyclic heteroaromatic ring having 1-4 heteroatoms independently selected from nitrogen, oxygen, or sulfur. In some embodiments, $R^3$ is a substituted 6-membered monocyclic heteroaromatic ring having 1-4 heteroatoms independently selected from nitrogen, oxygen or sulfur. In some embodiments, $R^3$ is an unsubstituted 6-membered monocyclic heteroaromatic ring having 1-4 heteroatoms independently selected from nitrogen, oxygen or sulfur.

In some embodiments, $R^3$ is an optionally substituted 5-membered heteroaryl ring having one heteroatom selected from nitrogen, oxygen, or sulfur. In some embodiments, $R^3$ is selected from optionally substituted pyrrolyl, furanyl, or thienyl.

In some embodiments, $R^3$ is an optionally substituted 5-membered heteroaryl ring having two heteroatoms independently selected from nitrogen, oxygen, or sulfur. In certain embodiments, $R^3$ is an optionally substituted 5-membered heteroaryl ring having one nitrogen atom, and an additional heteroatom selected from sulfur or oxygen. Exemplary $R^3$ groups include but are not limited to optionally substituted pyrazolyl, imidazolyl, thiazolyl, isothiazolyl, oxazolyl or isoxazolyl.

In some embodiments, $R^3$ is an optionally substituted 5-membered heteroaryl ring having three heteroatoms independently selected from nitrogen, oxygen, or sulfur. Exemplary $R^3$ groups include but are not limited to optionally substituted triazolyl, oxadiazolyl or thiadiazolyl.

In some embodiments, $R^3$ is an optionally substituted 5-membered heteroaryl ring having four heteroatoms independently selected from nitrogen, oxygen, or sulfur. Exemplary $R^3$ groups include but are not limited to optionally substituted tetrazolyl, oxatriazolyl and thiatriazolyl.

In some embodiments, $R^3$ is a 6-membered heteroaryl ring having 1-4 nitrogen atoms. In some embodiments, $R^3$ is a 6-membered heteroaryl ring having 1-3 nitrogen atoms. In other embodiments, $R^3$ is an optionally substituted 6-membered heteroaryl ring having 1-2 nitrogen atoms. In some embodiments, $R^3$ is an optionally substituted 6-membered heteroaryl ring having four nitrogen atoms. In some embodiments, $R^3$ is an optionally substituted 6-membered heteroaryl ring having three nitrogen atoms. In some embodiments, $R^3$ is an optionally substituted 6-membered heteroaryl ring having two nitrogen atoms. In certain embodiments, $R^3$ is an optionally substituted 6-membered heteroaryl ring having one nitrogen atom. Exemplary $R^3$ groups include but are not limited to optionally substituted pyridinyl, pyrimidinyl, pyrazinyl, pyridazinyl, triazinyl, or tetrazinyl.

In some embodiments, $R^3$ is an optionally substituted 8-10 membered bicyclic heteroaryl ring having 1-5 heteroatoms independently selected from nitrogen, oxygen, or sulfur. In some embodiments, $R^3$ is a substituted 8-10 membered bicyclic heteroaryl ring having 1-5 heteroatoms independently selected from nitrogen, oxygen, or sulfur. In some embodiments, $R^3$ is an unsubstituted 8-10 membered bicyclic heteroaryl ring having 1-5 heteroatoms independently selected from nitrogen, oxygen, or sulfur. In some embodiments, $R^3$ is an optionally substituted 8-membered bicyclic heteroaryl ring having 1-5 heteroatoms independently selected from nitrogen, oxygen, or sulfur. In some embodiments, $R^3$ is a substituted 8-membered bicyclic heteroaryl ring having 1-5 heteroatoms independently selected from nitrogen, oxygen, or sulfur. In some embodiments, $R^3$ is an unsubstituted 8-membered bicyclic heteroaryl ring having 1-5 heteroatoms independently selected from nitrogen, oxygen, or sulfur. In some embodiments, $R^3$ is an optionally substituted 9-membered bicyclic heteroaryl ring having 1-5 heteroatoms independently selected from nitrogen, oxygen, or sulfur. In some embodiments, $R^3$ is a substituted 9-membered bicyclic heteroaryl ring having 1-5 heteroatoms independently selected from nitrogen, oxygen, or sulfur. In some embodiments, $R^3$ is an unsubstituted 9-membered bicyclic heteroaryl ring having 1-5 heteroatoms independently selected from nitrogen, oxygen, or sulfur. In some embodiments, $R^3$ is an optionally substituted 10-membered bicyclic heteroaryl ring having 1-5 heteroatoms independently selected from nitrogen, oxygen, or sulfur. In some embodiments, $R^3$ is a substituted 10-membered bicyclic heteroaryl ring having 1-5 heteroatoms independently selected from nitrogen, oxygen, or sulfur. In some embodiments, $R^3$ is an unsubstituted 10-membered bicyclic heteroaryl ring having 1-5 heteroatoms independently selected from nitrogen, oxygen, or sulfur.

In some embodiments, $R^3$ is an optionally substituted 5,6-fused heteroaryl ring having 1-5 heteroatoms independently selected from nitrogen, oxygen, or sulfur. In some embodiments, $R^3$ is an optionally substituted 5,6-fused heteroaryl ring having 1-4 heteroatoms independently selected from nitrogen, oxygen, or sulfur. In some embodiments, $R^3$ is an optionally substituted 5,6-fused heteroaryl ring having 1-3 heteroatoms independently selected from nitrogen, oxygen, or sulfur. In some embodiments, $R^3$ is an optionally substituted 5,6-fused heteroaryl ring having two heteroatoms independently selected from nitrogen, oxygen, or sulfur. In some embodiments, $R^3$ is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, $R^3$ is an optionally substituted 5,6-fused heteroaryl ring having three heteroatoms independently selected from nitrogen, oxygen, or sulfur. In some embodiments, $R^3$ is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, $R^3$ is an optionally substituted 5,6-fused heteroaryl ring having four heteroatoms independently selected from nitrogen, oxygen, or sulfur. In some embodiments, $R^3$ is an optionally substituted 5,6-fused heteroaryl ring having five heteroatoms independently selected from nitrogen, oxygen, or sulfur.

In some embodiments, $R^3$ is an optionally substituted 5,6-fused heteroaryl ring having 1-5 heteroatoms independently selected from nitrogen, oxygen, or sulfur. In other embodiments, $R^3$ is an optionally substituted 5,6-fused heteroaryl ring having 1-2 heteroatoms independently selected from nitrogen, oxygen, or sulfur. In certain embodiments, $R^3$ is an optionally substituted 5,6-fused heteroaryl ring having one heteroatom independently selected from nitrogen, oxygen, or sulfur. In some embodiments, $R^3$ is optionally substituted indolyl. In some embodiments, $R^3$ is optionally substituted benzofuranyl. In some embodiments, $R^3$ is optionally substituted benzo[b]thienyl. In certain embodiments, $R^3$ is an optionally substituted 5,6-fused heteroaryl ring having two heteroatoms independently selected from nitrogen, oxygen, or sulfur. In some embodiments, $R^3$ is optionally substituted azaindolyl. In some embodiments, $R^3$ is optionally substituted benzimidazolyl. In some embodiments, $R^3$ is optionally substituted benzothiazolyl. In some embodiments, $R^3$ is optionally substituted benzoxazolyl. In some embodiments, $R^3$ is an optionally substituted indazolyl. In certain embodiments, $R^3$ is an optionally substituted 5,6-fused heteroaryl ring having three heteroatoms independently selected from nitrogen, oxygen, or sulfur. In some embodiments, $R^3$ is optionally substituted oxazolopyridiyl, thiazolopyridinyl or imidazopyridinyl. In certain embodiments, $R^3$ is an optionally substituted 5,6-fused heteroaryl ring having four heteroatoms independently selected from nitrogen, oxygen, or sulfur. In some embodiments, $R^3$ is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, $R^3$ is an optionally substituted 5,6-fused heteroaryl ring having five heteroatoms independently selected from nitrogen, oxygen, or sulfur.

In certain embodiments, $R^3$ is an optionally substituted 6,6-fused heteroaryl ring having 1-5 heteroatoms independently selected from nitrogen, oxygen, or sulfur. In some embodiments, $R^3$ is an optionally substituted 6,6-fused heteroaryl ring having 1-2 heteroatoms independently selected from nitrogen, oxygen, or sulfur. In other embodiments, $R^3$ is an optionally substituted 6,6-fused heteroaryl ring having one heteroatom selected from nitrogen, oxygen, or sulfur. In some embodiments, $R^3$ is optionally substituted quinolinyl. In some embodiments, $R^3$ is optionally substituted isoquinolinyl. In some embodiments, $R^3$ is an optionally substituted 6,6-fused heteroaryl ring having two heteroatoms independently selected from nitrogen, oxygen, or sulfur. In some embodiments, $R^3$ is optionally substituted quinazolinyl, phthalazinyl, quinoxalinyl or naphthyridinyl. In some embodiments, $R^3$ is an optionally substituted 6,6-fused heteroaryl ring having three heteroatoms independently selected from nitrogen, oxygen, or sulfur. In some embodiments, $R^3$ is optionally substituted pyridopyrimidinyl, pyridopyridazinyl, pyridopyrazinyl, or benzotriazinyl. In some embodiments, $R^3$ is an optionally substituted 6,6-fused heteroaryl ring having four heteroatoms independently selected from nitrogen, oxygen, or sulfur. In some embodiments, $R^3$ is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, $R^3$ is an optionally substituted 6,6-fused heteroaryl ring having five heteroatoms independently selected from nitrogen, oxygen, or sulfur.

As defined generally above, $R^4$ of formula I or II is selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^4$ is R. In some embodiments, $R^4$ is hydrogen. In some embodiments, $R^4$ is optionally substituted $C_{1-6}$ aliphatic. In some embodiments, $R^4$ is $C_{1-6}$ alkyl. In some embodiments, $R^4$ is methyl.

In some embodiments, $R^4$ is halogen. In some embodiments, $R^4$ is —F. In some embodiments, $R^4$ is —Cl. In some embodiments, $R^4$ is —Br. In some embodiments, $R^4$ is —I.

In some embodiments, $R^4$ is —CN. In some embodiments, $R^4$ is —NO$_2$. In some embodiments, $R^4$ is —C(O)OR'. In some embodiments, $R^4$ is —OR'. In some embodiments, $R^4$ is —SR'. In some embodiments, $R^4$ is —C(O)N(R')$_2$. In some embodiments, $R^4$ is —N(R')$_2$. In some embodiments, $R^4$ is —S(O)$_2$N(R)$_2$. In some embodiments, $R^4$ is —N(R')S(O)$_2$CF$_3$. In some embodiments, $R^4$ is —C(O)R'. In some embodiments, $R^4$ is —N(R')C(O)R'. In some embodiments, $R^4$ is —S(O)R'. In some embodiments, $R^4$ is —S(O)$_2$R'. In some embodiments, $R^4$ is —N(R')C(O)OR. In some embodiments, $R^4$ is —N(R')S(O)$_2$R'.

As defined generally above, $R^5$ of formula I, II, III, IV, V, VI, or VII is selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^5$ is R. In some embodiments, $R^5$ is hydrogen. In some embodiments, $R^5$ is optionally substituted $C_{1-6}$ aliphatic. In some embodiments, $R^5$ is $C_{1-6}$ alkyl. In some embodiments, $R^5$ is methyl.

In some embodiments, $R^5$ is halogen. In some embodiments, $R^5$ is —F. In some embodiments, $R^5$ is —Cl. In some embodiments, $R^5$ is —Br. In some embodiments, $R^5$ is —I.

In some embodiments, $R^5$ is —CN. In some embodiments, $R^5$ is —NO$_2$. In some embodiments, $R^5$ is —C(O)OR'. In some embodiments, $R^5$ is —OR'. In some embodiments, $R^5$ is —SR'. In some embodiments, $R^5$ is —C(O)N(R')$_2$. In some embodiments, $R^5$ is —N(R')$_2$. In some embodiments, $R^5$ is —S(O)$_2$N(R)$_2$. In some embodiments, $R^5$ is —N(R')S(O)$_2$CF$_3$. In some embodiments, $R^5$ is —C(O)R'. In some embodiments, $R^5$ is —N(R')C(O)R'. In some embodiments, $R^5$ is —S(O)R'. In some embodiments, $R^5$ is —S(O)$_2$R'. In some embodiments, $R^5$ is —N(R')C(O)OR. In some embodiments, $R^5$ is —N(R')S(O)$_2$R'.

As defined generally above, $R^6$ of formula I, II, III, IV, V, VI, or VII is selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^6$ is R. In some embodiments, $R^6$ is hydrogen. In some embodiments, $R^6$ is optionally substituted $C_{1-6}$ aliphatic. In some embodiments, $R^6$ is optionally substituted $C_{1-6}$ alkyl. In some embodiments, $R^6$ is substituted $C_{1-6}$ alkyl. In some embodiments, $R^6$ is unsubstituted $C_{1-6}$ alkyl. In some embodiments, $R^6$ is methyl. In some embodiments, $R^6$ is $C_{1-6}$ alkyl optionally substituted with one or more halogen. In some embodiments, $R^6$ is $C_6$ haloalkyl. In some embodiments, $R^6$ is —CF$_3$. In some embodiments, $R^6$ is optionally substituted $C_{3-6}$ cycloalkyl. In some embodiments, $R^6$ is substituted $C_{3-6}$ cycloalkyl. In some embodiments, $R^6$ is unsubstituted $C_{3-6}$ cycloalkyl. In some embodiments, $R^6$ is optionally substituted cyclopropyl. In some embodiments, $R^6$ is substituted cyclopropyl. In some embodiments, $R^6$ is unsubstituted cyclopropyl. In some embodiments, $R^6$ is optionally substituted cyclobutyl. In some embodiments, $R^6$ is substituted cyclobutyl. In some embodiments, $R^6$ is unsubstituted cyclobutyl. In some embodiments, $R^6$ is optionally substituted cyclopentyl. In some embodiments, $R^6$ is substituted cyclopentyl. In some embodiments, $R^6$ is unsubstituted cyclopentyl. In some embodiments, $R^6$ is optionally substituted cyclohexyl. In some embodiments, $R^6$ is substituted cyclohexyl. In some embodiments, $R^6$ is unsubstituted cyclohexyl.

In some embodiments, $R^6$ is halogen. In some embodiments, $R^6$ is —F. In some embodiments, $R^6$ is —Cl. In some embodiments, $R^6$ is —Br. In some embodiments, $R^6$ is —I.

In some embodiments, $R^6$ is —CN. In some embodiments, $R^6$ is —NO$_2$. In some embodiments, $R^6$ is —C(O)OR'. In some embodiments, $R^6$ is —OR'. In some embodiments, $R^6$ is —SR'. In some embodiments, $R^6$ is —C(O)N(R')$_2$. In some embodiments, $R^6$ is —N(R')$_2$. In some embodiments, $R^6$ is —S(O)$_2$N(R)$_2$. In some embodiments, $R^6$ is —N(R')S(O)$_2$CF$_3$. In some embodiments, $R^6$ is —C(O)R'. In some embodiments, $R^6$ is —N(R')C(O)R'. In some embodiments, $R^6$ is —S(O)R'. In some embodiments, $R^6$ is —S(O)$_2$R'. In some embodiments, $R^6$ is —N(R')C(O)OR. In some embodiments, $R^6$ is —N(R')S(O)$_2$R'.

As defined generally above, $R^7$ of formula I, II, III, IV, or V is hydrogen, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R, or an optionally substituted group selected from C$_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In some embodiments, $R^7$ is selected from R, halogen, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —N(R)S(O)$_2$CF$_3$, —C(O)N(R)S(O)$_2$R, —S(O)$_2$N(R)C(O)OR, —S(O)$_2$N(R)C(O)N(R)$_2$, —C(O)R, —C(O)N(R)S(O)$_2$CF$_3$, —N(R)C(O)R, —OC(O)R, —OC(O)N(R)$_2$, —C(NR)N(R)$_2$, —N(R)C(NR)N(R)$_2$, —S(O)R, —S(O)$_2$R, —N(R)C(O)OR, or —N(R)S(O)$_2$R.

In some embodiments, $R^7$ is an optionally substituted group selected from C$_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In some embodiments, $R^7$ is an optionally substituted ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In some embodiments, $R^7$ is an optionally substituted ring selected from phenyl, a 5-6 membered heteroaryl ring having 1-4 heteroatoms independently selected from nitrogen, oxygen, or sulfur, an 8-14 membered bicyclic or polycyclic saturated, partially unsaturated or aryl ring, or an 8-14 membered bicyclic or polycyclic heteroaryl ring having 1-5 heteroatoms independently selected from nitrogen, oxygen, or sulfur.

In some embodiments, $R^7$ is R. In some embodiments, $R^7$ is hydrogen.

In some embodiments, $R^7$ is optionally substituted C$_{1-12}$ aliphatic. In some embodiments, $R^7$ is optionally substituted C$_{1-10}$ aliphatic. In some embodiments, $R^7$ is optionally substituted C$_{1-8}$ aliphatic. In some embodiments, $R^7$ is optionally substituted C$_{1-6}$ aliphatic. In some embodiments, $R^7$ is optionally substituted C$_{1-6}$ alkyl. In some embodiments, $R^7$ is substituted C$_{1-6}$ alkyl. In some embodiments, $R^7$ is unsubstituted C$_{1-6}$ alkyl. In some embodiments, $R^7$ is optionally substituted hexyl. In some embodiments, $R^7$ is substituted hexyl. In some embodiments, $R^7$ is unsubstituted hexyl. In some embodiments, $R^7$ is optionally substituted pentyl. In some embodiments, $R^7$ is substituted pentyl. In some embodiments, $R^7$ is unsubstituted pentyl. In some embodiments, $R^7$ is optionally substituted butyl. In some embodiments, $R^7$ is substituted butyl. In some embodiments, $R^7$ is unsubstituted butyl. In some embodiments, $R^7$ is optionally substituted propyl. In some embodiments, $R^7$ is substituted propyl. In some embodiments, $R^7$ is unsubstituted propyl. In some embodiments, $R^7$ is optionally substituted ethyl. In some embodiments, $R^7$ is substituted ethyl. In some embodiments, $R^7$ is unsubstituted ethyl. In some embodiments, $R^7$ is optionally substituted methyl. In some embodiments, $R^7$ is substituted methyl. In some embodiments, $R^7$ is unsubstituted methyl.

In some embodiments, $R^7$ is optionally substituted C$_{3-6}$ carbocyclyl. In some embodiments, $R^7$ is substituted C$_{3-6}$ carbocyclyl. In some embodiments, $R^7$ is unsubstituted C$_{3-6}$ carbocyclyl. In some embodiments, $R^7$ is optionally substituted cyclohexyl. In some embodiments, $R^7$ is substituted cyclohexyl. In some embodiments, $R^7$ is unsubstituted cyclohexyl. In some embodiments, $R^7$ is optionally substituted cyclopentyl. In some embodiments, $R^7$ is substituted cyclopentyl. In some embodiments, $R^7$ is unsubstituted cyclopentyl. In some embodiments, $R^7$ is optionally substituted cyclobutyl. In some embodiments, $R^7$ is substituted cyclobutyl. In some embodiments, $R^7$ is unsubstituted cyclobutyl. In some embodiments, $R^7$ is optionally substituted cyclopropyl. In some embodiments, $R^7$ is substituted cyclopropyl. In some embodiments, $R^7$ is unsubstituted cyclopropyl.

In some embodiments, $R^7$ is halogen. In some embodiments, $R^7$ is —F. In some embodiments, $R^7$ is —Cl. In some embodiments, $R^7$ is —Br. In some embodiments, $R^7$ is —I.

In some embodiments, $R^7$ is —CN. In some embodiments, $R^7$ is —NO$_2$. In some embodiments, $R^7$ is —C(O)

OR. In some embodiments, $R^7$ is —OCF$_3$. In some embodiments, $R^7$ is —OR. In some embodiments, $R^7$ is —SR. In some embodiments, $R^7$ is —S(O)$_2$OR. In some embodiments, $R^7$ is —P(O)(OH)$_2$. In some embodiments, $R^7$ is —C(O)N(R). In some embodiments, $R^7$ is —N(R)$_2$. In some embodiments, $R^7$ is —S(O)$_2$N(R)$_2$. In some embodiments, $R^7$ is —N(R)S(O)$_2$CF$_3$. In some embodiments, $R^7$ is —C(O)N(R)S(O)$_2$R. In some embodiments, $R^7$ is —S(O)$_2$N(R)C(O)OR. In some embodiments, $R^7$ is —S(O)$_2$N(R)C(O)N(R)$_2$. In some embodiments, $R^7$ is —C(O)R. In some embodiments, $R^7$ is —C(O)N(R)S(O)$_2$CF$_3$. In some embodiments, $R^7$ is —N(R)C(O)R. In some embodiments, $R^7$ is —OC(O)R. In some embodiments, $R^7$ is —OC(O)N(R)$_2$. In some embodiments, $R^7$ is —C(NR)N(R)$_2$. In some embodiments, $R^7$ is —N(R)C(NR)N(R)$_2$. In some embodiments, $R^7$ is —S(O)R. In some embodiments, $R^7$ is —S(O)$_2$R. In some embodiments, $R^7$ is —N(R)C(O)OR. In some embodiments, $R^7$ is —N(R)S(O)$_2$R.

In some embodiments, $R^7$ is an optionally substituted 3-8 membered saturated or partially unsaturated carbocyclic ring. In some embodiments, $R^7$ is an optionally substituted 3-membered saturated or partially unsaturated carbocyclic ring. In some embodiments, $R^7$ is an optionally substituted 4-membered saturated or partially unsaturated carbocyclic ring. In some embodiments, $R^7$ is an optionally substituted 5-membered saturated or partially unsaturated carbocyclic ring. In some embodiments, $R^7$ is an optionally substituted 6-membered saturated or partially unsaturated carbocyclic ring. In some embodiments, $R^7$ is an optionally substituted 7-membered saturated or partially unsaturated carbocyclic ring. In some embodiments, $R^7$ is an optionally substituted 8-membered saturated or partially unsaturated carbocyclic ring.

In some embodiments, $R^7$ is an optionally substituted 3-8 membered saturated monocyclic carbocyclic ring. In some embodiments, $R^7$ is an optionally substituted cycloheptyl. In some embodiments, $R^7$ is an optionally substituted cyclohexyl. In some embodiments, $R^7$ is an optionally substituted cyclopentyl. In some embodiments, $R^7$ is an optionally substituted cyclobutyl. In some embodiments, $R^7$ is an optionally substituted cyclopropyl.

In some embodiments, $R^7$ is an optionally substituted 3-8 membered unsaturated carbocyclic ring. In some embodiments, $R^7$ is an optionally substituted cycloheptenyl. In some embodiments, $R^7$ is an optionally substituted cyclohexenyl. In some embodiments, $R^7$ is an optionally substituted cyclopentenyl. In some embodiments, $R^7$ is an optionally substituted cyclobutenyl.

In some embodiments, $R^7$ is optionally substituted phenyl. In some embodiments, $R^7$ is substituted phenyl. In some embodiments, $R^7$ is 2-methylphenyl. In some embodiments, $R^7$ is phenyl.

In some embodiments, $R^7$ is an optionally substituted 3-8 membered saturated or partially unsaturated heterocyclic ring having 1-2 heteroatoms independently selected from nitrogen, oxygen, or sulfur. In some embodiments, $R^7$ is an optionally substituted 3-8 membered saturated heterocyclic ring having 1-2 heteroatoms independently selected from nitrogen, oxygen, or sulfur. In some embodiments, $R^7$ is an optionally substituted 3-8 membered partially unsaturated heterocyclic ring having 1-2 heteroatoms independently selected from nitrogen, oxygen, or sulfur. Exemplary suitable embodiments for $R^7$ include but are not limited to those heterocyclic embodiments described for R.

In some embodiments, $R^7$ is an optionally substituted 5-6 membered heteroaryl ring having 1-4 heteroatoms independently selected from nitrogen, oxygen or sulfur. In some embodiments, $R^7$ is an optionally substituted 5-membered heteroaryl ring having 1-4 heteroatoms independently selected from nitrogen, oxygen or sulfur. In some embodiments, $R^7$ is an optionally substituted 5-membered heteroaryl ring having 1-4 nitrogen atoms. In some embodiments, $R^7$ is optionally substituted pyrrolyl. In some embodiments, $R^7$ is substituted pyrrolyl. In some embodiments, $R^7$ is unsubstituted pyrrolyl. In some embodiments, $R^7$ is optionally substituted pyrazolyl. In some embodiments, $R^7$ is substituted pyrazolyl. In some embodiments, $R^7$ is

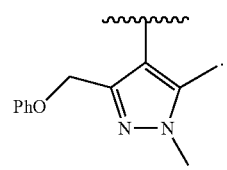

In some embodiments, $R^7$ is

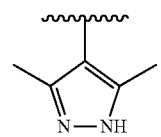

In some embodiments, $R^7$ is

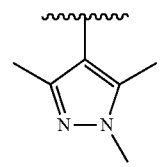

In some embodiments, $R^7$ is

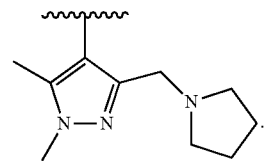

In some embodiments, $R^7$ is

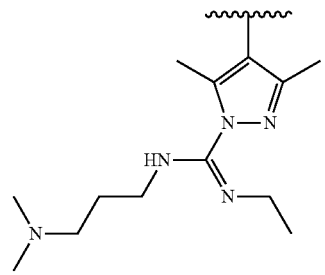

In some embodiments, $R^7$ is

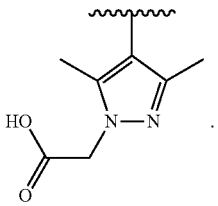 [SMILES: *c1c(C)nn(CC(=O)O)c1C]

In some embodiments, $R^7$ is

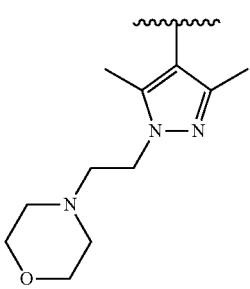

In some embodiments, $R^7$ is pyrazolyl. In some embodiments, $R^7$ is

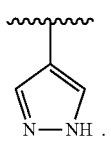

In some embodiments, $R^7$ is

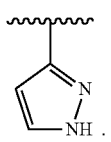

In some embodiments, $R^7$ is optionally substituted isoxazolyl. In some embodiments, $R^7$ is substituted isoxazolyl. In some embodiments, $R^7$ is unsubstituted isoxazolyl. In some embodiments, $R^7$ is optionally substituted isothiazolyl. In some embodiments, $R^7$ is substituted isothiazolyl. In some embodiments, $R^7$ is unsubstituted isothiazolyl. In some embodiments, $R^7$ is optionally substituted thienyl. In some embodiments, $R^7$ is substituted thienyl. In some embodiments, $R^7$ is unsubstituted thienyl. In some embodiments, $R^7$ is optionally substituted furanyl. In some embodiments, $R^7$ is substituted furanyl. In some embodiments, $R^7$ is unsubstituted furanyl. Other exemplary suitable $R^7$ embodiments include but are not limited to those described for R.

In some embodiments, $R^7$ is an optionally substituted 6-membered heteroaryl ring having 1-4 heteroatoms independently selected from nitrogen, oxygen or sulfur. In some embodiments, $R^7$ is an optionally substituted 6-membered heteroaryl ring having 1-4 nitrogen atoms. In some embodiments, $R^7$ is optionally substituted pyridinyl. In some embodiments, $R^7$ is substituted pyridinyl. In some embodiments, $R^7$ is

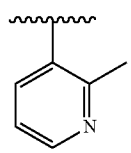

In some embodiments, $R^7$ is pyridinyl. In some embodiments, $R^7$ is 3-pyridinyl. In some embodiments, $R^7$ is 4-pyridinyl. Other exemplary suitable $R^7$ embodiments include but are not limited to those described for R.

In some embodiments, $R^7$ is an optionally substituted 8-14 membered bicyclic or polycyclic saturated, partially unsaturated or aryl ring. In some embodiments, $R^7$ is an optionally substituted 8-14 membered bicyclic or polycyclic saturated ring. In some embodiments, $R^7$ is an optionally substituted 8-14 membered bicyclic or polycyclic partially saturated ring. In some embodiments, $R^7$ is an optionally substituted 8-14 membered bicyclic or polycyclic aryl ring. In some embodiments, $R^7$ is an optionally substituted 8-10 membered bicyclic saturated, partially unsaturated or aryl ring. In some embodiments, $R^7$ is an optionally substituted 8-10 membered bicyclic saturated ring. In some embodiments, $R^7$ is an optionally substituted 8-10 membered bicyclic partially unsaturated ring. In some embodiments, $R^7$ is an optionally substituted 8-10 membered bicyclic aryl ring. In some embodiments, $R^7$ is optionally substituted naphthyl. In some embodiments, $R^7$ is optionally substituted anthracenyl. In some embodiments, $R^7$ is optionally substituted 9-anthracenyl.

In some embodiments, $R^7$ is an optionally substituted 7-14 membered bicyclic or polycyclic saturated or partially unsaturated heterocyclic ring having 1-5 heteroatoms independently selected from nitrogen, oxygen, or sulfur. In some embodiments, $R^7$ is an optionally substituted 7-10 membered bicyclic saturated or partially unsaturated heterocyclic ring having 1-5 heteroatoms independently selected from nitrogen, oxygen, or sulfur. In some embodiments, $R^7$ is optionally substituted indolinyl. In some embodiments, $R^7$ is optionally substituted isoindolinyl. In some embodiments, $R^7$ is optionally substituted 1, 2, 3, 4-tetrahydroquinolinyl. In some embodiments, $R^7$ is optionally substituted 1, 2, 3, 4-tetrahydroisoquinolinyl. In some embodiments, $R^7$ is an optionally substituted azabicyclo[3.2.1]octanyl.

In some embodiments, $R^7$ is an optionally substituted 8-14 membered bicyclic or polycyclic heteroaryl ring having 1-5 heteroatoms independently selected from nitrogen, oxygen, or sulfur. In some embodiments, $R^7$ is an optionally substituted 8-14 membered bicyclic or tricyclic heteroaryl ring having 1-5 heteroatoms independently selected from nitrogen, oxygen, or sulfur. In some embodiments, $R^7$ is an optionally substituted 8-14 membered bicyclic heteroaryl ring having 1-5 heteroatoms independently selected from nitrogen, oxygen, or sulfur. In some embodiments, $R^7$ is an 8-10 membered bicyclic heteroaryl ring having 1-5 heteroatoms independently selected from nitrogen, oxygen, or sulfur.

In some embodiments, $R^7$ is an optionally substituted 5,6-fused heteroaryl ring having 1-5 heteroatoms independently selected from nitrogen, oxygen, or sulfur. In some embodiments, $R^7$ is an optionally substituted 5,6-fused heteroaryl ring having 1-4 heteroatoms independently selected from nitrogen, oxygen, or sulfur. In some embodiments, $R^7$ is an optionally substituted 5,6-fused heteroaryl ring having 1-3 heteroatoms independently selected from nitrogen, oxygen, or sulfur. In some embodiments, $R^7$ is an optionally substituted 5,6-fused heteroaryl ring having two heteroatoms independently selected from nitrogen, oxygen, or sulfur. In some embodiments, $R^7$ is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, $R^7$ is an optionally substituted 5,6-fused heteroaryl ring having three heteroatoms independently selected from nitrogen, oxygen, or sulfur. In some embodiments, $R^7$ is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, $R^7$ is an optionally substituted 5,6-fused heteroaryl ring having four heteroatoms independently selected from nitrogen, oxygen, or sulfur. In some embodiments, $R^7$ is an optionally substituted 5,6-fused heteroaryl ring having five heteroatoms independently selected from nitrogen, oxygen, or sulfur.

In some embodiments, $R^7$ is an optionally substituted 5,6-fused heteroaryl ring having 1-5 heteroatoms independently selected from nitrogen, oxygen, or sulfur. In other embodiments, $R^7$ is an optionally substituted 5,6-fused heteroaryl ring having 1-2 heteroatoms independently selected from nitrogen, oxygen, or sulfur. In certain embodiments, $R^7$ is an optionally substituted 5,6-fused heteroaryl ring having one heteroatom independently selected from nitrogen, oxygen, or sulfur. In some embodiments, $R^7$ is optionally substituted indolyl. In some embodiments, $R^7$ is optionally substituted benzofuranyl. In some embodiments, $R^7$ is optionally substituted benzo[b]thienyl. In certain embodiments, $R^7$ is an optionally substituted 5,6-fused heteroaryl ring having two heteroatoms independently selected from nitrogen, oxygen, or sulfur. In some embodiments, $R^7$ is optionally substituted azaindolyl. In some embodiments, $R^7$ is optionally substituted benzimidazolyl. In some embodiments, $R^7$ is optionally substituted benzothiazolyl. In some embodiments, $R^7$ is optionally substituted benzoxazolyl. In some embodiments, $R^7$ is an optionally substituted indazolyl. In certain embodiments, $R^7$ is an optionally substituted 5,6-fused heteroaryl ring having three heteroatoms independently selected from nitrogen, oxygen, or sulfur. In some embodiments, $R^7$ is optionally substituted oxazolopyridiyl, thiazolopyridinyl or imidazopyridinyl. In certain embodiments, $R^7$ is an optionally substituted 5,6-fused heteroaryl ring having four heteroatoms independently selected from nitrogen, oxygen, or sulfur. In some embodiments, $R^7$ is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, $R^7$ is an optionally substituted 5,6-fused heteroaryl ring having five heteroatoms independently selected from nitrogen, oxygen, or sulfur.

In certain embodiments, $R^7$ is an optionally substituted 6,6-fused heteroaryl ring having 1-5 heteroatoms independently selected from nitrogen, oxygen, or sulfur. In some embodiments, $R^7$ is an optionally substituted 6,6-fused heteroaryl ring having 1-2 heteroatoms independently selected from nitrogen, oxygen, or sulfur. In other embodiments, $R^7$ is an optionally substituted 6,6-fused heteroaryl ring having one heteroatom selected from nitrogen, oxygen, or sulfur. In some embodiments, $R^7$ is optionally substituted quinolinyl. In some embodiments, $R^7$ is optionally substituted isoquinolinyl. In some embodiments, $R^7$ is an optionally substituted 6,6-fused heteroaryl ring having two heteroatoms independently selected from nitrogen, oxygen, or sulfur. In some embodiments, $R^7$ is optionally substituted quinazolinyl, phthalazinyl, quinoxalinyl or naphthyridinyl. In some embodiments, $R^7$ is an optionally substituted 6,6-fused heteroaryl ring having three heteroatoms independently selected from nitrogen, oxygen, or sulfur. In some embodiments, $R^7$ is optionally substituted pyridopyrimidinyl, pyridopyridazinyl, pyridopyrazinyl, or benzotriazinyl. In some embodiments, $R^7$ is an optionally substituted 6,6-fused heteroaryl ring having four heteroatoms independently selected from nitrogen, oxygen, or sulfur. In some embodiments, $R^7$ is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, $R^7$ is an optionally substituted 6,6-fused heteroaryl ring having five heteroatoms independently selected from nitrogen, oxygen, or sulfur.

In some embodiments, each of $R^4$, $R^5$ and $R^6$ is hydrogen. In some embodiments, each of $R^4$ and $R^5$ is hydrogen, and $R^6$ is halogen. In some embodiments, each of $R^4$ and $R^5$ is hydrogen, and $R^6$ is —Cl. In some embodiments, each of $R^4$ and $R^6$ is hydrogen, and $R^5$ is —Cl. In some embodiments, each of $R^4$, $R^5$ and $R^6$ is hydrogen, and $R^7$ is an optionally substituted ring selected from phenyl, a 5-6 membered heteroaryl ring having 1-4 heteroatoms independently selected from nitrogen, oxygen, or sulfur, an 8-14 membered bicyclic or polycyclic saturated, partially unsaturated or aryl ring, or an 8-14 membered bicyclic or polycyclic heteroaryl ring having 1-5 heteroatoms independently selected from nitrogen, oxygen, or sulfur. In some embodiments, each of $R^4$ and $R^5$ is hydrogen, $R^6$ is halogen, and $R^7$ is an optionally substituted ring selected from phenyl, a 5-6 membered heteroaryl ring having 1-4 heteroatoms independently selected from nitrogen, oxygen, or sulfur, an 8-14 membered bicyclic or polycyclic saturated, partially unsaturated or aryl ring, or an 8-14 membered bicyclic or polycyclic heteroaryl ring having 1-5 heteroatoms independently selected from nitrogen, oxygen, or sulfur. In some embodiments, each of $R^4$ and $R^5$ is hydrogen, $R^6$ is —Cl, and $R^7$ is an optionally substituted ring selected from phenyl, a 5-6 membered heteroaryl ring having 1-4 heteroatoms independently selected from nitrogen, oxygen, or sulfur, an 8-14 membered bicyclic or polycyclic saturated, partially unsaturated or aryl ring, or an 8-14 membered bicyclic or polycyclic heteroaryl ring having 1-5 heteroatoms independently selected from nitrogen, oxygen, or sulfur. In some embodiments, each of $R^4$ and $R^6$ is hydrogen, $R^5$ is halogen, and $R^7$ is an optionally substituted ring selected from phenyl, a 5-6 membered heteroaryl ring having 1-4 heteroatoms independently selected from nitrogen, oxygen, or sulfur, an 8-14 membered bicyclic or polycyclic saturated, partially unsaturated or aryl ring, or an 8-14 membered bicyclic or polycyclic heteroaryl ring having 1-5 heteroatoms independently selected from nitrogen, oxygen, or sulfur. In some embodiments, each of $R^4$ and $R^6$ is hydrogen, $R^5$ is —Cl, and $R^7$ is an optionally substituted ring selected from phenyl, a 5-6 membered heteroaryl ring having 1-4 heteroatoms independently selected from nitrogen, oxygen, or sulfur, an 8-14 membered bicyclic or polycyclic saturated, partially unsaturated or aryl ring, or an 8-14 membered bicyclic or polycyclic heteroaryl ring having 1-5 heteroatoms independently selected from nitrogen, oxygen, or sulfur.

In some embodiments, optionally $R^1$ and $R^2$, $R^1$ and $R^{2'}$, $R^1$ and $R^7$, $R^4$ and $R^5$, $R^5$ and $R^6$ and/or $R^6$ and $R^7$ of formula I, II, III, IV, V, VI, or VII are taken together with their intervening atoms to form an optionally substituted ring selected from a 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur. In some embodiments, optionally one of $R^4$ and $R^5$, $R^5$ and $R^6$, $R^6$ and $R^7$, $R^7$ and $R^1$, $R^1$ and $R^{2\prime}$, or $R^2$ and $R^1$ is taken together with their intervening atoms to form an optionally substituted ring selected from a 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur. In some embodiments, optionally one of $R^4$ and $R^5$, $R^5$ and $R^6$, $R^6$ and $R^7$, $R^7$ and $R^1$, $R^1$ and $R^{2\prime}$, or $R^2$ and $R^1$ is taken together with their intervening atoms to form an optionally substituted 3-8 membered saturated or partially unsaturated carbocyclic ring. In some embodiments, optionally one of $R^4$ and $R^5$, $R^5$ and $R^6$, $R^6$ and $R^7$, $R^7$ and $R^1$, $R^1$ and $R^{2\prime}$, or $R^2$ and $R^1$ is taken together with their intervening atoms to form an optionally substituted phenyl. In some embodiments, optionally one of $R^4$ and $R^5$, $R^5$ and $R^6$, $R^6$ and $R^7$, $R^7$ and $R^1$, $R^1$ and $R^{2\prime}$, or $R^2$ and $R^1$ is taken together with their intervening atoms to form an optionally substituted 3-8 membered saturated or partially unsaturated heterocyclic ring having 1-4 heteroatoms independently selected from nitrogen, oxygen. In some embodiments, optionally one of $R^4$ and $R^5$, $R^5$ and $R^6$, $R^6$ and $R^7$, $R^7$ and $R^1$, $R^1$ and $R^{2\prime}$, or $R^2$ and $R^1$ is taken together with their intervening atoms to form an optionally substituted 5-6 membered heteroaryl ring having 1-4 heteroatoms independently selected from nitrogen, oxygen, or sulfur.

In some embodiments, $R^4$ and $R^5$ are taken together with their intervening atoms to form an optionally substituted ring selected from 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, $R^5$ and $R^6$ are taken together with their intervening atoms to form an optionally substituted ring selected from 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur. In some embodiments, $R^6$ and $R^7$ are taken together with their intervening atoms to form an optionally substituted ring selected from 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, $R^7$ and $R^1$ are taken together with their intervening atoms to form an optionally substituted ring selected from a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, $R^1$ and $R^2$ are taken together with their intervening atoms to form an optionally substituted ring selected from a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur. In some embodiments, $R^1$ and $R^2$ are taken together with their intervening atoms to form an optionally substituted ring selected from a 3-8 membered saturated or partially unsaturated heterocyclic ring having 2-4 heteroatoms independently selected from nitrogen, oxygen, or sulfur, or a 5-6 membered heteroaryl ring having 2-4 heteroatoms independently selected from nitrogen, oxygen, or sulfur.

In some embodiments, $R^2$ is —C(O)N(R)-$L^3$-$R^z$ or —C(O)N(R)—C(R)$_2$-$L^3$-$R^z$, wherein one R group and $R^1$ are optionally taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein one R group and $R^1$ are optionally taken together with their intervening atoms to form an optionally substituted 4-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein one R group and $R^1$ are optionally taken together with their intervening atoms to form an optionally substituted 4-8 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein one R group and $R^1$ are optionally taken together with their intervening atoms to form an optionally substituted 5-8 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein one R group and $R^1$ are optionally taken together with their intervening atoms to form an optionally substituted 6-8 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein one R group and $R^1$ are optionally taken together with their intervening atoms to form an optionally substituted 6-7 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein one R group and $R^1$ are optionally taken together with their intervening atoms to form an optionally substituted 6-membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein one R group and $R^1$ are optionally taken together with their intervening atoms to form an optionally substituted 7-membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein one R group and $R^1$ are optionally taken together with their intervening atoms to form an optionally substituted 8-membered saturated or partially unsaturated heterocyclic ring having 2-4 heteroatoms independently selected from nitrogen, oxygen, or sulfur.

In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are optionally taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are optionally taken together with their intervening atoms to form an optionally substituted 4-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 4-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 5-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 6-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 6-7 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur.

In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 4-8 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein The R group attached to the nitrogen atom and $R^1$ are taken together with their intervening atoms to form an optionally substituted 5-8 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 6-8 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 6-7 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 4-membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 5-membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 6-membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 7-membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 8-membered saturated or partially unsaturated heterocyclic ring having 2-4 heteroatoms independently selected from nitrogen, oxygen, or sulfur.

In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are taken together with their intervening atoms to form an optionally substituted 5-6 membered heteroaryl ring having 2-4 heteroatoms independently selected from nitrogen, oxygen, or sulfur.

In some embodiments, $R^2$ is —C(O)N(R)-$L^3$-$R^z$, wherein $R^1$ and the R group are optionally taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 4-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 5-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 6-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 6-7 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur.

In some embodiments, $R^2$ is —C(O)N(R)-$L^3$-$R^z$, wherein $R^1$ and the R group are optionally taken together with their intervening atoms to form an optionally substituted 4-8 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 5-8 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 6-8 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 6-7 membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 4-membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 5-membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 6-membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 7-membered saturated or partially unsaturated heterocyclic ring having 2-4 heteroatoms independently selected from nitrogen, oxygen, or sulfur. In some embodiments, $R^2$ is —C(O)N(R)-$L^3$-$R^z$, wherein $R^1$ and the R group are optionally taken together with their intervening atoms to form an optionally substituted 8-membered saturated or partially unsaturated heterocyclic ring having 2-4 heteroatoms independently selected from nitrogen, oxygen, or sulfur.

In some embodiments, $R^2$ is —C(O)N(R)-$L^3$-$R^z$, wherein $R^1$ and the R group are optionally taken together with their intervening atoms to form an optionally substituted 5-6 membered heteroaryl ring having 2-4 heteroatoms independently selected from nitrogen, oxygen, or sulfur.

In some embodiments, $R^2$ is —C(O)N(R)—C(R)$_2$-$L^3$-$R^z$, wherein $R^1$ and one of the R groups are optionally taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^2$ is —C(O)N(R)—C(R)$_2$-$L^3$-$R^z$, wherein the R group attached to the nitrogen atom and $R^1$ are optionally taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^2$ is —C(O)N(R)—C(R)$_2$-$L^3$-$R^z$, wherein the R group attached to the nitrogen atom and $R^1$ are taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^2$ is —C(O)N(R)—C(R)$_2$-$L^3$-$R^z$, wherein the R group attached to the nitrogen atom and $R^1$ are taken together with their intervening atoms to form an optionally substituted 4-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur.

In some embodiments, $R^2$ is —C(O)N(R)—C(R)$_2$-$L^3$-$R^z$, wherein the R group attached to the nitrogen atom and $R^1$ are taken together with their intervening atoms to form an optionally substituted 4-8 membered saturated or partially unsaturated heterocyclic ring having 2-4 heteroatoms independently selected from nitrogen, oxygen, or sulfur. In some embodiments, $R^2$ is —C(O)N(R)—C(R)$_2$-$L^3$-$R^z$, wherein the R group attached to the nitrogen atom and $R^1$ are taken together with their intervening atoms to form an optionally substituted 5-8 membered saturated or partially unsaturated heterocyclic ring having 2-4 heteroatoms independently selected from nitrogen, oxygen, or sulfur. In some embodiments, $R^2$ is —C(O)N(R)—C(R)$_2$-$L^3$-$R^z$, wherein the R group attached to the nitrogen atom and $R^1$ are taken together with their intervening atoms to form an optionally substituted 6-8 membered saturated or partially unsaturated heterocyclic ring having 2-4 heteroatoms independently selected from nitrogen, oxygen, or sulfur. In some embodiments, $R^2$ is —C(O)N(R)—C(R)$_2$-L$^3$-R$^z$, wherein the R group attached to the nitrogen atom and $R^1$ are taken together with their intervening atoms to form an optionally substituted 7-8 membered saturated or partially unsaturated heterocyclic ring having 2-4 heteroatoms independently selected from nitrogen, oxygen, or sulfur. In some embodiments, $R^2$ is —C(O)N(R)—C(R)$_2$-L$^3$-R$^z$, wherein the R group attached to the nitrogen atom and $R^1$ are taken together with their intervening atoms to form an optionally substituted 6-7 membered saturated or partially unsaturated heterocyclic ring having 2-4 heteroatoms independently selected from nitrogen, oxygen, or sulfur. In some embodiments, $R^2$ is —C(O)N(R)—C(R)$_2$-L$^3$-R$^z$, wherein the R group attached to the nitrogen atom and $R^1$ are taken together with their intervening atoms to form an optionally substituted 4-membered saturated or partially unsaturated heterocyclic ring having 2-4 heteroatoms independently selected from nitrogen, oxygen, or sulfur. In some embodiments, $R^2$ is —C(O)N(R)—C(R)$_2$-L$^3$-R$^z$, wherein the R group attached to the nitrogen atom and $R^1$ are taken together with their intervening atoms to form an optionally substituted 5-membered saturated or partially unsaturated heterocyclic ring having 2-4 heteroatoms independently selected from nitrogen, oxygen, or sulfur. In some embodiments, $R^2$ is —C(O)N(R)—C(R)$_2$-L$^3$-R$^z$, wherein the R group attached to the nitrogen atom and $R^1$ are taken together with their intervening atoms to form an optionally substituted 6-membered saturated or partially unsaturated heterocyclic ring having 2-4 heteroatoms independently selected from nitrogen, oxygen, or sulfur. In some embodiments, $R^2$ is —C(O)N(R)—C(R)$_2$-L$^3$-R$^z$, wherein the R group attached to the nitrogen atom and $R^1$ are taken together with their intervening atoms to form an optionally substituted 7-membered saturated or partially unsaturated heterocyclic ring having 2-4 heteroatoms independently selected from nitrogen, oxygen, or sulfur. In some embodiments, $R^2$ is —C(O)N(R)—C(R)$_2$-L$^3$-R$^z$, wherein the R group attached to the nitrogen atom and $R^1$ are taken together with their intervening atoms to form an optionally substituted 8-membered saturated or partially unsaturated heterocyclic ring having 2-4 heteroatoms independently selected from nitrogen, oxygen, or sulfur.

In some embodiments, $R^2$ is —C(O)N(R)—C(R)$_2$-L$^3$-R$^z$, wherein the R group attached to the nitrogen atom and $R^1$ are taken together with their intervening atoms to form an optionally substituted 5-6 membered heteroaryl ring having 2-4 heteroatoms independently selected from nitrogen, oxygen, or sulfur.

In some embodiments, $R^1$ and $R^{2'}$ are taken together with their intervening atoms to form an optionally substituted ring selected from a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur. In some embodiments, $R^1$ and $R^{2'}$ are taken together with their intervening atoms to form an optionally substituted ring selected from a 3-8 membered saturated or partially unsaturated heterocyclic ring having 2-4 heteroatoms independently selected from nitrogen, oxygen, or sulfur, or a 5-6 membered heteroaryl ring having 2-4 heteroatoms independently selected from nitrogen, oxygen, or sulfur.

In some embodiments, $R^{2'}$ is —C(O)N(R)-L$^4$-R$^w$ or —C(O)N(R)—C(R)$_2$-L$^4$-R$^w$, wherein one R group and $R^1$ are optionally taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein one R group and $R^1$ are optionally taken together with their intervening atoms to form an optionally substituted 4-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein one R group and $R^1$ are optionally taken together with their intervening atoms to form an optionally substituted 4-8 membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein one R group and $R^1$ are optionally taken together with their intervening atoms to form an optionally substituted 5-8 membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein one R group and $R^1$ are optionally taken together with their intervening atoms to form an optionally substituted 6-8 membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein one R group and $R^1$ are optionally taken together with their intervening atoms to form an optionally substituted 6-7 membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein one R group and $R^1$ are optionally taken together with their intervening atoms to form an optionally substituted 6-membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein one R group and $R^1$ are optionally taken together with their intervening atoms to form an optionally substituted 7-membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein one R group and $R^1$ are optionally taken together with their intervening atoms to form an optionally substituted 8-membered saturated or partially unsaturated heterocyclic ring having 2-4 heteroatoms independently selected from nitrogen, oxygen, or sulfur.

In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are optionally taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are optionally taken together with their intervening atoms to form an optionally substituted 4-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 4-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 5-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 6-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 6-7 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur.

In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 4-8 membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein The R group attached to the nitrogen atom and $R^1$ are taken together with their intervening atoms to form an optionally substituted 5-8 membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 6-8 membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 6-7 membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 4-membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 5-membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 6-membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 7-membered saturated or partially unsaturated heterocyclic ring having 2-4 heteroatoms independently selected from nitrogen, oxygen, or sulfur. In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 8-membered saturated or partially unsaturated heterocyclic ring having 2-4 heteroatoms independently selected from nitrogen, oxygen, or sulfur.

In some embodiments, $R^{2'}$ is —C(O)N(R)-L$^4$-R$^w$ or —C(O)N(R)—C(R)$_2$-L$^4$-R$^w$, wherein the R group attached to the nitrogen atom and $R^1$ are taken together with their intervening atoms to form an optionally substituted 5-6 membered heteroaryl ring having 2-4 heteroatoms independently selected from nitrogen, oxygen, or sulfur.

In some embodiments, $R^{2'}$ is —C(O)N(R)-L$^4$-R$^w$, wherein $R^1$ and the R group are optionally taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^{2'}$ is —C(O)N(R)-L$^4$-R$^w$, wherein $R^1$ and the R group are optionally taken together with their intervening atoms to form an optionally substituted 4-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^{2'}$ is —C(O)N(R)-L$^4$-R$^w$, wherein $R^1$ and the R group are optionally taken together with their intervening atoms to form an optionally substituted 5-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^{2'}$ is —C(O)N(R)-$L^4$-$R^w$, wherein $R^1$ and the R group are optionally taken together with their intervening atoms to form an optionally substituted 6-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur. In some embodiments, $R^{2'}$ is —C(O)N(R)-$L^4$-$R^w$, wherein $R^1$ and the R group are optionally taken together with their intervening atoms to form an optionally substituted 6-7 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur.

In some embodiments, $R^{2'}$ is —C(O)N(R)-$L^4$-$R^w$, wherein $R^1$ and the R group are optionally taken together with their intervening atoms to form an optionally substituted 4-8 membered saturated or partially unsaturated heterocyclic ring having 2-4 heteroatoms independently selected from nitrogen, oxygen, or sulfur. In some embodiments, $R^{2'}$ is —C(O)N(R)-$L^4$-$R^w$, wherein $R^1$ and the R group are optionally taken together with their intervening atoms to form an optionally substituted 5-8 membered saturated or partially unsaturated heterocyclic ring having 2-4 heteroatoms independently selected from nitrogen, oxygen, or sulfur. In some embodiments, $R^{2'}$ is —C(O)N(R)-$L^4$-$R^w$, wherein $R^1$ and the R group are optionally taken together with their intervening atoms to form an optionally substituted 6-8 membered saturated or partially unsaturated heterocyclic ring having 2-4 heteroatoms independently selected from nitrogen, oxygen, or sulfur. In some embodiments, $R^{2'}$ is —C(O)N(R)-$L^4$-$R^w$, wherein $R^1$ and the R group are optionally taken together with their intervening atoms to form an optionally substituted 6-7 membered saturated or partially unsaturated heterocyclic ring having 2-4 heteroatoms independently selected from nitrogen, oxygen, or sulfur. In some embodiments, $R^{2'}$ is —C(O)N(R)-$L^4$-$R^w$, wherein $R^1$ and the R group are optionally taken together with their intervening atoms to form an optionally substituted 4-membered saturated or partially unsaturated heterocyclic ring having 2-4 heteroatoms independently selected from nitrogen, oxygen, or sulfur. In some embodiments, $R^{2'}$ is —C(O)N(R)-$L^4$-$R^w$, wherein $R^1$ and the R group are optionally taken together with their intervening atoms to form an optionally substituted 5-membered saturated or partially unsaturated heterocyclic ring having 2-4 heteroatoms independently selected from nitrogen, oxygen, or sulfur. In some embodiments, $R^{2'}$ is —C(O)N(R)-$L^4$-$R^w$, wherein $R^1$ and the R group are optionally taken together with their intervening atoms to form an optionally substituted 6-membered saturated or partially unsaturated heterocyclic ring having 2-4 heteroatoms independently selected from nitrogen, oxygen, or sulfur. In some embodiments, $R^{2'}$ is —C(O)N(R)-$L^4$-$R^w$, wherein $R^1$ and the R group are optionally taken together with their intervening atoms to form an optionally substituted 7-membered saturated or partially unsaturated heterocyclic ring having 2-4 heteroatoms independently selected from nitrogen, oxygen, or sulfur. In some embodiments, $R^{2'}$ is —C(O)N(R)-$L^4$-$R^w$, wherein $R^1$ and the R group are optionally taken together with their intervening atoms to form an optionally substituted 8-membered saturated or partially unsaturated heterocyclic ring having 2-4 heteroatoms independently selected from nitrogen, oxygen, or sulfur.

In some embodiments, $R^{2'}$ is —C(O)N(R)-$L^4$-$R^w$, wherein $R^1$ and the R group are optionally taken together with their intervening atoms to form an optionally substituted 5-6 membered heteroaryl ring having 2-4 heteroatoms independently selected from nitrogen, oxygen, or sulfur.

In some embodiments, $R^{2'}$ is —C(O)N(R)—C(R)$_2$-$L^4$-$R^w$, wherein $R^1$ and one of the R groups are optionally taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^{2'}$ is —C(O)N(R)—C(R)$_2$-$L^4$-$R^w$, wherein the R group attached to the nitrogen atom and $R^1$ are optionally taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^{2'}$ is —C(O)N(R)—C(R)$_2$-$L^4$-$R^w$, wherein the R group attached to the nitrogen atom and $R^1$ are taken together with their intervening atoms to form an optionally substituted 3-8 membered saturated or partially unsaturated heterocyclic ring having 1-4 heteroatoms independently selected from nitrogen, oxygen, or sulfur, or an optionally substituted 5-6 membered heteroaryl ring having 1-4 heteroatoms independently selected from nitrogen, oxygen, or sulfur. In some embodiments, $R^{2'}$ is —C(O)N(R)—C(R)$_2$-$L^4$-$R^w$, wherein the R group attached to the nitrogen atom and $R^1$ are taken together with their intervening atoms to form an optionally substituted 4-8 membered saturated or partially unsaturated heterocyclic ring having 2-4 heteroatoms independently selected from nitrogen, oxygen, or sulfur, or an optionally substituted 5-6 membered heteroaryl ring having 2-4 heteroatoms independently selected from nitrogen, oxygen, or sulfur.

In some embodiments, $R^{2'}$ is —C(O)N(R)—C(R)$_2$-$L^4$-$R^w$, wherein the R group attached to the nitrogen atom and $R^1$ are taken together with their intervening atoms to form an optionally substituted 4-8 membered saturated or partially unsaturated heterocyclic ring having 2-4 heteroatoms independently selected from nitrogen, oxygen, or sulfur. In some embodiments, $R^{2'}$ is —C(O)N(R)—C(R)$_2$-$L^4$-$R^w$, wherein the R group attached to the nitrogen atom and $R^1$ are taken together with their intervening atoms to form an optionally substituted 5-8 membered saturated or partially unsaturated heterocyclic ring having 2-4 heteroatoms independently selected from nitrogen, oxygen, or sulfur. In some embodiments, $R^{2'}$ is —C(O)N(R)—C(R)$_2$-$L^4$-$R^w$, wherein the R group attached to the nitrogen atom and $R^1$ are taken together with their intervening atoms to form an optionally substituted 6-8 membered saturated or partially unsaturated heterocyclic ring having 2-4 heteroatoms independently selected from nitrogen, oxygen, or sulfur. In some embodiments, $R^{2'}$ is —C(O)N(R)—C(R)$_2$-$L^4$-$R^w$, wherein the R group attached to the nitrogen atom and $R^1$ are taken together with their intervening atoms to form an optionally substituted 7-8 membered saturated or partially unsaturated heterocyclic ring having 2-4 heteroatoms independently selected from nitrogen, oxygen, or sulfur. In some embodiments, $R^{2'}$ is —C(O)N(R)—C(R)$_2$-$L^4$-$R^w$, wherein the R group attached to the nitrogen atom and $R^1$ are taken together with their intervening atoms to form an optionally substituted 6-7 membered saturated or partially unsaturated heterocyclic ring having 2-4 heteroatoms independently selected from nitrogen, oxygen, or sulfur. In some embodiments, $R^{2'}$ is —C(O)N(R)—C(R)$_2$-L$^4$-R$^w$, wherein the R group attached to the nitrogen atom and $R^1$ are taken together with their intervening atoms to form an optionally substituted 4-membered saturated or partially unsaturated heterocyclic ring having 2-4 heteroatoms independently selected from nitrogen, oxygen, or sulfur. In some embodiments, $R^{2'}$ is —C(O)N(R)—C(R)$_2$-L$^4$-R$^w$, wherein the R group attached to the nitrogen atom and $R^1$ are taken together with their intervening atoms to form an optionally substituted 5-membered saturated or partially unsaturated heterocyclic ring having 2-4 heteroatoms independently selected from nitrogen, oxygen, or sulfur. In some embodiments, $R^{2'}$ is —C(O)N(R)—C(R)$_2$-L$^4$-R$^w$, wherein the R group attached to the nitrogen atom and $R^1$ are taken together with their intervening atoms to form an optionally substituted 6-membered saturated or partially unsaturated heterocyclic ring having 2-4 heteroatoms independently selected from nitrogen, oxygen, or sulfur. In some embodiments, $R^{2'}$ is —C(O)N(R)—C(R)$_2$-L$^4$-R$^w$, wherein the R group attached to the nitrogen atom and $R^1$ are taken together with their intervening atoms to form an optionally substituted 7-membered saturated or partially unsaturated heterocyclic ring having 2-4 heteroatoms independently selected from nitrogen, oxygen, or sulfur. In some embodiments, $R^{2'}$ is —C(O)N(R)—C(R)$_2$-L$^4$-R$^w$, wherein the R group attached to the nitrogen atom and $R^1$ are taken together with their intervening atoms to form an optionally substituted 8-membered saturated or partially unsaturated heterocyclic ring having 2-4 heteroatoms independently selected from nitrogen, oxygen, or sulfur.

In some embodiments, $R^{2'}$ is —C(O)N(R)—C(R)$_2$-L$^4$-R$^w$, wherein the R group attached to the nitrogen atom and $R^1$ are taken together with their intervening atoms to form an optionally substituted 5-6 membered heteroaryl ring having 2-4 heteroatoms independently selected from nitrogen, oxygen, or sulfur.

As defined generally above, each $R^8$ of formula III or VI is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^8$ is selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'. In some embodiments, $R^8$ is R. In some embodiments, $R^8$ is hydrogen. In some embodiments, $R^8$ is $C_{1-12}$ aliphatic. In some embodiments, $R^8$ is $C_{1-6}$ aliphatic. In some embodiments, $R^8$ is $C_{1-3}$ aliphatic. In some embodiments, $R^8$ is methyl.

As defined generally above, each $R^9$ of formula III is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^9$ is selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'. In some embodiments, $R^9$ is R. In some embodiments, $R^9$ is hydrogen. In some embodiments, $R^9$ is $C_{1-12}$ aliphatic. In some embodiments, $R^9$ is $C_{1-6}$ aliphatic. In some embodiments, $R^9$ is $C_{1-3}$ aliphatic. In some embodiments, $R^9$ is methyl.

As defined generally above, each $R^{10}$ of formula IV is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^{10}$ is selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'. In some embodiments, $R^{10}$ is R. In some embodiments, $R^{10}$ is hydrogen. In some embodiments, $R^{10}$ is $C_{1-12}$ aliphatic. In some embodiments, $R^{10}$ is $C_{1-6}$ aliphatic. In some embodiments, $R^{10}$ is $C_{1-3}$ aliphatic. In some embodiments, $R^{10}$ is methyl.

As defined generally above, each $R^{11}$ of formula IV is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^{11}$ is selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'. In some embodiments, $R^{11}$ is R. In some embodiments, $R^{11}$ is hydrogen. In some embodiments, $R^{11}$ is $C_{1-12}$ aliphatic. In some embodiments, $R^{11}$ is $C_{1-6}$ aliphatic. In some embodiments, $R^{11}$ is $C_{1-3}$ aliphatic. In some embodiments, $R^{11}$ is methyl.

As defined generally above, each $R^{12}$ of formula IV is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^{12}$ is selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'. In some embodiments, $R^{12}$ is R. In some embodiments, $R^{12}$ is hydrogen. In some embodiments, $R^{12}$ is $C_{1-12}$ aliphatic. In some embodiments, $R^{12}$ is $C_{1-6}$ aliphatic. In some embodiments, $R^{12}$ is $C_{1-3}$ aliphatic. In some embodiments, $R^{12}$ is methyl.

As defined generally above, each $R^{13}$ of formula VI or VII is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^{13}$ is selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'. In some embodiments, $R^{13}$ is R. In some embodiments, $R^{13}$ is hydrogen. In some embodiments, $R^{13}$ is $C_{1-12}$ aliphatic. In some embodiments, $R^{13}$ is $C_{1-6}$ aliphatic. In some embodiments, $R^{13}$ is $C_{1-3}$ aliphatic. In some embodiments, $R^{13}$ is methyl. In some embodiments, $R^{13}$ is

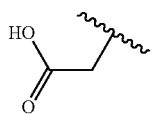
In some embodiments, $R^{13}$ is
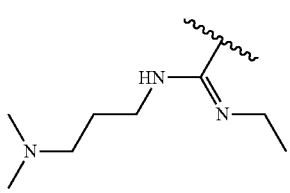
In some embodiments, $R^{13}$ is
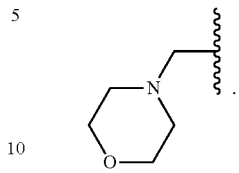
Exemplary compounds are set forth in Table 1, below:
TABLE 1
Exemplary compounds.
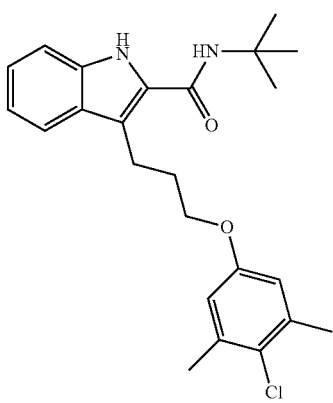 [SMILES: Cc1cc(OCCCc2c(C(=O)NC(C)(C)C)[nH]c3ccccc23)cc(C)c1Cl]
I-1
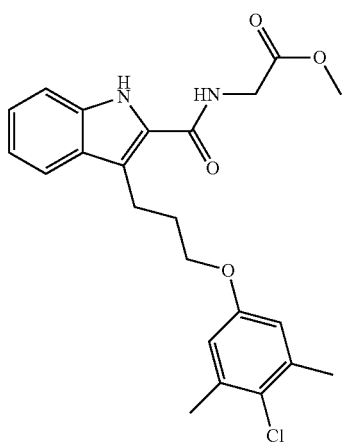 [SMILES: COC(=O)CNC(=O)c1[nH]c2ccccc2c1CCCOc1cc(C)c(Cl)c(C)c1]
I-2

TABLE 1-continued
Exemplary compounds.
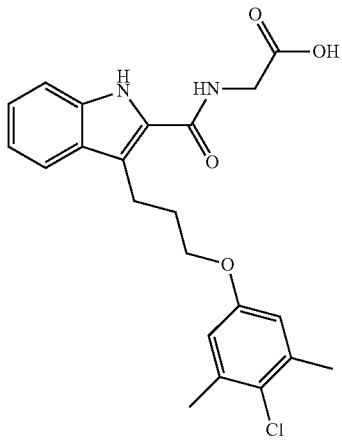 [SMILES: Cc1cc(OCCCc2c(C(=O)NCC(=O)O)[nH]c3ccccc23)cc(C)c1Cl]
I-3
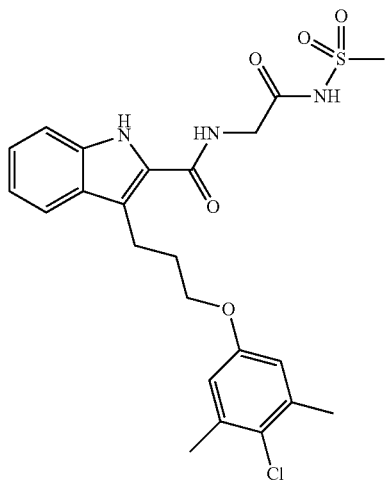 [SMILES: Cc1cc(OCCCc2c(C(=O)NCC(=O)NS(C)(=O)=O)[nH]c3ccccc23)cc(C)c1Cl]
I-4
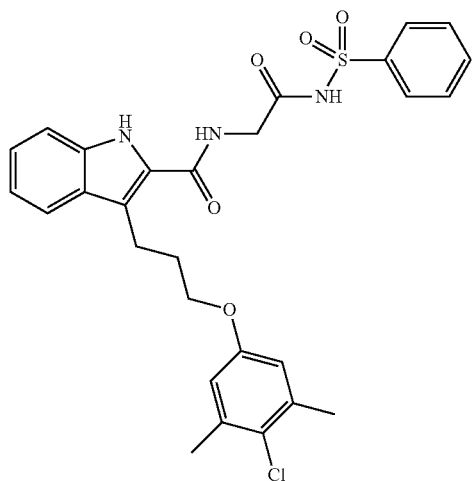 [SMILES: Cc1cc(OCCCc2c(C(=O)NCC(=O)NS(=O)(=O)c3ccccc3)[nH]c3ccccc23)cc(C)c1Cl]
I-5

TABLE 1-continued
Exemplary compounds.
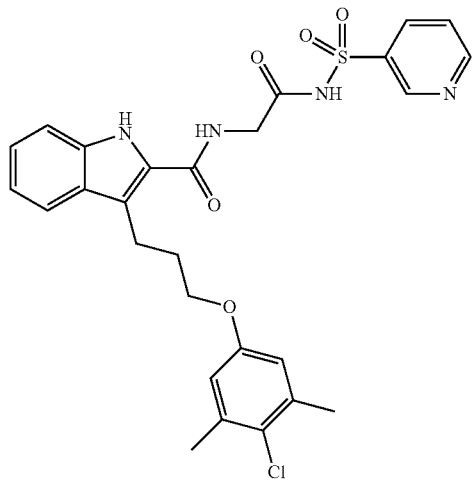 [SMILES: Cc1cc(OCCCc2c(C(=O)NCC(=O)NS(=O)(=O)c3cccnc3)[nH]c3ccccc23)cc(C)c1Cl]
I-6
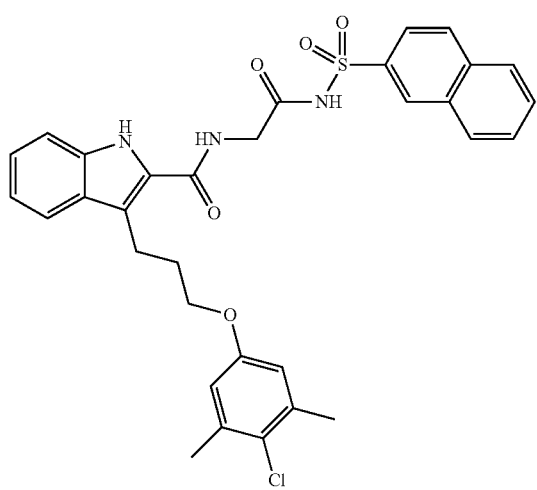 [SMILES: Cc1cc(OCCCc2c(C(=O)NCC(=O)NS(=O)(=O)c3ccc4ccccc4c3)[nH]c3ccccc23)cc(C)c1Cl]
I-7
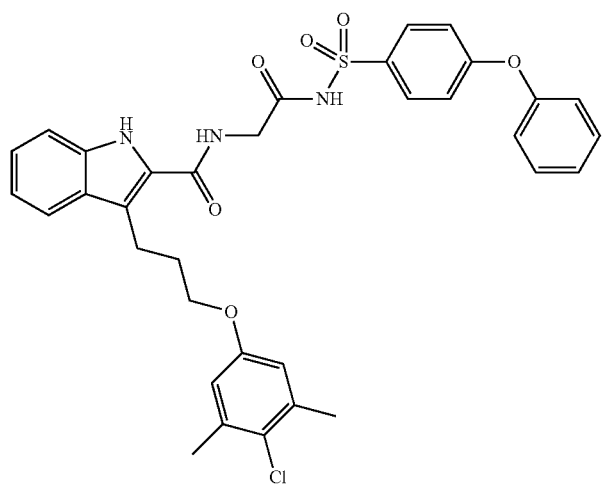 [SMILES: Cc1cc(OCCCc2c(C(=O)NCC(=O)NS(=O)(=O)c3ccc(Oc4ccccc4)cc3)[nH]c3ccccc23)cc(C)c1Cl]
I-8

TABLE 1-continued
Exemplary compounds.
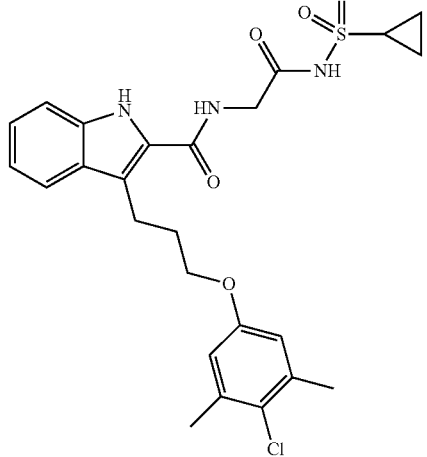
I-9
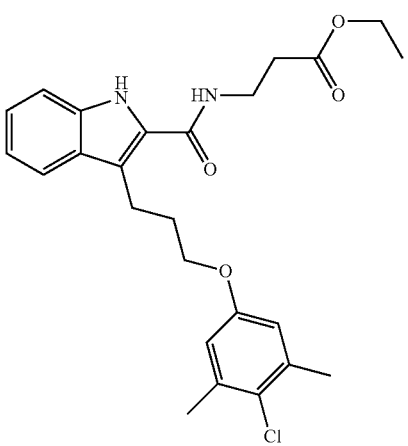 [SMILES: CCOC(=O)CCNC(=O)c1[nH]c2ccccc2c1CCCOc1cc(C)c(Cl)c(C)c1]
I-10
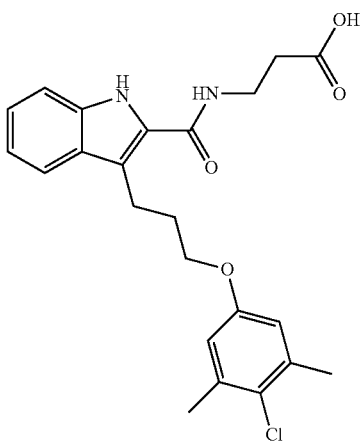 [SMILES: Cc1cc(OCCCc2c(C(=O)NCCC(=O)O)[nH]c3ccccc23)cc(C)c1Cl]
I-11

TABLE 1-continued
Exemplary compounds.
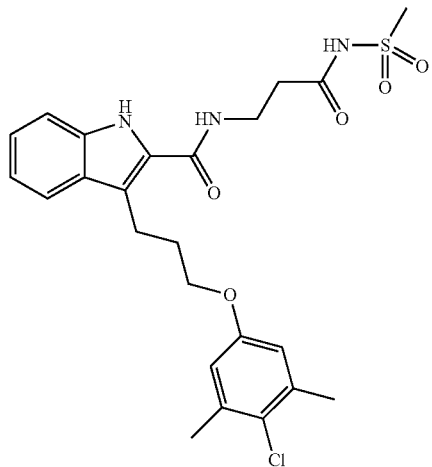 [SMILES: Cc1cc(OCCCc2c(C(=O)NCCC(=O)NS(C)(=O)=O)[nH]c3ccccc23)cc(C)c1Cl]
I-12
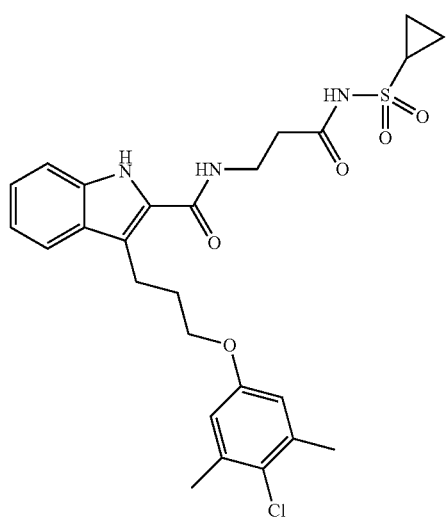 [SMILES: Cc1cc(OCCCc2c(C(=O)NCCC(=O)NS(=O)(=O)C3CC3)[nH]c3ccccc23)cc(C)c1Cl]
I-13
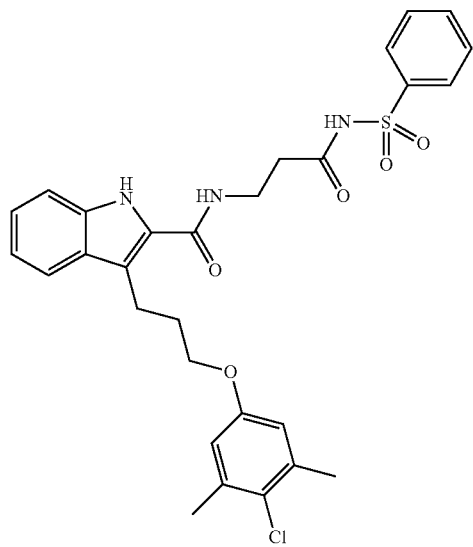 [SMILES: Cc1cc(OCCCc2c(C(=O)NCCC(=O)NS(=O)(=O)c3ccccc3)[nH]c3ccccc23)cc(C)c1Cl]
I-14

TABLE 1-continued
Exemplary compounds.
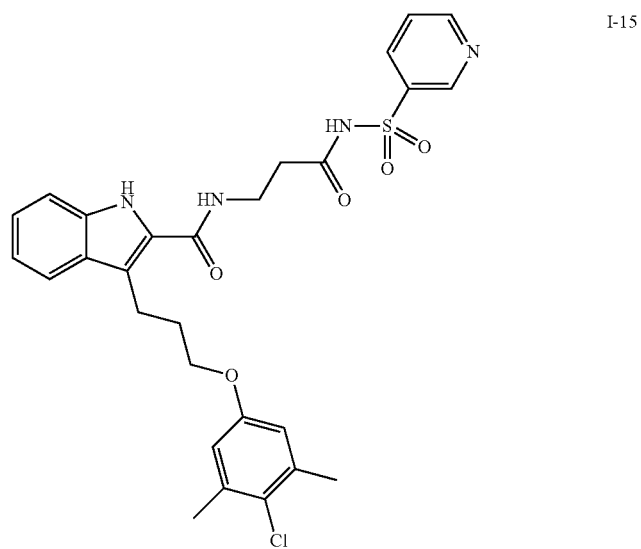
I-15
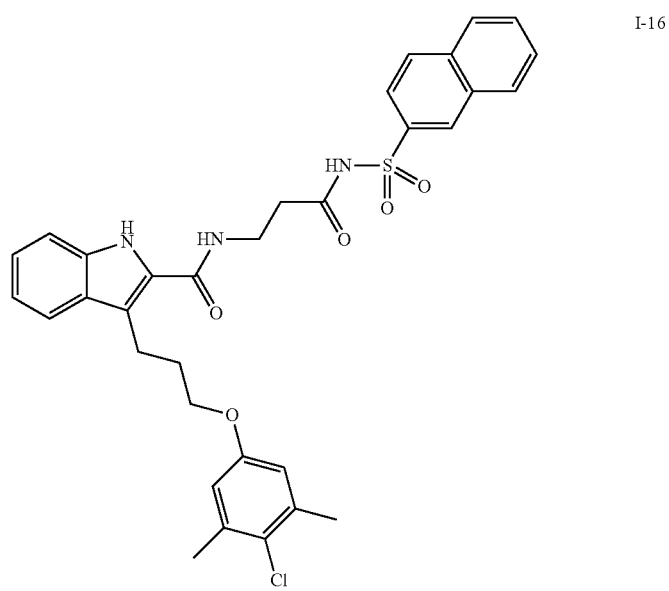
I-16

TABLE 1-continued
Exemplary compounds.
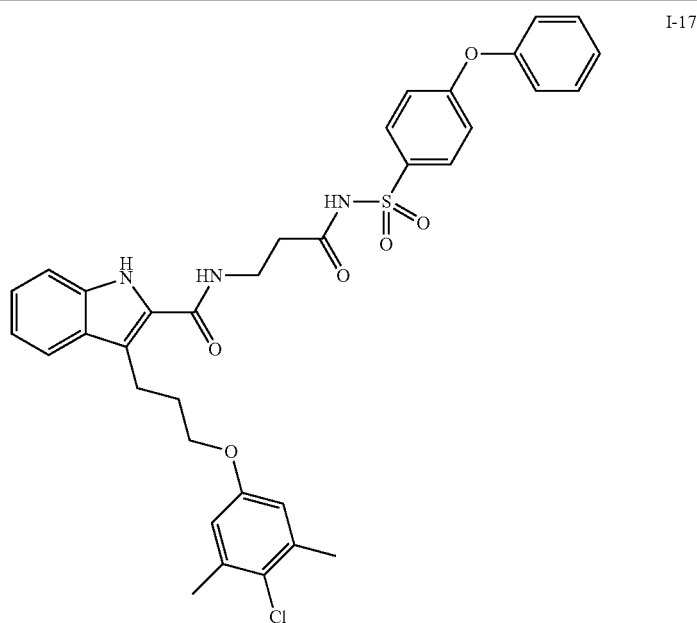
I-17
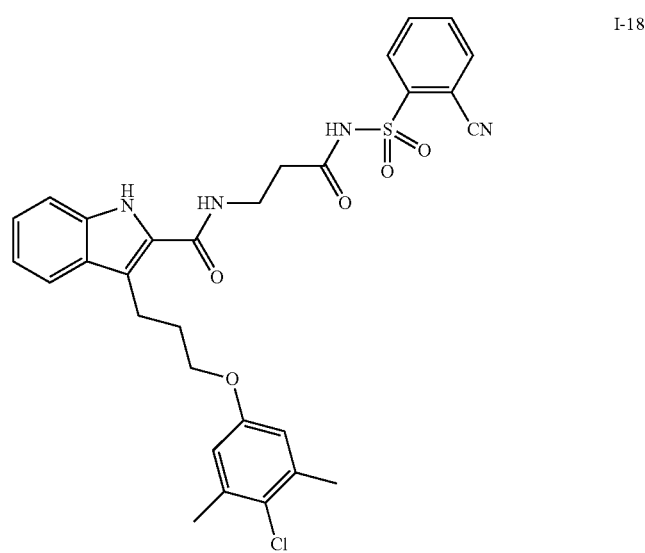
I-18

TABLE 1-continued
Exemplary compounds.
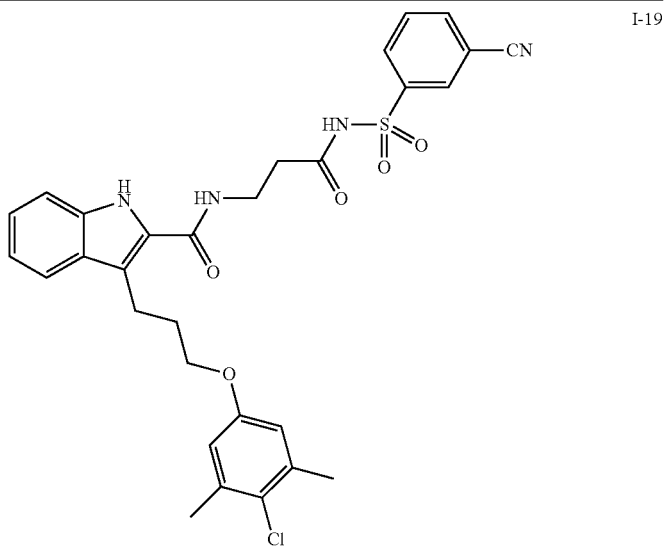
I-19
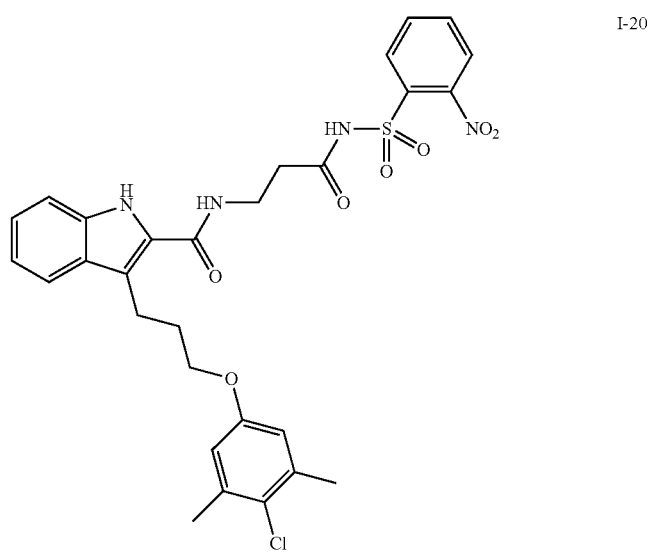
I-20
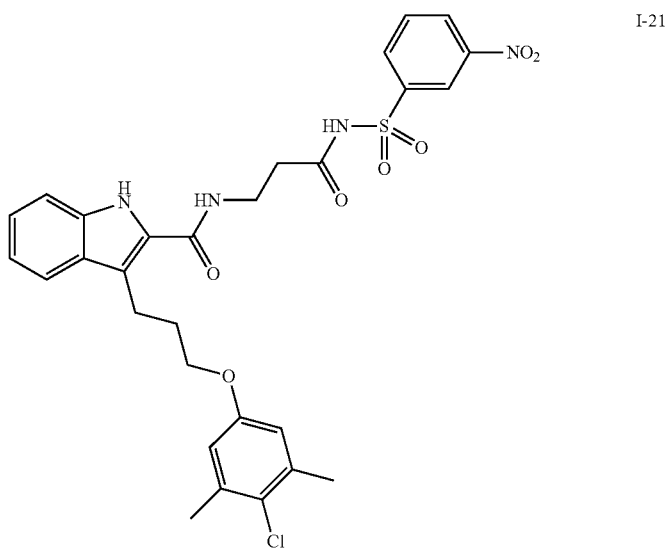
I-21

TABLE 1-continued
Exemplary compounds.
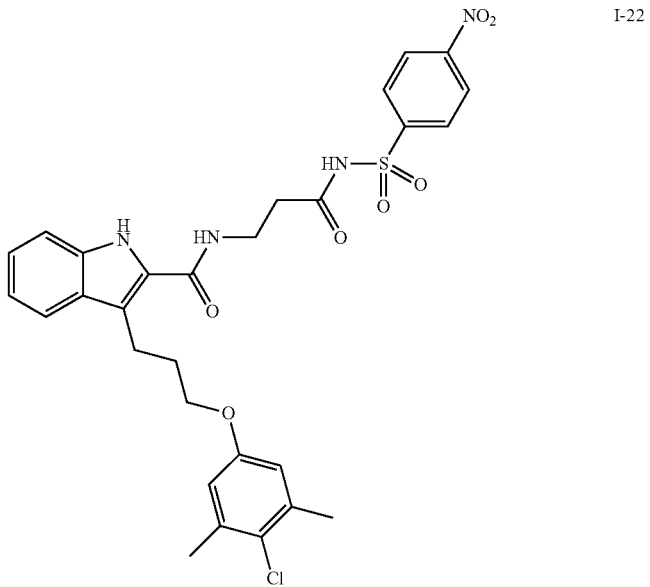
I-22
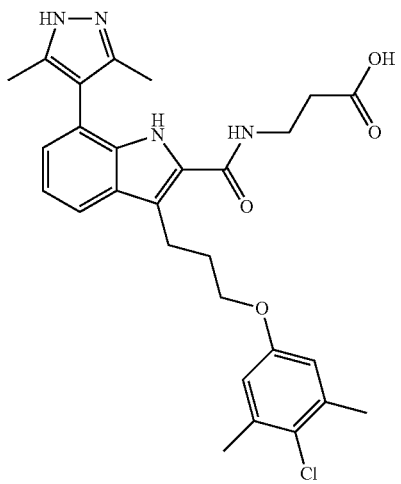 [SMILES: Cc1cc(OCCCc2c(C(=O)NCCC(=O)O)[nH]c3c(-c4c(C)n[nH]c4C)cccc23)cc(C)c1Cl]
I-23

TABLE 1-continued
Exemplary compounds.
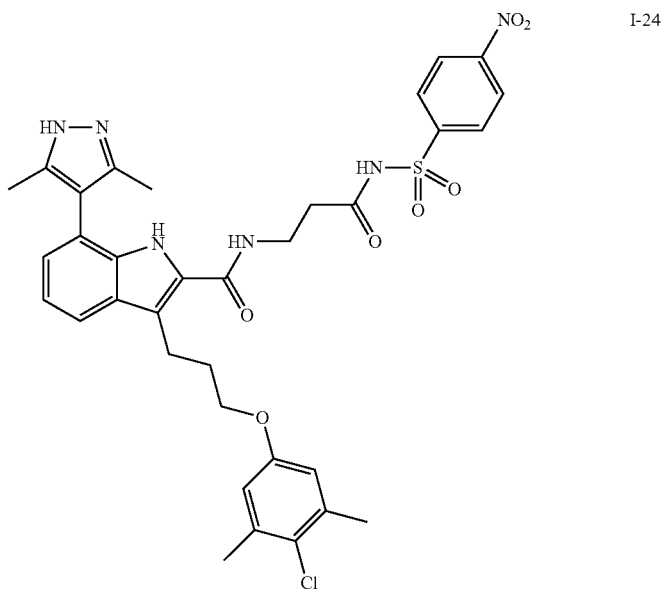
I-24
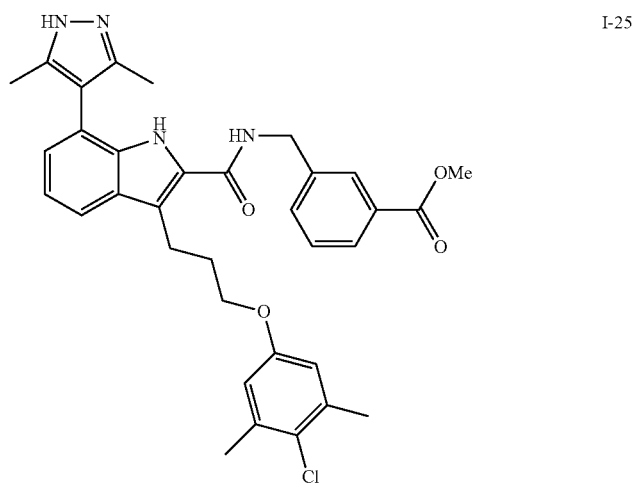
I-25
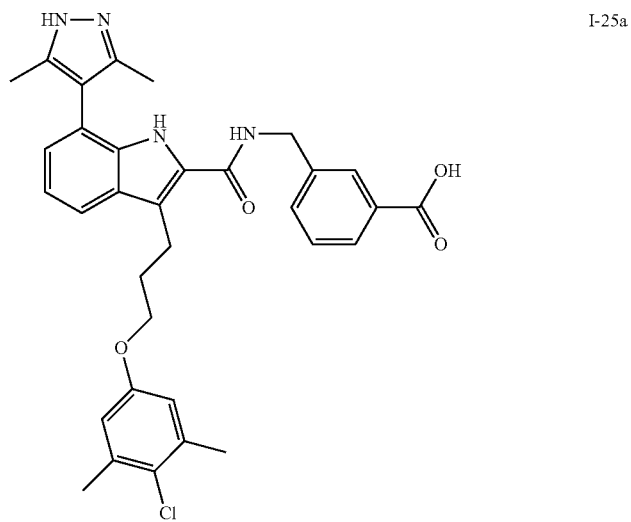
I-25a TABLE 1-continued
Exemplary compounds.
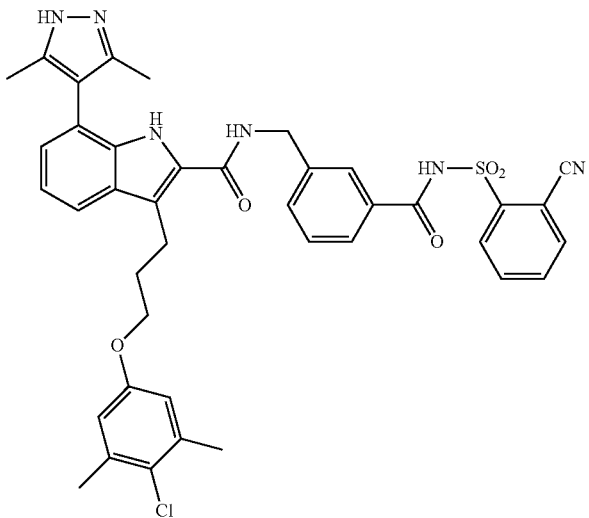 [SMILES: Cc1cc(OCCCc2c(C(=O)NCc3cccc(C(=O)NS(=O)(=O)c4ccccc4C#N)c3)[nH]c3c(-c4c(C)n[nH]c4C)cccc23)cc(C)c1Cl]
I-26
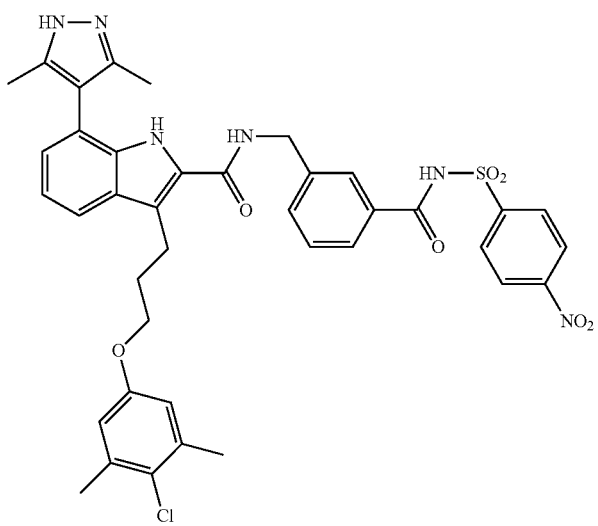 [SMILES: Cc1cc(OCCCc2c(C(=O)NCc3cccc(C(=O)NS(=O)(=O)c4ccc([N+](=O)[O-])cc4)c3)[nH]c3c(-c4c(C)n[nH]c4C)cccc23)cc(C)c1Cl]
I-27
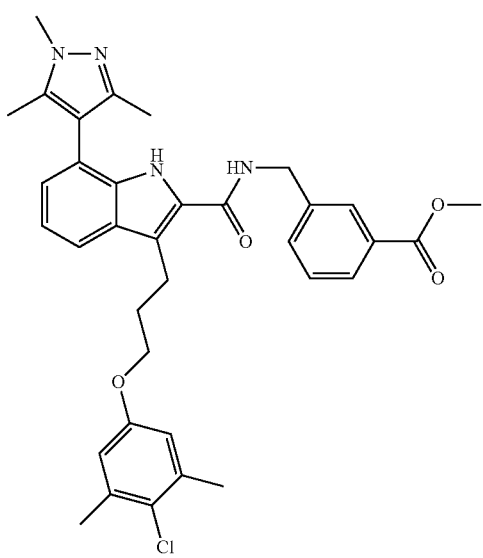
I-28

TABLE 1-continued
Exemplary compounds.
I-29
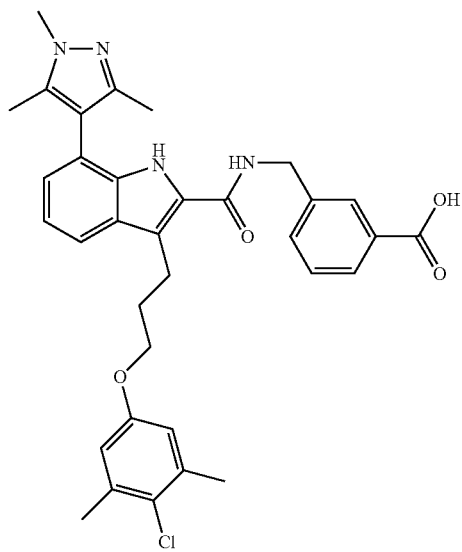 [SMILES: Cc1cc(OCCCc2c(C(=O)NCc3cccc(C(=O)O)c3)[nH]c3c(-c4c(C)nn(C)c4C)cccc23)cc(C)c1Cl]
I-30
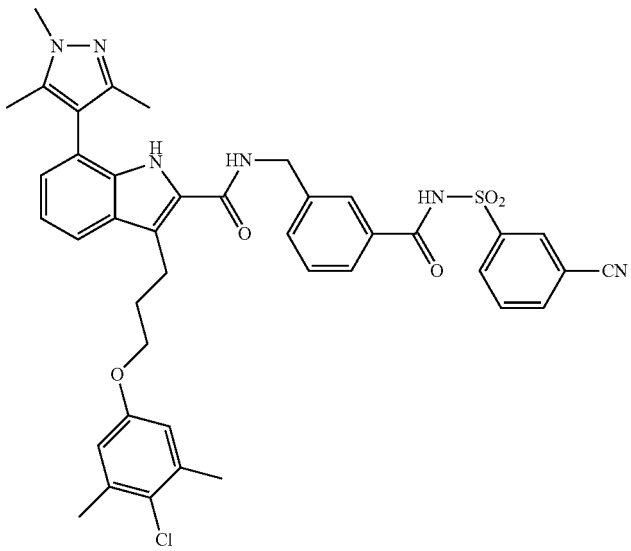 [SMILES: Cc1cc(OCCCc2c(C(=O)NCc3cccc(C(=O)NS(=O)(=O)c4cccc(C#N)c4)c3)[nH]c3c(-c4c(C)nn(C)c4C)cccc23)cc(C)c1Cl]

TABLE 1-continued
Exemplary compounds.
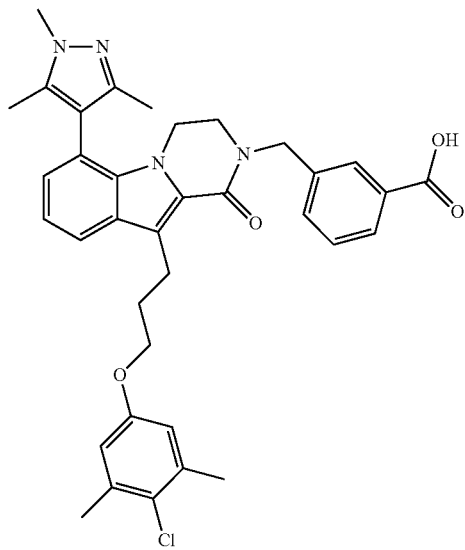 [SMILES: Cc1cc(OCCCc2c3n(c4c(-c5c(C)nn(C)c5C)cccc24)CCN(Cc2cccc(C(=O)O)c2)C3=O)cc(C)c1Cl]
I-31
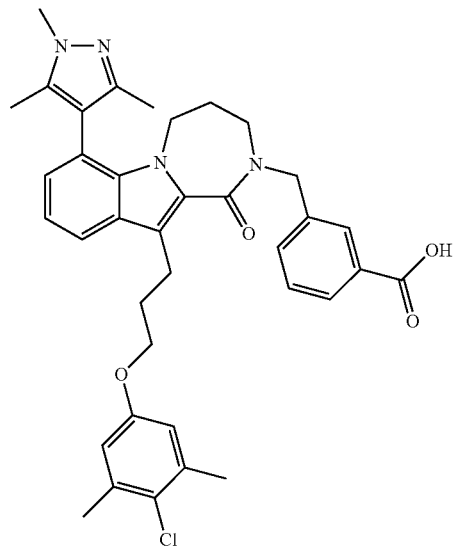 [SMILES: Cc1cc(OCCCc2c3n(c4c(-c5c(C)nn(C)c5C)cccc24)CCCN(Cc2cccc(C(=O)O)c2)C3=O)cc(C)c1Cl]
I-32

TABLE 1-continued
Exemplary compounds.
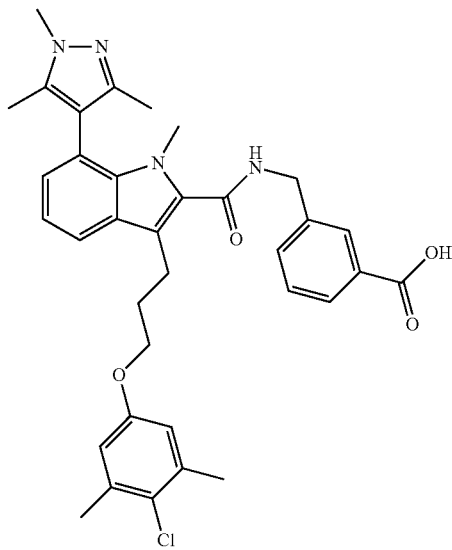 [SMILES: Cc1cc(OCCCc2c(C(=O)NCc3cccc(C(=O)O)c3)n(C)c3c(-c4c(C)nn(C)c4C)cccc23)cc(C)c1Cl]
I-33
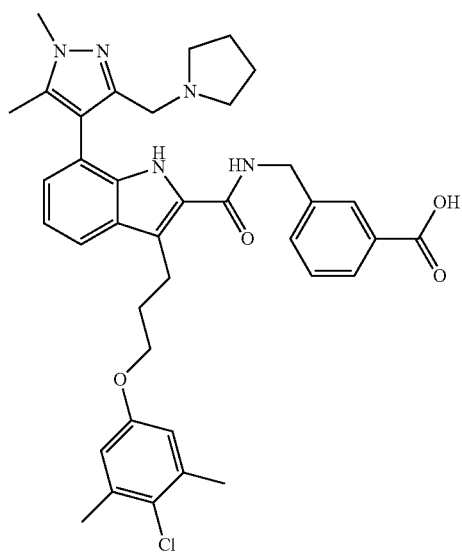 [SMILES: Cc1cc(OCCCc2c(C(=O)NCc3cccc(C(=O)O)c3)[nH]c3c(-c4c(CN5CCCC5)nn(C)c4C)cccc23)cc(C)c1Cl]
I-34

TABLE 1-continued
Exemplary compounds.
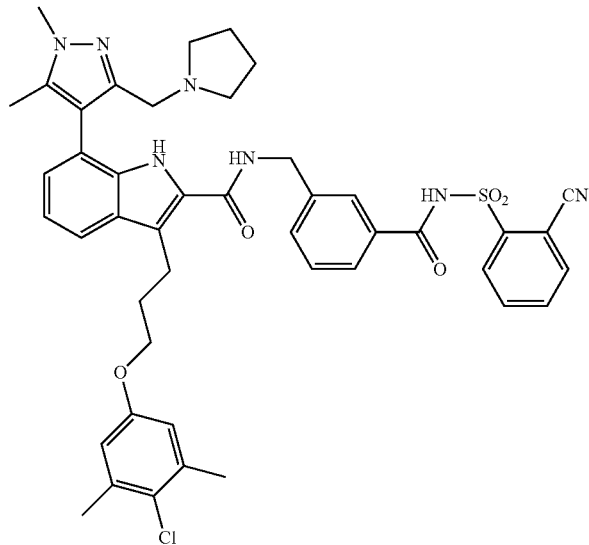 [SMILES: Cc1cc(OCCCc2c(C(=O)NCc3cccc(C(=O)NS(=O)(=O)c4ccccc4C#N)c3)[nH]c3c(-c4c(CN5CCCC5)nn(C)c4C)cccc23)cc(C)c1Cl]
I-35
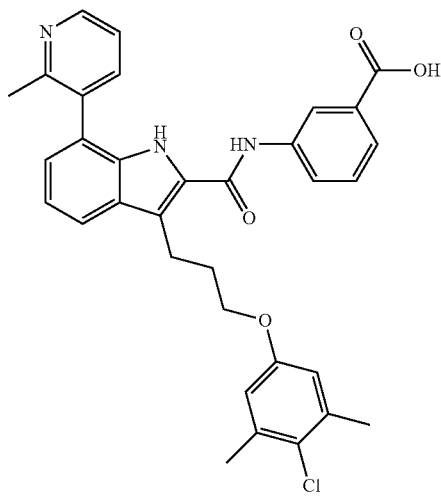 [SMILES: Cc1cc(OCCCc2c(C(=O)Nc3cccc(C(=O)O)c3)[nH]c3c(-c4cccnc4C)cccc23)cc(C)c1Cl]
I-36
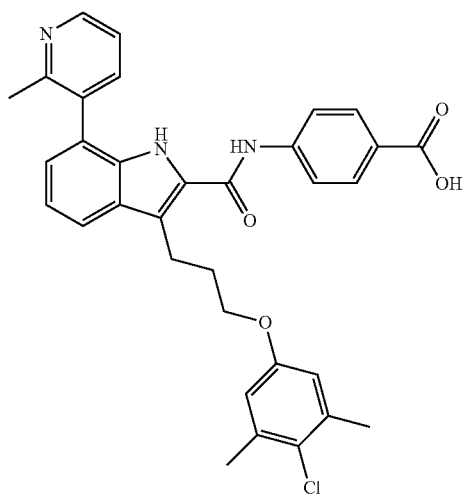 [SMILES: Cc1cc(OCCCc2c(C(=O)Nc3ccc(C(=O)O)cc3)[nH]c3c(-c4cccnc4C)cccc23)cc(C)c1Cl]
I-37

TABLE 1-continued
Exemplary compounds.
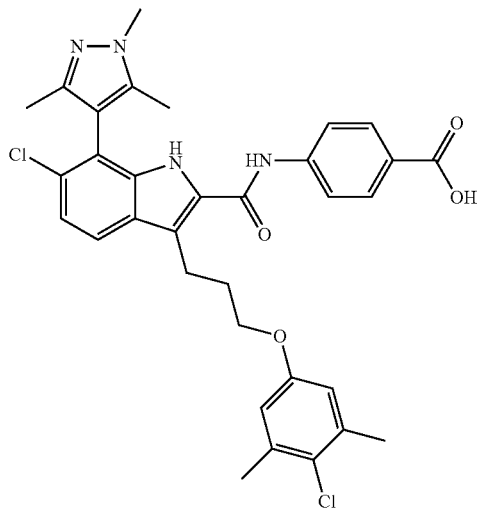 [SMILES: Cc1cc(OCCCc2c(C(=O)Nc3ccc(C(=O)O)cc3)[nH]c3c(-c4c(C)nn(C)c4C)c(Cl)ccc23)cc(C)c1Cl]
I-38
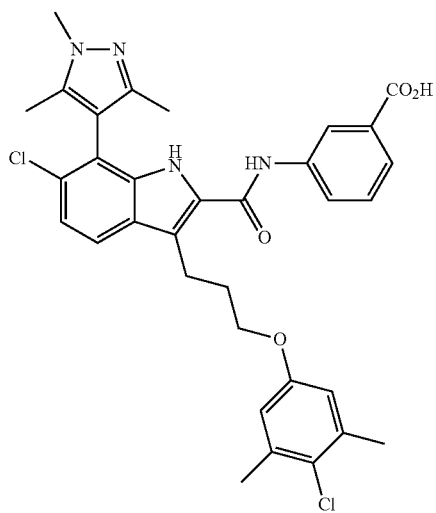 [SMILES: Cc1cc(OCCCc2c(C(=O)Nc3cccc(C(=O)O)c3)[nH]c3c(-c4c(C)nn(C)c4C)c(Cl)ccc23)cc(C)c1Cl]
I-39
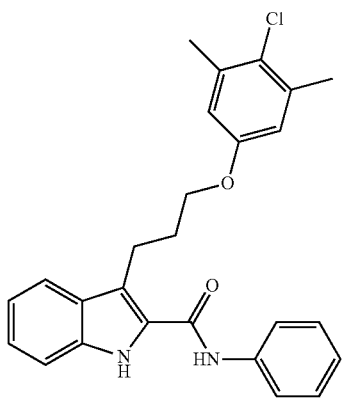 [SMILES: Cc1cc(OCCCc2c(C(=O)Nc3ccccc3)[nH]c3ccccc23)cc(C)c1Cl]
I-40

TABLE 1-continued
Exemplary compounds.
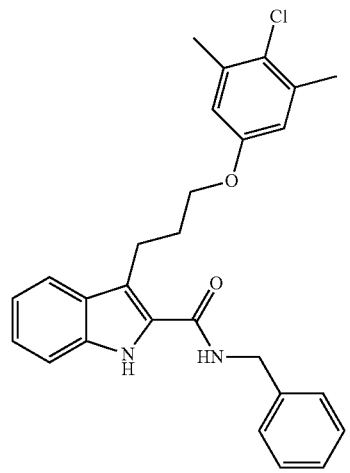 [SMILES: Cc1cc(OCCCc2c(C(=O)NCc3ccccc3)[nH]c3ccccc23)cc(C)c1Cl]
I-41
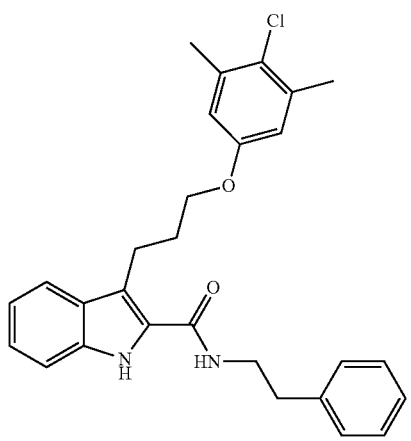 [SMILES: Cc1cc(OCCCc2c(C(=O)NCCc3ccccc3)[nH]c3ccccc23)cc(C)c1Cl]
I-42
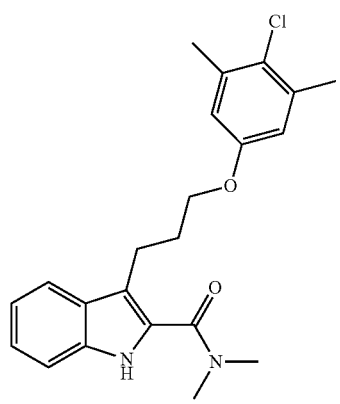 [SMILES: Cc1cc(OCCCc2c(C(=O)N(C)C)[nH]c3ccccc23)cc(C)c1Cl]
I-43

TABLE 1-continued
Exemplary compounds.
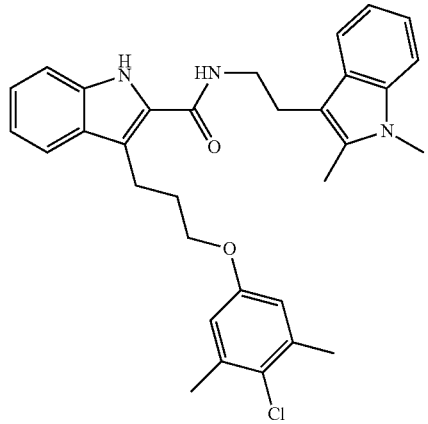 [SMILES: Cc1cc(OCCCc2c(C(=O)NCCc3c(C)n(C)c4ccccc34)[nH]c3ccccc23)cc(C)c1Cl]
I-44
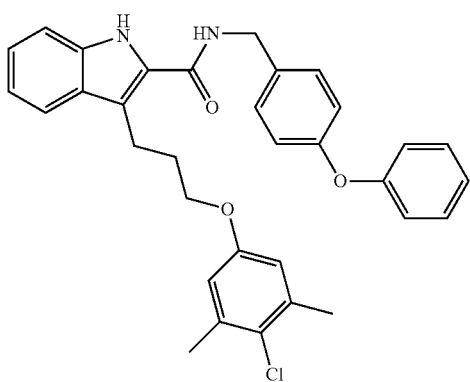 [SMILES: Cc1cc(OCCCc2c(C(=O)NCc3ccc(Oc4ccccc4)cc3)[nH]c3ccccc23)cc(C)c1Cl]
I-45
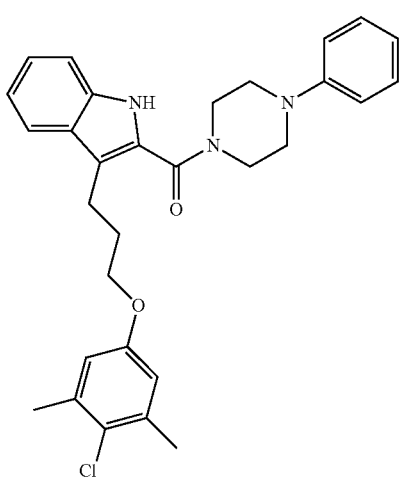 [SMILES: Cc1cc(OCCCc2c(C(=O)N3CCN(c4ccccc4)CC3)[nH]c3ccccc23)cc(C)c1Cl]
I-46

TABLE 1-continued
Exemplary compounds.
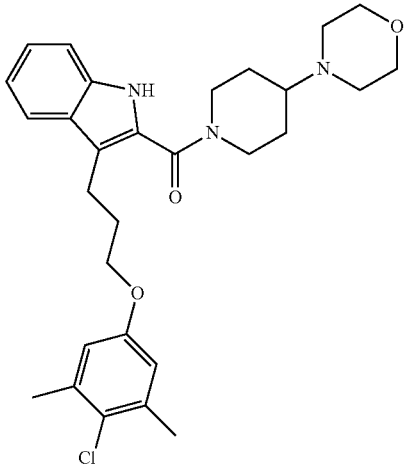 [SMILES: Cc1cc(OCCCc2c(C(=O)N3CCC(N4CCOCC4)CC3)[nH]c3ccccc23)cc(C)c1Cl]
I-47
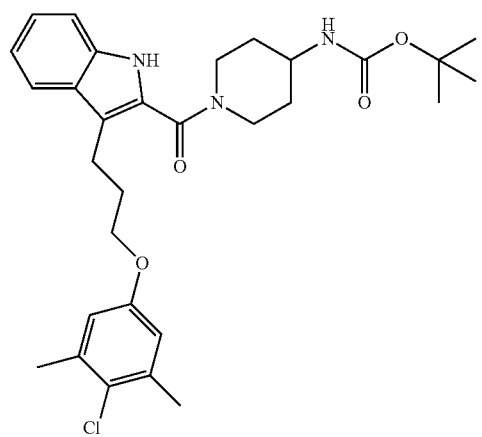 [SMILES: Cc1cc(OCCCc2c(C(=O)N3CCC(NC(=O)OC(C)(C)C)CC3)[nH]c3ccccc23)cc(C)c1Cl]
I-48
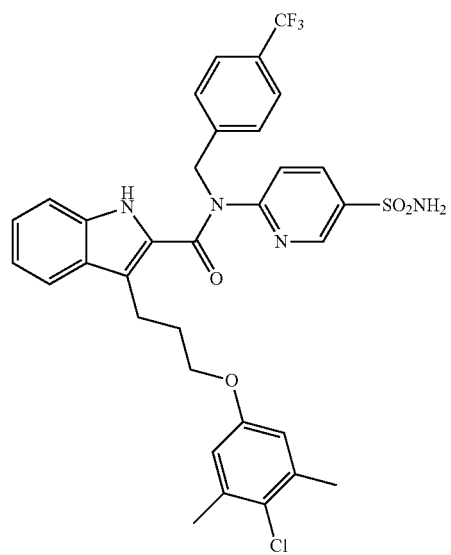 [SMILES: Cc1cc(OCCCc2c(C(=O)N(Cc3ccc(C(F)(F)F)cc3)c3ccc(S(N)(=O)=O)cn3)[nH]c3ccccc23)cc(C)c1Cl]
I-49

147 148
TABLE 1-continued
Exemplary compounds.
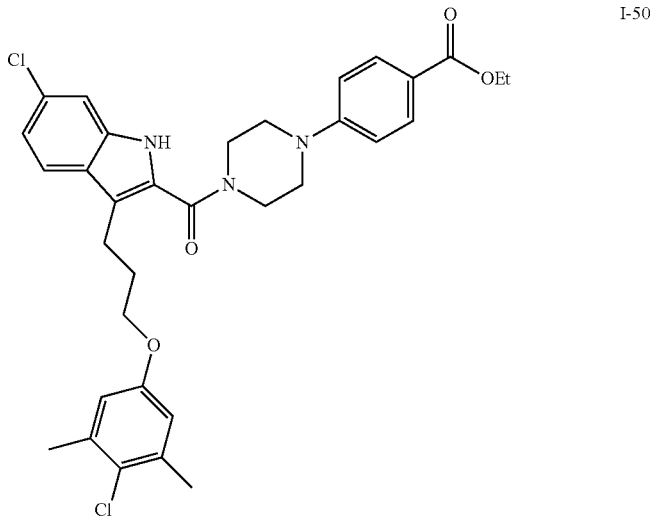
I-50
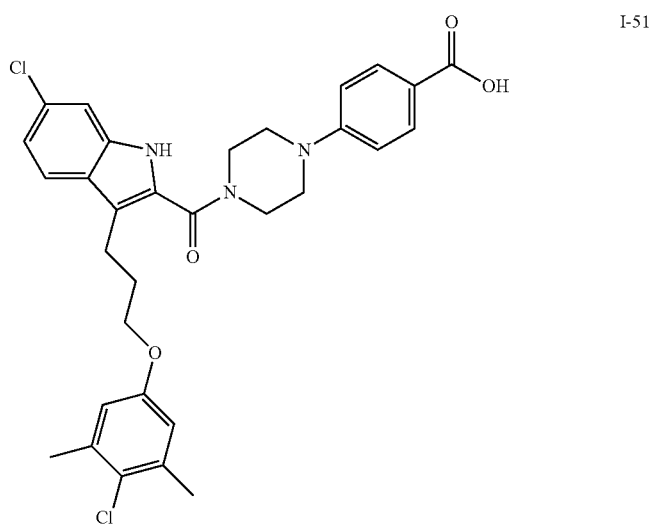
I-51
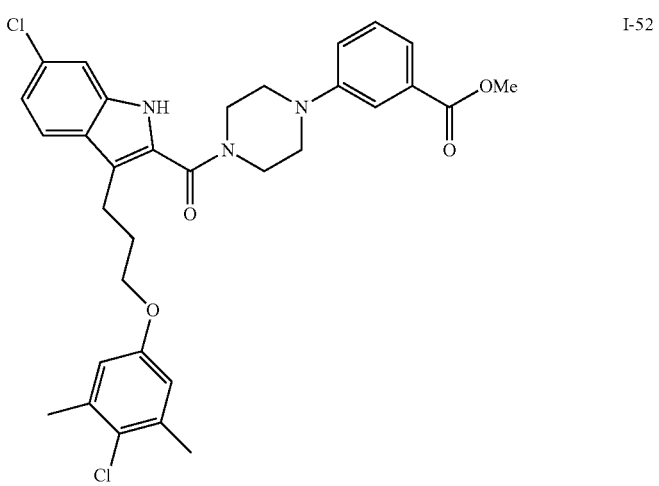
I-52

TABLE 1-continued
Exemplary compounds.
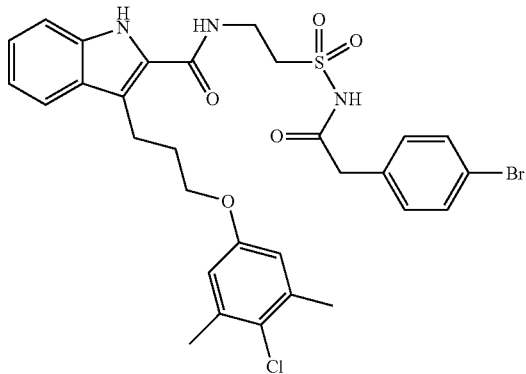 [SMILES: Cc1cc(OCCCc2c(C(=O)NCCS(=O)(=O)NC(=O)Cc3ccc(Br)cc3)[nH]c3ccccc23)cc(C)c1Cl]
I-53
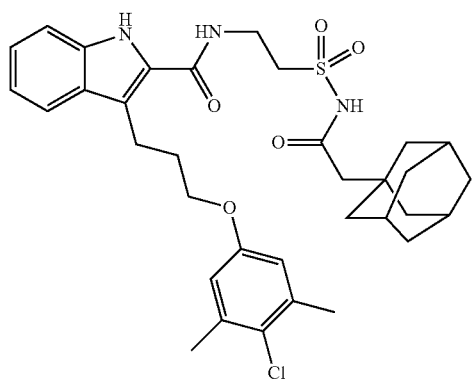 [SMILES: Cc1cc(OCCCc2c(C(=O)NCCS(=O)(=O)NC(=O)CC34CC5CC(CC(C5)C3)C4)[nH]c3ccccc23)cc(C)c1Cl]
I-54
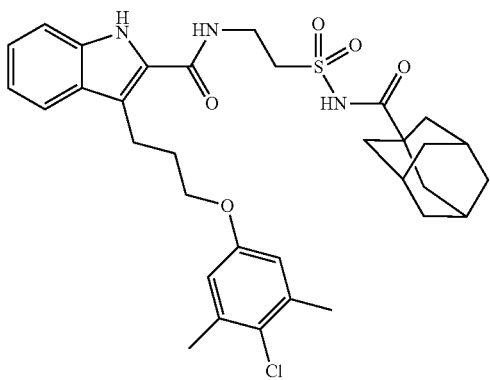 [SMILES: Cc1cc(OCCCc2c(C(=O)NCCS(=O)(=O)NC(=O)C34CC5CC(CC(C5)C3)C4)[nH]c3ccccc23)cc(C)c1Cl]
I-55
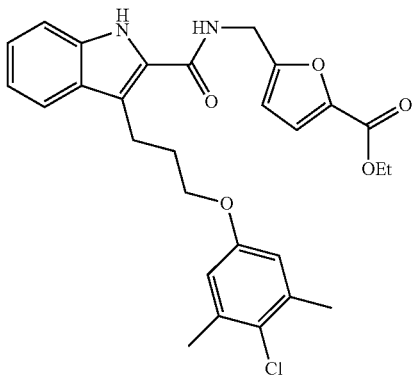 [SMILES: Cc1cc(OCCCc2c(C(=O)NCc3ccc(C(=O)O)o3)[nH]c3ccccc23)cc(C)c1Cl]
I-56

TABLE 1-continued
Exemplary compounds.
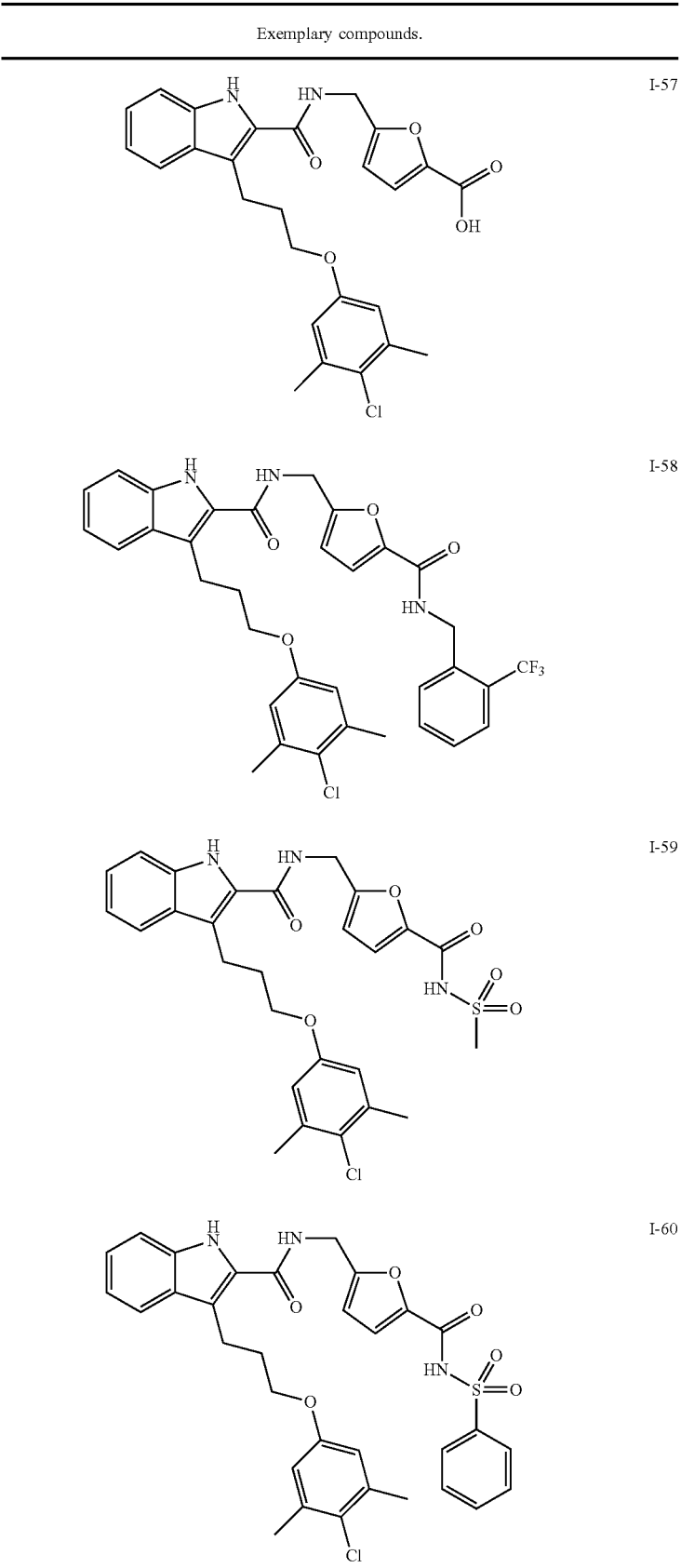
I-57
I-58
I-59
I-60

TABLE 1-continued
Exemplary compounds.
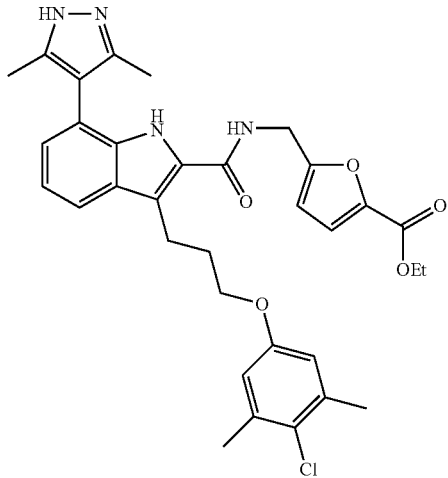
I-61
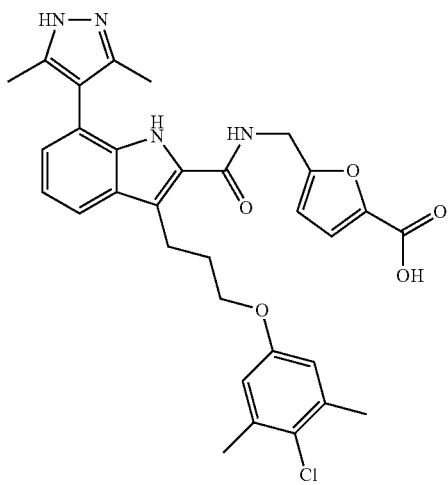 [SMILES: Cc1cc(OCCCc2c(C(=O)NCc3ccc(C(=O)O)o3)[nH]c3c(-c4c(C)n[nH]c4C)cccc23)cc(C)c1Cl]
I-62
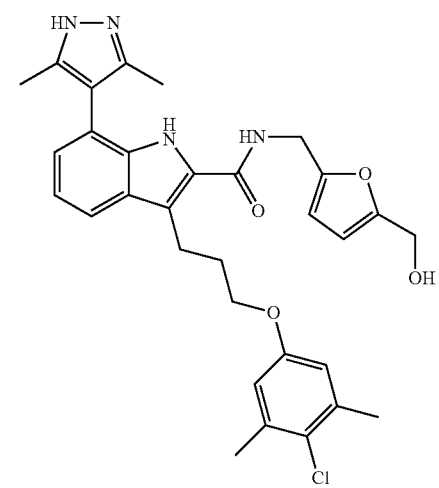 [SMILES: Cc1cc(OCCCc2c(C(=O)NCc3ccc(CO)o3)[nH]c3c(-c4c(C)n[nH]c4C)cccc23)cc(C)c1Cl]
I-63

TABLE 1-continued
Exemplary compounds.
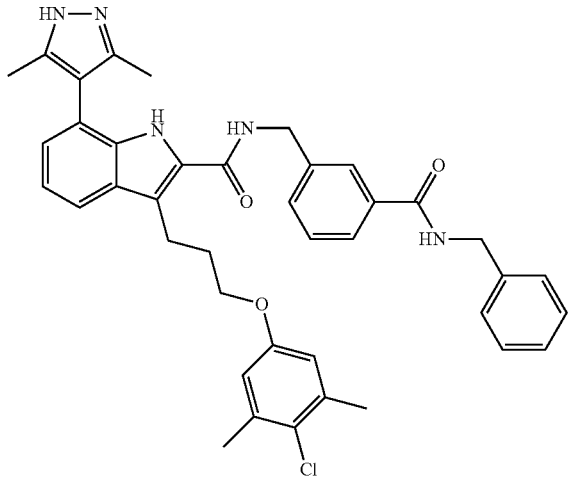 [SMILES: Cc1cc(OCCCc2c(C(=O)NCc3cccc(C(=O)NCc4ccccc4)c3)[nH]c3c(-c4c(C)n[nH]c4C)cccc23)cc(C)c1Cl]
I-64
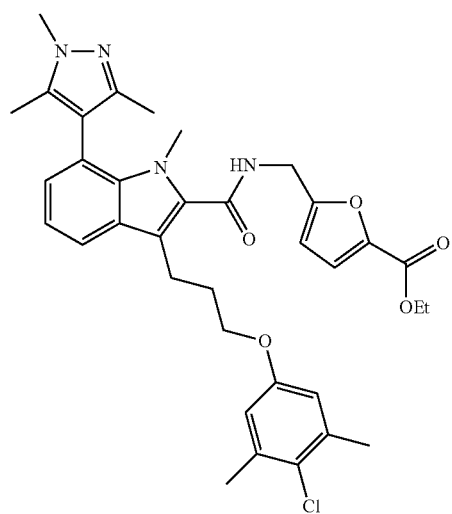
I-65
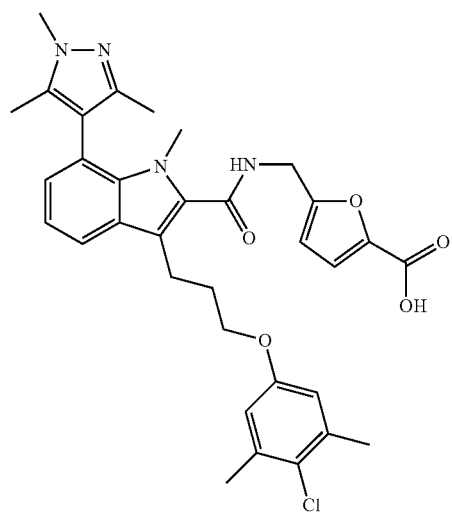 [SMILES: Cc1cc(OCCCc2c(C(=O)NCc3ccc(C(=O)O)o3)n(C)c3c(-c4c(C)nn(C)c4C)cccc23)cc(C)c1Cl]
I-66

TABLE 1-continued
Exemplary compounds.
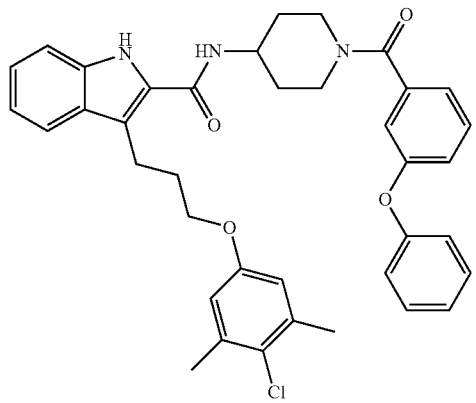 [SMILES: Cc1cc(OCCCc2c(C(=O)NC3CCN(C(=O)c4cccc(Oc5ccccc5)c4)CC3)[nH]c3ccccc23)cc(C)c1Cl]
I-67
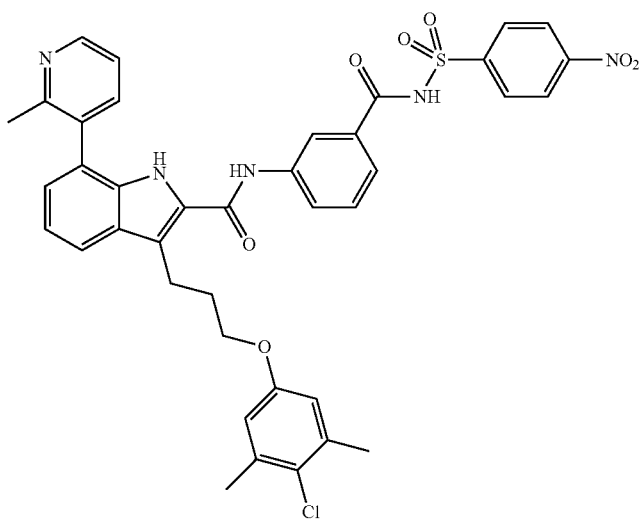 [SMILES: Cc1cc(OCCCc2c(C(=O)Nc3cccc(C(=O)NS(=O)(=O)c4ccc([N+](=O)[O-])cc4)c3)[nH]c3c(-c4cccnc4C)cccc23)cc(C)c1Cl]
I-68
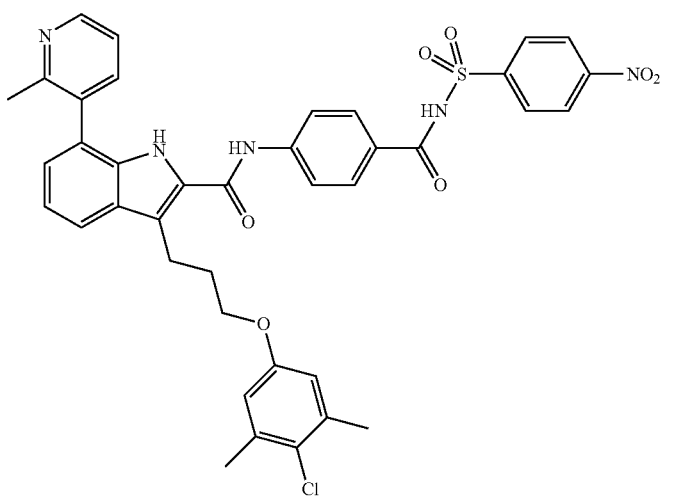 [SMILES: Cc1cc(OCCCc2c(C(=O)Nc3ccc(C(=O)NS(=O)(=O)c4ccc([N+](=O)[O-])cc4)cc3)[nH]c3c(-c4cccnc4C)cccc23)cc(C)c1Cl]
I-69

TABLE 1-continued
Exemplary compounds.
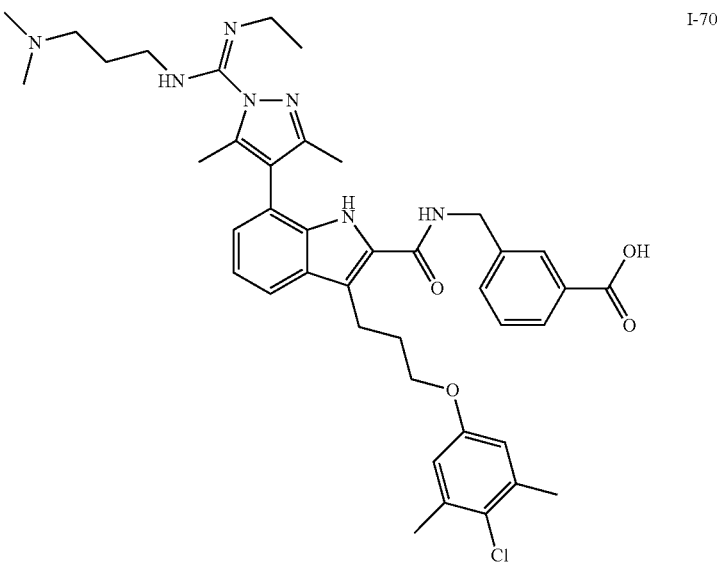
I-70
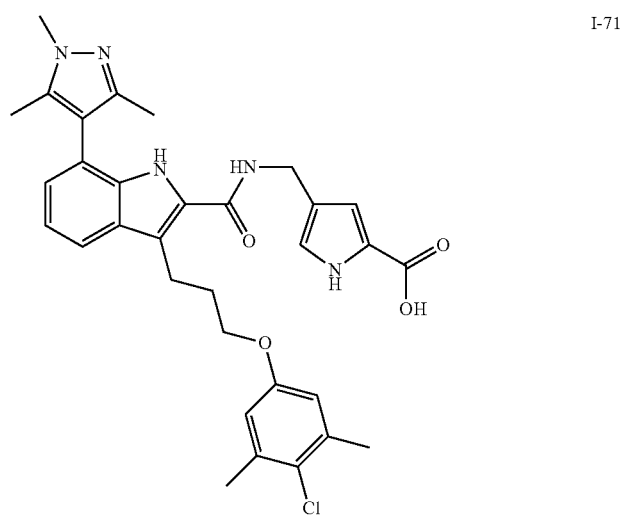
I-71
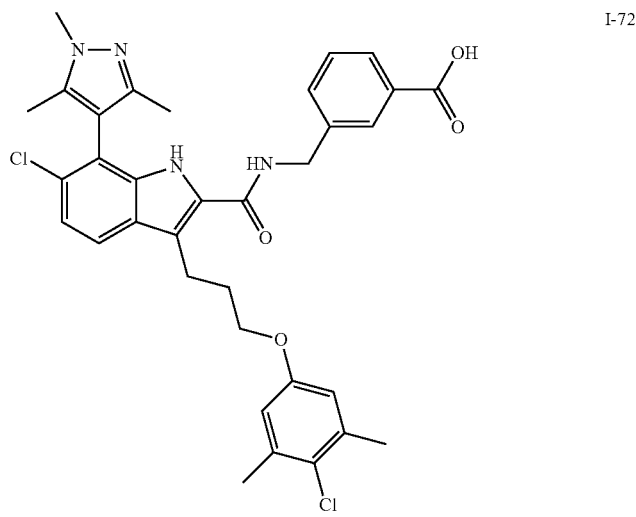
I-72

TABLE 1-continued
Exemplary compounds.
I-73
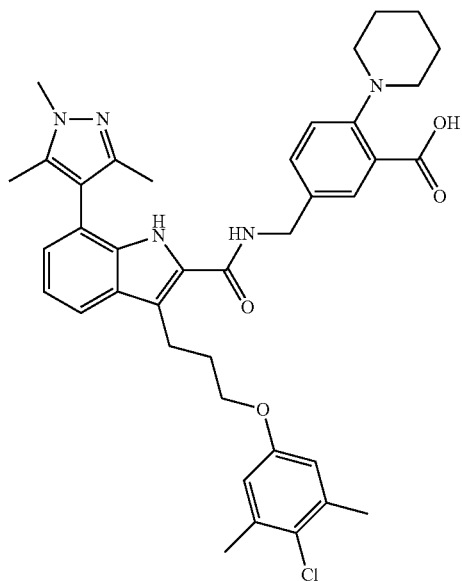 [SMILES: Cc1cc(OCCCc2c(C(=O)NCc3ccc(N4CCCCC4)c(C(=O)O)c3)[nH]c3c(-c4c(C)nn(C)c4C)cccc23)cc(C)c1Cl]
I-74
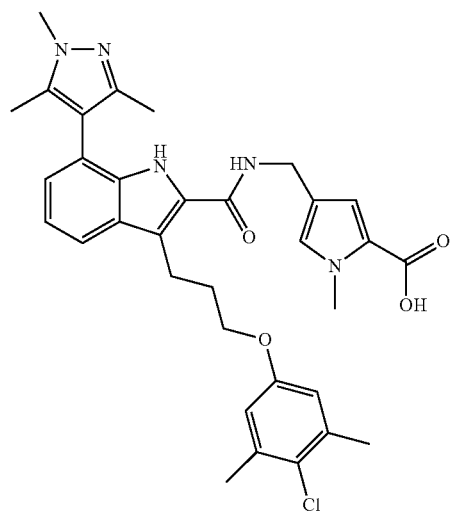 [SMILES: Cc1cc(OCCCc2c(C(=O)NCc3cc(C(=O)O)n(C)c3)[nH]c3c(-c4c(C)nn(C)c4C)cccc23)cc(C)c1Cl]
I-75
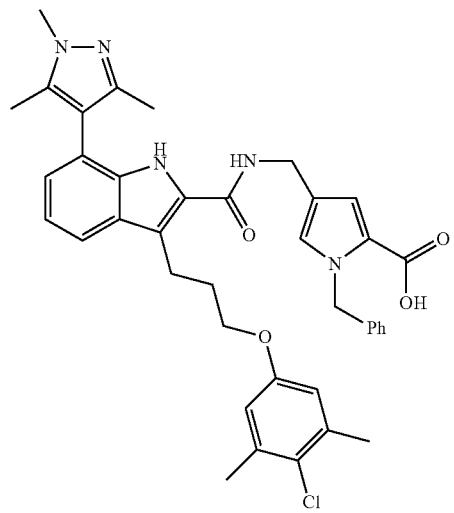 [SMILES: Cc1cc(OCCCc2c(C(=O)NCc3cc(C(=O)O)n(Cc4ccccc4)c3)[nH]c3c(-c4c(C)nn(C)c4C)cccc23)cc(C)c1Cl]

TABLE 1-continued
Exemplary compounds.
I-76
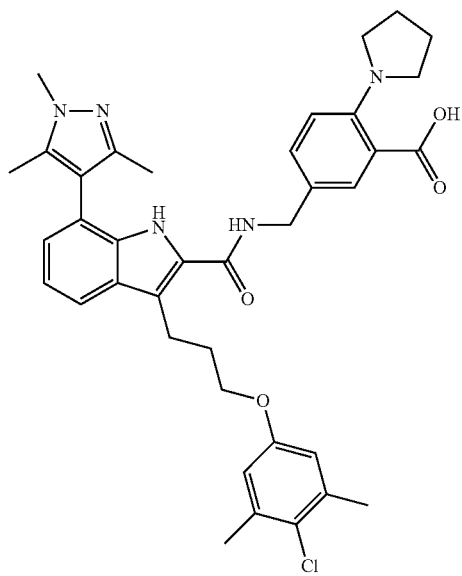 [SMILES: Cc1cc(OCCCc2c(C(=O)NCc3ccc(N4CCCC4)c(C(=O)O)c3)[nH]c3c(-c4c(C)nn(C)c4C)cccc23)cc(C)c1Cl]
I-77
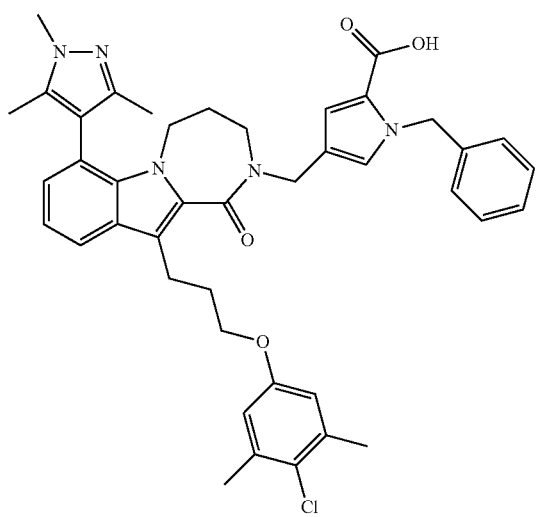 [SMILES: Cc1cc(OCCCc2c3n(c4c(-c5c(C)nn(C)c5C)cccc24)CCCN(Cc2cc(C(=O)O)n(Cc4ccccc4)c2)C3=O)cc(C)c1Cl]
I-78
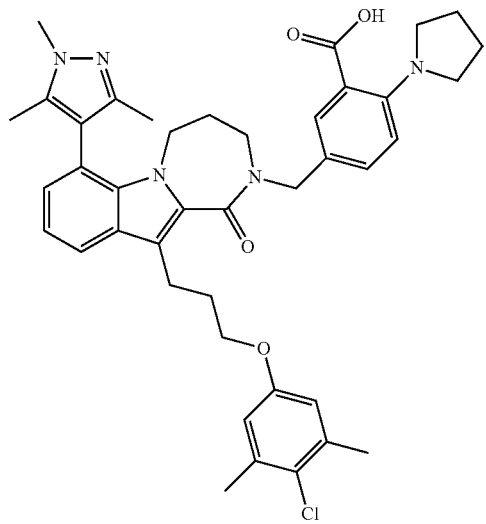 [SMILES: Cc1cc(OCCCc2c3n(c4c(-c5c(C)nn(C)c5C)cccc24)CCCN(Cc2ccc(N4CCCC4)c(C(=O)O)c2)C3=O)cc(C)c1Cl]

TABLE 1-continued
Exemplary compounds.
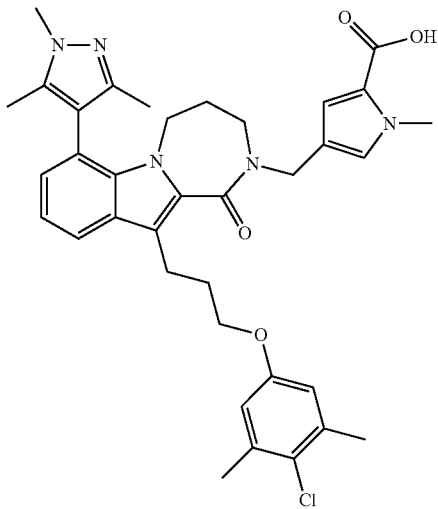
I-79
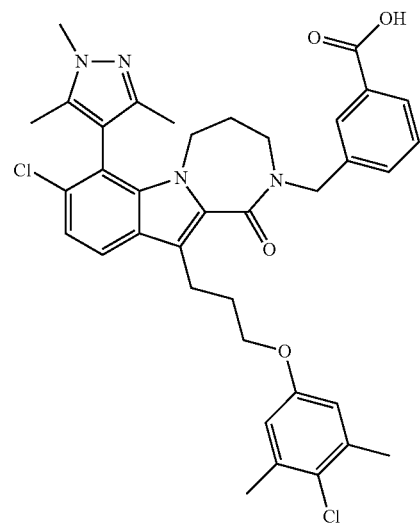 [SMILES: Cc1cc(OCCCc2c3n(c4c(-c5c(C)nn(C)c5C)c(Cl)ccc24)CCCN(Cc2cccc(C(=O)O)c2)C3=O)cc(C)c1Cl]
I-80
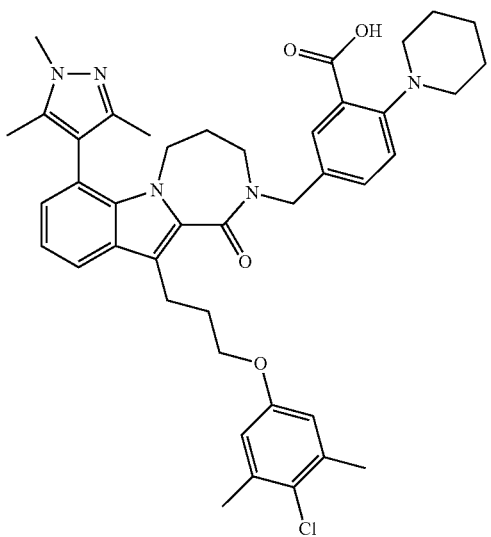 [SMILES: Cc1cc(OCCCc2c3n(c4c(-c5c(C)nn(C)c5C)cccc24)CCCN(Cc2ccc(N4CCCCC4)c(C(=O)O)c2)C3=O)cc(C)c1Cl]
I-81

TABLE 1-continued
Exemplary compounds.
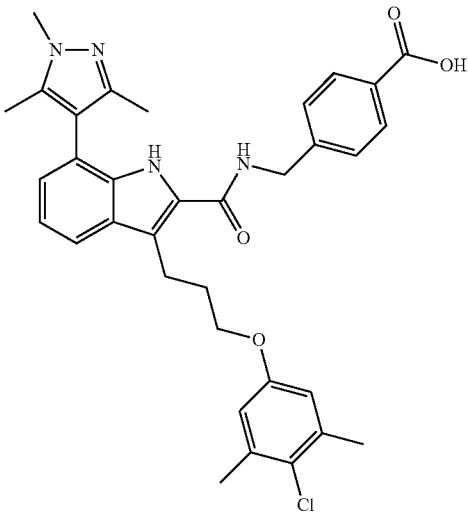 [SMILES: Cc1cc(OCCCc2c(C(=O)NCc3ccc(C(=O)O)cc3)[nH]c3c(-c4c(C)nn(C)c4C)cccc23)cc(C)c1Cl]
I-82
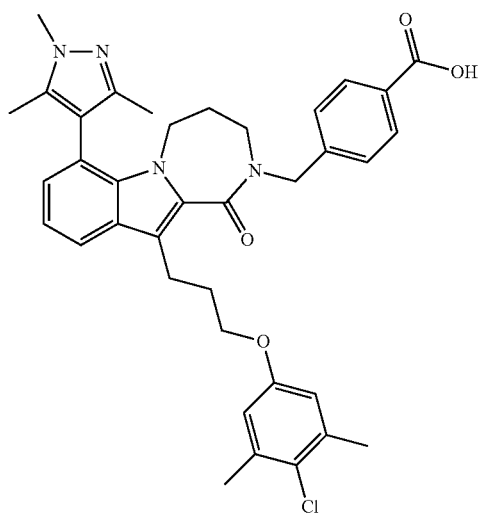 [SMILES: Cc1cc(OCCCc2c3n(c4c(-c5c(C)nn(C)c5C)cccc24)CCCN(Cc2ccc(C(=O)O)cc2)C3=O)cc(C)c1Cl]
I-83
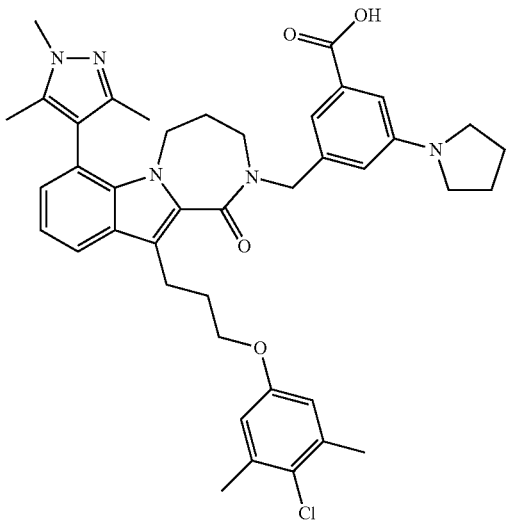 [SMILES: Cc1cc(OCCCc2c3n(c4c(-c5c(C)nn(C)c5C)cccc24)CCCN(Cc2cc(C(=O)O)cc(N4CCCC4)c2)C3=O)cc(C)c1Cl]
I-84

TABLE 1-continued
Exemplary compounds.
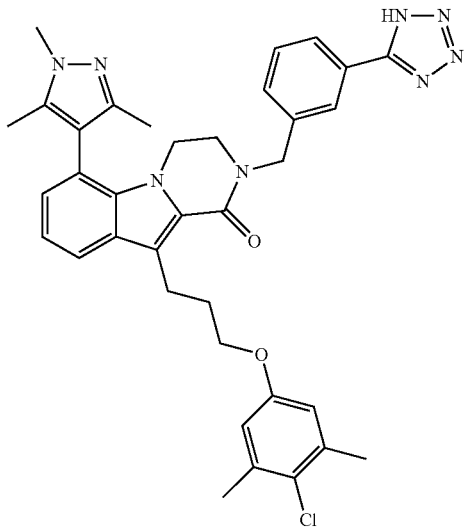 [SMILES: Cc1cc(OCCCc2c3n(c4c(-c5c(C)nn(C)c5C)cccc24)CCN(Cc2cccc(-c4nnn[nH]4)c2)C3=O)cc(C)c1Cl]
I-85
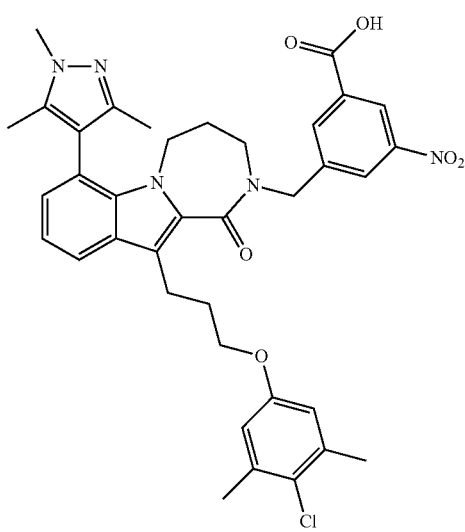 [SMILES: Cc1cc(OCCCc2c3n(c4c(-c5c(C)nn(C)c5C)cccc24)CCCN(Cc2cc(C(=O)O)cc([N+](=O)[O-])c2)C3=O)cc(C)c1Cl]
I-86
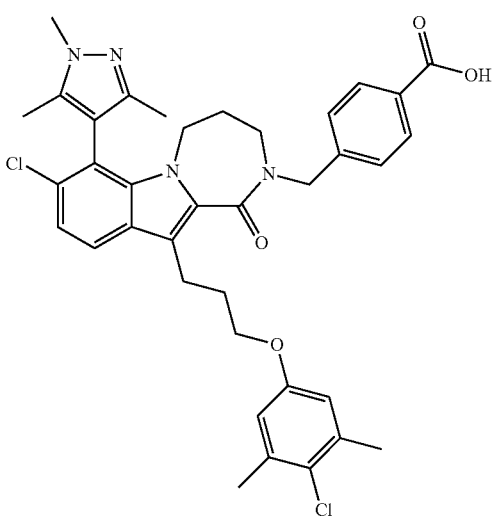 [SMILES: Cc1cc(OCCCc2c3n(c4c(-c5c(C)nn(C)c5C)c(Cl)ccc24)CCCN(Cc2ccc(C(=O)O)cc2)C3=O)cc(C)c1Cl]
I-87

TABLE 1-continued
Exemplary compounds.
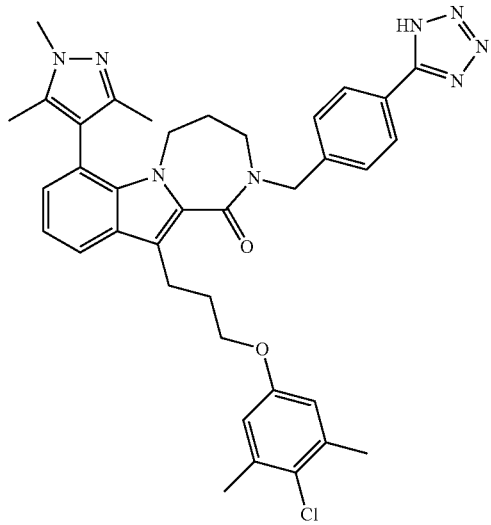 [SMILES: Cc1cc(OCCCc2c3n(c4c(-c5c(C)nn(C)c5C)cccc24)CCCN(Cc2ccc(-c4nnn[nH]4)cc2)C3=O)cc(C)c1Cl]
I-88
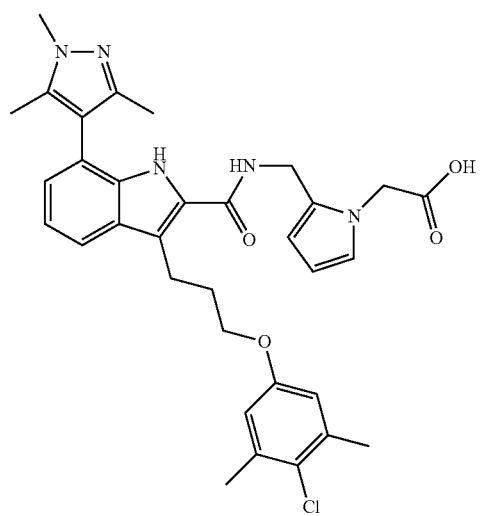 [SMILES: Cc1cc(OCCCc2c(C(=O)NCc3cccn3CC(=O)O)[nH]c3c(-c4c(C)nn(C)c4C)cccc23)cc(C)c1Cl]
I-89
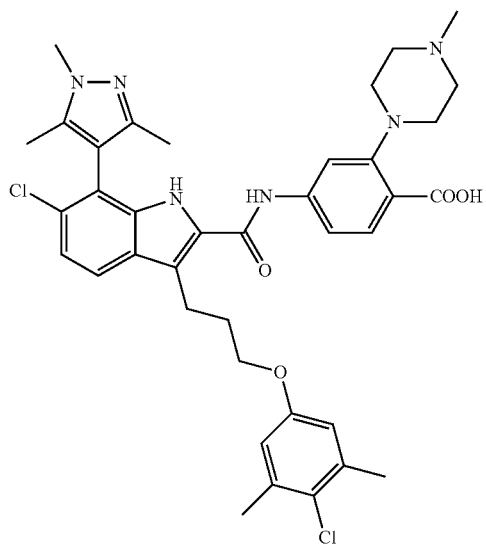 [SMILES: Cc1cc(OCCCc2c(C(=O)Nc3ccc(C(=O)O)c(N4CCN(C)CC4)c3)[nH]c3c(-c4c(C)nn(C)c4C)c(Cl)ccc23)cc(C)c1Cl]
I-90

TABLE 1-continued
Exemplary compounds.
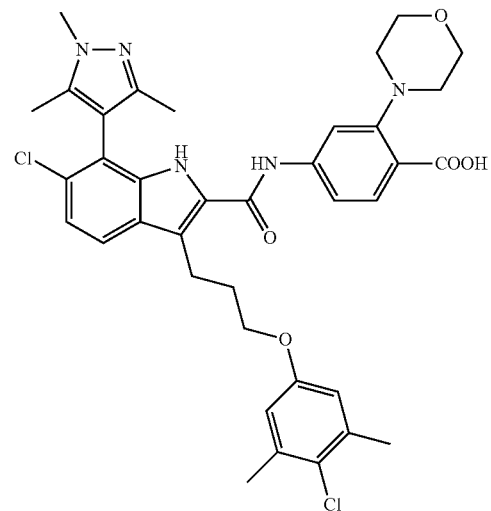 [SMILES: Cc1cc(OCCCc2c(C(=O)Nc3ccc(C(=O)O)c(N4CCOCC4)c3)[nH]c3c(-c4c(C)nn(C)c4C)c(Cl)ccc23)cc(C)c1Cl]
I-91
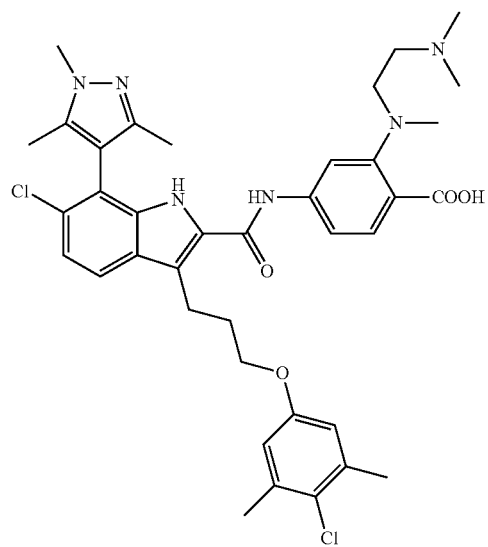 [SMILES: Cc1cc(OCCCc2c(C(=O)Nc3ccc(C(=O)O)c(N(C)CCN(C)C)c3)[nH]c3c(-c4c(C)nn(C)c4C)c(Cl)ccc23)cc(C)c1Cl]
I-92
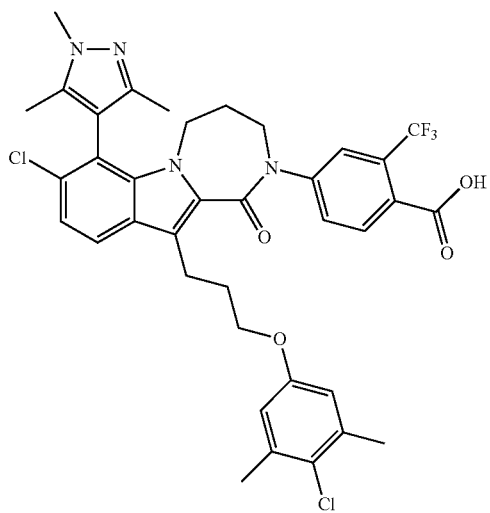 [SMILES: Cc1cc(OCCCc2c3n(c4c(-c5c(C)nn(C)c5C)c(Cl)ccc24)CCCN(c2ccc(C(=O)O)c(C(F)(F)F)c2)C3=O)cc(C)c1Cl]
I-93

TABLE 1-continued
Exemplary compounds.
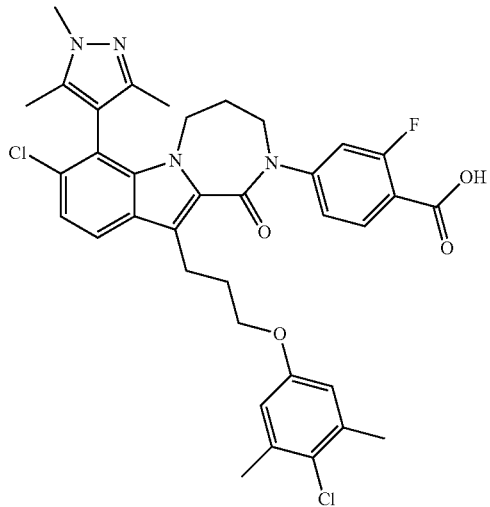 [SMILES: Cc1cc(OCCCc2c3n(c4c(-c5c(C)nn(C)c5C)c(Cl)ccc24)CCCN(c2ccc(C(=O)O)c(F)c2)C3=O)cc(C)c1Cl]
I-94
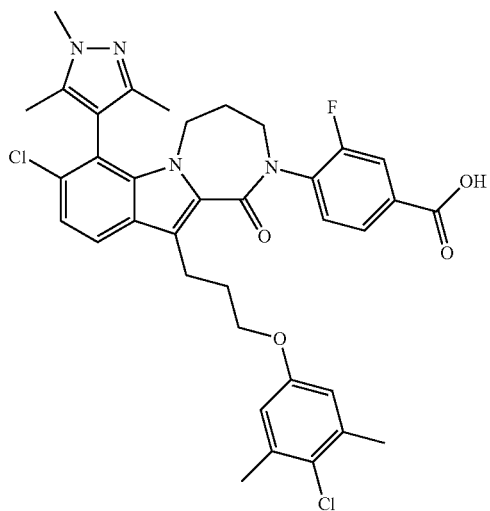 [SMILES: Cc1cc(OCCCc2c3n(c4c(-c5c(C)nn(C)c5C)c(Cl)ccc24)CCCN(c2ccc(C(=O)O)cc2F)C3=O)cc(C)c1Cl]
I-95
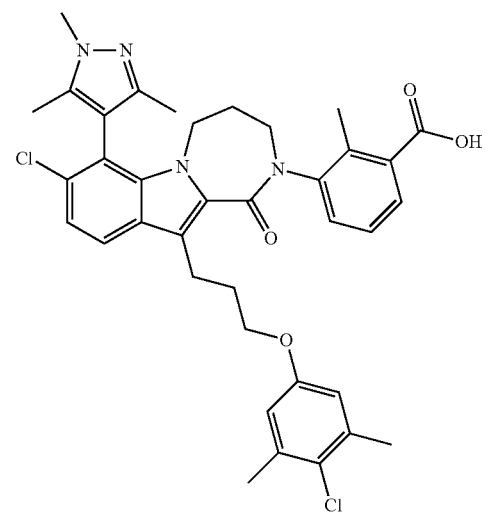 [SMILES: Cc1cc(OCCCc2c3n(c4c(-c5c(C)nn(C)c5C)c(Cl)ccc24)CCCN(c2cccc(C(=O)O)c2C)C3=O)cc(C)c1Cl]
I-96

TABLE 1-continued
Exemplary compounds.
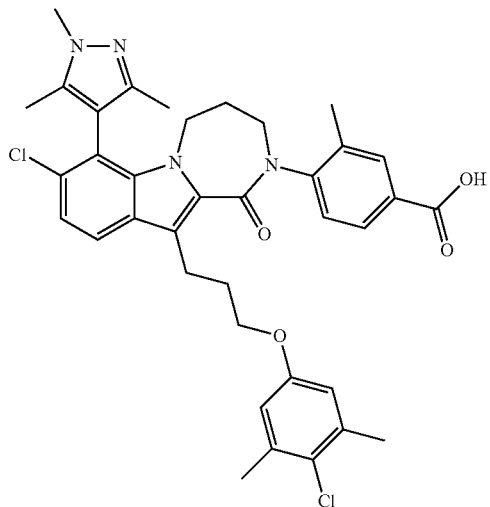 [SMILES: Cc1cc(C(=O)O)ccc1N1CCCn2c(c(CCCOc3cc(C)c(Cl)c(C)c3)c3ccc(Cl)c(-c4c(C)nn(C)c4C)c32)C1=O]
I-97
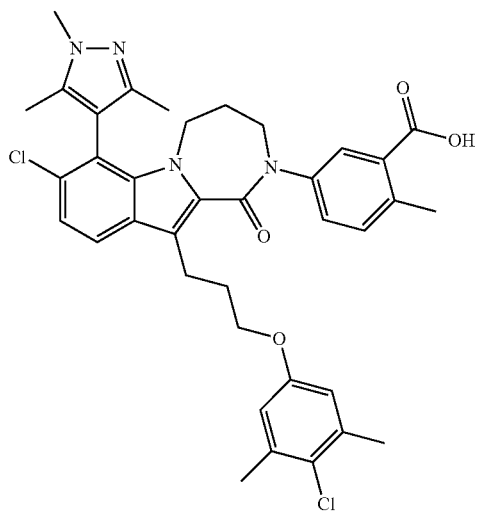 [SMILES: Cc1ccc(N2CCCn3c(c(CCCOc4cc(C)c(Cl)c(C)c4)c4ccc(Cl)c(-c5c(C)nn(C)c5C)c43)C2=O)cc1C(=O)O]
I-98
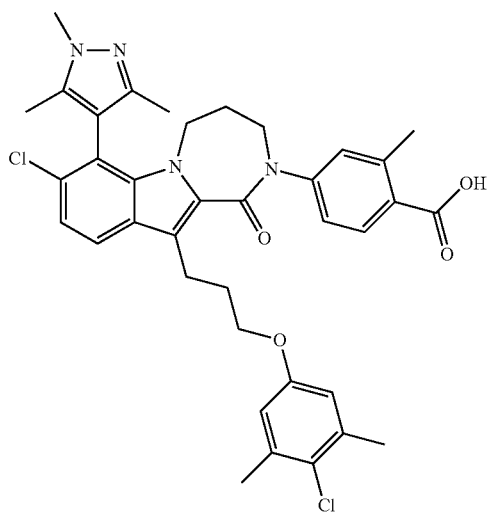 [SMILES: Cc1cc(N2CCCn3c(c(CCCOc4cc(C)c(Cl)c(C)c4)c4ccc(Cl)c(-c5c(C)nn(C)c5C)c43)C2=O)ccc1C(=O)O]
I-99

TABLE 1-continued
Exemplary compounds.
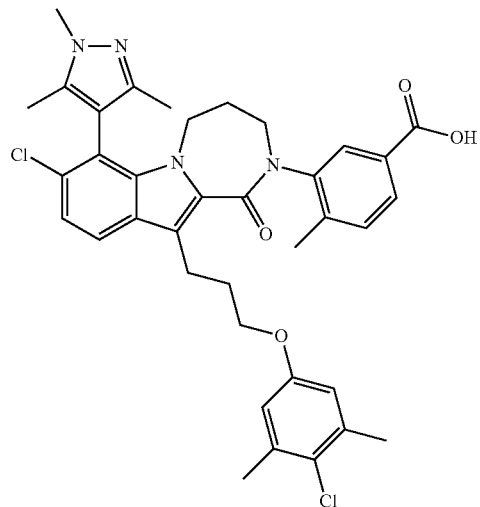 [SMILES: Cc1ccc(C(=O)O)cc1N1CCCn2c(c(CCCOc3cc(C)c(Cl)c(C)c3)c3ccc(Cl)c(-c4c(C)nn(C)c4C)c32)C1=O]
I-100
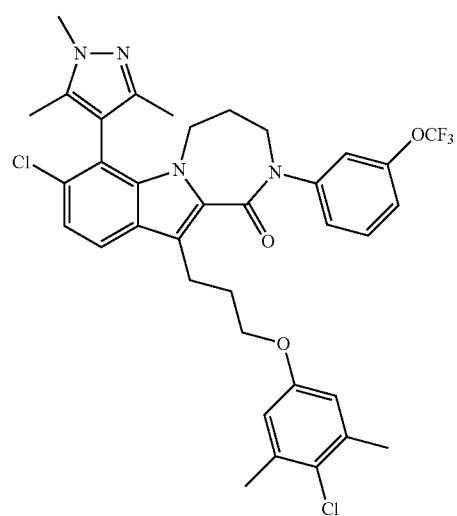 [SMILES: Cc1cc(OCCCc2c3n(c4c(-c5c(C)nn(C)c5C)c(Cl)ccc24)CCCN(c2cccc(OC(F)(F)F)c2)C3=O)cc(C)c1Cl]
I-101
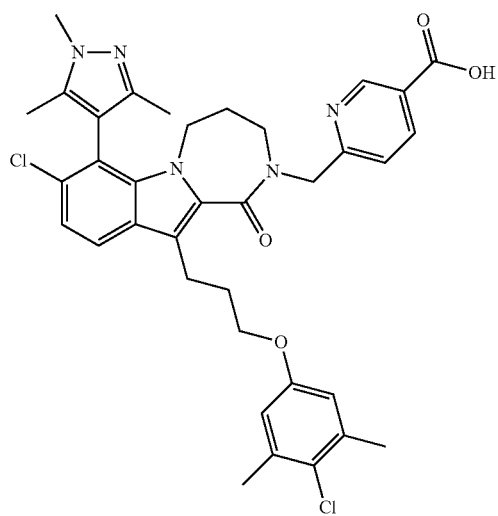 [SMILES: Cc1cc(OCCCc2c3n(c4c(-c5c(C)nn(C)c5C)c(Cl)ccc24)CCCN(Cc2ccc(C(=O)O)cn2)C3=O)cc(C)c1Cl]
I-102

TABLE 1-continued
Exemplary compounds.
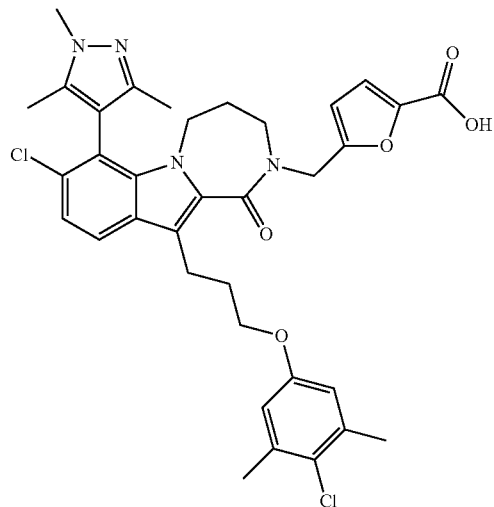 [SMILES: Cc1cc(OCCCc2c3n(c4c(-c5c(C)nn(C)c5C)c(Cl)ccc24)CCCN(Cc2ccc(C(=O)O)o2)C3=O)cc(C)c1Cl]
I-103
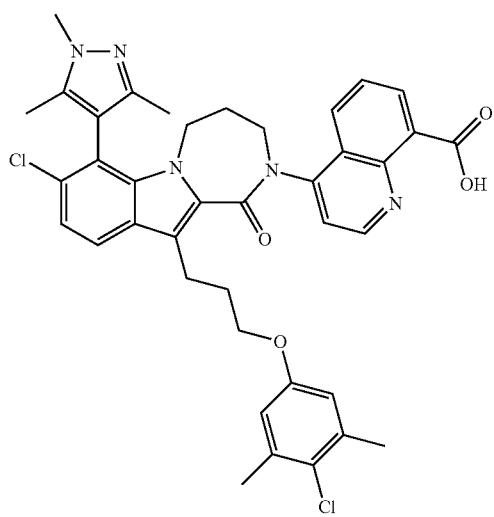 [SMILES: Cc1cc(OCCCc2c3n(c4c(-c5c(C)nn(C)c5C)c(Cl)ccc24)CCCN(c2ccnc4c(C(=O)O)cccc24)C3=O)cc(C)c1Cl]
I-104
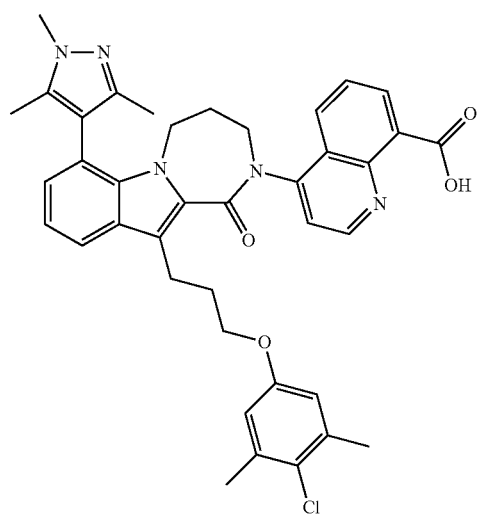 [SMILES: Cc1cc(OCCCc2c3n(c4c(-c5c(C)nn(C)c5C)cccc24)CCCN(c2ccnc4c(C(=O)O)cccc24)C3=O)cc(C)c1Cl]
I-105

TABLE 1-continued
Exemplary compounds.
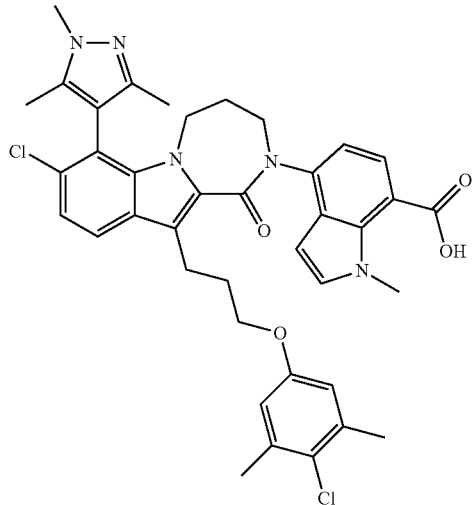 [SMILES: Cc1cc(OCCCc2c3n(c4c(-c5c(C)nn(C)c5C)c(Cl)ccc24)CCCN(c2ccc(C(=O)O)c4c2ccn4C)C3=O)cc(C)c1Cl]
I-106
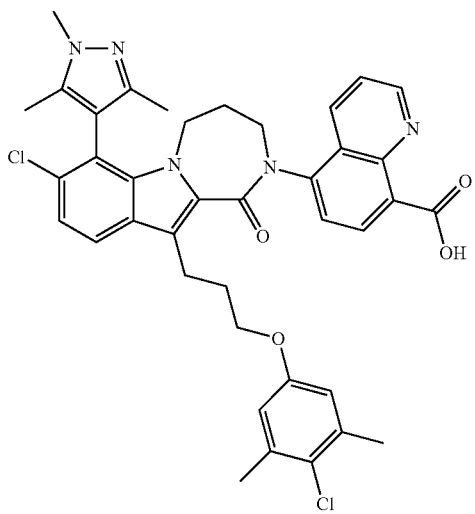 [SMILES: Cc1cc(OCCCc2c3n(c4c(-c5c(C)nn(C)c5C)c(Cl)ccc24)CCCN(c2ccc(C(=O)O)c4ncccc24)C3=O)cc(C)c1Cl]
I-107
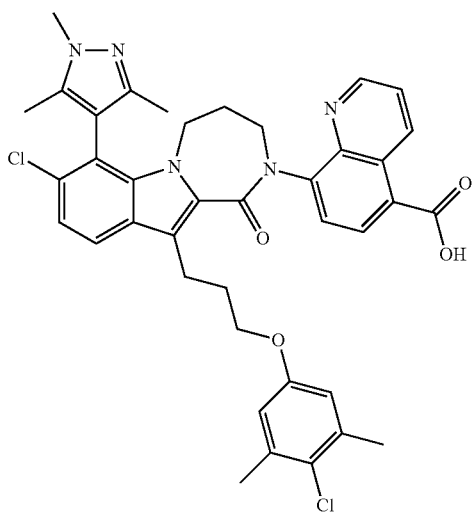 [SMILES: Cc1cc(OCCCc2c3n(c4c(-c5c(C)nn(C)c5C)c(Cl)ccc24)CCCN(c2ccc(C(=O)O)c4cccnc24)C3=O)cc(C)c1Cl]
I-108

TABLE 1-continued
Exemplary compounds.
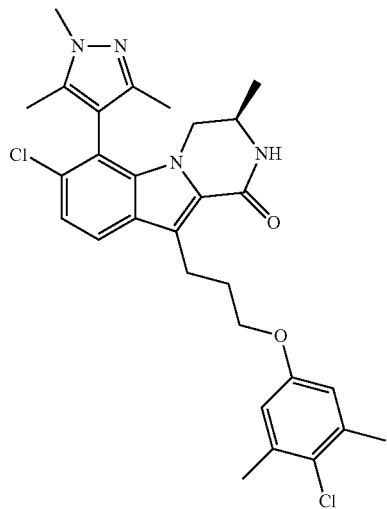 [SMILES: Cc1cc(OCCCc2c3n(c4c(-c5c(C)nn(C)c5C)c(Cl)ccc24)C[C@@H](C)NC3=O)cc(C)c1Cl]
I-109
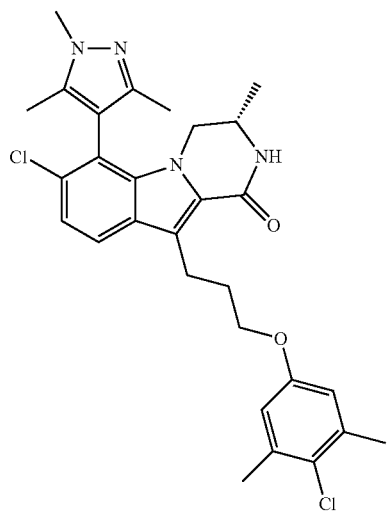 [SMILES: Cc1cc(OCCCc2c3n(c4c(-c5c(C)nn(C)c5C)c(Cl)ccc24)C[C@H](C)NC3=O)cc(C)c1Cl]
I-110
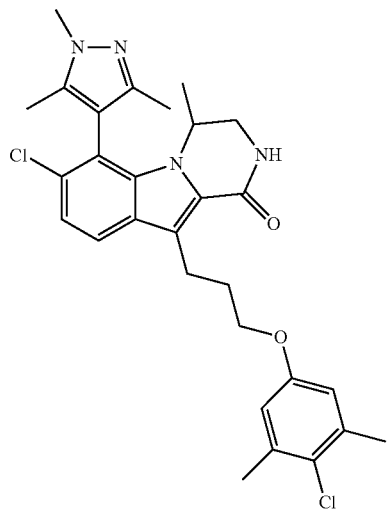 [SMILES: Cc1cc(OCCCc2c3n(c4c(-c5c(C)nn(C)c5C)c(Cl)ccc24)C(C)CNC3=O)cc(C)c1Cl]
I-111

TABLE 1-continued
Exemplary compounds.
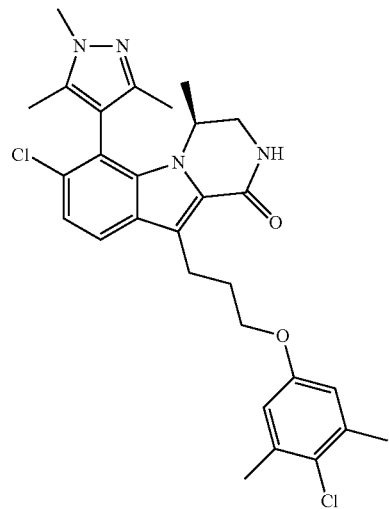 [SMILES: Cc1cc(OCCCc2c3n(c4c(-c5c(C)nn(C)c5C)c(Cl)ccc24)[C@@H](C)CNC3=O)cc(C)c1Cl]
I-112
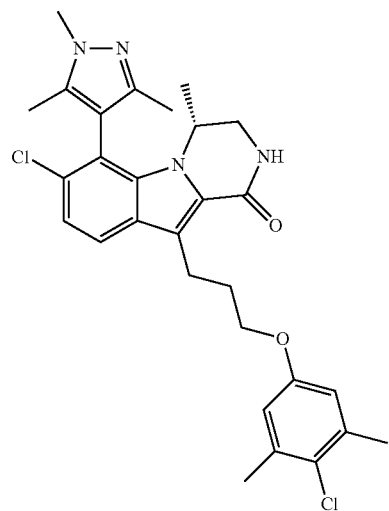 [SMILES: Cc1cc(OCCCc2c3n(c4c(-c5c(C)nn(C)c5C)c(Cl)ccc24)[C@H](C)CNC3=O)cc(C)c1Cl]
I-113
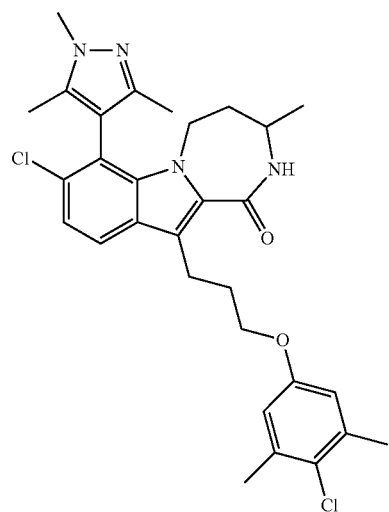 [SMILES: Cc1cc(OCCCc2c3n(c4c(-c5c(C)nn(C)c5C)c(Cl)ccc24)CCC(C)NC3=O)cc(C)c1Cl]
I-114

TABLE 1-continued
Exemplary compounds.
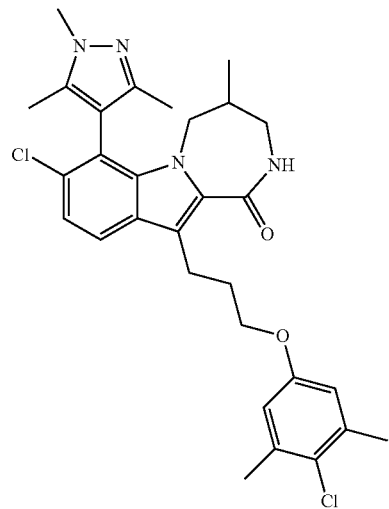 [SMILES: Cc1cc(OCCCc2c3n(c4c(-c5c(C)nn(C)c5C)c(Cl)ccc24)CC(C)CNC3=O)cc(C)c1Cl]
I-115
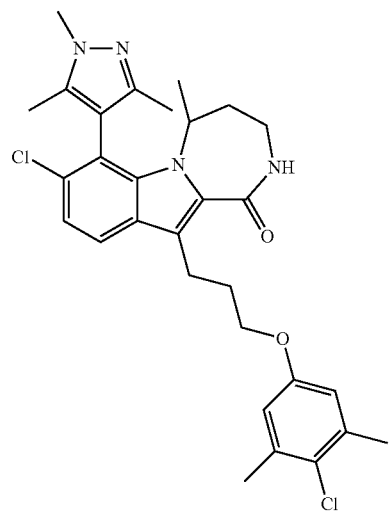 [SMILES: Cc1cc(OCCCc2c3n(c4c(-c5c(C)nn(C)c5C)c(Cl)ccc24)C(C)CCNC3=O)cc(C)c1Cl]
I-116
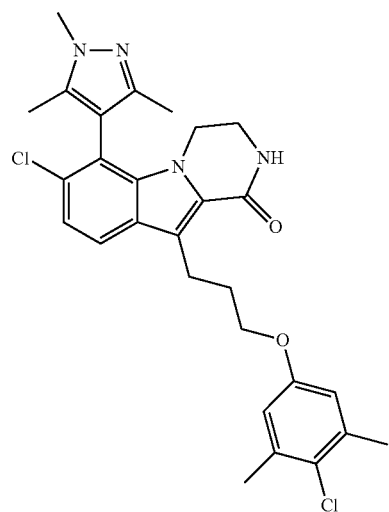 [SMILES: Cc1cc(OCCCc2c3n(c4c(-c5c(C)nn(C)c5C)c(Cl)ccc24)CCNC3=O)cc(C)c1Cl]
I-117

TABLE 1-continued
Exemplary compounds.
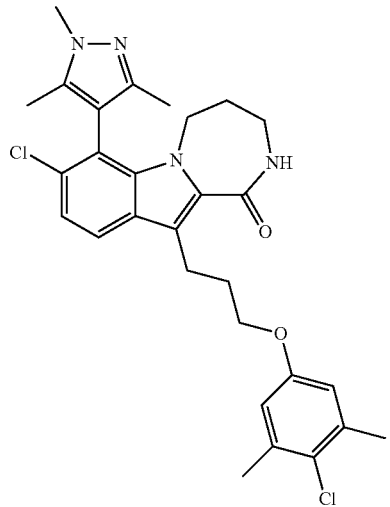 [SMILES: Cc1cc(OCCCc2c3n(c4c(-c5c(C)nn(C)c5C)c(Cl)ccc24)CCCNC3=O)cc(C)c1Cl]
I-118
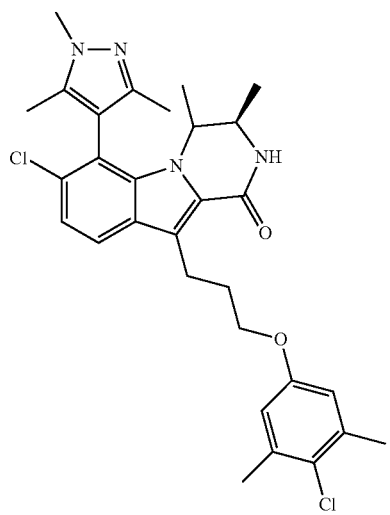 [SMILES: Cc1cc(OCCCc2c3n(c4c(-c5c(C)nn(C)c5C)c(Cl)ccc24)C(C)[C@@H](C)NC3=O)cc(C)c1Cl]
I-119
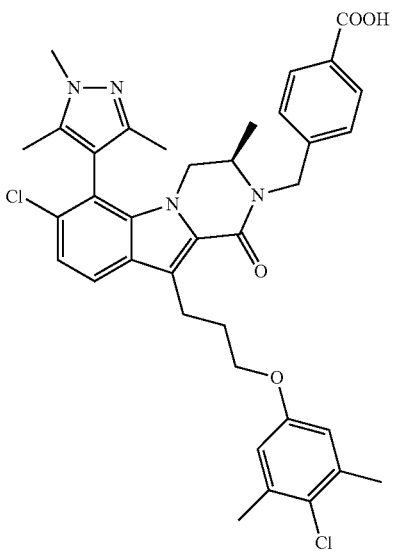 [SMILES: Cc1cc(OCCCc2c3n(c4c(-c5c(C)nn(C)c5C)c(Cl)ccc24)C[C@@H](C)N(Cc2ccc(C(=O)O)cc2)C3=O)cc(C)c1Cl]
I-120

TABLE 1-continued
Exemplary compounds.
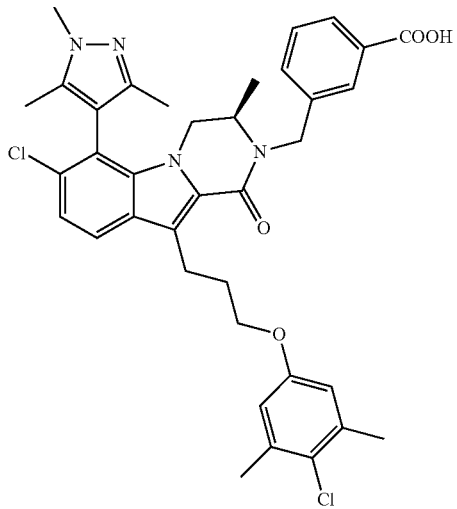 [SMILES: Cc1cc(OCCCc2c3n(c4c(-c5c(C)nn(C)c5C)c(Cl)ccc24)C[C@@H](C)N(Cc2cccc(C(=O)O)c2)C3=O)cc(C)c1Cl]
I-121
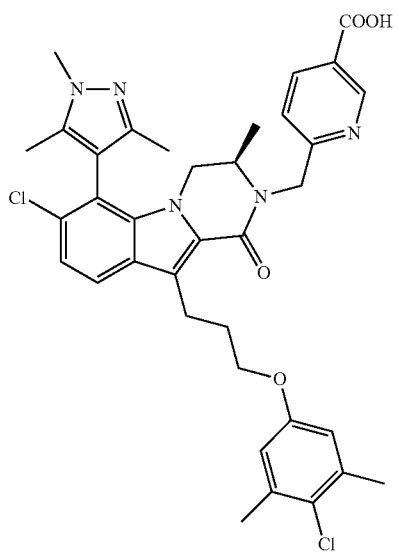 [SMILES: Cc1cc(OCCCc2c3n(c4c(-c5c(C)nn(C)c5C)c(Cl)ccc24)C[C@@H](C)N(Cc2ccc(C(=O)O)cn2)C3=O)cc(C)c1Cl]
I-122
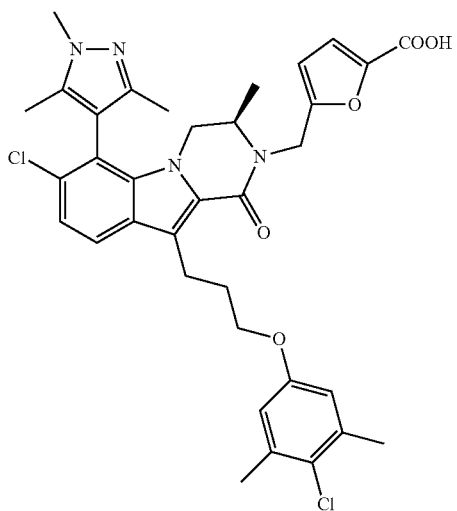 [SMILES: Cc1cc(OCCCc2c3n(c4c(-c5c(C)nn(C)c5C)c(Cl)ccc24)C[C@@H](C)N(Cc2ccc(C(=O)O)o2)C3=O)cc(C)c1Cl]
I-123

TABLE 1-continued
Exemplary compounds.
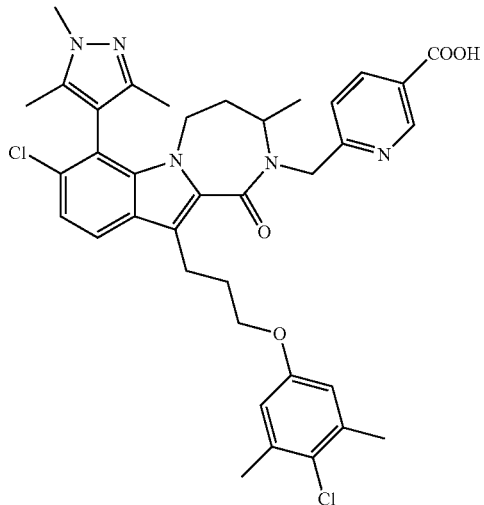 [SMILES: Cc1cc(OCCCc2c3n(c4c(-c5c(C)nn(C)c5C)c(Cl)ccc24)CCC(C)N(Cc2ccc(C(=O)O)cn2)C3=O)cc(C)c1Cl]
I-124
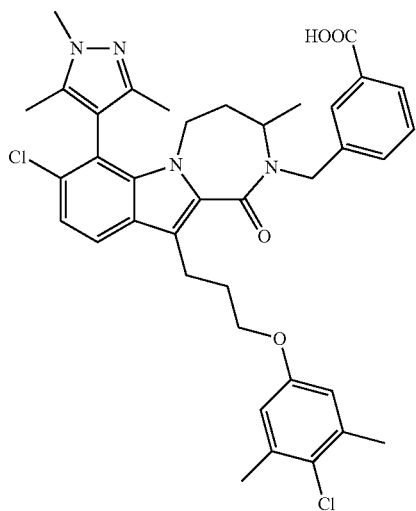 [SMILES: Cc1cc(OCCCc2c3n(c4c(-c5c(C)nn(C)c5C)c(Cl)ccc24)CCC(C)N(Cc2cccc(C(=O)O)c2)C3=O)cc(C)c1Cl]
I-125
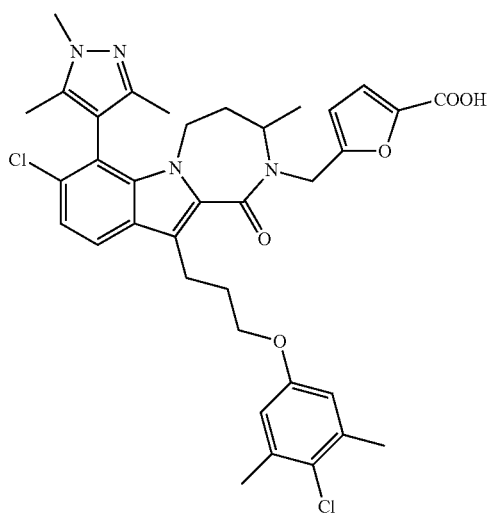 [SMILES: Cc1cc(OCCCc2c3n(c4c(-c5c(C)nn(C)c5C)c(Cl)ccc24)CCC(C)N(Cc2ccc(C(=O)O)o2)C3=O)cc(C)c1Cl]
I-126

TABLE 1-continued
Exemplary compounds.
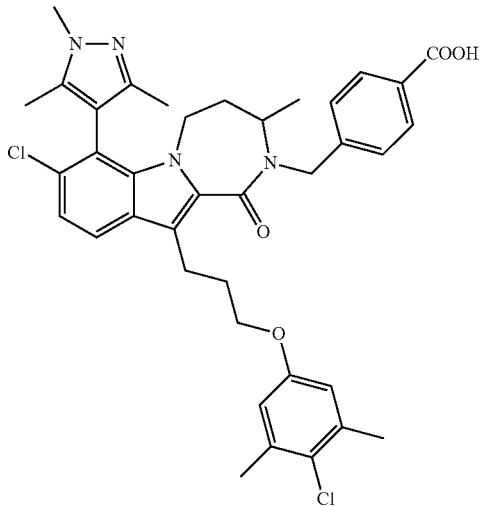 [SMILES: Cc1cc(OCCCc2c3n(c4c(-c5c(C)nn(C)c5C)c(Cl)ccc24)CCC(C)N(Cc2ccc(C(=O)O)cc2)C3=O)cc(C)c1Cl]
I-127
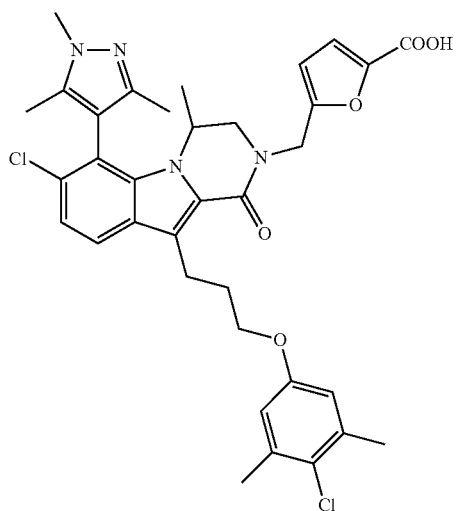 [SMILES: Cc1cc(OCCCc2c3n(c4c(-c5c(C)nn(C)c5C)c(Cl)ccc24)C(C)CN(Cc2ccc(C(=O)O)o2)C3=O)cc(C)c1Cl]
I-128
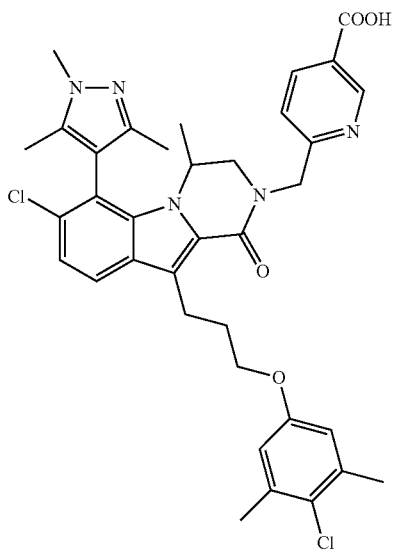 [SMILES: Cc1cc(OCCCc2c3n(c4c(-c5c(C)nn(C)c5C)c(Cl)ccc24)C(C)CN(Cc2ccc(C(=O)O)cn2)C3=O)cc(C)c1Cl]
I-129

TABLE 1-continued
Exemplary compounds.
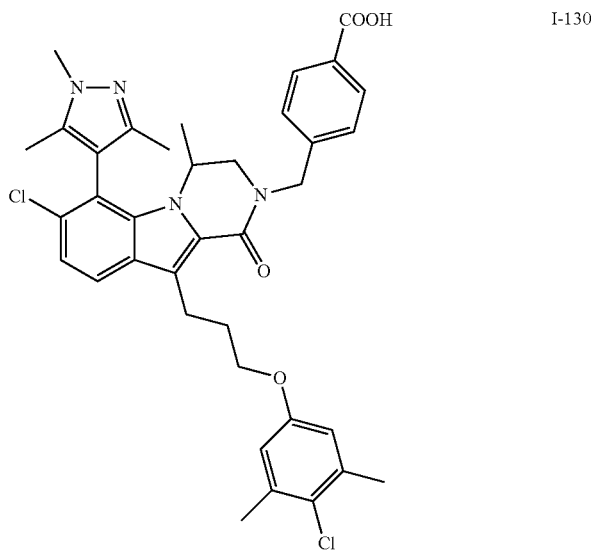
I-130
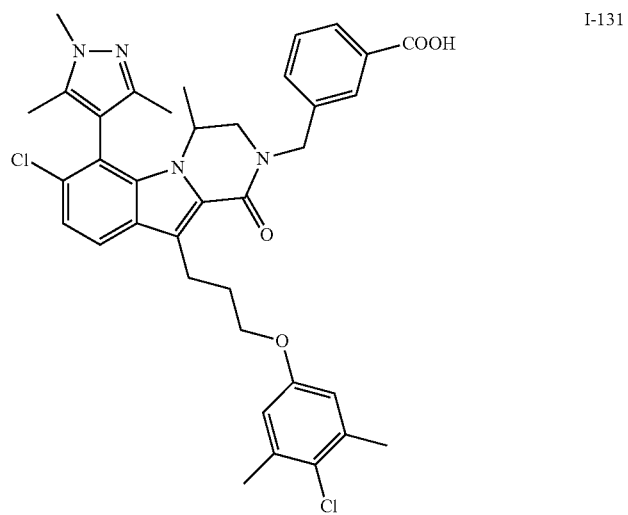
I-131
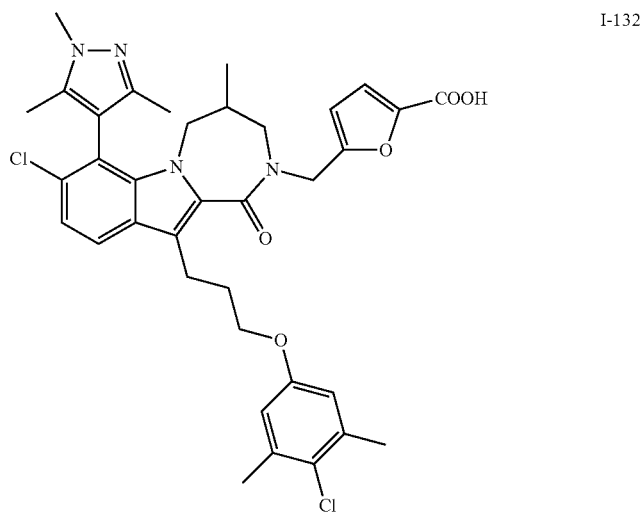
I-132

TABLE 1-continued
Exemplary compounds.
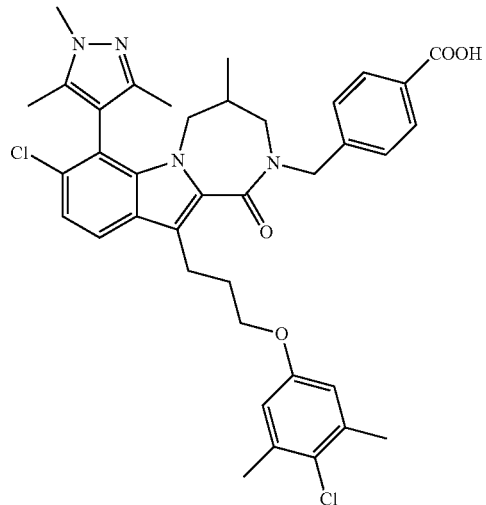 [SMILES: Cc1cc(OCCCc2c3n(c4c(-c5c(C)nn(C)c5C)c(Cl)ccc24)CC(C)CN(Cc2ccc(C(=O)O)cc2)C3=O)cc(C)c1Cl]
I-133
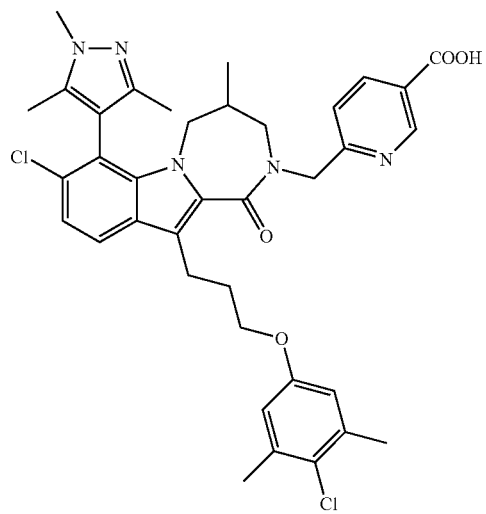 [SMILES: Cc1cc(OCCCc2c3n(c4c(-c5c(C)nn(C)c5C)c(Cl)ccc24)CC(C)CN(Cc2ccc(C(=O)O)cn2)C3=O)cc(C)c1Cl]
I-134
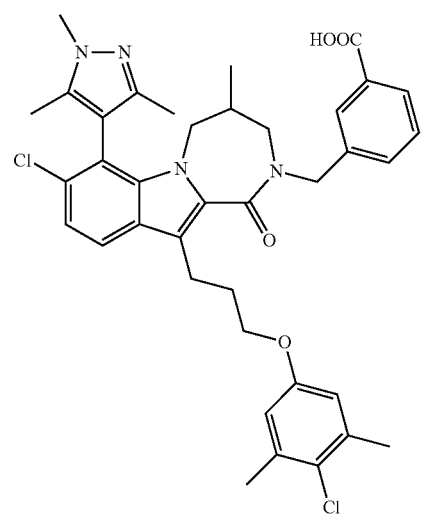 [SMILES: Cc1cc(OCCCc2c3n(c4c(-c5c(C)nn(C)c5C)c(Cl)ccc24)CC(C)CN(Cc2cccc(C(=O)O)c2)C3=O)cc(C)c1Cl]
I-135

TABLE 1-continued
Exemplary compounds.
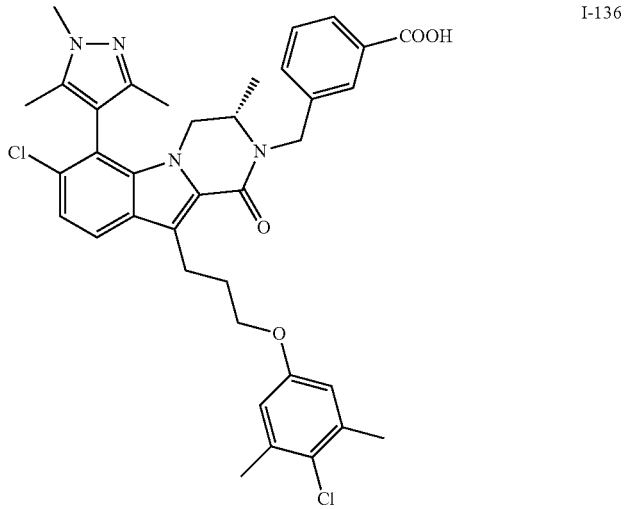
I-136
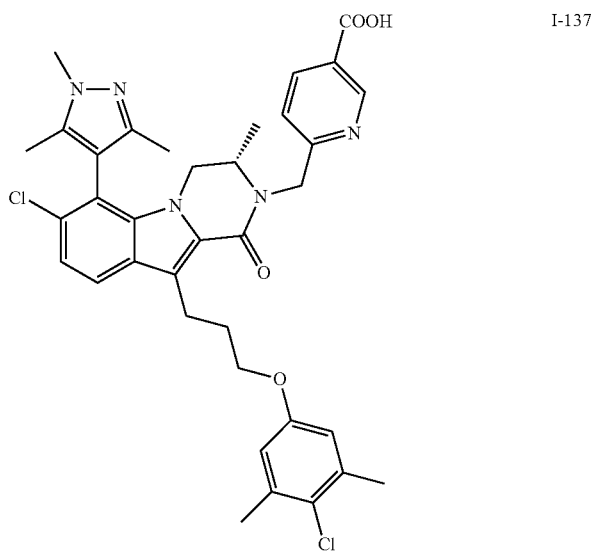
I-137
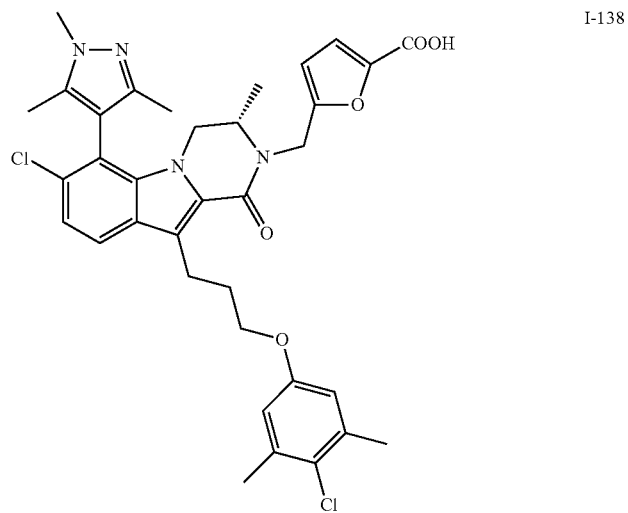
I-138

TABLE 1-continued
Exemplary compounds.
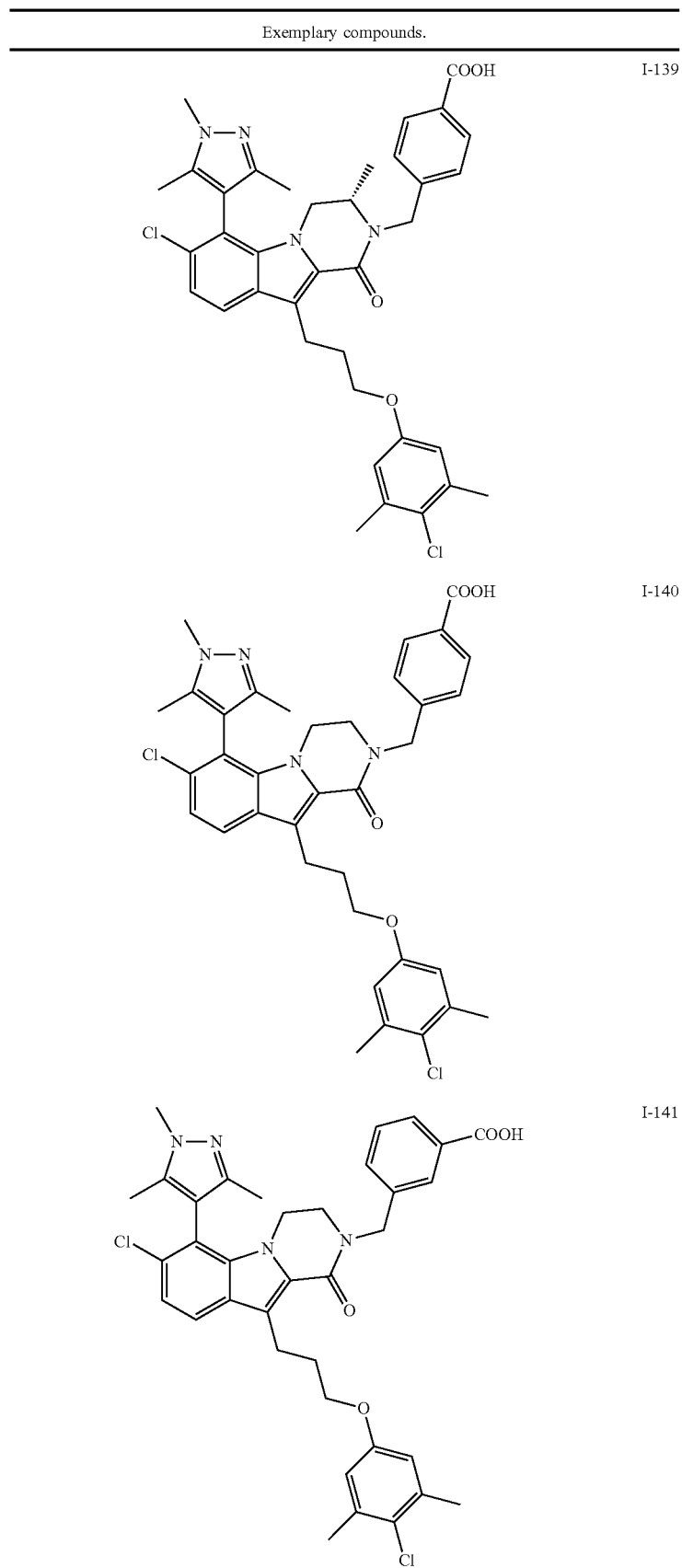
I-139
I-140
I-141

TABLE 1-continued
Exemplary compounds.
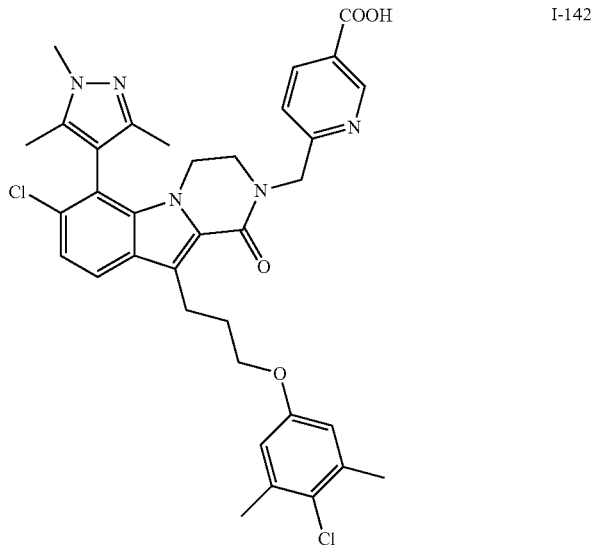
I-142
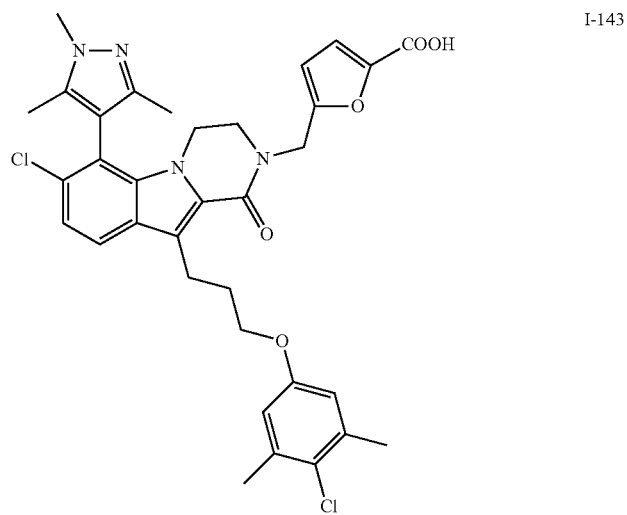
I-143
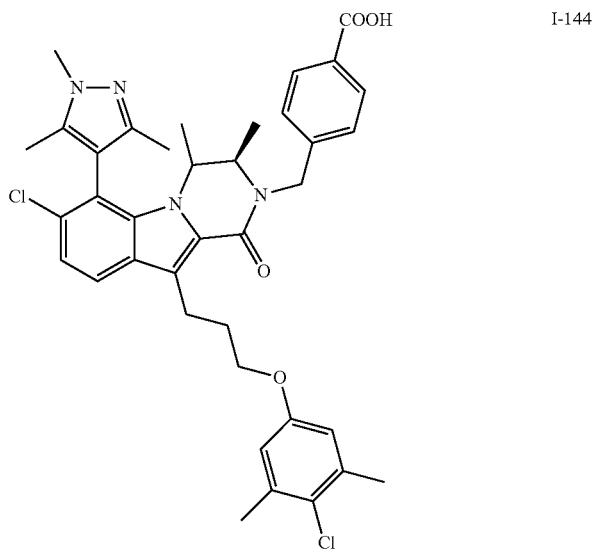
I-144

TABLE 1-continued
Exemplary compounds.
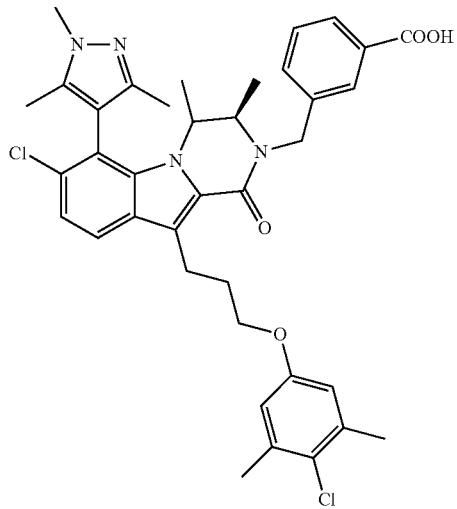 [SMILES: Cc1cc(OCCCc2c3n(c4c(-c5c(C)nn(C)c5C)c(Cl)ccc24)C(C)[C@@H](C)N(Cc2cccc(C(=O)O)c2)C3=O)cc(C)c1Cl]
I-145
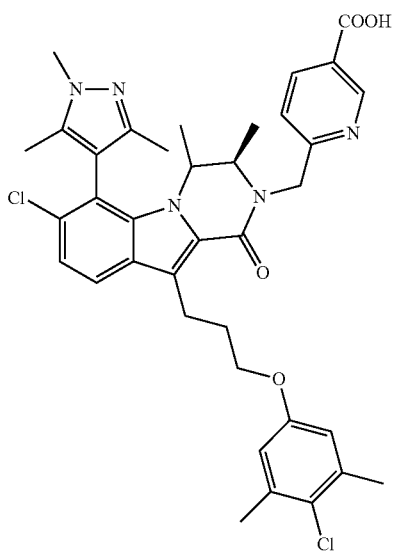 [SMILES: Cc1cc(OCCCc2c3n(c4c(-c5c(C)nn(C)c5C)c(Cl)ccc24)C(C)[C@@H](C)N(Cc2ccc(C(=O)O)cn2)C3=O)cc(C)c1Cl]
I-146
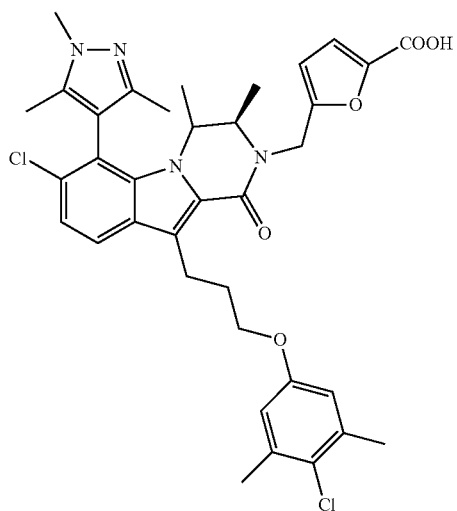 [SMILES: Cc1cc(OCCCc2c3n(c4c(-c5c(C)nn(C)c5C)c(Cl)ccc24)C(C)[C@@H](C)N(Cc2ccc(C(=O)O)o2)C3=O)cc(C)c1Cl]
I-147

TABLE 1-continued
Exemplary compounds.
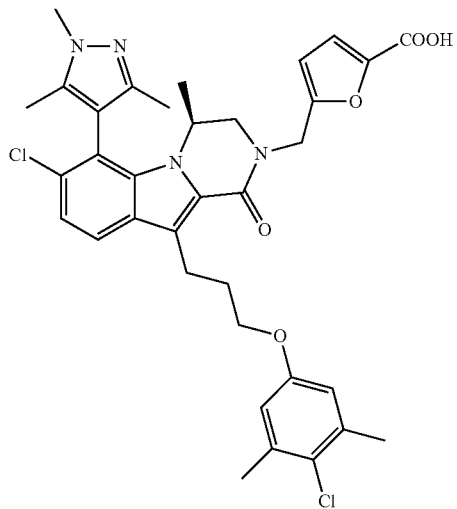 [SMILES: Cc1cc(OCCCc2c3n(c4c(-c5c(C)nn(C)c5C)c(Cl)ccc24)[C@@H](C)CN(Cc2ccc(C(=O)O)o2)C3=O)cc(C)c1Cl]
I-148
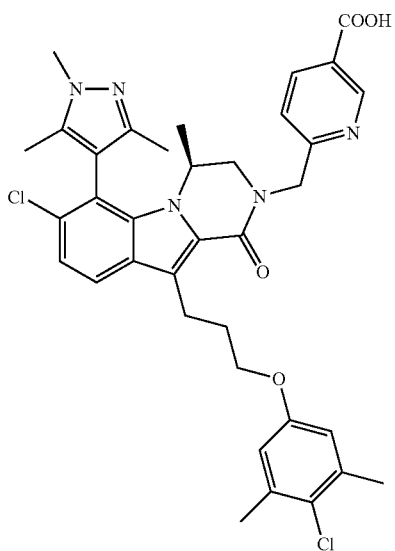 [SMILES: Cc1cc(OCCCc2c3n(c4c(-c5c(C)nn(C)c5C)c(Cl)ccc24)[C@@H](C)CN(Cc2ccc(C(=O)O)cn2)C3=O)cc(C)c1Cl]
I-149
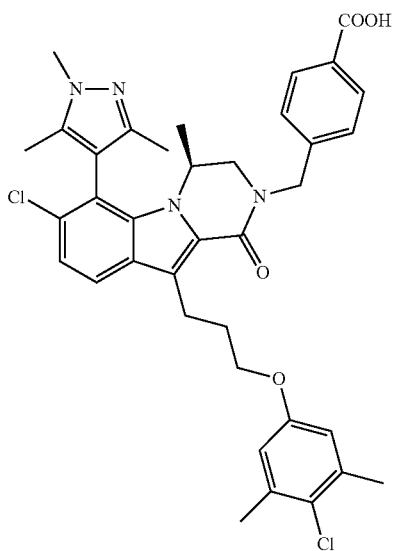 [SMILES: Cc1cc(OCCCc2c3n(c4c(-c5c(C)nn(C)c5C)c(Cl)ccc24)[C@@H](C)CN(Cc2ccc(C(=O)O)cc2)C3=O)cc(C)c1Cl]
I-150

TABLE 1-continued
Exemplary compounds.
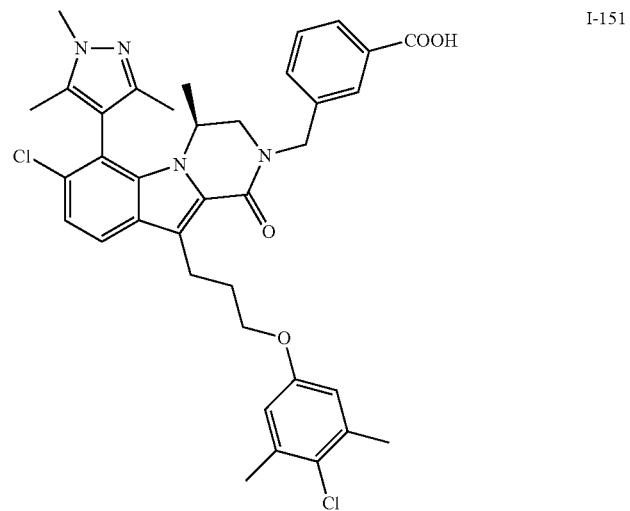
I-151
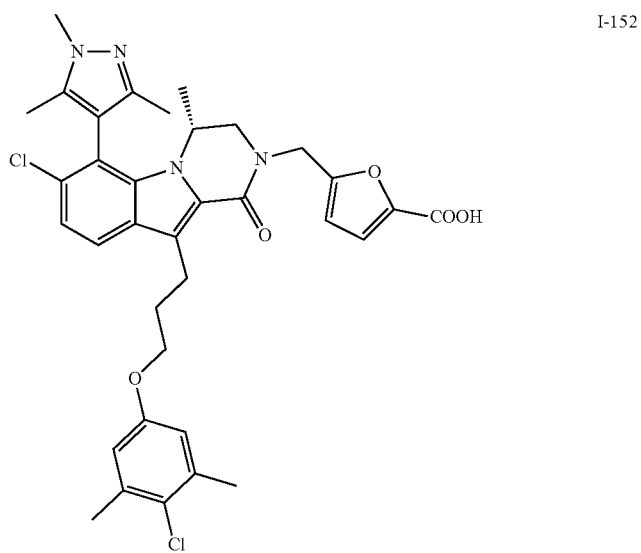
I-152
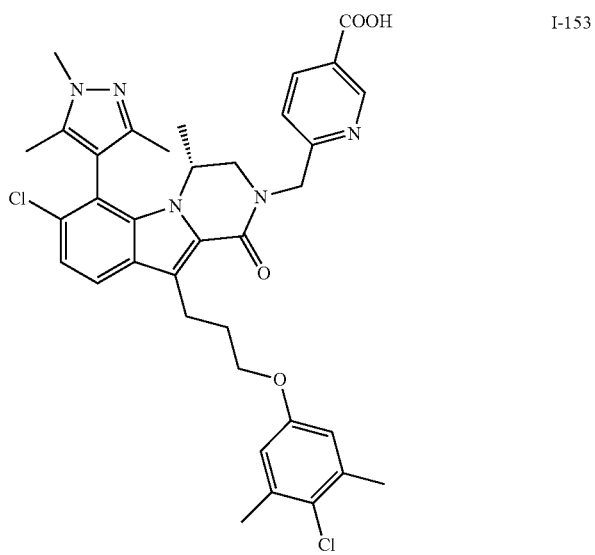
I-153

TABLE 1-continued
Exemplary compounds.
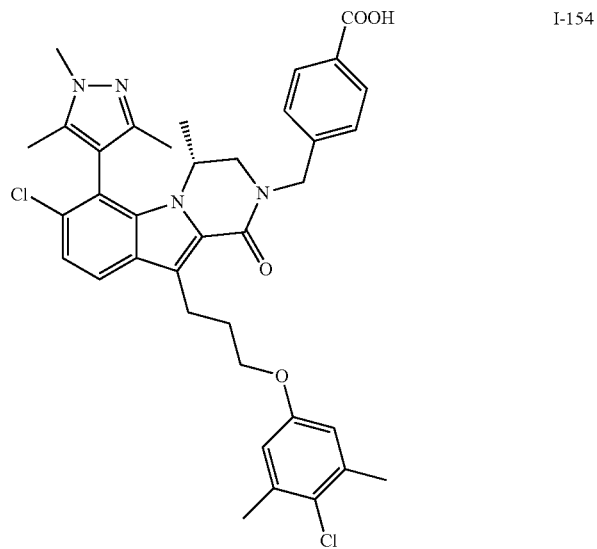
I-154
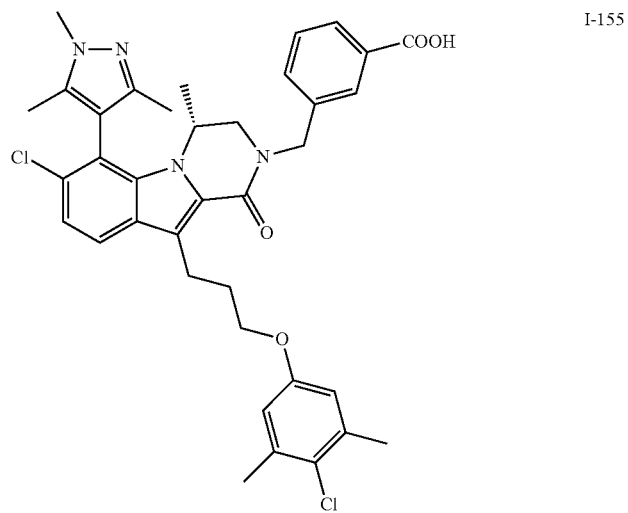
I-155
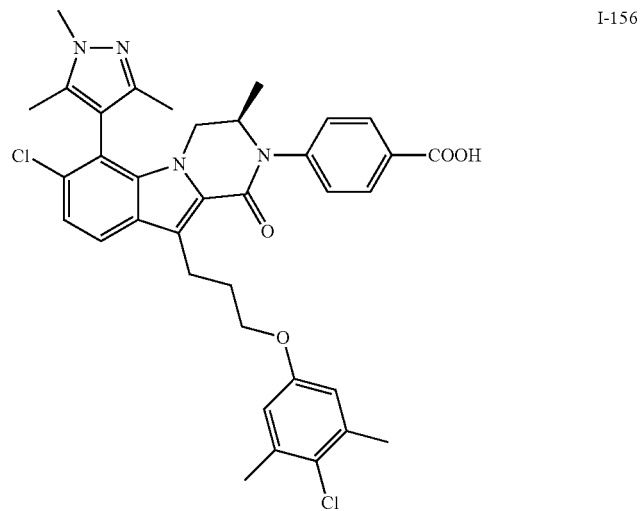
I-156

TABLE 1-continued
Exemplary compounds.
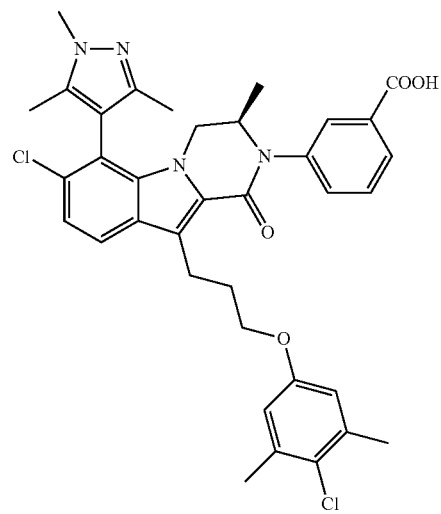 [SMILES: Cc1cc(OCCCc2c3n(c4c(-c5c(C)nn(C)c5C)c(Cl)ccc24)C[C@@H](C)N(c2cccc(C(=O)O)c2)C3=O)cc(C)c1Cl]
I-157
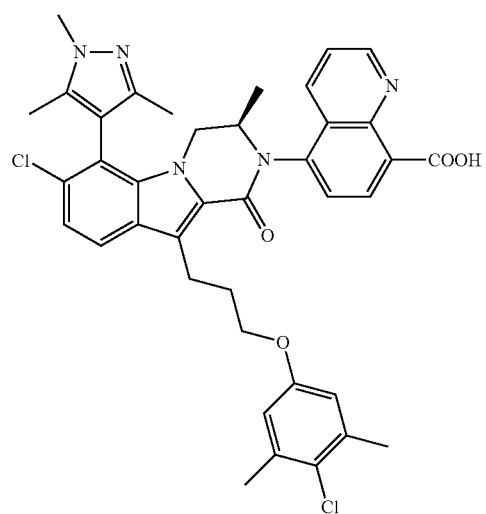 [SMILES: Cc1cc(OCCCc2c3n(c4c(-c5c(C)nn(C)c5C)c(Cl)ccc24)C[C@@H](C)N(c2ccc(C(=O)O)c4ncccc24)C3=O)cc(C)c1Cl]
I-158
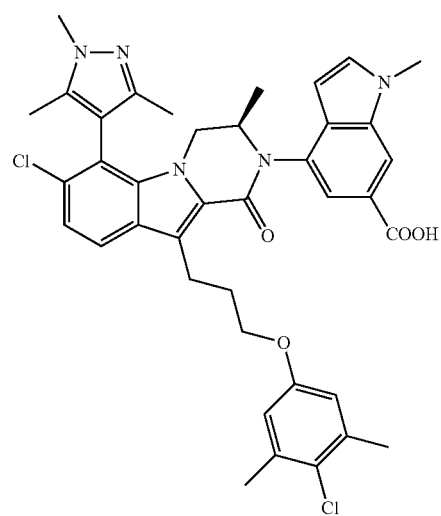 [SMILES: Cc1cc(OCCCc2c3n(c4c(-c5c(C)nn(C)c5C)c(Cl)ccc24)C[C@@H](C)N(c2cc(C(=O)O)cc4c2ccn4C)C3=O)cc(C)c1Cl]
I-159

TABLE 1-continued
Exemplary compounds.
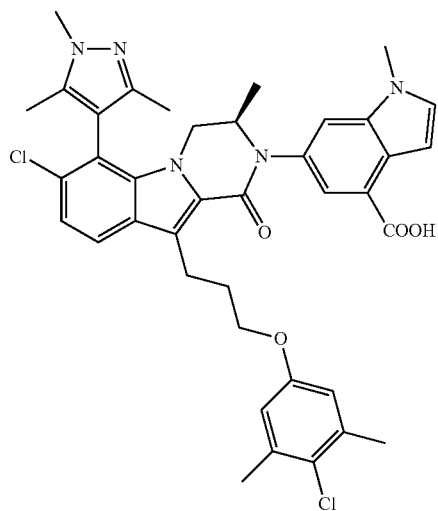 [SMILES: Cc1cc(OCCCc2c3n(c4c(-c5c(C)nn(C)c5C)c(Cl)ccc24)C[C@@H](C)N(c2cc(C(=O)O)c4ccn(C)c4c2)C3=O)cc(C)c1Cl]
I-160
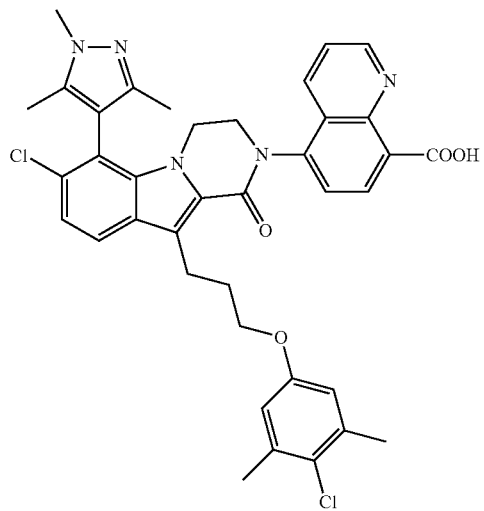 [SMILES: Cc1cc(OCCCc2c3n(c4c(-c5c(C)nn(C)c5C)c(Cl)ccc24)CCN(c2ccc(C(=O)O)c4ncccc24)C3=O)cc(C)c1Cl]
I-161
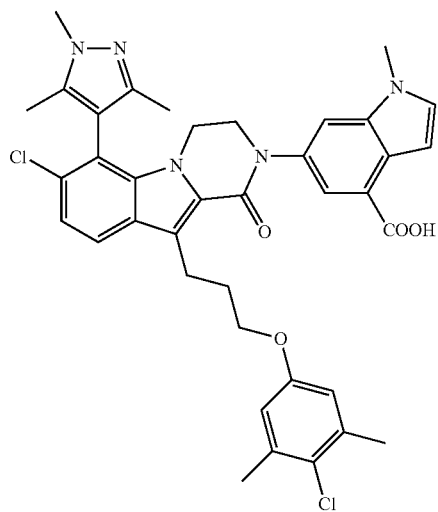 [SMILES: Cc1cc(OCCCc2c3n(c4c(-c5c(C)nn(C)c5C)c(Cl)ccc24)CCN(c2cc(C(=O)O)c4ccn(C)c4c2)C3=O)cc(C)c1Cl]
I-162

TABLE 1-continued
Exemplary compounds.
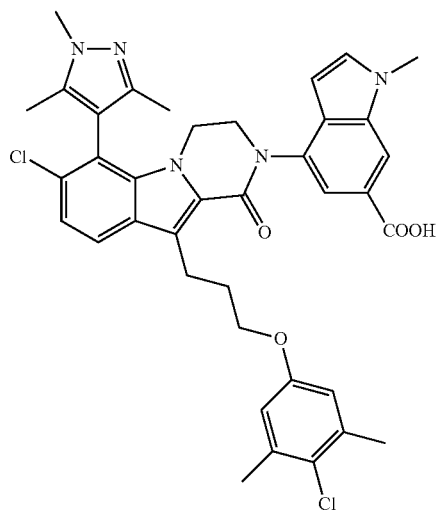 [SMILES: Cc1cc(OCCCc2c3n(c4c(-c5c(C)nn(C)c5C)c(Cl)ccc24)CCN(c2cc(C(=O)O)cc4c2ccn4C)C3=O)cc(C)c1Cl]
I-163
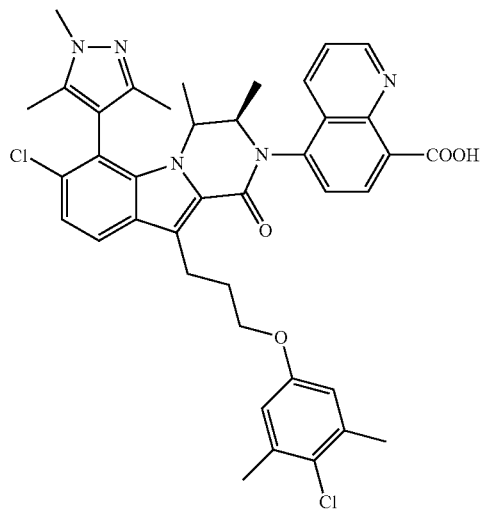 [SMILES: Cc1cc(OCCCc2c3n(c4c(-c5c(C)nn(C)c5C)c(Cl)ccc24)C(C)[C@@H](C)N(c2ccc(C(=O)O)c4ncccc24)C3=O)cc(C)c1Cl]
I-164
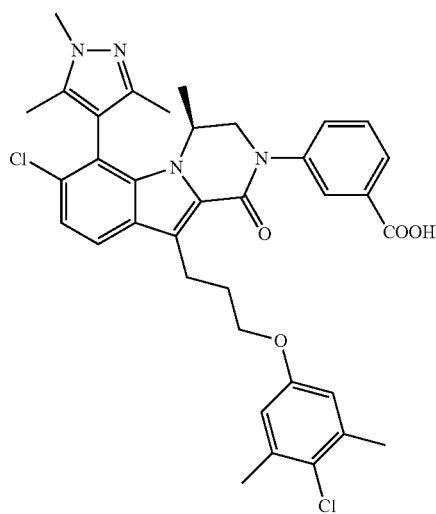 [SMILES: Cc1cc(OCCCc2c3n(c4c(-c5c(C)nn(C)c5C)c(Cl)ccc24)[C@@H](C)CN(c2cccc(C(=O)O)c2)C3=O)cc(C)c1Cl]
I-165

TABLE 1-continued
Exemplary compounds.
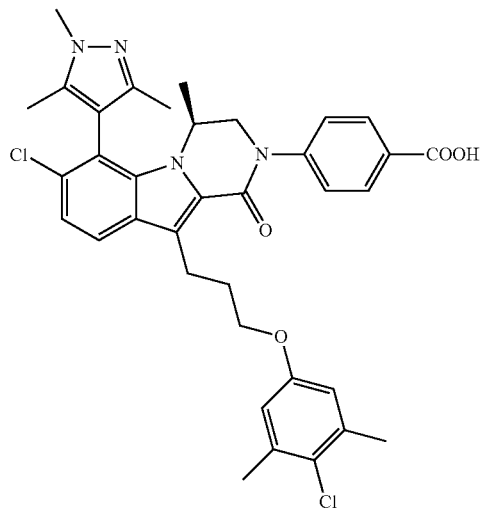 [SMILES: Cc1cc(OCCCc2c3n(c4c(-c5c(C)nn(C)c5C)c(Cl)ccc24)[C@@H](C)CN(c2ccc(C(=O)O)cc2)C3=O)cc(C)c1Cl]
I-166
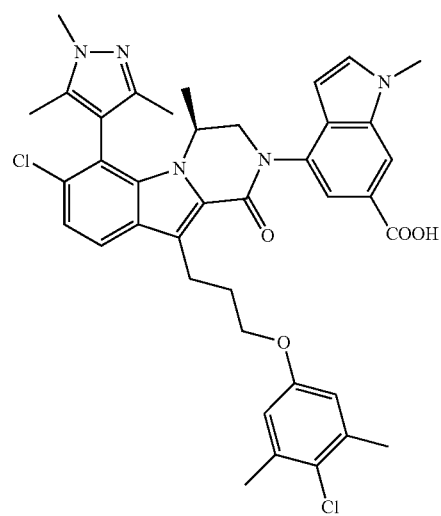 [SMILES: Cc1cc(OCCCc2c3n(c4c(-c5c(C)nn(C)c5C)c(Cl)ccc24)[C@@H](C)CN(c2cc(C(=O)O)cc4c2ccn4C)C3=O)cc(C)c1Cl]
I-167
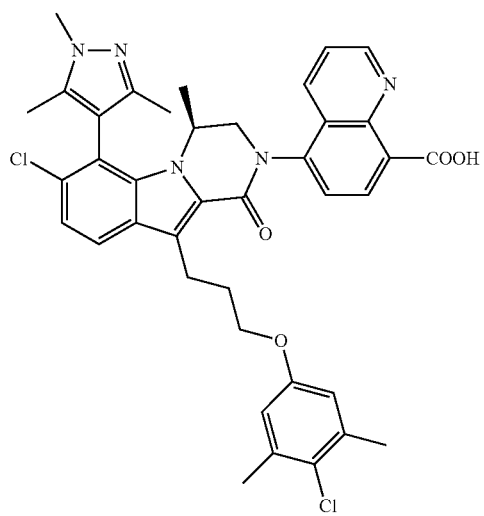 [SMILES: Cc1cc(OCCCc2c3n(c4c(-c5c(C)nn(C)c5C)c(Cl)ccc24)[C@@H](C)CN(c2ccc(C(=O)O)c4ncccc24)C3=O)cc(C)c1Cl]
I-168

TABLE 1-continued
Exemplary compounds.
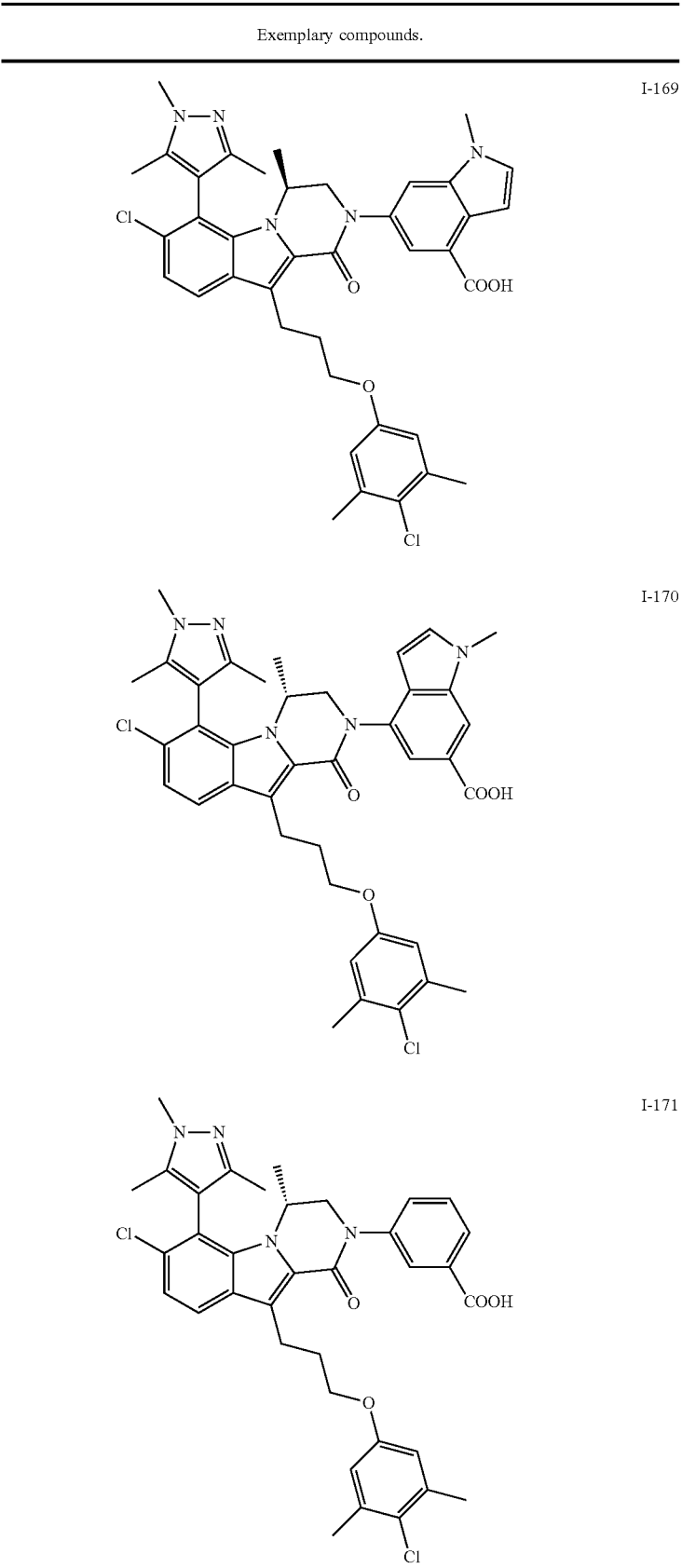
I-169
I-170
I-171

TABLE 1-continued
Exemplary compounds.
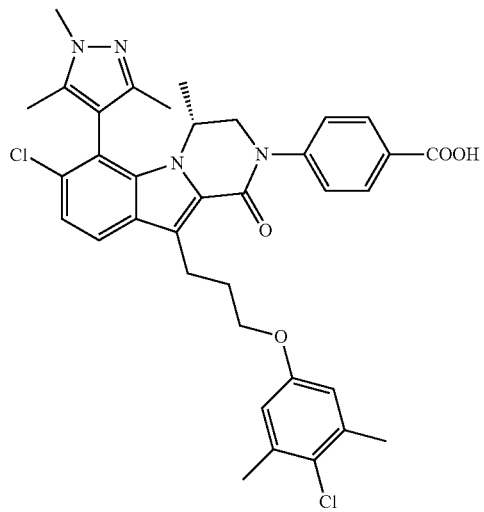 [SMILES: Cc1cc(OCCCc2c3n(c4c(-c5c(C)nn(C)c5C)c(Cl)ccc24)[C@H](C)CN(c2ccc(C(=O)O)cc2)C3=O)cc(C)c1Cl]
I-172
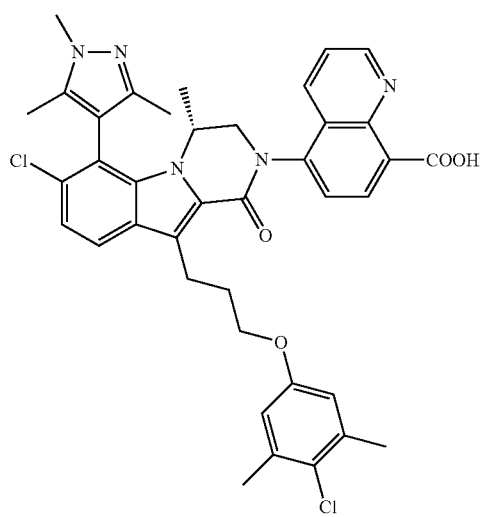 [SMILES: Cc1cc(OCCCc2c3n(c4c(-c5c(C)nn(C)c5C)c(Cl)ccc24)[C@H](C)CN(c2ccc(C(=O)O)c4ncccc24)C3=O)cc(C)c1Cl]
I-173
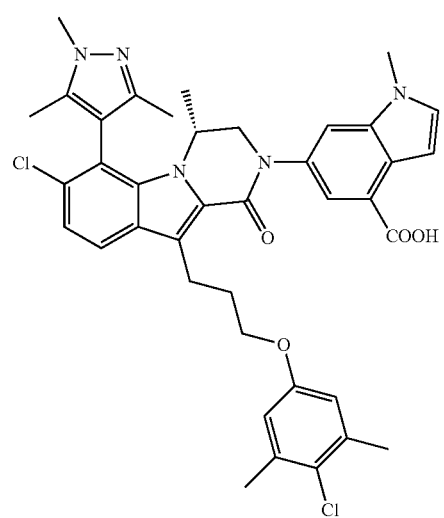 [SMILES: Cc1cc(OCCCc2c3n(c4c(-c5c(C)nn(C)c5C)c(Cl)ccc24)[C@H](C)CN(c2cc(C(=O)O)c4ccn(C)c4c2)C3=O)cc(C)c1Cl]
I-174

TABLE 1-continued
Exemplary compounds.
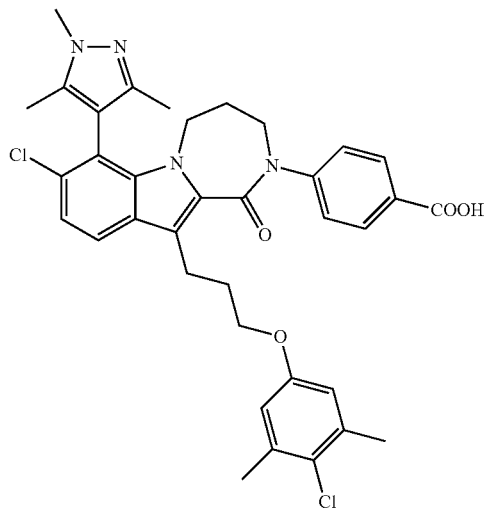 [SMILES: Cc1cc(OCCCc2c3n(c4c(-c5c(C)nn(C)c5C)c(Cl)ccc24)CCCN(c2ccc(C(=O)O)cc2)C3=O)cc(C)c1Cl]
I-175
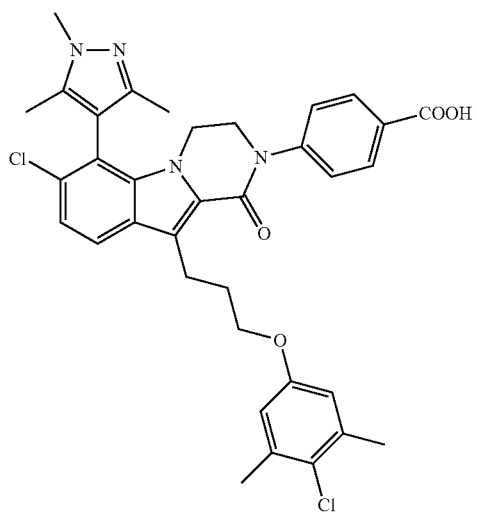 [SMILES: Cc1cc(OCCCc2c3n(c4c(-c5c(C)nn(C)c5C)c(Cl)ccc24)CCN(c2ccc(C(=O)O)cc2)C3=O)cc(C)c1Cl]
I-176
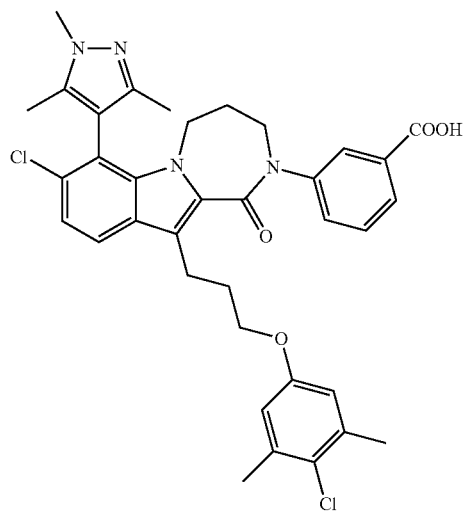 [SMILES: Cc1cc(OCCCc2c3n(c4c(-c5c(C)nn(C)c5C)c(Cl)ccc24)CCCN(c2cccc(C(=O)O)c2)C3=O)cc(C)c1Cl]
I-177

TABLE 1-continued
Exemplary compounds.
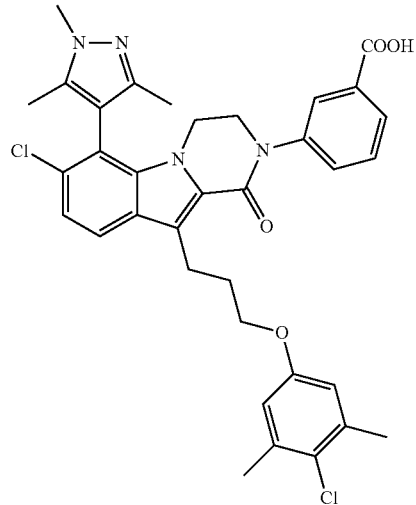 [SMILES: Cc1cc(OCCCc2c3n(c4c(-c5c(C)nn(C)c5C)c(Cl)ccc24)CCN(c2cccc(C(=O)O)c2)C3=O)cc(C)c1Cl]
I-178
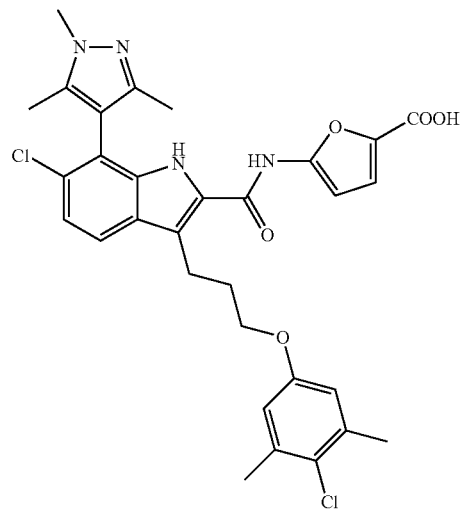 [SMILES: Cc1cc(OCCCc2c(C(=O)Nc3ccc(C(=O)O)o3)[nH]c3c(-c4c(C)nn(C)c4C)c(Cl)ccc23)cc(C)c1Cl]
I-179
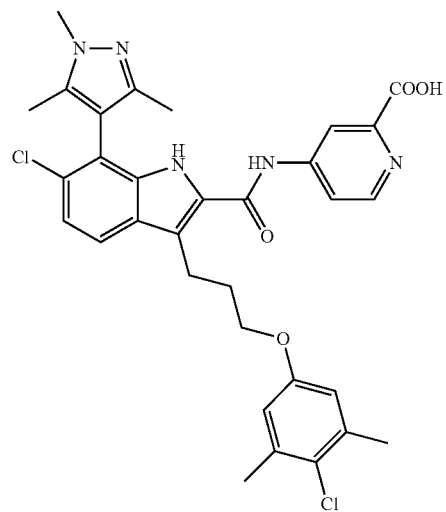 [SMILES: Cc1cc(OCCCc2c(C(=O)Nc3ccnc(C(=O)O)c3)[nH]c3c(-c4c(C)nn(C)c4C)c(Cl)ccc23)cc(C)c1Cl]
I-180

TABLE 1-continued
Exemplary compounds.
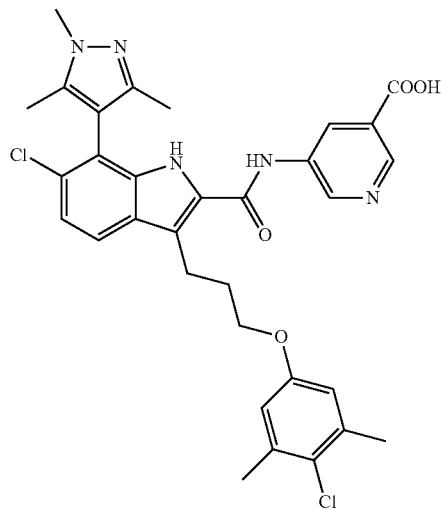 [SMILES: Cc1cc(OCCCc2c(C(=O)Nc3cncc(C(=O)O)c3)[nH]c3c(-c4c(C)nn(C)c4C)c(Cl)ccc23)cc(C)c1Cl]
I-181
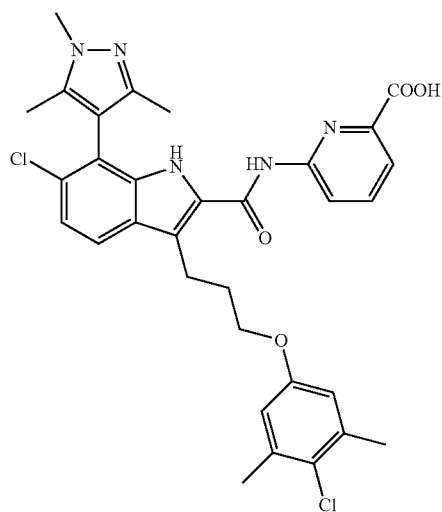 [SMILES: Cc1cc(OCCCc2c(C(=O)Nc3cccc(C(=O)O)n3)[nH]c3c(-c4c(C)nn(C)c4C)c(Cl)ccc23)cc(C)c1Cl]
I-182
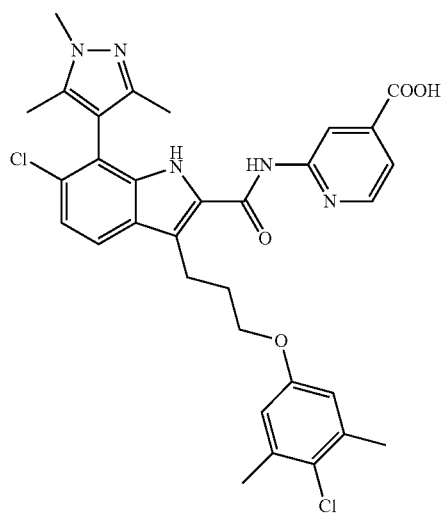 [SMILES: Cc1cc(OCCCc2c(C(=O)Nc3cc(C(=O)O)ccn3)[nH]c3c(-c4c(C)nn(C)c4C)c(Cl)ccc23)cc(C)c1Cl]
I-183

TABLE 1-continued
Exemplary compounds.
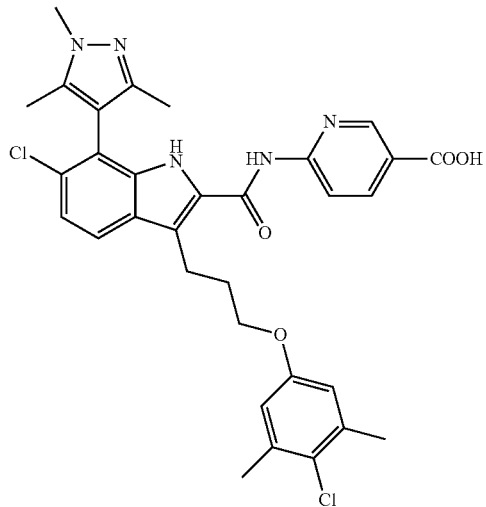 [SMILES: Cc1cc(OCCCc2c(C(=O)Nc3ccc(C(=O)O)cn3)[nH]c3c(-c4c(C)nn(C)c4C)c(Cl)ccc23)cc(C)c1Cl]
I-184
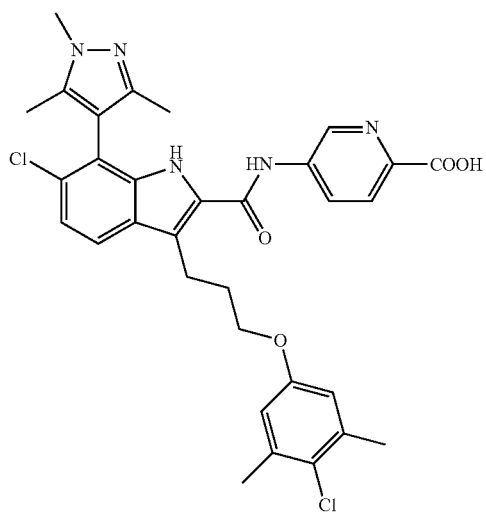 [SMILES: Cc1cc(OCCCc2c(C(=O)Nc3ccc(C(=O)O)nc3)[nH]c3c(-c4c(C)nn(C)c4C)c(Cl)ccc23)cc(C)c1Cl]
I-185
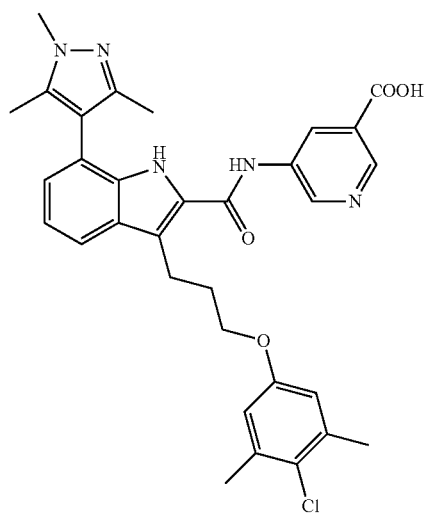 [SMILES: Cc1cc(OCCCc2c(C(=O)Nc3cncc(C(=O)O)c3)[nH]c3c(-c4c(C)nn(C)c4C)cccc23)cc(C)c1Cl]
I-186

TABLE 1-continued
Exemplary compounds.
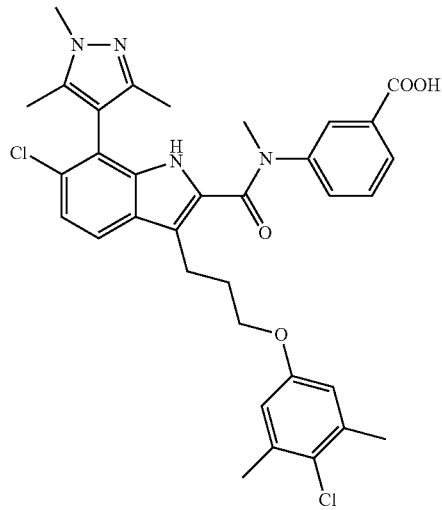 [SMILES: Cc1cc(OCCCc2c(C(=O)N(C)c3cccc(C(=O)O)c3)[nH]c3c(-c4c(C)nn(C)c4C)c(Cl)ccc23)cc(C)c1Cl]
I-187
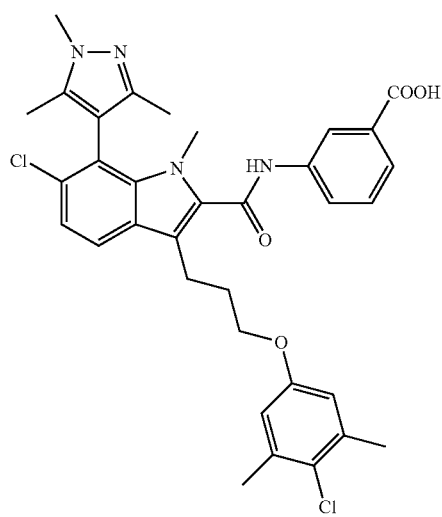 [SMILES: Cc1cc(OCCCc2c(C(=O)Nc3cccc(C(=O)O)c3)n(C)c3c(-c4c(C)nn(C)c4C)c(Cl)ccc23)cc(C)c1Cl]
I-188
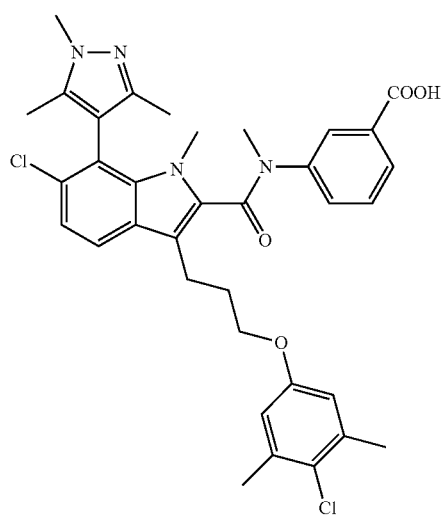 [SMILES: Cc1cc(OCCCc2c(C(=O)N(C)c3cccc(C(=O)O)c3)n(C)c3c(-c4c(C)nn(C)c4C)c(Cl)ccc23)cc(C)c1Cl]
I-189

TABLE 1-continued
Exemplary compounds.
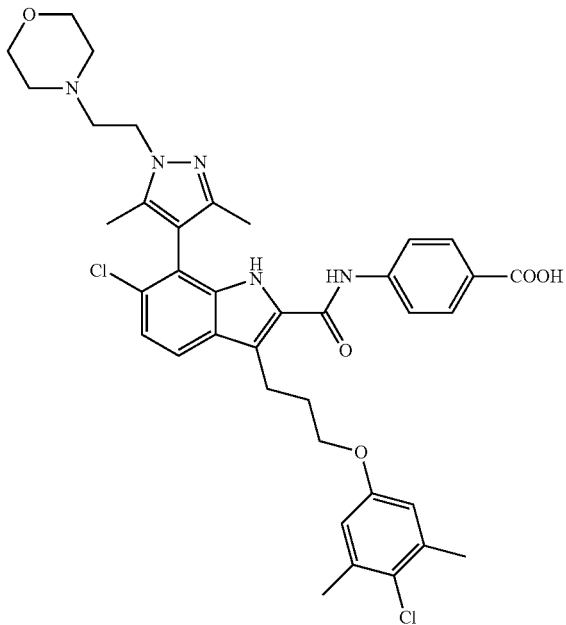 [SMILES: Cc1cc(OCCCc2c(C(=O)Nc3ccc(C(=O)O)cc3)[nH]c3c(-c4c(C)nn(CCN5CCOCC5)c4C)c(Cl)ccc23)cc(C)c1Cl]
I-190
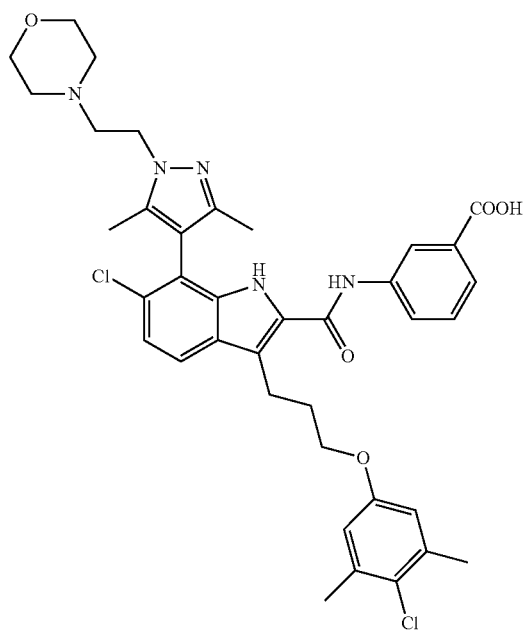 [SMILES: Cc1cc(OCCCc2c(C(=O)Nc3cccc(C(=O)O)c3)[nH]c3c(-c4c(C)nn(CCN5CCOCC5)c4C)c(Cl)ccc23)cc(C)c1Cl]
I-191

TABLE 1-continued
Exemplary compounds.
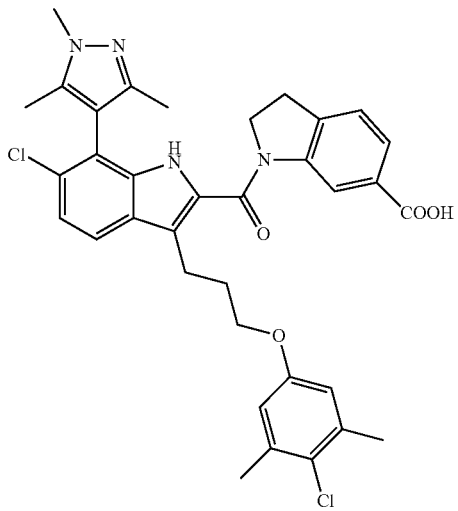 [SMILES: Cc1cc(OCCCc2c(C(=O)N3CCc4ccc(C(=O)O)cc43)[nH]c3c(-c4c(C)nn(C)c4C)c(Cl)ccc23)cc(C)c1Cl]
I-192
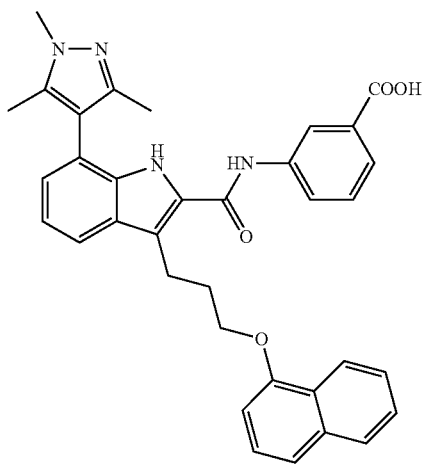 [SMILES: Cc1nn(C)c(C)c1-c1cccc2c(CCCOc3cccc4ccccc34)c(C(=O)Nc3cccc(C(=O)O)c3)[nH]c12]
I-193
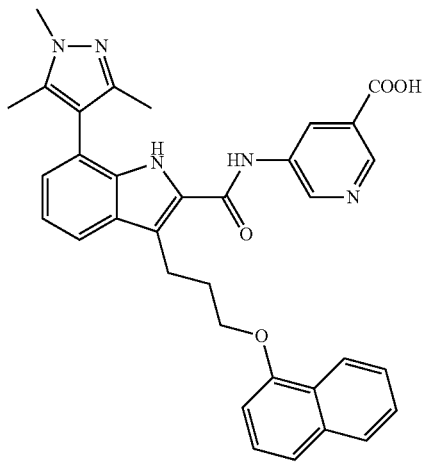 [SMILES: Cc1nn(C)c(C)c1-c1cccc2c(CCCOc3cccc4ccccc34)c(C(=O)Nc3cncc(C(=O)O)c3)[nH]c12]
I-194

TABLE 1-continued
Exemplary compounds.
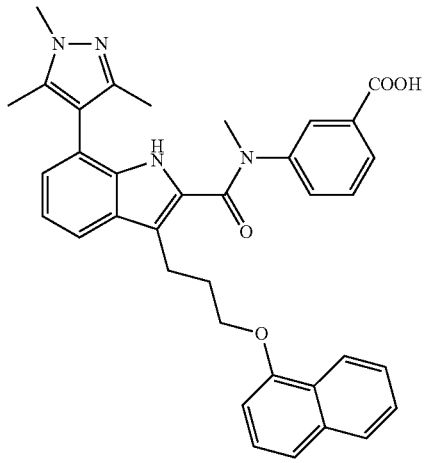 [SMILES: Cc1nn(C)c(C)c1-c1cccc2c(CCCOc3cccc4ccccc34)c(C(=O)N(C)c3cccc(C(=O)O)c3)[nH]c12]
I-195
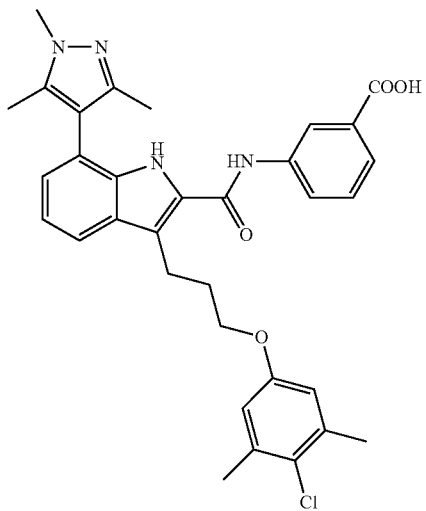 [SMILES: Cc1cc(OCCCc2c(C(=O)Nc3cccc(C(=O)O)c3)[nH]c3c(-c4c(C)nn(C)c4C)cccc23)cc(C)c1Cl]
I-196
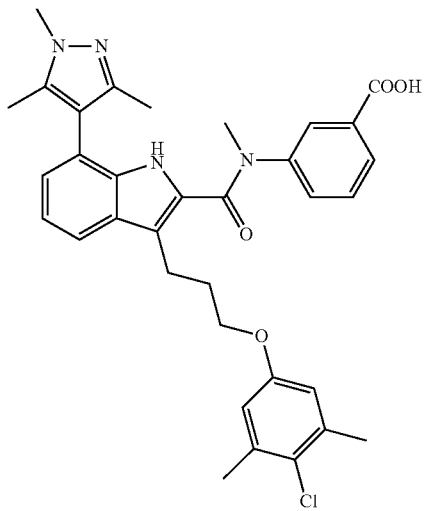 [SMILES: Cc1cc(OCCCc2c(C(=O)N(C)c3cccc(C(=O)O)c3)[nH]c3c(-c4c(C)nn(C)c4C)cccc23)cc(C)c1Cl]
I-197

TABLE 1-continued
Exemplary compounds.
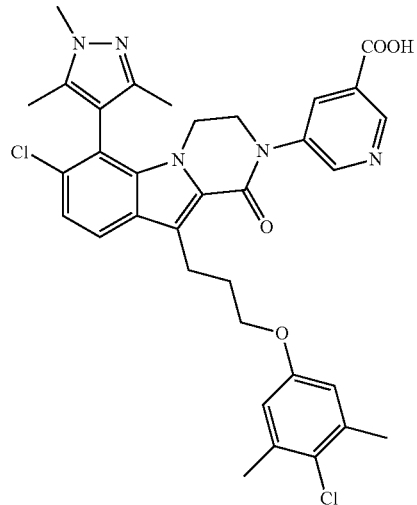 [SMILES: Cc1cc(OCCCc2c3n(c4c(-c5c(C)nn(C)c5C)c(Cl)ccc24)CCN(c2cncc(C(=O)O)c2)C3=O)cc(C)c1Cl]
I-198
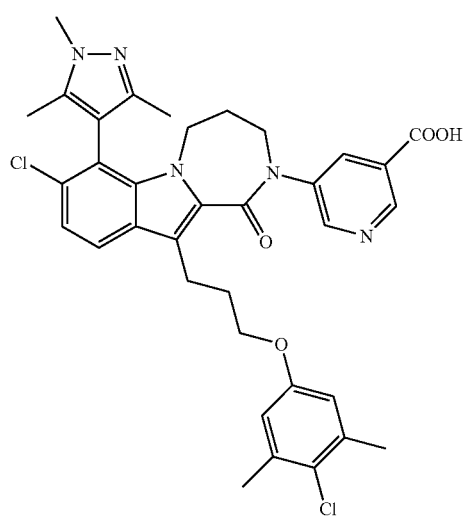 [SMILES: Cc1cc(OCCCc2c3n(c4c(-c5c(C)nn(C)c5C)c(Cl)ccc24)CCCN(c2cncc(C(=O)O)c2)C3=O)cc(C)c1Cl]
I-199
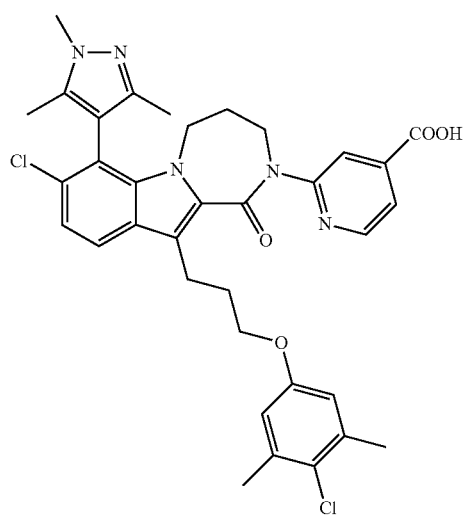 [SMILES: Cc1cc(OCCCc2c3n(c4c(-c5c(C)nn(C)c5C)c(Cl)ccc24)CCCN(c2cc(C(=O)O)ccn2)C3=O)cc(C)c1Cl]
I-200

TABLE 1-continued
Exemplary compounds.
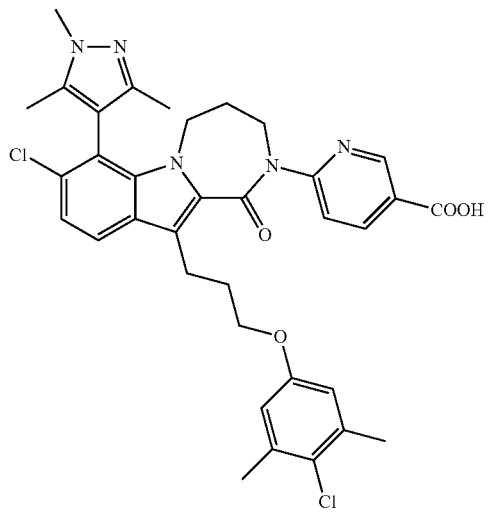 [SMILES: Cc1cc(OCCCc2c3n(c4c(-c5c(C)nn(C)c5C)c(Cl)ccc24)CCCN(c2ccc(C(=O)O)cn2)C3=O)cc(C)c1Cl]
I-201
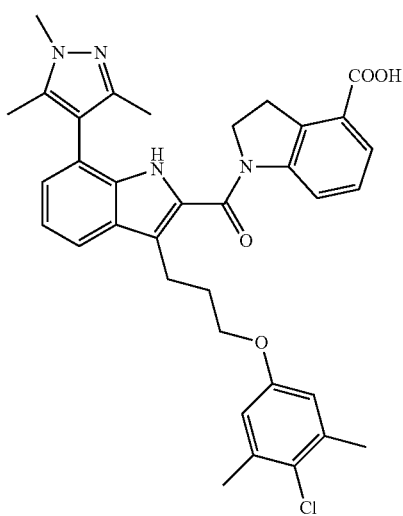 [SMILES: Cc1cc(OCCCc2c(C(=O)N3CCc4c(C(=O)O)cccc43)[nH]c3c(-c4c(C)nn(C)c4C)cccc23)cc(C)c1Cl]
I-202
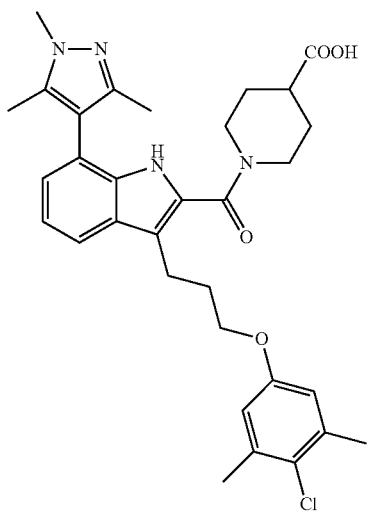
I-203

TABLE 1-continued
Exemplary compounds.
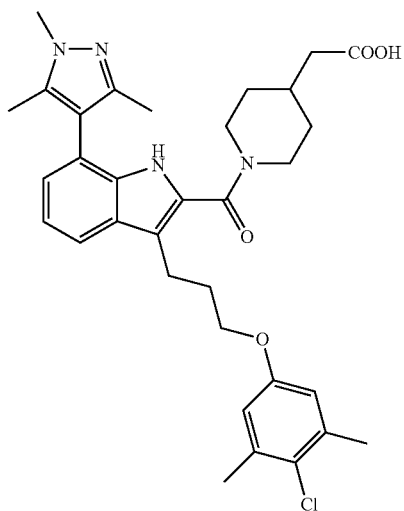
I-204
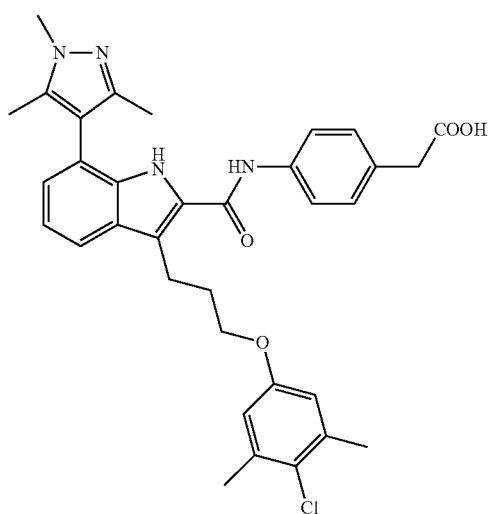 [SMILES: Cc1cc(OCCCc2c(C(=O)Nc3ccc(CC(=O)O)cc3)[nH]c3c(-c4c(C)nn(C)c4C)cccc23)cc(C)c1Cl]
I-205
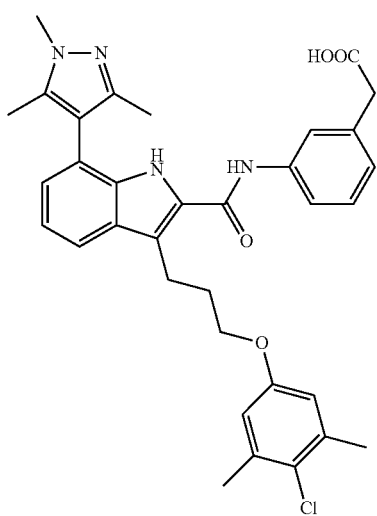 [SMILES: Cc1cc(OCCCc2c(C(=O)Nc3cccc(CC(=O)O)c3)[nH]c3c(-c4c(C)nn(C)c4C)cccc23)cc(C)c1Cl]
I-206

TABLE 1-continued
Exemplary compounds.
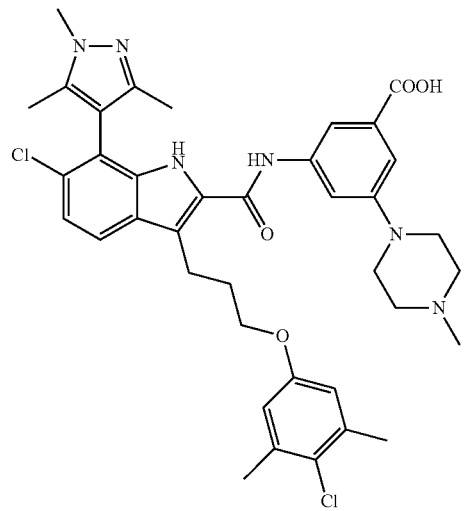 [SMILES: Cc1cc(OCCCc2c(C(=O)Nc3cc(C(=O)O)cc(N4CCN(C)CC4)c3)[nH]c3c(-c4c(C)nn(C)c4C)c(Cl)ccc23)cc(C)c1Cl]
I-207
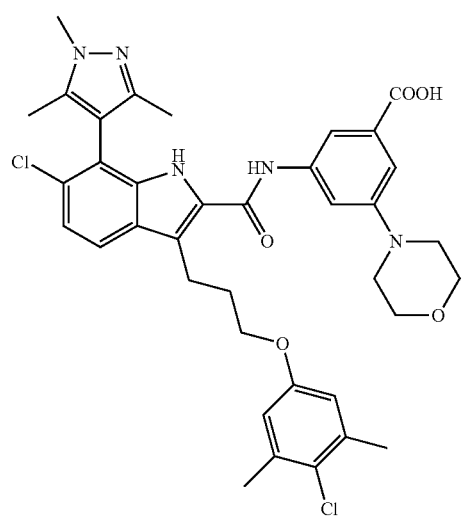 [SMILES: Cc1cc(OCCCc2c(C(=O)Nc3cc(C(=O)O)cc(N4CCOCC4)c3)[nH]c3c(-c4c(C)nn(C)c4C)c(Cl)ccc23)cc(C)c1Cl]
I-208
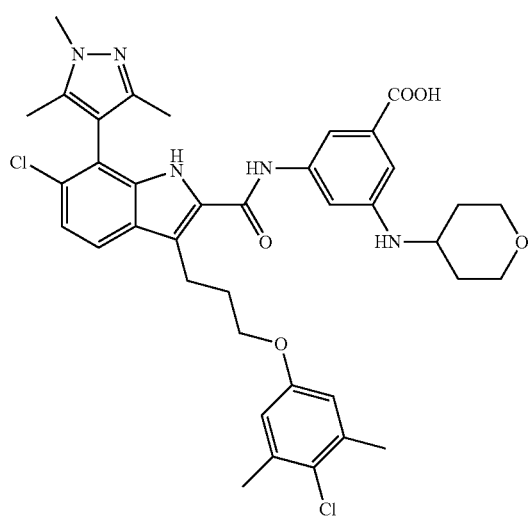 [SMILES: Cc1cc(OCCCc2c(C(=O)Nc3cc(NC4CCOCC4)cc(C(=O)O)c3)[nH]c3c(-c4c(C)nn(C)c4C)c(Cl)ccc23)cc(C)c1Cl]
I-209

TABLE 1-continued
Exemplary compounds.
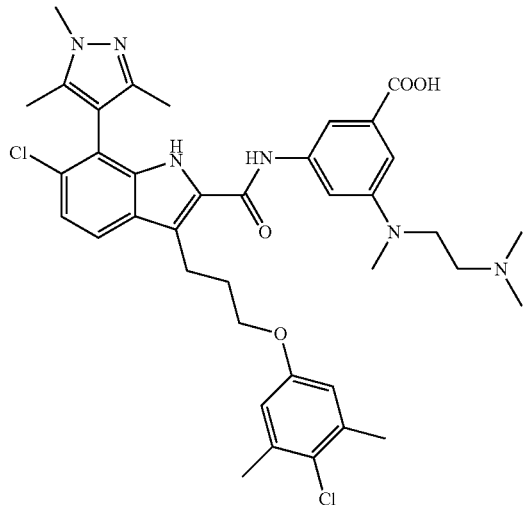 [SMILES: Cc1cc(OCCCc2c(C(=O)Nc3cc(C(=O)O)cc(N(C)CCN(C)C)c3)[nH]c3c(-c4c(C)nn(C)c4C)c(Cl)ccc23)cc(C)c1Cl]
I-210
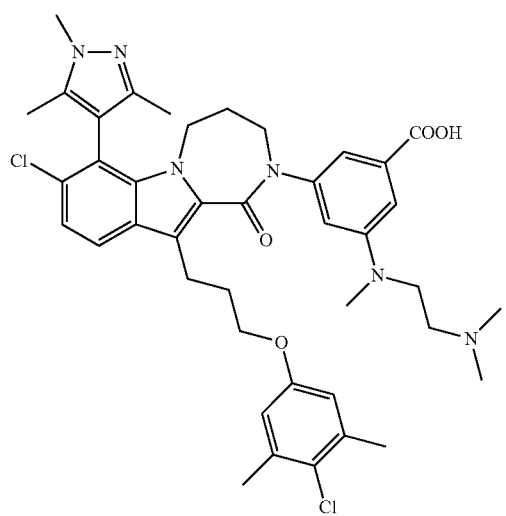 [SMILES: Cc1cc(OCCCc2c3n(c4c(-c5c(C)nn(C)c5C)c(Cl)ccc24)CCCN(c2cc(C(=O)O)cc(N(C)CCN(C)C)c2)C3=O)cc(C)c1Cl]
I-211
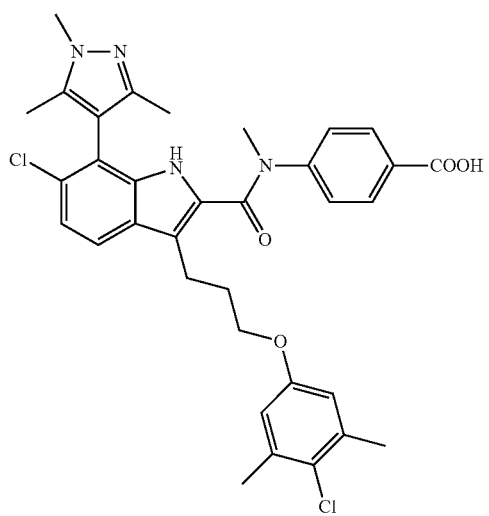 [SMILES: Cc1cc(OCCCc2c(C(=O)N(C)c3ccc(C(=O)O)cc3)[nH]c3c(-c4c(C)nn(C)c4C)c(Cl)ccc23)cc(C)c1Cl]
I-212

TABLE 1-continued
Exemplary compounds.
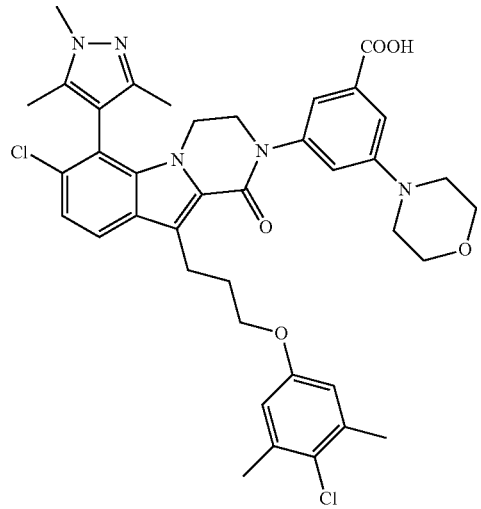 [SMILES: Cc1cc(OCCCc2c3n(c4c(-c5c(C)nn(C)c5C)c(Cl)ccc24)CCN(c2cc(C(=O)O)cc(N4CCOCC4)c2)C3=O)cc(C)c1Cl]
I-213
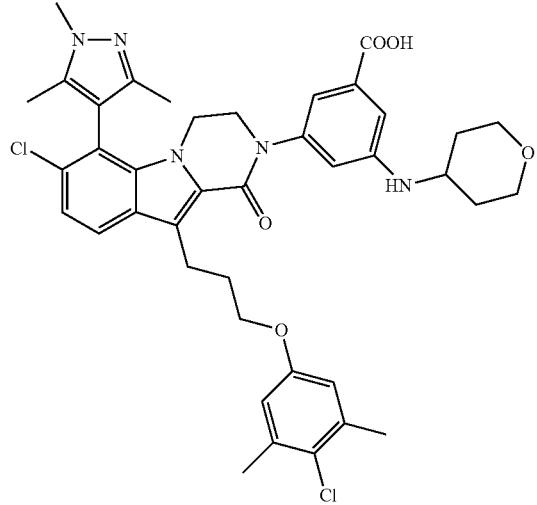 [SMILES: Cc1cc(OCCCc2c3n(c4c(-c5c(C)nn(C)c5C)c(Cl)ccc24)CCN(c2cc(NC4CCOCC4)cc(C(=O)O)c2)C3=O)cc(C)c1Cl]
I-214
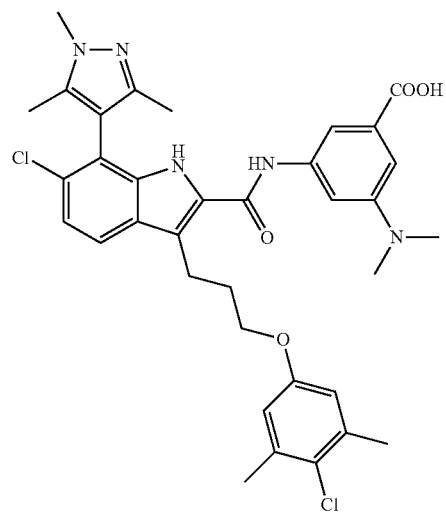 [SMILES: Cc1cc(OCCCc2c(C(=O)Nc3cc(C(=O)O)cc(N(C)C)c3)[nH]c3c(-c4c(C)nn(C)c4C)c(Cl)ccc23)cc(C)c1Cl]
I-215

TABLE 1-continued
Exemplary compounds.
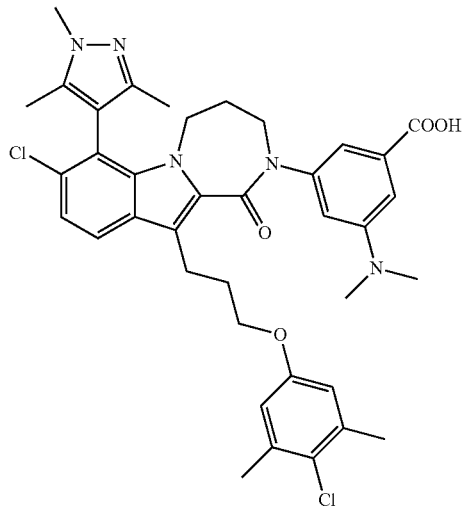 [SMILES: Cc1cc(OCCCc2c3n(c4c(-c5c(C)nn(C)c5C)c(Cl)ccc24)CCCN(c2cc(C(=O)O)cc(N(C)C)c2)C3=O)cc(C)c1Cl]
I-216
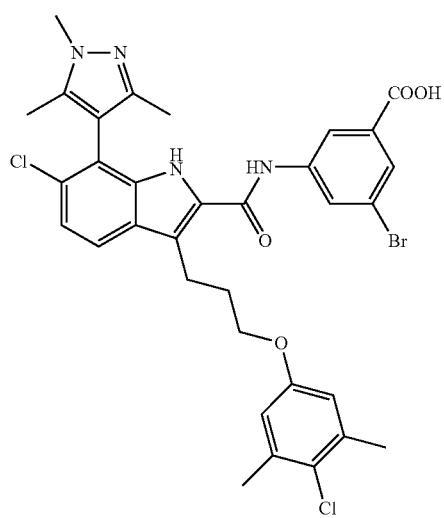 [SMILES: Cc1cc(OCCCc2c(C(=O)Nc3cc(Br)cc(C(=O)O)c3)[nH]c3c(-c4c(C)nn(C)c4C)c(Cl)ccc23)cc(C)c1Cl]
I-217
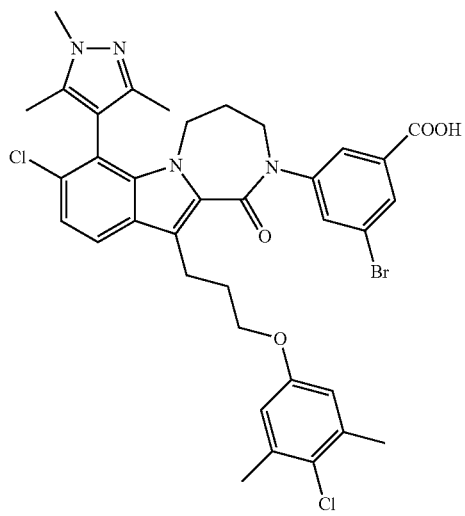
I-218

TABLE 1-continued
Exemplary compounds.
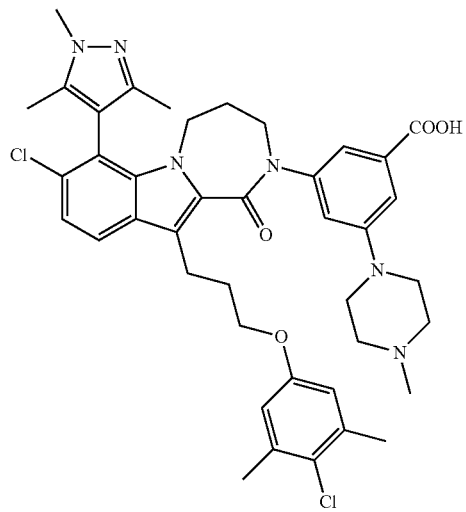 [SMILES: Cc1cc(OCCCc2c3n(c4c(-c5c(C)nn(C)c5C)c(Cl)ccc24)CCCN(c2cc(C(=O)O)cc(N4CCN(C)CC4)c2)C3=O)cc(C)c1Cl]
I-219
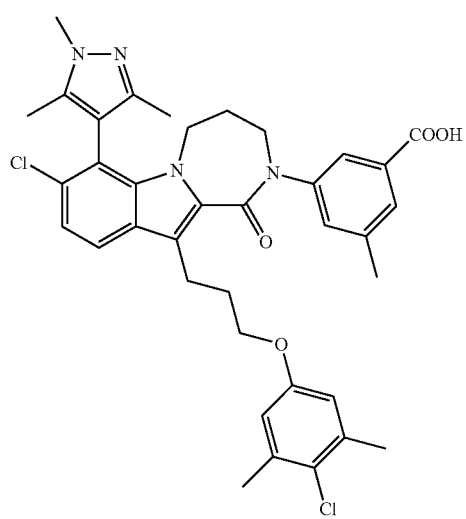 [SMILES: Cc1cc(C(=O)O)cc(N2CCCn3c(c(CCCOc4cc(C)c(Cl)c(C)c4)c4ccc(Cl)c(-c5c(C)nn(C)c5C)c43)C2=O)c1]
I-220
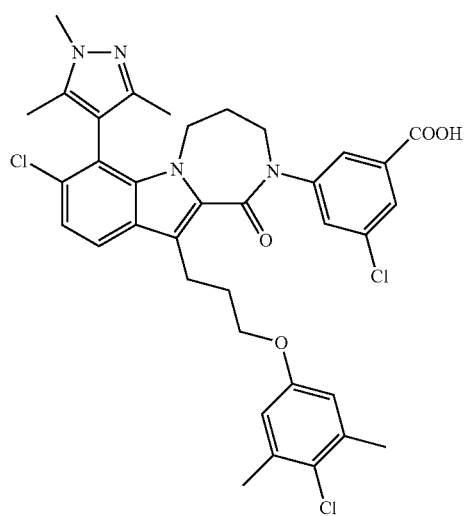
I-221

TABLE 1-continued
Exemplary compounds.
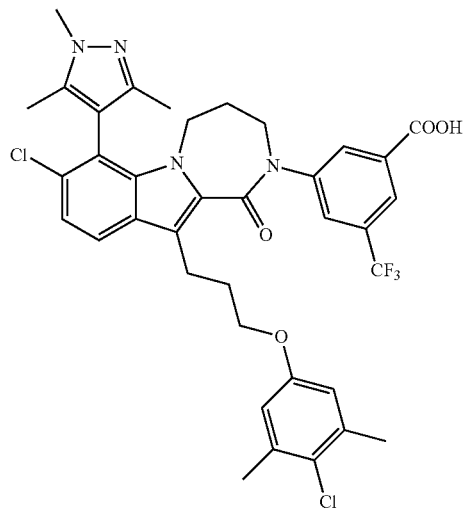
I-222
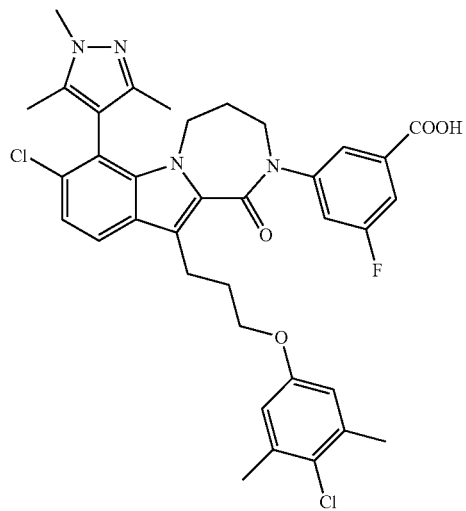 [SMILES: Cc1cc(OCCCc2c3n(c4c(-c5c(C)nn(C)c5C)c(Cl)ccc24)CCCN(c2cc(F)cc(C(=O)O)c2)C3=O)cc(C)c1Cl]
I-223
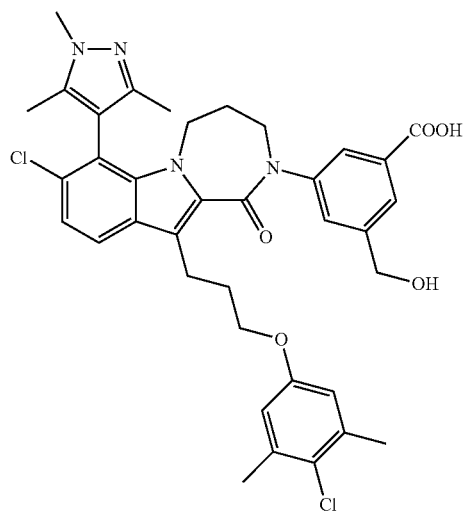 [SMILES: Cc1cc(OCCCc2c3n(c4c(-c5c(C)nn(C)c5C)c(Cl)ccc24)CCCN(c2cc(CO)cc(C(=O)O)c2)C3=O)cc(C)c1Cl]
I-224

TABLE 1-continued
Exemplary compounds.
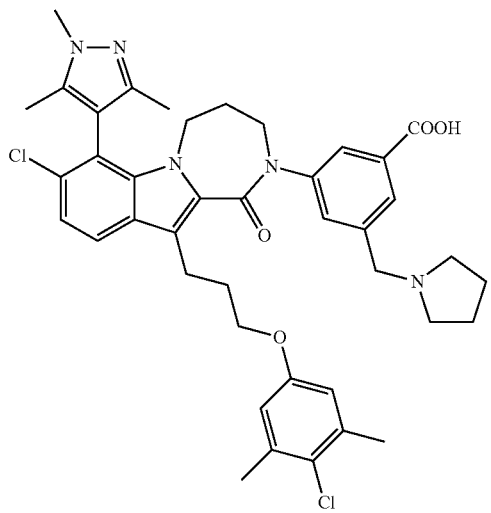 [SMILES: Cc1cc(OCCCc2c3n(c4c(-c5c(C)nn(C)c5C)c(Cl)ccc24)CCCN(c2cc(CN4CCCC4)cc(C(=O)O)c2)C3=O)cc(C)c1Cl]
I-225
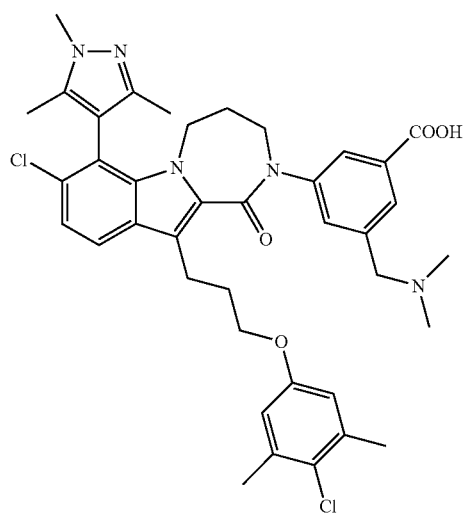 [SMILES: Cc1cc(OCCCc2c3n(c4c(-c5c(C)nn(C)c5C)c(Cl)ccc24)CCCN(c2cc(CN(C)C)cc(C(=O)O)c2)C3=O)cc(C)c1Cl]
I-226
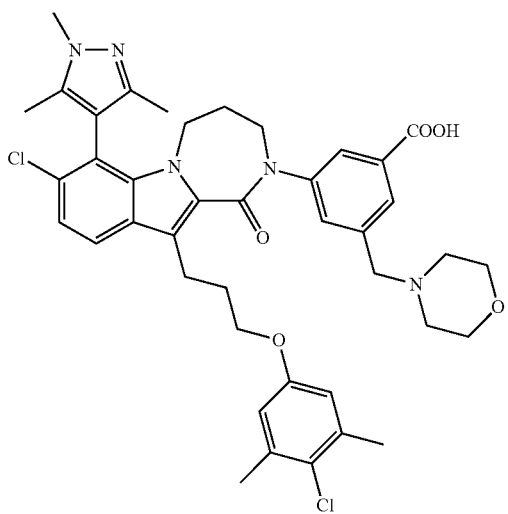 [SMILES: Cc1cc(OCCCc2c3n(c4c(-c5c(C)nn(C)c5C)c(Cl)ccc24)CCCN(c2cc(CN4CCOCC4)cc(C(=O)O)c2)C3=O)cc(C)c1Cl]
I-227

TABLE 1-continued
Exemplary compounds.
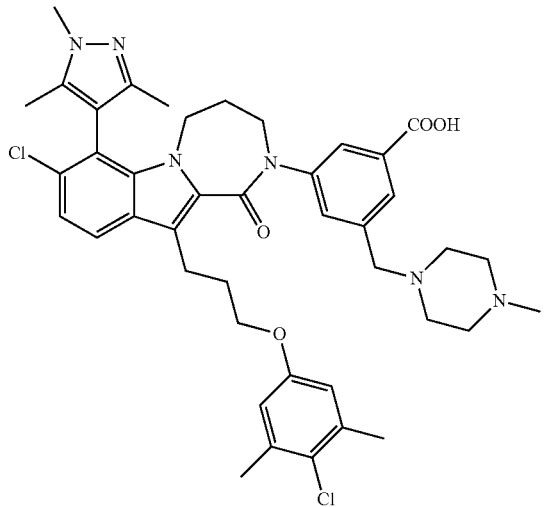 [SMILES: Cc1cc(OCCCc2c3n(c4c(-c5c(C)nn(C)c5C)c(Cl)ccc24)CCCN(c2cc(CN4CCN(C)CC4)cc(C(=O)O)c2)C3=O)cc(C)c1Cl]
I-228
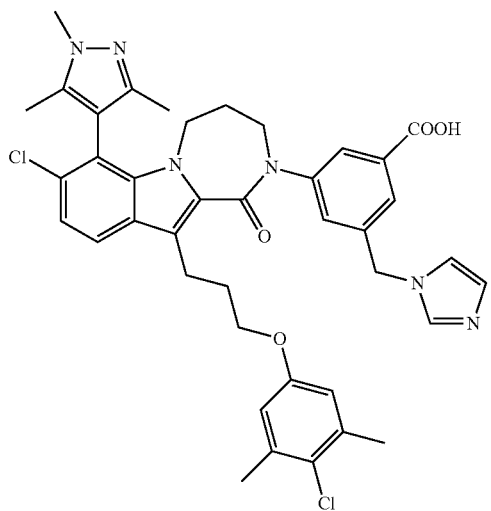 [SMILES: Cc1cc(OCCCc2c3n(c4c(-c5c(C)nn(C)c5C)c(Cl)ccc24)CCCN(c2cc(Cn4ccnc4)cc(C(=O)O)c2)C3=O)cc(C)c1Cl]
I-229
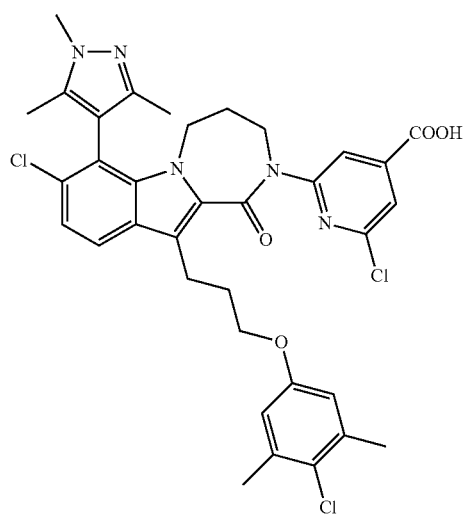 [SMILES: Cc1cc(OCCCc2c3n(c4c(-c5c(C)nn(C)c5C)c(Cl)ccc24)CCCN(c2cc(C(=O)O)cc(Cl)n2)C3=O)cc(C)c1Cl]
I-230

TABLE 1-continued
Exemplary compounds.
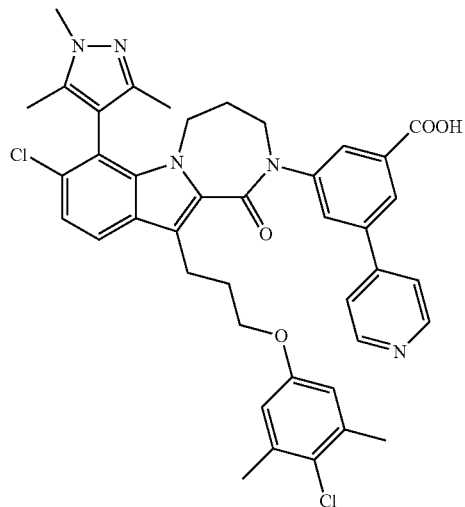 [SMILES: Cc1cc(OCCCc2c3n(c4c(-c5c(C)nn(C)c5C)c(Cl)ccc24)CCCN(c2cc(C(=O)O)cc(-c4ccncc4)c2)C3=O)cc(C)c1Cl]
I-231
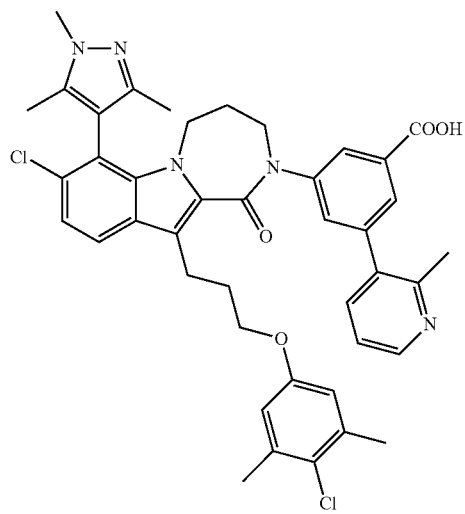 [SMILES: Cc1cc(OCCCc2c3n(c4c(-c5c(C)nn(C)c5C)c(Cl)ccc24)CCCN(c2cc(C(=O)O)cc(-c4cccnc4C)c2)C3=O)cc(C)c1Cl]
I-232
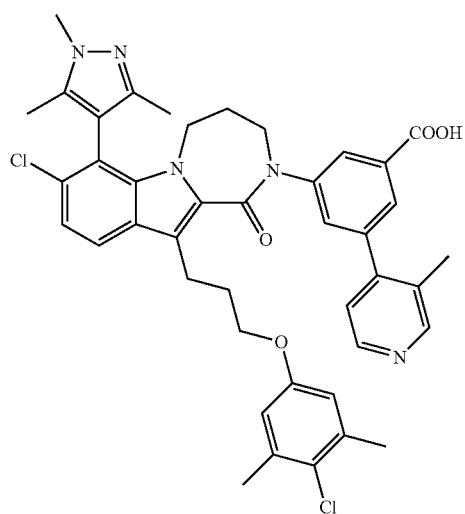 [SMILES: Cc1cnccc1-c1cc(C(=O)O)cc(N2CCCn3c(c(CCCOc4cc(C)c(Cl)c(C)c4)c4ccc(Cl)c(-c5c(C)nn(C)c5C)c43)C2=O)c1]
I-233

TABLE 1-continued
Exemplary compounds.
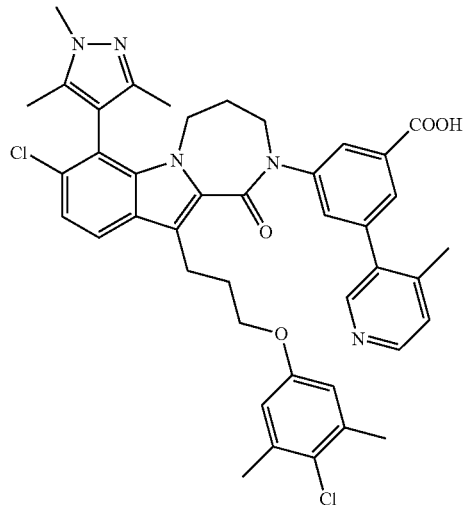 [SMILES: Cc1ccncc1-c1cc(C(=O)O)cc(N2CCCn3c(c(CCCOc4cc(C)c(Cl)c(C)c4)c4ccc(Cl)c(-c5c(C)nn(C)c5C)c43)C2=O)c1]
I-234
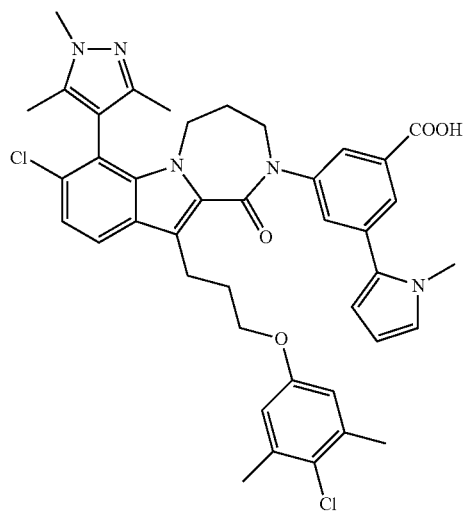 [SMILES: Cc1cc(OCCCc2c3n(c4c(-c5c(C)nn(C)c5C)c(Cl)ccc24)CCCN(c2cc(C(=O)O)cc(-c4cccn4C)c2)C3=O)cc(C)c1Cl]
I-235
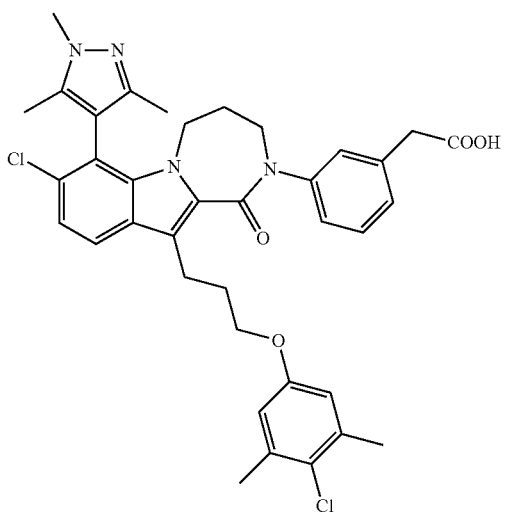 [SMILES: Cc1cc(OCCCc2c3n(c4c(-c5c(C)nn(C)c5C)c(Cl)ccc24)CCCN(c2cccc(CC(=O)O)c2)C3=O)cc(C)c1Cl]
I-236

TABLE 1-continued
Exemplary compounds.
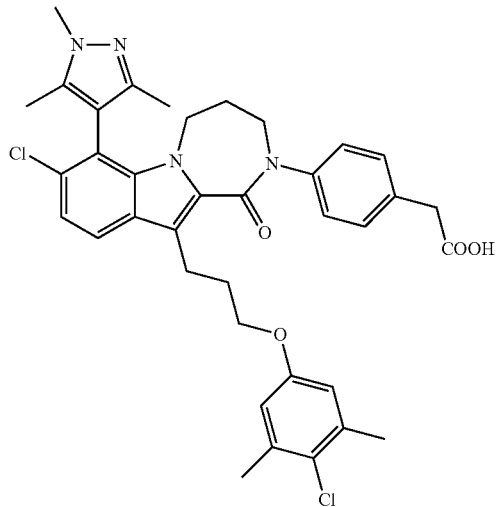 [SMILES: Cc1cc(OCCCc2c3n(c4c(-c5c(C)nn(C)c5C)c(Cl)ccc24)CCCN(c2ccc(CC(=O)O)cc2)C3=O)cc(C)c1Cl]
I-237
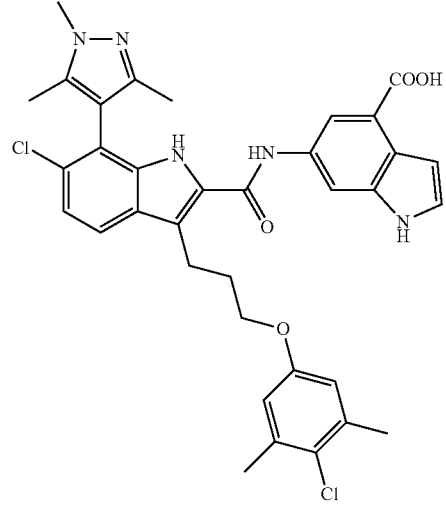 [SMILES: Cc1cc(OCCCc2c(C(=O)Nc3cc(C(=O)O)c4cc[nH]c4c3)[nH]c3c(-c4c(C)nn(C)c4C)c(Cl)ccc23)cc(C)c1Cl]
I-238
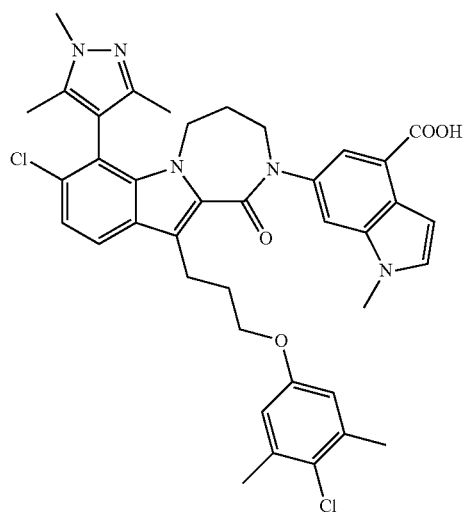 [SMILES: Cc1cc(OCCCc2c3n(c4c(-c5c(C)nn(C)c5C)c(Cl)ccc24)CCCN(c2cc(C(=O)O)c4ccn(C)c4c2)C3=O)cc(C)c1Cl]
I-239

TABLE 1-continued
Exemplary compounds.
I-240
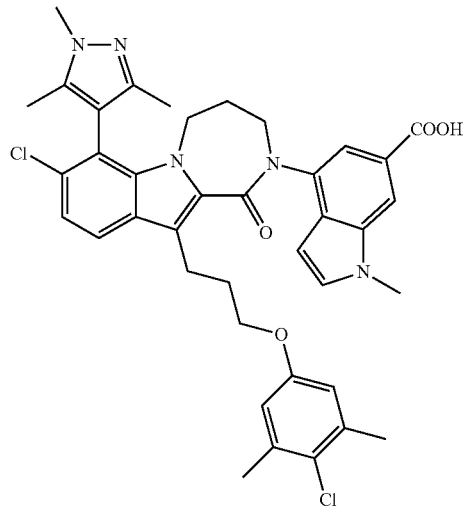 [SMILES: Cc1cc(OCCCc2c3n(c4c(-c5c(C)nn(C)c5C)c(Cl)ccc24)CCCN(c2cc(C(=O)O)cc4c2ccn4C)C3=O)cc(C)c1Cl]
I-241
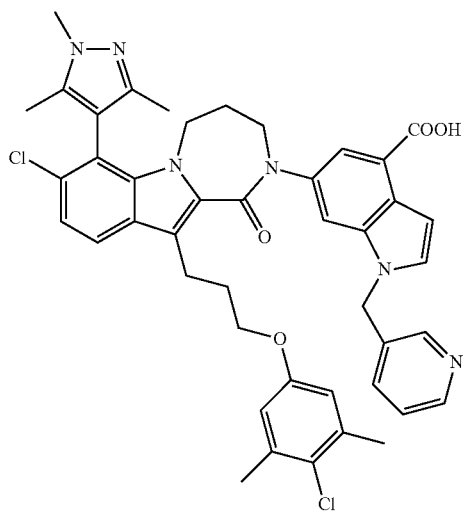 [SMILES: Cc1cc(OCCCc2c3n(c4c(-c5c(C)nn(C)c5C)c(Cl)ccc24)CCCN(c2cc(C(=O)O)c4ccn(Cc5cccnc5)c4c2)C3=O)cc(C)c1Cl]
I-242
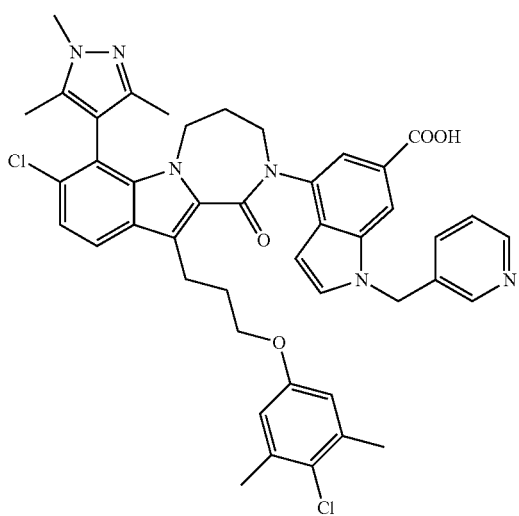 [SMILES: Cc1cc(OCCCc2c3n(c4c(-c5c(C)nn(C)c5C)c(Cl)ccc24)CCCN(c2cc(C(=O)O)cc4c2ccn4Cc2cccnc2)C3=O)cc(C)c1Cl]

TABLE 1-continued
Exemplary compounds.
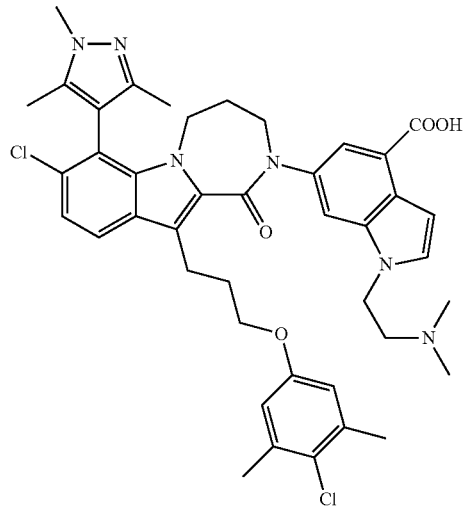 [SMILES: Cc1cc(OCCCc2c3n(c4c(-c5c(C)nn(C)c5C)c(Cl)ccc24)CCCN(c2cc(C(=O)O)c4ccn(CCN(C)C)c4c2)C3=O)cc(C)c1Cl]
I-243
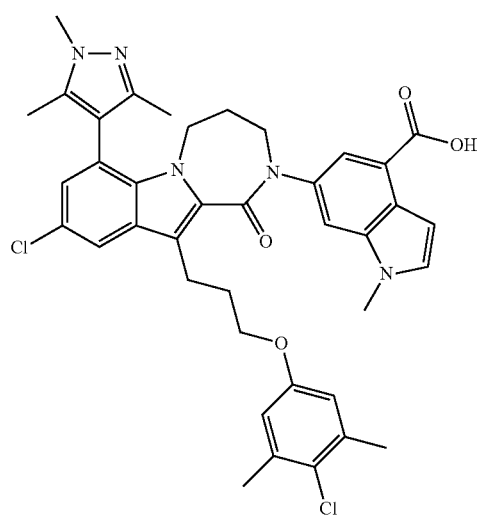 [SMILES: Cc1cc(OCCCc2c3n(c4c(-c5c(C)nn(C)c5C)cc(Cl)cc24)CCCN(c2cc(C(=O)O)c4ccn(C)c4c2)C3=O)cc(C)c1Cl]
I-244
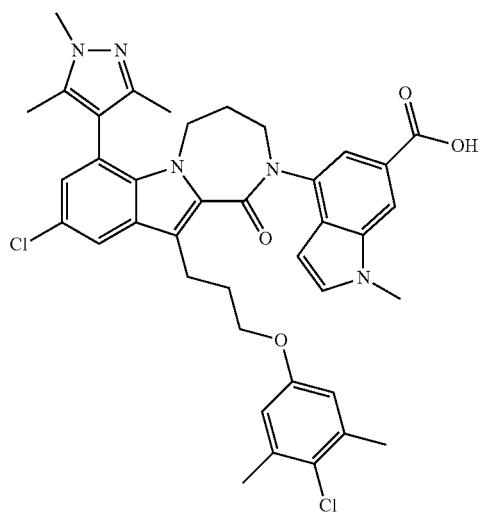 [SMILES: Cc1cc(OCCCc2c3n(c4c(-c5c(C)nn(C)c5C)cc(Cl)cc24)CCCN(c2cc(C(=O)O)cc4c2ccn4C)C3=O)cc(C)c1Cl]
I-245

TABLE 1-continued
Exemplary compounds.
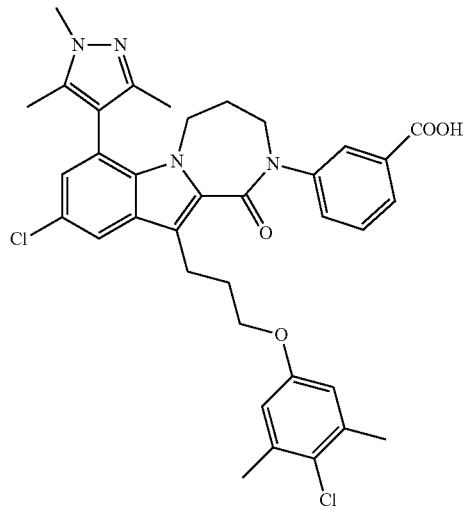 [SMILES: Cc1cc(OCCCc2c3n(c4c(-c5c(C)nn(C)c5C)cc(Cl)cc24)CCCN(c2cccc(C(=O)O)c2)C3=O)cc(C)c1Cl]
I-246
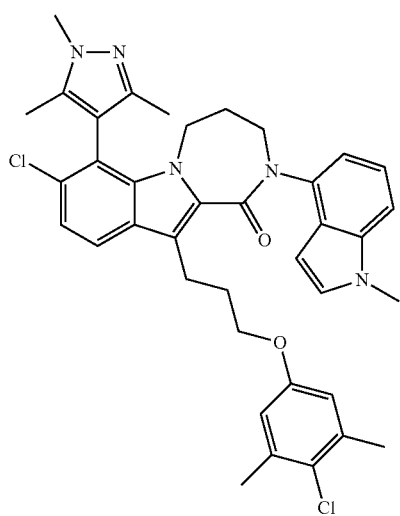 [SMILES: Cc1cc(OCCCc2c3n(c4c(-c5c(C)nn(C)c5C)c(Cl)ccc24)CCCN(c2cccc4c2ccn4C)C3=O)cc(C)c1Cl]
I-247
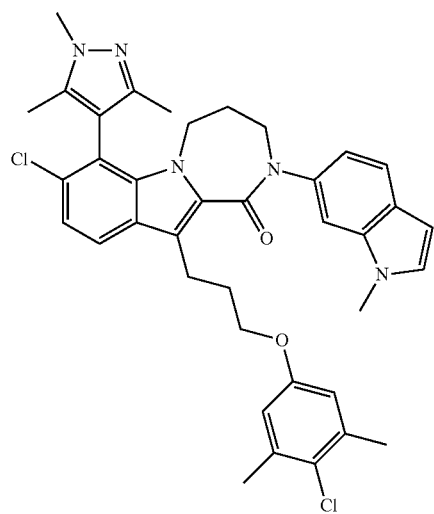 [SMILES: Cc1cc(OCCCc2c3n(c4c(-c5c(C)nn(C)c5C)c(Cl)ccc24)CCCN(c2ccc4ccn(C)c4c2)C3=O)cc(C)c1Cl]
I-248

TABLE 1-continued
Exemplary compounds.
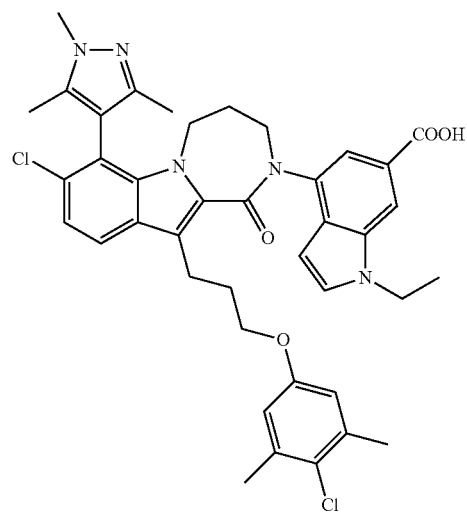 [SMILES: CCn1ccc2c(N3CCCn4c(c(CCCOc5cc(C)c(Cl)c(C)c5)c5ccc(Cl)c(-c6c(C)nn(C)c6C)c54)C3=O)cc(C(=O)O)cc21]
I-249
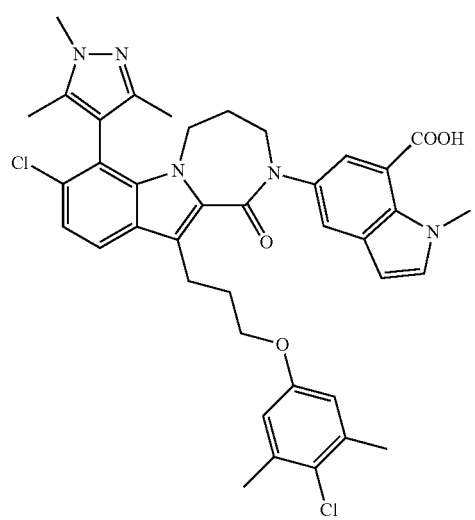 [SMILES: Cc1cc(OCCCc2c3n(c4c(-c5c(C)nn(C)c5C)c(Cl)ccc24)CCCN(c2cc(C(=O)O)c4c(ccn4C)c2)C3=O)cc(C)c1Cl]
I-250
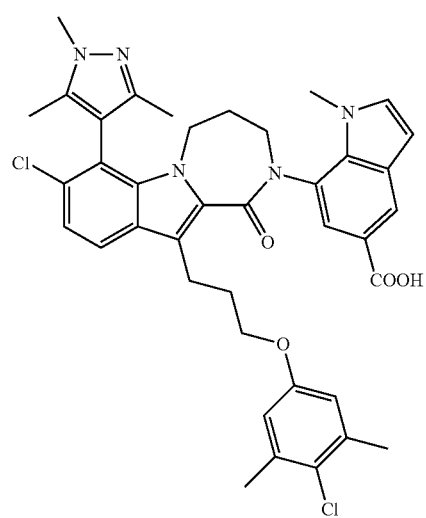 [SMILES: Cc1cc(OCCCc2c3n(c4c(-c5c(C)nn(C)c5C)c(Cl)ccc24)CCCN(c2cc(C(=O)O)cc4ccn(C)c24)C3=O)cc(C)c1Cl]
I-251

TABLE 1-continued
Exemplary compounds.
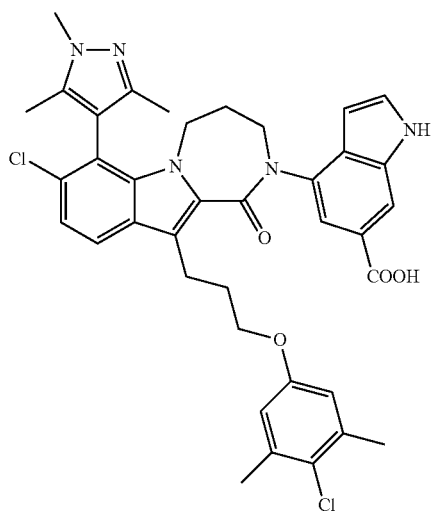 [SMILES: Cc1cc(OCCCc2c3n(c4c(-c5c(C)nn(C)c5C)c(Cl)ccc24)CCCN(c2cc(C(=O)O)cc4[nH]ccc24)C3=O)cc(C)c1Cl]
I-252
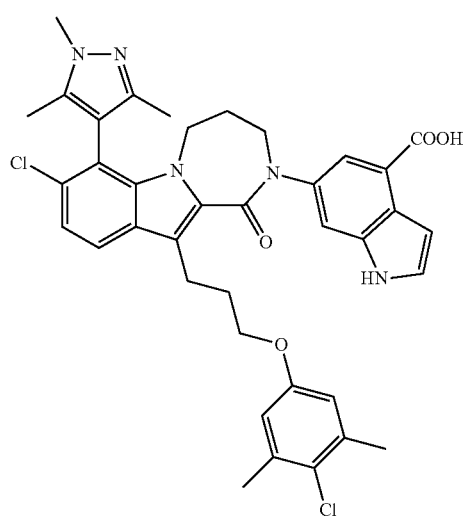 [SMILES: Cc1cc(OCCCc2c3n(c4c(-c5c(C)nn(C)c5C)c(Cl)ccc24)CCCN(c2cc(C(=O)O)c4cc[nH]c4c2)C3=O)cc(C)c1Cl]
I-253
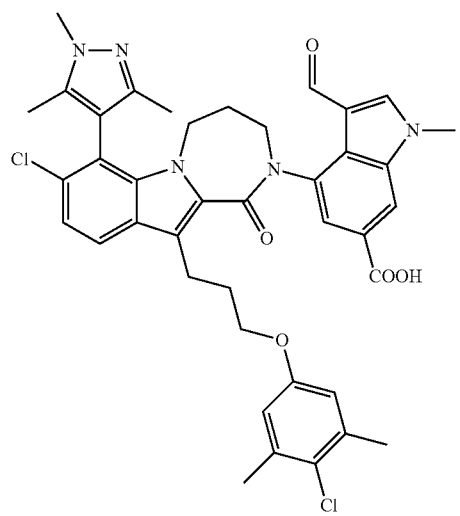 [SMILES: Cc1cc(OCCCc2c3n(c4c(-c5c(C)nn(C)c5C)c(Cl)ccc24)CCCN(c2cc(C(=O)O)cc4c2c(C=O)cn4C)C3=O)cc(C)c1Cl]
I-254

TABLE 1-continued
Exemplary compounds.
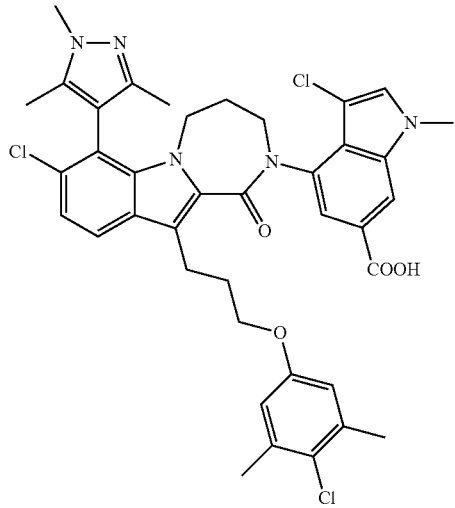 [SMILES: Cc1cc(OCCCc2c3n(c4c(-c5c(C)nn(C)c5C)c(Cl)ccc24)CCCN(c2cc(C(=O)O)cc4c2c(Cl)cn4C)C3=O)cc(C)c1Cl]
I-255
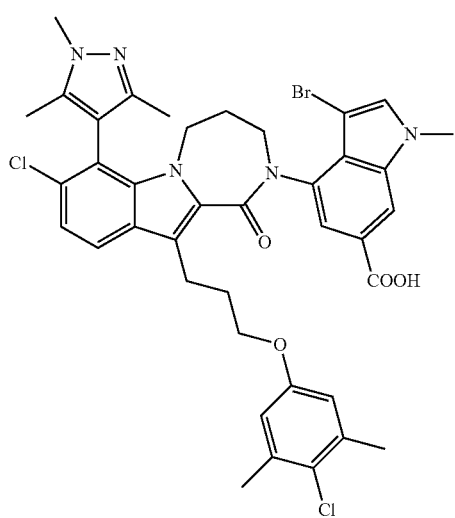 [SMILES: Cc1cc(OCCCc2c3n(c4c(-c5c(C)nn(C)c5C)c(Cl)ccc24)CCCN(c2cc(C(=O)O)cc4c2c(Br)cn4C)C3=O)cc(C)c1Cl]
I-256
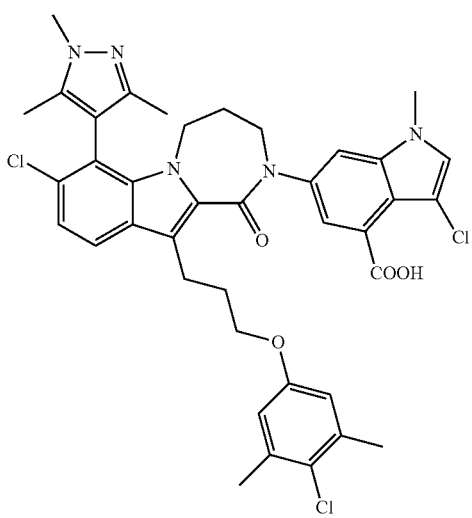 [SMILES: Cc1cc(OCCCc2c3n(c4c(-c5c(C)nn(C)c5C)c(Cl)ccc24)CCCN(c2cc(C(=O)O)c4c(Cl)cn(C)c4c2)C3=O)cc(C)c1Cl]
I-257

TABLE 1-continued
Exemplary compounds.
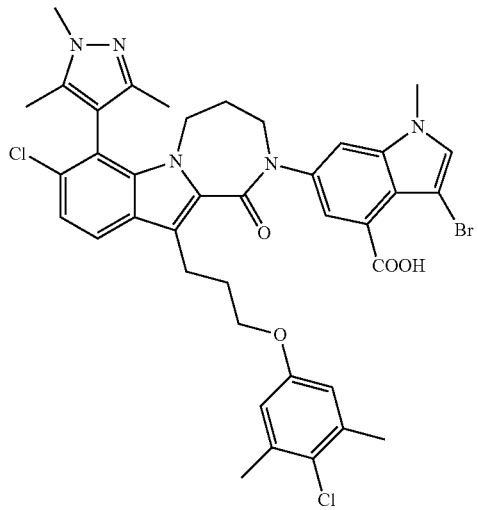 [SMILES: Cc1cc(OCCCc2c3n(c4c(-c5c(C)nn(C)c5C)c(Cl)ccc24)CCCN(c2cc(C(=O)O)c4c(Br)cn(C)c4c2)C3=O)cc(C)c1Cl]
I-258
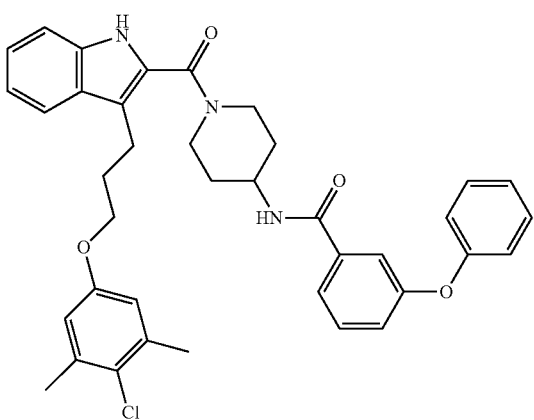 [SMILES: Cc1cc(OCCCc2c(C(=O)N3CCC(NC(=O)c4cccc(Oc5ccccc5)c4)CC3)[nH]c3ccccc23)cc(C)c1Cl]
I-259
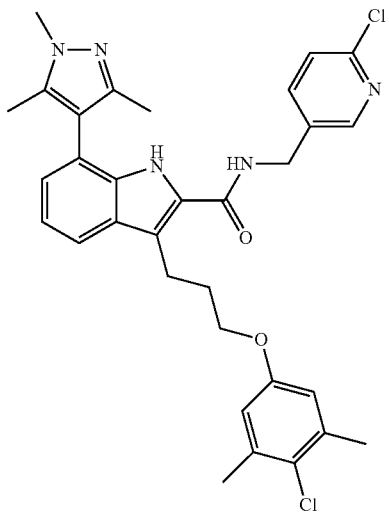 [SMILES: Cc1cc(OCCCc2c(C(=O)NCc3ccc(Cl)nc3)[nH]c3c(-c4c(C)nn(C)c4C)cccc23)cc(C)c1Cl]
I-260

TABLE 1-continued
Exemplary compounds.
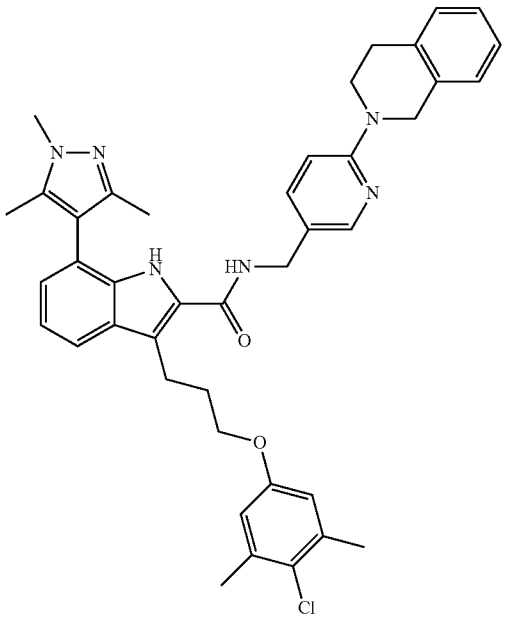 [SMILES: Cc1cc(OCCCc2c(C(=O)NCc3ccc(N4CCc5ccccc5C4)nc3)[nH]c3c(-c4c(C)nn(C)c4C)cccc23)cc(C)c1Cl]
I-261
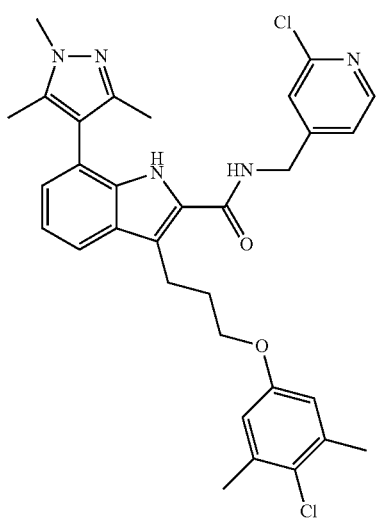 [SMILES: Cc1cc(OCCCc2c(C(=O)NCc3ccnc(Cl)c3)[nH]c3c(-c4c(C)nn(C)c4C)cccc23)cc(C)c1Cl]
I-262

TABLE 1-continued
Exemplary compounds.
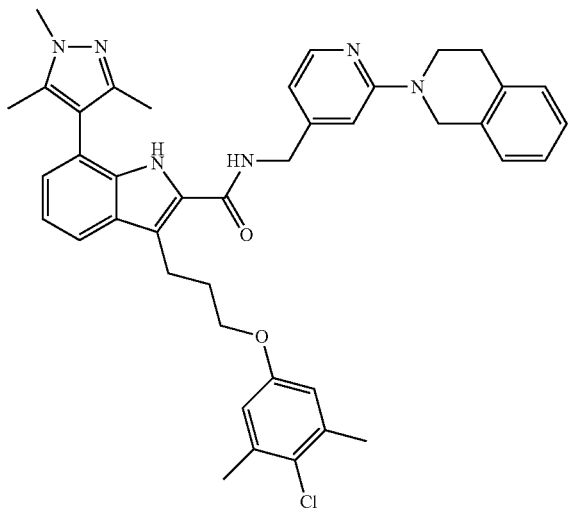 [SMILES: Cc1cc(OCCCc2c(C(=O)NCc3ccnc(N4CCc5ccccc5C4)c3)[nH]c3c(-c4c(C)nn(C)c4C)cccc23)cc(C)c1Cl]
I-263
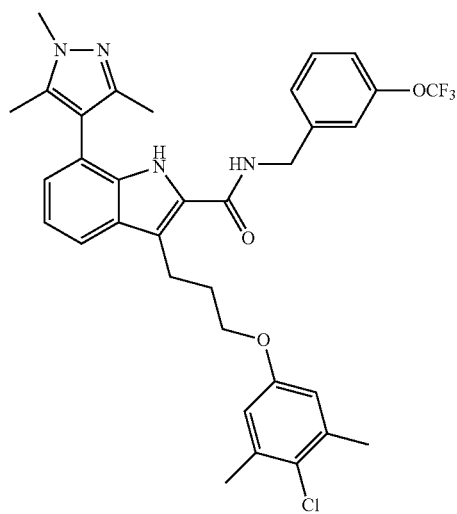 [SMILES: Cc1cc(OCCCc2c(C(=O)NCc3cccc(OC(F)(F)F)c3)[nH]c3c(-c4c(C)nn(C)c4C)cccc23)cc(C)c1Cl]
I-264
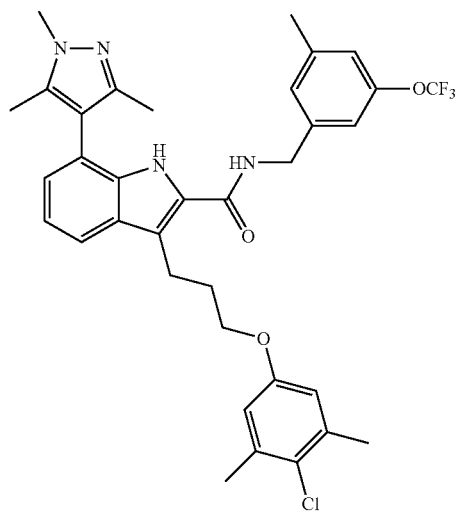 [SMILES: Cc1cc(CNC(=O)c2[nH]c3c(-c4c(C)nn(C)c4C)cccc3c2CCCOc2cc(C)c(Cl)c(C)c2)cc(OC(F)(F)F)c1]
I-265

TABLE 1-continued
Exemplary compounds.
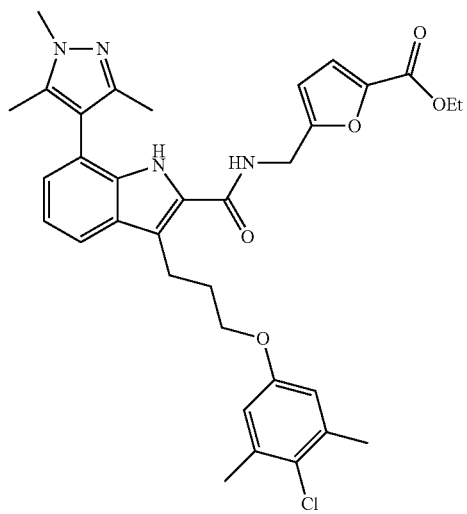 [SMILES: CCOC(=O)c1ccc(CNC(=O)c2[nH]c3c(-c4c(C)nn(C)c4C)cccc3c2CCCOc2cc(C)c(Cl)c(C)c2)o1]
I-266
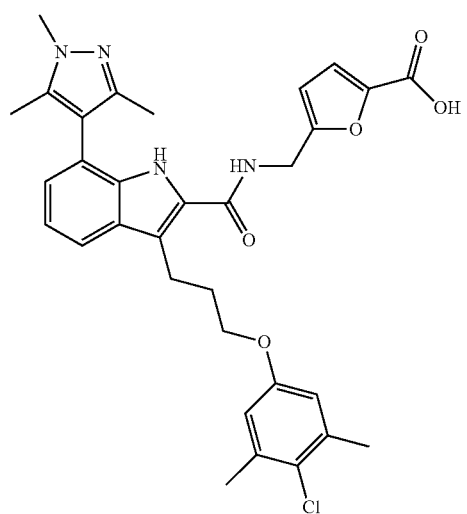 [SMILES: Cc1cc(OCCCc2c(C(=O)NCc3ccc(C(=O)O)o3)[nH]c3c(-c4c(C)nn(C)c4C)cccc23)cc(C)c1Cl]
I-267
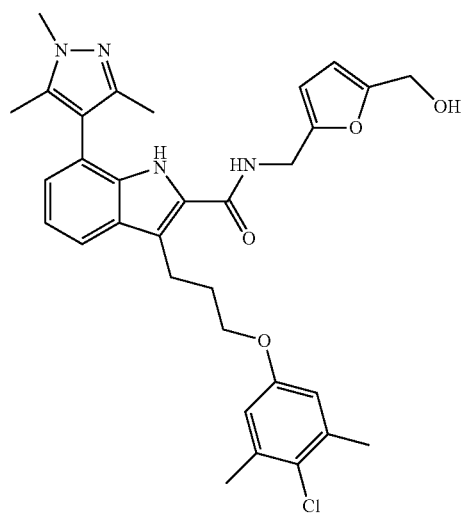 [SMILES: Cc1cc(OCCCc2c(C(=O)NCc3ccc(CO)o3)[nH]c3c(-c4c(C)nn(C)c4C)cccc23)cc(C)c1Cl]
I-268

TABLE 1-continued
Exemplary compounds.
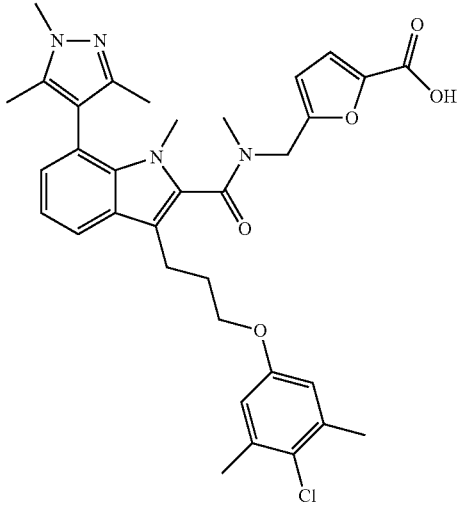 [SMILES: Cc1cc(OCCCc2c(C(=O)N(C)Cc3ccc(C(=O)O)o3)n(C)c3c(-c4c(C)nn(C)c4C)cccc23)cc(C)c1Cl]
I-269
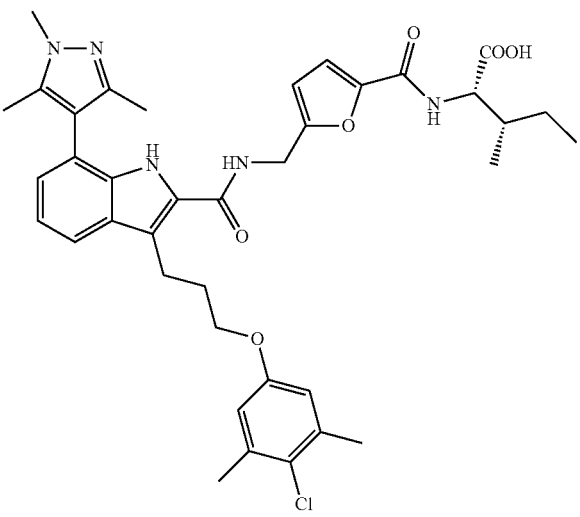 [SMILES: CC[C@H](C)[C@H](NC(=O)c1ccc(CNC(=O)c2[nH]c3c(-c4c(C)nn(C)c4C)cccc3c2CCCOc2cc(C)c(Cl)c(C)c2)o1)C(=O)O]
I-270
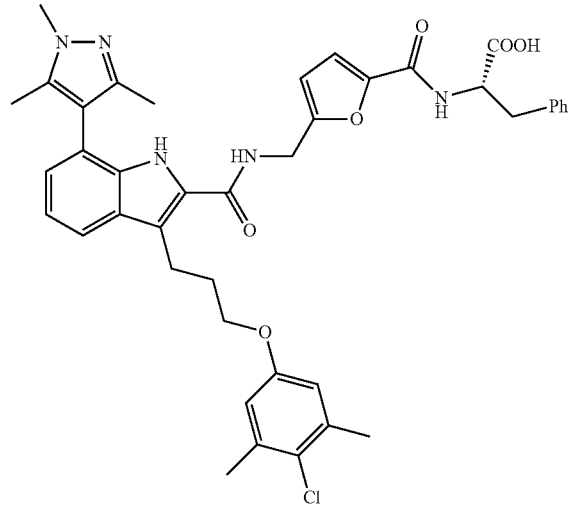 [SMILES: Cc1cc(OCCCc2c(C(=O)NCc3ccc(C(=O)N[C@@H](Cc4ccccc4)C(=O)O)o3)[nH]c3c(-c4c(C)nn(C)c4C)cccc23)cc(C)c1Cl]
I-271

TABLE 1-continued
Exemplary compounds.
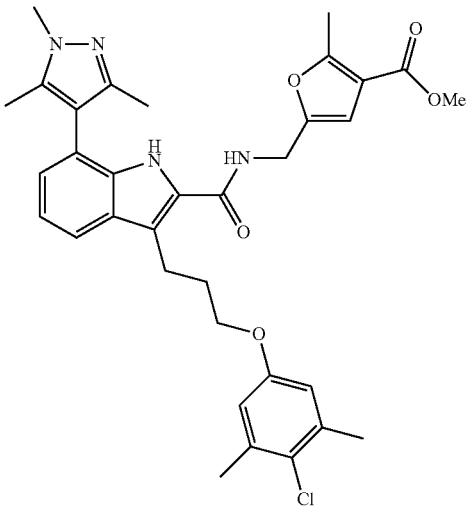 [SMILES: COC(=O)c1cc(CNC(=O)c2[nH]c3c(-c4c(C)nn(C)c4C)cccc3c2CCCOc2cc(C)c(Cl)c(C)c2)oc1C]
I-272
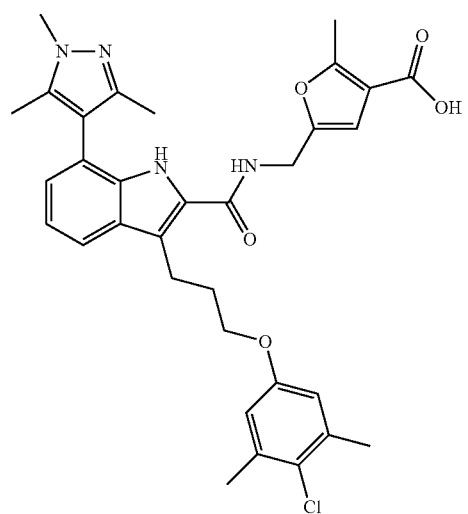 [SMILES: Cc1cc(OCCCc2c(C(=O)NCc3cc(C(=O)O)c(C)o3)[nH]c3c(-c4c(C)nn(C)c4C)cccc23)cc(C)c1Cl]
I-273
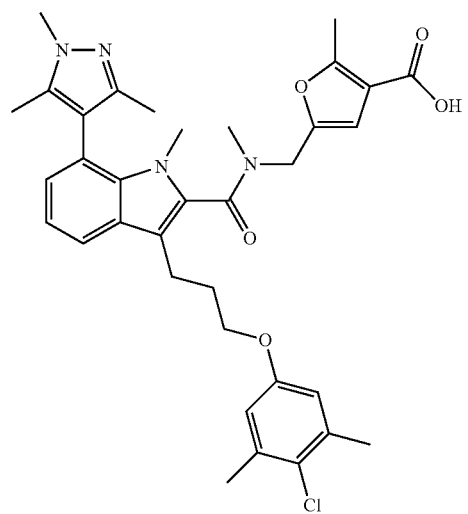 [SMILES: Cc1cc(OCCCc2c(C(=O)N(C)Cc3cc(C(=O)O)c(C)o3)n(C)c3c(-c4c(C)nn(C)c4C)cccc23)cc(C)c1Cl]
I-274

TABLE 1-continued
Exemplary compounds.
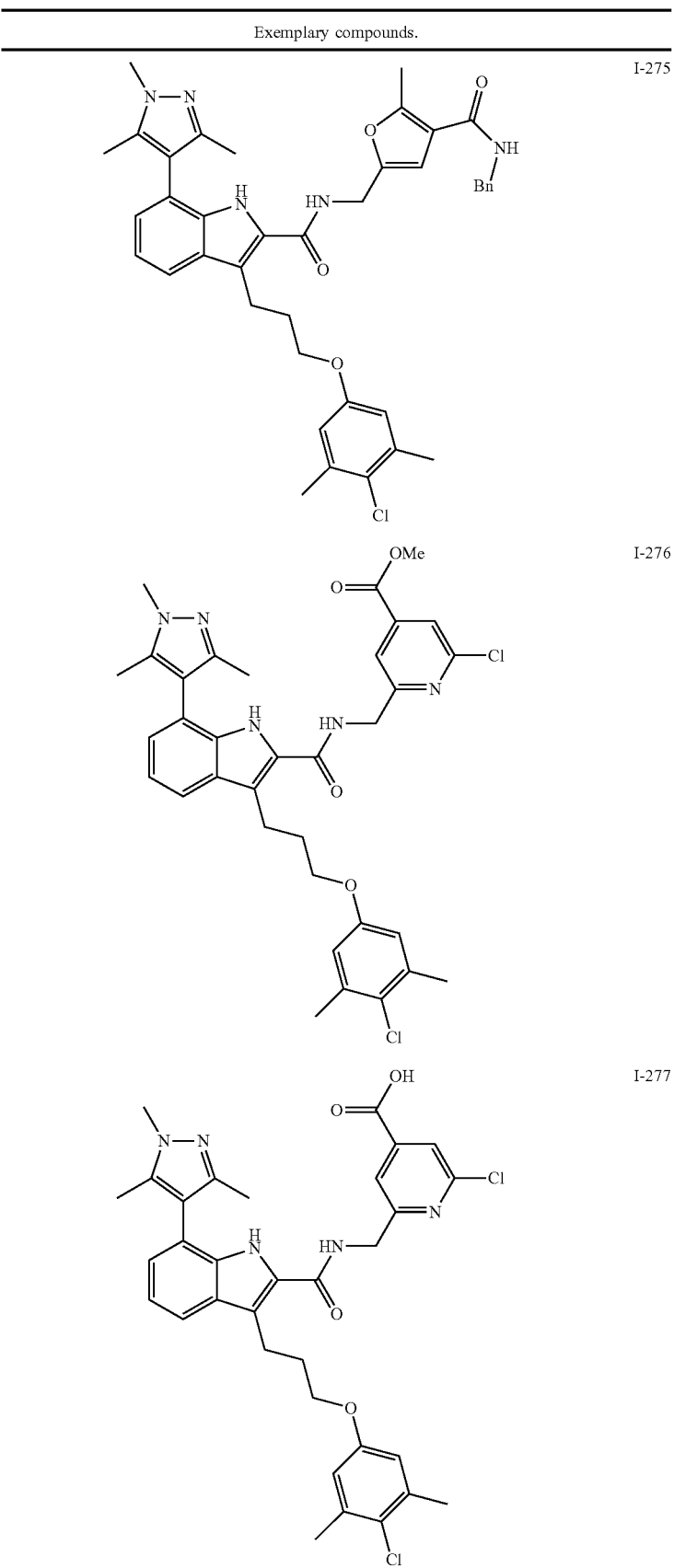
I-275
I-276
I-277

TABLE 1-continued
Exemplary compounds.
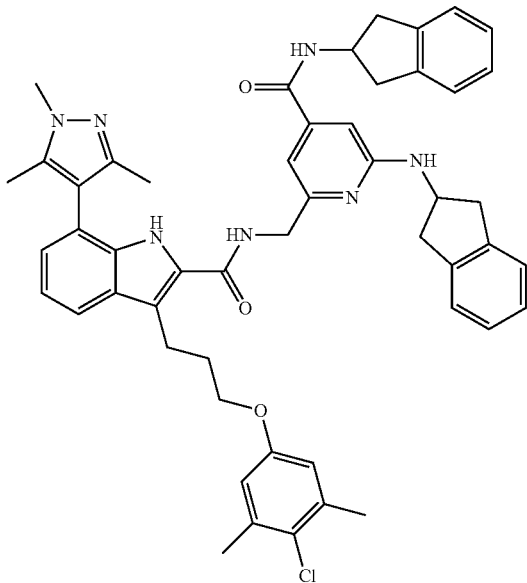 [SMILES: Cc1cc(OCCCc2c(C(=O)NCc3cc(C(=O)NC4Cc5ccccc5C4)cc(NC4Cc5ccccc5C4)n3)[nH]c3c(-c4c(C)nn(C)c4C)cccc23)cc(C)c1Cl]
I-278
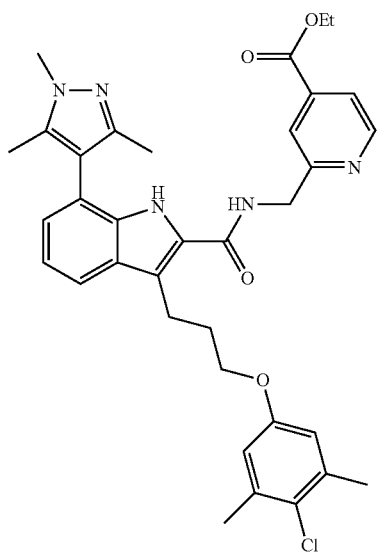 [SMILES: Cc1cc(OCCCc2c(C(=O)NCc3cc(C(=O)O)ccn3)[nH]c3c(-c4c(C)nn(C)c4C)cccc23)cc(C)c1Cl]
I-279

TABLE 1-continued
Exemplary compounds.
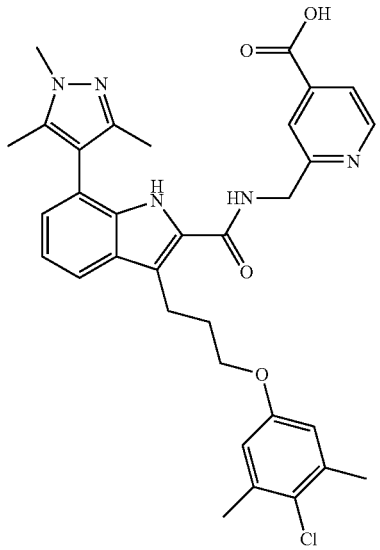
I-280
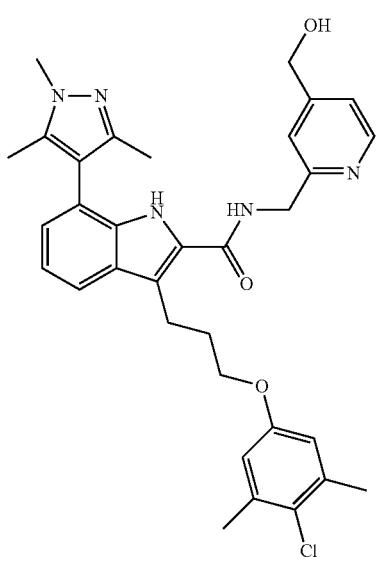 [SMILES: Cc1cc(OCCCc2c(C(=O)NCc3cc(CO)ccn3)[nH]c3c(-c4c(C)nn(C)c4C)cccc23)cc(C)c1Cl]
I-281

TABLE 1-continued
Exemplary compounds.
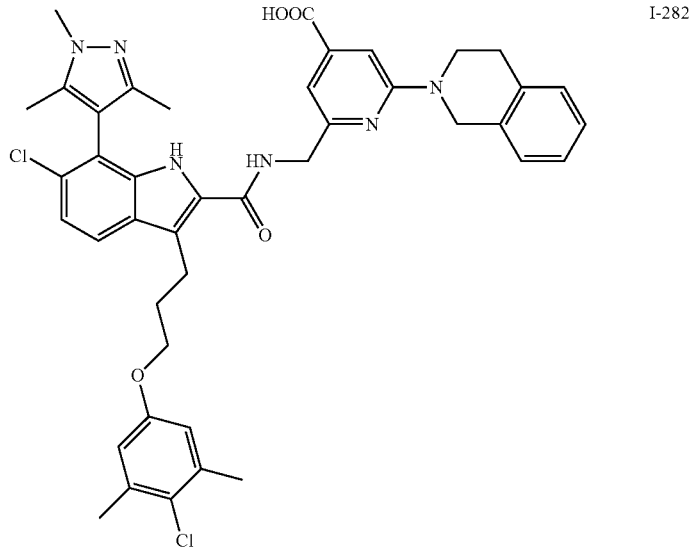
I-282
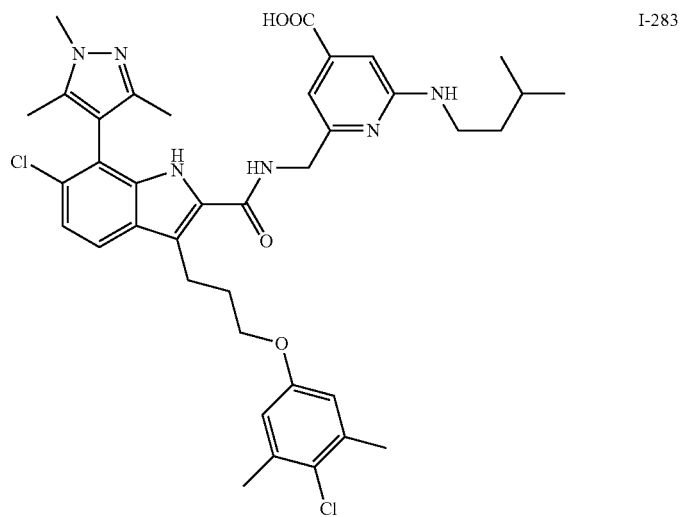
I-283
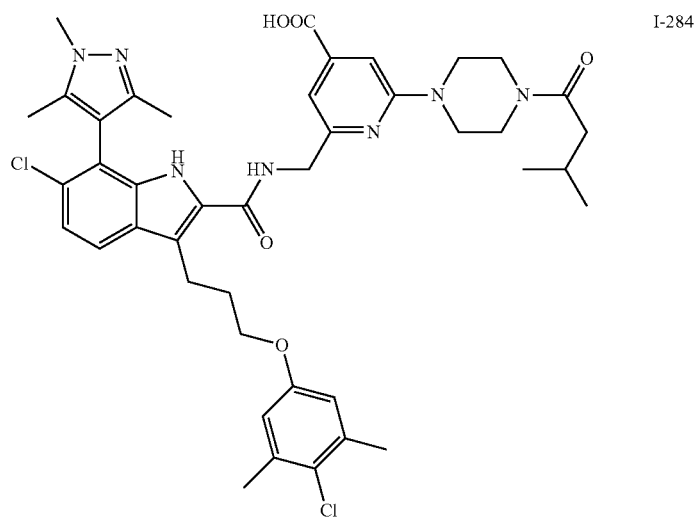
I-284

TABLE 1-continued
Exemplary compounds.
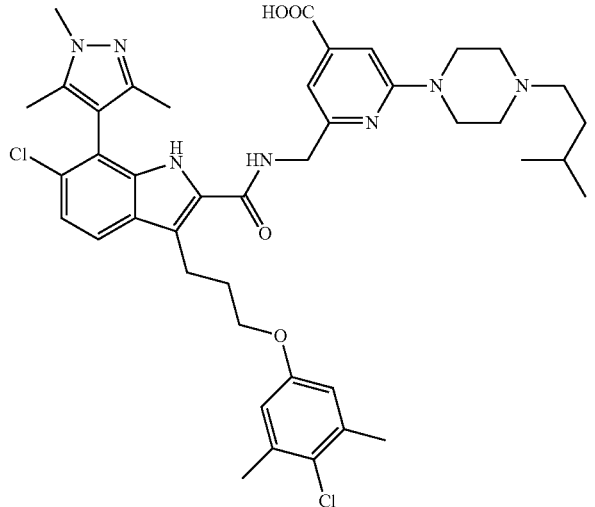 [SMILES: Cc1cc(OCCCc2c(C(=O)NCc3cc(C(=O)O)cc(N4CCN(CCC(C)C)CC4)n3)[nH]c3c(-c4c(C)nn(C)c4C)c(Cl)ccc23)cc(C)c1Cl]
I-285
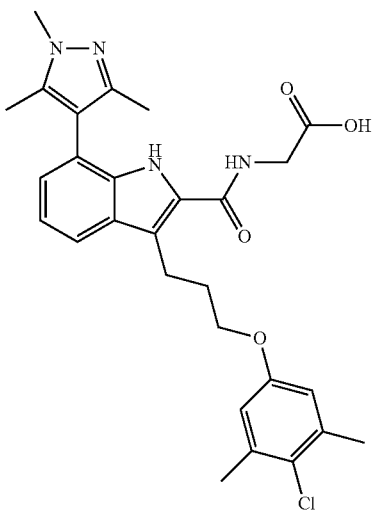
I-286
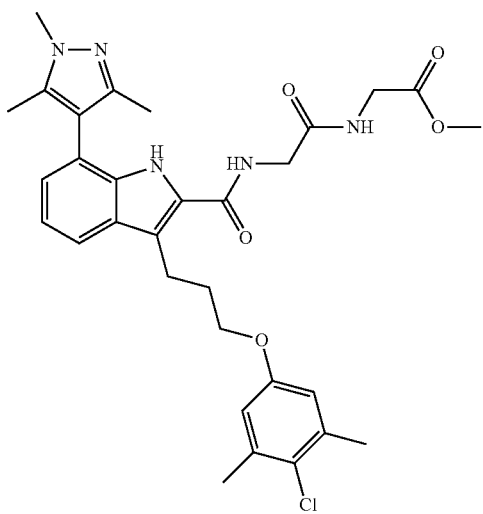
I-287

TABLE 1-continued
Exemplary compounds.
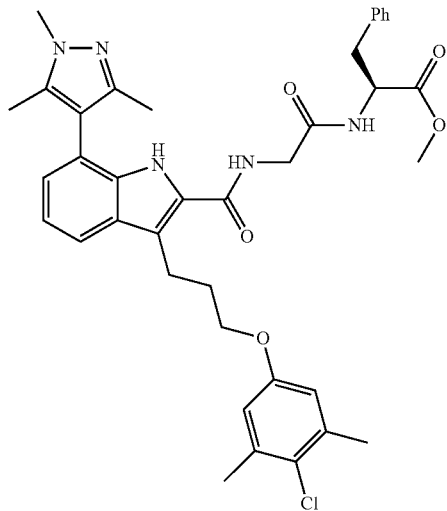 [SMILES: COC(=O)[C@H](Cc1ccccc1)NC(=O)CNC(=O)c1[nH]c2c(-c3c(C)nn(C)c3C)cccc2c1CCCOc1cc(C)c(Cl)c(C)c1]
I-288
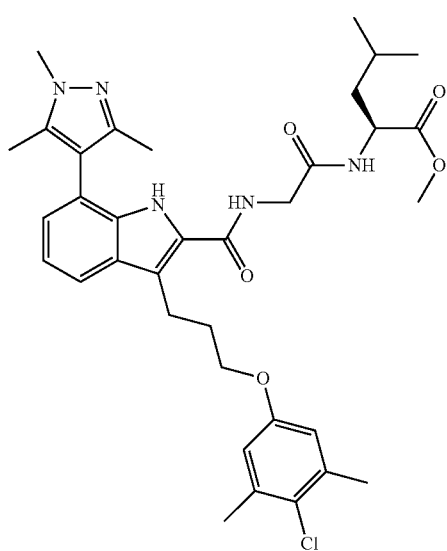 [SMILES: COC(=O)[C@H](CC(C)C)NC(=O)CNC(=O)c1[nH]c2c(-c3c(C)nn(C)c3C)cccc2c1CCCOc1cc(C)c(Cl)c(C)c1]
I-289
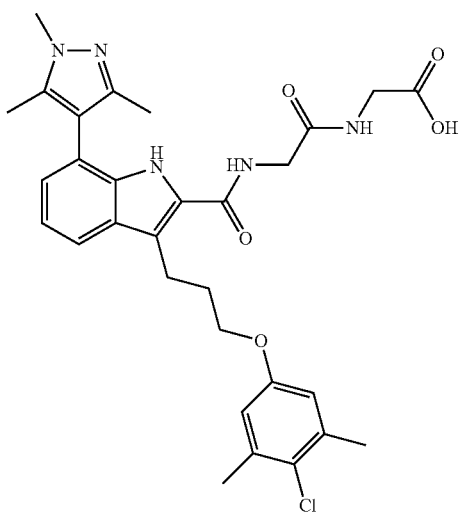 [SMILES: Cc1cc(OCCCc2c(C(=O)NCC(=O)NCC(=O)O)[nH]c3c(-c4c(C)nn(C)c4C)cccc23)cc(C)c1Cl]
I-290

TABLE 1-continued
Exemplary compounds.
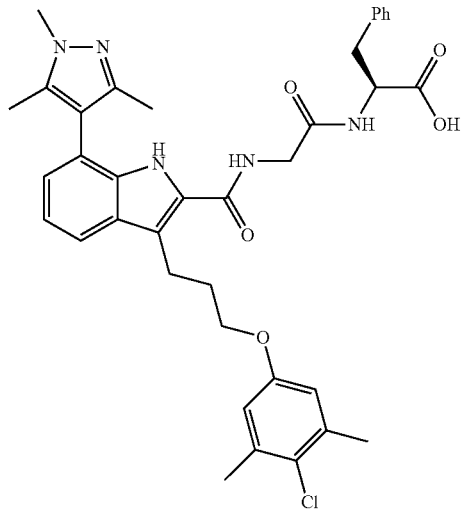 [SMILES: Cc1cc(OCCCc2c(C(=O)NCC(=O)N[C@@H](Cc3ccccc3)C(=O)O)[nH]c3c(-c4c(C)nn(C)c4C)cccc23)cc(C)c1Cl]
I-291
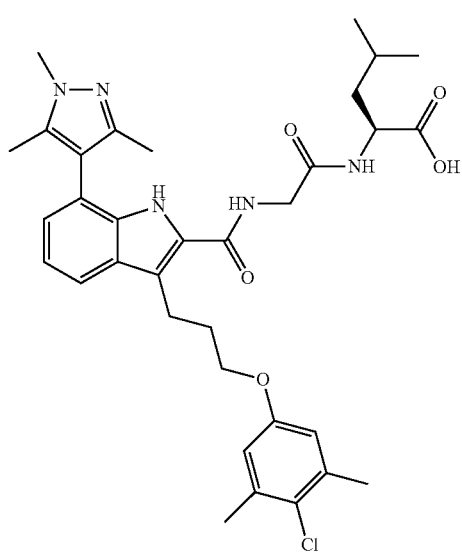 [SMILES: Cc1cc(OCCCc2c(C(=O)NCC(=O)N[C@@H](CC(C)C)C(=O)O)[nH]c3c(-c4c(C)nn(C)c4C)cccc23)cc(C)c1Cl]
I-292

TABLE 1-continued
Exemplary compounds.
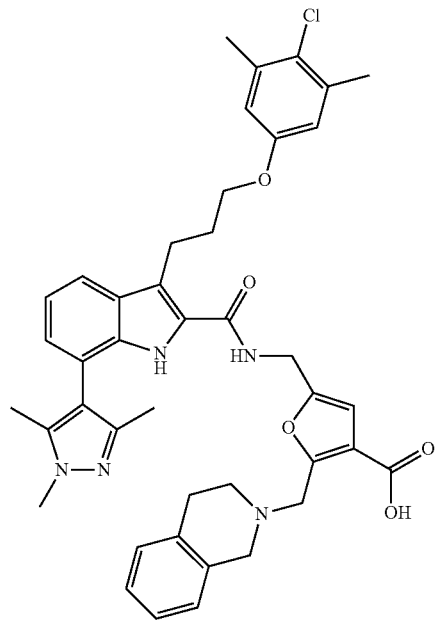 [SMILES: Cc1cc(OCCCc2c(C(=O)NCc3cc(C(=O)O)c(CN4CCc5ccccc5C4)o3)[nH]c3c(-c4c(C)nn(C)c4C)cccc23)cc(C)c1Cl] I-293
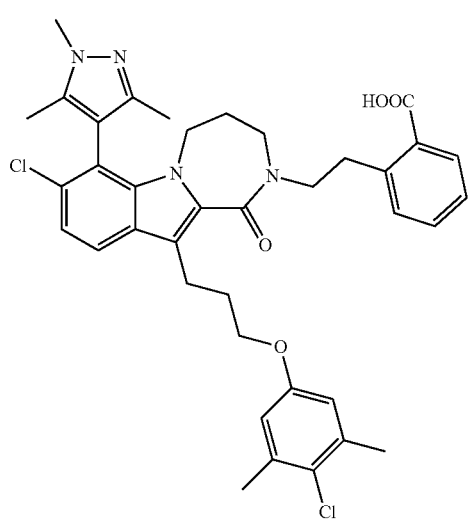 [SMILES: Cc1cc(OCCCc2c3n(c4c(-c5c(C)nn(C)c5C)c(Cl)ccc24)CCCN(CCc2ccccc2C(=O)O)C3=O)cc(C)c1Cl] I-294

TABLE 1-continued
Exemplary compounds.
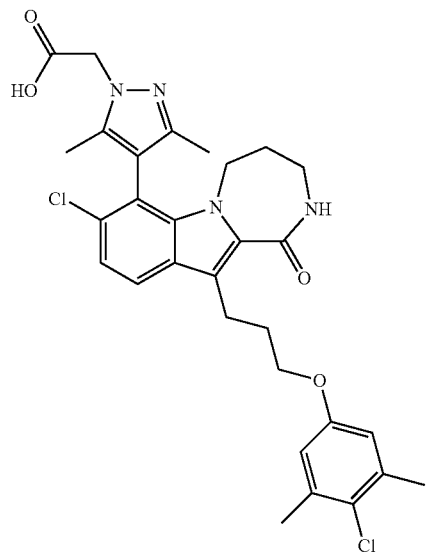 [SMILES: Cc1cc(OCCCc2c3n(c4c(-c5c(C)nn(CC(=O)O)c5C)c(Cl)ccc24)CCCNC3=O)cc(C)c1Cl]
I-295
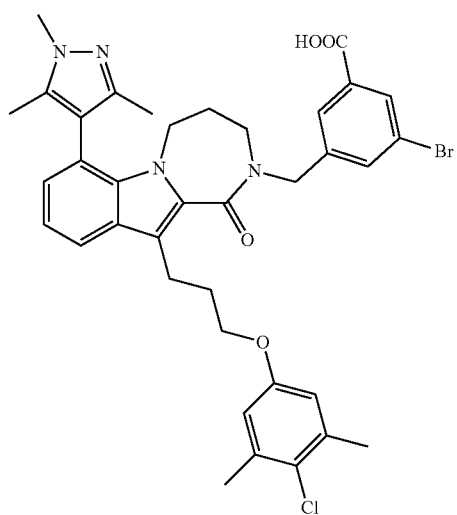 [SMILES: Cc1cc(OCCCc2c3n(c4c(-c5c(C)nn(C)c5C)cccc24)CCCN(Cc2cc(Br)cc(C(=O)O)c2)C3=O)cc(C)c1Cl]
I-296
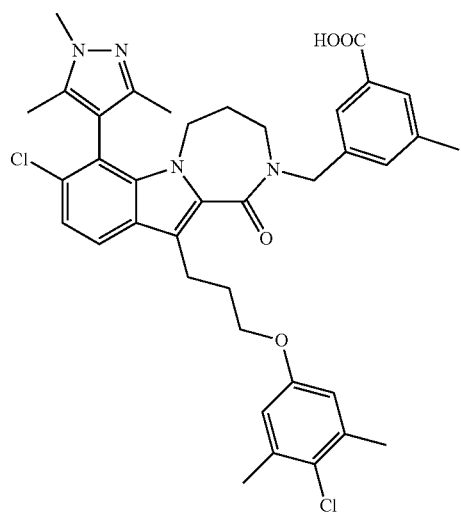 [SMILES: Cc1cc(CN2CCCn3c(c(CCCOc4cc(C)c(Cl)c(C)c4)c4ccc(Cl)c(-c5c(C)nn(C)c5C)c43)C2=O)cc(C(=O)O)c1]
I-297

TABLE 1-continued
Exemplary compounds.
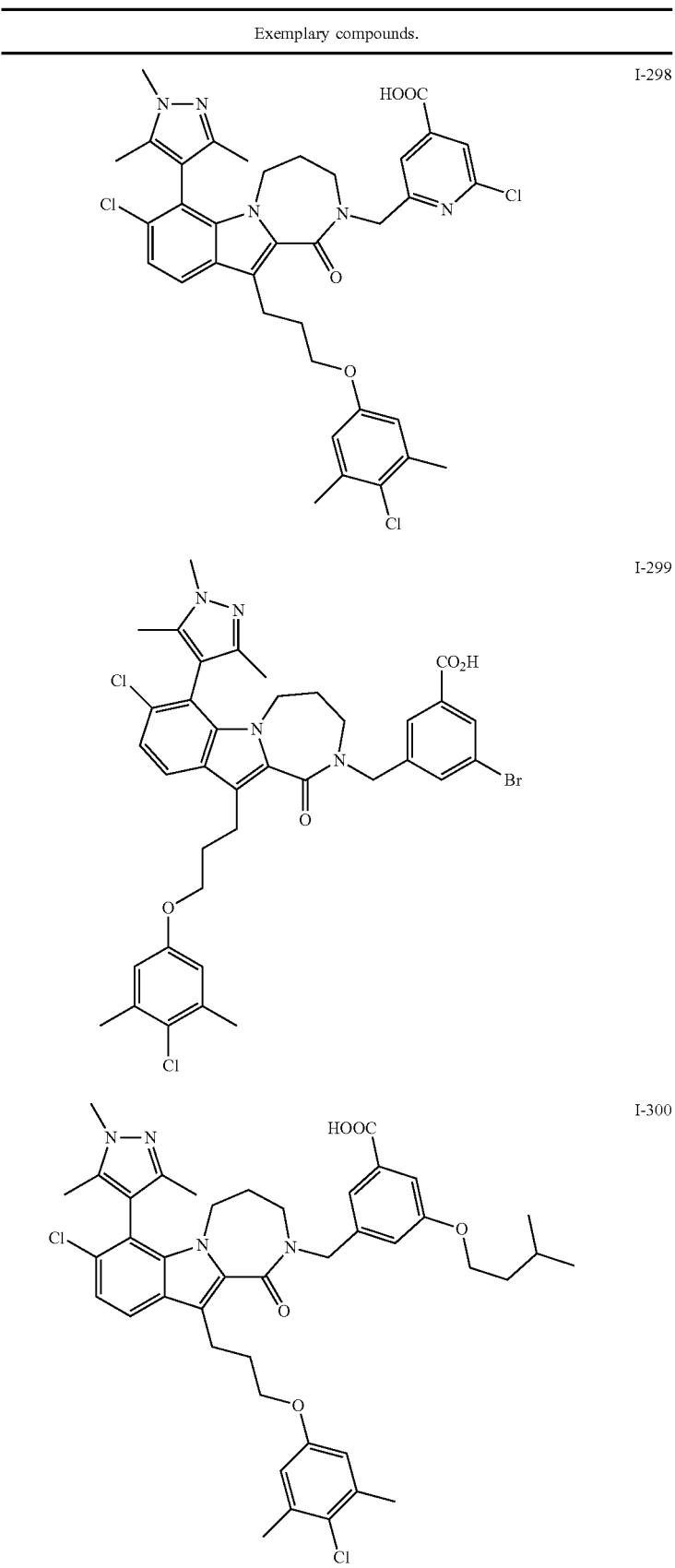
I-298
I-299
I-300

TABLE 1-continued
Exemplary compounds.
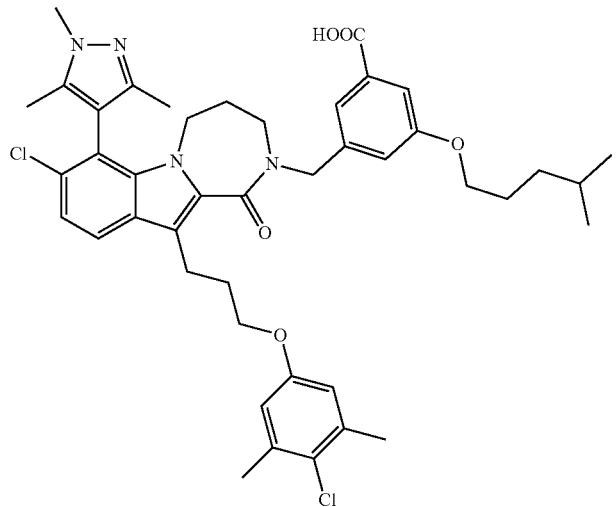 [SMILES: Cc1cc(OCCCc2c3n(c4c(-c5c(C)nn(C)c5C)c(Cl)ccc24)CCCN(Cc2cc(OCCCC(C)C)cc(C(=O)O)c2)C3=O)cc(C)c1Cl]
I-301
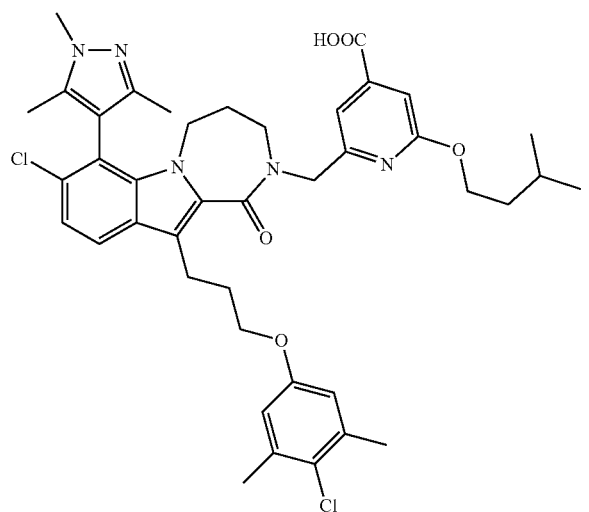 [SMILES: Cc1cc(OCCCc2c3n(c4c(-c5c(C)nn(C)c5C)c(Cl)ccc24)CCCN(Cc2cc(C(=O)O)cc(OCCC(C)C)n2)C3=O)cc(C)c1Cl]
I-302
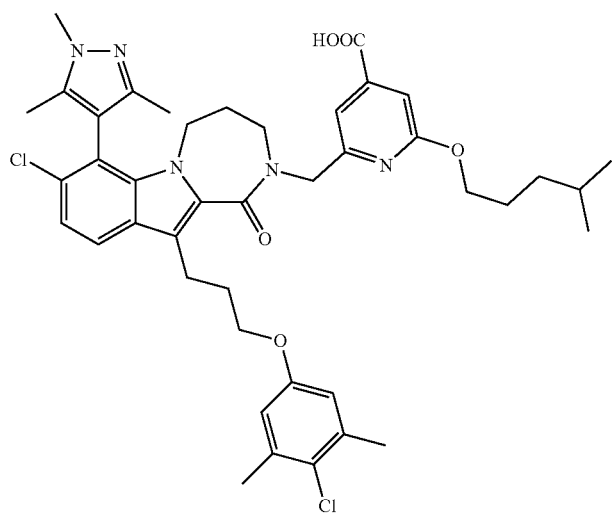 [SMILES: Cc1cc(OCCCc2c3n(c4c(-c5c(C)nn(C)c5C)c(Cl)ccc24)CCCN(Cc2cc(C(=O)O)cc(OCCCC(C)C)n2)C3=O)cc(C)c1Cl]
I-303

TABLE 1-continued
Exemplary compounds.
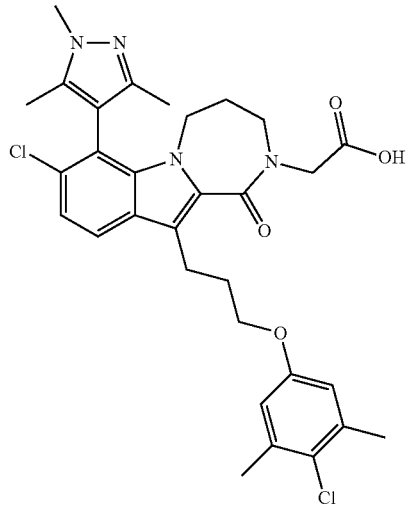 [SMILES: Cc1cc(OCCCc2c3n(c4c(-c5c(C)nn(C)c5C)c(Cl)ccc24)CCCN(CC(=O)O)C3=O)cc(C)c1Cl]
I-304
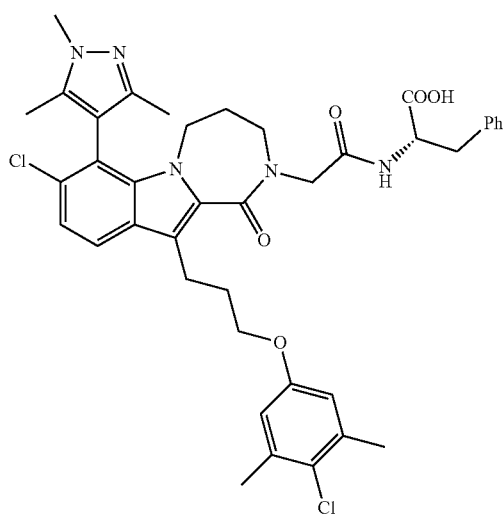 [SMILES: Cc1cc(OCCCc2c3n(c4c(-c5c(C)nn(C)c5C)c(Cl)ccc24)CCCN(CC(=O)N[C@@H](Cc2ccccc2)C(=O)O)C3=O)cc(C)c1Cl]
I-305
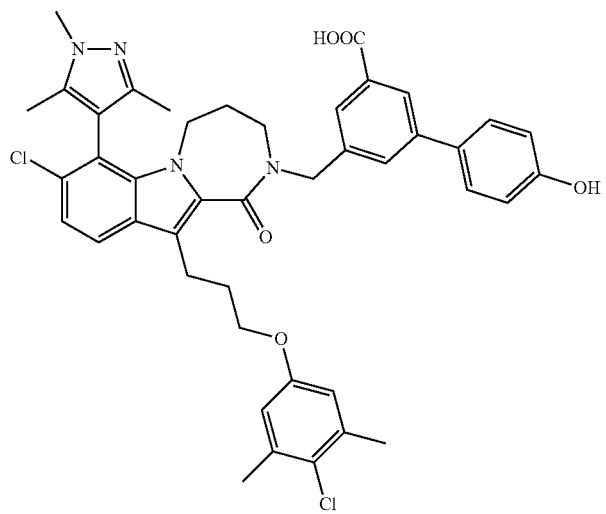 [SMILES: Cc1cc(OCCCc2c3n(c4c(-c5c(C)nn(C)c5C)c(Cl)ccc24)CCCN(Cc2cc(C(=O)O)cc(-c4ccc(O)cc4)c2)C3=O)cc(C)c1Cl]
I-306

TABLE 1-continued
Exemplary compounds.
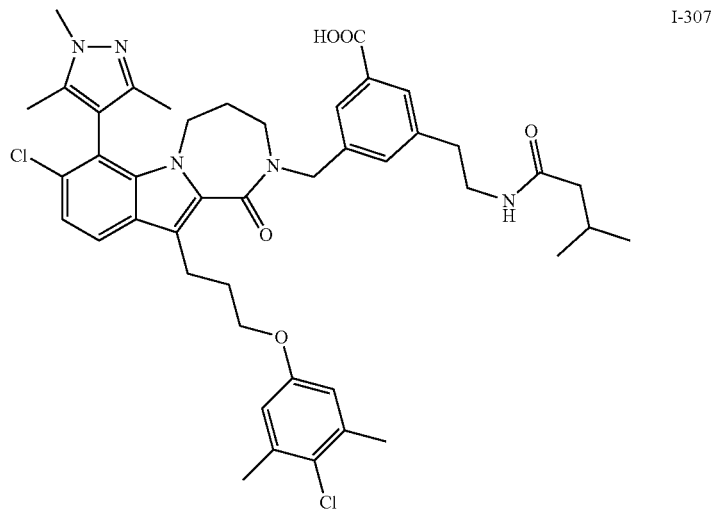
I-307
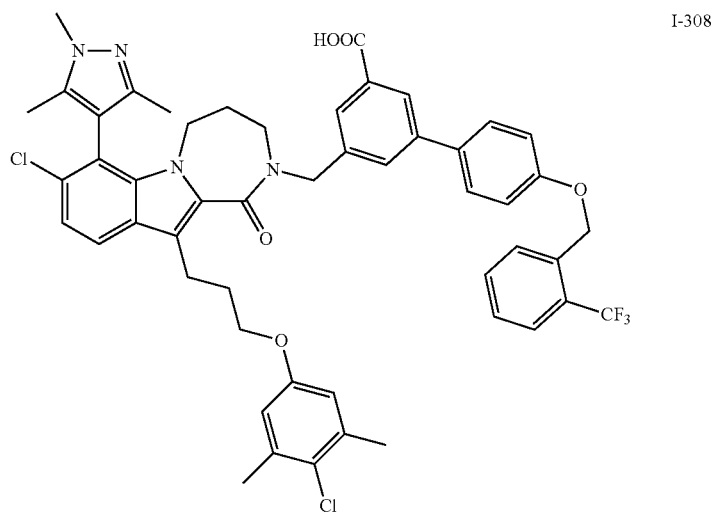
I-308
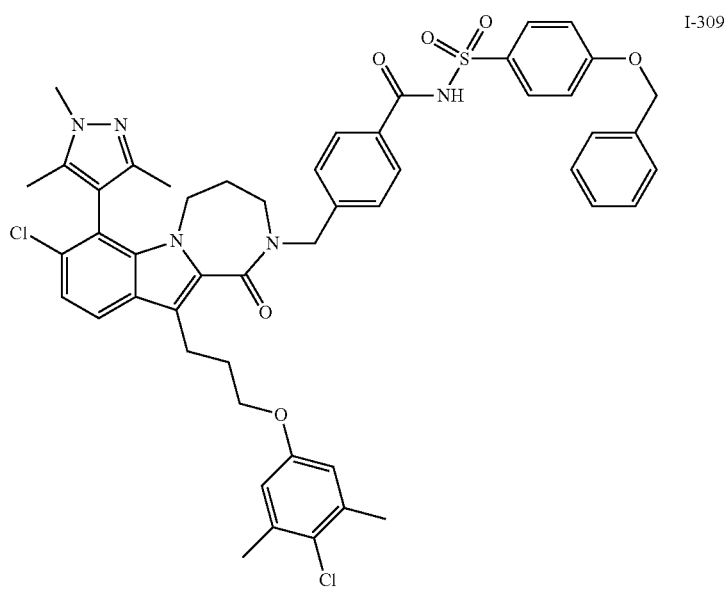
I-309

TABLE 1-continued
Exemplary compounds.
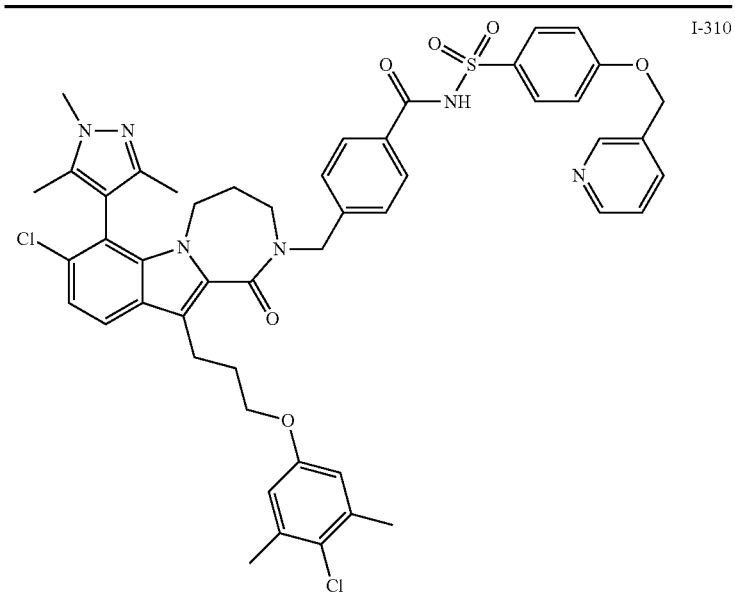
I-310
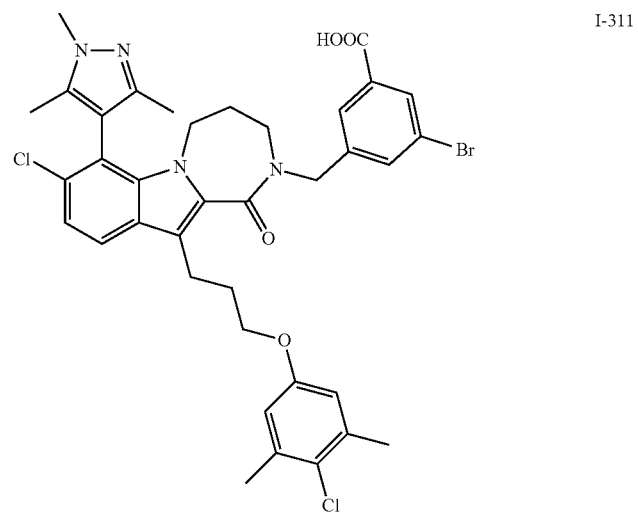 [SMILES: Cc1cc(OCCCc2c3n(c4c(-c5c(C)nn(C)c5C)c(Cl)ccc24)CCCN(Cc2cc(CCNC(=O)CC(C)C)cc(C(=O)O)c2)C3=O)cc(C)c1Cl]
I-311
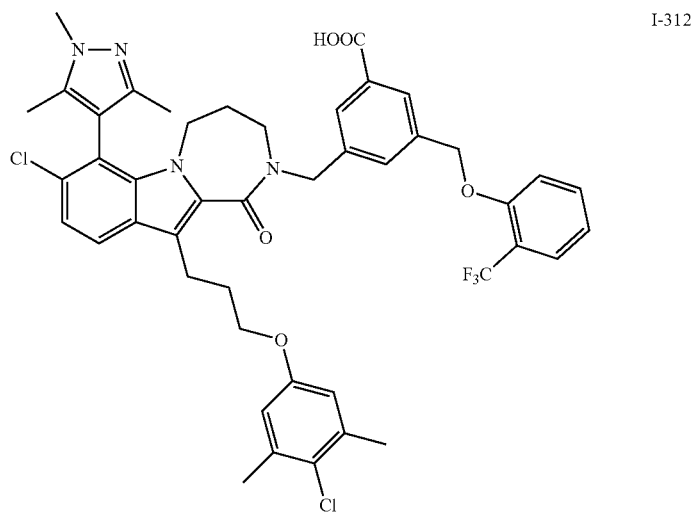
I-312

TABLE 1-continued
Exemplary compounds.
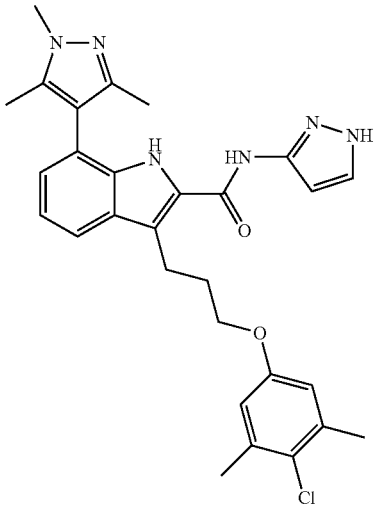
I-313
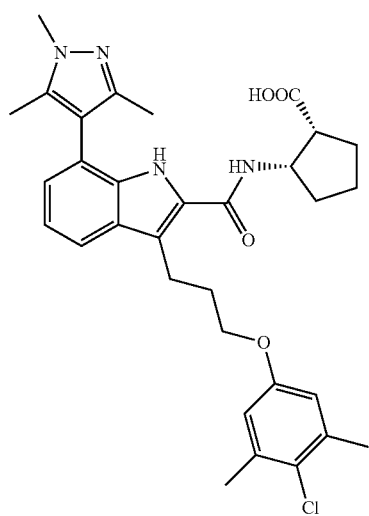
I-314
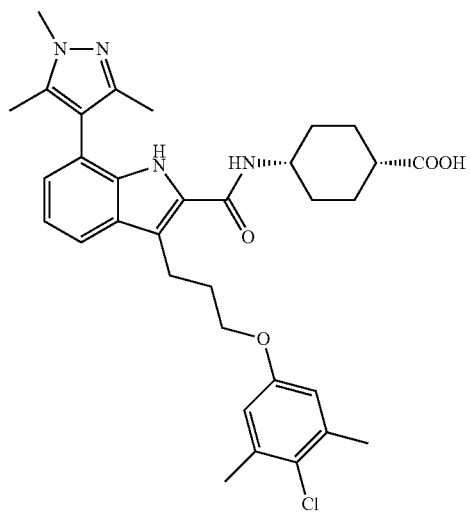 [SMILES: Cc1cc(OCCCc2c(C(=O)N[C@H]3CC[C@@H](C(=O)O)CC3)[nH]c3c(-c4c(C)nn(C)c4C)cccc23)cc(C)c1Cl]
I-315

TABLE 1-continued
Exemplary compounds.
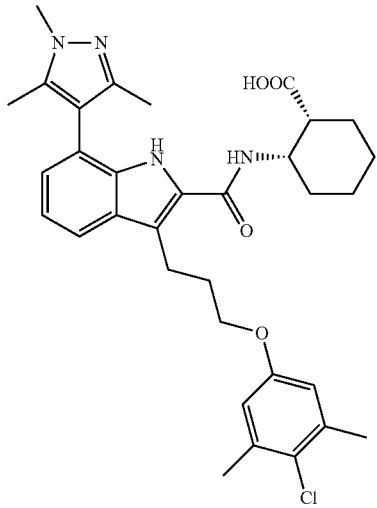 [SMILES: Cc1cc(OCCCc2c(C(=O)N[C@H]3CCCC[C@H]3C(=O)O)[nH]c3c(-c4c(C)nn(C)c4C)cccc23)cc(C)c1Cl]
I-316
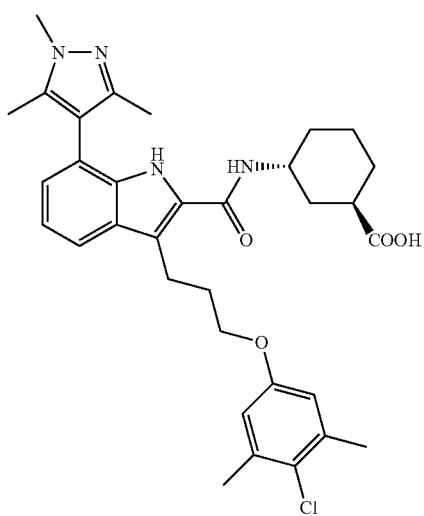 [SMILES: Cc1cc(OCCCc2c(C(=O)N[C@@H]3CCC[C@@H](C(=O)O)C3)[nH]c3c(-c4c(C)nn(C)c4C)cccc23)cc(C)c1Cl]
I-317
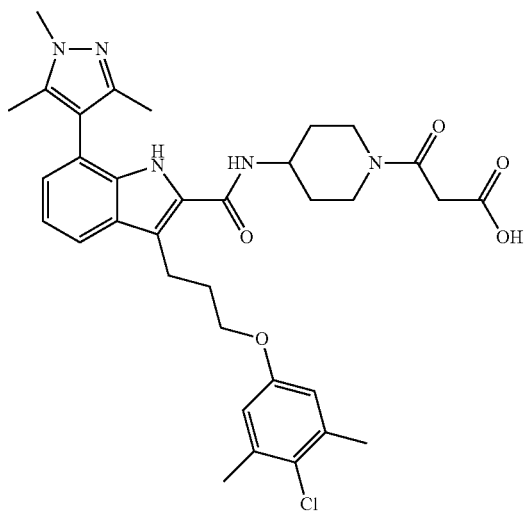 [SMILES: Cc1cc(OCCCc2c(C(=O)NC3CCN(C(=O)CC(=O)O)CC3)[nH]c3c(-c4c(C)nn(C)c4C)cccc23)cc(C)c1Cl]
I-318

TABLE 1-continued
Exemplary compounds.
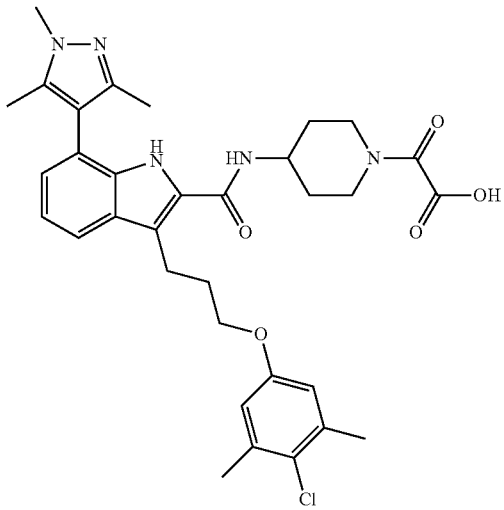 [SMILES: Cc1cc(OCCCc2c(C(=O)NC3CCN(C(=O)C(=O)O)CC3)[nH]c3c(-c4c(C)nn(C)c4C)cccc23)cc(C)c1Cl]
I-319
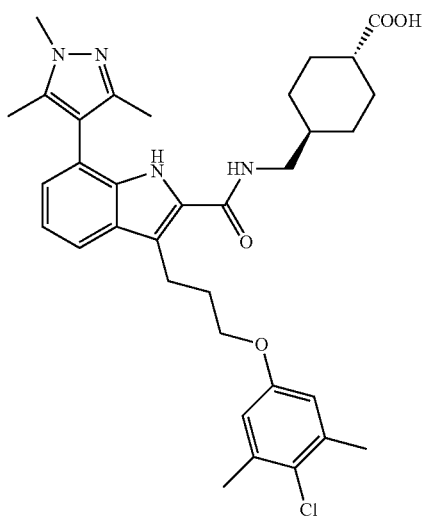 [SMILES: Cc1cc(OCCCc2c(C(=O)NC[C@H]3CC[C@H](C(=O)O)CC3)[nH]c3c(-c4c(C)nn(C)c4C)cccc23)cc(C)c1Cl]
I-320
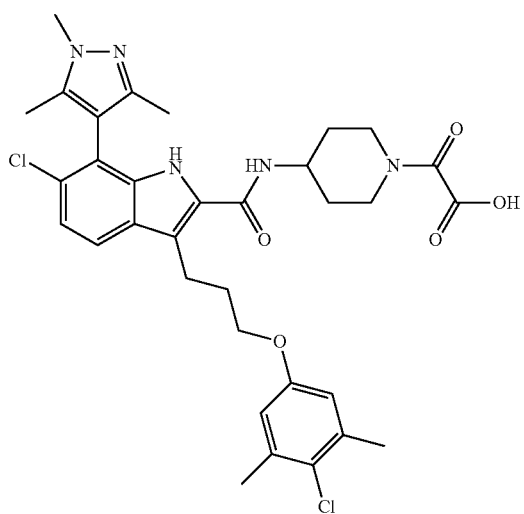 [SMILES: Cc1cc(OCCCc2c(C(=O)NC3CCN(C(=O)C(=O)O)CC3)[nH]c3c(-c4c(C)nn(C)c4C)c(Cl)ccc23)cc(C)c1Cl]
I-321

TABLE 1-continued
Exemplary compounds.
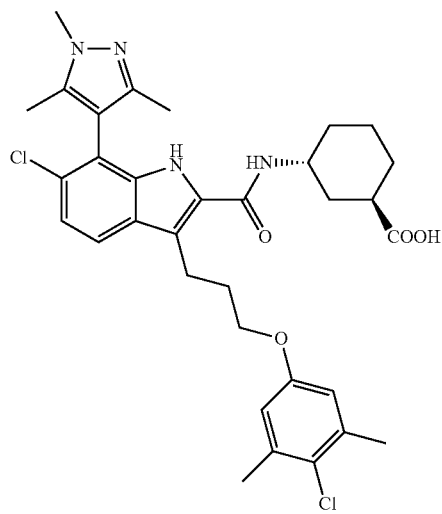 [SMILES: Cc1cc(OCCCc2c(C(=O)N[C@@H]3CCC[C@@H](C(=O)O)C3)[nH]c3c(-c4c(C)nn(C)c4C)c(Cl)ccc23)cc(C)c1Cl]
I-322
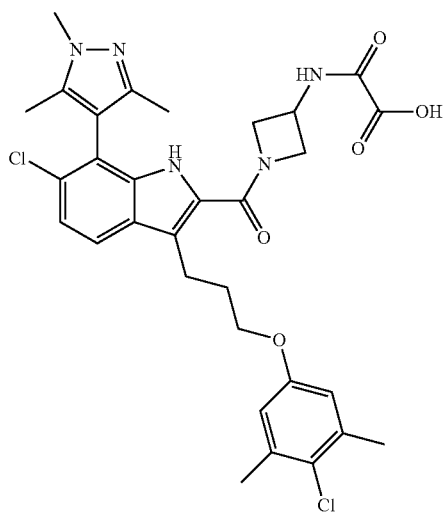 [SMILES: Cc1cc(OCCCc2c(C(=O)N3CC(NC(=O)C(=O)O)C3)[nH]c3c(-c4c(C)nn(C)c4C)c(Cl)ccc23)cc(C)c1Cl]
I-323
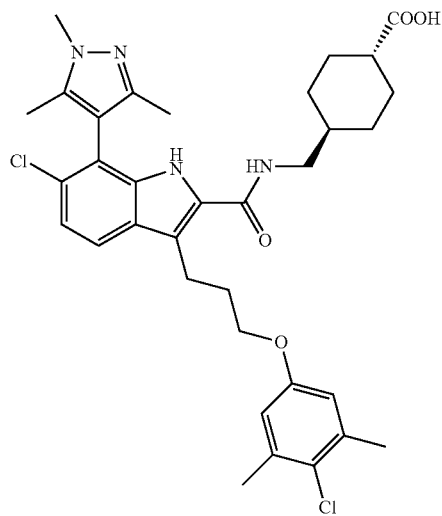 [SMILES: Cc1cc(OCCCc2c(C(=O)NC[C@H]3CC[C@H](C(=O)O)CC3)[nH]c3c(-c4c(C)nn(C)c4C)c(Cl)ccc23)cc(C)c1Cl]
I-324

TABLE 1-continued
Exemplary compounds.
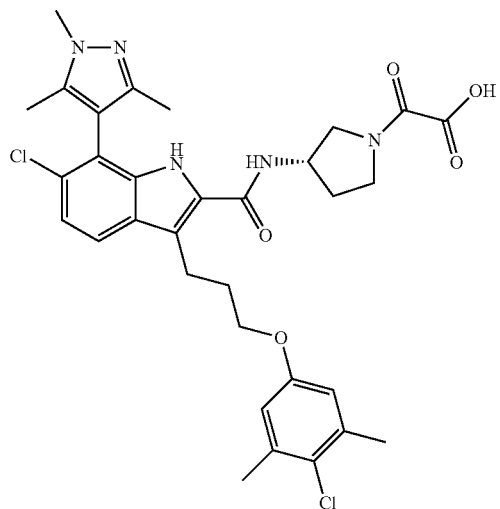 [SMILES: Cc1cc(OCCCc2c(C(=O)N[C@H]3CCN(C(=O)C(=O)O)C3)[nH]c3c(-c4c(C)nn(C)c4C)c(Cl)ccc23)cc(C)c1Cl]
I-325
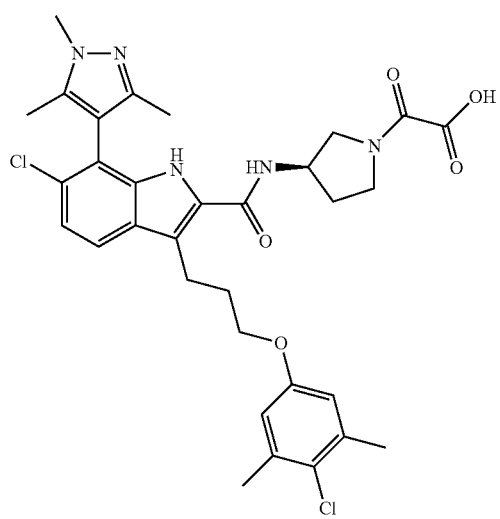 [SMILES: Cc1cc(OCCCc2c(C(=O)N[C@@H]3CCN(C(=O)C(=O)O)C3)[nH]c3c(-c4c(C)nn(C)c4C)c(Cl)ccc23)cc(C)c1Cl]
I-326
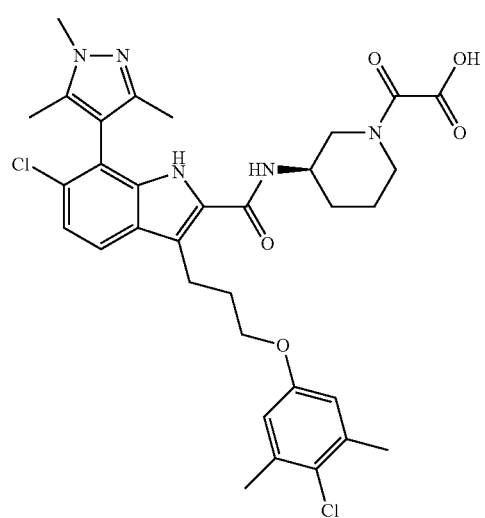 [SMILES: Cc1cc(OCCCc2c(C(=O)N[C@@H]3CCCN(C(=O)C(=O)O)C3)[nH]c3c(-c4c(C)nn(C)c4C)c(Cl)ccc23)cc(C)c1Cl]
I-327

TABLE 1-continued
Exemplary compounds.
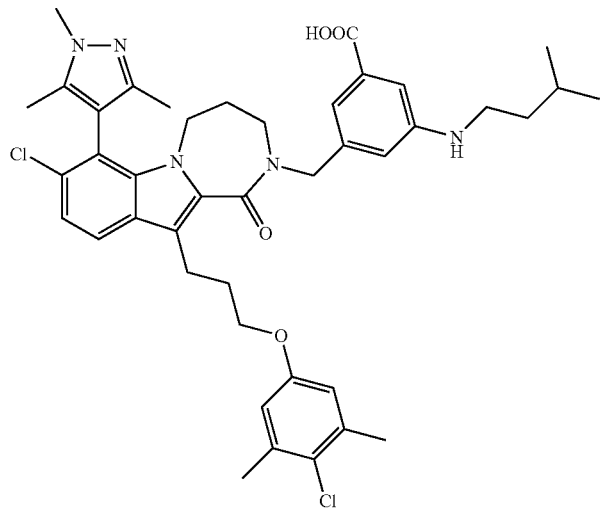 [SMILES: Cc1cc(OCCCc2c3n(c4c(-c5c(C)nn(C)c5C)c(Cl)ccc24)CCCN(Cc2cc(NCCC(C)C)cc(C(=O)O)c2)C3=O)cc(C)c1Cl]
I-328
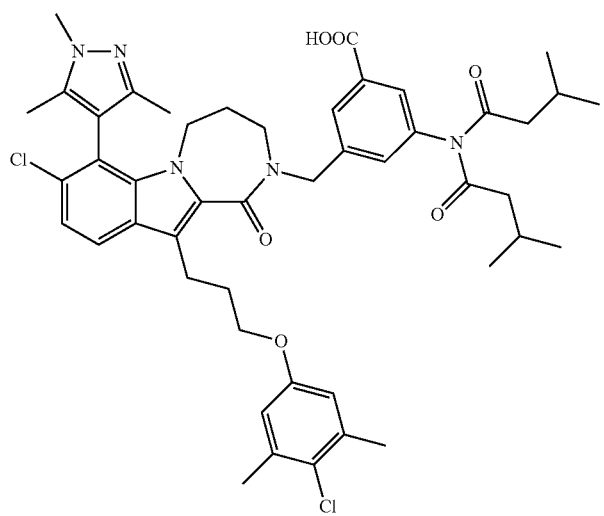 [SMILES: Cc1cc(OCCCc2c3n(c4c(-c5c(C)nn(C)c5C)c(Cl)ccc24)CCCN(Cc2cc(C(=O)O)cc(N(C(=O)CC(C)C)C(=O)CC(C)C)c2)C3=O)cc(C)c1Cl]
I-329
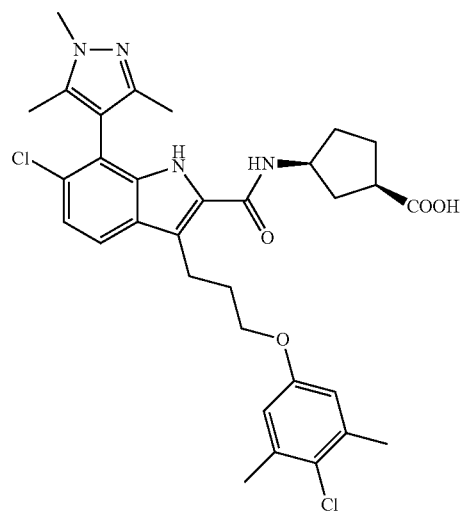 [SMILES: Cc1cc(OCCCc2c(C(=O)N[C@H]3CC[C@@H](C(=O)O)C3)[nH]c3c(-c4c(C)nn(C)c4C)c(Cl)ccc23)cc(C)c1Cl]
I-330

TABLE 1-continued
Exemplary compounds.
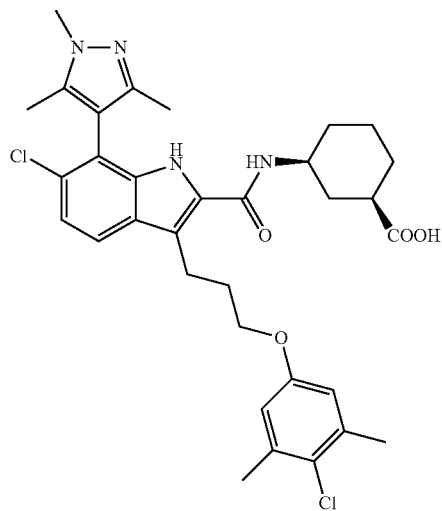 [SMILES: Cc1cc(OCCCc2c(C(=O)N[C@H]3CCC[C@@H](C(=O)O)C3)[nH]c3c(-c4c(C)nn(C)c4C)c(Cl)ccc23)cc(C)c1Cl]
I-331
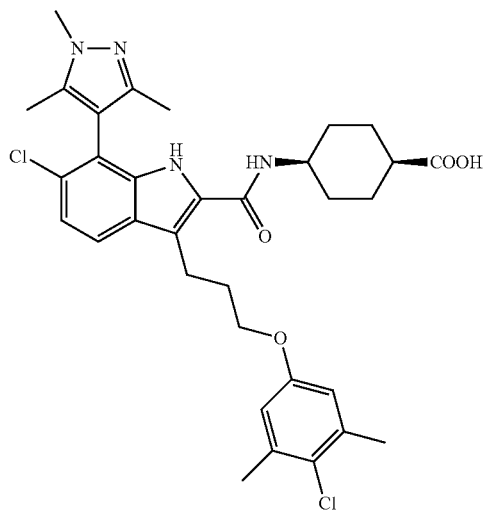 [SMILES: Cc1cc(OCCCc2c(C(=O)N[C@H]3CC[C@@H](C(=O)O)CC3)[nH]c3c(-c4c(C)nn(C)c4C)c(Cl)ccc23)cc(C)c1Cl]
I-332
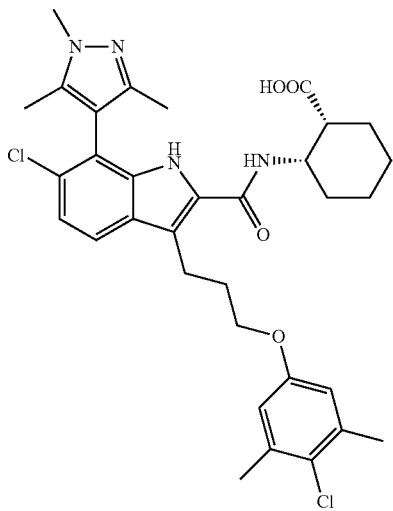 [SMILES: Cc1cc(OCCCc2c(C(=O)N[C@H]3CCCC[C@H]3C(=O)O)[nH]c3c(-c4c(C)nn(C)c4C)c(Cl)ccc23)cc(C)c1Cl]
I-333

TABLE 1-continued
Exemplary compounds.
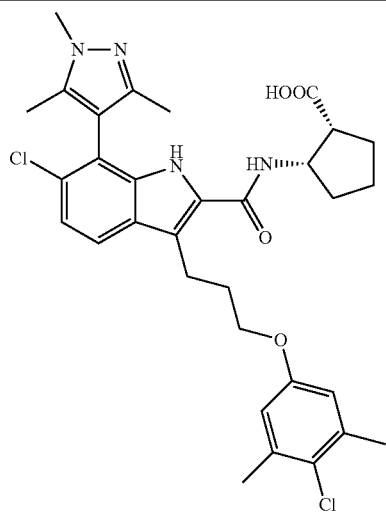
I-334
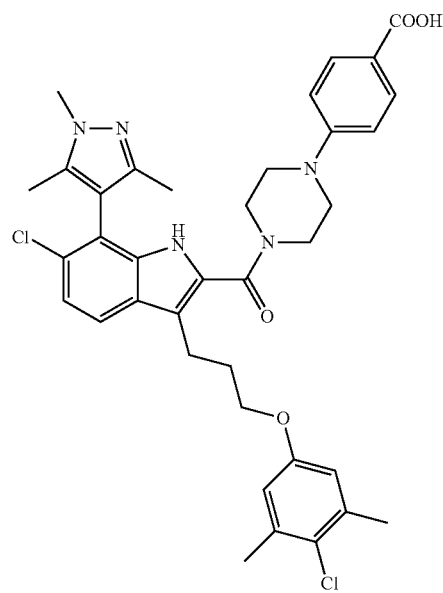 [SMILES: Cc1cc(OCCCc2c(C(=O)N3CCN(c4ccc(C(=O)O)cc4)CC3)[nH]c3c(-c4c(C)nn(C)c4C)c(Cl)ccc23)cc(C)c1Cl]
I-335
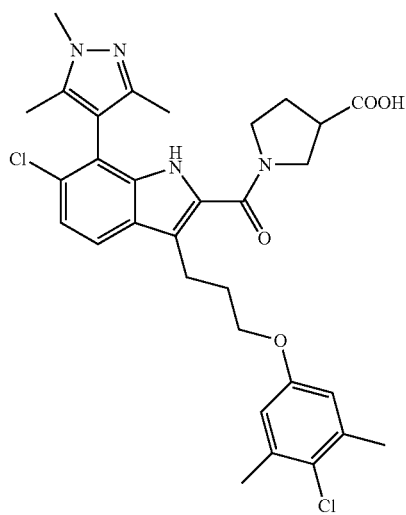 [SMILES: Cc1cc(OCCCc2c(C(=O)N3CCC(C(=O)O)C3)[nH]c3c(-c4c(C)nn(C)c4C)c(Cl)ccc23)cc(C)c1Cl]
I-336

TABLE 1-continued
Exemplary compounds.
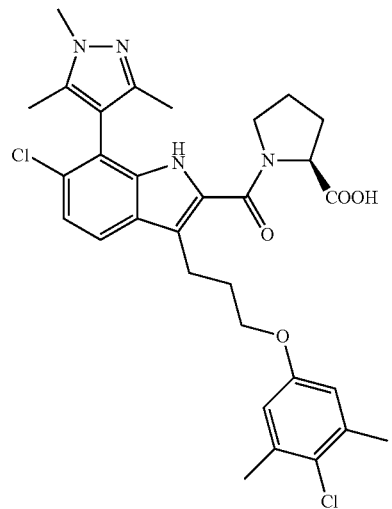 [SMILES: Cc1cc(OCCCc2c(C(=O)N3CCC[C@H]3C(=O)O)[nH]c3c(-c4c(C)nn(C)c4C)c(Cl)ccc23)cc(C)c1Cl]
I-337
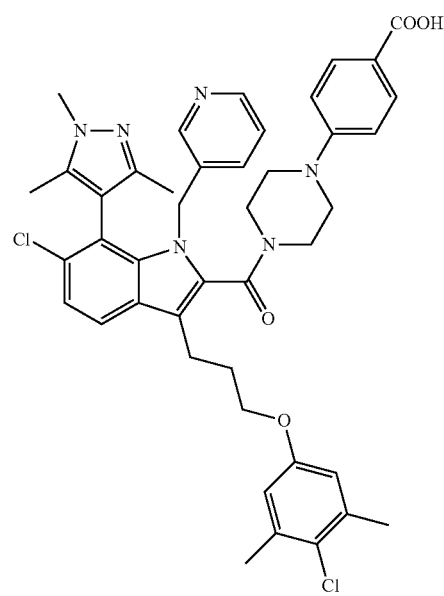 [SMILES: Cc1cc(OCCCc2c(C(=O)N3CCN(c4ccc(C(=O)O)cc4)CC3)n(Cc3cccnc3)c3c(-c4c(C)nn(C)c4C)c(Cl)ccc23)cc(C)c1Cl]
I-338

TABLE 1-continued
Exemplary compounds.
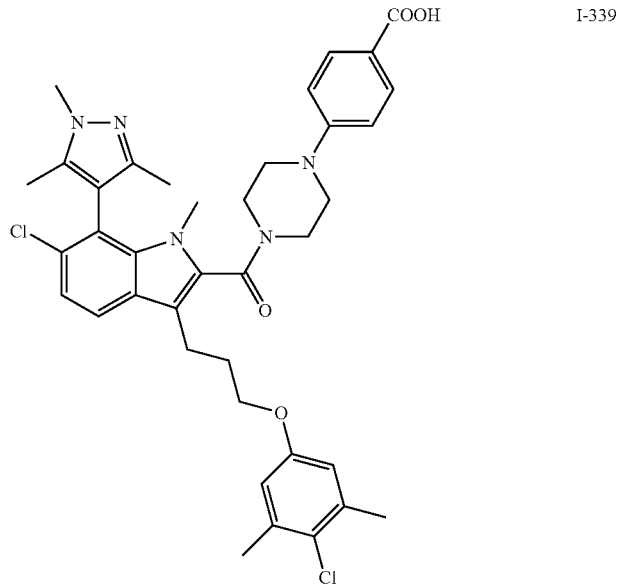
I-339
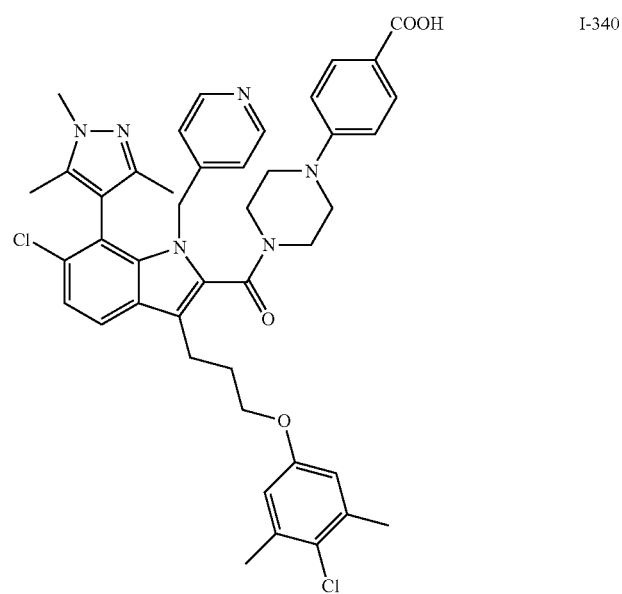
I-340

TABLE 1-continued
Exemplary compounds.
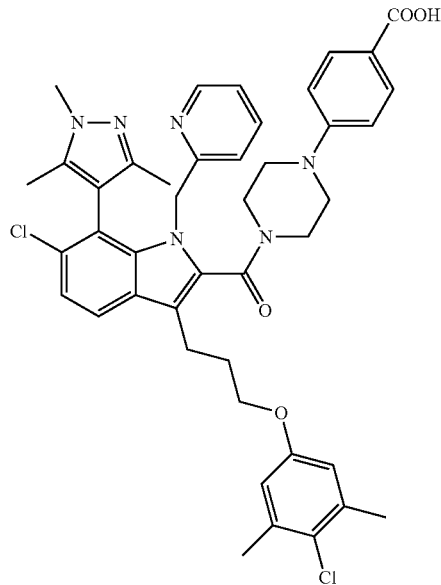 [SMILES: Cc1cc(OCCCc2c(C(=O)N3CCN(c4ccc(C(=O)O)cc4)CC3)n(Cc3ccccn3)c3c(-c4c(C)nn(C)c4C)c(Cl)ccc23)cc(C)c1Cl]
I-341
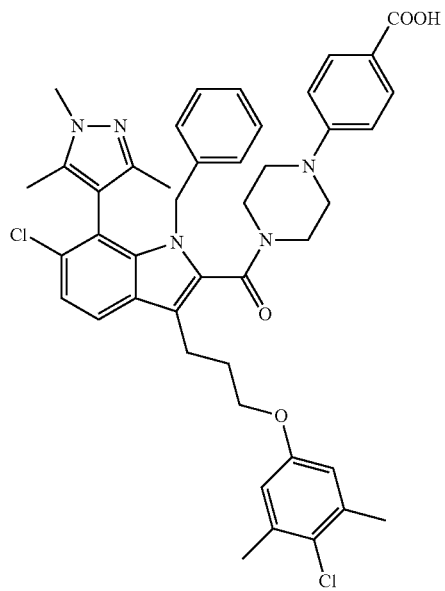 [SMILES: Cc1cc(OCCCc2c(C(=O)N3CCN(c4ccc(C(=O)O)cc4)CC3)n(Cc3ccccc3)c3c(-c4c(C)nn(C)c4C)c(Cl)ccc23)cc(C)c1Cl]
I-342

TABLE 1-continued
Exemplary compounds.
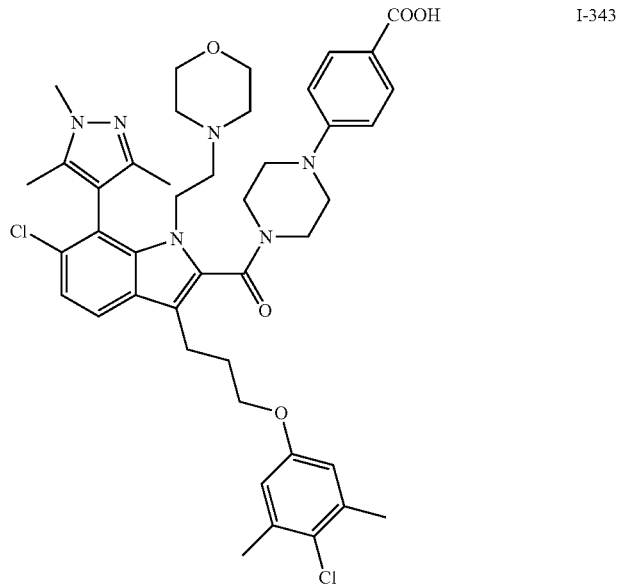
I-343
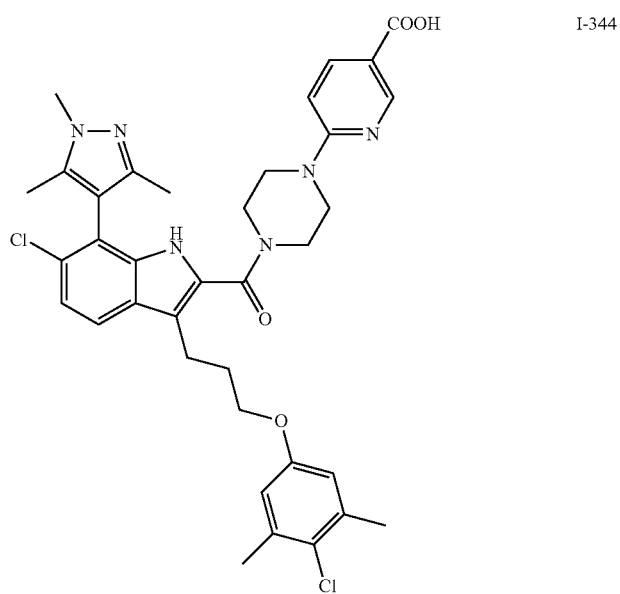
I-344

TABLE 1-continued
Exemplary compounds.
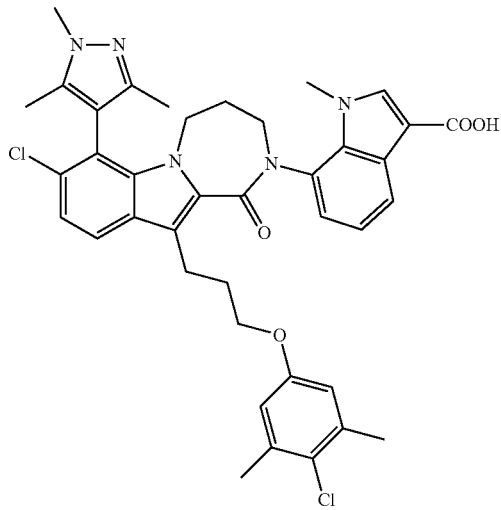 [SMILES: Cc1cc(OCCCc2c3n(c4c(-c5c(C)nn(C)c5C)c(Cl)ccc24)CCCN(c2cccc4c(C(=O)O)cn(C)c24)C3=O)cc(C)c1Cl]
I-345
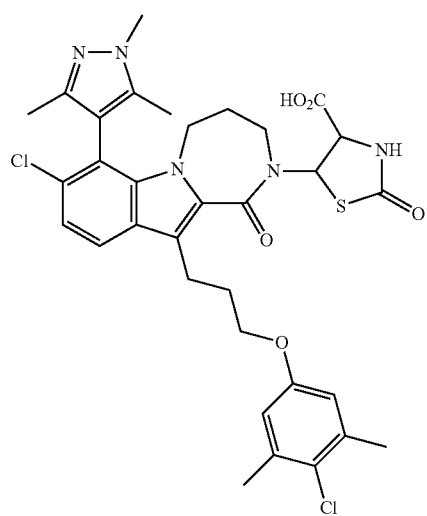 [SMILES: Cc1cc(OCCCc2c3n(c4c(-c5c(C)nn(C)c5C)c(Cl)ccc24)CCCN(C2SC(=O)NC2C(=O)O)C3=O)cc(C)c1Cl]
I-346
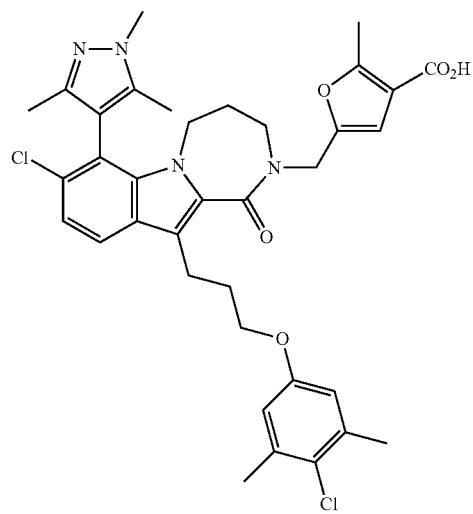 [SMILES: Cc1cc(OCCCc2c3n(c4c(-c5c(C)nn(C)c5C)c(Cl)ccc24)CCCN(Cc2cc(C(=O)O)c(C)o2)C3=O)cc(C)c1Cl]
I-347

TABLE 1-continued
Exemplary compounds.
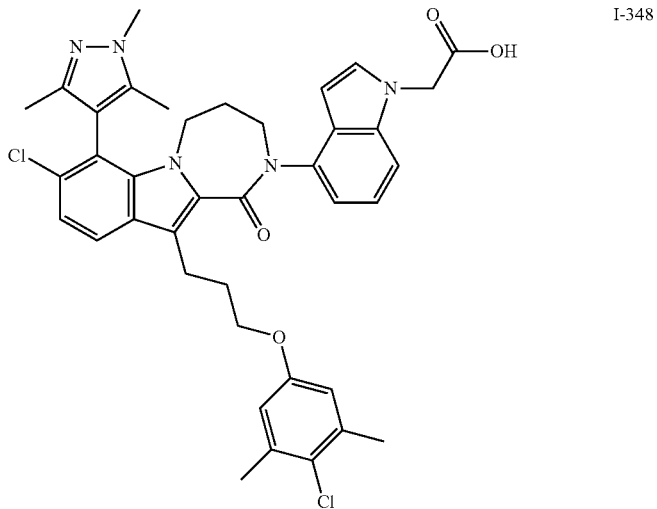
I-348
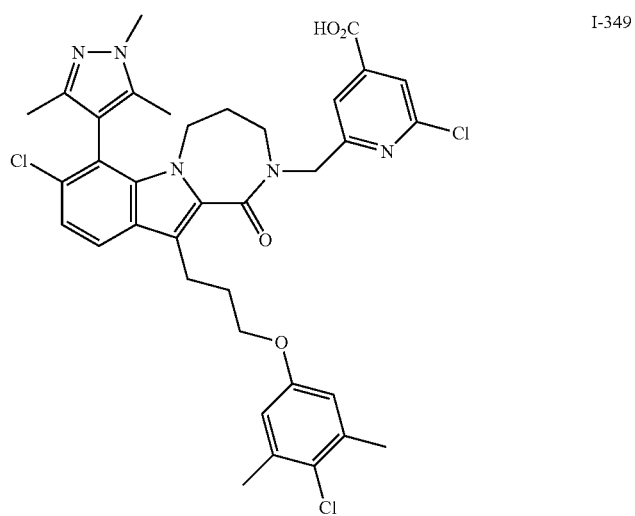
I-349
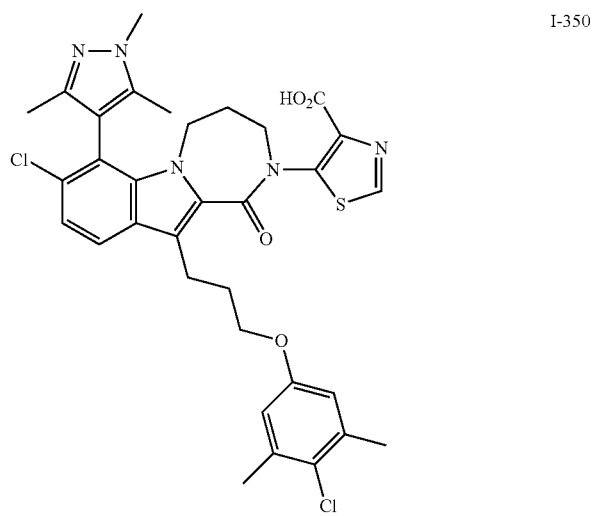
I-350

TABLE 1-continued
Exemplary compounds.
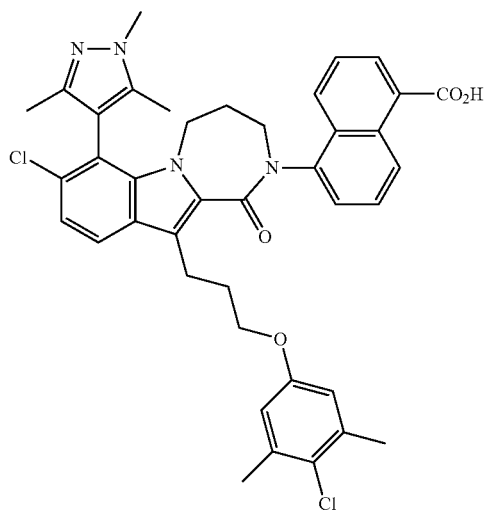 [SMILES: Cc1cc(OCCCc2c3n(c4c(-c5c(C)nn(C)c5C)c(Cl)ccc24)CCCN(c2cccc4c(C(=O)O)cccc24)C3=O)cc(C)c1Cl]
I-351
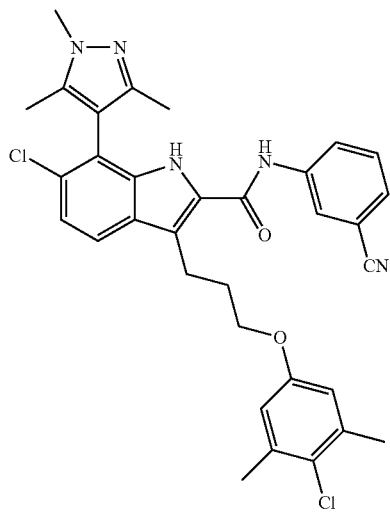 [SMILES: Cc1cc(OCCCc2c(C(=O)Nc3cccc(C#N)c3)[nH]c3c(-c4c(C)nn(C)c4C)c(Cl)ccc23)cc(C)c1Cl]
I-352
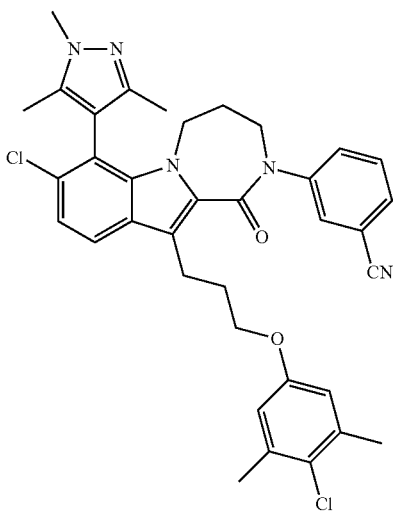 [SMILES: Cc1cc(OCCCc2c3n(c4c(-c5c(C)nn(C)c5C)c(Cl)ccc24)CCCN(c2cccc(C#N)c2)C3=O)cc(C)c1Cl]
I-353

TABLE 1-continued
Exemplary compounds.
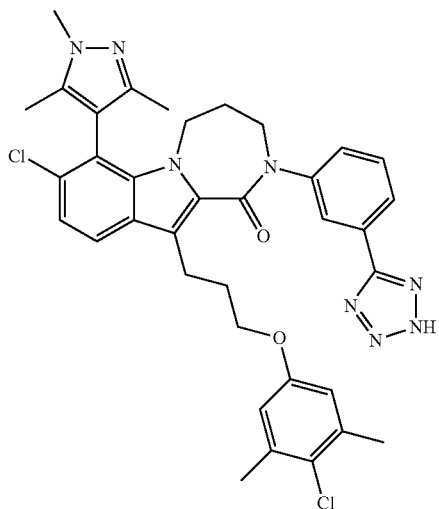 [SMILES: Cc1cc(OCCCc2c3n(c4c(-c5c(C)nn(C)c5C)c(Cl)ccc24)CCCN(c2cccc(-c4nn[nH]n4)c2)C3=O)cc(C)c1Cl]
I-354
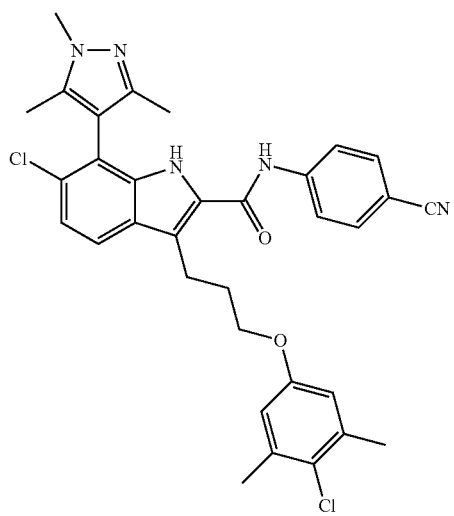 [SMILES: Cc1cc(OCCCc2c(C(=O)Nc3ccc(C#N)cc3)[nH]c3c(-c4c(C)nn(C)c4C)c(Cl)ccc23)cc(C)c1Cl]
I-355
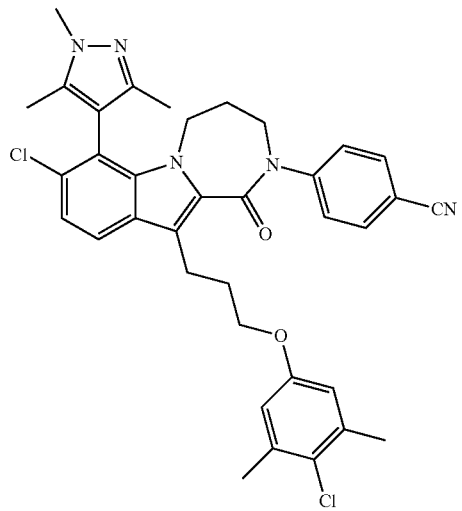 [SMILES: Cc1cc(OCCCc2c3n(c4c(-c5c(C)nn(C)c5C)c(Cl)ccc24)CCCN(c2ccc(C#N)cc2)C3=O)cc(C)c1Cl]
I-356

TABLE 1-continued
Exemplary compounds.
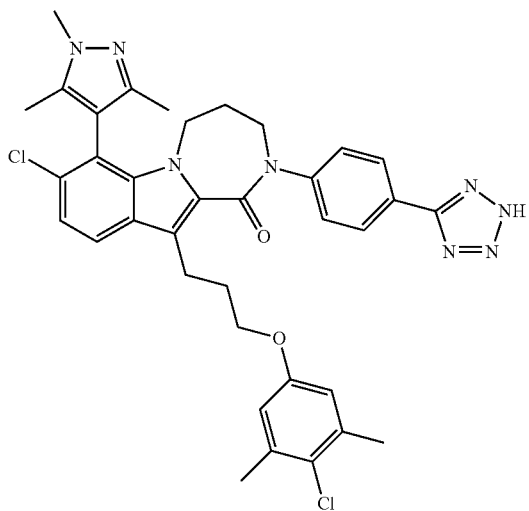 [SMILES: Cc1cc(OCCCc2c3n(c4c(-c5c(C)nn(C)c5C)c(Cl)ccc24)CCCN(c2ccc(-c4nn[nH]n4)cc2)C3=O)cc(C)c1Cl]
I-357
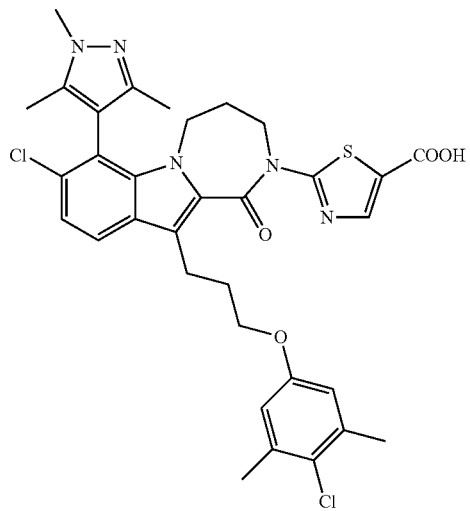 [SMILES: Cc1cc(OCCCc2c3n(c4c(-c5c(C)nn(C)c5C)c(Cl)ccc24)CCCN(c2ncc(C(=O)O)s2)C3=O)cc(C)c1Cl]
I-358
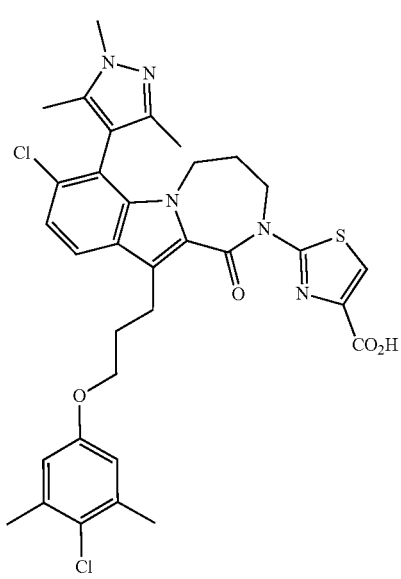 [SMILES: Cc1cc(OCCCc2c3n(c4c(-c5c(C)nn(C)c5C)c(Cl)ccc24)CCCN(c2nc(C(=O)O)cs2)C3=O)cc(C)c1Cl]
I-359

TABLE 1-continued
Exemplary compounds.
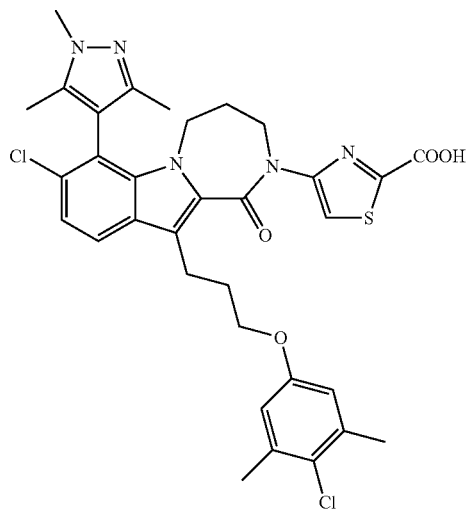 [SMILES: Cc1cc(OCCCc2c3n(c4c(-c5c(C)nn(C)c5C)c(Cl)ccc24)CCCN(c2csc(C(=O)O)n2)C3=O)cc(C)c1Cl]
I-360
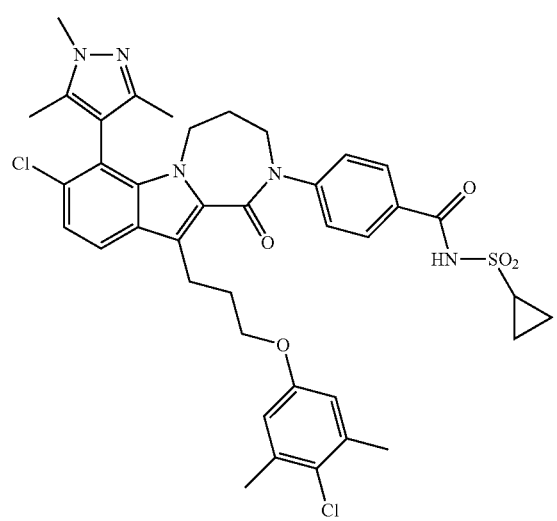 [SMILES: Cc1cc(OCCCc2c3n(c4c(-c5c(C)nn(C)c5C)c(Cl)ccc24)CCCN(c2ccc(C(=O)NS(=O)(=O)C4CC4)cc2)C3=O)cc(C)c1Cl]
I-361
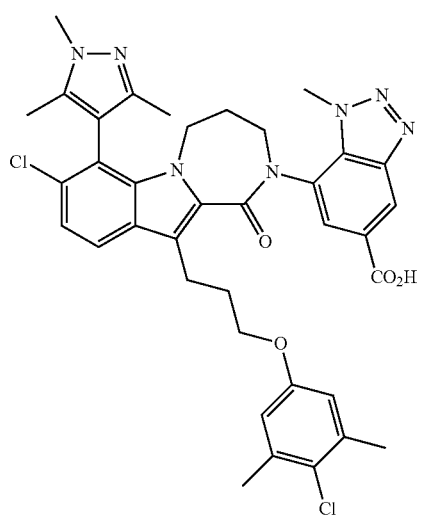 [SMILES: Cc1cc(OCCCc2c3n(c4c(-c5c(C)nn(C)c5C)c(Cl)ccc24)CCCN(c2cc(C(=O)O)cc4nnn(C)c24)C3=O)cc(C)c1Cl]
I-362

TABLE 1-continued
Exemplary compounds.
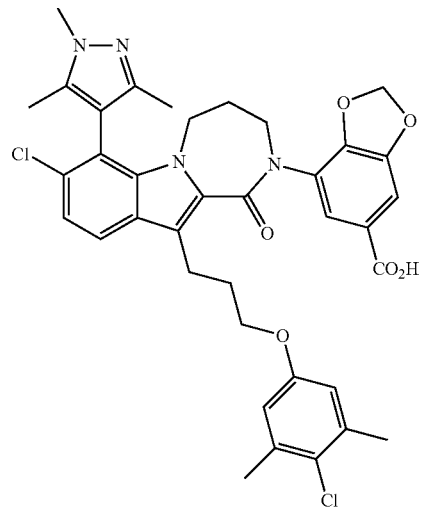 [SMILES: Cc1cc(OCCCc2c3n(c4c(-c5c(C)nn(C)c5C)c(Cl)ccc24)CCCN(c2cc(C(=O)O)cc4c2OCO4)C3=O)cc(C)c1Cl]
I-363
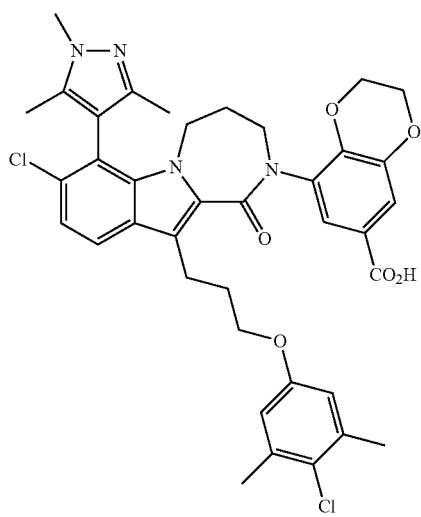 [SMILES: Cc1cc(OCCCc2c3n(c4c(-c5c(C)nn(C)c5C)c(Cl)ccc24)CCCN(c2cc(C(=O)O)cc4c2OCCO4)C3=O)cc(C)c1Cl]
I-364
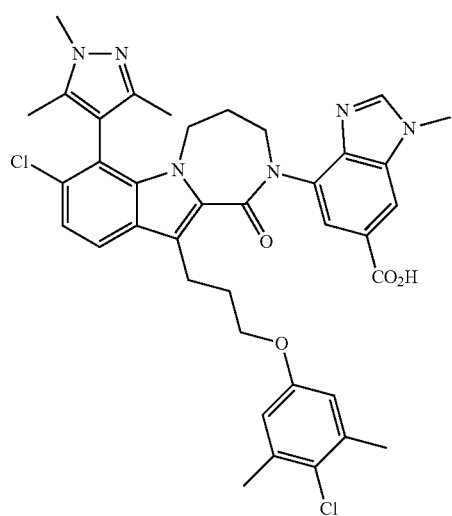 [SMILES: Cc1cc(OCCCc2c3n(c4c(-c5c(C)nn(C)c5C)c(Cl)ccc24)CCCN(c2cc(C(=O)O)cc4c2ncn4C)C3=O)cc(C)c1Cl]
I-365

TABLE 1-continued
Exemplary compounds.
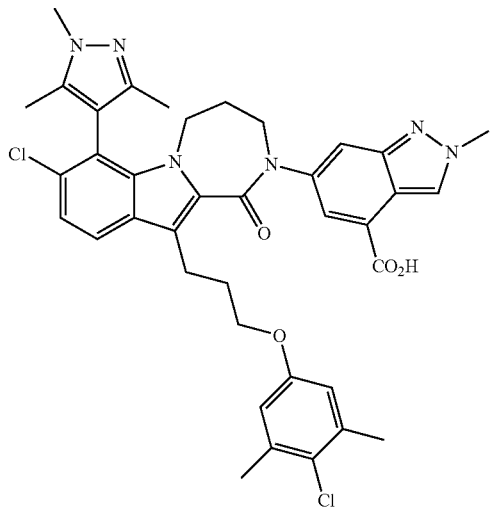 [SMILES: Cc1cc(OCCCc2c3n(c4c(-c5c(C)nn(C)c5C)c(Cl)ccc24)CCCN(c2cc(C(=O)O)c4cn(C)nc4c2)C3=O)cc(C)c1Cl]
I-366
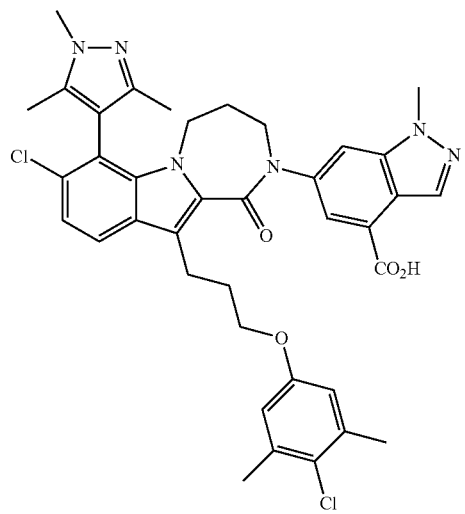 [SMILES: Cc1cc(OCCCc2c3n(c4c(-c5c(C)nn(C)c5C)c(Cl)ccc24)CCCN(c2cc(C(=O)O)c4cnn(C)c4c2)C3=O)cc(C)c1Cl]
I-367
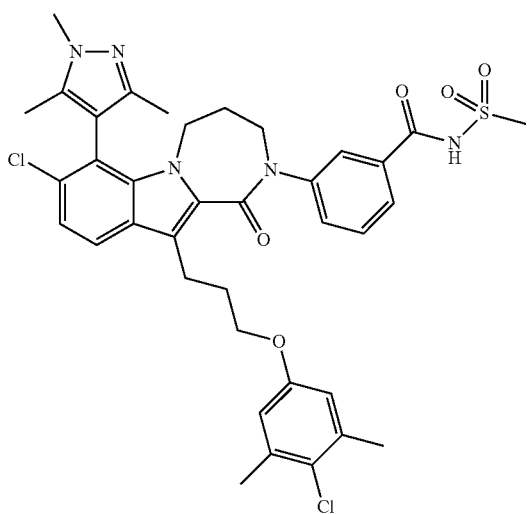 [SMILES: Cc1cc(OCCCc2c3n(c4c(-c5c(C)nn(C)c5C)c(Cl)ccc24)CCCN(c2cccc(C(=O)NS(C)(=O)=O)c2)C3=O)cc(C)c1Cl]
I-368

TABLE 1-continued
Exemplary compounds.
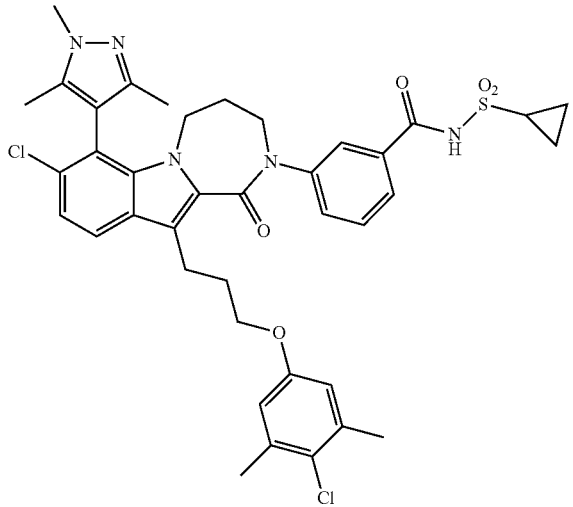 [SMILES: Cc1cc(OCCCc2c3n(c4c(-c5c(C)nn(C)c5C)c(Cl)ccc24)CCCN(c2cccc(C(=O)NS(=O)(=O)C4CC4)c2)C3=O)cc(C)c1Cl]
I-369
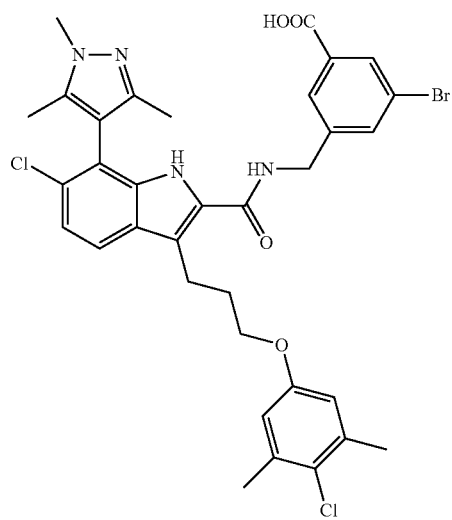 [SMILES: Cc1cc(OCCCc2c(C(=O)NCc3cc(Br)cc(C(=O)O)c3)[nH]c3c(-c4c(C)nn(C)c4C)c(Cl)ccc23)cc(C)c1Cl]
I-370
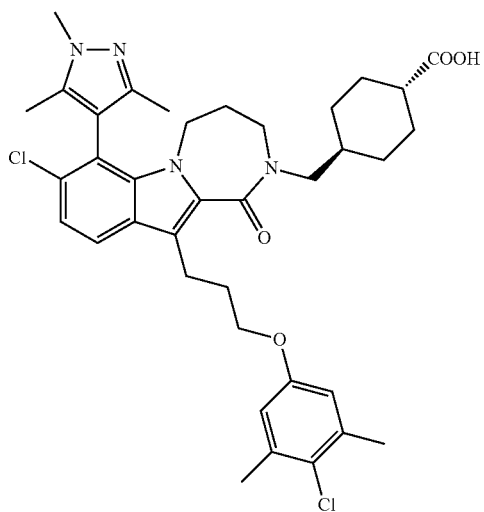 [SMILES: Cc1cc(OCCCc2c3n(c4c(-c5c(C)nn(C)c5C)c(Cl)ccc24)CCCN(C[C@H]2CC[C@H](C(=O)O)CC2)C3=O)cc(C)c1Cl]
I-371

TABLE 1-continued
Exemplary compounds.
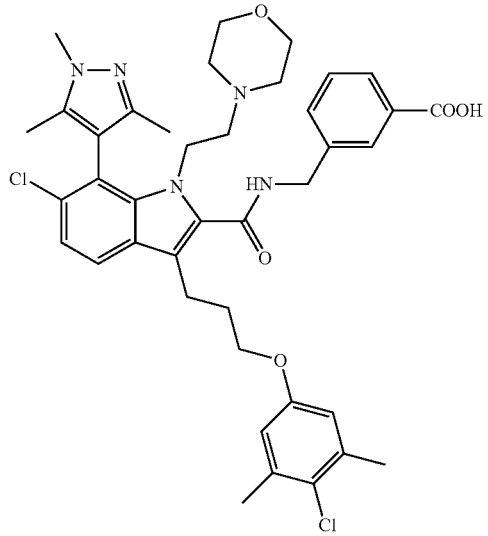 [SMILES: Cc1cc(OCCCc2c(C(=O)NCc3cccc(C(=O)O)c3)n(CCN3CCOCC3)c3c(-c4c(C)nn(C)c4C)c(Cl)ccc23)cc(C)c1Cl]
I-372
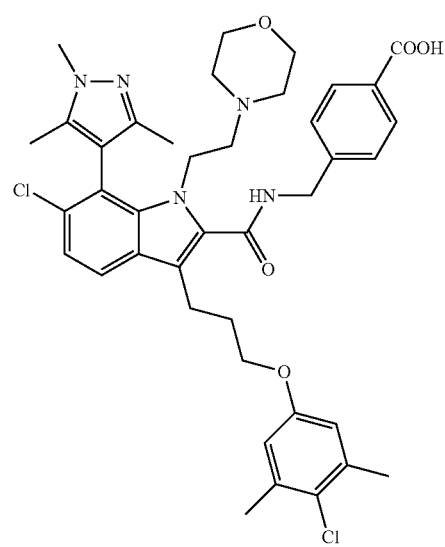 [SMILES: Cc1cc(OCCCc2c(C(=O)NCc3ccc(C(=O)O)cc3)n(CCN3CCOCC3)c3c(-c4c(C)nn(C)c4C)c(Cl)ccc23)cc(C)c1Cl]
I-373
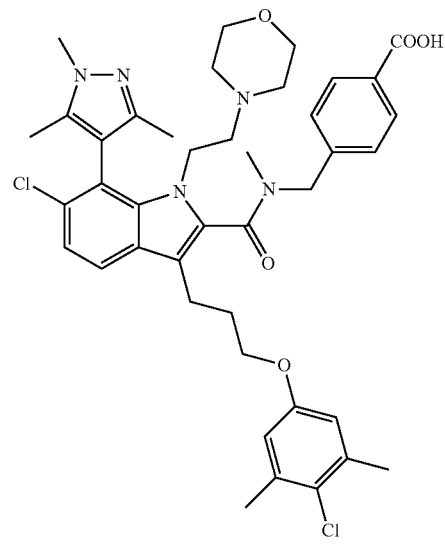 [SMILES: Cc1cc(OCCCc2c(C(=O)N(C)Cc3ccc(C(=O)O)cc3)n(CCN3CCOCC3)c3c(-c4c(C)nn(C)c4C)c(Cl)ccc23)cc(C)c1Cl]
I-374

TABLE 1-continued

Exemplary compounds.

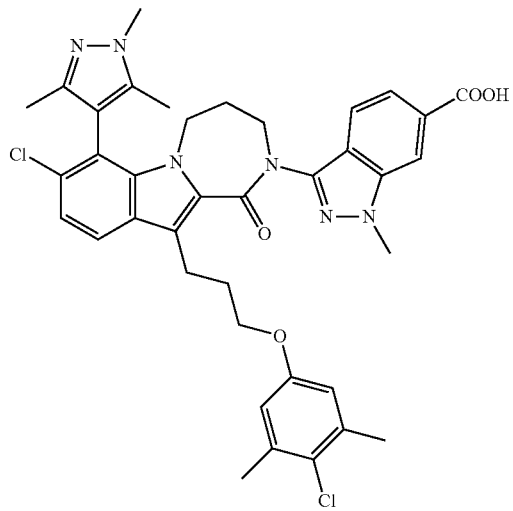 [SMILES: Cc1cc(OCCCc2c3n(c4c(-c5c(C)nn(C)c5C)c(Cl)ccc24)CCCN(c2nn(C)c4cc(C(=O)O)ccc24)C3=O)cc(C)c1Cl]

I-375

In certain embodiments, the present invention provides any compound selected from those depicted in Table 1, above, or a pharmaceutically acceptable salt thereof.

In some embodiments, a provided compound has a $K_i$ value less than about 0.011 µM for inhibition of Mcl-1. In some embodiments, a provided compound has a $K_i$ value less than about 0.1 µM for inhibition of Mcl-1. In some embodiments, a provided compound has a $K_i$ value less than about 0.2 µM for inhibition of Mcl-1. In some embodiments, a provided compound has a $K_i$ value less than about 0.3 µM for inhibition of Mcl-1. In some embodiments, a provided compound has a $K_i$ value less than about 0.4 µM for inhibition of Mcl-1. In some embodiments, a provided compound has a $K_i$ value less than about 0.5 µM for inhibition of Mcl-1. In some embodiments, a provided compound has a $K_i$ value less than about 0.6 µM for inhibition of Mcl-1. In some embodiments, a provided compound has a $K_i$ value less than about 0.7 µM for inhibition of Mcl-1. In some embodiments, a provided compound has a $K_i$ value less than about 0.8 µM for inhibition of Mcl-1. In some embodiments, a provided compound has a $K_i$ value less than about 0.9 µM for inhibition of Mcl-1. In some embodiments, a provided compound has a $K_i$ value less than about 1 µM for inhibition of Mcl-1. In some embodiments, a provided compound has a $K_i$ value less than about 2 µM for inhibition of Mcl-1. In some embodiments, a provided compound has a $K_i$ value less than about 3 µM for inhibition of Mcl-1. In some embodiments, a provided compound has a $K_i$ value less than about 4 µM for inhibition of Mcl-1. In some embodiments, a provided compound has a $K_i$ value less than about 5 µM for inhibition of Mcl-1. Exemplary assays for measuring $K_i$ value for inhibition of Mcl-1 is widely known in the art, including but not limited to those described in the examples herein. In some embodiments, an assay for measuring $K_i$ value for inhibition of Mcl-1 is described in Example 377.

4. Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit Mcl-1, in a biological sample or in a patient. In certain embodiments, the amount of compound in compositions of this invention is such that is effective to measurably inhibit Mcl-1, in a biological sample or in a patient. In certain embodiments, a composition of this invention is formulated for administration to a patient in need of such composition. In some embodiments, a composition of this invention is formulated for oral administration to a patient.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Mcl-1, or a mutant thereof, activity in a biological sample is useful for a variety of purposes that are known to one of skill in the art. Examples of such purposes include, but are not limited to, blood transfusion, organ transplantation, biological specimen storage, and biological assays.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In another aspect the present disclosure provides a method of treating a disease or disorder associated with the expression or over-expression of anti-apoptotic Bcl-2 family protein members, and in certain embodiments those diseases characterized by the expression or the over-expression of Mcl-1 proteins, comprising administering to a mammalian patient a therapeutically effective amount of a compound of formula I, II, III, IV, V, VI, or VII, or a pharmaceutically acceptable salt or solvate or a pharmaceutically acceptable carrier thereof.

Further, in accordance with the present invention, a method is provided for preventing, modulating, or treating the progression or onset of diseases or disorders associated with the upregulated activity of the Bcl-2 family of proteins, specifically Mcl-1 protein, such as defined above and hereinafter, wherein a therapeutically effective amount of a compound of formula I, II, III, IV, V, VI, or VII is administered to a mammalian, i.e., human, patient in need of treatment.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting Mcl-1, or a mutant thereof, activity in a patient comprising the step of administering to said patient a compound of the present invention, or a composition comprising said compound. In other embodiments, the present invention provides a method for treating a disorder mediated by Mcl-1, or a mutant thereof, in a patient in need thereof, comprising the step of administering to said patient a compound according to the present invention or pharmaceutically acceptable composition thereof. Such disorders are described in detail herein.

Compounds of the present invention modulate the activity of the Bcl-2 family of proteins. Preferably, compounds of the present invention inhibit the activity of one type or a subset of anti-apoptotic Bcl-2 family of proteins, for examples of Mcl-1, Bcl-2, Bcl-xL, and Bcl-w proteins. Consequently, the compounds of the present invention may be used in the treatment of multiple diseases or conditions of abnormal cell growth and/or dysregulated apoptosis, such as cancer, autoimmune disease and pro-thrombotic conditions. Examples of diseases or disorders associated with down-regulated apoptosis can be prevented, modulated, or treated according to the present invention include, but are not limited to, acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myeleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

The compounds of the present invention possess activity as inhibitors of the Bcl-2 family proteins, particularly Mcl-1 protein, and, therefore, may be used in the treatment of diseases associated with anti-apoptotic Bcl-2 family of proteins. Via the inhibitition of the activity of anti-apoptotic Bcl-2 family proteins, the compounds of the present invention may preferably be employed to release pro-apoptotic and promote apoptosis.

Accordingly, the compounds of the present invention can be administered to mammals, preferably humans, for the treatment of a variety of conditions and disorders, including, but not limited to, treating, preventing, or slowing the progression of various hematologic and solid tumor types and related conditions, resistance development associated with chemotherapy. Consequently, it is believed that the compounds of the present invention may be used in preventing, inhibiting, or treating acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myeleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

It is also expected that the compounds of the present invention may be used in preventing, inhibiting, or treating pediatric cancers or neoplasms including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like. (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Bf. 1. Haematol. 2000 September; 110(3): 584-90; Blood 2000 Feb. 15; 95(4): 1283-92; and New England Journal of Medicine 2004 September; 351(14): 1409-1418).

Involvement of Mcl-1 in acute lymphoblastic leukemia is reported in *Blood* (1998) 91, 991-1000.

Involvement of Mcl-1 in pancreatic carcinoma is reported in *Cancer Chemotherapeutic Pharmacology* (2008) 62, 1055-1064.

Involvement of Mcl-1 in breast cancer is reported in *Anticancer Research* (2004) 24, 473-482.

Involvement of Mcl-1 in breast and non small-cell lung cancer is also reported in *Nature* (2010) 463, 899-905

Involvement of Mcl-1 in non small-cell lung cancer is also reported in *Oncogene* (2011) 30, 1963-1968

Involvement of Mcl-1 in acute myelogenous leukemia is reported in *Blood* (1998) 91, 991-1000.

Involvement of Mcl-1 in cervical cancer is reported in *Cancer Letters* (Shannon, Ireland) (2002) 180, 63-68.

Involvement of Mcl-1 in cervical cancer is also reported in *Medical Oncology* (2011) 3, 673-677.

Involvement of Mcl-1 in chronic lymphocytic leukemia is reported in *Journal of the National Cancer Institute* (2004) 96, 673-682 and *Immunology* (2005) 114, 441-449.

Involvement of Mcl-1 in colorectal cancer, is reported in *Annals of oncology: Official Journal of the European Society for Medical Oncology/ESMO* (2001) 12, 779-785.

Involvement of Mcl-1 in gastric carcinoma, is reported in *Gastric Cancer* (2004) 7, 78-84.

Involvement of Mcl-1 in gestational trophobalstic disease is reported in *Cancer* (2005) 103, 268-276.

Involvement of Mcl-1 in glioblastoma is reported in *Journal of Neurology, Neurosurgery, and Psychiatry* (1999) 67, 763-768.

Involvement of Mcl-1 in head and neck cancer is reported in *Archives of Otolaryngology-Head and Neck Surgery* (1999) 125, 417-422.

Involvement of Mcl-1 in lung cancer is reported in *Pathology Oncology Research: POR* (1999) 5, 179-186.

Involvement of Mcl-1 in lung cancer is also reported in *Cancer Biology and Therapy* (2005) 4, 267-276.

Involvement of Mcl-1 in mesothioloma, is reported in *Clinical Cancer Research* (1999) 5, 3508-3515.

Involvement of Mcl-1 in mesothioloma, is also reported in *Carcinogenesis* (2010) 6, 984-993.

Involvement of Mcl-1 in multiple myeloma is reported in *European Journal of Immunology* (2004) 34, 3156-3164.

Involvement of Mcl-1 in non-Hodgkin's lymphoma is reported in *British Journal of Haematology* (2002) 116, 158-161.

Involvement of Mcl-1 in oligodenroglioma is reported in *Cancer* (1999) 86, 1832-1839.

Involvement of Mcl-1 in ovarian cancer is reported in *Journal of Clinical Oncology: Official Journal of the American Society of Clinical Oncology* (2000) 18, 3775-3781.

Involvement of Mcl-1 in ovarian cancer is also reported in *Molecular Genetics, Gastrointestinal Carcinoma and Ovarian Carcinoma* (2005) 4, 479-486.

Involvement of Mcl-1 in pancreatic cancer is reported in *Oncology* (2002) 62, 354-362.

Involvement of Mcl-1 in peripheral T-cell lymphoma is reported in *Journal of Pathology* (2003) 200, 240-248.

Over-expression of Bcl-2 family protein members is associated with resistance to chemotherapy and is correlated with clinical outcome, disease progression, overall prognosis or a combination thereof in various hematologic and solid tumor types Examples of diseases or disorders associated with the hyperactivity of the Bcl-2 family of proteins, particularly Mcl-1, that can be prevented, modulated, or treated according to the present invention include, but are not limited to, acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

It is also expected that compounds having formula I, II, III, IV, V, VI, or VII would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

In one embodiment, a compound of the invention (e.g., a compound of formula I, II, III, IV, V, VI, or VII), or stereoisomer, geometric isomer, tautomer, solvate, metabolite, or pharmaceutically acceptable salt, prodrug thereof, is used as an anticancer agent or as an adjunct agent for the treatment of cancer in a combination therapy. One of ordinary skill in the art is readily able to determine whether or not a candidate compound treats a cancerous condition for any particular cell type, either alone or in combination. Within certain aspects of this embodiment, compounds of the invention are used in adjunct with other therapies, including conventional surgery, radiotherapy and chemotherapy, for the treatment of cancer.

In another embodiment, the present invention provides for compositions for treating diseases in a patient during which is expressed or overexpressed an anti-apoptotic Bcl-2 family protein, said compositions comprising an excipient and a therapeutically effective amount of the compound of any of formula I, II, III, IV, V, VI, or VII and a therapeutically effective amount of one additional therapeutic agent or more than one additional therapeutic agent.

The compounds of the invention can be used alone, in combination with other compounds of the present invention, or in combination with one or more other agent(s). Further, the present invention provides a method for preventing, modulating, or treating the diseases as defined above and hereinafter, wherein a therapeutically effective amount of a combination of a compound of formula I, II, III, IV, V, VI, or VII and another compound of formula I, II, III, IV, V, VI, or VII and/or at least one other type of therapeutic agent, is administered to a mammalian, e.g., human, patient in need of treatment.

The present invention includes within its scope pharmaceutical compositions comprising, as an active ingredient, a therapeutically effective amount of at least one of the compounds of formula I, II, III, IV, V, VI, or VII, alone or in combination with a pharmaceutical carrier or diluent. Optionally, compounds of the present invention can be used alone, in combination with other compounds of the invention, or in combination with one or more other therapeutic agent(s), e.g., an anticancer agent or other pharmaceutically active material.

Depending upon the particular condition, or disease, to be treated, additional therapeutic agents, which are normally administered to treat that condition, are optionally present in the compositions of this invention. As used herein, additional therapeutic agents that are normally administered to treat a particular disease, or condition, are known as "appropriate for the disease, or condition, being treated."

For example, compounds of the present invention, or a pharmaceutically acceptable composition thereof, are administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, among others. In other embodiments, a compound of the present invention is administered in combination with a biologic agent, such as Avastin or VECTIBIX.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Other examples of agents the inhibitors of this invention are also combined with include, without limitation: treatments for Alzheimer's Disease such as donepezil hydrochloride (Aricept®) and rivastigmine (Exelon®); treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), glatiramer acetate (Copaxone®), and mitoxantrone; treatments for asthma such as albuterol and montelukast (Singulair®); agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents are optionally administered separately from an inventive compound-containing composition, as part of a multiple dosage regimen. Alternatively, those agents are optionally part of a single dosage form, mixed together with a compound of this invention in a single composition. If administered as part of a multiple dosage regime, the two active agents are submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention is administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that is combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, are optionally incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects are prevented or mitigated by pre-coating the device with a pharmaceutically acceptable composition comprising a kinase inhibitor. Implantable devices coated with a compound of this invention are another embodiment of the present invention.

The compounds of the present invention may be employed in adjunct with other therapies, including conventional surgery, radiotherapy and chemotherapy, for the treatment of cancer.

Such therapies can include one or more of the following categories of anti-cancer agents: alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, inhibitors of apoptosis proteins (IAPs), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Examples of suitable alkylating agents include altretamine, AMD-473, AP-5280, apaziquone, bendamustine, brostallicin, busulfan, carboquone, carmustine (BCNU), chlorambucil, Cloretazine™ (VNP 40101 M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, trofosfamide and the like.

Examples of suitable angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Examples of suitable aurora kinase inhibitors include AZD-1152, MLN-8054, VX-680 and the like.

Examples of suitable antimetabolites include ALIMTA® (pemetrexed disodium, L Y231514, MTA), 5 azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflomithine, E1CAR (5-ethynyl-1-–-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-I, tiazofurin, tegafur, TS-1, vidarabine, UFT and the like.

Examples of suitable Bcl protein family member inhibitors include AT-101 ((−)gossypol), GENASENSE® (G3139 or oblimersen (Bcl-2-targeting antisense oglionucleotide)), IPI-194, IPI-565, N-(4-(4-((4'-chloro(1,1'-biphenyl)-2-yl)methyl)piperazin-1-yl)benzoyl)-4-(((1R)-3-(dimethyl amino)-1-((phenylsulfanyl)methyl)propyl)amino)-3-nitrobenzenesulfonamide) (AB T-737), N-(4-(4-((2-(4-chlorophenyl)-5,5-dimethyl-1-cyclohex-I-en-1-yl)methyl)piperazin-1-yl)benzoyl)-4-(((1R)-3-(morpholin-4-yl)-I ((phenylsulfanyl)methyl)propyl) amino)-3-((trifluoromethyl) sulfonyl) benzenesulfonamide (ABT-263), N-(4-(4-((4'-chloro(1,1'-biphenyl)-2-yl)methyl) piperazin-1-yl)benzoyl)-4-(((1R)-3-(dimethylamino)-1-((phenylsulfanyl)methyl)propyl)amino)-3-nitro benzenesulfonamide) (ABT-737), ABT-199, GX-070 (obatoclax) and the like.

Examples of suitable Bcr-Abl kinase inhibitors include DASATINIB® (BMS-354825), GLEEVEC® (imatinib) and the like.

Examples of suitable CDK inhibitors include AZD-5438, BMI-I040, BMS-032, BMS-387, CVT-2584, flavopyridol, GPC-286199, MCS-5A, PD0332991, PHA-690509, seliciclib (CYC-202, R-roscovitine), ZK-304709 and the like.

Examples of suitable COX-2 inhibitors include ARCOXIA® (etoricoxib), BEXTRA® (valdecoxib), BMS347070, CELEBREX™ (celecoxib), COX-189 (lumiracoxib), CT-3, DERAMAXX® (deracoxib), ITE-522, 4-methyl-2-(3,4-dimethylphenyl)-I-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

Examples of suitable EGFR inhibitors include ABX-EGF, anti-EGFr immunoliposomes, EGF-vaccine, EMD-7200, ERBITUX® (cetuximab), HR3, 19A antibodies, IRESSA® (gefitinib), TARCEVA® (erlotinib or OS1-774), TP-38, EGFR fusion protein, TYKERB® (lapatinib) and the like.

Examples of suitable ErbB2 receptor inhibitors include CP-724-714, C1-I033 (canertinib), Herceptin® (trastuzumab), TYKERB® (lapatinib), OMNITARG® (2C4, petuzumab), TAK-165, GW-572016 (ionafamib), GW-282974, EKB-569, P1-166, dHER2 (HER2 vaccine), APC-8024 (HER-2 vaccine), anti-HER12neu bispecific antibody, B7.her21gG3, AS HER2 trifunctional bispecfic antibodies, mAB AR-209, mAB 2B-1 and the like.

Examples of suitable histone deacetylase inhibitors insule depsipeptide, LAQ-824, MS-275, trapoxin, suberoylanilide hydroxamic acid (SAHA), TSA, valproic acid and the like.

Examples of suitable HSP-90 inhibitors include 17-AAG-nab, 17-AAG, CNF-I01, CNF-I0I0, CNF-2024, 17-DMAG, geldanamycin, 1P1-504, KOS-953, MYCOGRAB®, NCS-683664, PU24FC1, PU3, radicicol, SNX-2112, STA-9090 VER49009 and the like.

Examples of suitable MEK inhibitors include ARRY-142886, ARRY-438162 PD-325901, PD-98059 and the like.

Examples of suitable activators of death receptor pathway include TRAIL, antibodies or other agents that target death receptors (e.g., DR4 and DR5) such as Apomab, conatumumab, ETR2-ST01, GDC0145, lexatumumab, HGS-1029, LBY-135, PRO-1762 and trastuzumab.

Examples of suitable mTOR inhibitors include AP-23573, CC1-779, everolimus, RAD-OO1, rapamycin, temsirolimus and the like.

Examples of suitable non-steroidal anti-inflammatory drugs include AM1GES1C® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetm), LODINE® (etodolac), TORADOL® (ketorolac), DAYPRO® (oxaprozin) and the like.

Examples of suitable platinum chemotherapeutics include cisplatin, ELOXATIN® (oxaliplatin) eptaplatin, lobaplatin, nedaplatin, PARAPLATIN® (carboplatin), satrap latin and the like.

Examples of suitable polo-like kinase inhibitors include B1-2536 and the like.

Examples of suitable thrombospondin analogs include TSP-1 and the like.

Examples of suitable VEGFR inhibitors include AVASTIN® (bevacizumab), AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), vatalanib (PTK-787, ZK-222584), SUTENT® (sunitinib, SU-11248), VEGF trap, vatalanib, ZACTIMA (vandetanib, ZD-6474) and the like.

Examples of suitable antibiotics include intercalating antibiotics aclarubicin, actinomycin D, amrubicin, annamycin, adriamycin, BLENOXANE® (bleomycin), daunorubicin, CAEL YX® or MYOCET® (doxorubicin), elsamitrucin, epirbucin, glarbuicin, ZA VEDOS® (idarubicin), mitomycin C, nemorubicin, neocarzinostatin, peplomycin, pirarubicin, rebeccamycin, stimalamer, streptozocin, VAL-STAR® (valrubicin), zinostatin and the like.

Examples of suitable topoisomerase inhibitors include aclarubicin, 9-aminocamptothecin, amonafide, BN-80915, CAMPTOSAR® (irinotecan hydrochloride), amptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Examples of suitable antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, P ANOREX® (edrecolomab), RENCAREX® (WX G250), RITUXAN® (rituximab), ticilimumab, trastuzimab and the like.

Examples of suitable hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Examples of suitable deltoids and retinoids include seocalcitol (EB1089, CB1093), lexacalcitrol (KH1060), fenretinide, PANRETIN® (aliretinoin), ATRAGEN® (liposomal tretinoin), TARGRETIN®(bexarotene), LGD-1550 and the like.

Examples of suitable plant alkaloids include, but are not limited to, vincristine, vinblastine, vindesine, vinorelbine and the like.

Examples of suitable PARP inhibitors include olaparib, KU-59436, ABT-888, AZD-2281, AG-014699, BSI-201, BGP-15, INO-IOOI, ONO-2231 and the like.

Examples of suitable proteasome inhibitors include VELCADE® (bortezomib), MG132, NPI-0052, PR-171 and the like.

Examples of suitable immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE®(lenograstim), lentinan, leukocyte alpha interferon, imiquimod, MDX-010, melanomavaccine, mitumomab, molgramostim, MYLOTARG™® (gemtuzumab ozogamicin). NEUPOGEN® (filgrastlm), OncoVAC-CL, OvaRex® (oregovomab), pemtumomab (Y-muH-MFG1), PROVENGE®, sargaramostim, sizofilan, teceleukin, TheraCys®, ubenimex, VIRULIZIN®, Z-1OO, WF-1O, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Examples of suitable purine analogs include LANVIS® (thioguanine) and PURI-NETHOL® (mercaptopurine).

Examples of suitable antimitotic agents include batabulin, epothilone D (KOS-862), N-(2-((4-hydroxyphenyl)amino) pyridin-3-yl)-4-methoxybenzenesulfonamide, ixabepilone (BMS 247550), paclitaxel, TAXOTERE® (docetaxel), PNUI00940 (109881), patupilone, XRP-9881(larotaxel), vinflunine, ZK-EPO and the like.

Compounds of the present invention can also be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having formula I or II may be combined with other chemotherapeutic agents such as ABRAXANE™ (ABI-007), ADVEXIN®, ALTOCOR® or MEVACOR® (lovastatin), AMPLIGEN® (polyl:poly CI2U, a synthetic RNA), APTOSYN™ (exisulind), AREDIA® (pamidronic acid), arglabin, L-asparaginase, atamestane (1-methyl-3, 17-dione-androsta-1,4-diene), A V AGE® (tazarotne), A VE-8062, BEC2 (mitumomab), cachectin or cachexin (tumor necrosis factor), canvaxin (vaccine), CeaVac™ (cancer vaccine), CELEUK® (celmoleukin), CEPLENE®(histamine dihydrochloride), CERVARIX™ (human papillomavirus vaccine), CHOP® (C:CYTOXAN® (cyclophosphamide); H: ADRIAMYCIN® (hydroxydoxorubicin); Vincristine (ONCOVIN®); P: prednisone), CyPat™, combrestatin A4P, DAB(389)EGF or TransMID-I007R™ (diphtheria toxins), dacarbazine, dactinomycin, 5,6-dimethylxanthenone-4-acetic acid (DMXAA), enilura-cil, EVIZON™ (squalamine lactate), DIMERICINE® (T4N5 liposome lotion), discodermolide, DX-8951f(exatecan mesylate), enzastaurin, EP0906, GARDASIL® (quadrivalent human papillomavirus (Types 6, 11, 16, 18) recombinantvaccine), gastrimmune, genasense, GMK (ganglioside conjugate vaccine), GVAX® (prostate cancer vaccine), halofuginone, histerelin, hydroxycarbamide, ibandronic acid, IGN-101, IL-3-PE38, IL-13-PE38QQR (cintredekin besudotox), IL-13-*pseudomonas* exotoxin, interferon-a, interferon-y, JUNOVAN™ or MEPACT™ (mifamurtide), lonafarnib, 5,10-25 methylenetetrahydrofolate, miltefosine (hexadecylphosphocholine), NEOVASTAT®(AE-941), NEUTREXIN® (trimetrexate glucuronate), NIPENT® (pentostatin), ONCONASE® (aribonuclease enzyme), ONCOPHAGE® (melanoma vaccine treatment), OncoVAX (IL-2Vaccine), ORATHECIN™ (rubitecan), OSIDEM® (antibody-based cell drug), OvaRex®MAb (murine monoclonal antibody), paditaxel, PANDIMEX™ (aglycone saponins from *ginseng* comprising 20(S)protopanaxadiol (aPPD) and 20(S)protopanaxatriol (aPPT)), panitumumab, PANVAC®-VF (investigational cancer vaccine), pegaspargase, PEGInterferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PTIOO), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio) quinazoline dihydrochloride), TNFerade™ (adenovector: DNA carrier containing the gene for tumor-necrosis factor-a), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alpha vbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

The combination therapy can be administered as a simultaneous or sequential regimen. When administered sequentially, the combination can be administered in two or more administrations. The combined administration includes co-administration, using separate formulations or a single pharmaceutical formulation, and consecutive administration in either order, wherein preferably there is a time period while both (or all) active agents simultaneously exert their biological activities.

The above other therapeutic agents, when employed in combination with the compounds of the present invention may be used, for example, in those amounts indicated in the *Physicians' Desk Reference*, as in the patents set out above, or can be lowered due to the combined action (synergy) of the newly identified agent and other chemotherapeutic agents or treatments as determined by one of ordinary skill in the art.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

The compounds of formula I, II, III, IV, V, VI, or VII can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating cancers and related diseases, a pharmaceutical composition will be employed containing the compounds of formula I, II, III, IV, V, VI, or VII, with or without other anticancer agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of formula I, II, III, IV, V, VI, or VII (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of a compound of formula I, II, III, IV, V, VI, or VII into a vial, aseptically freeze-drying and sealing. For use, the contents of the vial are mixed with 2 mL of physiological saline, to produce an injectable preparation.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference as to the subject matter referenced herein.

The compounds of the invention may be prepared using the exemplary reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One having ordinary skill in the art may adjust one or more of the conditions described herein. One skilled in the art of organic synthesis understands that the functionality present on various portions of the edict molecule must be compatible with the reagents and reactions proposed. Not all compounds of the invention falling into a given class may be compatible with some of the reaction conditions required in some of the methods described. Such restrictions to the substituents, which are compatible with the reaction conditions, will be readily apparent to one skilled in the art and alternate methods can be used.

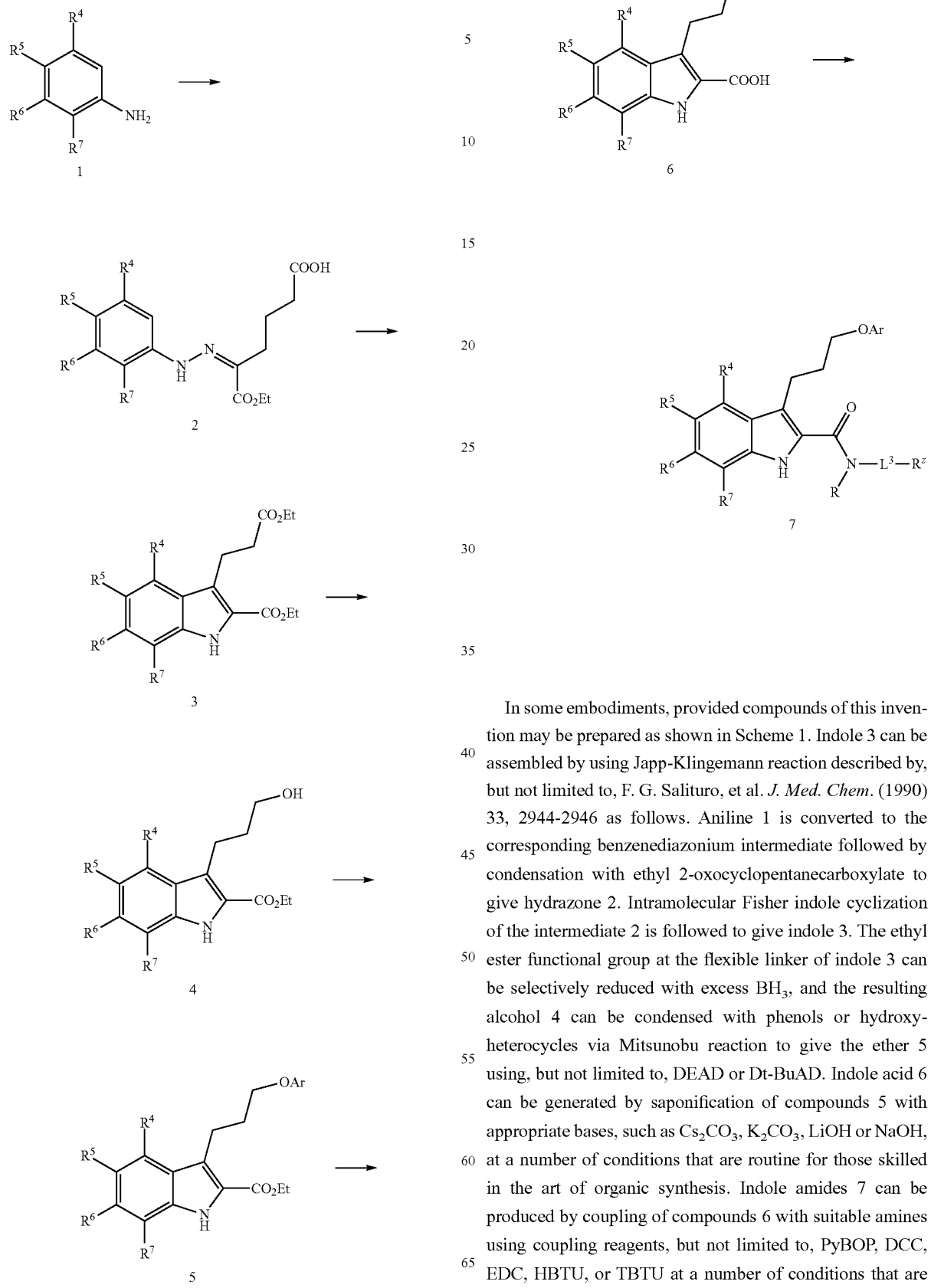

Scheme 1

In some embodiments, provided compounds of this invention may be prepared as shown in Scheme 1. Indole 3 can be assembled by using Japp-Klingemann reaction described by, but not limited to, F. G. Salituro, et al. *J. Med. Chem.* (1990) 33, 2944-2946 as follows. Aniline 1 is converted to the corresponding benzenediazonium intermediate followed by condensation with ethyl 2-oxocyclopentanecarboxylate to give hydrazone 2. Intramolecular Fisher indole cyclization of the intermediate 2 is followed to give indole 3. The ethyl ester functional group at the flexible linker of indole 3 can be selectively reduced with excess $BH_3$, and the resulting alcohol 4 can be condensed with phenols or hydroxy-heterocycles via Mitsunobu reaction to give the ether 5 using, but not limited to, DEAD or Dt-BuAD. Indole acid 6 can be generated by saponification of compounds 5 with appropriate bases, such as $Cs_2CO_3$, $K_2CO_3$, LiOH or NaOH, at a number of conditions that are routine for those skilled in the art of organic synthesis. Indole amides 7 can be produced by coupling of compounds 6 with suitable amines using coupling reagents, but not limited to, PyBOP, DCC, EDC, HBTU, or TBTU at a number of conditions that are routine for those skilled in the art of organic synthesis.

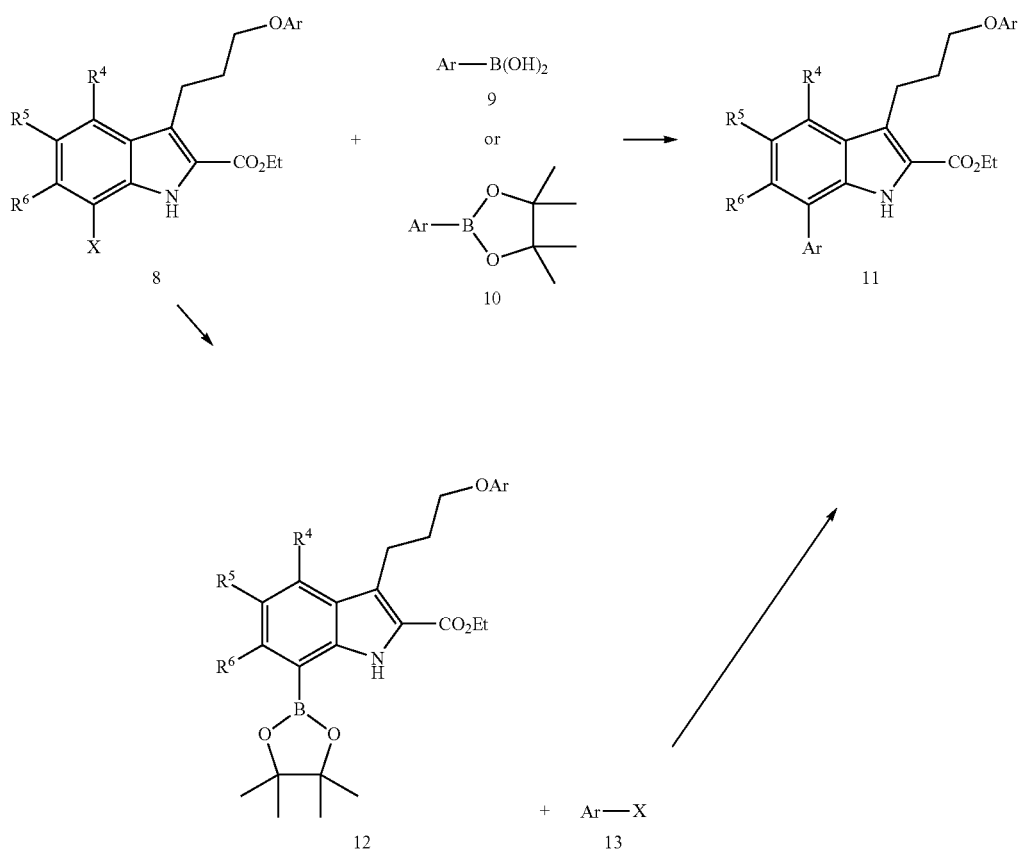

Scheme 2

In some embodiments, compounds of Formula 11 containing Ar or heteroaryl substituents as $R^7$ group may be synthesized by procedures illustrated in Scheme 2. Compounds of Formula 8, wherein X=Cl, Br, I, triflates or diazoderivatives, can be prepared as previously described in Scheme 1. A variety of boronic acids 9 or borates 10, which are commercially available or can be prepared, can be coupled with intermediates 8 via e.g., Suzuki coupling protocol to afford biaryl adducts 11 (Miyaura, N., Suzuki, A., Chem. Rev. (1995), 2457). In some embodiments, one exemplary such procedure entails treatment of the aryl bromide or iodide 8 with an aryl boronic acid in the presence of a catalytic Pd species, such as $Pd(PPh_3)_4$, $Pd(PPh_3)_2Cl_2$, $Pd(OAc)_2$, $Pd_2(dba)_3$ and a suitable ligand such as $PPh_3$, $AsPh_3$, etc., or other such Pd catalyst, and a base such as $Na_2CO_3$, $Cs_2CO_3$, $K_2CO_3$, $Ba(OH)_2$ or $Et_3N$. Alternatively, biaryl adducts 11 can be prepared from Pinacolborates 12 which can be prepared from compounds 8 via Pd, such as $Pd(PPh_3)_4$, $Pd(PPh_3)_2Cl_2$, $Pd(OAc)_2$, $Pd_2(dba)_3$, catalyzed coupling of bis(pinacolato)diboron. Intermediates 12 can be coupled with a variety of aryl-halides or heteroaryl-halides 13 using Suzuki coupling protocol described above to give compounds 11. In some embodiments, a provided approach allows for great diversity in the subsequent coupling of indole boronic acids or borates with commercially available haloaromatic derivatives.

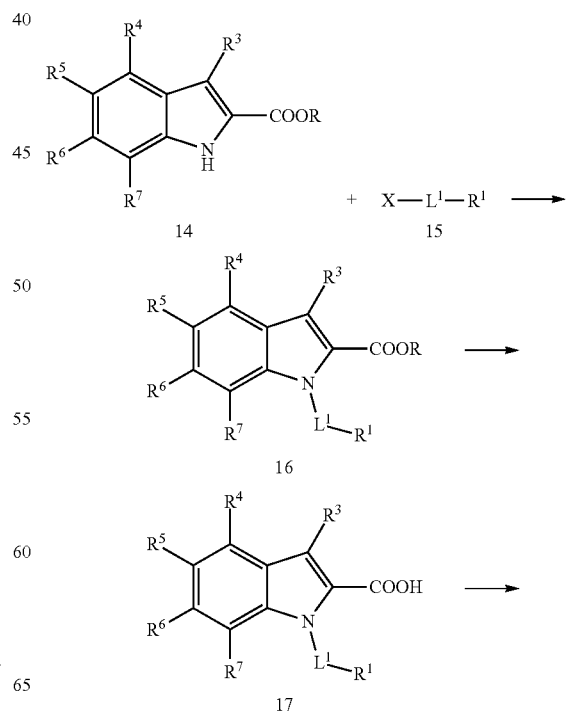

Scheme 3

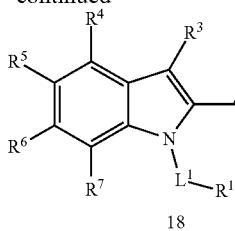

18

In some embodiments, provided compounds of Formula 18 may be prepared by procedures outlined in Scheme 3. Compounds of Formula 14 can be reacted with compounds of Formula 15, wherein X is Cl, Br, I, OMs, or OTs with a base such as NaH, $K_2CO_3$, $Cs_2CO_3$, $Et_3N$, or DIPEA in a suitable solvent such as DMF, THF, ether, DME, or the like, to give compounds of Formula 16. Applying the same reaction sequence as described in Scheme 1, compounds of Formula 16 can undergo saponification followed by coupling reaction to give compounds of Formula 18.

Scheme 4

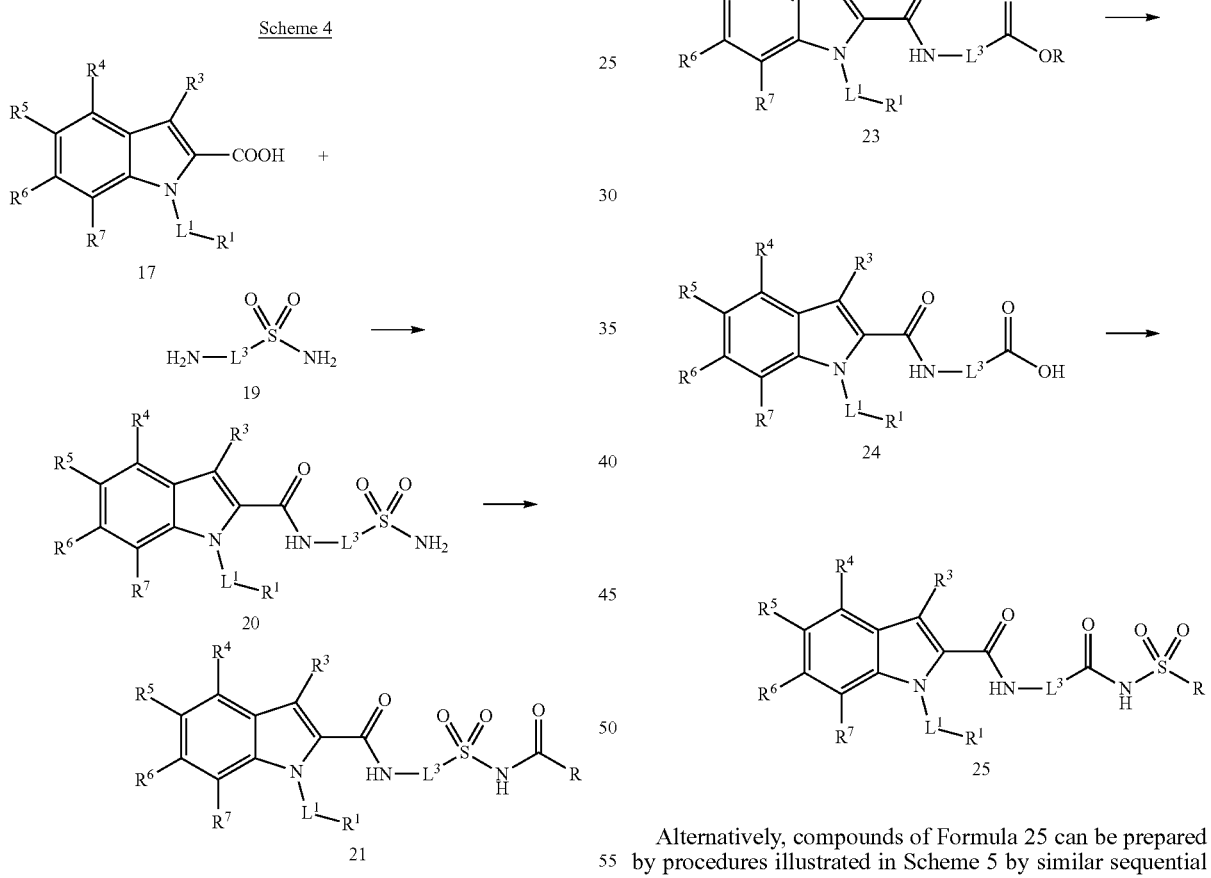

In some embodiments, compounds of Formula 21 can be synthesized by procedures depicted in Scheme 4 via selective sequential coupling reactions in one-pot. An amino group of compounds 19 can be coupled with compounds of Formula 17 as illustrated in Scheme 1 to afford intermediates 20. In the same pot, suitable carboxylic acids can be coupled to the sulfonamide group of compounds of Formula 20 using coupling reagents, but not limited to, PyBOP, DCC, EDC, HBTU, or TBTU at a number of conditions that are routine for those skilled in the art of organic synthesis, to yield acylsulfonamides of Formula 21.

Scheme 5

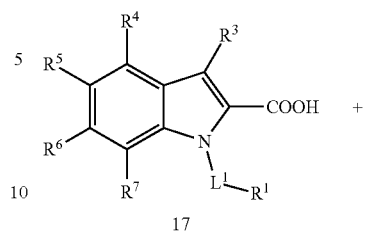

Alternatively, compounds of Formula 25 can be prepared by procedures illustrated in Scheme 5 by similar sequential coupling reactions. Compounds of Formula 17 can undergo coupling reactions with an amine functional group of compounds 22 as shown Scheme 1 to give intermediates 23. An ester group of Formula 23 can be saponificated using aqueous based, such as $Cs_2CO_3$, $K_2CO_3$, LiOH or NaOH, at a number of conditions that are routine for those skilled in the art of organic synthesis to generated compounds of Formula 24. Subsequent coupling reactions of acids 24 with suitable sulfonamides using coupling reagents at a number of conditions that are routine for those skilled in the art of organic synthesis to afford reverse acylsulfonamides of Formula 25.

Scheme 6

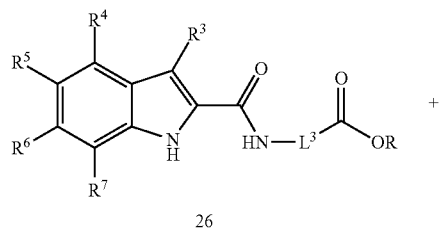

26

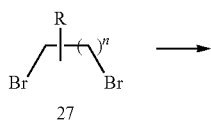

27

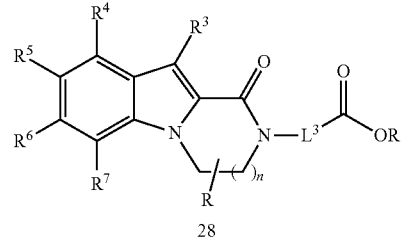

28

Exemplary method for preparing compounds of Formula 28, wherein the Ni position of indole and the amide NH is tethered to form rings, is described in Scheme 6 and proceeds from compounds of Formula 26. Optionally substituted di-bromo alkanes 27 can be used to react with indole amides 26. The cyclization may be accomplished with a variety of bases, but not limited to, DBU, Et$_3$N, DIPEA, Cs$_2$CO$_3$, K$_2$CO$_3$, NaH, or t-BuONa in a suitable solvent such as DMF, toluene, THF, DME, CH$_3$CN, 1,4-dioxane or the like, to afford compounds of Formula 28 at a number of conditions that are routine for those skilled in the art of organic synthesis. Compounds of Formula 28 can be employed to subsequent reactions as depicted in above Schemes.

Scheme 7

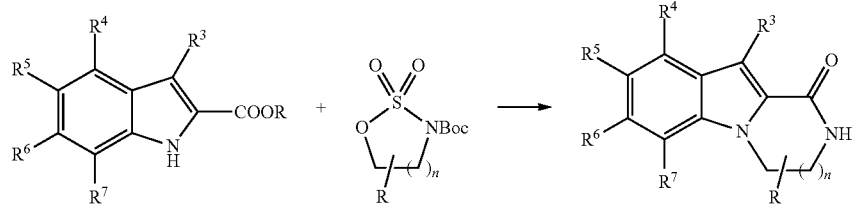

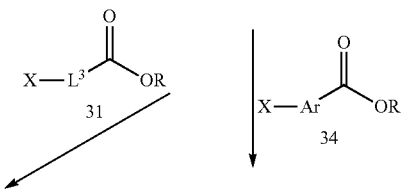

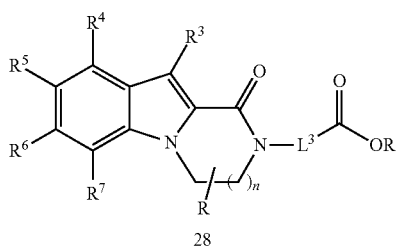

28

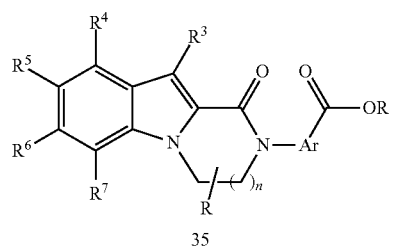

35

An alternate route to substituted tricyclic indole amides is shown in Scheme 7 and described here. The tricyclic amide intermediates of Formula 30 can be prepared by alkylation of the indole NH of ester 14 with optionally substituted cyclic sulfamidates 29 followed by cyclization upon removal of the Boc-protecting group (see, for example, Richter H. G. F. Bioorg. Med. Chem. Lett. 2010, 5713). The size and stereochemistry of the newly formed cyclic amide can be controlled by size and preset stereo-configuration of the reagent 29. The NH group of Formula 30 can undergo alkylation reactions with compounds of Formula 31, wherein X is Cl, Br, I, OMs, or OTs with a base such as NaH, $K_2CO_3$, $Cs_2CO_3$, $Et_3N$, or DIPEA in a suitable solvent such as DMF, THF, ether, DME, or the like, to give compounds of Formula 28. Corresponding compounds of Formulae 32 and 33 can be prepared from the ester 28 by saponification and coupling of sulfonamides to the carboxylic acid functional group of compounds 32 as described in Scheme 5. Alternatively, a variety of aryl or heteroaryl halides of Formula 34, wherein X is Br, I, or OTf can be coupled to the NH group of Formula 30 in the presence of a catalytic Pd species, such as $Pd(OAc)_2$, $Pd_2(dba)_3$ and a suitable ligand such as Xantphos and a base such as $Na_2CO_3$, $Cs_2CO_3$, or $K_2CO_3$ to generate compounds of Formula 35. Same saponification and coupling of sulfonamide coupling protocols described above can also be applied to prepare corresponding compounds of Formulae 36 and 37.

In some embodiments, compounds of Formula 39 containing tetrazole moiety can be generated by the procedure depicted in Scheme 8. A nitrile group of compounds 38 can undergo cyclization reaction with $NaN_3$ in the presence salt such as $NH_3Cl$, $Et_3N.HCl$ or catalytic amount of $I_2$, $AlCl_3$ or TMSCl in a suitable solvent such as DMF, $PhNO_2$ or NMP at a number of conditions that are routine for those skilled in the art of organic synthesis to give tetrazoles of Formula 39.

Abbreviations

The following abbreviations are employed in the Examples and elsewhere herein:
Dt-BuAD=di-tert-butyl azodicarboxylate
DCM=dichloromethane
EDC=1-Ethyl-3-(3-dimethylaminopropyl)carbodiimide
TEA=triethylamine
DMAP=dimethylamino pyridine
HOBT=hydroxybenzotriazole
DBU=1,8-Diazabicycloundec-7-ene
DMF=dimethylformamide
DMSO=dimethylsulfoxide
THF=tetrahydrofuran
$K_2CO_3$=potassium carbonate
$Cs_2CO_3$=cesium carbonate
DME=1,2-dimethoxyethane
t-BuONa=sodium tert-butoxide
LDA=lithium di-isopropylamide
NaHMDS=sodium hexamethyldisilazide
LiHMDS=lithium hexamethyldisilazide
n-BuLi=n-butyl lithium ether=diethyl ether
NaOH=sodium hydroxide
KOH=potassium hydroxide
EtOAc=ethyl acetate
$Na_2CO_3$=sodium carbonate
$Na_2SO_4$=sodium sulfate
$MgSO_4$=magnesium sulfate
$SiO_2$=silicon dioxide
$CH_2Cl_2$=methylene chloride
MeOH=methanol
EtOH=ethanol
Hex=hexanes
HCl=hydrochloric acid
Pd(dppf)$Cl_2$=[1,1'-bis(diphenylphosphino)ferrocene]dichloropalladium (II)
$Pd_2(dba)_3$=tris(dibenzylideneacetone)dipalladium (0)
Pd(PPh$_3$)$_4$=tetrakis(triphenylphosphine)palladium(0)
TFA=trifluoroacetic acid
Et$_3$N=triethylamine
DIPEA=N,N-diisopropylethylamine
SnCl$_2$=tin(II) chloride
DEAD=diethyl azodicarboxylate
TBAD=di-t-butyl azodicarboxylate
min=minute(s)
h or hr=hour(s)
mL or ml=milliliter
g=gram(s)
mg=milligram(s)
mmol=millimole(s)
LRMS=low resolution mass spectrometry
NMR=nuclear magnetic resonance

EXAMPLES

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

Example 1

Preparation of N-(tert-butyl)-3-(3-(4-chloro-3,5-dimethylphenoxy)propyl)-1H-indole-2-carboxamide

I-1

Step A. Preparation of 3-(1H-indol-3-yl)propanoic acid

To a solution of indole (1.35 g, 12 mmol) and acrylic acid (1.81 mL, 26.4 mmol) in acetic acid (12 mL) was added acetic anhydride (2.3 mL, 24 mmol). The reaction mixture was heated at 80° C. for 7 days. The reaction was monitored by LCMS and additional acrylic acid (0.9 mL, 12 mmol) was added on day 3 and 5. The reaction mixture was concentrated in vacuo, and the residue was purified by flash chromatography (Combi-flash Rf Hex/EtOAc 70% gradient) to give the title compound in 1.8 g (9.5 mmol). MS (ES) 190.1 (M+H).

Step B. Preparation of 3-(1H-indol-3-yl)propan-1-ol

To a solution of 3-(1H-indol-3-yl)propanoic acid (1.5 g, 7.9 mmol) in THF (20 mL) was added 1M BH$_3$ in THF (9 mL, 9 mmol) at 0° C. The reaction mixture was stirred for 1 h at 0° C. and quenched by addition of MeOH then concentrated in vacuo. The residue was purified by flash chromatography (Combi-flash Rf Hexane/EtOAc gradient 0-25%) to give the title compound as a white solid in 1.2 g (7.1 mmol). MS (ES) 176.1 (M+H).

Step C. Preparation of 3-(3-(4-chloro-3,5-dimethylphenoxy)propyl)-1H-indole

To a solution of 3-(1H-indol-3-yl)propan-1-ol (2.54 g, 14.5 mmol), PPh$_3$ (6.45 g, 24.6 mmol), and 3,5-diMe-4-Cl-phenol (4.0 g, 25.4 mmol) in THF (160 mL) was added Dt-BuAD (5.66 g, 24.6 mmol) at 20° C. The reaction mixture was stirred for 15 h at 20° C. then concentrated in vacuo. The residue was purified by flash chromatography (Combi-flash Rf Hexane/EtOAc gradient 0-10%) to give the desire compound as a colorless oil in 4.5 g (14.3 mmol). MS (ES) 314.1 (M+H).

Step D. Example 1

To a solution of 3-(3-(4-chloro-3,5-dimethylphenoxy)propyl)-1H-indole (115 mg, 0.37 mmol) and t-Bu-isocyanate (130 μL, 1.1 mmol) in CH$_2$Cl$_2$ (0.6 mL) was added BF$_3$-OEt$_2$ (180 μL, 1.5 mmol) at 20° C. The reaction mixture was warmed to 35° C. and stirred for 15 h. The reaction was quenched by addition of NaOAc aqueous solution. Organic layer was separated and concentrated. The residue was dissolved in CH$_2$Cl$_2$ (1.8 mL) and TFA (200 μL) was added at 20° C. The reaction mixture was stirred for 15 h then concentrated. The residue was directly purified by flash chromatography (Combi-flash Rf Hexane/EtOAc gradient 0-10%) to give the title compound as a yellow solid in 110 mg (0.27 mmol). MS (ES) 413.2 (M+H).

Example 2

Preparation of methyl (3-(3-(4-chloro-3,5-dimethylphenoxy)propyl)-1H-indole-2-carbonyl)glycinate

I-2

Step A. Preparation of 6-ethoxy-6-oxo-5-(2-phenylhydrazono)hexanoic acid

To a stirring mixture of aniline (1.8 mL, 20 mmol) in 1M HCl (25 mL) and water (5 mL) at 0° C. was added NaNO$_2$ (1.38 g, 20 mmol) in water (20 mL), NaCH$_3$COOH (9.23 g, 112 mmol) in water (25 mL) and ethyl 2-oxocyclopentane carboxylate (3.0 mL, 20 mmol) in sequence. The reaction mixture was stirred for 15 min at 0° C. then warmed to 20° C. over 2 h and extracted with CH$_2$Cl$_2$, dried over MgSO$_4$, filtered and concentrated in vacuo to give the title compound as a red oil in 5.2 g (90% crude).

Step B. Preparation of ethyl 3-(3-ethoxy-3-oxopropyl)-1H-indole-2-carboxylate

To a solution of 6-ethoxy-6-oxo-5-(2-phenylhydrazono)hexanoic acid (5.2 g, 18 mmol) in EtOH (30 mL) was added conc. H$_2$SO$_4$ (7.5 mL), slowly. The reaction mixture was refluxed for 1.5 h. The reaction was quenched by pouring into ice then extracted with CH$_2$Cl$_2$. The combined organic layer was washed with sat. NaHCO$_3$, water, brine, dried over MgSO$_4$, filtered and concentrated in vacuo. The residue was purified by flash chromatography (Combi-flash Rf Hex/EtOAc 25% gradient) to give the title compound as an off-white solid in 3.1 g (10.7 mmol). MS (ES) 290.1 (M+H).

Step C. Preparation of ethyl 3-(3-hydroxypropyl)-1H-indole-2-carboxylate

To a solution of ethyl 3-(3-ethoxy-3-oxopropyl)-1H-indole-2-carboxylate (1.4 g, 4.8 mmol) in THF (20 mmol) was added $BH_3$ in THF (20 mL, 20 mmol) at 20° C. The reaction mixture was stirred for 15 h at 20° C. and quenched by addition of MeOH then concentrated in vacuo. The residue was purified by flash chromatography (Combi-flash Rf Hexane/EtOAc gradient 0-50%) to give the title compound as a white solid in 940 mg (3.8 mmol). MS (ES) 248.1 (M+H).

Step D. Preparation of ethyl 3-(3-(4-chloro-3,5-dimethylphenoxy)propyl)-1H-indole-2-carboxylate To a solution of ethyl 3-(3-hydroxypropyl)-1H-indole-2-carboxylate (70 mg, 0.28 mmol), $PPh_3$ (110 mg, 0.51 mmol) and 3,5-diMe-4-Cl-phenol (81 mg, 0.52 mmol) in THF (3.5 mL) was added Dt-BuAD (99 mg, 0.51 mmol) at 20° C. The reaction mixture was stirred for 15 h at 20° C. then concentrated in vacuo. The residue was purified by flash chromatography (Combi-flash Rf Hexane/EtOAc gradient 0-10%) to give the title compound (81 mg, 0.21 mmol) as a colorless oil. MS (ES) 385.2 (M+H).

Step E. Preparation of 3-(3-(4-chloro-3,5-dimethylphenoxy)propyl)-1H-indole-2-carboxylic acid To a solution of ethyl 3-(3-(4-chloro-3,5-dimethylphenoxy)propyl)-1H-indole-2-carboxylate (70 mg, 0.18 mmol) in EtOH (2.0 mL) was added 50% NaOH $H_2O$ solution (100 µL) at 20° C. The reaction mixture was stirred for 3 h at 20° C. then acidified with 1N HCl solution. The mixture was extracted with EtOAc, dried over $MgSO_4$, filtered and concentrated in vacuo. The crude product was purified by reverse phase prep. HPLC (Phenomenex Gemini C18, $H_2O$/$CH_3CN$ gradient to 95% $CH_3CN$ 0.5% TFA) to yield the title compound (60 mg, 0.17 mmol) as a white solid. MS (ES) 358.1 (M+H).

Step F. Example 2

To a solution of 3-(3-(4-chloro-3,5-dimethylphenoxy)propyl)-1H-indole-2-carboxylic acid (100 mg, 0.28 mmol) and H-Gly-OMe HCl (53 mg, 0.42 mmol) in $CH_2Cl_2$ (3.0 mL) was added EDC.HCl (87 mg, 0.56 mmol) followed by DMAP (120 mg, 0.98 mmol) at 20° C. The reaction mixture was stirred for 15 h at 20° C. then quenched by addition of 0.5 N HCl. The quenched reaction mixture was extracted with $CH_2Cl_2$, washed with brine, dried by $MgSO_4$, filtered and concentrated in vacuo. The residue was purified by flash chromatography (Combi-flash Rf Hexane/EtOAc gradient 0-20%) to give the title compound (95 mg, 0.22 mmol) as a white solid. MS (ES) 429.2 (M+H).

Example 3

Preparation of (3-(3-(4-chloro-3,5-dimethylphenoxy)propyl)-1H-indole-2-carbonyl)glycine

I-3

To a solution of methyl (3-(3-(4-chloro-3,5-dimethylphenoxy)propyl)-1H-indole-2-carbonyl)glycinate (90 mg, 0.21 mmol) in EtOH (1.5 mL) was added 10% LiOH aqueous solution (150 µL, 0.63 mmol). The reaction mixture was stirred for 15 h at 20° C. then quenched by addition of 1M HCl. The reaction mixture was extracted with $CH_2Cl_2$ and concentrated in vacuo. The crude product was purified by reserve phase prep. HPLC (Phenomenex Gemini C18, $H_2O$/$CH_3CN$ 40-95% 0.01% TFA) to give the title product as a white solid in 75 mg (0.18 mmol). MS (ES) 415.1 (M+H).

Example 4

Preparation of 3-(3-(4-chloro-3,5-dimethylphenoxy)propyl)-N-(2-(methylsulfonamido)-2-oxoethyl)-1H-indole-2-carboxamide

I-4

To a solution of (3-(3-(4-chloro-3,5-dimethylphenoxy)propyl)-1H-indole-2-carbonyl)glycine (15 mg, 0.035 mmol) and methanesulfonamide (6.6 mmol, 0.070 mmol) in $CH_2Cl_2$ (1.0 mL) was added EDC HCl (11 mg, 0.070 mmol) followed by DMAP (13 mg, 0.11 mmol) at 20° C. The reaction mixture was stirred for 15 h at 20° C. then concentrated in vacuo. The residue was purified by reserve phase prep. HPLC (Phenomenex Gemini C18, $H_2O$/$CH_3CN$ 30-95% 0.01% TFA) to give the title product as a white solid in 15 mg (0.030 mmol). MS (ES) 492.1 (M+H).

Example 5

Preparation of 3-(3-(4-chloro-3,5-dimethylphenoxy)propyl)-N-(2-oxo-2-(phenylsulfonamido)ethyl)-1H-indole-2-carboxamide

I-5

Title compound was prepared (16 mg, 0.029 mmol) as a white solid according to procedures described in Example 4 using (3-(3-(4-chloro-3,5-dimethylphenoxy)propyl)-1H-indole-2-carbonyl)glycine (15 mg, 0.035 mmol) and substituting methanesulfonamide with benzenesulfonamide (9.0 mg, 0.70 mmol). MS (ES) 554.2 (M+H).

Example 6

Preparation of 3-(3-(4-chloro-3,5-dimethylphenoxy)propyl)-N-(2-oxo-2-(pyridine-3-sulfonamido)ethyl)-1H-indole-2-carboxamide

I-6

Title compound was prepared (18 mg, 0.028 mmol) as an off-white solid TFA salt according to procedures described in Example 4 using (3-(3-(4-chloro-3,5-dimethylphenoxy)propyl)-1H-indole-2-carbonyl)glycine (15 mg, 0.035 mmol) and substituting methanesulfonamide with pyridine-3-sulfonamide (9.0 mg, 0.70 mmol). MS (ES) 555.1 (M+H).

Example 7

Preparation of 3-(3-(4-chloro-3,5-dimethylphenoxy)propyl)-N-(2-(naphthalene-2-sulfonamido)-2-oxoethyl)-1H-indole-2-carboxamide

I-7

Title compound was prepared (16 mg, 0.026 mmol) as a white solid according to procedures described in Example 4 using (3-(3-(4-chloro-3,5-dimethylphenoxy)propyl)-1H-indole-2-carbonyl)glycine (15 mg, 0.035 mmol) and substituting methanesulfonamide with naphthalene-2-sulfonamide (15.0 mg, 0.70 mmol). MS (ES) 604.2 (M+H).

Example 8

Preparation of 3-(3-(4-chloro-3,5-dimethylphenoxy) propyl)-N-(2-oxo-2-((4-phenoxyphenyl)sulfonamido)ethyl)-1H-indole-2-carboxamide

I-8

Title compound was prepared (20 mg, 0.031 mmol) as a white solid according to procedures described in Example 4 using (3-(3-(4-chloro-3,5-dimethylphenoxy)propyl)-1H-indole-2-carbonyl)glycine (15 mg, 0.035 mmol) and substituting methanesulfonamide with 4-phenoxybenzenesulfonamide (18.0 mg, 0.70 mmol). MS (ES) 646.2 (M+H).

Example 9

Preparation of 3-(3-(4-chloro-3,5-dimethylphenoxy) propyl)-N-(2-(cyclopropanesulfonamido)-2-oxoethyl)-1H-indole-2-carboxamide

I-9

Title compound was prepared (16 mg, 0.031 mmol) as a white solid according to procedures described in Example 4 using (3-(3-(4-chloro-3,5-dimethylphenoxy)propyl)-1H-indole-2-carbonyl)glycine (15 mg, 0.035 mmol) and substituting methanesulfonamide with cyclopropanesulfonamide (9.0 mg, 0.70 mmol). MS (ES) 518.1 (M+H).

Example 10

Preparation of ethyl 3-(3-(3-(4-chloro-3,5-dimethylphenoxy)propyl)-1H-indole-2-carboxamido)propanoate

I-10

Title compound was prepared (112 mg, 0.24 mmol) as a white solid according to procedures described in Example 2 Step F using 3-(3-(4-chloro-3,5-dimethylphenoxy)propyl)-1H-indole-2-carboxylic acid (100 mg, 0.28 mmol) and substituting H-Gly-OMe HCl with ethyl 3-aminopropanoate hydrochloride (65 mg, 0.42 mmol). MS (ES) 457.2 (M+H).

Example 11

Preparation of 3-(3-(3-(4-chloro-3,5-dimethylphenoxy)propyl)-1H-indole-2-carboxamido)propanoic acid

I-11

Title compound was prepared (90 mg, 0.21 mmol) as a white solid according to procedures described in Example 3 using ethyl 3-(3-(3-(4-chloro-3,5-dimethylphenoxy)propyl)-1H-indole-2-carboxamido)propanoate (100 mg, 0.22 mmol). MS (ES) 429.2 (M+H).

Example 12

Preparation of 3-(3-(4-chloro-3,5-dimethylphenoxy) propyl)-N-(3-(methylsulfonamido)-3-oxopropyl)-1H-indole-2-carboxamide

I-12

Title compound was prepared (12 mg, 0.024 mmol) as a white solid according to procedures described in Example 4 using 3-(3-(3-(4-chloro-3,5-dimethylphenoxy)propyl)-1H-indole-2-carboxamido)propanoic acid (15 mg, 0.035 mmol). MS (ES) 505.1 (M+H).

Example 13

Preparation of 3-(3-(4-chloro-3,5-dimethylphenoxy) propyl)-N-(3-(cyclopropanesulfonamido)-3-oxopropyl)-1H-indole-2-carboxamide

I-13

Title compound was prepared (17 mg, 0.031 mmol) as a white solid according to procedures described in Example 9 using 3-(3-(3-(4-chloro-3,5-dimethylphenoxy)propyl)-1H-indole-2-carboxamido)propanoic acid (15 mg, 0.035 mmol). MS (ES) 532.2 (M+H).

Example 14

Preparation of 3-(3-(4-chloro-3,5-dimethylphenoxy) propyl)-N-(3-oxo-3-(phenylsulfonamido)propyl)-1H-indole-2-carboxamide

I-14

Title compound was prepared (19 mg, 0.033 mmol) as a white solid according to procedures described in Example 5 using 3-(3-(3-(4-chloro-3,5-dimethylphenoxy)propyl)-1H-indole-2-carboxamido)propanoic acid (15 mg, 0.035 mmol). MS (ES) 568.2 (M+H).

Example 15

Preparation of 3-(3-(4-chloro-3,5-dimethylphenoxy) propyl)-N-(3-oxo-3-(pyridine-3-sulfonamido)propyl)-1H-indole-2-carboxamide

I-15

Title compound was prepared (20 mg, 0.030 mmol) as an off-white solid TFA salt according to procedures described in Example 6 using 3-(3-(3-(4-chloro-3,5-dimethylphenoxy) propyl)-1H-indole-2-carboxamido)propanoic acid (15 mg, 0.035 mmol). MS (ES) 569.2 (M+H).

Example 16

Preparation of 3-(3-(4-chloro-3,5-dimethylphenoxy) propyl)-N-(3-(naphthalene-2-sulfonamido)-3-oxopropyl)-1H-indole-2-carboxamide

I-16

Title compound was prepared (21 mg, 0.034 mmol) as a white solid according to procedures described in Example 7 using 3-(3-(3-(4-chloro-3,5-dimethylphenoxy)propyl)-1H-indole-2-carboxamido)propanoic acid (15 mg, 0.035 mmol). MS (ES) 618.2 (M+H).

Example 17

Preparation of 3-(3-(4-chloro-3,5-dimethylphenoxy)propyl)-N-(3-oxo-3-((4-phenoxyphenyl)sulfonamido)propyl)-1H-indole-2-carboxamide

I-17

Title compound was prepared (19 mg, 0.029 mmol) as a white solid according to procedures described in Example 8 using 3-(3-(3-(4-chloro-3,5-dimethylphenoxy)propyl)-1H-indole-2-carboxamido)propanoic acid (15 mg, 0.035 mmol). MS (ES) 660.2 (M+H).

Example 18

Preparation of 3-(3-(4-chloro-3,5-dimethylphenoxy)propyl)-N-(3-((2-cyanophenyl)sulfonamido)-3-oxopropyl)-1H-indole-2-carboxamide

I-18

Title compound was prepared (17 mg, 0.029 mmol) as a white solid according to procedures described in Example 4 using 3-(3-(3-(4-chloro-3,5-dimethylphenoxy)propyl)-1H-indole-2-carboxamido)propanoic acid (15 mg, 0.035 mmol) and substituting methanesulfonamide with 2-cyanobenzenesulfonamide (13 mg, 0.035 mmol). MS (ES) 593.2 (M+H).

Example 19

Preparation of 3-(3-(4-chloro-3,5-dimethylphenoxy)propyl)-N-(3-((3-cyanophenyl)sulfonamido)-3-oxopropyl)-1H-indole-2-carboxamide

I-19

Title compound was prepared (19 mg, 0.032 mmol) as a white solid according to procedures described in Example 4 using 3-(3-(3-(4-chloro-3,5-dimethylphenoxy)propyl)-1H-indole-2-carboxamido)propanoic acid (15 mg, 0.035 mmol) and substituting methanesulfonamide with 3-cyanobenzenesulfonamide (13 mg, 0.035 mmol). MS (ES) 593.2 (M+H).

Example 20

Preparation of 3-(3-(4-chloro-3,5-dimethylphenoxy)propyl)-N-(3-((2-nitrophenyl)sulfonamido)-3-oxopropyl)-1H-indole-2-carboxamide

I-20

Title compound was prepared (18 mg, 0.029 mmol) as a white solid according to procedures described in Example 4 using 3-(3-(3-(4-chloro-3,5-dimethylphenoxy)propyl)-1H-indole-2-carboxamido)propanoic acid (15 mg, 0.035 mmol) and substituting methanesulfonamide with 2-nitrobenzenesulfonamide (14 mg, 0.035 mmol). MS (ES) 613.2 (M+H).

Example 21

Preparation of 3-(3-(4-chloro-3,5-dimethylphenoxy)propyl)-N-(3-((3-nitrophenyl)sulfonamido)-3-oxopropyl)-1H-indole-2-carboxamide

I-21

Title compound was prepared (19 mg, 0.030 mmol) as a white solid according to procedures described in Example 4 using 3-(3-(3-(4-chloro-3,5-dimethylphenoxy)propyl)-1H-indole-2-carboxamido)propanoic acid (15 mg, 0.035 mmol) and substituting methanesulfonamide with 3-nitrobenzenesulfonamide (14 mg, 0.035 mmol). MS (ES) 613.2 (M+H).

Example 22

Preparation of 3-(3-(4-chloro-3,5-dimethylphenoxy)propyl)-N-(3-((4-nitrophenyl)sulfonamido)-3-oxopropyl)-1H-indole-2-carboxamide

I-22

Title compound was prepared (17 mg, 0.028 mmol) as a white solid according to procedures described in Example 4 using 3-(3-(3-(4-chloro-3,5-dimethylphenoxy)propyl)-1H-indole-2-carboxamido)propanoic acid (15 mg, 0.035 mmol) and substituting methanesulfonamide with 4-nitrobenzenesulfonamide (14 mg, 0.035 mmol). MS (ES) 613.2 (M+H).

Example 23

Preparation of 3-(3-(3-(4-chloro-3,5-dimethylphenoxy)propyl)-7-(3,5-dimethyl-1H-pyrazol-4-yl)-1H-indole-2-carboxamido)propanoic acid

I-23

Step A. Preparation of 5-(2-(2-bromophenyl)hydrazono)-6-ethoxy-6-oxohexanoic acid Title compound was prepared as a red oil according to procedures described in Example 2 Step A using 2-bromoaniline and ethyl 2-oxocyclopentane carboxylate. MS (ES) 368.0 (M+H).

Step B. Preparation of ethyl 7-bromo-3-(3-ethoxy-3-oxopropyl)-1H-indole-2-carboxylate Title compound was prepared according to procedures described in Example 2 Step B using 5-(2-(2-bromophenyl)hydrazono)-6-ethoxy-6-oxohexanoic acid. MS (ES) 324.1 (M+H).

Step C. Preparation of ethyl 7-bromo-3-(3-hydroxypropyl)-1H-indole-2-carboxylate Title compound was prepared according to procedures described in Example 2 Step C using ethyl 7-bromo-3-(3-ethoxy-3-oxopropyl)-1H-indole-2-carboxylate. MS (ES) 326.0 (M+H).

Step D. Preparation of ethyl 7-bromo-3-(3-(4-chloro-3,5-dimethylphenoxy)propyl)-1H-indole-2-carboxylate Title compound was prepared according to procedures described in Example 2 Step D using ethyl 7-bromo-3-(3-hydroxypropyl)-1H-indole-2-carboxylate and 4-chloro-3,5-dimethylphenol. MS (ES) 464.1 (M+H).

Step E. Preparation of 3-(3-(4-chloro-3,5-dimethylphenoxy)propyl)-7-(3,5-dimethyl-1H-pyrazol-4-yl)-1H-indole-2-carboxylic acid To a solution of ethyl 7-bromo-3-(3-(4-chloro-3,5-dimethylphenoxy)propyl)-1H-indole-2-carboxylate (50 mg) in DME (837 µl), water (359 µl) and ethanol (239 µl) at 20 was added 3,5-dimethyl-4-(4,4,5,5-tetramethyl-1,3,2-dioxaborolan-2-yl)-1H-pyrazole (28.7 mg), bis(triphenylphosphine)palladium(II) chloride (7.55 mg) and $Na_2CO_3$ (114 mg, 1.076 mmol). The mixture was then heated to 150° C. in Biotage Initiator for 30 min. After heating, LiOH (269 µl) was added to the mixture and the mixture heated at 100° C. in Biotage Initiator for 10 min. The mixture was cooled, acidified (6M HCl), extracted with EtOAc, dried ($MgSO_4$) and concentrated. The residue was purified by reverse phase preparatory HPLC (Phenomenex Gemini C18, $H_2O/CH_3CN$ gradient to 95% $CH_3CN$ 0.1% TFA) to yield the title compound as a white solid. MS (ES) 452.2 (M+H).

Step F. Preparation of ethyl 3-(3-(3-(4-chloro-3,5-dimethylphenoxy)propyl)-7-(3,5-dimethyl-1H-pyrazol-4-yl)-1H-indole-2-carboxamido)propanoate Title compound was prepared (51 mg, 0.091 mmol) as a white solid according to procedures described in Example 10 using 3-(3-(4-chloro-3,5-dimethylphenoxy)propyl)-7-(3,5-dimethyl-1H-pyrazol-4-yl)-1H-indole-2-carboxylic acid (64 mg, 0.14 mmol) and ethyl 3-aminopropanoate hydrochloride (26 mg, 0.17 mmol). MS (ES) 551.2 (M+H).

Step G. Example 23

Title compound was prepared (40 mg, 0.076 mmol) as a white solid according to procedures described in Example 11 using ethyl 3-(3-(3-(4-chloro-3,5-dimethylphenoxy)propyl)-7-(3,5-dimethyl-1H-pyrazol-4-yl)-1H-indole-2-carboxamido)propanoate (48 mg, 0.087 mmol). MS (ES) 523.2 (M+H).

Example 24

Preparation of 3-(3-(4-chloro-3,5-dimethylphenoxy)propyl)-7-(3,5-dimethyl-1H-pyrazol-4-yl)-N-(3-((4-nitrophenyl)sulfonamido)-3-oxopropyl)-1H-indole-2-carboxamide

I-24

Title compound was prepared (7 mg, 0.010 mmol) as a white solid according to procedures described in Example 4 using 3-(3-(3-(4-chloro-3,5-dimethylphenoxy)propyl)-7-(3,5-dimethyl-1H-pyrazol-4-yl)-1H-indole-2-carboxamido)propanoic acid (10 mg, 0.019 mmol) and 4-nitrobenzenesulfonamide (4.7 mg, 0.038 mmol). MS (ES) 707.2 (M+H).

Example 25

Preparation of methyl 3-((3-(3-(4-chloro-3,5-dimethylphenoxy)propyl)-7-(3,5-dimethyl-1H-pyrazol-4-yl)-1H-indole-2-carboxamido)methyl)benzoate

I-25

To a stirred solution of EDC (0.243 mmol), HOBT (0.022 mmol), 3-(3-(4-chloro-3,5-dimethylphenoxy)propyl)-7-(3,5-dimethyl-1H-pyrazol-4-yl)-1H-indole-2-carboxylic acid (0.221 mmol), and TEA (0.664 mmol) in DCM (0.1M) was added methyl 3-(aminomethyl)benzoate hydrochloride (0.221 mmol). The reaction mixture was stirred for 15 h then concentrated in vacuo. The residue was slurred in 1 mL of 1:1 mix of acetonitrile and methanol and filtered. The filtrate was purified by reverse phase preparatory HPLC (Phenomenex Gemini C18, $H_2O/CH_3CN$ gradient to 5-95% $CH_3CN$ 0.1% TFA) to yield the title compound as a white solid. MS (ES) 599.2 (M+H).

Example 25a

Preparation of 3-((3-(3-(4-chloro-3,5-dimethylphenoxy)propyl)-7-(3,5-dimethyl-1H-pyrazol-4-yl)-1H-indole-2-carboxamido)methyl)benzoic acid I-25a To a stirred solution of methyl 3-((3-(3-(4-chloro-3,5-dimethylphenoxy)propyl)-7-(3,5-dimethyl-1H-pyrazol-4-yl)-1H-indole-2-carboxamido)methyl)benzoate (0.2 mmol) in THF (2 mL) was added a drop of MeOH followed by an aqueous solution of 2M LiOH (0.7 mL). The reaction was then heated at 50° C. for 5 hours then cooled to room temperature. The traction mixture was acidified to pH 2 with 3M HCl and extracted with ethyl acetate. The organic layer was washed with brine, dried over $MgSO_4$, filtered and concentrated in vacuo. The resultant solid was dissolved in 1 mL of 1:1 mix of acetonitrile and methanol. The slurry was filtered and the filtrate was purified by reverse phase preparatory HPLC (Phenomenex Gemini C18, $H_2O/CH_3CN$ gradient to 5-95% $CH_3CN$ 0.1% TFA) to yield the title compound (0.18 mmol) as a white solid. MS (ES) 585.2 (M+H).

Example 26

Preparation of 3-(3-(4-chloro-3,5-dimethylphenoxy)propyl)-N-(3-(((2-cyanophenyl)sulfonyl)carbamoyl)benzyl)-7-(3,5-dimethyl-1H-pyrazol-4-yl)-1H-indole-2-carboxamide

I-26

Title compound was prepared (11 mg, 0.014 mmol) as a white solid according to procedures described in Example 4 using 3-((3-(3-(4-chloro-3,5-dimethylphenoxy)propyl)-7-(3,5-dimethyl-1H-pyrazol-4-yl)-1H-indole-2-carboxamido)methyl)benzoic acid (10 mg, 0.017 mmol) and substituting methanesulfonamide with 2-cyanobenzenesulfonamide (3.8 mg, 0.021 mmol). MS (ES) 748.9 (M+H).

Example 27

Preparation of 3-(3-(4-chloro-3,5-dimethylphenoxy)propyl)-7-(3,5-dimethyl-1H-pyrazol-4-yl)-N-(3-(((4-nitrophenyl)sulfonyl)carbamoyl)benzyl)-1H-indole-2-carboxamide

I-27

Title compound was prepared (11 mg, 0.014 mmol) as a white solid according to procedures described in Example 4 using 3-((3-(3-(4-chloro-3,5-dimethylphenoxy)propyl)-7-(3,5-dimethyl-1H-pyrazol-4-yl)-1H-indole-2-carboxamido)methyl)benzoic acid (10 mg, 0.017 mmol) and substituting methanesulfonamide with 4-nitrobenzenesulfonamide (4.2 mg, 0.021 mmol). MS (ES) 769.0 (M+H).

Example 28

Preparation of methyl 3-((3-(3-(4-chloro-3,5-dimethylphenoxy)propyl)-7-(1,3,5-trimethyl-1H-pyrazol-4-yl)-1H-indole-2-carboxamido)methyl)benzoate

I-28

Step A. Preparation of ethyl 3-(3-(4-chloro-3,5-dimethylphenoxy)propyl)-7-(1,3,5-trimethyl-1H-pyrazol-4-yl)-1H-indole-2-carboxylate To a solution of ethyl 7-bromo-3-(3-(4-chloro-3,5-dimethylphenoxy)propyl)-1H-indole-2-carboxylate (300 mg, 0.64 mmol) in dioxane (3.0 ml) and water (2.0 ml) at 20 was added 1,3,5-trimethyl-4-(4,4,5,5-tetramethyl-1,3,2-dioxaborolan-2-yl)-1H-pyrazole (168 mg, 0.71 mmol), Pd(PPh$_3$)$_4$ (37 mg, 0.032 mmol) and K$_2$CO$_3$ (267 mg, 1.94 mmol). The mixture was degassed then heated to 125° C. in Biotage Initiator for 40 min. The reaction was quenched by addition of water, extracted with EtOAc, dried over MgSO4, filtered and concentrated in vacuo. The residue was purified by flash chromatography (Combi-flash Rf Hexane/EtOAc gradient 0-15%) to give the title compound (175 mg, 0.35 mmol) as a white solid. MS (ES) 494.2 (M+H)

Step B. Preparation of 3-(3-(4-chloro-3,5-dimethylphenoxy)propyl)-7-(1,3,5-trimethyl-1H-pyrazol-4-yl)-1H-indole-2-carboxylic acid To a solution of ethyl 3-(3-(4-chloro-3,5-dimethylphenoxy)propyl)-7-(1,3,5-trimethyl-1H-pyrazol-4-yl)-1H-indole-2-carboxylate (175 mg, 0.35 mmol) in EtOH (1.6 mL) and THF (0.4 mL) was added 2N aqueous solution of LiOH (1.0 mL) then the mixture was stirred for 24 h at 40° C. The reaction mixture was concentrated in vacuo, and residue was re-dissolved in water (1.0 mL). The solution was acidified (6M HCl), and white solid was filtered to give the title compound (160 mg, 0.34 mmol). MS (ES) 466.2 (M+H).

Step C. Example 28

A mixture of 3-(3-(4-chloro-3,5-dimethylphenoxy)propyl)-7-(1,3,5-trimethyl-1H-pyrazol-4-yl)-1H-indole-2-carboxylic acid (0.055 g, 0.118 mmol), methyl 3-(aminomethyl)benzoate hydrochloride (0.024 g, 0.118 mmol), 1-(3-dimethylaminopropyl)-3-ethylcarbodiimide hydrochloride (0.024 g, 0.124 mmol) and DMAP (0.016 g, 0.130 mmol) in THF (1.18 ml) was stirred at rt. After 90 min, the mixture was concentrated in vacuo. The residue was purified via reverse-phase preparative HPLC (Phenomenex Gemini C18, H$_2$O/CH$_3$CN gradient to 40-95% MeCN 0.1% TFA) to give the title compound. MS (ES) 613.0 (M+H).

Example 29

Preparation of 3-((3-(3-(4-chloro-3,5-dimethylphenoxy)propyl)-7-(1,3,5-trimethyl-1H-pyrazol-4-yl)-1H-indole-2-carboxamido)methyl)benzoic acid

I-29

A mixture of 3-(3-(4-chloro-3,5-dimethylphenoxy)propyl)-7-(1,3,5-trimethyl-1H-pyrazol-4-yl)-1H-indole-2-carboxylic acid (0.055 g, 0.118 mmol), methyl 3-(aminomethyl)benzoate hydrochloride (0.024 g, 0.118 mmol), 1-(3-dimethylaminopropyl)-3-ethylcarbodiimide hydrochloride (0.024 g, 0.124 mmol) and DMAP (0.016 g, 0.130 mmol) in THF (1.18 ml) was stirred at rt. After 15 h, LiOH (2M, 1.0 ml) and EtOH (0.5 ml) were added and the mixture was warmed to 60° C. After 3 h, the mixture was acidified (1M HCl), extracted with EtOAc, dried, filtered and concentrated in vacuo. The residue was purified via reverse-phase preparative HPLC (Phenomenex Gemini C18, H$_2$O/CH$_3$CN gradient to 40-95% MeCN 0.1% TFA) to give the title compound. MS (ES) 599.1 (M+H).

Example 30

Preparation of 3-(3-(4-chloro-3,5-dimethylphenoxy)propyl)-N-(3-(((3-cyanophenyl)sulfonyl)carbamoyl)benzyl)-7-(1,3,5-trimethyl-1H-pyrazol-4-yl)-1H-indole-2-carboxamide

I-30

A mixture of 3-((3-(3-(4-chloro-3,5-dimethylphenoxy)propyl)-7-(1,3,5-trimethyl-1H-pyrazol-4-yl)-1H-indole-2-carboxamido)methyl)benzoic acid (0.025 g, 0.042 mmol), 3-cyanobenzenesulfonamide (0.011 g, 0.063 mmol), 1-(3-dimethylaminopropyl)-3-ethylcarbodiimide hydrochloride (0.012 g, 0.063 mmol) and DMAP (7.65 mg, 0.063 mmol) in dichloromethane (0.835 ml) was stirred at rt. After 90 min, the mixture was concentrated in vacuo. The residue was purified via reverse-phase preparative HPLC (Phenomenex Gemini C18, H$_2$O/CH$_3$CN gradient to 50-95% MeCN 0.1% TFA) to give the title compound. MS (ES) 763.0. (M+H).

Example 31

Preparation of 3-((10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)methyl)benzoic acid

I-31

A mixture of methyl 3-((3-(3-(4-chloro-3,5-dimethylphenoxy)propyl)-7-(1,3,5-trimethyl-1H-pyrazol-4-yl)-1H-indole-2-carboxamido)methyl)benzoate (0.035 g, 0.057 mmol), 1,2-dibromoethane (0.017 ml, 0.200 mmol) and cesium carbonate (0.074 g, 0.228 mmol) in DMF (0.571 ml) was stirred at 100° C. After 48 h, the mixture was concentrated in vacuo. A mixture of the intermediate ester and LiOH (2M, 0.285 ml) in THF (0.3 ml) and EtOH (0.15 ml) was stirred at 50° C. After 15 h, the mixture was acidified (1M HCl), extracted with EtOAc, dried, filtered and concentrated in vacuo. The residue was purified via reverse-phase preparative HPLC (Phenomenex Gemini C18, H$_2$O/CH$_3$CN gradient to 50-80% MeCN 0.1% TFA) to give the title compound. MS (ES) 625.0 (M+H).

Example 32

Preparation of 3-((11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid

I-32

Title compound was prepared (18 mg, 0.013 mmol) as a white solid according to procedures described in Example 31 using 3-((3-(3-(4-chloro-3,5-dimethylphenoxy)propyl)-7-((1,3,5-trimethyl-1H-pyrazol-4-yl)-1H-indole-2-carboxamido)methyl)benzoate (0.01 g, 0.016 mmol), and substituting 1,2-dibromoethane 1,3-dibromopropane (8.28 μl, 0.082 mmol). MS (ES) 639.1 (M+H). $^1$H NMR (400 MHz, CDCl$_3$): 8.04 (m, 2H), 7.73 (d, J=7.2 Hz, 1H), 7.63 (d, J=7.7 Hz, 1H), 7.47 (t, J=7.6 Hz, 1H), 7.15 (t, J=7.8 Hz, 1H), 6.94 (d, J=6.3 Hz, 1H), 6.65 (s, 2H), 4.77 (s, 2H), 4.02 (t, J=6.3 Hz, 2H), 3.89 (m, 5H), 3.25 (m, 4), 2.35 (s, 6H), 2.26 (t, J=6.6 Hz, 2H), 2.11 (s, 6H), 1.53 (m, 2).

Example 33

Preparation of 3-((3-(3-(4-chloro-3,5-dimethylphenoxy)propyl)-1-methyl-7-(1,3,5-trimethyl-1H-pyrazol-4-yl)-1H-indole-2-carboxamido)methyl)benzoic acid

I-33

Step A. Preparation of 3-(3-(4-chloro-3,5-dimethylphenoxy)propyl)-1-methyl-7-(1,3,5-trimethyl-1H-pyrazol-4-yl)-1H-indole-2-carboxylic acid To a solution of ethyl 3-(3-(4-chloro-3,5-dimethylphenoxy)propyl)-7-(1,3,5-trimethyl-1H-pyrazol-4-yl)-1H-indole-2-carboxylate (0.081 g, 0.164 mmol) in DMF (1.09 ml) at rt was added sodium hydride (0.016 g, 0.394 mmol). After 15 min, dimethyl sulfate (0.047 ml, 0.492 mmol) was added to the mixture. After 5 h, the mixture was concentrated in vacuo. A mixture of the crude ester and LiOH (2M, 0.820 ml) in EtOH (0.547 ml) and THF (1.09 ml) was stirred at 60° C. After 6 h, the mixture was acidified (1M HCl), extracted with EtOAc, dried, filtered and concentrated in vacuo. The residue was purified via reverse-phase preparative HPLC (Phenomenex Gemini C18, H$_2$O/CH$_3$CN gradient to 40-95% MeCN 0.1% TFA) to give the title compound. MS (ES) 480.1 (M+H).

Step B. Example 33

A mixture of 3-(3-(4-chloro-3,5-dimethylphenoxy)propyl)-1-methyl-7-(1,3,5-trimethyl-1H-pyrazol-4-yl)-1H-indole-2-carboxylic acid (0.010 g, 0.021 mmol), methyl 3-(aminomethyl)benzoate hydrochloride (4.62 mg, 0.023 mmol), 1-(3-dimethylaminopropyl)-3-ethylcarbodiimide hydrochloride (4.39 mg, 0.023 mmol) and DMAP (2.80 mg, 0.023 mmol) in THF (0.208 ml) was stirred at rt. After 5 h, the mixture was concentrated in vacuo. A mixture of the intermediate ester and LiOH (2M, 0.177 ml) in THF (0.208 ml) and EtOH (0.100 ml) was stirred at 60° C. After 3 h, the mixture was acidified (1M HCl), extracted with EtOAc, dried, filtered and concentrated in vacuo. The residue was purified via reverse-phase preparative HPLC (Phenomenex Gemini C18, H$_2$O/CH$_3$CN gradient to 40-80% MeCN 0.1% TFA) to give the title compound. MS (ES) 613.0 (M+H). $^1$H NMR (400 MHz, CDCl$_3$): 7.99 (m, 2H), 7.68 (d, J=7.6 Hz, 1H), 7.52 (d, J=7.6 Hz, 1H), 7.43 (t, J=7.6 Hz, 1H), 7.25 (t, J=6.0 Hz, 1H), 7.18 (t, J=7.4 Hz, 1H), 6.98 (d, J=6.5 Hz, 1H), 6.50 (s, 2H), 4.68 (m, 2H), 4.00 (s, 3H), 3.91 (t, J=5.4 Hz, 2H), 3.47 (s, 3H), 3.21 (t, J=6.1 Hz, 2H), 2.27 (m, 8H), 2.22 (s, 3H), 2.17 (s, 3H).

Example 34

Preparation of 3-((3-(3-(4-chloro-3,5-dimethylphenoxy)propyl)-7-(1,5-dimethyl-3-(pyrrolidin-1-ylmethyl)-1H-pyrazol-4-yl)-1H-indole-2-carboxamido)methyl)benzoic acid

I-34

Step A. Preparation of ethyl 3-(3-(4-chloro-3,5-dimethylphenoxy)propyl)-7-(4,4,5,5-tetramethyl-1,3,2-dioxaborolan-2-yl)-1H-indole-2-carboxylate To a solution of ethyl 7-bromo-3-(3-(4-chloro-3,5-dimethylphenoxy)propyl)-1H-indole-2-carboxylate (0.84 g) in DMF (9.0 ml) was added bis(pinacolato)diboron (0.551 g), potassium acetate (0.82 g) and Pd(dppf)Cl$_2$ (66 mg). The mixture was warmed to 60° C. After 15 h, the mixture was concentrated in vacuo. The residue was taken up in CH$_2$Cl$_2$, washed with H$_2$O, filtered and concentrated in vacuo. The crude residue was purified by flash column chromatography (Combi-Flash Rf, Hex/EtOAc 0-10% gradient) to give the title compounds. MS (ES) 512.2 (M+H).

Step B. Preparation of ethyl 3-(3-(4-chloro-3,5-dimethylphenoxy)propyl)-7-(3-(hydroxymethyl)-1,5-dimethyl-1H-pyrazol-4-yl)-1H-indole-2-carboxylate To a solution of ethyl 3-(3-(4-chloro-3,5-dimethylphenoxy)propyl)-7-(4,4,5,5-tetramethyl-1,3,2-dioxaborolan-2-yl)-1H-indole-2-carboxylate (0.79 g) in DME (5.8 ml) and ethanol (2.9 ml) was added (4-bromo-1,5-dimethyl-1H-pyrazol-3-yl)methanol (0.348 g), Pd(PPh$_3$)$_4$ (89 mg) and cesium fluoride (0.703 g). The mixture was heated to 120° C. in Biotage Initiator for 45 min. The crude residue was purified by flash column chromatography (Combi-Flash Rf, CH$_2$Cl$_2$/MeOH 0-10% gradient) to give the title compounds. MS (ES) 510.3 (M+H).

Step C. Preparation of 3-(3-(4-chloro-3,5-dimethylphenoxy)propyl)-7-(1,5-dimethyl-3-(pyrrolidin-1-ylmethyl)-1H-pyrazol-4-yl)-1H-indole-2-carboxylic acid To a solution of ethyl 3-(3-(4-chloro-3,5-dimethylphenoxy)propyl)-7-(3-(hydroxymethyl)-1,5-dimethyl-1H-pyrazol-4-yl)-1H-indole-2-carboxylate (0.23 g, 0.451 mmol) and N,N-diisopropylethylamine (0.236 ml, 1.353 mmol) in dichloromethane (3.39 ml) at 0° C. was added methanesulfonyl chloride (0.070 ml, 0.902 mmol). After 30 min, pyrrolidine (0.186 ml, 2.255 mmol) was added to the mixture. The mixture was then warmed to rt. After 15 h at rt, the reaction mixture was diluted with dichloromethane. The combined organics were washed with H$_2$O, filtered and concentrated in vacuo. A mixture of the crude ester intermediate and LiOH (2N, 2.2 ml, 4.51 mmol) in THF (2.0 ml) and EtOH (1.0 ml) was stirred at 60° C. After 3 h, the mixture was acidified (1M HCl), extracted with EtOAc, dried, filtered and concentrated in vacuo. The residue was purified via reverse-phase preparative HPLC (Phenomenex Gemini C18, $H_2O/CH_3CN$ gradient to 40-80% MeCN 0.1% $NH_4OH$) to give the title compound. MS (ES) 535.2 (M+H).

Step C. Example 34

A mixture of 3-(3-(4-chloro-3,5-dimethylphenoxy)propyl)-7-(1,5-dimethyl-3-(pyrrolidin-1-ylmethyl)-1H-pyrazol-4-yl)-1H-indole-2-carboxylic acid (0.028 g, 0.052 mmol), methyl 3-(aminomethyl)benzoate (0.011 g, 0.068 mmol), 1-(3-dimethylaminopropyl)-3-ethylcarbodiimide hydrochloride (10.53 mg, 0.055 mmol) and DMAP (7.03 mg, 0.058 mmol) in THF (0.52 ml) was stirred at rt. After 15 h, LiOH (0.445 ml, 0.890 mmol) was added to the mixture. The mixture was then warmed to 60° C. After 3 h, the mixture was acidified (1M HCl), extracted with EtOAc, dried, filtered and concentrated in vacuo. The residue was purified via reverse-phase preparative HPLC (Phenomenex Gemini C18, $H_2O/CH_3CN$ gradient to 30-70% MeCN 0.1% $NH_4OH$) to give the title compound. MS (ES) 668.1 (M+H).

Example 35

Preparation of 3-(3-(4-chloro-3,5-dimethylphenoxy) propyl)-N-(3-(((2-cyanophenyl)sulfonyl)carbamoyl) benzyl)-7-(1,5-dimethyl-3-(pyrrolidin-1-ylmethyl)-1H-pyrazol-4-yl)-1H-indole-2-carboxamide

I-35

A mixture of 3-((3-(3-(4-chloro-3,5-dimethylphenoxy) propyl)-7-(1,5-dimethyl-3-(pyrrolidin-1-ylmethyl)-1H-pyrazol-4-yl)-1H-indole-2-carboxamido)methyl)benzoic acid (0.013 g, 0.019 mmol), 2-cyanobenzenesulfonamide (5.32 mg, 0.029 mmol), 1-(3-dimethylaminopropyl)-3-ethylcarbodiimide hydrochloride (5.59 mg, 0.029 mmol) and DMAP (3.57 mg, 0.029 mmol) in dichloromethane (0.389 ml) was stirred at rt. After 15 h, the mixture was concentrated in vacuo. The residue was purified via reverse-phase preparative HPLC (Phenomenex Gemini C18, $H_2O/CH_3CN$ gradient to 20-80% MeCN 0.1% $NH_4OH$) to give the title compound. MS (ES) 832.0 (M+H).

Example 36

Preparation of 3-(3-(3-(4-chloro-3,5-dimethylphenoxy)propyl)-7-(2-methylpyridin-3-yl)-1H-indole-2-carboxamido)benzoic acid

I-36

Step A: Preparation of ethyl 3-(3-(4-chloro-3,5-dimethylphenoxy)propyl)-7-(2-methylpyridin-3-yl)-1H-indole-2-carboxylate A solution of ethyl 7-bromo-3-(3-(4-chloro-3,5-dimethylphenoxy)propyl)-1H-indole-2-carboxylate (60 mg, 0.129 mmol), (2-methylpyridin-3-yl)boronic acid (20 mg, 0.15 mmol), $Pd(PPh_3)_4$ (7.46 mg, 6.45 µmol) and CsF (58.8 mg, 0.387 mmol) in ethanol (0.22 ml) and DME (0.44 ml) was degassed under Argon for 10 min. The mixture was then heated to 120° C. in Biotage Initiator for 25 min. The reaction mixture was concentrated under vacuum, and the residue was purified by flash chromatography (Combi-flash Rf Hexane/EtOAc gradient 0-15%) to yield the title compound (59 mg). MS (ES) 477.3 (M+H).

Step B: Preparation of 3-(3-(4-chloro-3,5-dimethylphenoxy)propyl)-7-(2-methylpyridin-3-yl)-1H-indole-2-carboxylic acid A solution of ethyl 3-(3-(4-chloro-3,5-dimethylphenoxy)propyl)-7-(2-methylpyridin-3-yl)-1H-indole-2-carboxylate (38 mg, 0.080 mmol) and LiOH (2N, 200 µl, 0.4 mmol) in EtOH (400 µl) and THF (100 µl) was heated to 40° C. for 16 h. The reaction mixture was concentrated in vacuo, and the residue was purified by reverse phase prep. HPLC (Phenomenex Gemini C18, $H_2O/CH_3CN$ gradient to 95% $CH_3CN$ 0.1% TFA) to yield the title compound (32 mg 0.071 mmol). MS (ES) 449.2 (M+H).

Step C: Example 36

A solution of 3-(3-(4-chloro-3,5-dimethylphenoxy)propyl)-7-(2-methylpyridin-3-yl)-1H-indole-2-carboxylic acid (20 mg, 0.045 mmol), methyl 3-aminobenzoate (7.4 mg, 0.049 mmol), EDC (9.4 mg, 0.049 mmol) and DMAP (1.1 mg, 8.91 µmol) in $CH_2Cl_2$ (890 µl) was stirred 15 h at rt. The solvent was removed and the residue was dissolved in a mixture of LiOH (2N, 0.1 ml, 0.2 mmol), EtOH (0.4 ml) and THF (0.1 ml). The reaction mixture was stirred at 40° C. for 16 h. The reaction mixture was cooled to rt and concentrated in vacuo. The residue was purified by reverse phase prep. HPLC (Phenomenex Gemini C18, $H_2O/CH_3CN$ gradient to 30-80% $CH_3CN$ 0.1% TFA) to give the title compound (12.6 mg) as a white solid. MS (ES) 568.0 (M+H).

Example 37

Preparation of 4-(3-(3-(4-chloro-3,5-dimethylphenoxy)propyl)-7-(2-methylpyridin-3-yl)-1H-indole-2-carboxamido)benzoic acid

I-37

The title compound was prepared (22 mg, 0.039 mmol) according to procedures described in Example 36 Step A and B using 3-(3-(4-chloro-3,5-dimethylphenoxy)propyl)-7-(2-methylpyridin-3-yl)-1H-indole-2-carboxylic acid (30 mg, 0.067 mmol) and substituting methyl 3-aminobenzoate with methyl 4-aminobenzoate (11 mg, 0.074 mmol). MS (ES) 568.0 (M+H).

Example 38

Preparation of 4-(6-chloro-3-(3-(4-chloro-3,5-dimethylphenoxy)propyl)-7-(1,3,5-trimethyl-1H-pyrazol-4-yl)-1H-indole-2-carboxamido)benzoic acid

I-38

Step A. Preparation of ethyl 7-bromo-6-chloro-3-(3-ethoxy-3-oxopropyl)-1H-indole-2-carboxylate Title compounds were prepared according to procedures described in Example 2 Step A and B using 2-bromo-3-chloroaniline. MS (ES) 402.0 (M+H).

Step B. Preparation of ethyl 7-bromo-6-chloro-3-(3-hydroxypropyl)-1H-indole-2-carboxylate Title compound was prepared according to the procedure in Example 2 Step C using ethyl 7-bromo-6-chloro-3-(3-ethoxy-3-oxopropyl)-1H-indole-2-carboxylate. MS (ES) 360.1 (M+H).

Step C. Preparation ethyl 7-bromo-6-chloro-3-(3-(4-chloro-3,5-dimethylphenoxy)propyl)-1H-indole-2-carboxylate Title compound was prepared as a colorless oil according to procedures described in Example 2 Step D using 7-bromo-6-chloro-3-(3-hydroxypropyl)-1H-indole-2-carboxylate. MS (ES) 498.0 (M+H).

Step D. Preparation of ethyl 6-chloro-3-(3-(4-chloro-3,5-dimethylphenoxy)propyl)-7-(1,3,5-trimethyl-1H-pyrazol-4-yl)-1H-indole-2-carboxylate Title compound was prepared as a colorless oil according to procedures described in Example 28 Step A using 7-bromo-6-chloro-3-(3-hydroxypropyl)-1H-indole-2-carboxylate. MS (ES) 528.2 (M+H).

Step E. Preparation of 6-chloro-3-(3-(4-chloro-3,5-dimethylphenoxy)propyl)-7-(1,3,5-trimethyl-1H-pyrazol-4-yl)-1H-indole-2-carboxylic acid Title compound was prepared as a colorless oil according to procedures described in Example 28 Step B using ethyl 6-chloro-3-(3-(4-chloro-3,5-dimethylphenoxy)propyl)-7-(1,3,5-trimethyl-1H-pyrazol-4-yl)-1H-indole-2-carboxylate. MS (ES) 500.2 (M+H).

Step F. Example 38

The title compound was prepared (15 mg, 0.024 mmol) according to procedures described in Example 36 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid (40 mg, 0.080 mmol) and methyl 4-aminobenzoate (13.29 mg, 0.088 mmol). MS (ES) 619.0 (M+H).

Example 39

Preparation of 3-(6-chloro-3-(3-(4-chloro-3,5-dimethylphenoxy)propyl)-7-(1,3,5-trimethyl-1H-pyrazol-4-yl)-1H-indole-2-carboxamido)benzoic acid

I-39

The title compound was prepared (16 mg, 0.026 mmol) according to procedures described in Example 36 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid (20 mg, 0.040 mmol) and methyl 3-aminobenzoate (6.65 mg, 0.044 mmol). MS (ES) 619.2 (M+H).

Example 40

Preparation of 3-(3-(4-chloro-3,5-dimethylphenoxy)propyl)-N-phenyl-1H-indole-2-carboxamide

I-40

To a stirred solution of EDC (0.088 mmol), HOBT (0.014 mmol), 3-(3-(4-chloro-3,5-dimethylphenoxy)propyl)-1H-indole-2-carboxylic acid (0.07 mmol) in DCM (0.1M) and TEA (0.28 mmol) was added aniline (0.077 mmol). The reaction mixture was allowed to stir for 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (Phenomenex Gemini C18, H$_2$O/CH$_3$CN gradient to 5-95% CH$_3$CN 0.1% TFA) to yield the title compound as a white solid. $^1$H NMR (CDCl$_3$, 400 MHz, 25° C.): 9.10 (br s, 1H), 8.35 (br s, 1H), 7.68 (d, J=8.0 Hz, 1H), 7.58 (d, J=8.0 Hz, 2H), 7.43 (d, J=8.0 Hz, 1H), 7.36-7.31 (m, 3H), 7.17 (2, J=6.0 Hz, 2H), 6.56 (s, 2H), 4.01 (t, J=6.0 Hz, 2H), 2.34-2.25 (m, 2H), 2.25 (s, 6H); MS (ES) 433.2 (M+H).

Example 41

Preparation of N-benzyl-3-(3-(4-chloro-3,5-dimethylphenoxy)propyl)-1H-indole-2-carboxamide

I-41

Title compound was prepared according to the procedure used in Example 40 using the requisite amine. $^1$H NMR (CDCl$_3$, 400 MHz, 25° C.): 9.06 (br s, 1H), 7.64 (d, J=8.0 Hz, 1H), 7.41 (d, J=8.0 Hz, 1H), 7.32-7.24 (m, 5H), 7.19-7.12 (m, 2H), 6.44 (s, 2H), 4.57 (d, J=4.0 Hz, 2H), 3.88 (t, J=6.0 Hz, 2H), 3.25 (t, J=6 Hz, 2H), 2.26 (s, 6H), 2.24-2.18 (m, 2H); MS (ES) 447.3 (M+H). MS (ES) 447.2 (M+H).

Example 42

Preparation of 3-(3-(4-chloro-3,5-dimethylphenoxy)propyl)-N-phenethyl-1H-indole-2-carboxamide

I-42

Title compound was prepared according to the procedure used in Example 40 using the requisite amine. $^1$H NMR (CDCl3, 400 MHz, 25° C.): 9.02 (br s, 1H), 7.61 (d, J=8.0 Hz, 1H), 7.40 (d, J=8.0 Hz, 1H), 7.32-7.27 (m, 3H), 7.24-7.10 (m, 4H), 6.71 (br t, J=4.0 Hz, 1H), 6.57 (s, 2H), 3.81 (t, J=6.0 Hz, 2H), 3.60 (q, J=6.0 Hz, 2H), 3.09 (t, J=8.0 Hz, 2H), 2.83 (t, J=8.0 Hz, 2H), 2.33 (s, 6H), 2.12-2.05 (m, 2H); MS (ES) 461.2 (M+H).

Example 43

Preparation of 3-(3-(4-chloro-3,5-dimethylphenoxy)propyl)-N,N-dimethyl-1H-indole-2-carboxamide

I-43

Title compound was prepared according to the procedure used in Example 40 using the requisite amine. $^1$H NMR (CDCl$_3$, 400 MHz, 25° C.): 8.41 (br s, 1H), 7.64 (d, J=8.0 Hz, 1H), 7.36 (d, J=8.0 Hz, 1H), 7.27-7.24 (m, 1H), 7.13 (t, J=8.0 Hz, 1H), 6.61 (s, 2H), 3.89 (t, J=6.0 Hz, 2H), 3.08 (s, 6H), 3.00 (t, J=8.0 Hz, 2H), 2.33 (s, 6H), 2.18-2.11 (m, 2H); MS (ES) 385.2 (M+H).

Example 44

Preparation of 3-(3-(4-chloro-3,5-dimethylphenoxy)propyl)-N-(2-(1,2-dimethyl-1H-indol-3-yl)ethyl)-1H-indole-2-carboxamide

I-44

Title compound was prepared according to the procedure used in Example 40 using the requisite amine. $^1$H NMR (CDCl$_3$, 400 MHz, 25° C.): 9.11 (br s, 1H), 7.59 (d, J=8.0 Hz, 1H), 7.47 (d, J=8.0 Hz, 1H), 7.40 (d, J=8.0 Hz, 1H), 7.30-7.22 (m, 2H), 7.17-7.09 (m, 2H), 7.04 (t, J=6.0 Hz, 1H), 6.72 (br t, J=6.0 Hz, 1H), 6.53 (s, 2H), 3.68-3.60 (m, 4H), 3.60 (s, 3H), 3.02 (t, J=6.0 Hz, 2H), 2.96 (t, J=8.0 Hz, 2H), 2.32 (s, 6H), 2.30 (s, 3H), 1.95-1.90 (m, 2H); MS (ES) 528.3 (M+H).

Example 45

Preparation of 3-(3-(4-chloro-3,5-dimethylphenoxy) propyl)-N-(4-phenoxybenzyl)-1H-indole-2-carboxamide

I-45

Title compound was prepared according to the procedure used in Example 40 using the requisite amine. $^1$H NMR (CDCl$_3$, 400 MHz, 25° C.): 9.13 (br s, 1H), 7.64 (d, J=8.0 Hz, 1H), 7.41 (d, J=8.0 Hz, 1H), 7.34-7.29 (m, 3H), 7.22-7.08 (m, 5H), 6.99 (d, J=4.0 Hz 2H), 6.93 (d, J=12.0 Hz 2H), 6.48 (s, 2H), 4.53 (d, J=6.0 Hz, 2H), 3.90 (t, J=6.0 Hz, 2H), 3.24 (t, J=8.0 Hz, 2H), 2.28 (s, 6H), 2.25-2.18 (m, 2H); MS (ES) 539.2 (M+H).

Example 46

Preparation of (3-(3-(4-chloro-3,5-dimethylphenoxy)propyl)-1H-indol-2-yl)(4-phenylpiperazin-1-yl)methanone

I-46

Title compound was prepared according to the procedure used in Example 40 using the requisite amine. $^1$H NMR (CDCl$_3$, 400 MHz, 25° C.): 8.42 (br s, 1H), 7.66 (d, J=8.0 Hz, 1H), 7.39 (d, J=8.0 Hz, 1H), 7.31-7.27 (m, 3H), 7.15 (t, J=8.0 Hz, 1H), 6.96-6.93 (m, 3H), 6.59 (s, 2H), 3.90 (t, J=6.0 Hz, 2H), 3.84 (br t, J=4.0 Hz, 4H), 3.21 (br t, J=4.0 Hz, 4H), 3.04 (t, J=6.0 Hz, 2H), 2.29 (s, 6H), 2.19-2.12 (m, 2H); MS (ES) 502.2 (M+H).

Example 47

Preparation of (3-(3-(4-chloro-3,5-dimethylphenoxy)propyl)-1H-indol-2-yl)(4-morpholinopiperidin-1-yl)methanone

I-47

Title compound was prepared according to the procedure used in Example 40 using the requisite amine. $^1$H NMR (CDCl$_3$, 400 MHz, 25° C.): 9.12 (br s, 1H), 7.63 (d, J=8.0 Hz, 1H), 7.38 (d, J=8.0 Hz, 1H), 7.28 (t, J=6.0 Hz 1H), 7.14 (t, J=6.0 Hz, 1H), 6.59 (s, 2H), 4.42 (br t, J=12.0 Hz, 2H), 3.97-3.84 (m, 6H), 3.44-3.31 (m, 3H), 2.97 (t, J=8.0 Hz, 2H), 2.97-2.79 (m, 4H), 2.32 (s, 6H), 2.14-2.01 (m, 4H), 1.84-1.75 (m, 2H); MS (ES) 510.3 (M+H).

Example 48

Preparation of tert-butyl (1-(3-(3-(4-chloro-3,5-dimethylphenoxy)propyl)-1H-indole-2-carbonyl)piperidin-4-yl)carbamate

I-48

To a stirred solution of EDC (0.175 mmol), HOBT (0.028 mmol), 3-(3-(4-chloro-3,5-dimethylphenoxy)propyl)-1H-indole-2-carboxylic acid (0.07 mmol) in DCM (0.1M) and TEA (0.559 mmol) was added tert-butyl piperidin-4-ylcarbamate (0.153 mmol). The reaction mixture was allowed to stir for 15 hours. Upon completion the volatiles were removed via rotary evaporation and the remaining material adsorbed onto silica gel. The material was isolated via silica gel chromatography using a gradient up to 10% methanol in DCM to yield the Title compound as a yellow foam. MS (ES) 540.3 (M+H).

Example 49

Preparation of 3-(3-(4-chloro-3,5-dimethylphenoxy) propyl)-N-(5-sulfamoylpyridin-2-yl)-N-(4-(trifluoromethyl)benzyl)-1H-indole-2-carboxamide

I-49

Step A. Preparation of 6-chloropyridine-3-sulfonamide

To a 20 mL scintillation vial with an inlaid septum cap was added a stir bar, 6-chloropyridine-3-sulfonyl chloride (2 mmol) and 8 mL of acetonitrile (0.25 M). The solution was cooled to −78° C. and ammonia gas was bubbled through the solution for 10 seconds. The reaction was then allowed to warm to room temperature, at which time the reaction was vented with a syringe needle and allowed to stir for two hours. The resultant white slurry was then filtered and the filtrate concentrated in vacuo to yield title compound as a white solid.

Step B. Preparation of 6-((4-(trifluoromethyl)benzyl)amino)pyridine-3-sulfonamide To a suspension of 6-chloropyridine-3-sulfonamide in ethanol (0.3 M) in a microwave compatible vessel was added (4-(trifluoromethyl)phenyl)methylamine. The reaction mixture was heated at 150° C. in Biotage Initiator for 1 hour. The reaction mixture was quenched by addition of H$_2$O, extracted with EtOAc, dried over MgSO$_4$, filtered and concentrated in vacuo to give the title compound as an off-white solid.

Step C. Example 49

Title compound was prepared according to the procedure used in Example 40 using 6-((4-(trifluoromethyl)benzyl)amino)pyridine-3-sulfonamide. MS (ES) 671.2 (M+H).

Example 50

Preparation of ethyl 4-(4-(6-chloro-3-(3-(4-chloro-3,5-dimethylphenoxy)propyl)-1H-indole-2-carbonyl)piperazin-1-yl)benzoate

I-50

To a stirred solution of EDC (0.153 mmol), DMAP (0.153 mmol), 3-(3-(4-chloro-3,5-dimethylphenoxy)propyl)-1H-indole-2-carboxylic acid (0.076 mmol) in DCM (0.1M) and TEA (0.28 mmol) was added ethyl 4-(piperazin-1-yl)benzoate (0.077 mmol). The reaction mixture was allowed to stir for 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H₂O/CH₃CN gradient to 95% CH₃CN 0.1% TFA) to yield the title compound as a white solid. ¹H NMR (CDCl₃, 400 MHz, 25° C.): 8.92 (br s, 1H), 7.95 (d, J=8.0 Hz, 2H), 7.55 (d, J=8.0 Hz, 1H), 7.37 (br s, 1H), 7.11 (d, J=8.0 Hz, 1H), 6.86 (d, J=12.0 Hz, 2H), 6.55 (s, 2H), 4.35 (q, J=8.0 Hz, 2H), 3.87 (t, J=6.0 Hz, 2H), 3.81 (br t, J=4.0 Hz, 4H), 3.00 (t, J=8.0 Hz, 2H), 2.28 (s, 6H), 2.13-2.09 (m, 2H); MS (ES) 608.2 (M+H).

Example 51

Preparation of 4-(4-(6-chloro-3-(3-(4-chloro-3,5-dimethylphenoxy)propyl)-1H-indole-2-carbonyl)piperazin-1-yl)benzoic acid

I-51

To a stirred solution of ethyl 4-(4-(6-chloro-3-(3-(4-chloro-3,5-dimethylphenoxy)propyl)-1H-indole-2-carbonyl)piperazin-1-yl)benzoate (0.123 mmol) in THF (0.075M) was added a drop of MeOH, and an aqueous solution of 2M LiOH (1 mL). The reaction was then heated at 50° C. for 15 hours, after which it was cooled to room temperature, acidified to pH 2 with 3M HCl and extracted with EtOAc. The organic layer was washed with brine, dried over MgSO₄, filtered and concentrated in vacuo. The resultant solid was dissolved in 1 mL of 1:1 mix of acetonitrile and methanol. The slurry was filtered and the filtrate was purified by reverse phase preparatory HPLC (Phenomenex Gemini C18, H₂O/CH₃CN gradient to 5-95% CH₃CN 0.1% TFA) to yield the title compound as a white solid. ¹H NMR (d6-DMSO 400 MHz, 25° C.): 11.48 (s, 1H), 7.79 (d, J=8.0 Hz, 2H), 7.64 (d, J=8.0 Hz, 1H), 7.40 (d, J=2.0 Hz, 1H), 7.05 (br d, J=12.0 Hz, 1H), 6.96 (br d, J=8.0 Hz, 2H), 6.69 (s, 2H), 3.91 (t, J=4.0 Hz, 2H), 3.62 (br s, 4H), 2.90 (t, J=8.0 Hz, 2H), 2.21 (s, 6H), 2.04-1.88 (m, 2H); MS (ES) 580.0 (M+H). MS (ES).

Example 52

Preparation of methyl 3-(4-(6-chloro-3-(3-(4-chloro-3,5-dimethylphenoxy)propyl)-1H-indole-2-carbonyl)piperazin-1-yl)benzoate

I-52

Title compound was prepared according to the procedure used in Example 50 using the requisite amine and 6-chloro-3-(3-(4-chloro-3,5-dimethylphenoxy)propyl)-1H-indole-2-carboxylic acid. ¹H NMR (d6-DMSO, 400 MHz, 25° C.): 7.64 (d, J=8.0 Hz, 2H), 7.46 (m, 1H), 7.43-7.36 (m, 3H), 7.25-7.21 (m, 1H), 7.08-7.03 (m, 1H), 6.69 (s, 2H), 3.92 (t, J=8.0 Hz, 2H), 3.83 (s, 3H), 3.64 (br s, 4H), 3.21 (br s, 4H), 2.90 (t, J=8.0 Hz, 2H), 2.20 (s, 6H), 2.04-1.96 (m, 2H); MS (ES) 594.1 (M+H).

Example 53

Preparation of N-(2-(N-(2-(4-bromophenyl)acetyl)sulfamoyl)ethyl)-3-(3-(4-chloro-3,5-dimethylphenoxy)propyl)-1H-indole-2-carboxamide

I-53

To a stirred solution of 3-(3-(4-chloro-3,5-dimethylphenoxy)propyl)-1H-indole-2-carboxylic acid (0.062 mmol), EDC (0.068 mmol), HOBT (0.006 mmol), and TEA (0.187 mmol) in DCM (0.1M) at 0° C. was added 2-aminoethanesulfonamide hydrochloride. The reaction mixture was then slowly warmed to room temperature and stirred for 15 hours. After the allotted time, EDC (0.125 mmol), DMAP (0.187 mmol) and 2-(4-bromophenyl)acetic acid (0.062 mmol) were added to the reaction, and it was allowed to stir for another 15 hours. The reaction mixture was then concentrated in vacuo, and the remaining material slurried in 1 mL of 1:1 mix of acetonitrile and methanol. The slurry was filtered and the filtrate was purified by reverse phase preparatory HPLC (Phenomenex Gemini C18, H₂O/CH₃CN gradient to 5-95% CH₃CN 0.1% TFA) to yield the title compound as a white solid. MS (ES) 660.1 (M+H).

Example 54

Preparation of N-(2-(N-(2-((3r,5r,7r)-adamantan-1-yl)acetyl)sulfamoyl)ethyl)-3-(3-(4-chloro-3,5-dimethylphenoxy)propyl)-1H-indole-2-carboxamide

I-54

Title compound was prepared according to the procedure used in Example 53 by substituting 2-((3r,5r,7r)-adamantan-1-yl)acetic acid for 2-(4-bromophenyl)acetic acid. ¹H NMR (CDCl₃, 400 MHz, 25° C.): 9.18 (br s, 1H), 8.50 (br s, 1H), 7.59 (d, J=8.0 Hz, 1H), 7.37 (d, J=8.0 Hz, 1H), 7.30-7.23 (m, 2H), 7.11 (t, J=6.0 Hz, 1H), 6.69 (s, 2H), 3.93 (t, J=6.0 Hz, 2H), 3.88 (q, J=6.0 Hz, 2H), 3.57 (br t, J=6.0 Hz, 2H), 3.19 (t, J=8.0 Hz, 2H), 2.35 (s, 6H), 2.23-2.16 (m, 2H), 1.96-1.83 (br m, 7H), 1.70-1.55 (br m, 6H); MS (ES) 640.2 (M+H).

Example 55

Preparation of N-(2-(N-((3r,5r,7r)-adamantane-1-carbonyl)sulfamoyl)ethyl)-3-(3-(4-chloro-3,5-dimethylphenoxy)propyl)-1H-indole-2-carboxamide

I-55

Title compound was prepared according to the procedure used in Example 53 by substituting (3r,5r,7r)-adamantane-1-carboxylic acid for 2-(4-bromophenyl)acetic acid. ¹H NMR (CDCl₃, 400 MHz, 25° C.): 9.13 (br s, 1H), 8.13 (br s, 1H), 7.62 (d, J=8.0 Hz, 1H), 7.39 (d, J=8.0 Hz, 1H), 7.30 (t, J=6.0 Hz, 1H), 7.27 (t, J=8.0 Hz, 1H), 7.13 (t, J=6.0 Hz, 1H), 6.68 (s, 2H), 3.93 (t, J=6.0 Hz, 2H), 3.84 (q, J=6.0 Hz, 2H), 3.55 (br t, J=6.0 Hz, 2H), 3.22 (t, J=6.0 Hz, 2H), 2.34 (s, 6H), 2.24-2.19 (m, 2H), 2.02 (br m, 4H), 1.83 (br m, 6H), 1.73-1.60 (br m, 6H); MS (ES) 626.2 (M+H).

Example 56

Preparation of ethyl 5-((3-(3-(4-chloro-3,5-dimethylphenoxy)propyl)-1H-indole-2-carboxamido)methyl)furan-2-carboxylate

I-56

To a stirred solution of EDC (0.553 mmol), HOBT (0.05 mmol), 3-(3-(4-chloro-3,5-dimethylphenoxy)propyl)-1H-indole-2-carboxylic acid (0.503 mmol), and TEA (1.51 mmol) in DCM (0.1M) was added ethyl 5-(aminomethyl)furan-2-carboxylate (0.503 mmol). The reaction mixture was allowed to stir for 15 hours. The reaction mixture was concentrated in vacuo, and the residue was slurried in 1 mL of 1:1 mix of acetonitrile and methanol. The slurry was filtered and the filtrate was purified by reverse phase preparatory HPLC (Phenomenex Gemini C18, H$_2$O/CH$_3$CN gradient to 5-95% CH$_3$CN 0.1% TFA) to yield the title compound as a white solid. MS (ES) 509.2 (M+H).

Example 57

Preparation of 5-((3-(3-(4-chloro-3,5-dimethylphenoxy)propyl)-1H-indole-2-carboxamido)methyl)furan-2-carboxylic acid

I-57

To a stirred solution of ethyl 5-((3-(3-(4-chloro-3,5-dimethylphenoxy)propyl)-1H-indole-2-carboxamido)methyl)furan-2-carboxylate (0.295 mmol) in THF (0.1M) was added a drop of MeOH, and an aqueous solution of 2M LiOH (1 mL). The reaction was then heated at 50° C. for 15 hours, after which it was cooled to room temperature, acidified to pH 2 with 3M HCl and extracted with ethyl acetate. The organic layer was washed with brine, dried over MgSO$_4$, filtered and concentrated in vacuo. The resultant solid was dissolved in 1 mL of 1:1 mix of acetonitrile and methanol. The slurry was filtered and the filtrate was purified by reverse phase preparatory HPLC (Phenomenex Gemini C18, H$_2$O/CH$_3$CN gradient to 5-95% CH$_3$CN 0.1% TFA) to yield the title compound as a white solid. $^1$H NMR (d6-DMSO, 400 MHz, 25° C.): 8.51 (t, J=8.0 Hz, 1H), 7.62 (d, J=8.0 Hz, 1H), 7.40 (d, J=8.0 Hz, 1H), 7.21 (t, J=6.0 Hz, 1H), 7.15 (d, J=8.0 Hz, 1H), 7.02 (t, J=6.0 Hz, 1H), 6.73 (s, 2H), 6.51 (d, J=4.0 Hz, 1H), 3.92 (t, J=8.0 Hz, 2H), 3.18 (t, J=8.0 Hz, 2H), 2.26 (s, 6H), 2.04-1.96 (m, 2H), MS (ES) 481.2 (M+H).

Example 58

Preparation 3-(3-(4-chloro-3,5-dimethylphenoxy)propyl)-N-((5-((2-(trifluoromethyl)benzyl)carbamoyl)furan-2-yl)methyl)-1H-indole-2-carboxamide

I-58

To a stirred solution of EDC (0.125 mmol), HOBT (0.01 mmol), 5-((3-(3-(4-chloro-3,5-dimethylphenoxy)propyl)-1H-indole-2-carboxamido)methyl)furan-2-carboxylic acid (0.062 mmol), and TEA (0.187 mmol) in DCM (0.1M) was added (2-(trifluoromethyl)phenyl)methylamine (0.075 mmol). The reaction mixture was stirred for 15 h then concentrated in vacuo. The residue was slurred in 1 mL of 1:1 mix of acetonitrile and methanol and filtered. The filtrate was purified by reverse phase preparatory HPLC (Phenomenex Gemini C18, H$_2$O/CH$_3$CN gradient to 5-95% CH$_3$CN 0.1% TFA) to yield the title compound as a white solid. $^1$H NMR (d6-DMSO, 400 MHz, 25° C.): 11.25 (s, 1H), 8.91 (m, 1H), 8.48 (m, 1H), 7.73 (d, J=8.0 Hz, 1H), 7.63 (m, 2H), 7.50-7.39 (m, 3H), 7.21 (t, J=6.0 Hz, 1H), 7.17 (m, 1H), 7.02 (t, J=6.0 Hz, 1H), 6.73 (s, 2H), 6.52 (m, 1H), 4.59 (m, 3H), 3.92 (t, J=8.0 Hz, 2H), 3.18 (t, J=8.0 Hz, 2H), 2.26 (s, 6H), 2.04-1.96 (m, 2H), MS (ES) 638.2 (M+H).

Example 59

Preparation of 3-(3-(4-chloro-3,5-dimethylphenoxy)propyl)-N-((5-((methylsulfonyl)carbamoyl)furan-2-yl)methyl)-1H-indole-2-carboxamide

I-59

To a stirred solution of EDC (0.125 mmol), DMAP (0.187 mmol), 5-((3-(3-(4-chloro-3,5-dimethylphenoxy)propyl)-1H-indole-2-carboxamido)methyl)furan-2-carboxylic acid (0.062 mmol), and TEA (0.187 mmol) in DCM (0.1M) was added methanesulfonamide (0.187 mmol). The reaction mixture was allowed to stir for 15 hours. The reaction mixture was stirred for 15 h then concentrated in vacuo. The residue was slurred in 1 mL of 1:1 mix of acetonitrile and methanol and filtered. The filtrate was purified by reverse phase preparatory HPLC (Phenomenex Gemini C18, H$_2$O/CH$_3$CN gradient to 5-95% CH$_3$CN 0.1% TFA) to yield the title compound as a white solid. MS (ES) 558.1 (M+H).

Example 60

Preparation of 3-(3-(4-chloro-3,5-dimethylphenoxy)propyl)-N-((5-((phenylsulfonyl)carbamoyl)furan-2-yl)methyl)-1H-indole-2-carboxamide

I-60

Title compound was prepared according to the procedure used in Example 59 using the requisite sulfonamide. MS (ES) 620.2 (M+H).

Example 61

Preparation of ethyl 5-((3-(3-(4-chloro-3,5-dimethylphenoxy)propyl)-7-(3,5-dimethyl-1H-pyrazol-4-yl)-1H-indole-2-carboxamido)methyl)furan-2-carboxylate

I-61

Title compound was prepared according to the procedure used in Example 56 by substituting 3-(3-(4-chloro-3,5-dimethylphenoxy)propyl)-7-(3,5-dimethyl-1H-pyrazol-4-yl)-1H-indole-2-carboxylic acid for 3-(3-(4-chloro-3,5-dimethylphenoxy)propyl)-1H-indole-2-carboxylic acid. $^1$H NMR (d6-DMSO, 400 MHz, 25° C.): 10.55 (s, 1H), 8.93 (m, 1H), 7.60 (d, J=8.0 Hz, 1H), 7.23 (d, J=4.0 Hz, 1H), 7.11-7.04 (m, 2H), 6.75 (s, 2H), 6.51 (m, 1H), 4.56 (d, J=8.0 Hz, 2H), 4.26 (q, J=8.0 Hz, 2H), 3.97 (t, J=6.0 Hz, 2H), 3.24 (t, J=8.0 Hz, 2H), 2.27 (s, 6H), 2.09 (s, 6H), 2.06-2.02 (m, 2H), 1.27 (t, J=8.0 Hz, 3H), MS (ES) 603.2 (M+H).

Example 62

Preparation of 5-((3-(3-(4-chloro-3,5-dimethylphenoxy)propyl)-7-(3,5-dimethyl-1H-pyrazol-4-yl)-1H-indole-2-carboxamido)methyl)furan-2-carboxylic acid

I-62

Title compound was prepared according to the procedure used in Example 57 by substituting ethyl 5-((3-(3-(4-chloro-3,5-dimethylphenoxy)propyl)-7-(3,5-dimethyl-1H-pyrazol-4-yl)-1H-indole-2-carboxamido)methyl)furan-2-carboxylate for ethyl 5-((3-(3-(4-chloro-3,5-dimethylphenoxy)propyl)-1H-indole-2-carboxamido)methyl)furan-2-carboxylate. MS (ES) 575.2 (M+H).

Example 63

Preparation of 3-(3-(4-chloro-3,5-dimethylphenoxy)propyl)-7-(3,5-dimethyl-1H-pyrazol-4-yl)-N-((5-(hydroxymethyl)furan-2-yl)methyl)-1H-indole-2-carboxamide

I-63

To a stirred solution of ethyl 5-((3-(3-(4-chloro-3,5-dimethylphenoxy)propyl)-7-(3,5-dimethyl-1H-pyrazol-4-yl)-

1H-indole-2-carboxamido)methyl)furan-2-carboxylate (0.05 mmol) in THF (0.1M) at 0° C. was added dropwise 2M Lithium borohydride solution in THF (0.497 mmol). The reaction was allowed to slowly warm to rt and stir for an additional 15 h. The mixture was then cooled to 0° C. and acidified to pH 6 with 3N aqueous HCl. The mixture was extracted with ethyl acetate and the organic layer washed with brine, dried over $Na_2SO_4$, filtered and concentrated in vacuo. The solid was then dissolved in 1 mL of a 1:1 mix of acetonitrile and methanol and was purified by reverse phase preparatory HPLC (Phenomenex Gemini C18, $H_2O/CH_3CN$ gradient to 5-95% $CH_3CN$ 0.1% TFA) to yield the title compound as a white solid. MS (ES) 561.2 (M+H).

Example 64

Preparation of N-(3-(benzylcarbamoyl)benzyl)-3-(3-(4-chloro-3,5-dimethylphenoxy)propyl)-7-(3,5-dimethyl-1H-pyrazol-4-yl)-1H-indole-2-carboxamide

I-64

To a stirred solution of EDC (0.055 mmol), HOBT (0.003 mmol), 3-((3-(3-(4-chloro-3,5-dimethylphenoxy)propyl)-7-(3,5-dimethyl-1H-pyrazol-4-yl)-1H-indole-2-carboxamido)methyl)benzoic acid (0.062 mmol), and TEA (0.109 mmol) in DCM (0.1M) was added benzylamine (0.055 mmol). The reaction mixture was stirred for 15 h then concentrated in vacuo. The residue was dissolved in 1 mL of 1:1 mix of acetonitrile and methanol and filtered. The filtrate was purified by reverse phase preparatory HPLC (Phenomenex Gemini C18, $H_2O/CH_3CN$ gradient to 5-95% $CH_3CN$ 0.1% TFA) to yield the title compound as a white solid. MS (ES) 674.1 (M+H).

Example 65

Preparation of ethyl 5-((3-(3-(4-chloro-3,5-dimethylphenoxy)propyl)-1-methyl-7-(1,3,5-trimethyl-1H-pyrazol-4-yl)-1H-indole-2-carboxamido)methyl)furan-2-carboxylate

I-65

Title compound was prepared according to the procedure used in Example 56 by substituting 3-(3-(4-chloro-3,5-dimethylphenoxy)propyl)-1-methyl-7-(1,3,5-trimethyl-1H-pyrazol-4-yl)-1H-indole-2-carboxylic acid for 3-(3-(4-chloro-3,5-dimethylphenoxy)propyl)-1H-indole-2-carboxylic acid. MS (ES) 631.3 (M+H).

Example 66

Preparation of 5-((3-(3-(4-chloro-3,5-dimethylphenoxy)propyl)-1-methyl-7-(1,3,5-trimethyl-1H-pyrazol-4-yl)-1H-indole-2-carboxamido)methyl)furan-2-carboxylic acid

I-66

Title compound was prepared according to the procedure used in Example 57 by substituting ethyl 5-((3-(3-(4-chloro-3,5-dimethylphenoxy)propyl)-1-methyl-7-(1,3,5-trimethyl-1H-pyrazol-4-yl)-1H-indole-2-carboxamido)methyl)furan-2-carboxylate for ethyl 5-((3-(3-(4-chloro-3,5-dimethylphenoxy)propyl)-1H-indole-2-carboxamido)methyl)furan-2-carboxylate. MS (ES) 603.1 (M+H).

Example 67

Preparation of 3-(3-(4-chloro-3,5-dimethylphenoxy)propyl)-N-(1-(3-phenoxybenzoyl)piperidin-4-yl)-1H-indole-2-carboxamide

I-67

Step A. Preparation of tert-butyl (1-(3-phenoxybenzoyl)piperidin-4-yl)carbamate

To a stirred solution of EDC (0.292 mmol), HOBT (0.0474 mmol), 3-phenoxybenzoic acid (0.233 mmol) in DCM (0.1M) and TEA (0.934 mmol) was added tert-butyl piperidin-4-ylcarbamate (0.257 mmol). The reaction mixture was stirred for 15 h then concentrated in vacuo. The residue was purified by flash column chromatography (Combi-Flash Rf, Hex/EtOAc 0-70% gradient) yield the title compound as a white solid.

Step B. Preparation of (4-aminopiperidin-1-yl)(3-phenoxyphenyl)methanone 2,2,2-trifluoroacetate To a stirred solution of tert-butyl (1-(3-phenoxybenzoyl)piperidin-4-yl)carbamate (0.214 mmol) in DCM (0.2 M) was added TFA (0.2 mL). The reaction was allowed to stir for two hours then concentrated to give the title compound. It was directly used for subsequent step without further purification.

Step C. Example 67

Title compound was prepared according to the procedure used in Example 40 using (4-aminopiperidin-1-yl)(3-phenoxyphenyl)methanone 2,2,2-trifluoroacetate. MS (ES) 636.3 (M+H).

Example 68

Preparation of 3-(3-(4-chloro-3,5-dimethylphenoxy)propyl)-7-(2-methylpyridin-3-yl)-N-(3-(((4-nitrophenyl)sulfonyl)carbamoyl)phenyl)-1H-indole-2-carboxamide

I-68

A solution of 3-(3-(3-(4-chloro-3,5-dimethylphenoxy)propyl)-7-(2-methylpyridin-3-yl)-1H-indole-2-carboxamido)benzoic acid (12.6 mg, 0.022 mmol), 4-nitrobenzenesulfonamide (5.38 mg, 0.027 mmol), EDC (4.68 mg, 0.024 mmol) and DMAP (5.42 mg, 0.044 mmol) in DCM (444 µl) was stirred 5 h at rt. The reaction mixture was concentrated in vacuo, and the residue was purified by reverse phase preparatory HPLC (Phenomenex Gemini C18, $H_2O/CH_3CN$ gradient to 40-85% $CH_3CN$ 0.1% TFA) to give the title compound (8.1 mg) as a yellow solid. MS (ES) 751.90 (M+H). MS (ES) 751.90 (M+H).

Example 69

Preparation of 3-(3-(4-chloro-3,5-dimethylphenoxy)propyl)-7-(2-methylpyridin-3-yl)-N-(4-(((4-nitrophenyl)sulfonyl)carbamoyl)phenyl)-1H-indole-2-carboxamide

I-69

The title compound was prepared (11.6 mg, 0.015 mmol) according to procedures described in Example 70 using 4-(3-(3-(4-chloro-3,5-dimethylphenoxy)propyl)-7-(2-methylpyridin-3-yl)-1H-indole-2-carboxamido)benzoic acid (22 mg, 0.039 mmol), 4-nitrobenzenesulfonamide (9.40 mg, 0.046 mmol), EDC (8.17 mg, 0.043 mmol) and DMAP (9.46 mg, 0.077 mmol) in DCM (775 µl). MS (ES) 751.90 (M+H).

Example 70

Preparation of 3-((3-(3-(4-chloro-3,5-dimethylphenoxy)propyl)-7-(1-(N-(3-(dimethylamino)propyl)-N'-ethylcarbamimidoyl)-3,5-dimethyl-1H-pyrazol-4-yl)-1H-indole-2-carboxamido)methyl)benzoic acid

I-70

To a solution of 3-(3-(4-chloro-3,5-dimethylphenoxy)propyl)-7-(3,5-dimethyl-1H-pyrazol-4-yl)-1H-indole-2-carboxylic acid (50 mg, 0.111 mmol) in $CH_2Cl_2$ (2.2 mL) at rt was added methyl 3-(aminomethyl)benzoate hydrochloride (0.027 g, 0.133 mmol), EDC (32 mg, 0.166 mmol) and DMAP (20 mg, 0.166 mmol). The reaction was stirred for 1.5 h at rt then aqueous HCl (1 M) was added to the mixture. The mixture was extracted with $CH_2Cl_2$ and concentrated in vacuo. The crude ester was dissolved in a mixture of THF (1.0 mL)/EtOH (0.5 mL), and 2M LiOH (1.0 mL) and stirred for 15 h at rt. The reaction mixture was concentrated and the residue was purified by reverse phase preparatory HPLC (Phenomenex Gemini C18, $H_2O/CH_3CN$ gradient to 30-65% $CH_3CN$ 0.1% TFA) to give Example 25a and the title compound (5.1 mg) as a side product. MS (ES) 740.1 (M+H).

Example 71

Preparation of 4-((3-(3-(4-chloro-3,5-dimethylphenoxy)propyl)-7-(1,3,5-trimethyl-1H-pyrazol-4-yl)-1H-indole-2-carboxamido)methyl)-1H-pyrrole-2-carboxylic acid

I-71

A mixture of 3-(3-(4-chloro-3,5-dimethylphenoxy)propyl)-7-(1,3,5-trimethyl-1H-pyrazol-4-yl)-1H-indole-2-carboxylic acid (55 mg, 0.118 mmol), methyl 4-(aminomethyl)-1H-pyrrole-2-carboxylate hydrochloride (25 mg, 0.130 mmol), EDC (24 mg, 0.124 mmol) and DMAP (16 mg, 0.130 mmol) in THF (1.2 mL) was stirred at rt for 15 h then aqueous HCl (1 M) was added to the mixture. The mixture was extracted with $CH_2Cl_2$ and concentrated in vacuo. The residue was dissolved in a mixture of THF (0.4 mL), EtOH (0.2 mL), and 2M LiOH (0.33 mL) and stirred for 45 h at rt. The mixture was acidified with 1M HCl, extracted with EtOAc, dried (MgSO4), filtered and concentrated in vacuo. The residue was purified by reverse phase preparatory HPLC (Phenomenex Gemini C18, $H_2O/CH_3CN$ gradient to 30-90% $CH_3CN$ 0.1% TFA) to give the title compound (40 mg) as an off-white solid. MS (ES) 588.1 (M+H).

Example 72

Preparation of 3-((6-chloro-3-(3-(4-chloro-3,5-dimethylphenoxy)propyl)-7-(1,3,5-trimethyl-1H-pyrazol-4-yl)-1H-indole-2-carboxamido)methyl)benzoic acid

I-72

Step A. Preparation of methyl 3-((6-chloro-3-(3-(4-chloro-3,5-dimethylphenoxy)propyl)-7-(1,3,5-trimethyl-1H-pyrazol-4-yl)-1H-indole-2-carboxamido)methyl)benzoate A mixture of 6-chloro-3-(3-(4-chloro-3,5-dimethylphenoxy)propyl)-7-(1,3,5-trimethyl-1H-pyrazol-4-yl)-1H-indole-2-carboxylic acid (100 mg, 0.20 mmol), methyl 3-(aminomethyl)benzoate hydrochloride (42 mg, 0.21 mmol), EDC (57 mg, 0.30 mmol) and DMAP (37 mg, 0.30 mmol) in THF (2.0 mL) was stirred at rt for 15 h then concentrated in vacuo. The residue was purified by reverse phase preparatory HPLC (Phenomenex Gemini C18, $H_2O/CH_3CN$ gradient to 50-95% $CH_3CN$ 0.1% TFA) to give the title compound (55 mg) as a white solid. MS (ES) 647.1 (M+H).

Step B. Example 72

A mixture of methyl 3-((6-chloro-3-(3-(4-chloro-3,5-dimethylphenoxy)propyl)-7-(1,3,5-trimethyl-1H-pyrazol-4-yl)-1H-indole-2-carboxamido)methyl)benzoate (40 mg, 0.062 mmol) and 2 M LiOH aqueous solution (0.31 mL, 0.62 mmol) in THF (0.41 mL) and Ethanol (0.21 mL) was stirred for 40 h at rt. The reaction mixture was acidified with 1M HCl, extracted with EtOAc, dried over MgSO$_4$, filtered and concentrated in vacuo. The residue was purified by reverse phase preparatory HPLC (Phenomenex Gemini C18, $H_2O/CH_3CN$ gradient to 30-95% $CH_3CN$ 0.1% TFA) to give the title compound (31 mg) as a white solid. MS (ES) 633.2 (M+H).

Example 73

Preparation of 5-((3-(3-(4-chloro-3,5-dimethylphenoxy)propyl)-7-(1,3,5-trimethyl-1H-pyrazol-4-yl)-1H-indole-2-carboxamido)methyl)-2-(piperidin-1-yl)benzoic acid

I-73

Step A. Preparation of methyl 5-((3-(3-(4-chloro-3,5-dimethylphenoxy)propyl)-7-(1,3,5-trimethyl-1H-pyrazol-4-yl)-1H-indole-2-carboxamido)methyl)-2-(piperidin-1-yl)benzoate The title compound (60 mg) was prepared according to procedures described in Example 72 A using 3-(3-(4-chloro-3,5-dimethylphenoxy)propyl)-7-(1,3,5-trimethyl-1H-pyrazol-4-yl)-1H-indole-2-carboxylic acid (82 mg, 0.176 mmol) and methyl 5-(aminomethyl)-2-(piperidin-1-yl)benzoate 2,2,2-trifluoroacetate (96 mg, 0.264 mmol). MS (ES) 696.3 (M+H).

Step B. Example 73

The title compound (8.1 mg) was prepared according to procedures described in Example 72 B using methyl 5-((3-

(3-(4-chloro-3,5-dimethylphenoxy)propyl)-7-(1,3,5-trimethyl-1H-pyrazol-4-yl)-1H-indole-2-carboxamido)methyl)-2-(piperidin-1-yl)benzoate (13 mg, 0.019 mmol). MS (ES) 682.2 (M+H).

Example 74

Preparation of 4-((3-(3-(4-chloro-3,5-dimethylphenoxy)propyl)-7-(1,3,5-trimethyl-1H-pyrazol-4-yl)-1H-indole-2-carboxamido)methyl)-1-methyl-1H-pyrrole-2-carboxylic acid

I-74

Step A. Preparation of methyl 4-((3-(3-(4-chloro-3,5-dimethylphenoxy)propyl)-7-(1,3,5-trimethyl-1H-pyrazol-4-yl)-1H-indole-2-carboxamido)methyl)-1-methyl-1H-pyrrole-2-carboxylate The title compound (22 mg) was prepared according to procedures described in Example 72 A using 3-(3-(4-chloro-3,5-dimethylphenoxy)propyl)-7-(1,3,5-trimethyl-1H-pyrazol-4-yl)-1H-indole-2-carboxylic acid (20 mg, 0.044 mmol) and methyl 4-(aminomethyl)-1-methyl-1H-pyrrole-2-carboxylate hydrochloride (9 mg, 0.044 mmol).

Step B. Example 74

The title compound (4.5 mg) was prepared according to procedures described in Example 72 B using methyl 4-((3-(3-(4-chloro-3,5-dimethylphenoxy)propyl)-7-(1,3,5-trimethyl-1H-pyrazol-4-yl)-1H-indole-2-carboxamido)methyl)-1-methyl-1H-pyrrole-2-carboxylate (6 mg, 9.74 μmol). MS (ES) 602.2 (M+H).

Example 75

Preparation of 1-benzyl-4-((3-(3-(4-chloro-3,5-dimethylphenoxy)propyl)-7-(1,3,5-trimethyl-1H-pyrazol-4-yl)-1H-indole-2-carboxamido)methyl)-1H-pyrrole-2-carboxylic acid

I-75

Step A. Preparation of methyl 1-benzyl-4-((3-(3-(4-chloro-3,5-dimethylphenoxy)propyl)-7-(1,3,5-trimethyl-1H-pyrazol-4-yl)-1H-indole-2-carboxamido)methyl)-1H-pyrrole-2-carboxylate The title compound (81 mg) was prepared according to procedures described in Example 72 A using 3-(3-(4-chloro-3,5-dimethylphenoxy)propyl)-7-(1,3,5-trimethyl-1H-pyrazol-4-yl)-1H-indole-2-carboxylic acid (61 mg, 0.132 mmol) and methyl 4-(aminomethyl)-1-benzyl-1H-pyrrole-2-carboxylate hydrochloride (37 mg, 0.132 mmol). MS (ES) 692.3 (M+H).

Step B. Example 75

The title compound (8.5 mg) was prepared according to procedures described in Example 72 B using methyl 1-benzyl-4-((3-(3-(4-chloro-3,5-dimethylphenoxy)propyl)-7-(1,3,5-trimethyl-1H-pyrazol-4-yl)-1H-indole-2-carboxamido)methyl)-1H-pyrrole-2-carboxylate (10 mg, 0.014 mmol). MS (ES) 678.2 (M+H).

Example 76

Preparation of 5-((3-(3-(4-chloro-3,5-dimethylphenoxy)propyl)-7-(1,3,5-trimethyl-1H-pyrazol-4-yl)-1H-indole-2-carboxamido)methyl)-2-(pyrrolidin-1-yl)benzoic acid

I-76

Step A. Preparation of methyl 5-((3-(3-(4-chloro-3,5-dimethylphenoxy)propyl)-7-(1,3,5-trimethyl-1H-pyrazol-4-yl)-1H-indole-2-carboxamido)methyl)-2-(pyrrolidin-1-yl)benzoate The title compound (56 mg) was prepared according to procedures described in Example 72 A using 3-(3-(4-chloro-3,5-dimethylphenoxy)propyl)-7-(1,3,5-trimethyl-1H-pyrazol-4-yl)-1H-indole-2-carboxylic acid (61 mg, 0.132 mmol) and methyl 5-(aminomethyl)-2-(pyrrolidin-1-yl)benzoate (31 mg, 0.132 mmol). MS (ES) 682.3 (M+H).

Step B. Example 76

The title compound (7.5 mg) was prepared according to procedures described in Example 72 B using methyl 5-((3-(3-(4-chloro-3,5-dimethylphenoxy)propyl)-7-(1,3,5-trimethyl-1H-pyrazol-4-yl)-1H-indole-2-carboxamido)methyl)-2-(pyrrolidin-1-yl)benzoate (10 mg, 0.015 mmol). MS (ES) 668.2 (M+H).

Example 77

Preparation of 1-benzyl-4-((1-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-1H-pyrrole-2-carboxylic acid

I-77

A mixture of methyl 1-benzyl-4-((3-(3-(4-chloro-3,5-dimethylphenoxy)propyl)-7-(1,3,5-trimethyl-1H-pyrazol-4-yl)-1H-indole-2-carboxamido)methyl)-1H-pyrrole-2-carboxylate (45 mg, 0.065 mmol), 1,3-dibromopropane (33 μL, 0.325 mmol) and $Cs_2CO_3$ (212 mg, 0.650 mmol) in DMF (0.650 mL) was stirred for 40 h at 100° C. The reaction was quenched with 10% $Na_2S_2O_3$. The mixture was extracted with EtOAc and concentrated in vacuo. The crude ester was dissolved in EtOH (2.6 mL), and KOH (365 mg, 0.65 mmol) was added. The reaction mixture was stirred for 15 h at 60° C. then concentrated in vacuo. The residue was purified by reverse phase preparatory HPLC (Phenomenex Gemini C18, $H_2O/CH_3CN$ gradient to 40-80% $CH_3CN$ 0.1% TFA) to give the title compound (20 mg) as a white solid. MS (ES) 718.3 (M+H).

Example 78

Preparation of 5-((11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-2-(pyrrolidin-1-yl)benzoic acid

I-78

The title compound was prepared (16 mg) according to procedures described in Example 77 using methyl 5-((3-(3-

(4-chloro-3,5-dimethylphenoxy)propyl)-7-(1,3,5-trimethyl-1H-pyrazol-4-yl)-1H-indole-2-carboxamido)methyl)-2-(pyrrolidin-1-yl)benzoate (40 mg, 0.059 mmol). MS (ES) 708.3 (M+H).

Example 79

Preparation of 4-((11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-1-methyl-1H-pyrrole-2-carboxylic acid

I-79

The title compound was prepared (5.6 mg) according to procedures described in Example 77 using methyl 4-((3-(3-(4-chloro-3,5-dimethylphenoxy)propyl)-7-(1,3,5-trimethyl-1H-pyrazol-4-yl)-1H-indole-2-carboxamido)methyl)-1-methyl-1H-pyrrole-2-carboxylate (10 mg, 0.016 mmol) and 1,3-dibromopropane (8.24 µl, 0.081 mmol). MS (ES) 642.3 (M+H).

Example 80

Preparation of 3-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid

I-80

The title compound was prepared (49 mg) according to procedures described in Example 77 using methyl 3-((6-chloro-3-(3-(4-chloro-3,5-dimethylphenoxy)propyl)-7-(1,3,5-trimethyl-1H-pyrazol-4-yl)-1H-indole-2-carboxamido)methyl)benzoate (68 mg, 0.105 mmol) and 1,3-dibromopropane (53 µl, 0.525 mmol). MS (ES) 673.2 (M+H).

Example 81

Preparation of 5-((11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-2-(piperidin-1-yl)benzoic acid

I-81

The title compound was prepared (15 mg) according to procedures described in Example 77 using methyl 5-((3-(3-(4-chloro-3,5-dimethylphenoxy)propyl)-7-(1,3,5-trimethyl-1H-pyrazol-4-yl)-1H-indole-2-carboxamido)methyl)-2-(piperidin-1-yl)benzoate (24 mg, 0.034 mmol) and 1,3-dibromopropane (17 µl, 0.17 mmol). MS (ES) 722.3 (M+H).

Example 82

Preparation of 4-((3-(3-(4-chloro-3,5-dimethylphenoxy)propyl)-7-(1,3,5-trimethyl-1H-pyrazol-4-yl)-1H-indole-2-carboxamido)methyl)benzoic acid

I-82

Step A. Preparation of methyl 4-((3-(3-(4-chloro-3,5-dimethylphenoxy)propyl)-7-(1,3,5-trimethyl-1H-pyrazol-4-yl)-1H-indole-2-carboxamido)methyl)benzoate The title compound (150 mg) was prepared according to procedures described in Example 72 A using 3-(3-(4-chloro-3,5-dimethylphenoxy)propyl)-7-(1,3,5-trimethyl-1H-pyrazol-4-yl)-1H-indole-2-carboxylic acid (116 mg, 0.25 mmol) and methyl 4-(aminomethyl)benzoate hydrochloride (50 mg, 0.25 mmol). MS (ES) 613.2 (M+H).

Step B. Example 82

The title compound (22 mg) was prepared according to procedures described in Example 72 B using methyl 4-((3-(3-(4-chloro-3,5-dimethylphenoxy)propyl)-7-(1,3,5-trimethyl-1H-pyrazol-4-yl)-1H-indole-2-carboxamido)methyl)benzoate (30 g, 0.049 mmol). MS (ES) 599.2 (M+H).

Example 83

Preparation of 4-((11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid

I-83

The title compound was prepared (75 mg) according to procedures described in Example 77 using methyl 4-((3-(3-(4-chloro-3,5-dimethylphenoxy)propyl)-7-(1,3,5-trimethyl-1H-pyrazol-4-yl)-1H-indole-2-carboxamido)methyl)benzoate (120 mg, 0.20 mmol) and 1,3-dibromopropane (99 µl, 0.98 mmol). MS (ES) 639.3 (M+H).

Example 84

Preparation of 3-((11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-5-(pyrrolidin-1-yl)benzoic acid

I-84

Step A. Preparation of methyl 3-((3-(3-(4-chloro-3,5-dimethylphenoxy)propyl)-7-(1,3,5-trimethyl-1H-pyrazol-4-yl)-1H-indole-2-carboxamido)methyl)-5-(pyrrolidin-1-yl)benzoate The title compound (50 mg) was prepared according to procedures described in Example 72 A using 3-(3-(4-chloro-3,5-dimethylphenoxy)propyl)-7-(1,3,5-trimethyl-1H-pyrazol-4-yl)-1H-indole-2-carboxylic acid (74 mg, 0.159 mmol) and methyl 3-(aminomethyl)-5-(pyrrolidin-1-yl)benzoate hydrochloride (56 mg, 0.207 mmol).

Step B. Example 84

The title compound was prepared (8 mg) according to procedures described in Example 77 using methyl 3-((3-(3-(4-chloro-3,5-dimethylphenoxy)propyl)-7-(1,3,5-trimethyl-1H-pyrazol-4-yl)-1H-indole-2-carboxamido)methyl)-5-(pyrrolidin-1-yl)benzoate (15 mg, 0.022 mmol) and (11 µl, 0.11 mmol). MS (ES) 708.3 (M+H).

Example 85

Preparation of 2-(3-(1H-tetrazol-5-yl)benzyl)-10-(3-(4-chloro-3,5-dimethylphenoxy)propyl)-6-(1,3,5-trimethyl-1H-pyrazol-4-yl)-3,4-dihydropyrazino[1,2-a]indol-1(2H)-one

I-85

Step A. Preparation of ethyl 1-(2-((tert-butoxycarbonyl)amino)ethyl)-3-(3-(4-chloro-3,5-dimethylphenoxy)propyl)-7-(1,3,5-trimethyl-1H-pyrazol-4-yl)-1H-indole-2-carboxylate To a solution of ethyl 3-(3-(4-chloro-3,5-dimethylphenoxy)propyl)-7-(1,3,5-trimethyl-1H-pyrazol-4-yl)-1H-indole-2-carboxylate (60 mg, 0.121 mmol) and tert-butyl 1,2,3-oxathiazolidine-3-carboxylate 2,2-dioxide (33 mg, 0.146 mmol) in DMF (0.4 mL) was added NaH (4.37 mg, 0.182 mmol) at rt. The reaction mixture was stirred for 15 h at rt, quenched by addition of $H_2O$ extracted with EtOAc. The combined organic layer was washed with $H_2O$ followed by brine, dried over $MgSO_4$, filtered and concentrated in vacuo. The crude product was directly used for the next step without further purification. MS (ES) 637.2 (M+H).

Step B. Preparation of 10-(3-(4-chloro-3,5-dimethylphenoxy)propyl)-6-(1,3,5-trimethyl-1H-pyrazol-4-yl)-3,4-dihydropyrazino[1,2-a]indol-1(2H)-one A mixture of ethyl 1-(2-((tert-butoxycarbonyl)amino)ethyl)-3-(3-(4-chloro-3,5-dimethylphenoxy)propyl)-7-(1,3,5-trimethyl-1H-pyrazol-4-yl)-1H-indole-2-carboxylate (64 mg, 0.101 mmol) and TFA (0.2 ml, 2.53 mmol) in $CH_2Cl_2$ (0.45 mL) was stirred at rt for 30 min then concentrated in vacuo. The residue was dissolved in MeOH (0.4 mL), and $K_2CO_3$ (49 mg, 0.35 mmol) was added at rt. The reaction mixture was stirred at 50° C. for 90 h. The reaction mixture was filtered through a hydrophobic frit and concentrated. The residue was purified by reverse phase preparatory HPLC (Phenomenex Gemini C18, $H_2O/CH_3CN$ gradient to 40-80% $CH_3CN$ 0.1% TFA) to give the title compound (35 mg) as a white solid. MS (ES) 491.1 (M+H).

Step C. Preparation of 3-((10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)methyl)benzonitrile A mixture of 10-(3-(4-chloro-3,5-dimethylphenoxy)propyl)-6-(1,3,5-trimethyl-1H-pyrazol-4-yl)-3,4-dihydropyrazino[1,2-a]indol-1 (2H)-one (21 mg, 0.043 mmol) and NaH (2.1 mg, 0.086 mmol) in DMF (0.43 ml) was stirred at 0° C. After 30 min, 3-(bromomethyl)benzonitrile (17 mg, 0.086 mmol) was added to the mixture. The mixture was then warmed to rt and stirred for additional 1 h. The mixture was quenched with sat. $NH_4Cl$ aqueous solution, extracted with $Et_2O$, dried over $Na_2SO_4$, filtered and concentrated in vacuo to give the tile compound, which was used directly without further purification. MS (ES) 606.1 (M+H).

Step D. Example 85

A mixture of 3-((10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)methyl)benzonitrile (26 mg, 0.043 mmol), sodium azide (17 mg, 0.26 mmol) and $NH_4Cl$ (14 mg, 0.26 mmol) in DMF (0.15 mL) was stirred at 120° C. for 15 h.

The cooled reaction mixture was filtered and purified by reverse phase preparatory HPLC (Phenomenex Gemini C18, $H_2O/CH_3CN$ gradient to 40-80% $CH_3CN$ 0.1% TFA) to give the title compound (15 mg) as a white solid. MS (ES) 649.3 (M+H).

Example 86

Preparation of 3-((11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-5-nitrobenzoic acid

I-86

Step A. Preparation of methyl 3-((3-(3-(4-chloro-3,5-dimethylphenoxy)propyl)-7-(1,3,5-trimethyl-1H-pyrazol-4-yl)-1H-indole-2-carboxamido)methyl)-5-nitrobenzoate The title compound (119 mg) was prepared according to procedures described in Example 72 A using 3-(3-(4-chloro-3,5-dimethylphenoxy)propyl)-7-(1,3,5-trimethyl-1H-pyrazol-4-yl)-1H-indole-2-carboxylic acid (100 mg, 0.22 mmol) and methyl 3-(aminomethyl)-5-nitrobenzoate 2,2,2-trifluoroacetate (104 mg, 0.322 mmol). MS (ES) 658.2 (M+H).

Step B. Example 86

The title compound was prepared (18 mg) according to procedures described in Example 77 using methyl 3-((3-(3-(4-chloro-3,5-dimethylphenoxy)propyl)-7-(1,3,5-trimethyl-1H-pyrazol-4-yl)-1H-indole-2-carboxamido)methyl)-5-nitrobenzoate (59 mg, 0.090 mmol) and 1,3-dibromopropane (45 μl, 0.045 mmol). MS (ES) 684.2 (M+H).

Example 87

Preparation of 4-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid

I-87

Step A. Preparation of methyl 4-((6-chloro-3-(3-(4-chloro-3,5-dimethylphenoxy)propyl)-7-(1,3,5-trimethyl-1H-pyrazol-4-yl)-1H-indole-2-carboxamido)methyl)benzoate The title compound was prepared according to procedures described in Example 72 A using 6-chloro-3-(3-(4-chloro-3,5-dimethylphenoxy)propyl)-7-(1,3,5-trimethyl-1H-pyrazol-4-yl)-1H-indole-2-carboxylic acid (75 mg, 0.15 mmol) and methyl 4-(aminomethyl)benzoate hydrochloride (32 mg, 0.16 mmol). MS (ES) 647.2 (M+H).

Step B. Example 87

The title compound was prepared (55 mg) according to procedures described in Example 77 using methyl 4-((6-chloro-3-(3-(4-chloro-3,5-dimethylphenoxy)propyl)-7-(1,3, 5-trimethyl-1H-pyrazol-4-yl)-1H-indole-2-carboxamido)

methyl)benzoate (0.15 mmol) and 1,3-dibromopropane (76 µL, 0.75 mmol). MS (ES) 673.2 (M+H).

Example 88

Preparation of 2-(4-(1H-tetrazol-5-yl)benzyl)-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one

I-88

Step A. Preparation of 3-(3-(4-chloro-3,5-dimethylphenoxy)propyl)-N-(4-cyanobenzyl)-7-(1,3,5-trimethyl-1H-pyrazol-4-yl)-1H-indole-2-carboxamide The title compound was prepared according to procedures described in Example 72 A using 3-(3-(4-chloro-3,5-dimethylphenoxy)propyl)-7-(1,3,5-trimethyl-1H-pyrazol-4-yl)-1H-indole-2-carboxylic acid (75 mg, 0.161 mmol) and 4-(aminomethyl)benzonitrile hydrochloride (28 mg, 0.169 mmol). MS (ES) 580.2 (M+H).

Step B. Preparation of 4-((11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzonitrile The title compound was prepared according to procedures described in Example 77 using 3-(3-(4-chloro-3,5-dimethylphenoxy)propyl)-N-(4-cyanobenzyl)-7-(1,3,5-trimethyl-1H-pyrazol-4-yl)-1H-indole-2-carboxamide (0.093 g, 0.161 mmol) and 1,3-dibromopropane (82 µL, 0.81 mmol). MS (ES) 620.2 (M+H).

Step B. Example 88

The title compound was prepared (45 mg) according to procedures described in Example 85 Step D using of 4-((11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzonitrile (100 mg, 0.16 mmol), sodium azide (63 mg, 0.97 mmol) and ammonium chloride (52 mg, 0.97 mmol). MS (ES) 663.3 (M+H).

Example 89

Preparation of 2-(2-((3-(3-(4-chloro-3,5-dimethylphenoxy)propyl)-7-(1,3,5-trimethyl-1H-pyrazol-4-yl)-1H-indole-2-carboxamido)methyl)-1H-pyrrol-1-yl)acetic acid

I-89

Step A. Preparation of methyl 2-(2-((3-(3-(4-chloro-3,5-dimethylphenoxy)propyl)-7-(1,3,5-trimethyl-1H-pyrazol-4-yl)-1H-indole-2-carboxamido)methyl)-1H-pyrrol-1-yl)acetate The title compound (74 mg) was prepared according to procedures described in Example 72 A using 3-(3-(4-chloro-3,5-dimethylphenoxy)propyl)-7-(1,3,5-trimethyl-1H-pyrazol-4-yl)-1H-indole-2-carboxylic acid (58 mg, 0.13 mmol) and methyl 2-(2-(aminomethyl)-1H-pyrrol-1-yl)acetate (0.034 g, 0.20 mmol). MS (ES) 616.3 (M+H).

Step B. Example 89

The title compound (65 mg) was prepared according to procedures described in Example 72 B using methyl 2-(2-((3-(3-(4-chloro-3,5-dimethylphenoxy)propyl)-7-(1,3,5-trimethyl-1H-pyrazol-4-yl)-1H-indole-2-carboxamido)methyl)-1H-pyrrol-1-yl)acetate (74 mg, 0.12 mmol). MS (ES) 602.2 (M+H).

Example 90

Preparation of 4-(6-chloro-3-(3-(4-chloro-3,5-dimethylphenoxy)propyl)-7-(1,3,5-trimethyl-1H-pyrazol-4-yl)-1H-indole-2-carboxamido)-2-(4-methylpiperazin-1-yl)benzoic acid

I-90

Step A. Preparation of 6-chloro-3-(3-(4-chloro-3,5-dimethylphenoxy)propyl)-7-(1,3,5-trimethyl-1H-pyrazol-4-yl)-1H-indole-2-carbonyl Chloride To a solution of 6-chloro-3-(3-(4-chloro-3,5-dimethylphenoxy)propyl)-7-(1,3,5-trimethyl-1H-pyrazol-4-yl)-1H-indole-2-carboxylic acid (275 mg, 0.550 mmol) in $CH_2Cl_2$ (11 mL) was added oxalyl chloride (0.2 mL, 2.2 mmol) and DMF (2.1 µL, 0.028 mmol) rt. The reaction mixture was stirred at rt for 3 h then concentrated in vacuo to give the crude title compound, which was used in subsequent reactions without further purification.

Step B. Preparation of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-(4-methylpiperazin-1-yl)benzoate A mixture of 6-chloro-3-(3-(4-chloro-3,5-dimethylphenoxy)propyl)-7-(1,3,5-trimethyl-1H-pyrazol-4-yl)-1H-indole-2-carbonyl chloride (83 mg, 0.16 mmol), methyl 4-amino-2-(4-methylpiperazin-1-yl)benzoate (40 mg, 0.16 mmol) and DIPEA (84 µl, 0.481 mmol) in $CH_2Cl_2$ (3.2 mL) was stirred at rt for 4 h then concentrated in vacuo. The residue was purified by reverse phase preparatory HPLC (Phenomenex Gemini C18, $H_2O/CH_3CN$ gradient to 30-95% $CH_3CN$ 0.1% TFA) to give the title compound (55 mg) as a white solid. MS (ES) 731.3 (M+H).

Step C. Example 90

A mixture of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-(4-methylpiperazin-1-yl)benzoate (55 mg, 0.075 mmol) and 2M LiOH (400 µL, 0.80 mmol) in THF (2.0 mL) was stirred at 50° C. for 3 h. The reaction mixture was acidified with 1M HCl, extracted with EtOAc, dried over $MgSO_4$, filtered and concentrated in vacuo. The residue was purified by reverse phase preparatory HPLC (Phenomenex Gemini C18, $H_2O/CH_3CN$ gradient to 15-95% $CH_3CN$ 0.1% $NH_4OH$) to give the title compound (35 mg) as a white solid. MS (ES) 717.3 (M+H).

Example 91

Preparation of 4-(6-chloro-3-(3-(4-chloro-3,5-dimethylphenoxy)propyl)-7-(1,3,5-trimethyl-1H-pyrazol-4-yl)-1H-indol-2-carboxamido)-2-morpholinobenzoic acid

I-91

Step A. Preparation of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-morpholinobenzoate The title compound (24 mg) was prepared according to procedures described in Example 90 B using 6-chloro-3-(3-(4-chloro-3,5-dimethylphenoxy)propyl)-7-(1,3,5-trimethyl-1H-pyrazol-4-yl)-1H-indole-2-carbonyl chloride (35 mg, 0.068 mmol) and methyl 4-amino-2-morpholinobenzoate (16 mg, 0.068 mmol). MS (ES) 718.2 (M+H).

Step B. Example 91

The title compound (18 mg) was prepared according to procedures described in Example 90 C using methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-morpholinobenzoate (24 mg, 0.033 mmol). MS (ES) 704.2 (M+H).

Example 92

Preparation of 4-(6-chloro-3-(3-(4-chloro-3,5-dimethylphenoxy)propyl)-7-(1,3,5-trimethyl-1H-pyrazol-4-yl)-1H-indol-2-carboxamido)-2-((2-(dimethylamino)ethyl)(methyl)amino)benzoic acid

I-92

Step A. Preparation of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-((2-(dimethylamino)ethyl)(methyl)amino)benzoate The title compound (50 mg) was prepared according to procedures described in Example 90 B using 6-chloro-3-(3-(4-chloro-3,5-dimethylphenoxy)propyl)-7-(1,3,5-trimethyl-1H-pyrazol-4-yl)-1H-indole-2-carbonyl chloride (51 mg, 0.099 mmol) and methyl 4-amino-2-((2-(dimethylamino)ethyl)(methyl)amino)benzoate (25 mg, 0.099 mmol). MS (ES) 733.3 (M+H).

Step B. Example 92

The title compound (41 mg) was prepared according to procedures described in Example 90 C using methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-((2-(dimethylamino)ethyl)(methyl)amino)benzoate (45 mg, 0.061 mmol). MS (ES) 719.3 (M+H).

Example 93

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-2-(trifluoromethyl)benzoic acid

I-93

Step A. Preparation of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-(trifluoromethyl)benzoate The title compound (49 mg) was prepared according to procedures described in Example 90 B using 6-chloro-3-(3-(4-chloro-3,5-dimethylphenoxy)propyl)-7-(1,3,5-trimethyl-1H-pyrazol-4-yl)-1H-indole-2-carbonyl chloride (52 mg, 0.10 mmol) and methyl 4-amino-2-(trifluoromethyl)benzoate (22 mg, 0.10 mmol). MS (ES) 700.2 (M+H).

Step B. Example 93

A mixture of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-(trifluoromethyl)benzoate (20 mg, 0.029 mmol), 1,3-dibromopropane (7.2 µL, 0.071 mmol) and $Cs_2CO_3$ (46 mg, 0.14 mmol) in DMF (0.57 mL) was stirred for 15 h at 80° C. The reaction was quenched with 10% $Na_2S_2O_3$. The mixture was extracted with EtOAc and concentrated in vacuo. The crude ester was dissolved in THF (0.30 mL), and 2M LiOH aqueous solution (73 µL, 0.15 mmol) was added. The reaction mixture was stirred for 3 h at 50° C. then concentrated in vacuo. The residue was purified by reverse phase preparatory HPLC (Phenomenex Gemini C18, $H_2O$/$CH_3CN$ gradient to 45-95% $CH_3CN$ 0.1% TFA) to give the title compound (8 mg) as a white solid. MS (ES) 727.2 (M+H).

Example 94

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-2-fluorobenzoic acid

I-94

Step A. Preparation of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-fluorobenzoate The title compound (45 mg) was prepared according to procedures described in Example 90 B using 6-chloro-3-(3-(4-chloro-3,5-dimethylphenoxy)propyl)-7-(1,3,5-trimethyl-1H-pyrazol-4-yl)-1H-indole-2-carbonyl chloride (52 mg, 0.10 mmol) and methyl 4-amino-2-fluorobenzoate (17 mg, 0.10 mmol). MS (ES) 651.2 (M+H).

Step B. Example 94

The title compound (14 mg) was prepared according to procedures described in Example 93 B using methyl 4-(6- chloro-3-(3-(4-chloro-3,5-dimethylphenoxy)propyl)-7-(1,3,5-trimethyl-1H-pyrazol-4-yl)-1H-indole-2-carboxamido)-2-fluorobenzoate (25 mg, 0.038 mmol) and 1,3-dibromopropane (9.7 μL, 0.096 mmol). MS (ES) 677.2 (M+H).

Example 95

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-3-fluorobenzoic acid

I-95

Step A. Preparation of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-3-fluorobenzoate The title compound (35 mg) was prepared according to procedures described in Example 90 B using 6-chloro-3-(3-(4-chloro-3,5-dimethylphenoxy)propyl)-7-(1,3,5-trimethyl-1H-pyrazol-4-yl)-1H-indole-2-carbonyl chloride (52 mg, 0.10 mmol) and methyl 4-amino-3-fluorobenzoate (17 mg, 0.10 mmol). MS (ES) 651.2 (M+H).

Step B. Example 95

The title compound (17 mg) was prepared according to procedures described in Example 93 B using methyl 4-(6-chloro-3-(3-(4-chloro-3,5-dimethylphenoxy)propyl)-7-(1,3,5-trimethyl-1H-pyrazol-4-yl)-1H-indole-2-carboxamido)-3-fluorobenzoate (25 mg, 0.038 mmol) and 1,3-dibromopropane (9.7 μL, 0.096 mmol). MS (ES) 677.2 (M+H).

Example 96

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-2-methylbenzoic acid

I-96

Step A. Preparation of methyl 3-(6-chloro-3-(3-(4-chloro-3,5-dimethylphenoxy)propyl)-7-(1,3,5-trimethyl-1H-pyrazol-4-yl)-1H-indole-2-carboxamido)-2-methylbenzoate The title compound (60 mg) was prepared according to procedures described in Example 90 B using 6-chloro-3-(3-(4-chloro-3,5-dimethylphenoxy)propyl)-7-(1,3,5-trimethyl-1H-pyrazol-4-yl)-1H-indole-2-carbonyl chloride (52 mg, 0.10 mmol) and methyl 3-amino-4-methylbenzoate (18 mg, 0.11 mmol). MS (ES) 647.2 (M+H).

Step B. Example 96

The title compound (31 mg) was prepared according to procedures described in Example 93 B using methyl 3-(6-chloro-3-(3-(4-chloro-3,5-dimethylphenoxy)propyl)-7-(1,3,5-trimethyl-1H-pyrazol-4-yl)-1H-indole-2-carboxamido)-2-methylbenzoate (60 mg, 0.092 mmol) and 1,3-dibromopropane (25.4 μL, 0.250 mmol). MS (ES) 673.2 (M+H).

Example 97

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-3-methylbenzoic acid

I-97

Step A. Preparation of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-3-methylbenzoate The title compound (55 mg) was prepared according to procedures described in Example 90 B using 6-chloro-3-(3-(4-chloro-3,5-dimethylphenoxy)propyl)-7-(1,3,5-trimethyl-1H-pyrazol-4-yl)-1H-indole-2-carbonyl chloride (52 mg, 0.10 mmol) and methyl 4-amino-3-methylbenzoate (18 mg, 0.11 mmol). MS (ES) 647.2 (M+H).

Step B. Example 97

The title compound (27 mg) was prepared according to procedures described in Example 93 B using methyl 3-(6-chloro-3-(3-(4-chloro-3,5-dimethylphenoxy)propyl)-7-(1,3,5-trimethyl-1H-pyrazol-4-yl)-1H-indole-2-carboxamido)-2-methylbenzoate (55 mg, 0.092 mmol) and 1,3-dibromopropane (25 μL, 0.25 mmol). MS (ES) 673.2 (M+H).

Example 98

Preparation of 5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-2-methylbenzoic acid

I-98

Step A. Preparation of methyl 5-(6-chloro-3-(3-(4-chloro-3,5-dimethylphenoxy)propyl)-7-(1,3,5-trimethyl-1H-pyrazol-4-yl)-1H-indole-2-carboxamido)-2-methylbenzoate The title compound was prepared according to procedures described in Example 90 B using 6-chloro-3-(3-(4-chloro-3,5-dimethylphenoxy)propyl)-7-(1,3,5-trimethyl-1H-pyrazol-4-yl)-1H-indole-2-carbonyl chloride (50 mg, 0.10 mmol) and methyl 5-amino-2-methylbenzoate (18 mg, 0.11 mmol). MS (ES) 647.2 (M+H).

Step B. Example 98

The title compound (33 mg) was prepared according to procedures described in Example 93 B using methyl 5-(6-chloro-3-(3-(4-chloro-3,5-dimethylphenoxy)propyl)-7-(1,3,5-trimethyl-1H-pyrazol-4-yl)-1H-indole-2-carboxamido)-2-methylbenzoate (64 mg, 0.10 mmol) and 1,3-dibromopropane (25 μL, 0.25 mmol). MS (ES) 673.2 (M+H).

Example 99

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-2-methylbenzoic acid

I-99

Step A. Preparation of methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-methylbenzoate The title compound was prepared according to procedures described in Example 90 B using 6-chloro-3-(3-(4-chloro-3,5-dimethylphenoxy)propyl)-7-(1,3,5-trimethyl-1H-pyrazol-4-yl)-1H-indole-2-carbonyl chloride (52 mg, 0.10 mmol) and methyl 4-amino-2-methylbenzoate (18 mg, 0.11 mmol). MS (ES) 647.2 (M+H).

Step B. Example 99

The title compound (29 mg) was prepared according to procedures described in Example 93 B using methyl 4-(6-chloro-3-(3-(4-chloro-3,5-dimethylphenoxy)propyl)-7-(1,3,5-trimethyl-1H-pyrazol-4-yl)-1H-indole-2-carboxamido)-2-methylbenzoate (64 mg, 0.10 mmol) and 1,3-dibromopropane (25 µL, 0.25 mmol). MS (ES) 673.2 (M+H).

Example 100

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-4-methylbenzoic acid

I-100

Step A. Preparation of methyl 3-(6-chloro-3-(3-(4-chloro-3,5-dimethylphenoxy)propyl)-7-(1,3,5-trimethyl-1H-pyrazol-4-yl)-1H-indole-2-carboxamido)-4-methylbenzoate The title compound was prepared according to procedures described in Example 90 B using 6-chloro-3-(3-(4-chloro-3,5-dimethylphenoxy)propyl)-7-(1,3,5-trimethyl-1H-pyrazol-4-yl)-1H-indole-2-carbonyl chloride (52 mg, 0.10 mmol) and methyl 3-amino-4-methylbenzoate (18 mg, 0.11 mmol). MS (ES) 647.2 (M+H).

Step B. Example 100

The title compound (39 mg) was prepared according to procedures described in Example 93 B using methyl 3-(6-chloro-3-(3-(4-chloro-3,5-dimethylphenoxy)propyl)-7-(1,3,5-trimethyl-1H-pyrazol-4-yl)-1H-indole-2-carboxamido)-4-methylbenzoate (64 mg, 0.10 mmol) and 1,3-dibromopropane (25 µL, 0.25 mmol). MS (ES) 673.2 (M+H).

Example 101

Preparation of 8-chloro-11-(3-(4-chloro-3,5-dimethylphenoxy)propyl)-2-(3-(trifluoromethoxy)phenyl)-7-(1,3,5-trimethyl-1H-pyrazol-4-yl)-2,3,4,5-tetrahydro-1H-[1,4]diazepino[1,2-a]indol-1-one

I-101

Step A. Preparation of 6-chloro-3-(3-(4-chloro-3,5-dimethylphenoxy)propyl)-N-(3-(trifluoromethoxy)phenyl)-7-(1,3,5-trimethyl-1H-pyrazol-4-yl)-1H-indole-2-carboxamide The title compound was prepared according to procedures described in Example 72 A using 6-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.10 mmol) and 3-(trifluoromethoxy)aniline (16 µL, 0.12 mmol). MS (ES) 659.2 (M+H).

Step B. Example 101

The title compound (46 mg) was prepared according to procedures described in Example 93 B using 6-chloro-3-(3-(4-chloro-3,5-dimethylphenoxy)propyl)-N-(3-(trifluoromethoxy)phenyl)-7-(1,3,5-trimethyl-1H-pyrazol-4-yl)-1H-indole-2-carboxanide mmol) and 1,3-dibromopropane (25 µL, 0.25 mmol). MS (ES) 673.2 (M+H).

Example 102

Preparation of 6-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)nicotinic acid

I-102

Step A. Preparation of 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one The title compound was prepared according to procedures described in Example 85 A and B using ethyl 3-(3-(4-chloro-3,5-dimethylphenoxy)propyl)-7-(1,3,5-trimethyl-1H-pyrazol-4-yl)-1H-indole-2-carboxylate and substituting tert-butyl 1,2,3-oxathiazolidine-3-carboxylate 2,2-dioxide with tert-butyl 1,2,3-oxathiazinane-3-carboxylate 2,2-dioxide in 75% yield.

Step B. Preparation of methyl 6-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl) Nicotinate To a solution of 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (20 mg, 0.037 mmol) in DMF (1 mL) was added a mixture of NaH (1.8 mg, 0.045 mmol) and catalytic amount of TBAI, followed by addition of methyl 6-(bromomethyl)nicotinate (14 mg, 0.063 mmol) at 0° C. The reaction mixture was stirred for 2 h at room temperature and diluted with EtOAc (5 mL) then quenched with water (3 mL). The organic layer was washed with water (3×5 mL), dried over $MgSO_4$, and concentrated in vacuo to give the crude title product, which was used to next step without further purification.

Step C. Example 102

To a solution of methyl 6-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl) nicotinate (crude, 0.037 mmol) in mixture of MeOH and dioxane (1 mL/2 mL) was added sodium hydroxide (0.2 mL, 2M solution). The reaction mixture was stirred for 3 h at rt, acidified with 1 N HCl (2 mL), and then concentrated in vacuo. The residue was purified by column chromatography using DCM/MeOH (Combi-flash Rf, 0 to 30% MeOH gradient) to afford the title compound as a yellow solid (14 mg, 57%). $^1$H NMR (MeOD, 400 MHz) δ (ppm) 9.06 (s, 1H), 8.29 (dd, J=8.0, 1.6 Hz, 1H), 7.68 (d, J=8.8 Hz, 1H), 7.46 (d, J=8.0 Hz, 1H), 7.23 (d, J=8.0 Hz, 1H), 6.66 (s, 2H), 4.82 (d, J=3.6 Hz, 2H), 3.93 (t, J=6.0 Hz, 4H), 3.83 (s, 3H), 3.19 (t, J=7.2 Hz, 2H), 2.38-2.25 (m, 2H), 2.31 (s, 6H), 2.16 (q, J=6.4 Hz, 1H), 2.06 (s, 3H), 1.97 (s, 3H), 1.75-1.63 (m, 2H); LCMS (ES) tR: 0.776 min (>99%, ELSD), 674.2 [M+1]

Example 103

Preparation of 5-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)furan-2-carboxylic acid

I-103

The title compound was prepared according to procedures described in Example 102 B and C using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one and methyl 5-(chloromethyl)furan-2-carboxylate; $^1$H NMR (MeOD, 400 MHz) δ (ppm) 7.67 (d, J=8.8 Hz, 1H), 7.22 (d, J=8.4 Hz, 1H), 6.99 (d, J=3.2 Hz, 1H), 6.66 (s, 2H), 6.44 (d, J=3.6 Hz, 1H), 4.62 (s, 2H), 3.90 (t, J=6.0 Hz, 2H), 3.83 (s, 3H), 3.82-3.80 (m, 2H), 3.29 (t, J=6.4 Hz, 2H), 3.18 (t, J=7.2 Hz, 2H), 2.32 (s, 6H), 2.17-2.13 (m, 2H), 2.04 (s, 3H), 1.95 (s, 3H), 1.58-1.53 (m, 2H); LCMS (ES) tR: 0.796 min (>99%, ELSD), 663.2 [M+1]

Example 104

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)quinoline-8-carboxylic acid

I-104

Step A. Preparation of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)quinoline-8-carboxylate A flame dried flask was charged with Pd$_2$(dba)$_3$ (1 mg, 0.5 mol %), Xantphos (2 mg, 1 mol %), cesium carbonate (27 mg, 0.084 mmol), 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 4-bromoquinoline-8-carboxylate (18 mg, 0.067 mmol), and 1,4-dioxane (1 mL). The reaction mixture was degassed for 10 min under argon and stirred for 16 h at 110° C. then solvent was concentrated in vacuo. The residue was filtered through celite pad with MeOH then solvent was removed in vacuo to give the crude title compound which was used in the next reaction without further purification.

Step B. Example 104

To a solution of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)quinoline-8-carboxylate (crude, 0.056 mmol) in mixture of methanol and dioxane (1 mL/2 mL) was added sodium hydroxide (0.2 mL, 2M solution). The reaction mixture was stirred for 3 h at room temperature and then concentrated in vacuo. The residue was purified by reverse phase preparatory HPLC (Phenomenex Gemini C18, H$_2$O/CH$_3$CN gradient to 45-95% CH$_3$CN 0.1% TFA) to give the title compound (22 mg, 58%) as a yellow solid. $^1$H NMR (DMSO-d$^6$, 400 MHz) δ (ppm) 9.17 (d, J=4.8 Hz, 1H), 8.59 (d, J=7.6 Hz, 1H), 8.23 (d, J=8.4 Hz, 1H), 7.79 (dd, J=12.8, 8.0 Hz, 2H), 7.74 (d, J=8.8 Hz, 1H), 7.28 (d, J=8.4 Hz, 1H), 6.70 (s, 2H), 4.20 (t, J=6.0 Hz, 2H), 3.96 (t, J=6.0 Hz, 2H), 3.77 (s, 3H), 3.75-3.50 (m, 2H), 3.04 (t, J=7.2 Hz, 2H), 2.22 (s, 6H), 2.20-2.05 (m, 2H), 2.04 (s, 3H), 1.93 (s, 3H), 1.87-1.73 (m, 2H); LCMS (ES) tR: 1.392 min (>99%, ELSD), 711.2 [M+1].

Example 105

Preparation of 4-(11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)quinoline-8-carboxylic acid

I-105

The title compound was prepared according to procedures described in Example 104 Step A and B using 11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one and 4-bromoquinoline-8-carboxylate; $^1$H NMR (DMSO, 400 MHz) δ (ppm) 9.17 (d, J=5.2 Hz, 1H), 8.59 (d, J=6.8 Hz, 1H), 8.24 (d, J=8.4 Hz, 1H), 7.79 (dd, J=12.4, 7.6 Hz, 2H), 7.72 (d, J=8.0 Hz, 1H), 7.14 (t, J=7.6 Hz, 1H), 6.97 (d, J=7.6 Hz, 1H), 6.71 (s, 2H), 4.29 (t, J=6.0 Hz, 2H), 3.97 (t, J=6.4 Hz, 2H), 3.75 (s, 3H), 3.74-3.67 (m, 2H), 3.06 (t, J=7.2 Hz, 2H), 2.26 (s, 6H), 2.15-2.01 (m, 2H), 2.05 (s, 3H), 1.95 (s, 3H), 1.88-1.78 (m, 2H); LCMS (ES) tR: 1.318 min (>99%, ELSD), m/z: 677.1 [M+1].

Example 106

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-7-carboxylic acid

I-106

The title compound was prepared according to procedures described in Example 104 A and B using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2- a]indol-1-one and methyl 4-bromo-1-methyl-3a,7a-dihydro-1H-indole-7-carboxylate; $^1$H NMR (DMSO, 400 MHz) δ (ppm) 7.70 (d, J=8.4 Hz, 1H), 7.51 (d, J=8.0 Hz, 1H), 7.36 (d, J=3.2 Hz, 1H), 7.25 (d, J=8.4 Hz, 1H), 6.92 (d, J=8.0 Hz, 1H), 6.70 (s, 2H), 6.36 (d, J=3.2 Hz, 1H), 4.09 (t, J=6.4 Hz, 2H), 3.95 (t, J=6.4 Hz, 2H), 3.85 (s, 3H), 3.76 (s, 3H), 3.65 (t, J=6.0 Hz, 2H), 3.03 (t, J=6.8 Hz, 2H), 2.23 (s, 6H), 2.09-2.03 (m, 2H), 2.01 (s, 3H), 1.91 (s, 3H), 1.79-1.70 (m, 2H); LCMS (ES) tR: 1.515 min (>99%, ELSD), m/z: 713.2 [M+1].

Example 107

Preparation of 5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)quinoline-8-carboxylic acid

I-107

The title compound was prepared according to procedures described in Example 104 A and B using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one and methyl 5-bromoquinoline-8-carboxylate; $^1$H NMR (DMSO, 400 MHz) δ (ppm) 9.15 (d, J=4.4 Hz, 1H), 8.58 (d, J=8.0 Hz, 1H), 8.54 (d, J=8.0 Hz, 1H), 7.80-7.72 (m, 3H), 7.28 (d, J=8.4 Hz, 1H), 6.70 (s, 2H), 4.20 (t, J=6.0 Hz, 2H), 3.96 (t, J=6.0 Hz, 2H), 3.77 (s, 3H), 3.75-3.50 (m, 2H), 3.03 (t, J=6.4 Hz, 2H), 2.22 (s, 6H), 2.12-2.05 (m, 2H), 2.05 (s, 3H), 1.94 (s, 3H), 1.89-1.69 (m, 2H); LCMS (ES) tR: 1.377 min (>99%, ELSD), m/z: 711.1 [M+1].

Example 108

Preparation of 8-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)quinoline-5-carboxylic acid

I-108

The title compound was prepared according to procedures described in Example 104 A and B using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one and methyl 8-bromoquinoline-5-carboxylate; $^1$H NMR (DMSO, 400 MHz) δ (ppm) 9.32 (dd, J=8.8, 1.6 Hz, 1H), 8.90 (dd, J=4.0, 1.6 Hz, 1H), 8.25 (d, J=7.6 Hz, 1H), 7.71 (d, J=8.0 Hz, 1H), 7.66 (dd, J=8.8, 3.6 Hz, 2H), 7.25 (d, J=8.4 Hz, 1H), 6.72 (s, 2H), 4.33 (t, J=6.4 Hz, 2H), 3.94 (t, J=6.4 Hz, 2H), 3.76 (s, 3H), 3.71 (t, J=6.4 Hz, 2H), 3.02 (t, J=6.8 Hz, 2H), 2.22 (s, 6H), 2.06 (t, J=6.8 Hz, 2H), 2.03 (s, 3H), 1.92 (s, 3H), 1.80-1.68 (m, 2H); LCMS (ES) tR: 1.380 min (>99%, ELSD), m/z: 711.1 [M+1].

Example 109

Preparation of (R)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one

I-109

Step A. Preparation of ethyl (R)-1-(2-((tert-butoxycarbonyl)amino)propyl)-6-chloro-3-(3-(4-chloro-3,5-dimethylphenoxy)propyl)-7-(1,3,5-trimethyl-1H-pyrazol-4-yl)-1H-indole-2-carboxylate To a flame dried round bottom flask (50 mL) equipped with magnetic stir bar was added ethyl 6-chloro-3-(3-(4-chloro-3,5-dimethylphenoxy)propyl)-7-(1,3,5-trimethyl-1H-pyrazol-4-yl)-1H-indole-2-carboxylate (360 mg, 0.683 mol) and anhydrous DMF (2 mL) and the solution was stirred in ice bath under nitrogen atmosphere. Sodium hydride (60%) (25 mg, 0.62 mol) was added and after 3 min tert-butyl (R)-4-methyl-1,2,3-oxathiazolidine-3-carboxylate 2,2-dioxide was added. The reaction mixture was stirred in the ice bath for 20 min and then at rt for overnight. The reaction mixture was diluted with ethyl acetate (50 mL) and washed with brine (2×30 mL), dried with anhydrous MgSO$_4$, filtered off and concentrated down using rotary evaporator. The residue was purified by flash chromatography (Combi-flash Rf, Hex/acetone 80/20) to give the title compound (305 mg, 65%). $^1$H NMR (CDCl$_3$) δ 7.66 (d, 1H, J=8 Hz), 7.32 (d, 1H, J=8 Hz), 6.65 (s, 2H), 4.30 (q, 2H, J 1=8 Hz), 4.20 (m, 2H), 4.03 (t, 2H, J=8 Hz), 3.87 (s, 3H), 3.39-3.30 (m, 4H), 3.09 (m, 2H), 2.35 (two s, 6H), 2.09-2.00 (m, 2H), 1.45 (s, 9H), 1.29-1.18 (multiple d, total 3H), 0.99 (tr, 3H, J=8 Hz). MS (ES) 686.3 (M+H).

Step B. Example 109

The solution of ethyl (R)-1-(2-((tert-butoxycarbonyl)amino)propyl)-6-chloro-3-(3-(4-chloro-3,5-dimethylphenoxy)propyl)-7-(1,3,5-trimethyl-1H-pyrazol-4-yl)-1H-indole-2-carboxylate (218 mg, 0.32 mol) in anhydrous CH$_2$Cl$_2$ was cooled at 0° C. in ice bath. TFA (1.5 mL) was added dropwise, and the reaction mixture was stirred at rt for 2 h. The solvent was removed in vacuo and anhydrous ethanol (10 mL) was added followed by anhydrous K$_2$CO$_3$ (829 mg, 1.92 mmols). The reaction mixture was stirred at rt for overnight. The reaction mixture was diluted with ethyl acetate (60 mL) and washed with brine (2×30 mL). The organic layers were dried with anhydrous MgSO$_4$, filtered and concentrated in vacuo. The residue was purified by flash chromatography (Combi-flash Rf, CH$_2$Cl$_2$/methanol=0-10% gradient) to give the title compound (150 mg, 87%). $^1$H NMR (CDCl$_3$) δ 7.64 (d, 1H, J=8 Hz), 7.31 (d, 1H, J=8 Hz), 6.65 (s, 2H), 5.63 (d, 1H, J=12 Hz), 4.03 (t, 2H, J=8 Hz), 3.87 (s, 3H), 3.85-3.73 (m, 2H), 3.39-3.30 (m, 2H), 2.35 (s, 6H), 2.25 (tr, 2H, J=8 Hz), 2.07-2.05 (s, 6H), 1.18 (m, 3H). MS (ES) 539.5 (M+H).

Example 110

Preparation of (S)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one

I-110

The title compound was prepared according to procedures described in Example 109 A and B using ethyl 6-chloro-3-

(3-(4-chloro-3,5-dimethylphenoxy)propyl)-7-(1,3,5-trimethyl-1H-pyrazol-4-yl)-1H-indole-2-carboxylate and tert-butyl (S)-4-methyl-1,2,3-oxathiazolidine-3-carboxylate 2,2-dioxide. MS (ES) 539.2 (M+H)

Example 111

Preparation of 7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one

I-111

The title compound was prepared according to procedures described in Example 109 A and B using ethyl 6-chloro-3-(3-(4-chloro-3,5-dimethylphenoxy)propyl)-7-(1,3,5-trimethyl-1H-pyrazol-4-yl)-1H-indole-2-carboxylate and tert-butyl-5-methyl-1,2,3-oxathiazolidine-3-carboxylate 2,2-dioxide. MS (ES) 539.2 (M+H)

Example 112

Preparation of (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one

I-112

The title compound was prepared according to procedures described in Example 109 A and B using ethyl 6-chloro-3-(3-(4-chloro-3,5-dimethylphenoxy)propyl)-7-(1,3,5-trimethyl-1H-pyrazol-4-yl)-1H-indole-2-carboxylate and tert-butyl (R)-5-methyl-1,2,3-oxathiazolidine-3-carboxylate 2,2-dioxide. MS (ES) 539.2 (M+H)

Example 113

Preparation of (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one

I-113

The title compound was prepared according to procedures described in Example 109 A and B using ethyl 6-chloro-3-(3-(4-chloro-3,5-dimethylphenoxy)propyl)-7-(1,3,5-trimethyl-1H-pyrazol-4-yl)-1H-indole-2-carboxylate and tert-butyl (S)-5-methyl-1,2,3-oxathiazolidine-3-carboxylate 2,2-dioxide. MS (ES) 539.2 (M+H).

Example 114

Preparation of 8-chloro-1-(3-(4-chloro-3,5-dimethylphenoxy)propyl)-3-methyl-7-(1,3,5-trimethyl-1H-pyrazol-4-yl)-2,3,4,5-tetrahydro-1H-[1,4]diazepino[1,2-a]indol-1-one

I-114

The title compound was prepared according to procedures described in Example 109 A and B using ethyl 6-chloro-3-(3-(4-chloro-3,5-dimethylphenoxy)propyl)-7-(1,3,5-trimethyl-1H-pyrazol-4-yl)-1H-indole-2-carboxylate and tert-butyl 4-methyl-1,2,3-oxathiazinane-3-carboxylate 2,2-dioxide. MS (ES) 553.2 (M+H).

Example 115

Preparation of 8-chloro-1-(3-(4-chloro-3,5-dimethylphenoxy)propyl)-4-methyl-7-(1,3,5-trimethyl-1H-pyrazol-4-yl)-2,3,4,5-tetrahydro-1H-[1,4]diazepino[1,2-a]indol-1-one

I-115

The title compound was prepared according to procedures described in Example 109 A and B using ethyl 6-chloro-3-(3-(4-chloro-3,5-dimethylphenoxy)propyl)-7-(1,3,5-trimethyl-1H-pyrazol-4-yl)-1H-indole-2-carboxylate and tert-butyl 5-methyl-1,2,3-oxathiazinane-3-carboxylate 2,2-dioxide. MS (ES) 553.2 (M+H).

Example 116

Preparation of 8-chloro-1-(3-(4-chloro-3,5-dimethylphenoxy)propyl)-5-methyl-7-(1,3,5-trimethyl-1H-pyrazol-4-yl)-2,3,4,5-tetrahydro-1H-[1,4]diazepino[1,2-a]indol-1-one

I-116

The title compound was prepared according to procedures described in Example 109 A and B using ethyl 6-chloro-3-(3-(4-chloro-3,5-dimethylphenoxy)propyl)-7-(1,3,5-trimethyl-1H-pyrazol-4-yl)-1H-indole-2-carboxylate and tert-butyl 6-methyl-1,2,3-oxathiazinane-3-carboxylate 2,2-dioxide. MS (ES) 553.2 (M+H).

Example 117

Preparation of 7-chloro-10-(3-(4-chloro-3,5-dimethylphenoxy)propyl)-6-(1,3,5-trimethyl-1H-pyrazol-4-yl)-3,4-dihydropyrazino[1,2-a]indol-1(2H)-one

I-117

The title compound was prepared according to procedures described in Example 109 A and B using ethyl 6-chloro-3-(3-(4-chloro-3,5-dimethylphenoxy)propyl)-7-(1,3,5-trimethyl-1H-pyrazol-4-yl)-1H-indole-2-carboxylate and tert-butyl 1,2,3-oxathiazolidine-3-carboxylate 2,2-dioxide. MS (ES) 525.2 (M+H).

Example 118

Preparation of 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one

I-118

The title compound was prepared according to procedures described in Example 109 A and B using ethyl 6-chloro-3-(3-(4-chloro-3,5-dimethylphenoxy)propyl)-7-(1,3,5-trimethyl-1H-pyrazol-4-yl)-1H-indole-2-carboxylate and tert-butyl 1,2,3-oxathiazinane-3-carboxylate 2,2-dioxide. MS (ES) 539.2 (M+H).

Example 119

Preparation of (3R)-7-chloro-10-(3-(4-chloro-3,5-dimethylphenoxy)propyl)-3,4-dimethyl-6-(1,3,5-trimethyl-1H-pyrazol-4-yl)-3,4-dihydropyrazino[1,2-a]indol-1(2H)-one

I-119

The title compound was prepared according to procedures described in Example 109 A and B using ethyl 6-chloro-3-(3-(4-chloro-3,5-dimethylphenoxy)propyl)-7-(1,3,5-trimethyl-1H-pyrazol-4-yl)-1H-indole-2-carboxylate and tert-butyl (4R)-4,5-dimethyl-1,2,3-oxathiazolidine-3-carboxylate 2,2-dioxide. MS (ES) 553.2 (M+H).

Example 120

Preparation of (R)-4-((7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)methyl)benzoic acid

I-120

To a flame dried round bottom flask (25 mL) equipped with magnetic stir bar was added (R)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1 (2H)-one (25 mg, 46.3 mmol) and anhydrous DMF (2 mL) and the solution was stirred in ice bath under nitrogen atmosphere. Sodium hydride (60%) (5.5 mg, 78.7 mmol) was added to the reaction mixture and stirred for 10 min. Methyl 4-(bromomethyl)benzoate (1.7 eq) was added to the reaction mixture then stirred in the ice bath for 10 min. The reaction mixture was warmed to rt, stirred for additional 1 h then diluted with ethyl acetate (20 mL). The organic solution was washed with brine (2×10 mL), dried over anhydrous $MgSO_4$, filtered and concentrated in vacuo. The residue was dissolved in a mixture of THF and MeOH (4 mL, 1:1) and NaOH (2M, 1 mL) aqueous solution was added. The reaction was stirred at rt while monitoring progress by LCMS until completion. The reaction mixture was acidified with HCl (1.2 M), concentrated to ½ of its original volume, diluted with ethyl acetate and washed with water. The organic layer was concentrated in vacuo. The residue was purified by reverse phase preparatory HPLC (Phenomenex Gemini C18, $H_2O/CH_3CN$ gradient to 50-95% $CH_3CN$ 0.1% TFA) to give the title compound (22 mg, 58%) as a yellow solid.down using rotary evaporator and dissolved in a mixture of DMSO and MEOH and purified by HPLC (Phenomenex Gemini C18, $H_2O/CH_3CN$ gradient 50-95% $CH_3CN$, 0.1% TFA) to give the title compound (81% yield) as a white solid. $^1$H NMR (CDCl$_3$) δ 8.04 (d, 2H, J=8 Hz), 7.70-7.67 (m, 1H), 7.14 (m, 2H), 7.31 (m, 1H), 6.67 (s, 2H), 5.59 (tr, 1H, J=16 Hz), 4.04-4.00 (m, 4H), 3.93 and 3.89 (s, 3H), 3.64-3.37 (m, 4H), 2.35 (s, 6H), 2.25 (m, 2H), 2.07-2.05 (s, 6H), 1.13 and 1.08 (d, 3H, J=8 Hz). MS (ES) 673.2 (M+H).

Example 121

Preparation of (R)-3-((7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)methyl)benzoic acid

I-121

The title compound was prepared according to procedures described in Example 120 using (R)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1 (2H)-one and methyl 3-(bromomethyl)benzoate (68% yield). $^1$H NMR (CDCl$_3$) δ 8.02 (m, 2H), 7.68 (d, 1H, J=8 Hz), 7.59 (m, 1H), 7.48 (m, 1H), 7.27 (m, 1H), 6.67 (s, 2H), 5.55 (m, 1H), 4.04 (m, 4H), 3.99 and 3.89 (s, 3H), 3.60-3.55 (m, 2H), 3.45-3.37 (m, 2H), 2.35 (s, 6H), 2.25 (m, 2H), 2.07-2.05 (multiple s, 6H), 1.12 and 1.08 (d, 3H, J=8 Hz). MS (ES) 673.2 (M+H).

Example 122

Preparation of (R)-6-((7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)methyl)nicotinic acid

I-122

The title compound was prepared according to procedures described in Example 120 using (R)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1 (2H)-one and methyl 6-(bromomethyl)nicotinate (78% yield). $^1$H NMR (CDCl$_3$) δ 9.10 (d, 1H, J=8 Hz), 8.29 (m, 1H), 7.58 (d, 1H, J=8 Hz), 7.48 (tr, 1H, J=8 Hz), 7.27 (d, 1H, J=8 Hz), 6.56 (s, 2H), 5.58 and 5.48 (dd, 1H, J1=24 Hz, J2=64 Hz), 4.28 and 4.17 (dd, 1H, J1=24 Hz, J2=64 Hz), 4.04-3.73 (m, 7H), 3.73-3.547 (m, 2H), 3.35-3.24 (m, 2H), 2.25 (s, 6H), 2.18-2.10 (m, 2H), 2.07-2.05 (multiple s, 6H), 1.08 and 1.03 (d, 3H, J=8 Hz). MS (ES) 674.2 (M+H).

Example 123

Preparation of (R)-5-((7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)methyl)furan-2-carboxylic acid

I-123

The title compound was prepared according to procedures described in Example 120 using (R)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1 (2H)-one and methyl 5-(bromomethyl)furan-2-carboxylate (78% yield). $^1$H NMR (CDCl$_3$) δ 7.67 (d, 1H, J=8 Hz), 7.27-7.15 (m, 2H), 6.56 (s, 2H), 6.49 (d, 1H, J=3 Hz) 5.43 and 5.26 (dd, 1H, J$_1$=16 Hz, J$_2$=60 Hz), 4.31 and 4.15 (dd, 1H, J$_1$=16 Hz, J$_2$=60 Hz), 4.04-3.73 (m, 7H), 3.73-3.54 (m, 2H), 3.35-3.24 (m, 2H), 2.25 (s, 6H), 2.18-2.10 (m, 2H), 2.07-2.05 (multiple s, 3H), 1.08 and 1.03 (d, 3H, J=8 Hz). MS (ES) 663.2 (M+H).

Example 124-155 was prepared in parallel manner with 47-88% yield.

Example 124

Preparation of 6-((8-chloro-11-(3-(4-chloro-3,5-dimethylphenoxy)propyl)-3-methyl-1-oxo-7-(1,3,5-trimethyl-1H-pyrazol-4-yl)-4,5-dihydro-1H-[1,4]diazepino[1,2-a]indol-2(3H)-yl)methyl)nicotinic acid

I-124

The title compound was prepared according to procedures described in Example 120 using 8-chloro-11-(3-(4-chloro-

447

3,5-dimethylphenoxy)propyl)-3-methyl-7-(1,3,5-trimethyl-1H-pyrazol-4-yl)-2,3,4,5-tetrahydro-1H-[1,4]diazepino[1,2-a]indol-1-one and methyl 6-(bromomethyl)nicotinate. MS (ES) 688.2 (M+H).

Example 125

Preparation of 3-((8-chloro-11-(3-(4-chloro-3,5-dimethylphenoxy)propyl)-3-methyl-1-oxo-7-(1,3,5-trimethyl-1H-pyrazol-4-yl)-4,5-dihydro-1H-[1,4]diazepino[1,2-a]indol-2(3H)-yl)methyl)benzoic acid

I-125

The title compound was prepared according to procedures described in Example 120 using 8-chloro-11-(3-(4-chloro-3,5-dimethylphenoxy)propyl)-3-methyl-7-(1,3,5-trimethyl-1H-pyrazol-4-yl)-2,3,4,5-tetrahydro-1H-[1,4]diazepino[1,2-a]indol-1-one and methyl 3-(bromomethyl)benzoate. MS (ES) 687.2 (M+H).

Example 126

Preparation of 5-((8-chloro-1-(3-(4-chloro-3,5-dimethylphenoxy)propyl)-3-methyl-1-oxo-7-(1,3,5-trimethyl-1H-pyrazol-4-yl)-4,5-dihydro-1H-[1,4]diazepino[1,2-a]indol-2(3H)-yl)methyl)furan-2-carboxylic acid

I-126

The title compound was prepared according to procedures described in Example 120 using 8-chloro-11-(3-(4-chloro-3,5-dimethylphenoxy)propyl)-3-methyl-7-(1,3,5-trimethyl-1H-pyrazol-4-yl)-2,3,4,5-tetrahydro-1H-[1,4]diazepino[1,2-a]indol-1-one and methyl 5-(bromomethyl)furan-2-carboxylate. MS (ES) 677.2 (M+H).

Example 127

Preparation of 4-((8-chloro-11-(3-(4-chloro-3,5-dimethylphenoxy)propyl)-3-methyl-1-oxo-7-(1,3,5-trimethyl-1H-pyrazol-4-yl)-4,5-dihydro-1H-[1,4]diazepino[1,2-a]indol-2(3H)-yl)methyl)benzoic acid

I-127

The title compound was prepared according to procedures described in Example 120 using 8-chloro-11-(3-(4-chloro-3,5-dimethylphenoxy)propyl)-3-methyl-7-(1,3,5-trimethyl-1H-pyrazol-4-yl)-2,3,4,5-tetrahydro-1H-[1,4]diazepino[1,2-a]indol-1-one and methyl 4-(bromomethyl)benzoate. MS (ES) 687.2 (M+H).

Example 128

Preparation of 5-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)furan-2-carboxylic acid

I-128

The title compound was prepared according to procedures described in Example 120 using 7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1 (2H)-one and methyl 5-(bromomethyl)furan-2-carboxylate. MS (ES) 663.2 (M+H).

Example 129

Preparation of 6-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)nicotinic acid

I-129

The title compound was prepared according to procedures described in Example 120 using 7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1 (2H)-one and methyl 6-(bromomethyl)nicotinate. MS (ES) 674.2 (M+H).

Example 130

Preparation of 4-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)benzoic acid

I-130

The title compound was prepared according to procedures described in Example 120 using 7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1 (2H)-one and methyl 4-(bromomethyl)benzoate. MS (ES) 673.2 (M+H).

Example 131

Preparation of 3-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)benzoic acid

I-131

The title compound was prepared according to procedures described in Example 120 using 7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1 (2H)-one and methyl 3-(bromomethyl)benzoate. MS (ES) 673.2 (M+H).

Example 132

Preparation of 5-((8-chloro-1-(3-(4-chloro-3,5-dimethylphenoxy)propyl)-4-methyl-1-oxo-7-(1,3,5-trimethyl-1H-pyrazol-4-yl)-4,5-dihydro-1H-[1,4]diazepino[1,2-a]indol-2(3H)-yl)methyl)furan-2-carboxylic acid

I-132

The title compound was prepared according to procedures described in Example 120 using 8-chloro-11-(3-(4-chloro-3,5-dimethylphenoxy)propyl)-4-methyl-7-(1,3,5-trimethyl-1H-pyrazol-4-yl)-2,3,4,5-tetrahydro-1H-[1,4]diazepino[1,2- a]indol-1-one and methyl 5-(bromomethyl)furan-2-carboxylate. MS (ES) 677.2 (M+H).

Example 133

Preparation of 4-((8-chloro-11-(3-(4-chloro-3,5-dimethylphenoxy)propyl)-4-methyl-1-oxo-7-(1,3,5-trimethyl-1H-pyrazol-4-yl)-4,5-dihydro-1H-[1,4]diazepino[1,2-a]indol-2(3H)-yl)methyl)benzoic acid

I-133

The title compound was prepared according to procedures described in Example 120 using 8-chloro-11-(3-(4-chloro-3,5-dimethylphenoxy)propyl)-4-methyl-7-(1,3,5-trimethyl-1H-pyrazol-4-yl)-2,3,4,5-tetrahydro-1H-[1,4]diazepino[1,2-a]indol-1-one and methyl 4-(bromomethyl)benzoate. MS (ES) 687.2 (M+H).

Example 134

Preparation of 6-((8-chloro-11-(3-(4-chloro-3,5-dimethylphenoxy)propyl)-4-methyl-1-oxo-7-(1,3,5-trimethyl-1H-pyrazol-4-yl)-4,5-dihydro-1H-[1,4]diazepino[1,2-a]indol-2(3H)-yl)methyl)nicotinic acid

I-134

The title compound was prepared according to procedures described in Example 120 using 8-chloro-11-(3-(4-chloro-3,5-dimethylphenoxy)propyl)-4-methyl-7-(1,3,5-trimethyl-1H-pyrazol-4-yl)-2,3,4,5-tetrahydro-1H-[1,4]diazepino[1,2-a]indol-1-one and methyl 6-(bromomethyl)nicotinate. MS (ES) 688.2 (M+H).

Example 135

Preparation of 3-((8-chloro-11-(3-(4-chloro-3,5-dimethylphenoxy)propyl)-4-methyl-1-oxo-7-(1,3,5-trimethyl-1H-pyrazol-4-yl)-4,5-dihydro-1H-[1,4]diazepino[1,2-a]indol-2(3H)-yl)methyl)benzoic acid

I-135

The title compound was prepared according to procedures described in Example 120 using 8-chloro-11-(3-(4-chloro-3,5-dimethylphenoxy)propyl)-4-methyl-7-(1,3,5-trimethyl-1H-pyrazol-4-yl)-2,3,4,5-tetrahydro-1H-[1,4]diazepino[1,2-a]indol-1-one and methyl 3-(bromomethyl)benzoate. MS (ES) 687.2 (M+H).

Example 136

Preparation of (S)-3-((7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)methyl)benzoic acid

I-136

The title compound was prepared according to procedures described in Example 120 using (S)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one and methyl 3-(bromomethyl)benzoate. MS (ES) 673.2 (M+H).

Example 137

Preparation of (S)-6-((7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)methyl)nicotinic acid

I-137

The title compound was prepared according to procedures described in Example 120 using (S)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one and methyl 6-(bromomethyl)nicotinate. MS (ES) 674.2 (M+H).

Example 138

Preparation of (S)-5-((7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)methyl)furan-2-carboxylic acid

I-138

The title compound was prepared according to procedures described in Example 120 using (S)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one and methyl 5-(bromomethyl)furan-2-carboxylate. MS (ES) 663.2 (M+H).

Example 139

Preparation of (S)-4-((7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)methyl)benzoic acid

I-139

The title compound was prepared according to procedures described in Example 120 using (S)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one and methyl 4-(bromomethyl)benzoate. MS (ES) 673.2 (M+H).

Example 140

Preparation of 4-((7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)methyl)benzoic acid

I-140

The title compound was prepared according to procedures described in Example 120 using 7-chloro-10-(3-(4-chloro-3,5-dimethylphenoxy)propyl)-6-(1,3,5-trimethyl-1H-pyrazol-4-yl)-3,4-dihydropyrazino[1,2-a]indol-1 (2H)-one and methyl 4-(bromomethyl)benzoate. MS (ES) 659.2 (M+H).

Example 141

Preparation of 3-((7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)methyl)benzoic acid

I-141

The title compound was prepared according to procedures described in Example 120 using 7-chloro-10-(3-(4-chloro-3,5-dimethylphenoxy)propyl)-6-(1,3,5-trimethyl-1H-pyrazol-4-yl)-3,4-dihydropyrazino[1,2-a]indol-1 (2H)-one and methyl 3-(bromomethyl)benzoate. MS (ES) 659.2 (M+H).

Example 142

Preparation of 6-((7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)methyl)nicotinic acid

I-142

The title compound was prepared according to procedures described in Example 120 using 7-chloro-10-(3-(4-chloro-3,5-dimethylphenoxy)propyl)-6-(1,3,5-trimethyl-1H-pyrazol-4-yl)-3,4-dihydropyrazino[1,2-a]indol-1 (2H)-one and methyl 6-(bromomethyl)nicotinate. MS (ES) 660.2 (M+H).

Example 143

Preparation of 5-((7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)methyl)furan-2-carboxylic acid

I-143

The title compound was prepared according to procedures described in Example 120 using 7-chloro-10-(3-(4-chloro-3,5-dimethylphenoxy)propyl)-6-(1,3,5-trimethyl-1H-pyrazol-4-yl)-3,4-dihydropyrazino[1,2-a]indol-1 (2H)-one and methyl 5-(bromomethyl)furan-2-carboxylate. MS (ES) 649.2 (M+H).

Example 144

Preparation of 4-(((3R)-7-chloro-10-(3-(4-chloro-3,5-dimethylphenoxy)propyl)-3,4-dimethyl-1-oxo-6-(1,3,5-trimethyl-1H-pyrazol-4-yl)-3,4-dihydropyrazino[1,2-a]indol-2(1H)-yl)methyl)benzoic acid

I-144

The title compound was prepared according to procedures described in Example 120 using (3R)-7-chloro-10-(3-(4-chloro-3,5-dimethylphenoxy)propyl)-3,4-dimethyl-6-(1,3,5-trimethyl-1H-pyrazol-4-yl)-3,4-dihydropyrazino[1,2-a]indol-1 (2H)-one and methyl 4-(bromomethyl)benzoate. MS (ES) 687.2 (M+H).

Example 145

Preparation of 3-(((3R)-7-chloro-10-(3-(4-chloro-3,5-dimethylphenoxy)propyl)-3,4-dimethyl-1-oxo-6-(1,3,5-trimethyl-1H-pyrazol-4-yl)-3,4-dihydropyrazino[1,2-a]indol-2(1H)-yl)methyl)benzoic acid

I-145

The title compound was prepared according to procedures described in Example 120 using (3R)-7-chloro-10-(3-(4-chloro-3,5-dimethylphenoxy)propyl)-3,4-dimethyl-6-(1,3,5-trimethyl-1H-pyrazol-4-yl)-3,4-dihydropyrazino[1,2-a]indol-1 (2H)-one and methyl 3-(bromomethyl)benzoate. MS (ES) 687.2 (M+H).

Example 146

Preparation of 6-(((3R)-7-chloro-10-(3-(4-chloro-3,5-dimethylphenoxy)propyl)-3,4-dimethyl-1-oxo-6-(1,3,5-trimethyl-1H-pyrazol-4-yl)-3,4-dihydropyrazino[1,2-a]indol-2(1H)-yl)methyl)nicotinic acid

I-146

The title compound was prepared according to procedures described in Example 120 using (3R)-7-chloro-10-(3-(4-chloro-3,5-dimethylphenoxy)propyl)-3,4-dimethyl-6-(1,3,5-trimethyl-1H-pyrazol-4-yl)-3,4-dihydropyrazino[1,2-a]indol-1 (2H)-one and methyl 6-(bromomethyl)nicotinate. MS (ES) 688.2 (M+H).

Example 147

Preparation of 5-(((3R)-7-chloro-10-(3-(4-chloro-3,5-dimethylphenoxy)propyl)-3,4-dimethyl-1-oxo-6-(1,3,5-trimethyl-1H-pyrazol-4-yl)-3,4-dihydropyrazino[1,2-a]indol-2(1H)-yl)methyl)furan-2-carboxylic acid

I-147

The title compound was prepared according to procedures described in Example 120 using (3R)-7-chloro-10-(3-(4-chloro-3,5-dimethylphenoxy)propyl)-3,4-dimethyl-6-(1,3,5-trimethyl-1H-pyrazol-4-yl)-3,4-dihydropyrazino[1,2-a]indol-1(2H)-one and methyl 5-(bromomethyl)furan-2-carboxylate. MS (ES) 677.2 (M+H).

Example 148

Preparation of (S)-5-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)furan-2-carboxylic acid

I-148

The title compound was prepared according to procedures described in Example 120 using (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]in-

Example 149

Preparation of (S)-6-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)nicotinic acid

I-149

The title compound was prepared according to procedures described in Example 120 using (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 6-(bromomethyl)nicotinate. MS (ES) 674.2 (M+H).

Example 150

Preparation of (S)-4-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)benzoic acid

I-150

The title compound was prepared according to procedures described in Example 120 using (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 4-(bromomethyl)benzoate. MS (ES) 673.2 (M+H).

Example 151

Preparation of (S)-3-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)benzoic acid

I-151

The title compound was prepared according to procedures described in Example 120 using (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 3-(bromomethyl)benzoate. MS (ES) 673.2 (M+H).

Example 152

Preparation of (R)-5-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)furan-2-carboxylic acid

I-152

The title compound was prepared according to procedures described in Example 120 using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 5-(bromomethyl)furan-2-carboxylate. MS (ES) 663.2 (M+H).

Example 153

Preparation of (R)-6-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)nicotinic acid

I-153

The title compound was prepared according to procedures described in Example 120 using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 6-(bromomethyl)nicotinate. MS (ES) 674.2 (M+H).

Example 154

Preparation of (R)-4-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)benzoic acid

I-154

The title compound was prepared according to procedures described in Example 120 using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 4-(bromomethyl)benzoate. MS (ES) 673.2 (M+H).

Example 155

Preparation of (R)-3-((7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)methyl)benzoic acid

I-155

The title compound was prepared according to procedures described in Example 120 using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 3-(bromomethyl)benzoate. MS (ES) 673.2 (M+H).

Example 156

Preparation of (R)-4-(7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)benzoic acid

I-156

To a flame dried round bottom flask (25 mL) equipped with magnetic stir bar was added (R)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one (25 mg, 46.3 mmol) and anhydrous 1,4-dioxane (2 mL). Sequentially, $Cs_2CO_3$ (28 mg, 83.7 mmol), $Pd_2(dba)_3$ (1 mg, 1.1 mmol), Xanthpos (2 mg, 3.3 mmol) and methyl 4-bromobenzoate (1.2 eq) were added. The reaction mixture was stirred at 120° C. for overnight. The reaction mixture concentrated in vacuo and the residue was purified by flash chromatography (Combi-flash Rf, DCM/methanol=0-10% gradient) to give the ester intermediate which was dissolved in a mixture of THF and MeOH (4 mL, 1:1) followed by addition of NaOH (2M, 1 mL) aqueous solution. The reaction was stirred at rt until completion of saponification while monitoring progress by LCMS. The reaction mixture was acidified with HCl (1.2M), concentrated to 12 of its original volume and diluted with ethyl acetate. The resulting solution was washed with water, dried over $MgSO_4$ and concentrated in vacuo. The residue was purified by the reverse phase HPLC (Phenomenex Gemini C18, $H_2O/CH_3CN$ gradient from 50-95% $CH_3CN$, 0.1% TFA) to give the title compound (65%) as a white solid. $^1H$ NMR ($CDCl_3$) δ 8.14 (m, 2H), 7.69 (d, 1H, J=8 Hz), 7.42 (d, 1H, J=8 Hz), 7.14 (m, 2H), 7.31 (m, 1H), 6.64 (s, 2H), 4.09-4.06 (m, 4H), 3.76 (s, 3H), 3.76 (m, 2H), 3.40-3.36 (m, 2H), 2.35 (s, 6H), 2.25 (m, 2H), 2.07-2.05 (s, 6H), 1.13 and 1.08 (d, 3H, J=8 Hz). MS (ES) 659.2 (M+H).

Example 157

Preparation of (R)-3-(7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)benzoic acid

I-157

The title compound (55%) was prepared according to procedures described in Example 156 using (R)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one and methyl 3-bromobenzoate. $^1H$ NMR ($CDCl_3$) δ 8.04 (m, 2H), 7.68 (d, 1H, J=8 Hz), 7.60 (m, 1H), 7.54 (m, 1H), 7.27 (m, 1H), 6.67 (s, 2H), 4.13 (m, 1H), 4.01-3.99 (m, 2H), 3.92 and 3.90 (s, 3H), 3.60-3.55 (m, 2H), 3.40-3.36 (m, 2H), 2.33 (s, 6H), 2.25 (m, 2H), 2.07-2.05 (multiple s, 6H), 1.24 and 1.17 (d, 3H, J=8 Hz). MS (ES) 659.2 (M+H).

Example 158

Preparation of (R)-5-(7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)quinoline-8-carboxylic acid

I-158

The title compound (44%) was prepared according to procedures described in Example 156 using (R)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one and methyl 5-bromoquinoline-8-carboxylate. $^1H$ NMR (MeOH-d4) δ 9.14 (m, 1H), 8.82 (dd, 1H, $J_1$=8 Hz, $J_2$=16 Hz), 8.81 and 8.79 (m, 1H), 7.68 (m, 2H), 7.58 (d, 1H, J=8 Hz), 7.81 and 7.68 (m, 1H), 7.32 (m, 1H), 6.31 and 6.31 (s, 1H), 4.49-4.24 (m, 1H), 4.22-3.95 (m, 3H), 3.98-3.85 (multiple s, 3H), 2.31 (multiple s, 6H), 2.18-2.05 (m, 8H), 1.31 and 1.13 (multiple s, 3H). MS (ES) 710.2 (M+H).

Example 159

Preparation of (R)-4-(7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)-1-methyl-1H-indole-6-carboxylic acid

I-159

The title compound (35%) was prepared according to procedures described in Example 156 using (R)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one and methyl 4-bromo-1-methyl-1H-indole-6-carboxylate. $^1H$ NMR ($CDCl_3$) δ 7.82 (s, 1H), 7.70 (d, 1H, J=8 Hz), 7.58 (d, 1H, J=8 Hz), 7.54 (d, 1H, J=8 Hz) 7.32-7.01 (m, 3H), 6.64 (s, 2H), 4.29-4.22 (m, 3H), 4.16-4.13 (m, 2H), 4.08-3.75 (multiple s, 6H), 3.73-3.38 (m, 2H), 3.37 (m, 2H), 2.33 (s, 6H), 2.18-2.05 (m, 2H), 2.12-2.19 (multiple S, 6H), 1.26 and 1.20 (d, 3H, J=8 Hz). MS (ES) 712.3 (M+H), Example 160

Preparation of (R)-6-(7-chloro-10-(3-(4-chloro-3,5-dimethylphenoxy)propyl)-3-methyl-1-oxo-6-(1,3,5-trimethyl-1H-pyrazol-4-yl)-3,4-dihydropyrazino[1,2-a]indol-2(1H)-yl)-1-methyl-1H-indole-4-carboxylic acid

I-160

The title compound (55%) was prepared according to procedures described in Example 156 using (R)-7-chloro-10-(3-(4-chloro-3,5-dimethylphenoxy)propyl)-3-methyl-6-(1,3,5-trimethyl-1H-pyrazol-4-yl)-3,4-dihydropyrazino[1,2-a]indol-1(2H)-one and methyl 6-bromo-1-methyl-1H-indole-4-carboxylate. $^1H$ NMR ($CDCl_3$) δ 8.17 (d, 1H, J=8 Hz), 7.81 (d, 1H, J=8 Hz), 7.72 (d, 1H, J=8 Hz) 7.32 (m, 2H), 6.31 (s, 2H), 6.34 (tr, 1H, J=4 Hz), 4.29-4.22 (m, 3H), 4.19-4.16 (m, 2H), 4.02-3.90 (multiple s, 3H), 3.84-3.78 (multiple s, 3H), 3.39 (m, 3H), 2.31 (s, 6H), 2.18-2.05 (m, 2H), 2.15-2.12 (multiple S, 6H), 1.24 and 1.16 (d, 3H, J=8 Hz). MS (ES) 712.2 (M+H)

Example 161

Preparation of 5-(7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)quinoline-8-carboxylic acid

I-161

The title compound was prepared according to procedures described in Example 156 using 7-chloro-10-(3-(4-chloro-3,5-dimethylphenoxy)propyl)-6-(1,3,5-trimethyl-1H-pyrazol-4-yl)-3,4-dihydropyrazino[1,2-a]indol-1 (2H)-one and methyl 5-bromoquinoline-8-carboxylate. MS (ES) 696.2 (M+H).

Example 162

Preparation of 6-(7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)-1-methyl-1H-indole-4-carboxylic acid

I-162

The title compound was prepared according to procedures described in Example 156 using 7-chloro-10-(3-(4-chloro-3,5-dimethylphenoxy)propyl)-6-(1,3,5-trimethyl-1H-pyrazol-4-yl)-3,4-dihydropyrazino[1,2-a]indol-1 (2H)-one and methyl 6-bromo-1-methyl-1H-indole-4-carboxylate. MS (ES) 698.2 (M+H)

Example 163

Preparation of 4-(7-cholro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)-1-methyl-1H-indole-6-carboxylic acid

I-163

The title compound was prepared according to procedures described in Example 156 using 7-chloro-10-(3-(4-chloro-3,5-dimethylphenoxy)propyl)-6-(1,3,5-trimethyl-1H-pyrazol-4-yl)-3,4-dihydropyrazino[1,2-a]indol-1 (2H)-one and methyl 4-bromo-1-methyl-1H-indole-6-carboxylate. MS (ES) 698.2 (M+H)

Example 164

Preparation of 5-((3R)-7-chloro-10-(3-(4-chloro-3,5-dimethylphenoxy)propyl)-3,4-dimethyl-1-oxo-6-(1,3,5-trimethyl-1H-pyrazol-4-yl)-3,4-dihydropyrazino[1,2-a]indol-2(1H)-yl)quinoline-8-carboxylic acid

I-164

The title compound was prepared according to procedures described in Example 156 using (3R)-7-chloro-10-(3-(4-chloro-3,5-dimethylphenoxy)propyl)-3,4-dimethyl-6-(1,3,5-trimethyl-1H-pyrazol-4-yl)-3,4-dihydropyrazino[1,2-a]indol-1(2H)-one and methyl 5-bromoquinoline-8-carboxylate. MS (ES) 724.2 (M+H).

Example 165

Preparation of (S)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)benzoic acid

I-165

The title compound was prepared according to procedures described in Example 156 using (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 3-bromobenzoate. MS (ES) 659.2 (M+H).

Example 166

Preparation of (S)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)benzoic acid

I-166

The title compound was prepared according to procedures described in Example 156 using (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 4-bromobenzoate. MS (ES) 659.2 (M+H).

Example 167

Preparation of (S)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-6-carboxylic acid

I-167

The title compound was prepared according to procedures described in Example 156 using (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 4-bromo-1-methyl-1H-indole-6-carboxylate. MS (ES) 712.2 (M+H).

Example 168

Preparation of (S)-5-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-8-carboxylic acid

I-168

The title compound was prepared according to procedures described in Example 156 using (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 5-bromoquinoline-8-carboxylate. MS (ES) 710.2 (M+H).

Example 169

Preparation of (S)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-4-carboxylic acid

I-169

The title compound was prepared according to procedures described in Example 156 using (S)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 6-bromo-1-methyl-1H-indole-4-carboxylate. MS (ES) 712.2 (M+H).

Example 170

Preparation of (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-6-carboxylic acid

I-170

The title compound was prepared according to procedures described in Example 156 using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 4-bromo-1-methyl-1H-indole-6-carboxylate. MS (ES) 712.2 (M+H).

Example 171

Preparation of (R)-3-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)benzoic acid

I-171

The title compound was prepared according to procedures described in Example 156 using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 3-bromobenzoate. MS (ES) 659.2 (M+H).

Example 172

Preparation of (R)-4-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)benzoic acid

I-172

The title compound was prepared according to procedures described in Example 156 using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1 (2H)-one and methyl 4-bromobenzoate. MS (ES) 659.2 (M+H).

Example 173

Preparation of (R)-5-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)quinoline-8-carboxylic acid

I-173

The title compound was prepared according to procedures described in Example 156 using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1 (2H)-one and methyl 5-bromoquinoline-8-carboxylate. MS (ES) 659.2 (M+H).

Example 174

Preparation of (R)-6-(7-chloro-10-(3-(4-chloro-3,5-dimethylphenoxy)propyl)-4-methyl-1-oxo-6-(1,3,5-trimethyl-1H-pyrazol-4-yl)-3,4-dihydropyrazino[1,2-a]indol-2(1H)-yl)-1-methyl-1H-indole-4-carboxylic acid

I-174

The title compound was prepared according to procedures described in Example 156 using (R)-7-chloro-10-(3-(4-chloro-3,5-dimethylphenoxy)propyl)-4-methyl-6-(1,3,5-trimethyl-1H-pyrazol-4-yl)-3,4-dihydropyrazino[1,2-a]indol-1(2H)-one and methyl 6-bromo-1-methyl-1H-indole-4-carboxylate. MS (ES) 712.2 (M+H).

Example 175

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoic acid

I-175

A solution of methyl 4-(6-chloro-3-(3-(4-chloro-3,5-dimethylphenoxy)propyl)-7-(1,3,5-trimethyl-1H-pyrazol-4-yl)-1H-indole-2-carboxamido)benzoate (38 mg, 0.060 mmol), 1,3-dibromopropane (30.4 µl, 0.300 mmol), $Cs_2CO_3$ (195 mg, 0.600 mmol) in DMF (1.200 mL) was stirred at 100° C. for 20 h. The $Cs_2CO_3$ was filtered and the solution was concentrated. The residue was dissolved in mixture of EtOH (0.6 mL)/THF (0.15 mL), and 2 M LiOH (150 µl, 0.30 mmol) aqueous solution was added. The reaction mixture was stirred at rt for 48 h then concentrated in vacuo. The residue was purified by the reverse phase HPLC (Phenomenex Gemini C18, $H_2O/CH_3CN$ gradient from 40-95% $CH_3CN$, 0.1% TFA) to give the title compound (16 mg) as white solid. MS (ES) 659.0 (M+H). $^1$H NMR (400 MHz, DMSO-$d_6$): δ 7.94 (s, 1H), 7.92 (s, 1H), 7.72 (d, J=8.0 Hz, 1H), 7.46 (d, J=7.0 Hz, 1H), 7.27 (d, J=8.0 Hz, 1H), 6.73 (s, 2H), 3.98 (t, J=8.0 Hz, 2H), 3.93 (t, J=8.0 Hz, 2H), 3.78 (s, 3H), 3.60 (t, J=6.0 Hz, 2H), 3.07 (t, J=6.0 Hz, 2H), 2.22 (s, 6H), 2.09-2.06 (m, 2H), 2.01 (s, 3H), 1.91 (s, 3H), 1.80-1.77 (m, 2H).

Example 176

Preparation of 4-(7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)benzoic acid

I-176

The title compound was prepared (21 mg, 0.033 mmol) according to procedures described in Example 175 using methyl 4-(6-chloro-3-(3-(4-chloro-3,5-dimethylphenoxy)propyl)-7-(1,3,5-trimethyl-1H-pyrazol-4-yl)-1H-indole-2-carboxamido)benzoate (40 mg, 0.063 mmol), 1,2-dibromoethane (27.2 µl, 0.316 mmol), $Cs_2CO_3$ (206 mg, 0.631 mmol). MS (ES) 645.0 (M+H). $^1$H NMR (400 MHz, DMSO-$d_6$): δ 7.97 (s, 1H), 7.95 (s, 1H), 7.75 (d, J=8.0 Hz, 1H), 7.50 (d, J=8.0 Hz, 1H), 7.27 (d, J=8.0 Hz, 1H), 6.75 (s, 2H), 4.06-3.98 (comp, 4H), 3.85-3.82 (m, 2H), 3.87 (s, 3H), 3.26 (t, J=8.0 Hz, 2H), 2.26 (s, 6H), 2.09-2.06 (m, 2H), 2.02 (s, 3H), 1.93 (s, 3H).

Example 177

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoic acid

I-177

The title compound was prepared (18.1 mg, 0.027 mmol) according to procedures described in Example 175 using methyl 3-(6-chloro-3-(3-(4-chloro-3,5-dimethylphenoxy)propyl)-7-(1,3,5-trimethyl-1H-pyrazol-4-yl)-1H-indole-2-carboxamido)benzoate (50 mg, 0.079 mmol), 1,3-dibromopropane (40.1 µl, 0.395 mmol), Cs$_2$CO$_3$ (257 mg, 0.789 mmol). MS (ES) 659.1 (M+H). $^1$H NMR (400 MHz, DMSO-d$_6$): δ 7.93 (s, 1H), 7.85-7.82 (m, 1H), 7.71 (d, J=8.0 Hz, 1H), 7.54-7.49 (comp, 2H), 7.26 (d, J=8.0 Hz, 1H), 6.72 (s, 2H), 4.00 (t, J=6.0 Hz, 2H), 3.94 (t, J=6.0 Hz, 2H), 3.77 (s, 3H), 3.59 (t, J=6.0 Hz, 2H), 3.05 (t, J=6.0 Hz, 2H), 2.22 (s, 6H), 2.08-2.05 (m, 2H), 2.01 (s, 3H), 1.90 (s, 3H), 1.80-1.75 (m, 2H).

Example 178

Preparation of 3-(7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)benzoic acid

I-178

The title compound was prepared (11.3 mg, 0.018 mmol) according to procedures described in Example 175 using methyl 3-(6-chloro-3-(3-(4-chloro-3,5-dimethylphenoxy)propyl)-7-(1,3,5-trimethyl-1H-pyrazol-4-yl)-1H-indole-2-carboxamido)benzoate (50 mg, 0.079 mmol), 1,2-dibromoethane (34 µL, 0.395 mmol). MS (ES) 645.0 (M+H). $^1$H NMR (400 MHz, DMSO-d$_6$): δ 7.97 (t, J=1.8 Hz, 1H), 7.81 (dt, J=7.7, 1.3 Hz, 1H), 7.74 (d, J=8.4 Hz, 1H), 7.62 (d, J=8.0 Hz, 1H), 7.53 (d, J=7.8 Hz, 1H), 7.27 (d, J=8.5 Hz, 1H), 6.74 (s, 2H), 4.05-3.97 (comp, 4H), 3.87-3.80 (m, 2H), 3.77 (s, 3H), 3.25 (t, J=7.6 Hz, 2H), 2.25 (s, 6H), 2.10-2.06 (m, 2H), 2.02 (s, 3H), 1.92 (s, 3H).

Example 179

Preparation of 5-(6-chloro-3-(3-(4-chloro-3,5-dimethylphenoxy)propyl)-7-(1,3,5-trimethyl-1H-pyrazol-4-yl)-1H-indole-2-carboxamido)furan-2-carboxylic acid

I-179

Step A. Preparation of 6-chloro-3-(3-(4-chloro-3,5-dimethylphenoxy)propyl)-7-(1,3,5-trimethyl-1H-pyrazol-4-yl)-1H-indole-2-carbonyl Chloride To a stirred solution of 6-chloro-3-(3-(4-chloro-3,5-dimethylphenoxy)propyl)-7-(1,3,5-trimethyl-1H-pyrazol-4-yl)-1H-indole-2-carboxylic acid (100 mg, 0.200 mmol) in DCM (4.0 mL) and DMF (1 drop) was added oxalyl chloride (70.0 µL, 0.80 mmol) at rt. The reaction mixture was stirred for 2 h then concentrated to give the crude title compound as a yellow solid, which was used for the next step without further purification.

Step B. Example 179

A solution of 6-chloro-3-(3-(4-chloro-3,5-dimethylphenoxy)propyl)-7-(1,3,5-trimethyl-1H-pyrazol-4-yl)-1H-indole-2-carbonyl chloride (30 mg, 0.058 mmol), methyl 5-aminofuran-2-carboxylate (12.24 mg, 0.087 mmol), pyridine (23.4 µL, 0.29 mmol) in DCM (1.2 mL) was stirred at rt for 16 h. The reaction mixture was concentrated in vacuo. The residue was dissolved in the mixture of EtOH (0.6 mL)/THF (0.15 mL), and 2 M LiOH aqueous solution (0.1 mL) was added. The reaction mixture was stirred at rt for 20 h then acidified with HCl (aq.) (40 al, 6 N). The reaction mixture was concentrated, and the residue was purified by the reverse phase HPLC (Phenomenex Gemini C18, H$_2$O/CH$_3$CN gradient from 40-85% CH$_3$CN, 0.1% TFA) to give the title compound (9.7 mg, 0.016 mmol). MS (ES) 609.0 (M+H). $^1$H NMR (400 MHz, DMSO-d$_6$): δ 10.88 (s, 1H), 7.67 (d, J=8.6 Hz, 1H), 7.25 (d, J=3.6 Hz, 1H), 7.22 (d, J=8.6 Hz, 1H), 6.74 (s, 2H), 6.53 (d, J=3.6 Hz, 1H), 3.97 (t, J=6.3 Hz, 2H), 3.80 (s, 3H), 3.27 (t, J=7.2 Hz, 2H), 2.26 (s, 6H), 2.07-2.03 (m, 2H), 2.03 (s, 3H), 1.96 (s, 3H).

Example 180

Preparation of 4-(6-chloro-3-(3-(4-chloro-3,5-dimethylphenoxy)propyl)-7-(1,3,5-trimethyl-1H-pyrazol-4-yl)-1H-indole-2-carboxamido)picolinic acid

I-180

The title compound was prepared (5.3 mg, 0.009 mmol) according to procedures described in Example 179 A and B using 6-chloro-3-(3-(4-chloro-3,5-dimethylphenoxy)propyl)-7-(1,3,5-trimethyl-1H-pyrazol-4-yl)-1H-indole-2-carbonyl chloride (30 mg, 0.058 mmol), methyl 4-aminopicolinate (9.68 mg, 0.064 mmol) and pyridine (0.023 mL, 0.289 mmol). MS (ES) 620.0 (M+H).

Example 181

Preparation of 5-(6-chloro-3-(3-(4-chloro-3,5-dimethylphenoxy)propyl)-7-(1,3,5-trimethyl-1H-pyrazol-4-yl)-1H-indole-2-carboxamido)nicotinic acid

I-181

The title compound was prepared (15.9 mg, 0.026 mmol) according to procedures described in Example 179 A and B using 6-chloro-3-(3-(4-chloro-3,5-dimethylphenoxy)propyl)-7-(1,3,5-trimethyl-1H-pyrazol-4-yl)-1H-indole-2-carbonyl chloride (30 mg, 0.058 mmol), methyl 5-aminonicotinate (9.68 mg, 0.064 mmol), pyridine (9.35 µL, 0.116 mmol). MS (ES) 620.1 (M+H). $^1$H NMR (400 MHz, DMSO-d6): δ 10.87 (s, 1H), 10.37 (s, 1H), 9.02 (d, J=2.5 Hz, 1H), 8.79 (d, J=1.9 Hz, 1H), 8.60 (t, J=2.3 Hz, 1H), 7.68 (d, J=8.7 Hz, 1H), 7.23 (d, J=8.7 Hz, 1H), 6.70 (s, 2H), 3.97 (t, J=6.3 Hz, 2H), 3.79 (s, 3H), 3.25 (t, J=7.3 Hz, 2H), 2.22 (s, 6H), 2.08-2.03 (m, 2H), 2.04 (s, 3H), 1.96 (s, 3H).

Example 182

Preparation of 6-(6-chloro-3-(3-(4-chloro-3,5-dimethylphenoxy)propyl)-7-(1,3,5-trimethyl-1H-pyrazol-4-yl)-1H-indole-2-carboxamido)picolinic acid

I-182

The title compound was prepared (7.9 mg, 0.013 mmol) according to procedures described in Example 179 A and B using 6-chloro-3-(3-(4-chloro-3,5-dimethylphenoxy)propyl)-7-(1,3,5-trimethyl-1H-pyrazol-4-yl)-1H-indole-2-carbonyl chloride (30 mg, 0.058 mmol), methyl 6-aminopicolinate (9.68 mg, 0.064 mmol), pyridine (9.35 μL, 0.116 mmol). MS (ES) 620.0 (M+H).

Example 183

Preparation of 2-(6-chloro-3-(3-(4-chloro-3,5-dimethylphenoxy)propyl)-7-(1,3,5-trimethyl-1H-pyrazol-4-yl)-1H-indole-2-carboxamido)isonicotinic acid

I-183

The title compound was prepared (34 mg, 0.055 mmol) according to procedures described in Example 179 A and B using 6-chloro-3-(3-(4-chloro-3,5-dimethylphenoxy)propyl)-7-(1,3,5-trimethyl-1H-pyrazol-4-yl)-1H-indole-2-carbonyl chloride (40 mg, 0.077 mmol) and DMAP (19 mg, 0.154 mmol) in DCM (1.5 mL), pyridine (6.24 μL, 0.077 mmol). MS (ES) 620.1 (M+H).

Example 184

Preparation of 6-(6-chloro-3-(3-(4-chloro-3,5-dimethylphenoxy)propyl)-7-(1,3,5-trimethyl-1H-pyrazol-4-yl)-1H-indole-2-carboxamido)nicotinic acid

I-184

The title compound was prepared (14.5 mg, 0.023 mmol) according to procedures described in Example 179 A and B using 6-chloro-3-(3-(4-chloro-3,5-dimethylphenoxy)propyl)-7-(1,3,5-trimethyl-1H-pyrazol-4-yl)-1H-indole-2-carbonyl chloride (30 mg, 0.058 mmol), methyl 6-aminonicotinate (18 mg, 0.116 mmol), pyridine (4.68 μL, 0.058 mmol) and DMAP (14 mg, 0.116 mmol). MS (ES) 620.0 (M+H).

Example 185

Preparation of 5-(6-chloro-3-(3-(4-chloro-3,5-dimethylphenoxy)propyl)-7-(1,3,5-trimethyl-1H-pyrazol-4-yl)-1H-indole-2-carboxamido)picolinic acid

I-185

The title compound was prepared (9.7 mg, 0.016 mmol) according to procedures described in Example 179 A and B using 6-chloro-3-(3-(4-chloro-3,5-dimethylphenoxy)propyl)-7-(1,3,5-trimethyl-1H-pyrazol-4-yl)-1H-indole-2-carbonyl chloride (30 mg, 0.058 mmol), methyl 5-aminopicolinate (13 mg, 0.087 mmol), pyridine (9.35 μL, 0.116 mmol). MS (ES) 620.1 (M+H).

Example 186

Preparation of 5-(3-(3-(4-chloro-3,5-dimethylphenoxy)propyl)-7-(1,3,5-trimethyl-1H-pyrazol-4-yl)-1H-indole-2-carboxamido)nicotinic acid

I-186

The title compound was prepared (18 mg, 0.031 mmol) according to procedures described in Example 36 using 3-(3-(4-chloro-3,5-dimethylphenoxy)propyl)-7-(1,3,5-trimethyl-1H-pyrazol-4-yl)-1H-indole-2-carboxylic acid (40 mg, 0.086 mmol), methyl 5-aminonicotinate (26 mg, 0.172 mmol), DMAP (21 mg, 0.172 mmol) and EDC (33 mg, 0.172 mmol). MS (ES) 586.0 (M+H). $^1$H NMR (400 MHz, DMSO-$d_6$): δ 10.77 (s, 1H), 10.38 (s, 1H), 9.06 (d, J=2.5 Hz, 1H), 8.80 (d, J=1.8 Hz, 1H), 8.64 (t, J=2.2 Hz, 1H), 7.66 (d, J=7.4 Hz, 1H), 7.14 (t, J=7.6 Hz, 1H), 7.07 (dd, J=7.1, 1.0 Hz, 1H), 6.73 (s, 2H), 3.99 (t, J=6.2 Hz, 2H), 3.79 (s, 3H), 3.30 (t, J=7.2 Hz, 2H), 2.23 (s, 6H), 2.14 (s, 3H), 2.10-2.07 (m, 2H), 2.06 (s, 3H).

Example 187

Preparation of 3-(6-chloro-3-(3-(4-chloro-3,5-dimethylphenoxy)propyl)-N-methyl-7-(1,3,5-trimethyl-1H-pyrazol-4-yl)-1H-indole-2-carboxamido)benzoic acid

I-187

The title compound was prepared (6.9 mg, 0.011 mmol) according to procedures described in Example 36 using 6-chloro-3-(3-(4-chloro-3,5-dimethylphenoxy)propyl)-7-(1,3,5-trimethyl-1H-pyrazol-4-yl)-1H-indole-2-carboxylic acid (20 mg, 0.040 mmol), methyl 3-(methylamino)benzoate (13 mg, 0.080 mmol), DMAP (9.77 mg, 0.080 mmol) and EDC (11.5 mg, 0.060 mmol). MS (ES) 633.0 (M+H).

Example 188

Preparation of 3-(6-chloro-3-(3-(4-chloro-3,5-dimethylphenoxy)propyl)-1-methyl-7-(1,3,5-trimethyl-1H-pyrazol-4-yl)-1H-indole-2-carboxamido)benzoic acid

I-188

The title compound was prepared (5.5 mg, 0.001 mmol) according to procedures described in Example 36 using 6-chloro-3-(3-(4-chloro-3,5-dimethylphenoxy)propyl)-1-methyl-7-(1,3,5-trimethyl-1H-pyrazol-4-yl)-1H-indole-2-carboxylic acid (36 mg, 0.070 mmol), methyl 3-aminobenzoate (12.7 mg, 0.084 mmol), DMAP (17 mg, 0.140 mmol) and EDC (20 mg, 0.105 mmol). MS (ES) 633.0 (M+H).

Example 189

Preparation of 3-(6-chloro-3-(3-(4-chloro-3,5-dimethylphenoxy)propyl)-N,1-dimethyl-7-(1,3,5-trimethyl-1H-pyrazol-4-yl)-1H-indole-2-carboxamido) benzoic acid

I-189

To a stirred solution of methyl 3-(6-chloro-3-(3-(4-chloro-3,5-dimethylphenoxy)propyl)-7-(1,3,5-trimethyl- 1H-pyrazol-4-yl)-1H-indole-2-carboxamido)benzoate (46 mg, 0.073 mmol) and MeI (9.1 µL, 0.145 mmol) in THF (1.5 mL), NaH (1.7 mg, 0.073 mmol) was added. The resulting mixture was stirred over night at rt. After 16 h, the reaction mixture was concentrated, and the residue was purified by the reverse phase HPLC (Phenomenex Gemini C18, $H_2O$/$CH_3CN$ gradient from 30-90% $CH_3CN$, 0.1% TFA) to give the title compound (18 mg, 0.028 mmol). MS (ES) 647.1 (M+H).

Example 190

Preparation of 4-(6-chloro-3-(3-(4-chloro-3,5-dimethylphenoxy)propyl)-7-(3,5-dimethyl-1-(2-morpholinoethyl)-1H-pyrazol-4-yl)-1H-indole-2-carboxamido)benzoic acid

I-190

Step A. Preparation of ethyl 6-chloro-3-(3-(4-chloro-3,5-dimethylphenoxy)propyl)-7-(3,5-dimethyl-1-(2-morpholinoethyl)-1H-pyrazol-4-yl)-1H-indole-2-carboxylate A solution of ethyl 7-bromo-6-chloro-3-(3-(4-chloro-3,5-dimethylphenoxy)propyl)-1H-indole-2-carboxylate (200 mg, 0.40 mmol), 4-(2-(3,5-dimethyl-4-(4,4,5,5-tetramethyl-1,3,2-dioxaborolan-2-yl)-1H-pyrazol-1-yl)ethyl)morpholine (148 mg, 0.44 mmol), Pd(PPh$_3$)$_4$ (23 mg, 0.020 mmol) and $K_2CO_3$ (0.60 mL, 2N, 1.2 mmol) in 1,4-dioxane (1 mL) and water (0.5 mL) was degassed under Ar for 10 min. The mixture was then heated under microwave at 120° C. for 90 min in Biotage Initiator. The reaction mixture was cooled to rt then concentrated in vacuo. The residue was purified by flash chromatography (0-70% EtOAc/Hex gradient) to give the title compound (150 mg, 0.24 mmol). MS (ES) 627.1 (M+H).

Step B. Preparation of 6-chloro-3-(3-(4-chloro-3,5-dimethylphenoxy)propyl)-7-(3,5-dimethyl-1-(2-morpholinoethyl)-1H-pyrazol-4-yl)-1H-indole-2-carboxylic acid To a solution of ethyl 6-chloro-3-(3-(4-chloro-3,5-dimethylphenoxy)propyl)-7-(3,5-dimethyl-1-(2-morpholinoethyl)-1H-pyrazol-4-yl)-1H-indole-2-carboxylate (150 mg, 0.24 mmol) in a mixture of EtOH (2.0 mL) and THF (0.5 mL) was added LiOH (aq. 1.0 mL, 2N, 2.0 mmol). The resulting mixture was stirred at 40° C. for 20 h then cooled to rt. The reaction mixture was concentrated in vacuo, and the residue was purified by the reverse phase HPLC (Phenomenex Gemini C18, $H_2O$/$CH_3CN$ gradient from 30-80% $CH_3CN$, 0.1% TFA) to give the title compound (125 mg, 0.21 mmol) as colorless oil. MS (ES) 599.1 (M+H).

Step C. Example 190

A solution of 6-chloro-3-(3-(4-chloro-3,5-dimethylphenoxy)propyl)-7-(3,5-dimethyl-1-(2-morpholinoethyl)-1H-pyrazol-4-yl)-1H-indole-2-carboxylic acid (20 mg, 0.033 mmol), methyl 4-aminobenzoate (5.6 mg, 0.037 mmol), DMAP (8.2 mg, 0.067 mmol) and EDC (9.6 mg, 0.05 mmol) in DCM (0.7 mL) was stirred at rt for 16 h. The solution of crude product in EtOH (0.6 mL), THF (0.15 mL) and LiOH (0.1 mL) was stirred at 40° C. for 16 h. The reaction mixture was concentrated, and the residue was purified by the reverse phase HPLC (Phenomenex Gemini C18, $H_2O$/$CH_3CN$ gradient from 30-80% $CH_3CN$, 0.1% TFA) to give the title compound (4.4 mg, 0.006 mmol). MS (ES) 718.0 (M+H).

Example 191

Preparation of 3-(6-chloro-3-(3-(4-chloro-3,5-dimethylphenoxy)propyl)-7-(3,5-dimethyl-1-(2-morpholinoethyl)-1H-pyrazol-4-yl)-1H-indole-2-carboxamido)benzoic acid

I-191

A solution of 6-chloro-3-(3-(4-chloro-3,5-dimethylphenoxy)propyl)-7-(3,5-dimethyl-1-(2-morpholinoethyl)-1H-pyrazol-4-yl)-1H-indole-2-carboxylic acid (20 mg, 0.033 mmol), methyl 3-aminobenzoate (5.6 mg, 0.037 mmol), DMAP (8.2 mg, 0.067 mmol) and EDC (9.6 mg, 0.05 mmol) in DCM (0.7 mL) was stirred at rt for 16 h. EtOH (0.6 mL), THF (0.15 mL) and LiOH (0.1 mL) were added to the reaction solution and the resulting mixture was stirred at rt for 20 h. The reaction mixture was concentrated, and the residue was purified by the reverse phase HPLC (Phenomenex Gemini C18, $H_2O$/$CH_3CN$ gradient from 30-80% $CH_3CN$, 0.1% TFA) to give the title compound (9.0 mg, 0.013 mmol) as white solid. MS (ES) 718.0 (M+H).

Example 192

Preparation of 1-(6-chloro-3-(3-(4-chloro-3,5-dimethylphenoxy)propyl)-7-(1,3,5-trimethyl-1H-pyrazol-4-yl)-1H-indole-2-carbonyl)indoline-6-carboxylic acid

I-192

The title compound was prepared (8 mg, 0.012 mmol) according to procedures described in Example 36 using 6-chloro-3-(3-(4-chloro-3,5-dimethylphenoxy)propyl)-7-(1,3,5-trimethyl-1H-pyrazol-4-yl)-1H-indole-2-carboxylic acid (40 mg, 0.080 mmol), methyl indoline-6-carboxylate (21 mg, 0.120 mmol), DMAP (20 mg, 0.160 mmol) and EDC (23 mg, 0.120 mmol). MS (ES) 645.0 (M+H).

Example 193

Preparation of 3-(3-(3-(naphthalen-1-yloxy)propyl)-7-(1,3,5-trimethyl-1H-pyrazol-4-yl)-1H-indole-2-carboxamido)benzoic acid

I-193

The title compound was prepared (25 mg, 0.044 mmol) according to procedures described in Example 36 using 3-(3-(naphthalen-1-yloxy)propyl)-7-(1,3,5-trimethyl-1H-pyrazol-4-yl)-1H-indole-2-carboxylic acid (30 mg, 0.066 mmol), methyl 3-aminobenzoate (15 mg, 0.099 mmol), DMAP (16 mg, 0.132 mmol) and EDC (19 mg, 0.099 mmol). MS (ES) 573.1 (M+H). $^1$H NMR (400 MHz, DMSO-d6): δ 10.81 (s, 1H), 10.23 (s, 1H), 8.32 (t, J=1.8 Hz, 1H), 8.30-8.27 (m, 1H), 8.04-8.02 (m, 1H), 7.87-7.85 (m, 1H), 7.69-7.65 (comp, 2H), 7.54-7.43 (comp, 4H), 7.38 (d, J=7.8 Hz, 1H), 7.08 (t, J=7.4 Hz, 1H), 7.04 (dd, J=7.1, 1.2 Hz, 1H), 6.92 (d, J=7.2 Hz, 1H), 4.23 (t, J=6.0 Hz, 2H), 3.79 (s, 3H), 3.44 (t, J=7.5 Hz, 2H), 2.30-2.23 (m, 2H), 2.13 (s, 3H), 2.05 (s, 3H).

Example 194

Preparation of 5-(3-(3-(naphthalen-1-yloxy)propyl)-7-(1,3,5-trimethyl-1H-pyrazol-4-yl)-1H-indole-2-carboxamido)nicotinic acid

I-194

The title compound was prepared (17 mg, 0.030 mmol) according to procedures described in Example 36 using 3-(3-(naphthalen-1-yloxy)propyl)-7-(1,3,5-trimethyl-1H-pyrazol-4-yl)-1H-indole-2-carboxylic acid (30 mg, 0.066 mmol), methyl 5-aminonicotinate (15 mg, 0.099 mmol), DMAP (16 mg, 0.132 mmol) and EDC (19 mg, 0.099 mmol). MS (ES) 574.0 (M+H). $^1$H NMR (400 MHz, DMSO-d6): δ 10.79 (s, 1H), 10.42 (s, 1H), 9.09 (d, J=2.5 Hz, 1H), 8.81 (d, J=1.8 Hz, 1H), 8.68 (t, J=2.2 Hz, 1H), 8.29 (dd, J=7.6, 2.1 Hz, 1H), 7.86 (dd, J=6.5, 2.0 Hz, 1H), 7.69 (d, J=7.3 Hz, 1H), 7.54-7.46 (comp, 2H), 7.44 (d, J=8.2 Hz, 1H), 7.38 (t, J=8.0 Hz, 1H), 7.11 (t, J=7.5 Hz, 1H), 7.06 (dd, J=7.1, 1.2 Hz, 1H), 6.92 (d, J=7.0 Hz, 1H), 4.23 (t, J=6.0 Hz, 2H), 3.79 (s, 3H), 3.45 (t, J=7.4 Hz, 2H), 2.30-2.25 (m, 2H), 2.14 (s, 3H), 2.06 (s, 3H).

Example 195

Preparation of 3-(N-methyl-3-(3-(naphthalen-1-yloxy)propyl)-7-(1,3,5-trimethyl-1H-pyrazol-4-yl)-1H-indole-2-carboxamido)benzoic acid

I-195

The title compound was prepared (19 mg, 0.032 mmol) according to procedures described in Example 36 using 3-(3-(naphthalen-1-yloxy)propyl)-7-(1,3,5-trimethyl-1H-pyrazol-4-yl)-1H-indole-2-carboxylic acid (30 mg, 0.066 mmol), methyl 3-(methylamino)benzoate (16 mg, 0.099 mmol), DMAP (16 mg, 0.13 mmol) and EDC (19 mg, 0.099 mmol). MS (ES) 587.1 (M+H).

Example 196

Preparation of 3-(3-(3-(4-chloro-3,5-dimethylphenoxy)propyl)-7-(1,3,5-trimethyl-1H-pyrazol-4-yl)-1H-indole-2-carboxamido)benzoic acid

I-196

The title compound was prepared (29 mg, 0.050 mmol) according to procedures described in Example 36 using 3-(3-(4-chloro-3,5-dimethylphenoxy)propyl)-7-(1,3,5-trimethyl-1H-pyrazol-4-yl)-1H-indole-2-carboxylic acid (40 mg, 0.086 mmol), methyl 3-aminobenzoate (26 mg, 0.172 mmol), DMAP (21 mg, 0.172 mmol) and EDC (33 mg, 0.172 mmol). MS (ES) 585.1 (M+H). $^1$H NMR (400 MHz, DMSO-d6): δ 10.79 (s, 1H), 10.20 (s, 1H), 8.28 (t, J=1.8 Hz, 1H), 7.99 (ddd, J=8.2, 2.2, 0.9 Hz, 1H), 7.67 (dt, J=7.8, 1.3 Hz, 1H), 7.63 (d, J=7.7 Hz, 1H), 7.47 (d, J=7.8 Hz, 1H), 7.12 (t, J=7.5 Hz, 1H), 7.04 (dd, J=7.1, 1.1 Hz, 1H), 6.74 (s, 2H), 4.00 (t, J=6.3 Hz, 2H), 3.78 (s, 3H), 3.29 (t, J=7.3 Hz, 2H), 2.24 (s, 6H), 2.13 (s, 3H), 2.10-2.07 (m, 2H), 2.05 (s, 3H).

Example 197

Preparation of 3-(3-(3-(4-chloro-3,5-dimethylphenoxy)propyl)-N-methyl-7-(1,3,5-trimethyl-1H-pyrazol-4-yl)-1H-indole-2-carboxamido)benzoic acid

I-197

The title compound was prepared (13 mg, 0.022 mmol) according to procedures described in Example 1 using 3-(3-(4-chloro-3,5-dimethylphenoxy)propyl)-7-(1,3,5-trimethyl-1H-pyrazol-4-yl)-1H-indole-2-carboxylic acid (40 mg, 0.086 mmol), methyl 3-(methylamino)benzoate (28 mg, 0.172 mmol), DMAP (21 mg, 0.172 mmol) and EDC (33 mg, 0.172 mmol). MS (ES) 599.1 (M+H).

Example 198

Preparation of 5-(7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)nicotinic acid

I-198

The title compound was prepared (20 mg, 0.031 mmol) according to procedures described in Example 175 using methyl 5-(6-chloro-3-(3-(4-chloro-3,5-dimethylphenoxy)propyl)-7-(1,3,5-trimethyl-1H-pyrazol-4-yl)-1H-indole-2-carboxamido)nicotinate (38 mg, 0.060 mmol), 1,2-dibromoethane (26 µL, 0.299 mmol), Cs$_2$CO$_3$ (195 mg, 0.60 mmol). MS (ES) 646.0 (M+H). $^1$H NMR (400 MHz, DMSO-d6): δ 8.93 (s, 1H), 8.86 (s, 1H), 8.31 (s, 1H), 7.76 (d, J=8.0 Hz, 1H), 7.28 (d, J=8.0 Hz, 1H), 6.75 (s, 2H), 4.09-4.06 (m, 2H), 4.00 (t, J=6.0 Hz, 2H), 3.89-3.85 (m, 2H), 3.77 (s, 3H), 3.26 (t, J=8.0 Hz, 2H), 2.26 (s, 6H), 2.08-2.05 (m, 2H), 2.03 (s, 3H), 1.93 (s, 3H).

Example 199

Preparation of 5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)nicotinic acid

I-199

The title compound was prepared (5.7 mg, 0.009 mmol) according to procedures described in Example 175 using methyl 5-(6-chloro-3-(3-(4-chloro-3,5-dimethylphenoxy)propyl)-7-(1,3,5-trimethyl-1H-pyrazol-4-yl)-1H-indole-2-carboxamido)nicotinate (32 mg, 0.050 mmol), 1,3-dibromopropane (26 µL, 0.25 mmol), Cs2CO3 (164 mg, 0.50 mmol). MS (ES) 660.0 (M+H).

Example 200

Preparation of 2-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)isonicotinic acid

I-200

The title compound was prepared (6 mg, 0.009 mmol) according to procedures described in Example 175 using methyl 2-(6-chloro-3-(3-(4-chloro-3,5-dimethylphenoxy)propyl)-7-(1,3,5-trimethyl-1H-pyrazol-4-yl)-1H-indole-2-carboxamido)isonicotinate (60 mg, 0.095 mmol), 1,3-dibromopropane (48 μL, 0.47 mmol), Cs$_2$CO$_3$ (308 mg, 0.95 mmol). MS (ES) 660.0 (M+H).

Example 201

Preparation of 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)nicotinic acid

I-201

The title compound was prepared (5.6 mg) according to procedures described in Example 175 using methyl 6-(6-chloro-3-(3-(4-chloro-3,5-dimethylphenoxy)propyl)-7-(1,3,5-trimethyl-1H-pyrazol-4-yl)-1H-indole-2-carboxamido)nicotinate (40 mg, 0.063 mmol), 1,3-dibromopropane (32 μL, 0.315 mmol), Cs$_2$CO$_3$ (205 mg, 0.63 mmol). MS (ES) 660.0 (M+H).

Example 202

Preparation of 1-(3-(3-(4-chloro-3,5-dimethylphenoxy)propyl)-7-(1,3,5-trimethyl-1H-pyrazol-4-yl)-1H-indole-2-carbonyl)indoline-4-carboxylic acid

I-202

The title compound was prepared (36 mg, 0.059 mmol) according to procedures described in Example 36 using 3-(3-(4-chloro-3,5-dimethylphenoxy)propyl)-7-(1,3,5-trimethyl-1H-pyrazol-4-yl)-1H-indole-2-carboxylic acid (40 mg, 0.086 mmol), methyl indoline-4-carboxylate (30 mg, 0.17 mmol), DMAP (21 mg, 0.17 mmol) and EDC (33 mg, 0.17 mmol). MS (ES) 611.1 (M+H).

Example 203

Preparation of 1-(3-(3-(4-chloro-3,5-dimethylphenoxy)propyl)-7-(1,3,5-trimethyl-1H-pyrazol-4-yl)-1H-indole-2-carbonyl)piperidine-4-carboxylic acid

I-203

The title compound was prepared (38 mg, 0.066 mmol) according to procedures described in Example 36 using 3-(3-(4-chloro-3,5-dimethylphenoxy)propyl)-7-(1,3,5-trimethyl-1H-pyrazol-4-yl)-1H-indole-2-carboxylic acid (40 mg, 0.086 mmol), methyl piperidine-4-carboxylate (25 mg, 0.172 mmol), DMAP (21 mg, 0.172 mmol) and EDC (33 mg, 0.172 mmol). MS (ES) 577.1 (M+H).

Example 204

Preparation of 2-(1-(3-(3-(4-chloro-3,5-dimethylphenoxy)propyl)-7-(1,3,5-trimethyl-1H-pyrazol-4-yl)-1H-indole-2-carbonyl)piperidin-4-yl)acetic acid

I-204

The title compound was prepared (26 mg, 0.044 mmol) according to procedures described in Example 36 using 3-(3-(4-chloro-3,5-dimethylphenoxy)propyl)-7-(1,3,5-trimethyl-1H-pyrazol-4-yl)-1H-indole-2-carboxylic acid (40 mg, 0.086 mmol), ethyl 2-(piperidin-4-yl)acetate (29 mg, 0.172 mmol), DMAP (21 mg, 0.172 mmol) and EDC (33 mg, 0.172 mmol). MS (ES) 591.1 (M+H).

Example 205

Preparation of 2-(4-(3-(3-(4-chloro-3,5-dimethylphenoxy)propyl)-7-(1,3,5-trimethyl-1H-pyrazol-4-yl)-1H-indole-2-carboxamido)phenyl)acetic acid

I-205

The title compound was prepared (37 mg, 0.063 mmol) according to procedures described in Example 36 using 3-(3-(4-chloro-3,5-dimethylphenoxy)propyl)-7-(1,3,5-trimethyl-1H-pyrazol-4-yl)-1H-indole-2-carboxylic acid (40 mg, 0.086 mmol), methyl 2-(4-aminophenyl)acetate (28 mg, 0.17 mmol), DMAP (21 mg, 0.17 mmol) and EDC (33 mg, 0.17 mmol). MS (ES) 599.1 (M+H).

Example 206

Preparation of 2-(3-(3-(3-(4-chloro-3,5-dimethylphenoxy)propyl)-7-(1,3,5-trimethyl-1H-pyrazol-4-yl)-1H-indole-2-carboxamido)phenyl)acetic acid

I-206

The title compound was prepared (45 mg, 0.075 mmol) according to procedures described in Example 36 using 3-(3-(4-chloro-3,5-dimethylphenoxy)propyl)-7-(1,3,5-trimethyl-1H-pyrazol-4-yl)-1H-indole-2-carboxylic acid (40 mg, 0.086 mmol), methyl 2-(3-aminophenyl)acetate (28 mg, 0.17 mmol), DMAP (21 mg, 0.172 mmol) and EDC (33 mg, 0.17 mmol). MS (ES) 599.1 (M+H). $^1$H NMR (400 MHz, DMSO-d$_6$): δ 10.82 (s, 1H), 10.04 (s, 1H), 7.65-7.62 (comp, 2H), 7.58 (s, 1H), 7.29 (t, J=7.8 Hz, 1H), 7.12 (t, J=7.5 Hz, 1H), 7.04 (d, J=7.0 Hz, 1H), 7.00 (d, J=7.6 Hz, 1H), 6.76 (s, 2H), 4.00 (t, J=6.1 Hz, 2H), 3.79 (s, 3H), 3.58 (s, 2H), 3.29 (t, J=7.4 Hz, 2H), 2.26 (s, 6H), 2.13 (s, 3H), 2.10-2.07 (m, 2H), 2.06 (s, 3H).

Example 207

Preparation of 3-(6-chloro-3-(3-(4-chloro-3,5-dimethylphenoxy)propyl)-7-(1,3,5-trimethyl-1H-pyrazol-4-yl)-1H-indole-2-carboxamido)-5-(4-methylpiperazin-1-yl)benzoic acid

I-207

The title compound was prepared (9.1 mg, 0.013 mmol) according to procedures described in Example 36 using 6-chloro-3-(3-(4-chloro-3,5-dimethylphenoxy)propyl)-7-(1,3,5-trimethyl-1H-pyrazol-4-yl)-1H-indole-2-carboxylic acid (99 mg, 0.20 mmol), methyl 3-amino-5-(4-methylpiperazin-1-yl)benzoate (54 mg, 0.22 mmol), DMAP (48 mg, 0.39 mmol) and EDC (75 mg, 0.39 mmol). MS (ES) 717.1 (M+H).

Example 208

Preparation of 3-(6-chloro-3-(3-(4-chloro-3,5-dimethylphenoxy)propyl)-7-(1,3,5-trimethyl-1H-pyrazol-4-yl)-1H-indole-2-carboxamido)-5-morpholinobenzoic acid

I-208

The title compound was prepared (23 mg, 0.032 mmol) according to procedures described in Example 36 using 6-chloro-3-(3-(4-chloro-3,5-dimethylphenoxy)propyl)-7-(1,3,5-trimethyl-1H-pyrazol-4-yl)-1H-indole-2-carboxylic acid (68 mg, 0.136 mmol), methyl 3-amino-5-morpholinobenzoate (35.3 mg, 0.149 mmol), DMAP (33.2 mg, 0.272 mmol) and EDC (52.1 mg, 0.272 mmol). MS (ES) 704.1 (M+H).

Example 209

Preparation of 3-(6-chloro-3-(3-(4-chloro-3,5-dimethylphenoxy)propyl)-7-(1,3,5-trimethyl-1H-pyrazol-4-yl)-1H-indole-2-carboxamido)-5-((tetrahydro-2H-pyran-4-yl)amino)benzoic acid

I-209

The title compound was prepared (13 mg, 0.019 mmol) according to procedures described in Example 36 using 6-chloro-3-(3-(4-chloro-3,5-dimethylphenoxy)propyl)-7-(1,3,5-trimethyl-1H-pyrazol-4-yl)-1H-indole-2-carboxylic acid (73 mg, 0.15 mmol), methyl 3-amino-5-((tetrahydro-2H-pyran-4-yl)amino)benzoate (40 mg, 0.16 mmol), DMAP (36 mg, 0.29 mmol) and EDC (56 mg, 0.29 mmol). MS (ES) 718.0 (M+H).

Example 210

Preparation of 3-(6-chloro-3-(3-(4-chloro-3,5-dimethylphenoxy)propyl)-7-(1,3,5-trimethyl-1H-pyrazol-4-yl)-1H-indole-2-carboxamido)-5-((2-(dimethylamino)ethyl)(methyl)amino)benzoic acid

I-210

The title compound was prepared (19 mg, 0.026 mmol) according to procedures described in Example 36 using 6-chloro-3-(3-(4-chloro-3,5-dimethylphenoxy)propyl)-7-(1,3,5-trimethyl-1H-pyrazol-4-yl)-1H-indole-2-carboxylic acid (116 mg, 0.23 mmol), methyl 3-amino-5-((2-(dimethylamino)ethyl)(methyl)amino)benzoate (70 mg, 0.28 mmol), DMAP (57 mg, 0.46 mmol) and EDC (89 mg, 0.46 mmol). MS (ES) 719.1 (M+H).

Example 211

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-((2-(dimethylamino)ethyl)(methyl)amino)benzoic acid

I-211

The title compound was prepared (6.3 mg, 0.008 mmol) according to procedures described in Example 175 using methyl 3-(6-chloro-3-(3-(4-chloro-3,5-dimethylphenoxy)propyl)-7-(1,3,5-trimethyl-1H-pyrazol-4-yl)-1H-indole-2-carboxamido)-5-((2-(dimethylamino)ethyl)(methyl)amino)benzoate (60 mg, 0.082 mmol), 1,3-dibromopropane (42 µL, 0.41 mmol), $Cs_2CO_3$ (266 mg, 0.82 mmol). MS (ES) 759.1 (M+H).

Example 212

Preparation of 4-(6-chloro-3-(3-(4-chloro-3,5-dimethylphenoxy)propyl)-N-methyl-7-(1,3,5-trimethyl-1H-pyrazol-4-yl)-1H-indole-2-carboxamido)benzoic acid

I-212

The title compound was prepared (12 mg, 0.019 mmol) according to procedures described in Example 179 A and B using 6-chloro-3-(3-(4-chloro-3,5-dimethylphenoxy)propyl)-7-(1,3,5-trimethyl-1H-pyrazol-4-yl)-1H-indole-2-carbonyl chloride (40 mg, 0.077 mmol), methyl 4-(methylamino)benzoate (26 mg, 0.15 mmol), DMAP (19 mg, 0.15 mmol) and pyridine (6.2 µL, 0.077 mmol). MS (ES) 619.9 (M+H).

Example 213

Preparation of 3-(7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)-5-morpholinobenzoic acid

I-213

The title compound was prepared (10 mg, 0.014 mmol) according to procedures described in Example 179 A and B using methyl 3-(6-chloro-3-(3-(4-chloro-3,5-dimethylphenoxy)propyl)-7-(1,3,5-trimethyl-1H-pyrazol-4-yl)-1H-indole-2-carboxamido)-5-morpholinobenzoate (42 mg, 0.058 mmol), 1,2-dibromoethane (25 µL, 0.29 mmol) and $Cs_2CO_3$ (190 mg, 0.58 mmol). MS (ES) 730.0 (M+H).

Example 214

Preparation of 3-(7-chloro-10-(3-(4-chloro-3,5-dimethylphenoxy)propyl)-1-oxo-6-(1,3,5-trimethyl-1H-pyrazol-4-yl)-3,4-dihydropyrazino[1,2-a]indol-2(1H)-yl)-5-((tetrahydro-2H-pyran-4-yl)amino)benzoic acid

I-214

The title compound was prepared (11 mg, 0.015 mmol) according to procedures described in Example 179 A and B using methyl 3-(6-chloro-3-(3-(4-chloro-3,5-dimethylphenoxy)propyl)-7-(1,3,5-trimethyl-1H-pyrazol-4-yl)-1H-indole-2-carboxamido)-5-((tetrahydro-2H-pyran-4-yl)amino)benzoate (43 mg, 0.059 mmol), 1,2-dibromoethane (25 µL, 0.29 mmol) and $Cs_2CO_3$ (191 mg, 0.59 mmol). MS (ES) 744.1 (M+H).

Example 215

Preparation of 3-(6-chloro-3-(3-(4-chloro-3,5-dimethylphenoxy)propyl)-7-(1,3,5-trimethyl-1H-pyrazol-4-yl)-1H-indole-2-carboxamido)-5-(dimethylamino)benzoic acid

I-215

The title compound was prepared (7 mg, 0.011 mmol) according to procedures described in Example 36 using of 6-chloro-3-(3-(4-chloro-3,5-dimethylphenoxy)propyl)-7-(1,3,5-trimethyl-1H-pyrazol-4-yl)-1H-indole-2-carboxylic acid (100 mg, 0.20 mmol), methyl 3-amino-5-(dimethylamino)benzoate (43 mg, 0.22 mmol), DMAP (49 mg, 0.40 mmol) and EDC (77 mg, 0.40 mmol). MS (ES) 662.1 (M+H).

Example 216

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(dimethylamino)benzoic acid

I-216

The title compound was prepared (16 mg, 0.023 mmol) according to procedures described in Example 179 A and B using methyl 3-(6-chloro-3-(3-(4-chloro-3,5-dimethylphenoxy)propyl)-7-(1,3,5-trimethyl-1H-pyrazol-4-yl)-1H-indole-2-carboxamido)-5-(dimethylamino)benzoate (42 mg, 0.062 mmol), 1,3-dibromopropane (32 μL, 0.31 mmol) and Cs$_2$CO$_3$ (202 mg, 0.62 mmol). MS (ES) 702.0 (M+H).

Example 217

Preparation of 3-bromo-5-(6-chloro-3-(3-(4-chloro-3,5-dimethylphenoxy)propyl)-7-(1,3,5-trimethyl-1H-pyrazol-4-yl)-1H-indole-2-carboxamido)benzoic acid

I-217

Step A. Preparation of methyl 3-bromo-5-(6-chloro-3-(3-(4-chloro-3,5-dimethylphenoxy)propyl)-7-(1,3,5-trimethyl-1H-pyrazol-4-yl)-1H-indole-2-carboxamido)benzoate A solution of 6-chloro-3-(3-(4-chloro-3,5-dimethylphenoxy)propyl)-7-(1,3,5-trimethyl-1H-pyrazol-4-yl)-1H-indole-2-carboxylic acid (200 mg, 0.40 mmol), methyl 3-amino-5-bromobenzoate (101 mg, 0.44 mmol), DMAP (98 mg, 0.80 mmol) and EDC (153 mg, 0.80 mmol) in DCM (8.0 mL) was stirred at rt for 16 h. The reaction mixture was concentrated in vacuo, and the residue was purified by silica gel flash chromatography (ISCO, 0-70% EtOAc/Hex gradient) to give title compound (255 mg, 0.36 mmol). MS (ES) 712.9 (M+H).

Step B. Example 217

To a solution of methyl 3-bromo-5-(6-chloro-3-(3-(4-chloro-3,5-dimethylphenoxy)propyl)-7-(1,3,5-trimethyl-1H-pyrazol-4-yl)-1H-indole-2-carboxamido) (25 mg, 0.035 mol) in a mixture of EtOH (0.6 mL), THF (0.15 mL) was added LiOH (aq. 0.1 mL, 2N, 0.20 mmol) at rt. The reaction mixture was stirred for 20 h at rt then concentrated in vacuo. The residue was purified by the reverse phase HPLC (Phenomenex Gemini C18, H$_2$O/CH$_3$CN gradient from 30-90% CH$_3$CN, 0.1% TFA) to give the title compound (16.7 mg, 0.024 mmol) as white solid. MS (ES) 698.8 (M+H).

Example 218

Preparation of 3-bromo-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoic acid

I-218

Step A. Preparation of methyl 3-bromo-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoate A solution of methyl 3-bromo-5-(6-chloro-3-(3-(4-chloro-3,5-dimethylphenoxy)propyl)-7-(1,3,5-trimethyl-1H-pyrazol-4-yl)-1H-indole-2-carboxamido)benzoate (230 mg, 0.323 mmol), 1,3-dibromopropane (164 μL, 1.6 mmol), Cs$_2$CO$_3$ (1.05 g, 3.2 mmol) in DMF (6.5 mL) was stirred at 100° C. for 16 h. The Cs$_2$CO$_3$ was filtered, and the filtrate was concentrated in vacuo. The residue was purified by silica gel flash chromatography (ISCO 0-70% EtOAc/Hex gradient) to give the title compound (110 mg, 0.15 mmol). MS (ES) 752.9 (M+H).

Step B. Example 218

To a solution of methyl 3-bromo-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoate (20 mg, 0.027 mmol) in THF (266 μL) was added LiOH (aq. 2N, 66.4 μL, 0.133 mmol) at rt. The reaction mixture was stirred for 20 h at rt then concentrated. The residue was purified by the reverse phase HPLC (Phenomenex Gemini C18, H$_2$O/CH$_3$CN gradient from 40-95% CH$_3$CN, 0.1% TFA) to give title compound (10 mg, 0.014 mmol). MS (ES) 738.9 (M+H).

Example 219

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(4-methylpiperazin-1-yl)benzoic acid

I-219

Step A. Preparation of methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(4-methylpiperazin-1-yl)benzoate A solution of methyl 3-bromo-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoate (37 mg, 0.049 mmol), 1-methylpiperazine (7.39 mg, 0.074 mmol), BINAP (3.06 mg, 4.92 μmol) and Cs$_2$CO$_3$ (48.1 mg, 0.148 mmol) in Toluene (500 μL) was degassed under Argon for 10 min. palladium(II) acetate (1.1 mg, 4.9 μmol) was added and the resulting mixture was then heated to 100° C. for 16 h. The reaction mixture was filtered, and the filtrate was purified by the reverse phase HPLC (Phenomenex Gemini C18, H$_2$O/

CH₃CN gradient from 30-80% CH₃CN, 0.1% NH₄OH) to give the title compound (5 mg) as a brown solid. MS (ES) 771.1 (M+H).

Step B. Example 219

To a solution of methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(4-methylpiperazin-1-yl)benzoate (5 mg, 0.006 mmol) in a mixture of EtOH (100 μL) and THF (50 μL) was added LiOH (aq. 30 μL, 2N). The reaction mixture was stirred at 40° C. for 15 h, acidified by addition of TFA and concentrated. The residue was purified by the reverse phase HPLC (Phenomenex Gemini C18, H₂O/CH₃CN gradient from 30-80% CH₃CN, 0.1% NH₄OH) to give the title compound (3 mg). MS (ES) 757.0 (M+H).

Example 220

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-methylbenzoic acid

I-220

Step A. Preparation of methyl 3-(6-chloro-3-(3-(4-chloro-3,5-dimethylphenoxy)propyl)-7-(1,3,5-trimethyl-1H-pyrazol-4-yl)-1H-indole-2-carboxamido)-5-methylbenzoate A solution of 6-chloro-3-(3-(4-chloro-3,5-dimethylphenoxy)propyl)-7-(1,3,5-trimethyl-1H-pyrazol-4-yl)-1H-indole-2-carboxylic acid (100 mg, 0.200 mmol), methyl 3-amino-5-methylbenzoate (36 mg, 0.220 mmol), DMAP (49 mg, 0.400 mmol) and EDC (77 mg, 0.400 mmol) in DCM (4 mL) was stirred at rt for 16 h. The reaction mixture was concentrated in vacuo, and the residue was purified by silica gel flash chromatography (ISCO, 0-60% EtOAc/Hex gradient) to give the title compound (48 mg, 0.074 mmol). MS (ES) 647.1 (M+H).

Step B. Preparation of methyl 3-(8-chloro-11-(3-(4-chloro-3,5-dimethylphenoxy)propyl)-1-oxo-7-(1,3,5-trimethyl-1H-pyrazol-4-yl)-4,5-dihydro-H-[1,4]diazepino[1,2-a]indol-2(3H)-yl)-5-methylbenzoate A solution of methyl 3-(6-chloro-3-(3-(4-chloro-3,5-dimethylphenoxy)propyl)-7-(1,3,5-trimethyl-1H-pyrazol-4-yl)-1H-indole-2-carboxamido)-5-methylbenzoate (48 mg, 0.074 mmol), 1,3-dibromopropane (38 μL, 0.371 mmol), Cs₂CO₃ (241 mg, 0.74 mmol) in DMF (15 mL) was stirred at 100° C. for 16 h. The reaction mixture was cooled to rt, filtered, and the filtrate was concentrated. The residue was purified by silica gel flash chromatography (ISCO, 0-70% EtOAc/Hex gradient) to give the title compound (24 mg, 0.035 mmol). MS (ES) 687.0 (M+H).

Step C. Example 220

To a solution of methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-methylbenzoate (24 mg, 0.035 mmol) in THF (350 μl) was added LiOH (aq. 2N, 87 μL, 0.175 mmol). The reaction mixture was stirred at rt for 20 h then concentrated. The residue was purified by the reverse phase HPLC (Phenomenex Gemini C18, H₂O/CH₃CN gradient from 40-90% CH₃CN, 0.1% TFA) to give the title compound (8.2 mg, 0.012 mmol). MS (ES) 673.0 (M+H).

Example 221

Preparation of 3-chloro-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoic acid

I-221

Step A. Preparation of methyl 3-chloro-5-(6-chloro-3-(3-(4-chloro-3,5-dimethylphenoxy)propyl)-7-(1,3,5-trimethyl-1H-pyrazol-4-yl)-1H-indole-2-carboxamido)benzoate The title compound was prepared (73 mg, 0.109 mmol) according to procedures described in Example 220 Step A using of 6-chloro-3-(3-(4-chloro-3,5-dimethylphenoxy)propyl)-7-(1,3,5-trimethyl-1H-pyrazol-4-yl)-1H-indole-2-carboxylic acid (80 mg, 0.160 mmol), methyl 3-amino-5-chlorobenzoate (32.6 mg, 0.176 mmol), DMAP (39.1 mg, 0.320 mmol) and EDC (61.3 mg, 0.320 mmol). MS (ES) 667.0 (M+H).

Step B. Example 221

A solution of methyl 3-chloro-5-(6-chloro-3-(3-(4-chloro-3,5-dimethylphenoxy)propyl)-7-(1,3,5-trimethyl-1H-pyrazol-4-yl)-1H-indole-2-carboxamido)benzoate (73 mg, 0.109 mmol), 1,3-dibromopropane (0.033 ml, 0.328 mmol), Cs₂CO₃ (178 mg, 0.546 mmol) in DMF (1 mL) was stirred at 60° C. for 2 h. The reaction mixture was filtered and the filtrate was concentrated. The residue was dissolved in THF (0.5 mL) and LiOH (aq. 0.3 mL, 2N). The reaction mixture was stirred at 40° C. for 15 h then concentrated. The residue was purified by the reverse phase HPLC (Phenomenex Gemini C18, H₂O/CH₃CN gradient from 40-90% CH₃CN, 0.1% TFA) to give title compound (17 mg, 0.024 mmol). MS (ES) 693.0 (M+H), ¹H NMR (400 MHz, DMSO-d₆): δ 7.88 (m, 1H), 7.79 (m, 1H), 7.73-7.71 (comp, 2H), 7.27 (d, J=8.0 Hz, 1H), 6.73 (s, 2H), 4.01 (t, J=8.0 Hz, 2H), 3.94 (t, J=6.0 Hz, 2H), 3.78 (s, 3H), 3.63 (t, J=6.0 Hz, 2H), 3.06 (t, J=8.0 Hz, 2H), 2.23 (s, 6H), 2.09-2.06 (m, 2H), 2.01 (s, 3H), 1.91 (s, 3H), 1.77 (t, 2H).

Example 222

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(trifluoromethyl)benzoic acid

I-222

Step A. Preparation of methyl 3-(6-chloro-3-(3-(4-chloro-3,5-dimethylphenoxy)propyl)-7-(1,3,5-trimethyl-1H-pyrazol-4-yl)-1H-indole-2-carboxamido)-5-(trifluoromethyl)benzoate The title compound was prepared (72 mg, 0.10 mmol) according to procedures described in Example 220 Step A using of 6-chloro-3-(3-(4-chloro-3,5-dimethylphenoxy)propyl)-7-(1,3,5-trimethyl-1H-pyrazol-4-yl)-1H-indole-2-carboxylic acid (80 mg, 0.16 mmol), methyl 3-amino-5-(trifluoromethyl)benzoate (38 mg, 0.18 mmol), DMAP (39 mg, 0.32 mmol) and EDC (61 mg, 0.32 mmol). MS (ES) 700.9 (M+H).

Step B. Example 222

A solution of methyl 3-(6-chloro-3-(3-(4-chloro-3,5-dimethylphenoxy)propyl)-7-(1,3,5-trimethyl-1H-pyrazol-4-yl)-1H-indole-2-carboxamido)-5-(trifluoromethyl)benzoate (72 mg, 0.10 mmol), 1,3-dibromopropane (0.031 mL, 0.31 mmol), $Cs_2CO_3$ (167 mg, 0.51 mmol) in DMF (1 mL) was stirred at 60° C. for 2 h. The reaction mixture was filtered and the filtrate was concentrated. The residue was dissolved in THF (0.5 mL), and LiOH (aq. 2N, 0.3 mL, 0.6 mmol). The reaction mixture was stirred at 40° C. for 15 h then concentrated. The residue was purified by the reverse phase HPLC (Phenomenex Gemini C18, $H_2O/CH_3CN$ gradient from 40-90% $CH_3CN$, 0.1% TFA) to give the title compound (15 mg, 0.021 mmol). MS (ES) 727.0 (M+H), $^1H$ NMR (400 MHz, DMSO-$d_6$): δ 8.16 (s, 1H), 8.05 (s, 1H), 7.97 (s, 1H), 7.72 (d, J=8.0 Hz, 1H), 7.27 (d, J=8.0 Hz, 1H), 6.73 (s, 2H), 4.04 (t, J=8.0 Hz, 2H), 3.96 (t, J=6.0 Hz, 2H), 3.78 (s, 3H), 3.67 (t, J=6.0 Hz, 2H), 3.06 (t, J=8.0 Hz, 2H), 2.22 (s, 6H), 2.09-2.06 (m, 2H), 2.02 (s, 3H), 1.91 (s, 3H), 1.80-1.76 (m, 2H).

Example 223

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-fluorobenzoic acid

I-223

Step A. Preparation of methyl 3-(6-chloro-3-(3-(4-chloro-3,5-dimethylphenoxy)propyl)-7-(1,3,5-trimethyl-1H-pyrazol-4-yl)-1H-indole-2-carboxamido)-5-fluorobenzoate The title compound was prepared (75 mg, 0.115 mmol) according to procedures described in Example 220 Step A using 6-chloro-3-(3-(4-chloro-3,5-dimethylphenoxy)propyl)-7-(1,3,5-trimethyl-1H-pyrazol-4-yl)-1H-indole-2-carboxylic acid (80 mg, 0.16 mmol), methyl 3-amino-5-fluorobenzoate (41 mg, 0.24 mmol), DMAP (39 mg, 0.32 mmol) and EDC (61 mg, 0.32 mmol). MS (ES) 651.0 (M+H).

Step B. Example 223

A solution of methyl 3-(6-chloro-3-(3-(4-chloro-3,5-dimethylphenoxy)propyl)-7-(1,3,5-trimethyl-1H-pyrazol-4-yl)-1H-indole-2-carboxamido)-5-fluorobenzoate (75 mg, 0.11 mmol), 1,3-dibromopropane (0.035 mL, 0.34 mmol), $Cs_2CO_3$ (188 mg, 0.58 mmol) in DMF (2 mL) was stirred at 60° C. for 2 h. The reaction mixture was filtered and the filtrate was concentrated. The residue was dissolved in THF (0.5 mL) and LiOH (aq. 2N 0.3 mL, 0.6 mmol) was added. The reaction mixture was stirred at 40° C. for 15 h then concentrated. The residue was purified by the reverse phase HPLC (Phenomenex Gemini C18, $H_2O/CH_3CN$ gradient from 30-85% $CH_3CN$, 0.1% TFA) to give the title compound (28 mg, 0.041 mmol). MS (ES) 677.0 (M+H).

Example 224

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(hydroxymethyl)benzoic acid

I-224

Step A. Preparation of methyl 3-(((tert-butyldimethylsilyl)oxy)methyl)-5-(6-chloro-3-(3-(4-chloro-3,5-dimethylphenoxy)propyl)-7-(1,3,5-trimethyl-1H-pyrazol-4-yl)-1H-indole-2-carboxamido)benzoate The title compound was prepared (75 mg, 0.12 mmol) according to procedures described in Example 220 Step A using 6-chloro-3-(3-(4-chloro-3,5-dimethylphenoxy)propyl)-7-(1,3,5-trimethyl-1H-pyrazol-4-yl)-1H-indole-2-carboxylic acid (230 mg, 0.46 mmol), methyl 3-amino-5-(((tert-butyldimethylsilyl)oxy)methyl)benzoate (149 mg, 0.51 mmol), DMAP (112 mg, 0.92 mmol) and EDC (176 mg, 0.92 mmol). MS (ES) 777.1 (M+H).

Step B. Preparation of methyl 3-(8-chloro-11-(3-(4-chloro-3,5-dimethylphenoxy)propyl)-1-oxo-7-(1,3,5-trimethyl-1H-pyrazol-4-yl)-4,5-dihydro-H-[1,4]diazepino[1,2-a]indol-2(3H)-yl)-5-(hydroxymethyl)benzoate A solution of methyl 3-(((tert-butyldimethylsilyl)oxy)methyl)-5-(6-chloro-3-(3-(4-chloro-3,5-dimethylphenoxy)propyl)-7-(1,3,5-trimethyl-1H-pyrazol-4-yl)-1H-indole-2-carboxamido)benzoate (240 mg, 0.31 mmol), 1,3-dibromopropane (0.157 mL, 1.54 mmol), $Cs_2CO_3$ (503 mg, 1.54 mmol) in DMF (4 mL) was stirred at 60° C. for 2 h. The reaction mixture was filtered, and the filtrate was concentrated. The residue was dissolved in THF (5 mL), and TBAF (1 mL, 1.0 mmol, 1M in THF) was added. The reaction mixture was stirred at rt for 1 h then concentrated. The residue was purified by silica gel flash chromatography (ISCO 0-15% MeOH/DCM gradient) to give the title compound (214 mg, 0.30 mmol). MS (ES) 703.0 (M+H).

Step C. Example 224

To a solution of methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(hydroxymethyl)benzoate (40 mg, 0.057 mmol) in THF (0.6 mL) was added LiOH (aq. 2N, 140 µL, 0.28 mmol). The reaction mixture was stirred at rt for 20 h then concentrated. The residue was purified by the reverse phase HPLC (Phenomenex Gemini C18, $H_2O/CH_3CN$ gradient from 30-80% $CH_3CN$, 0.1% TFA) to give the title compound (28 mg, 0.041 mmol). MS (ES) 689.1 (M+H), $^1H$ NMR (400 MHz, DMSO-$d_6$): δ 7.84 (s, 1H), 7.81 (s, 1H), 7.71 (d, J=8.0 Hz, 1H), 7.51 (s, 1H), 7.26 (d, J=8.0 Hz, 1H), 6.74 (s, 2H), 2.51 (s, 2H), 4.02-3.94 (comp, J=4H), 3.78 (s, 3H), 3.60 (t, J=6.0 Hz, 2H), 3.05 (t, J=8.0 Hz, 2H), 2.28 (s, 6H), 2.08-2.06 (m, 2H), 2.01 (s, 3H), 1.91 (s, 3H), 1.80-1.76 (m, 2H).

Example 225

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(pyrrolidin-1-ylmethyl)benzoic acid

I-225

A solution of methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2 (3H)-yl)-5-(hydroxymethyl)benzoate (30 mg, 0.043 mmol), DIPEA (15 µL, 0.085 mmol) and MsCl (6.6 µl, 0.085 mmol) in DCM (400 µL) was stirred at 0° C. for 1 h then pyrrolidine (35 µL, 0.43 mmol) was added. The resulting mixture was warmed to rt, stirred additional 1 h then concentrated. The residue was dissolved in THF (0.2 mL) and LiOH (aq. 2N, 0.1 mL, 0.2 mmol) was added. The mixture was stirred at 40° C. for 15 h then concentrated. The residue was purified by the reverse phase HPLC (Phenomenex Gemini C18, $H_2O/CH_3CN$ gradient from 30-80% $CH_3CN$, 0.1% $NH_4OH$) to give the title compound (8.5 mg, 0.011 mmol). MS (ES) 742.0 (M+H).

Example 226

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-((dimethylamino)methyl)benzoic acid

I-226

The title compound was prepared (9 mg, 0.013 mmol) according to procedures described in Example 225 using methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(hydroxymethyl)benzoate (20 mg, 0.028 mmol), DIPEA (15 µL, 0.085 mmol) and MsCl (4.4 µL, 0.057 mmol) and dimethylamine (1M, 85 µL, 0.085 mmol). MS (ES) 716.1 (M+H), $^1$H NMR (400 MHz, DMSO-$d_6$): δ 8.10 (s, 1H), 8.02 (s, 1H), 7.77 (s, 1H), 7.73 (d, J=8.0 Hz, 1H), 7.28 (d, J=8.0 Hz, 1H), 6.73 (s, 2H), 4.36 (d, J=4.0 Hz, 2H), 4.02-3.94 (comp, 4H), 3.78 (s, 3H), 3.65 (t, J=6.0 Hz, 2H), 3.07 (t, J=6.0 Hz, 2H), 2.77 (s, 3H), 2.76 (s, 3H), 2.22 (s, 6H), 2.08-2.06 (m, 2H), 2.02 (s, 3H), 1.92 (s, 3H), 1.85-1.80 (m, 2H).

Example 227

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(morpholinomethyl)benzoic acid

I-227

The title compound was prepared (20 mg, 0.026 mmol) according to procedures described in Example 225 using of methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(hydroxymethyl)benzoate (30 mg, 0.043 mmol), DIPEA (15 µL, 0.085 mmol) and MsCl (6.6 µL, 0.085 mmol) and morpholine (19 µL, 0.21 mmol). MS (ES) 758.1 (M+H), $^1$H NMR (400 MHz, DMSO-$d_6$): δ 8.10 (s, 1H), 8.04 (s, 1H), 7.77 (s, 1H), 7.73 (d, J=8.0 Hz, 1H), 7.28 (d, J=8.0 Hz, 1H), 6.73 (s, 2H), 4.44 (s, 2H), 4.02-3.95 (comp, 6H), 3.78 (s, 3H), 3.70-3.64 (comp, 4H), 3.33-3.29 (m, 2H), 3.17-3.14 (m, 2H), 3.06 (t, J=8.0 Hz, 2H), 2.23 (s, 6H), 2.10-2.07 (m, 2H), 2.02 (s, 3H), 1.92 (s, 3H), 1.85-1.80 (m, 2H).

Example 228

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-((4-methylpiperazin-1-yl)methyl)benzoic acid

I-228

The title compound was prepared (17 mg, 0.021 mmol) according to procedures described in Example 225 using of methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(hydroxymethyl)benzoate (30 mg, 0.043 mmol), DIPEA (15 µL, 0.085 mmol) and MsCl (6.6 µl, 0.085 mmol) and 1-methylpiperazine (24 µL, 0.21 mmol). MS (ES) 771.1 (M+H), $^1$H NMR (400 MHz, DMSO-$d_6$): δ 7.91 (s, 1H), 7.87 (s, 1H), 7.72 (d, J=8.0 Hz, 1H), 7.56 (s, 1H), 7.27 (d, J=8.0 Hz, 1H), 6.73 (s, 2H), 4.01 (t, J=8.0 Hz, 2H), 3.96 (t, J=6.0 Hz, 2H), 3.79-3.75 (m, 2H), 3.78 (s, 3H), 3.62 (t, J=6.0 Hz, 2H), 3.42 (s, 2H), 3.09-3.05 (comp, 6H), 2.80 (s, 3H), 2.23 (s, 6H), 2.09-2.05 (m, 4H), 2.02 (s, 3H), 1.91 (s, 3H), 1.82-1.77 (m, 2H).

Example 229

Preparation of 3-((1H-imidazol-1-yl)methyl)-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoic acid

I-229

The title compound was prepared (13 mg, 0.021 mmol) according to procedures described in Example 225 using of methyl 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(hydroxymethyl)benzoate (30 mg, 0.043 mmol), DIPEA (15 µL, 0.085 mmol) and MsCl (6.6 µl, 0.085 mmol) and imidazole (14 mg, 0.21 mmol). MS (ES) 739.0 (M+H).

Example 230

Preparation of 2-chloro-6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)isonicotinic acid

I-230

Step A. Preparation of methyl 2-chloro-6-(6-chloro-3-(3-(4-chloro-3,5-dimethylphenoxy)propyl)-7-(1,3,5-trimethyl-1H-pyrazol-4-yl)-1H-indole-2-carboxamido)isonicotinate A solution of 6-chloro-3-(3-(4-chloro-3,5-dimethylphenoxy)propyl)-7-(1,3,5-trimethyl-1H-pyrazol-4-yl)-1H-indole-2-carbonyl chloride (100 mg, 0.19 mmol), DMAP (47 mg, 0.39 mmol), Pyridine (31 µL, 0.39 mmol) in DCM (3.8 mL) was stirred at rt for 10 min, and methyl 2-amino-6-chloroisonicotinate (40 mg, 0.21 mmol) was added. The resulting mixture was stirred at rt for 15 h then concentrated. The residue was purified by silica gel flash chromatography (ISCO, 0-60% EtOAc/Hex gradient) to give the title compound (100 mg, 0.149 mmol). MS (ES) 667.9 (M+H).

Step B. Example 230

A solution of methyl 2-chloro-6-(6-chloro-3-(3-(4-chloro-3,5-dimethylphenoxy)propyl)-7-(1,3,5-trimethyl-1H-pyrazol-4-yl)-1H-indole-2-carboxamido)isonicotinate (100 mg, 0.149 mmol), 1,3-dibromopropane (46 µL, 0.448 mmol), $Cs_2CO_3$ (244 mg, 0.747 mmol) in DMF (2.1 mL) was stirred at 60° C. for 2 h. The reaction mixture was filtered and the filtrate was concentrated. The residue was dissolved in THF (0.3 mL), and LiOH (aq. 2N, 0.1 mL, 0.2 mmol). The reaction mixture was stirred at 40° C. for 15 h then concentrated. The residue was purified by the reverse phase HPLC (Phenomenex Gemini C18, $H_2O/CH_3CN$ gradient from 30-90% $CH_3CN$, 0.1% TFA) to give the title compound (5 mg, 0.007 mmol). MS (ES) 696.0 (M+H).

Example 231

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(pyridin-4-yl)benzoic acid

I-231

A solution of methyl 3-bromo-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoate (30 mg, 0.040 mmol), pyridin-4-ylboronic acid (6.0 mg, 0.048 mmol), $Pd(PPh_3)_4$ (2.3 mg, 2.0 µmol) and CsF (18.17 mg, 0.120 mmol) in ethanol (100 µL) and DME (200 µL) was degassed under Ar for 10 min. The mixture was then heated under microwave at 120° C. (Biotage Initiator) for 25 min. The reaction mixture was cooled to rt then LiOH (aq. 2N, 0.3 mL) was added. The resulting mixture was heated under microwave at 100° C. (Biotage Initiator) for additional 20 min. The reaction mixture was concentrated, and the residue was purified by the reverse phase HPLC (Phenomenex Gemini C18, $H_2O/CH_3CN$ gradient from 30-75% $CH_3CN$, 0.1% TFA) to give the title compound (12 mg, 0.016 mmol). MS (ES) 736.0 (M+H).

Example 232

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(2-methylpyridin-3-yl)benzoic acid

I-232

The title compound was prepared (30 mg, 0.021 mmol) according to procedures described in Example 231 using 3-bromo-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoate (40 mg, 0.053 mmol), (2-methylpyridin-3-yl)boronic acid (8.74 mg, 0.064 mmol), $Pd(PPh_3)_4$ (3.07 mg, 2.66 µmol) and CsF (24.22 mg, 0.159 mmol). MS (ES) 750.0 (M+H), $^1$H NMR (400 MHz, DMSO-$d_6$): δ 8.77 (s, 1H), 8.31-8.28 (m, 1H), 8.09 (s, 1H), 7.90 (s, 1H), 7.83-7.79 (m, 1H), 7.76 (s, 1H), 7.73 (d, J=8 Hz, 1H), 7.27 (d, J=8.0 Hz, 1H), 6.72 (s, 2H), 4.02 (t, J=6.0 Hz, 2H), 3.95 (t, J=6.0 Hz, 2H), 3.77 (s, 3H), 3.68 (t, J=6.0 Hz, 2H), 3.07 (t, J=8.0 Hz, 2H), 2.61 (s, 3H), 2.21 (s, 6H), 2.12-2.06 (m, 2H), 2.01 (s, 3H), 1.91 (s, 3H), 1.83-1.78 (m, 2H).

Example 233

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(3-methylpyridin-4-yl)benzoic acid

I-233

The title compound was prepared (12 mg, 0.016 mmol) according to procedures described in Example 231 using 3-bromo-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoate (40 mg, 0.053 mmol), (3-methylpyridin-4-yl)boronic acid (9.0 mg, 0.064 mmol), $Pd(PPh_3)_4$ (3.1 mg, 2.7 µmol) and CsF (24 mg, 0.16 mmol). MS (ES) 750.0 (M+H), $^1$H NMR (400 MHz, DMSO-$d_6$): δ 8.79 (s, 1H), 8.72 (d, J=4.0 Hz, 1H), 8.09 (s, 1H), 7.89 (s, 1H), 7.74-7.72 (comp, 3H), 7.27 (d, J=8 Hz, 1H), 6.72 (s, 2H), 4.06-4.04 (m, 2H), 3.95 (t, J=6.0 Hz, 2H), 3.78 (s, 3H), 3.69 (t, J=6.0 Hz, 2H), 3.07 (t, J=8.0 Hz, 2H), 2.38 (s, 3H), 2.20 (s, 6H), 2.09-2.05 (m, 2H), 2.01 (s, 3H), 1.91 (s, 3H), 1.83-1.78 (m, 2H).

Example 234

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(4-methylpyridin-3-yl)benzoic acid

I-234

The title compound was prepared (14 mg, 0.019 mmol) according to procedures described in Example 231 using 3-bromo-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoate (40 mg, 0.053 mmol), (4-methylpyridin-3-yl)boronic acid (8.7 mg, 0.064 mmol), $Pd(PPh_3)_4$ (3.1 mg, 2.7 µmol) and CsF (24 mg, 0.16 mmol). MS (ES) 750.0 (M+H).

Example 235

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-5-(1-methyl-1H-pyrrol-2-yl)benzoic acid

I-235

The title compound was prepared (11 mg, 0.015 mmol) according to procedures described in Example 231 using 3-bromo-5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoate (40 mg, 0.053 mmol), 1-methyl-2-(4,4,5,5-tetramethyl-1,3,2-dioxaborolan-2-yl)-1H-pyrrole (13 mg, 0.064 mmol), Pd(PPh$_3$)$_4$ (3.1 mg, 2.7 µmol) and CsF (24 mg, 0.16 mmol). MS (ES) 738.0 (M+H).

Example 236

Preparation of 2-(3-(8-chloro-11-(3-(4-chloro-3,5-dimethylphenoxy)propyl)-1-oxo-7-(1,3,5-trimethyl-1H-pyrazol-4-yl)-4,5-dihydro-H-[1,4]diazepino[1,2-a]indol-2(3H)-yl)phenyl)acetic acid

I-236

Step A. Preparation of methyl 2-(3-(6-chloro-3-(3-(4-chloro-3,5-dimethylphenoxy)propyl)-7-(1,3,5-trimethyl-1H-pyrazol-4-yl)-1H-indole-2-carboxamido)phenyl)acetate A solution of 6-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.100 mmol), methyl 2-(3-aminophenyl)acetate (33 mg, 0.20 mmol), DMAP (24 mg, 0.20 mmol) and EDC (38 mg, 0.20 mmol) in DCM (2 mL) was stirred at rt for 16 h. The reaction mixture was concentrated, and the residue was purified by silica gel flash chromatography (ISCO 0-10% MeOH/DCM gradient) to give the title compound (40 mg, 0.062 mmol). MS (ES) 647.0 (M+H).

Step B. Example 236

A solution of methyl 2-(3-(6-chloro-3-(3-(4-chloro-3,5-dimethylphenoxy)propyl)-7-(1,3,5-trimethyl-1H-pyrazol-4-yl)-1H-indole-2-carboxamido)phenyl)acetate (40 mg, 0.062 mmol), 1,3-dibromopropane (0.019 ml, 0.19 mmol), Cs$_2$CO$_3$ (101 mg, 0.31 mmol) in DMF (2 ml) was stirred at 60° C. for 2 h. The reaction mixture was filtered and the filtrate was concentrated. The residue was dissolved in THF (0.5 mL) and LiOH (aq. 2N, 0.3 ml, 0.6 mmol) was added. The reaction mixture was stirred at 40° C. for 15 h then concentrated. The residue was purified by the reverse phase HPLC (Phenomenex Gemini C18, H$_2$O/CH$_3$CN gradient from 30-80% CH$_3$CN, 0.1% TFA) to give the title compound (15 mg, 0.022 mmol). MS (ES) 673.0 (M+H).

Example 237

Preparation of 2-(4-(8-chloro-11-(3-(4-chloro-3,5-dimethylphenoxy)propyl)-1-oxo-7-(1,3,5-trimethyl-1H-pyrazol-4-yl)-4,5-dihydro-H-[1,4]diazepino[1,2-a]indol-2(3H)-yl)phenyl)acetic acid

I-237

The title compound was prepared (10 mg, 0.015 mmol) according to procedures described in Example 236 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.10 mmol), methyl 2-(4-aminophenyl)acetate (33 mg, 0.20 mmol), DMAP (24 mg, 0.20 mmol) and EDC (38 mg, 0.20 mmol). MS (ES) 673.0 (M+H).

Example 238

Preparation of 6-(6-chloro-3-(3-(4-chloro-3,5-dimethylphenoxy)propyl)-7-(1,3,5-trimethyl-1H-pyrazol-4-yl)-1H-indole-2-carboxamido)-1H-indole-4-carboxylic acid

I-238

Step A. Preparation of methyl 6-(6-chloro-3-(3-(4-chloro-3,5-dimethylphenoxy)propyl)-7-(1,3,5-trimethyl-1H-pyrazol-4-yl)-1H-indole-2-carboxamido)-1H-indole-4-carboxylate A solution of 6-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.10 mmol), methyl 6-amino-1H-indole-4-carboxylate (23 mg, 0.12 mmol), DMAP (24 mg, 0.20 mmol) and EDC (38 mg, 0.20 mmol) in DCM (2 mL) was stirred at rt for 16 h. The reaction mixture was concentrated, and the residue was purified by silica gel flash chromatography (ISCO 0-70% EtOAc/Hex gradient) to give the title compound (35 mg, 0.052 mmol). MS (ES) 672.0 (M+H).

Step B. Example 238

A mixture of methyl 6-(6-chloro-3-(3-(4-chloro-3,5-dimethylphenoxy)propyl)-7-(1,3,5-trimethyl-1H-pyrazol-4-yl)-1H-indole-2-carboxamido)-1H-indole-4-carboxylate (35 mg, 0.052 mmol), LiOH (aq. 2N, 130 µL, 0.26 mmol) in THF (500 µL) was stirred at rt for 15. The reaction mixture was concentrated, and the residue was purified by the reverse phase HPLC (Phenomenex Gemini C18, H$_2$O/CH$_3$CN gradient from 30-80% CH$_3$CN, 0.1% TFA) to give the title compound (13 mg, 0.020 mmol). MS (ES) 658.0 (M+H).

Example 239

Preparation of 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-4-carboxylic acid

I-239

Step A. Preparation of methyl 6-(6-chloro-3-(3-(4-chloro-3,5-dimethylphenoxy)propyl)-7-(1,3,5-trimethyl-1H-pyrazol-4-yl)-1H-indole-2-carboxamido)-1-methyl-1H-indole-4-carboxylate A solution of 6-chloro-3-(3-(4-chloro-3,5-dimethylphenoxy)propyl)-7-(1,3,5-trimethyl-1H-pyrazol-4-yl)-1H-indole-2-carboxylic acid (100 mg, 0.20 mmol), methyl 6-amino-1-methyl-1H-indole-4-carboxylate (49 mg, 0.240 mmol), DMAP (49 mg, 0.40 mmol) and EDC (77 mg, 0.40 mmol) in DCM (4 mL) was stirred at rt for 16 h. The reaction mixture was concentrated, and the residue was purified by silica gel flash chromatography (ISCO 0-10% MeOH/DCM gradient) to give title compound (80 mg, 0.117 mmol). MS (ES) 686.0 (M+H).

Step B. Example 239

A mixture of methyl 6-(6-chloro-3-(3-(4-chloro-3,5-dimethylphenoxy)propyl)-7-(1,3,5-trimethyl-1H-pyrazol-4-yl)-

1H-indole-2-carboxamido)-1-methyl-1H-indole-4-carboxylate (80 mg, 0.117 mmol), 1,3-dibromopropane (36 μL, 0.35 mmol), $Cs_2CO_3$ (190 mg, 0.58 mmol) in DMF (1.5 mL) was stirred at 60° C. for 2 h. The reaction mixture was filtered, and the filtrate was concentrated. The residue was dissolved in a mixture of THF (0.5 mL) and LiOH (aq. 2N, 0.3 mL, 0.6 mmol) and stirred at 60° C. for 15 h. The reaction mixture was concentrated and the residue was purified by the reverse phase HPLC (Phenomenex Gemini C18, $H_2O/CH_3CN$ gradient from 35-85% $CH_3CN$, 0.1% TFA) to give the title compound (36 mg, 0.051 mmol). MS (ES) 712.0 (M+H). $^1H$ NMR (400 MHz, DMSO-$d_6$): δ 7.74-7.68 (comp, 3H), 7.53 (d, J=7.0 Hz, 1H), 7.26 (d, J=8.0 Hz, 1H), 6.794 (d, J=6.0 Hz, 1H), 6.75 (s, 2H), 4.08 (t, J=6.0 Hz, 2H), 3.98 (t, J=6.0 Hz, 2H), 3.83 (s, 3H), 3.79 (s, 3H), 3.65 (t, J=8.0 Hz, 2H), 3.06 (t, J=8.0 Hz, 2H), 2.24 (s, 6H), 2.09-2.06 (m, 2H), 2.03 (s, 3H), 1.93 (s, 3H), 1.76-1.72 (m, 2H).

Example 240

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-6-carboxylic acid

I-240

The title compound was prepared (40 mg, 0.056 mmol) according to procedures described in Example 239 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid (100 mg, 0.20 mmol), methyl 4-amino-1-methyl-1H-indole-6-carboxylate (49 mg, 0.24 mmol), DMAP (49 mg, 0.40 mmol) and EDC (77 mg, 0.40 mmol). MS (ES) 712.0 (M+H). $^1H$ NMR (400 MHz, DMSO-$d_6$): δ 8.07 (s, 1H), 7.72 (d, J=8.0 Hz, 1H), 7.56-7.55 (comp, 2H), 7.27 (d, J=8.0 Hz, 1H), 6.73 (s, 2H), 6.36 (d, J=4.0 Hz, 1H), 4.12 (t, J=6.0 Hz, 2H), 3.98 (t, J=6.0 Hz, 2H), 3.90 (s, 3H), 3.78 (s, 3H), 3.69 (t, J=6.0 Hz, 2H), 3.04 (t, J=8.0 Hz, 2H), 2.24 (s, 6H), 2.09-2.06 (m, 2H), 2.03 (s, 3H), 1.93 (s, 3H), 1.76-1.72 (m, 2H).

Example 241

Preparation of 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-(pyridin-3-ylmethyl)-1H-indole-4-carboxylic acid

I-241

The title compound was prepared (50 mg, 0.063 mmol) according to procedures described in Example 239 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid (70 mg, 0.14 mmol), methyl 6-amino-1-(pyridin-3-ylmethyl)-1H-indole-4-carboxylate (47 mg, 0.168 mmol), DMAP (34 mg, 0.28 mmol) and EDC (54 mg, 0.28 mmol). MS (ES) 789.0 (M+H).

Example 242

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-(pyridin-3-ylmethyl)-1H-indole-6-carboxylic acid

I-242

The title compound was prepared (35 mg, 0.044 mmol) according to procedures described in Example 239 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid (70 mg, 0.14 mmol), methyl 4-amino-1-(pyridin-3-ylmethyl)-1H-indole-6-carboxylate (47 mg, 0.17 mmol), DMAP (34 mg, 0.28 mmol) and EDC (54 mg, 0.28 mmol). MS (ES) 789.0 (M+H).

Example 243

Preparation of 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-(2-(dimethylamino)ethyl)-1H-indole-4-carboxylic acid

I-243

Step A. Preparation of methyl 6-(6-chloro-3-(3-(4-chloro-3,5-dimethylphenoxy)propyl)-7-(1,3,5-trimethyl-1H-pyrazol-4-yl)-1H-indole-2-carboxamido)-1-(2-(dimethylamino)ethyl)-1H-indole-4-carboxylate A solution of 6-chloro-3-(3-(4-chloro-3,5-dimethylphenoxy)propyl)-7-(1,3,5-trimethyl-1H-pyrazol-4-yl)-1H-indole-2-carboxylic acid (70 mg, 0.14 mmol), methyl 6-amino-1-(2-(dimethylamino)ethyl)-1H-indole-4-carboxylate (40 mg, 0.154 mmol), DMAP (34 mg, 0.28 mmol) and EDC (54 mg, 0.28 mmol) in DCM (2 mL) was stirred at rt for 16 h. The reaction mixture was concentrated, and the residue was purified by silica gel flash chromatography (ISCO 0-10% MeOH/DCM gradient) to give the title compound (36 mg, 0.048 mmol). MS (ES) 743.1 (M+H).

Step B. Example 243

A solution of methyl 6-(6-chloro-3-(3-(4-chloro-3,5-dimethylphenoxy)propyl)-7-(1,3,5-trimethyl-1H-pyrazol-4-yl)-1H-indole-2-carboxamido)-1-(2-(dimethylamino)ethyl)-1H-indole-4-carboxylate (36 mg, 0.048 mmol), 1,3-dibromopropane (15 μL, 0.15 mmol), $Cs_2CO_3$ (79 mg, 0.24 mmol) in DMF (1.5 mL) was stirred at 60° C. for 2 h. The reaction mixture was filtered and the filtrate was concentrated. The residue was dissolved in a mixture of THF (1.5 mL) and LiOH (aq. 2N, 0.3 mL, 0.6 mmol) and stirred at 40° C. for 15 h. The reaction mixture was concentrated, and the residue was purified by the reverse phase HPLC (Phenomenex Gemini C18, $H_2O/CH_3CN$ gradient from 30-80% $CH_3CN$, 0.1% $NH_4OH$) to give the title compound (5 mg, 0.007 mmol). MS (ES) 769.0 (M+H).

Example 244

Preparation of 6-(9-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-4-carboxylic acid

I-244

Step A. Preparation of ethyl 7-bromo-5-chloro-3-(3-ethoxy-3-oxopropyl)-1H-indole-2-carboxylate Title compounds were prepared according to procedures described in Example 2 Step A and B using 2-bromo-4-chloroaniline. MS (ES) 402.0 (M+H).

Step B. Preparation of ethyl 7-bromo-5-chloro-3-(3-hydroxypropyl)-1H-indole-2-carboxylate Title compound was prepared according to the procedure in Example 2 Step C using ethyl 7-bromo-5-chloro-3-(3-ethoxy-3-oxopropyl)-1H-indole-2-carboxylate. MS (ES) 360.1 (M+H).

Step C. Preparation ethyl 7-bromo-5-chloro-3-(3-(4-chloro-3,5-dimethylphenoxy)propyl)-1H-indole-2-carboxylate Title compound was prepared as a colorless oil according to procedures described in Example 2 Step D using 7-bromo-5-chloro-3-(3-hydroxypropyl)-1H-indole-2-carboxylate. MS (ES) 498.0 (M+H).

Step D. Preparation of ethyl 5-chloro-3-(3-(4-chloro-3,5-dimethylphenoxy)propyl)-7-(1,3,5-trimethyl-1H-pyrazol-4-yl)-1H-indole-2-carboxylate Title compound was prepared as a colorless oil according to procedures described in Example 28 Step A using 7-bromo-5-chloro-3-(3-hydroxypropyl)-1H-indole-2-carboxylate. MS (ES) 528.2 (M+H).

Step E. Preparation of 5-chloro-3-(3-(4-chloro-3,5-dimethylphenoxy)propyl)-7-(1,3,5-trimethyl-1H-pyrazol-4-yl)-1H-indole-2-carboxylic acid Title compound was prepared as a colorless oil according to procedures described in Example 28 Step B using ethyl 6-chloro-3-(3-(4-chloro-3,5-dimethylphenoxy)propyl)-7-(1,3,5-trimethyl-1H-pyrazol-4-yl)-1H-indole-2-carboxylate. MS (ES) 500.2 (M+H).

Step F. Preparation of methyl 6-(5-chloro-3-(3-(4-chloro-3,5-dimethylphenoxy)propyl)-7-(1,3,5-trimethyl-1H-pyrazol-4-yl)-1H-indole-2-carboxamido)-1-methyl-1H-indole-4-carboxylate A solution of 5-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.100 mmol), methyl 6-amino-1-methyl-1H-indole-4-carboxylate (25 mg, 0.12 mmol), DMAP (24 mg, 0.20 mmol) and EDC (38 mg, 0.20 mmol) in DCM (2 mL) was stirred at rt for 16 h. The reaction mixture was concentrated, and the residue was purified by silica gel flash chromatography (ISCO 0-10% MeOH/DCM gradient) to give the title compound (50 mg, 0.073 mmol). MS (ES) 686.0 (M+H).

Step G. Example 244

A solution of methyl 6-(5-chloro-3-(3-(4-chloro-3,5-dimethylphenoxy)propyl)-7-(1,3,5-trimethyl-1H-pyrazol-4-yl)-1H-indole-2-carboxamido)-1-methyl-1H-indole-4-carboxylate (50 mg, 0.073 mmol), 1,3-dibromopropane (22 µL, 0.22 mmol), $Cs_2CO_3$ (119 mg, 0.36 mmol) in DMF (1.5 mL) was stirred at 60° C. for 2 h. The reaction mixture was filtered and the filtrate was concentrated. The residue was dissolved in THF (0.5 mL) and LiOH (aq. 2N, 0.3 mL, 0.6 mmol) and stirred at 60° C. for 15 h. The reaction mixture was concentrated, and the residue was purified by the reverse phase HPLC (Phenomenex Gemini C18, $H_2O/CH_3CN$ gradient from 35-90% $CH_3CN$, 0.1% TFA) to give the title compound (10 mg, 0.014 mmol). MS (ES) 712.0 (M+H).

Example 245

Preparation of 4-(9-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-6-carboxylic acid

I-245

The title compound was prepared (10 mg, 0.014 mmol) according to procedures described in Example 244 Step F and G using 5-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.10 mmol) and methyl 4-amino-1-methyl-1H-indole-6-carboxylate (24 mg, 0.12 mmol). MS (ES) 712.0 (M+H).

Example 246

Preparation of 3-(9-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoic acid

I-246

The title compound was prepared (25 mg, 0.038 mmol) according to procedures described in Example 244 Step F and G using 5-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.10 mmol) and methyl 3-aminobenzoate (18 mg, 0.12 mmol). MS (ES) 659.2 (M+H).

Example 247

Preparation of 8-chloro-1-(3-(4-chloro-3,5-dimethylphenoxy)propyl)-2-(1-methyl-1H-indol-4-yl)-7-(1,3,5-trimethyl-1H-pyrazol-4-yl)-2,3,4,5-tetrahydro-1H-[1,4]diazepino[1,2-a]indol-1-one

I-247

The title compound was prepared (27 mg, 0.040 mmol) according to procedures described in Example 239 Step A and B using 6-chloro-3-(3-(4-chloro-3,5-dimethylphenoxy)propyl)-7-(1,3,5-trimethyl-1H-pyrazol-4-yl)-1H-indole-2- carboxylic acid (50 mg, 0.100 mmol) and 1-methyl-1H-indol-4-amine (18 mg, 0.12 mmol). MS (ES) 668.1 (M+H).

Example 248

Preparation of 8-chloro-1-(3-(4-chloro-3,5-dimethylphenoxy)propyl)-2-(1-methyl-1H-indol-6-yl)-7-(1,3,5-trimethyl-1H-pyrazol-4-yl)-2,3,4,5-tetrahydro-1H-[1,4]diazepino[1,2-a]indol-1-one

I-248

The title compound was prepared (14 mg, 0.021 mmol) according to procedures described in Example 239 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.100 mmol) and 1-methyl-1H-indol-6-amine (16 mg, 0.11 mmol). MS (ES) 668.1 (M+H), $^1$H NMR (400 MHz, DMSO-$d_6$): δ 7.71 (d, J=8.0 Hz, 1H), 7.52 (d, J=8.0 Hz, 1H), 7.42 (s, 1H), 7.37 (d, J=3.1 Hz, 1H), 7.26 (d, J=8.0 Hz, 1H), 6.88 (dd, J=8.3, 1.7 Hz, 1H), 6.75 (s, 2H), 6.45 (d, J=2.9 Hz, 1H), 4.07 (t, J=6.0 Hz, 2H), 3.97 (t, J=8.0 Hz, 2H), 3.79 (s, 3H), 3.77 (s, 3H), 3.59 (t, J=6.0 Hz, 2H), 3.06 (t, J=6.0 Hz, 2H), 2.25 (s, 6H), 2.09-2.06 (m, 2H), 2.03 (s, 3H), 1.92 (s, 3H), 1.82-1.77 (m, 2H).

Example 249

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-ethyl-1H-indole-6-carboxylic acid

I-249

The title compound was prepared (30 mg, 0.041 mmol) according to procedures described in Example 239 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid (60 mg, 0.12 mmol) and methyl 4-amino-1-ethyl-1H-indole-6-carboxylate (31.4 mg, 0.144 mmol). MS (ES) 726.1 (M+H).

Example 250

Preparation of 5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-7-carboxylic acid

I-250

The title compound was prepared (55 mg, 0.077 mmol) according to procedures described in Example 239 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid (80 mg, 0.160 mmol) and methyl 5-amino-1-methyl-1H-indole-7-carboxylate (45 mg, 0.220 mmol). MS (ES) 712.1 (M+H).

Example 251

Preparation of 7-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-5-carboxylic acid

I-251

The title compound was prepared (8.5 mg, 0.012 mmol) according to procedures described in Example 239 Step A and B using 6-chloro-3-(3-(4-chloro-3,5-dimethylphenoxy)propyl)-7-(1,3,5-trimethyl-1H-pyrazol-4-yl)-1H-indole-2-carboxylic acid (100 mg, 0.20 mmol) and methyl 7-amino-1-methyl-1H-indole-5-carboxylate (40.8 mg, 0.20 mmol). MS (ES) 712.1 (M+H).

Example 252

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1H-indole-6-carboxylic acid

I-252

Step A. Preparation of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1H-indole-6-carboxylate A mixture of 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (40 mg, 0.074 mmol), 1-(tert-butyl) 6-methyl 4-bromo-1H-indole-1,6-dicarboxylate (32 mg, 0.089 mmol), Xantphos (2.6 mg, 4.5 μmol), Pd2(dba)3 (1.4 mg, 1.5 μmol) and Cs2CO3 (36 mg, 0.11 mmol) was degassed for 10 min under Ar. 1,4-Dioxane (74.1 μl) was added and the resulting mixture was heated to 110° C. for 16 h. The reaction mixture was cooled to rt, and TFA (100 μL) was added. The resulting reaction mixture was stirred for 2 h at 60° C. then concentrated. The residue was purified by the reverse phase HPLC (Phenomenex Gemini C18, H2O/CH3CN gradient from 40-90% CH3CN, 0.1% TFA) to give title compound (12 mg, 0.017 mmol). MS (ES) 712.0 (M+H).

Step B. Example 252

A solution of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1H-indole-6-carboxylate (12 mg, 0.017 mmol) in THF (0.1 mL) and LiOH (aq. 2N, 0.05 mL, 0.1 mmol) was heated at 40° C. for 2 d. The reaction mixture was concentrated and the residue was purified by the reverse phase HPLC (Phenomenex Gemini C18, H2O/CH3CN gradient from 30-80% CH3CN, 0.1% TFA) to give the title compound (5 mg, 0.007 mmol). MS (ES) 698.1 (M+H).

Example 253

Preparation of 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1H-indole-4-carboxylic acid

I-253

The title compound was prepared (5.2 mg, 0.007 mmol) according to procedures described in Example 252 Step A and B using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (51 mg, 0.094 mmol) and 1-(tert-butyl) 4-methyl 6-bromo-1H-indole-1,4-dicarboxylate (40 mg, 0.11 mmol). MS (ES) 698.1 (M+H).

Example 254

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-3-formyl-1-methyl-1H-indole-6-carboxylic acid

I-254

Step A. Preparation of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-3-formyl-1-methyl-1H-indole-6-carboxylate Phosphorus oxychloride (7.70 μL, 0.083 mmol) was added to DMF (100 μL, 1.29 mmol) at 0° C., and the resulting mixture was stirred for 15 min. A solution of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-6-carboxylate (40 mg, 0.055 mmol) in DMF (0.2 mL) was added at 0° C. The resulting mixture was warmed to 50° C. for 1 h. H$_2$O (0.1 mL) was added to quench the reaction. The solution was concentrated and the residue was purified by the reverse phase HPLC (Phenomenex Gemini C18, H$_2$O/CH$_3$CN gradient from 50-90% CH$_3$CN, 0.1% TFA) to give the title compound (38 mg, 0.050 mmol). MS (ES) 754.0 (M+H).

Step B Example 254

The methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-3-formyl-1-methyl-1H-indole-6-carboxylate (38 mg, 0.050 mmol) was dissolved in THF (0.2 ml) and LiOH (aq. 2N, 0.13 mL, 0.26 mmol) and stirred at 60° C. for 15 h. The reaction mixture was concentrated, and the residue was purified by the reverse phase HPLC (Phenomenex Gemini C18, H$_2$O/CH$_3$CN gradient from 30-80% CH$_3$CN, 0.1% TFA) to give the title compound (25 mg, 0.034 mmol). MS (ES) 740.1 (M+H).

Example 255

Preparation of 3-chloro-4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-6-carboxylic acid

I-255

To a stirred solution of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-6-carboxylate (40 mg, 0.055 mmol), NCS (7.7 mg, 0.058 mmol) was added and the resulting mixture was stirred at rt for 15 h. LiOH (aq. 2N, 0.14 mL, 0.28 mmol) was added and the mixture was heated to 70° C. for 6 h. The reaction mixture was concentrated, and the residue was purified by the reverse phase HPLC (Phenomenex Gemini C18, H$_2$O/CH$_3$CN gradient from 40-90% CH$_3$CN, 0.1% TFA) to give the title compound (15 mg, 0.020 mmol). MS (ES) 746.2 (M+H).

Example 256

Preparation of 3-bromo-4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-6-carboxylic acid

I-256

To a stirred solution of methyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-6-carboxylate (40 mg, 0.055 mmol), NBS (12 mg, 0.066 mmol) was added and the resulting mixture was stirred at rt for 15 h. LiOH (aq. 2N, 0.14 mL, 0.28 mmol) was added and the mixture was heated to 70° C. for 6 h. The reaction mixture was concentrated, and the residue was purified by the reverse phase HPLC (Phenomenex Gemini C18, H$_2$O/CH$_3$CN gradient from 40-90% CH$_3$CN, 0.1% TFA) to give the title compound (18 mg, 0.023 mmol). MS (ES) 792.1 (M+H).

Example 257

Preparation of 3-chloro-6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-4-carboxylic acid

I-257

The title compound was prepared (18 mg, 0.024 mmol) according to procedures described in Example 225 using methyl 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-4-carboxylate (40 mg, 0.055 mmol), NCS (7.35 mg, 0.055 mmol). MS (ES) 748.2 (M+H). $^1$H NMR (400 MHz, DMSO-d$_6$): δ 7.73-7.69 (comp, 3H), 7.40 (s, 1H), 7.26 (d, J=8.0 Hz, 1H), 6.74 (s, 2H), 4.09-4.06 (m, 2H), 3.98 (t, J=8.0 Hz, 2H), 3.80 (s, 3H), 3.78 (s, 3H), 3.64 (t, J=6.0

Hz, 2H), 3.05 (t, J=8.0 Hz, 2H), 2.24 (s, 6H), 2.10-2.06 (m, 2H), 2.03 (s, 3H), 1.92 (s, 3H), 1.82-1.76 (m, 2H).

Example 258

Preparation of 3-bromo-6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-4-carboxylic acid

I-258

The title compound was prepared (5 mg, 0.006 mmol) according to procedures described in Example 226 using methyl 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-4-carboxylate (40 mg, 0.055 mmol), NBS (10 mg, 0.058 mmol). MS (ES) 792.1 (M+H).

Example 259

Preparation of N-(1-(3-(3-(4-chloro-3,5-dimethylphenoxy)propyl)-1H-indole-2-carbonyl)piperidin-4-yl)-3-phenoxybenzamide

I-259

Step A. Preparation of (4-aminopiperidin-1-yl)(3-(3-(4-chloro-3,5-dimethylphenoxy)propyl)-1H-indol-2-yl)methanone 2,2,2-trifluoroacetate To a stirred solution of tert-butyl (1-(3-(3-(4-chloro-3,5-dimethylphenoxy)propyl)-1H-indole-2-carbonyl)piperidin-4-yl)carbamate (0.037 mmol) in DCM (1 mL) was added TFA (0.2 mL). The reaction was stirred for 2 h then the volatiles were removed in vacuo to give the crude title product which was directly used in subsequent step without further purification.

Step B. Example 259

The title compound was prepared according to the procedure used in Example 40 by substituting (4-aminopiperidin-1-yl)(3-(3-(4-chloro-3,5-dimethylphenoxy)propyl)-1H-indol-2-yl)methanone 2,2,2-trifluoroacetate for aniline. $^1$H NMR (CDCl$_3$, 400 MHz, 25° C.): 8.41 (br s, 1H), 7.65 (d, J=8.0 Hz, 1H), 7.41-7.33 (m, 6H), 7.29 (m, 1H), 7.27 (t, J=8.0 Hz 1H), 7.14 (m, 3H), 7.01 (d, J=8.0 Hz, 2H), 6.61 (s, 2H), 5.92 (m, 1H), 4.33-4.18 (m, 3H), 3.90 (t, J=6.0 Hz, 2H), 3.46 (m, 2H), 3.55 (br t, J=6.0 Hz, 2H), 3.22 (t, J=6.0 Hz, 2H), 2.34 (s, 6H), 2.24-2.19 (m, 2H), 2.02 (t, J=8.0 Hz, 2H), 2.31 (s, 6H), 2.18-2.09 (m, 4H), 1.53-1.43 (m, 2H); MS (ES) 636.3 (M+H).

Example 260

Preparation of 3-(3-(4-chloro-3,5-dimethylphenoxy)propyl)-N-((6-chloropyridin-3-yl)methyl)-7-(1,3,5-trimethyl-1H-pyrazol-4-yl)-1H-indole-2-carboxamide

I-260

The title compound was prepared according to the procedure used in Example 40 using the requisite amine. MS (ES) 636.3 (M+H).

Example 261

Preparation of 3-(3-(4-chloro-3,5-dimethylphenoxy)propyl)-N-((6-(3,4-dihydroisoquinolin-2 (1H)-yl)pyridin-3-yl)methyl)-7-(1,3,5-trimethyl-1H-pyrazol-4-yl)-1H-indole-2-carboxamide

I-261

To a microwave reaction vial was added cesium carbonate (0.068 mmol), 3-(3-(4-chloro-3,5-dimethylphenoxy)propyl)-N-((6-chloropyridin-3-yl)methyl)-7-(1,3,5-trimethyl-1H-pyrazol-4-yl)-1H-indole-2-carboxamide (0.034 mmol), palladium acetate (0.0034 mmol), 2-dicyclohexylphosphino-2',6'-dimethoxybiphenyl (0.0042 mmol), and a stir bar. This mixture was suspended in dioxane (0.05 M) for the addition of 1,2,3,4-tetrahydroisoquinoline (0.037 mmol). The microwave vial was then crimped and immediately transferred to the microwave reactor for heating at 100° C. for a period of 35 minutes. The reaction was filtered through Celite and volatiles were removed in vacuo. The residue was then dissolved in 1 mL of a 1:1 mix of acetonitrile and methanol and was purified by reverse phase preparatory HPLC (H$_2$O/CH$_3$CN gradient to 95% CH$_3$CN 0.1% TFA) to yield the title compound as a white solid. MS (ES) 687.1 (M+H).

Example 262

Preparation of 3-(3-(4-chloro-3,5-dimethylphenoxy)propyl)-N-((2-chloropyridin-4-yl)methyl)-7-(1,3,5-trimethyl-1H-pyrazol-4-yl)-1H-indole-2-carboxamide

I-262

The title compound was prepared according to the procedure used in Example 40 using the requisite amine. MS (ES) 636.3 (M+H).

Example 263

Preparation of 3-(3-(4-chloro-3,5-dimethylphenoxy)propyl)-N-((2-(3,4-dihydroisoquinolin-2(1H)-yl)pyridin-4-yl)methyl)-7-(1,3,5-trimethyl-1H-pyrazol-4-yl)-1H-indole-2-carboxamide

I-263

The title compound was prepared according to the procedure used in Example 261 by substituting 3-(3-(4-chloro-3,5-dimethylphenoxy)propyl)-N-((2-chloropyridin-4-yl)methyl)-7-(1,3,5-trimethyl-1H-pyrazol-4-yl)-1H-indole-2-carboxamide for 3-(3-(4-chloro-3,5-dimethylphenoxy)propyl)-N-((6-chloropyridin-3-yl)methyl)-7-(1,3,5-trimethyl-1H-pyrazol-4-yl)-1H-indole-2-carboxamide. MS (ES) 687.1 (M+H).

Example 264

Preparation of 3-(3-(4-chloro-3,5-dimethylphenoxy)propyl)-N-(3-(trifluoromethoxy)benzyl)-7-(1,3,5-trimethyl-1H-pyrazol-4-yl)-1H-indole-2-carboxamide

I-264

The title compound was prepared according to the procedure used in Example 48 by substituting (3-(trifluoromethoxy)phenyl)methanamine for tert-butyl piperidin-4-ylcarbamate. MS (ES) 639.0 (M+H).

Example 265

Preparation of 3-(3-(4-chloro-3,5-dimethylphenoxy)propyl)-N-(3-methyl-5-(trifluoromethoxy)benzyl)-7-(1,3,5-trimethyl-1H-pyrazol-4-yl)-1H-indole-2-carboxamide

I-265

The title compound was prepared according to the procedure used in Example 48 by substituting (3-methyl-5-(trifluoromethoxy)phenyl)methanamine for tert-butyl piperidin-4-ylcarbamate. MS (ES) 653.1 (M+H).

Example 266

Preparation of ethyl 5-((3-(3-(4-chloro-3,5-dimethylphenoxy)propyl)-7-(1,3,5-trimethyl-1H-pyrazol-4-yl)-1H-indole-2-carboxamido)methyl)furan-2-carboxylate

I-266

To a stirred solution of EDC (0.502 mmol), HOBT (0.033 mmol), 3-(3-(4-chloro-3,5-dimethylphenoxy)propyl)-7-(1,3,5-trimethyl-1H-pyrazol-4-yl)-1H-indole-2-carboxylic acid (0.335 mmol) in DCM (0.1M) and TEA (1.34 mmol) was added ethyl 5-(aminomethyl)furan-2-carboxylate hydrochloride (0.368 mmol). The reaction mixture was allowed to stir for 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H2O/CH3CN gradient to 95% CH3CN 0.1% TFA) to yield the title compound as a white solid. MS (ES) 617.1 (M+H).

Example 267

Preparation of 5-((3-(3-(4-chloro-3,5-dimethylphenoxy)propyl)-7-(1,3,5-trimethyl-1H-pyrazol-4-yl)-1H-indole-2-carboxamido)methyl)furan-2-carboxylic acid

I-267

The title compound was prepared according to the procedure used in Example 57 by substituting ethyl 5-((3-(3-(4-chloro-3,5-dimethylphenoxy)propyl)-7-(1,3,5-trimethyl-1H-pyrazol-4-yl)-1H-indole-2-carboxamido)methyl)furan-2-carboxylate for ethyl 5-((3-(3-(4-chloro-3,5-dimethylphenoxy)propyl)-1H-indole-2-carboxamido)methyl)furan-2-carboxylate. $^1$H NMR (d6-DMSO, 400 MHz, 25° C.): 10.56 (s, 1H), 8.88 (m, 1H), 7.59 (d, J=8.0 Hz, 1H), 7.15 (d, J=4.0 Hz, 1H), 7.15-7.00 (m, 2H), 6.76 (s, 2H), 6.48 (m, 1H), 4.54 (d, J=8.0 Hz, 2H), 3.77 (s, 3H), 3.25 (t, J=6.0 Hz, 2H), 2.27 (s, 6H), 2.09 (s, 3H), 2.06-2.01 (m, 5H), MS (ES) 589.0 (M+H).

Example 268

Preparation of 3-(3-(4-chloro-3,5-dimethylphenoxy)propyl)-N-((5-(hydroxymethyl)furan-2-yl)methyl)-7-(1,3,5-trimethyl-1H-pyrazol-4-yl)-1H-indole-2-carboxamide

I-268

To a stirred solution of ethyl 5-((3-(3-(4-chloro-3,5-dimethylphenoxy)propyl)-7-(1,3,5-trimethyl-1H-pyrazol-4-yl)-1H-indole-2-carboxamido)methyl)furan-2-carboxylate (0.032 mmol) in THF (0.1M) at 0° C. was added 2M Lithium borohydride solution in THF (0.096 mmol). The reaction was allowed to slowly warm to room temperature and stir for an additional 15 h. The mixture was then cooled to 0° C. and acidified to pH 6 with 3N aqueous HCl. The mixture was extracted with ethyl acetate and the organic layer washed with brine, dried over sodium sulfate can concentrated via rotary evaporation. The solid was then dissolved in 1 mL of a 1:1 mix of acetonitrile and methanol and was purified by reverse phase preparatory HPLC (H$_2$O/CH$_3$CN gradient to 95% CH$_3$CN 0.1% TFA) to yield the title compound as a white solid. MS (ES) 575.1 (M+H).

Example 269

Preparation of 5-((3-(3-(4-chloro-3,5-dimethylphenoxy)propyl)-N,1-dimethyl-7-(1,3,5-trimethyl-1H-pyrazol-4-yl)-1H-indole-2-carboxamido)methyl)furan-2-carboxylic acid

I-269

To a stirred solution of ethyl 5-((3-(3-(4-chloro-3,5-dimethylphenoxy)propyl)-7-(1,3,5-trimethyl-1H-pyrazol-4-yl)-1H-indole-2-carboxamido)methyl)furan-2-carboxylate (0.043 mmol) in THF was added sodium hydride (0.43 mmol) at 0° C. After addition, the mixture was allowed to stir at room temperature for 30 minutes before the addition of iodomethane (0.43 mmol). After one hour the reaction was reverse-quenched into a mixture of 3M HCl and DCM. The aqueous phase was extracted with DCM, washed with brine, dried over magnesium sulfate and concentrated via rotary evaporation. The residue was then dissolved in 1 mL of a 1:1 mix of acetonitrile and methanol and was purified by reverse phase preparatory HPLC (H$_2$O/CH$_3$CN gradient to 95% CH$_3$CN 0.1% TFA) to yield the title compound as a white solid. MS (ES) 617.1 (M+H).

Example 270

Preparation of (5-((3-(3-(4-chloro-3,5-dimethylphenoxy)propyl)-7-(1,3,5-trimethyl-1H-pyrazol-4-yl)-1H-indole-2-carboxamido)methyl)furan-2-carbonyl)-L-isoleucine

I-270

Step A. Preparation of methyl (5-((3-(3-(4-chloro-3,5-dimethylphenoxy)propyl)-7-(1,3,5-trimethyl-1H-pyrazol-4-yl)-1H-indole-2-carboxamido)methyl)furan-2-carbonyl)-L-isoleucinate To a stirred solution of EDC (0.043 mmol), HOBT (0.003 mmol), 5-((3-(3-(4-chloro-3,5-dimethylphenoxy)propyl)-7-(1,3,5-trimethyl-1H-pyrazol-4-yl)-1H-indole-2-carboxamido)methyl)furan-2-carboxylic acid (0.028 mmol) in DCM (0.1M) and TEA (0.115 mmol) was added methyl L-isoleucinate hydrochloride (0.032 mmol). The reaction mixture was allowed to stir for 15 h. Upon completion the volatiles were removed via rotary evaporation and the remaining material adsorbed onto silica gel. The material was isolated via silica gel chromatography using a gradient up to 5% methanol in DCM to yield the title compound as a foam. MS (ES) 716.1 (M+H).

Step B. Example 270

Title compound was prepared according to the procedure used in Example 57 by substituting methyl (5-((3-(3-(4-chloro-3,5-dimethylphenoxy)propyl)-7-(1,3,5-trimethyl-1H-pyrazol-4-yl)-1H-indole-2-carboxamido)methyl)furan-2-carbonyl)-L-isoleucinate for ethyl 5-((3-(3-(4-chloro-3,5-dimethylphenoxy)propyl)-1H-indole-2-carboxamido)methyl)furan-2-carboxylate. MS (ES) 702.1 (M+H).

Example 271

Preparation of (5-((3-(3-(4-chloro-3,5-dimethylphenoxy)propyl)-7-(1,3,5-trimethyl-1H-pyrazol-4-yl)-1H-indole-2-carboxamido)methyl)furan-2-carbonyl)-L-phenylalanine

I-271

Step A. Preparation of methyl (5-((3-(3-(4-chloro-3,5-dimethylphenoxy)propyl)-7-(1,3,5-trimethyl-1H-pyrazol-4-yl)-1H-indole-2-carboxamido)methyl)furan-2-carbonyl)-L-phenylalaninate The title compound was prepared according to the procedure used in Example 270 Step A by substituting methyl L-phenylalaninate hydrochloride for methyl L-isoleucinate hydrochloride. MS (ES) 750.1 (M+H).

Step B. Example 271

The title compound was prepared according to the procedure used in Example 270 Step B by substituting methyl (5-((3-(3-(4-chloro-3,5-dimethylphenoxy)propyl)-7-(1,3,5-trimethyl-1H-pyrazol-4-yl)-1H-indole-2-carboxamido)methyl)furan-2-carbonyl)-L-phenylalaninate for methyl (5-((3-(3-(4-chloro-3,5-dimethylphenoxy)propyl)-7-(1,3,5-trimethyl-1H-pyrazol-4-yl)-1H-indole-2-carboxamido)methyl)furan-2-carbonyl)-L-isoleucinate. MS (ES) 736.0 (M+H).

Example 272

Preparation of methyl 5-((3-(3-(4-chloro-3,5-dimethylphenoxy)propyl)-7-(1,3,5-trimethyl-1H-pyrazol-4-yl)-1H-indole-2-carboxamido)methyl)-2-methylfuran-3-carboxylate

I-272

The title compound was prepared according to the procedure used in Example 266 by substituting methyl 5-(aminomethyl)-2-methylfuran-3-carboxylate hydrochloride for ethyl 5-(aminomethyl)furan-2-carboxylate hydrochloride. MS (ES) 617.1 (M+H).

Example 273

Preparation of 5-((3-(3-(4-chloro-3,5-dimethylphenoxy)propyl)-7-(1,3,5-trimethyl-1H-pyrazol-4-yl)-1H-indole-2-carboxamido)methyl)-2-methylfuran-3-carboxylic acid

I-273

The title compound was prepared according to the procedure used in Example 57 by substituting methyl 5-((3-(3-(4-chloro-3,5-dimethylphenoxy)propyl)-7-(1,3,5-trimethyl-1H-pyrazol-4-yl)-1H-indole-2-carboxamido)methyl)-2-methylfuran-3-carboxylate for ethyl 5-((3-(3-(4-chloro-3,5-dimethylphenoxy)propyl)-1H-indole-2-carboxamido)methyl)furan-2-carboxylate. MS (ES) 603.0 (M+H).

Example 274

Preparation of 5-((3-(3-(4-chloro-3,5-dimethylphenoxy)propyl)-N,1-dimethyl-7-(1,3,5-trimethyl-1H-pyrazol-4-yl)-1H-indole-2-carboxamido)methyl)-2-methylfuran-3-carboxylic acid

I-274

Title compound was prepared according to the procedure used in Example 269 by substituting methyl 5-((3-(3-(4-chloro-3,5-dimethylphenoxy)propyl)-7-(1,3,5-trimethyl-1H-pyrazol-4-yl)-1H-indole-2-carboxamido)methyl)-2-methylfuran-3-carboxylate for ethyl 5-((3-(3-(4-chloro-3,5-dimethylphenoxy)propyl)-7-(1,3,5-trimethyl-1H-pyrazol-4-yl)-1H-indole-2-carboxamido)methyl)furan-2-carboxylate. MS (ES) 617.1 (M+H).

Example 275

Preparation of N-((4-(benzylcarbamoyl)-5-methylfuran-2-yl)methyl)-3-(3-(4-chloro-3,5-dimethylphenoxy)propyl)-7-(1,3,5-trimethyl-1H-pyrazol-4-yl)-1H-indole-2-carboxamide

I-275

To a stirred solution of EDC (0.082 mmol), HOBT (0.005 mmol), 5-((3-(3-(4-chloro-3,5-dimethylphenoxy)propyl)-7-(1,3,5-trimethyl-1H-pyrazol-4-yl)-1H-indole-2-carboxamido)methyl)-2-methylfuran-3-carboxylic acid (0.055 mmol) in DCM (0.1M) and TEA (0.219 mmol) was added benzyl amine (0.060 mmol). The reaction mixture was allowed to stir for 15 hours. Upon completion the volatiles were removed via rotary evaporation and the residue was then dissolved in 1 mL of a 1:1 mix of acetonitrile and methanol and was purified by reverse phase preparatory HPLC ($H_2O/CH_3CN$ gradient to 95% $CH_3CN$ 0.1% TFA) to yield the title compound as a white solid. MS (ES) 692.1 (M+H).

Example 276

Preparation of methyl 2-chloro-6-((3-(3-(4-chloro-3,5-dimethylphenoxy)propyl)-7-(1,3,5-trimethyl-1H-pyrazol-4-yl)-1H-indole-2-carboxamido)methyl)isonicotinate

I-276

The title compound was prepared according to the procedure used in Example 266 by substituting methyl 2-(aminomethyl)-6-chloroisonicotinate for ethyl 5-(aminomethyl)furan-2-carboxylate hydrochloride. MS (ES) 648.0 (M+H).

Example 277

Preparation of 2-chloro-6-((3-(3-(4-chloro-3,5-dimethylphenoxy)propyl)-7-(1,3,5-trimethyl-1H-pyrazol-4-yl)-1H-indole-2-carboxamido)methyl)isonicotinic acid

I-277

The title compound was prepared according to the procedure used in Example 57 by substituting 2-chloro-6-((3-(3-(4-chloro-3,5-dimethylphenoxy)propyl)-7-(1,3,5-trimethyl-1H-pyrazol-4-yl)-1H-indole-2-carboxamido)methyl) isonicotinic acid for ethyl 5-((3-(3-(4-chloro-3,5-dimethylphenoxy)propyl)-1H-indole-2-carboxamido) methyl)furan-2-carboxylate. MS (ES) 633.2 (M+H).

Example 278

Preparation of 3-(3-(4-chloro-3,5-dimethylphenoxy)propyl)-N-((6-((2,3-dihydro-1H-inden-2-yl)amino)-4-((2,3-dihydro-1H-inden-2-yl)carbamoyl)pyridin-2-yl)methyl)-7-(1,3,5-trimethyl-1H-pyrazol-4-yl)-1H-indole-2-carboxamide

I-278

To a microwave compatible vessel containing methyl 2-chloro-6-((3-(3-(4-chloro-3,5-dimethylphenoxy)propyl)-7-(1,3,5-trimethyl-1H-pyrazol-4-yl)-1H-indole-2-carboxamido)methyl)isonicotinate (0.055 mmol) and a stir bar was added 2,3-dihydro-1H-inden-2-amine (0.139 mmol). The vessel was sealed and placed in the microwave for 1 h at 225° C. Upon completion the reaction was slurried in 1 mL of 1:1 mix of acetonitrile and methanol. The slurry was filtered and the filtrate was purified by reverse phase preparatory HPLC ($H_2O/CH_3CN$ gradient to 95% $CH_3CN$ 0.1% TFA) to yield the title compound an oil. MS (ES) 846.1 (M+H).

Example 279

Preparation of ethyl 2-((3-(3-(4-chloro-3,5-dimethylphenoxy)propyl)-7-(1,3,5-trimethyl-1H-pyrazol-4-yl)-1H-indole-2-carboxamido)methyl)isonicotinate

I-279

The title compound was prepared according to the procedure used in Example 266 by substituting ethyl 2-(aminomethyl)isonicotinate hydrochloride for ethyl 5-(aminomethyl)furan-2-carboxylate hydrochloride. MS (ES) 628.0 (M+H).

Example 280

Preparation of 2-((3-(3-(4-chloro-3,5-dimethylphenoxy)propyl)-7-(1,3,5-trimethyl-1H-pyrazol-4-yl)-1H-indole-2-carboxamido)methyl)isonicotinic acid

I-280

The title compound was prepared according to the procedure used in Example 57 by substituting ethyl 2-((3-(3-(4-chloro-3,5-dimethylphenoxy)propyl)-7-(1,3,5-trimethyl-1H-pyrazol-4-yl)-1H-indole-2-carboxamido)methyl) isonicotinate for ethyl 5-((3-(3-(4-chloro-3,5-dimethylphenoxy)propyl)-1H-indole-2-carboxamido) methyl)furan-2-carboxylate. MS (ES) 600.1 (M+H).

Example 281

Preparation of 3-(3-(4-chloro-3,5-dimethylphenoxy)propyl)-N-((4-(hydroxymethyl)pyridin-2-yl)methyl)-7-(1,3,5-trimethyl-1H-pyrazol-4-yl)-1H-indole-2-carboxamide

I-281

The title compound was prepared according to the procedure used in Example 268 by substituting ethyl 2-((3-(3-(4-chloro-3,5-dimethylphenoxy)propyl)-7-(1,3,5-trimethyl-1H-pyrazol-4-yl)-1H-indole-2-carboxamido)methyl) isonicotinate for ethyl 5-((3-(3-(4-chloro-3,5-dimethylphenoxy)propyl)-7-(1,3,5-trimethyl-1H-pyrazol-4-yl)-1H-indole-2-carboxamido)methyl)furan-2-carboxylate. $^1$H NMR (d6-DMSO, 400 MHz, 25° C.): 10.60 (s, 1H), 9.07 (m, 1H), 8.63 (d, J=8.0 Hz, 1H), 7.68-7.57 (m, 3H), 7.12-7.02 (m, 2H), 6.76 (s, 2H), 4.72 (m, 2H), 4.67 (s, 2H), 3.97 (m, 2H), 3.77 (s, 3H), 3.22 (m, 2H), 2.27 (s, 6H), 2.11 (s, 3H), 2.06-1.98 (m, 5H); MS (ES) 586.0 (M+H).

Example 282

Preparation of 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(3,4-dihydroisoquinolin-2(1H)-yl)isonicotinic acid

I-282

Step A. Preparation of methyl 2-(3,4-dihydroisoquinolin-2(1H)-yl)-6-((1,3-dioxoisoindolin-2-yl)methyl)isonicotinate To a microwave reaction vial was added cesium carbonate (0.151 mmol), methyl 2-chloro-6-((1,3-dioxoisoindolin-2-yl)methyl)isonicotinate (0.076 mmol), palladium acetate (0.0076 mmol), 2-Dicyclohexylphosphino-2',6'-dimethoxybiphenyl (0.0095 mmol), and a stir bar. This mixture was suspended in dioxane (0.05 M) for the addition of 1,2,3,4-tetrahydroisoquinoline (0.083 mmol). The microwave vial was then crimped and immediately transferred to the microwave reactor for heating at 110° C. for a period of 90 minutes. Upon completion the reaction was filtered through Celite and volatiles were removed in vacuo. The residue was then adsorbed onto silica gel. The material was isolated via silica gel chromatography using a gradient up to 50% ethyl acetate in hexanes to yield the Title compound white solid. MS (ES) 428.1 (M+H).

Step B. Preparation of methyl 2-(aminomethyl)-6-(3,4-dihydroisoquinolin-2(1H)-yl)isonicotinate To a stirred solution of methyl 2-(3,4-dihydroisoquinolin-2(1H)-yl)-6-((1,3-dioxoisoindolin-2-yl)methyl)isonicotinate (0.035 mmol) in methanol (0.05 M) was added hydrazine hydrate (0.070 mmol) at room temperature. Upon completion the volatiles were removed in vacuo, the residue was slurried in 1 mL of 1:1 mix of acetonitrile and methanol. The slurry was filtered and the filtrate was purified by reverse phase preparatory HPLC (H₂O/CH₃CN gradient to 95% CH₃CN 0.1% TFA) to yield the title compound as a yellow glass. MS (ES) 298.2 (M+H).

Step C. Preparation of methyl 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(3,4-dihydroisoquinolin-2(1H)-yl)isonicotinate To a stirred solution of EDC (0.015 mmol), HOBT (0.001 mmol), 6-chloro-3-(3-(4-chloro-3,5-dimethylphenoxy)propyl)-7-(1,3,5-trimethyl-1H-pyrazol-4-yl)-1H-indole-2-carboxylic acid (0.01 mmol) in DCM (0.1M) and TEA (0.04 mmol) was added methyl 2-(aminomethyl)-6-(3,4-dihydroisoquinolin-2(1H)-yl)isonicotinate. The reaction mixture was allowed to stir for 15 hours. Upon completion the volatiles were removed via rotary evaporation and the residue was then adsorbed onto silica gel. The material was isolated via silica gel chromatography using a gradient up to 10% methanol in DCM to yield methyl 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(3,4-dihydroisoquinolin-2(1H)-yl)isonicotinate. MS (ES) 779.1 (M+H).

Step D. Example 282

Title compound was prepared according to the procedure used in Example 57 by substituting methyl 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(3,4-dihydroisoquinolin-2(1H)-yl)isonicotinate for ethyl 5-((3-(3-(4-chloro-3,5-dimethylphenoxy)propyl)-1H-indole-2-carboxamido)methyl)furan-2-carboxylate. MS (ES) 765.0 (M+H).

Example 283

Preparation of 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(isopentylamino)isonicotinic acid

I-283

Step A. Preparation of methyl 2-((1,3-dioxoisoindolin-2-yl)methyl)-6-(isopentylamino)isonicotinate The title compound was prepared according to the procedure used in Example 282 Step A by substituting 3-methylbutan-1-amine for 1,2,3,4-tetrahydroisoquinoline MS (ES) 382.2 (M+H).

Step B. Preparation of methyl 2-(aminomethyl)-6-(3,4-dihydroisoquinolin-2(1H)-yl)isonicotinate The title compound was prepared according to the procedure used in Example 282 Step B by substituting methyl 2-((1,3-dioxoisoindolin-2-yl)methyl)-6-(isopentylamino)isonicotinate for methyl 2-(aminomethyl)-6-(3,4-dihydroisoquinolin-2(1H)-yl)isonicotinate. MS (ES) 252.3 (M+H).

Step C. Preparation of methyl 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(isopentylamino)isonicotinate The title compound was prepared according to the procedure used in Example 282 Step C by substituting methyl 2-(aminomethyl)-6-(isopentylamino)isonicotinate for methyl 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(3,4-dihydroisoquinolin-2(1H)-yl)isonicotinate. MS (ES) 733.0 (M+H).

Step D. Example 283

The title compound was prepared according to the procedure used in Example 57 by substituting methyl 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(isopentylamino)isonicotinate for ethyl 5-((3-(3-(4-chloro-3,5-dimethylphenoxy)propyl)-1H-indole-2-carboxamido)methyl)furan-2-carboxylate. MS (ES) 719.1 (M+H).

Example 284

Preparation of 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(4-(3-methylbutanoyl)piperazin-1-yl)isonicotinic acid

I-284

Step A. Preparation of methyl 2-((1,3-dioxoisoindolin-2-yl)methyl)-6-(piperazin-1-yl)isonicotinate Title compound was prepared according to the procedure used in Example 282 Step A by substituting piperazine for 1,2,3,4-tetrahydroisoquinoline. MS (ES) 381.1 (M+H).

Step B. Preparation of methyl 2-((1,3-dioxoisoindolin-2-yl)methyl)-6-(4-(3-methylbutanoyl)piperazin-1-yl)isonicotinate To a stirred solution of methyl 2-((1,3-dioxoisoindolin-2-yl)methyl)-6-(piperazin-1-yl)isonicotinate (0.050 mmol) in DCM (0.1M) and TEA (0.152 mmol) was added isovaleryl chloride (0.10 mmol). The reaction mixture was allowed to stir for 15 h at rt. Upon completion the volatiles were removed via rotary evaporation and the material used in the next step without further purification. MS (ES) 465.1 (M+H).

Step C. Preparation of methyl 2-(aminomethyl)-6-(4-(3-methylbutanoyl)piperazin-1-yl)isonicotinate To a stirred solution of methyl 2-((1,3-dioxoisoindolin-2-yl)methyl)-6-(4-(3-methylbutanoyl)piperazin-1-yl)isonicotinate (0.035 mmol) in methanol (0.05 M) was added hydrazine hydrate (0.070 mmol) at room temperature. Upon completion the volatiles were removed in vacuo, the residue was partitioned in DCM and saturated sodium bicarbonate. The aqueous phase was extracted with DCM, washed with brine, dried over magnesium sulfate and concentrated via rotary evaporation. The material used in the next step without further purification. MS (ES) 335.2 (M+H).

Step D. Preparation of methyl 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(4-(3-methylbutanoyl)piperazin-1-yl)isonicotinate The title compound was prepared according to the procedure used in Example 282 Step C by substituting methyl 2-(aminomethyl)-6-(4-(3-methylbutanoyl)piperazin-1-yl)isonicotinate for methyl 2-(aminomethyl)-6-(3,4-dihydroisoquinolin-2(1H)-yl)isonicotinate. MS (ES) 816.3 (M+H).

Step E. Example 284

The title compound was prepared according to the procedure used in Example 57 by methyl 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(4-(3-methylbutanoyl)piperazin-1-yl)isonicotinate for ethyl 5-((3-(3-(4-chloro-3,5-dimethylphenoxy)propyl)-1H-indole-2-carboxamido)methyl)furan-2-carboxylate. MS (ES) 802.0 (M+H).

Example 285

Preparation of 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(4-isopentylpiperazin-1-yl)isonicotinic acid

I-285

Step A. Preparation of methyl 2-((1,3-dioxoisoindolin-2-yl)methyl)-6-(piperazin-1-yl)isonicotinate The title compound was prepared according to the procedure used in Example 282 Step A by substituting piperazine for 1,2,3,4-tetrahydroisoquinoline. MS (ES) 381.1 (M+H).

Step B. Preparation of methyl 2-((1,3-dioxoisoindolin-2-yl)methyl)-6-(4-isopentylpiperazin-1-yl)isonicotinate To a stirred solution of product from Step A (0.050 mmol) in DCM (0.1M) and TEA (0.152 mmol) was added isovaleraldehyde (0.101 mmol). The reaction mixture was allowed to stir for 30 minutes at room temperature before the addition of sodium triacetoxyborohydride. Upon completion the reaction was quenched with saturated sodium bicarbonate, the aqueous phase was extracted with DCM, washed with brine, dried over magnesium sulfate and concentrated via rotary evaporation. The material was used in the next step without further purification. MS (ES) 451.2 (M+H).

Step C. Preparation of methyl 2-(aminomethyl)-6-(4-(3-methylbutanoyl)piperazin-1-yl)isonicotinate To a stirred solution of methyl 2-((1,3-dioxoisoindolin-2-yl)methyl)-6-(4-isopentylpiperazin-1-yl)isonicotinate (0.035 mmol) in methanol (0.05 M) was added hydrazine hydrate (0.070 mmol) at room temperature. Upon completion the volatiles were removed in vacuo, the residue was partitioned in DCM and saturated sodium bicarbonate. The aqueous phase was extracted with DCM, washed with brine, dried over magnesium sulfate and concentrated via rotary evaporation. The material used in the next step without further purification. MS (ES) 321.2 (M+H).

Step D. Preparation of methyl 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(4-(3-methylbutanoyl)piperazin-1-yl)isonicotinate The title compound was prepared according to the procedure used in Example 282 Step C by methyl 2-(aminomethyl)-6-(4-isopentylpiperazin-1-yl)isonicotinate for methyl 2-(aminomethyl)-6-(3,4-dihydroisoquinolin-2(1H)-yl)isonicotinate. MS (ES) 802.3 (M+H).

Step E. Example 285

The title compound was prepared according to the procedure used in Example 57 by substituting methyl 2-((6-chloro-3-(3-(4-chloro-3,5-dimethylphenoxy)propyl)-7-(1,3,5-trimethyl-1H-pyrazol-4-yl)-1H-indole-2-carboxamido)methyl)-6-(4-(3-methylbutanoyl)piperazin-1-yl)isonicotinate for ethyl 5-((3-(3-(4-chloro-3,5-dimethylphenoxy)propyl)-1H-indole-2-carboxamido)methyl)furan-2-carboxylate. MS (ES) 802.0 (M+H).

Example 286

Preparation of (3-(3-(4-chloro-3,5-dimethylphenoxy)propyl)-7-(1,3,5-trimethyl-1H-pyrazol-4-yl)-1H-indole-2-carbonyl)glycine

I-286

Step A. Preparation of methyl (3-(3-(4-chloro-3,5-dimethylphenoxy)propyl)-7-(1,3,5-trimethyl-1H-pyrazol-4-yl)-1H-indole-2-carbonyl)glycinate The title compound was prepared according to the procedure used in Example 40 using methyl glycinate hydrochloride in place of aniline. MS (ES) 537.3 (M+H).

Step B. Example 286

The title compound was prepared according to the procedure used in Example 57 by substituting methyl (3-(3-(4-chloro-3,5-dimethylphenoxy)propyl)-7-(1,3,5-trimethyl-1H-pyrazol-4-yl)-1H-indole-2-carbonyl)glycinate for ethyl 5-((3-(3-(4-chloro-3,5-dimethylphenoxy)propyl)-1H-indole-2-carboxamido)methyl)furan-2-carboxylate. MS (ES) 523.0 (M+H).

Example 287

Preparation of methyl (3-(3-(4-chloro-3,5-dimethylphenoxy)propyl)-7-(1,3,5-trimethyl-1H-pyrazol-4-yl)-1H-indole-2-carbonyl)glycylglycinate

I-287

To a stirred solution of EDC (0.072 mmol), HOBT (0.005 mmol), (3-(3-(4-chloro-3,5-dimethylphenoxy)propyl)-7-(1,3,5-trimethyl-1H-pyrazol-4-yl)-1H-indole-2-carbonyl)glycine (0.048 mmol) in DCM (0.1M) and TEA (0.191 mmol) was added methyl glycinate hydrochloride (0.057 mmol). The reaction mixture was allowed to stir for 15 h. Upon completion the volatiles were removed via rotary evaporation and the remaining material adsorbed onto silica gel. The material was isolated via silica gel chromatography using a gradient up to 10% methanol in DCM to yield the Title compound as a foam. MS (ES) 594.3 (M+H).

Example 288

Preparation of methyl (3-(3-(4-chloro-3,5-dimethylphenoxy)propyl)-7-(1,3,5-trimethyl-1H-pyrazol-4-yl)-1H-indole-2-carbonyl)glycyl-L-phenylalaninate

I-288

The title compound was prepared according to the procedure used in Example 328 by substituting methyl L-phenylalaninate hydrochloride for methyl glycinate hydrochloride. MS (ES) 684.1 (M+H).

Example 289

Preparation of methyl (3-(3-(4-chloro-3,5-dimethylphenoxy)propyl)-7-(1,3,5-trimethyl-1H-pyrazol-4-yl)-1H-indole-2-carbonyl)glycyl-L-leucinate

I-289

The title compound was prepared according to the procedure used in Example 328 by substituting methyl L-leucinate hydrochloride for methyl glycinate hydrochloride. MS (ES) 650.1 (M+H).

Example 290

Preparation of (3-(3-(4-chloro-3,5-dimethylphenoxy)propyl)-7-(1,3,5-trimethyl-1H-pyrazol-4-yl)-1H-indole-2-carbonyl)glycylglycine

I-290

The title compound was prepared according to the procedure used in Example 57 by substituting methyl (3-(3-(4-chloro-3,5-dimethylphenoxy)propyl)-7-(1,3,5-trimethyl-1H-pyrazol-4-yl)-1H-indole-2-carbonyl)glycylglycinate for ethyl 5-((3-(3-(4-chloro-3,5-dimethylphenoxy)propyl)-1H-indole-2-carboxamido)methyl)furan-2-carboxylate. MS (ES) 580.0 (M+H).

Example 291

Preparation of (3-(3-(4-chloro-3,5-dimethylphenoxy)propyl)-7-(1,3,5-trimethyl-1H-pyrazol-4-yl)-1H-indole-2-carbonyl)glycyl-L-phenylalanine

I-291

The title compound was prepared according to the procedure used in Example 57 by substituting methyl (3-(3-(4-chloro-3,5-dimethylphenoxy)propyl)-7-(1,3,5-trimethyl-1H-pyrazol-4-yl)-1H-indole-2-carbonyl)glycyl-L-phenylalaninate for ethyl 5-((3-(3-(4-chloro-3,5-dimethylphenoxy)propyl)-1H-indole-2-carboxamido)methyl)furan-2-carboxylate. MS (ES) 670.1 (M+H).

Example 292

Preparation of (3-(3-(4-chloro-3,5-dimethylphenoxy)propyl)-7-(1,3,5-trimethyl-1H-pyrazol-4-yl)-1H-indole-2-carbonyl)glycyl-L-leucine

I-292

The title compound was prepared according to the procedure used in Example 57 by substituting methyl (3-(3-(4-chloro-3,5-dimethylphenoxy)propyl)-7-(1,3,5-trimethyl-1H-pyrazol-4-yl)-1H-indole-2-carbonyl)glycyl-L-leucinate for ethyl 5-((3-(3-(4-chloro-3,5-dimethylphenoxy)propyl)-1H-indole-2-carboxamido)methyl)furan-2-carboxylate. MS (ES) 636.1 (M+H).

Example 293

Preparation of 5-((3-(3-(4-chloro-3,5-dimethylphenoxy)propyl)-7-(1,3,5-trimethyl-1H-pyrazol-4-yl)-1H-indole-2-carboxamido)methyl)-2-((3,4-dihydroisoquinolin-2(1H)-yl)methyl)furan-3-carboxylic acid

I-293

Step A. Preparation of methyl 5-((1,3-dioxoisoindolin-2-yl)methyl)-2-methylfuran-3-carboxylate To a microwave compatible vessel containing methyl 5-(aminomethyl)-2-methylfuran-3-carboxylate hydrochloride (1.2 mmol) and a stir bar was added isobenzofuran-1,3-dione (1.2 mmol). The vessel was sealed and placed in the microwave for 30 min at 150° C. Upon completion the material was partitioned in DCM and saturated sodium bicarbonate. The aqueous phase was extracted with DCM, washed with brine, dried over magnesium sulfate and concentrated via rotary evaporation. The material used in the next step without further purification. MS (ES) 300.1 (M+H).

Step B. Preparation of methyl 2-(bromomethyl)-5-((1,3-dioxoisoindolin-2-yl)methyl)furan-3-carboxylate To a solution of methyl 5-((1,3-dioxoisoindolin-2-yl)methyl)-2-methylfuran-3-carboxylate (0.84 mmol) in chlorobenzene (0.1M) was added NBS (0.92 mmol) and AIBN (0.17 mmol). The reaction mixture was allowed to stir for 15 h at 90° C. Upon completion the volatiles were removed via rotary evaporation and the residue was partitioned in DCM and saturated sodium bicarbonate. The aqueous phase was extracted with DCM, washed with brine, dried over magnesium sulfate and adsorbed onto silica gel. The material was isolated via silica gel chromatography using a gradient up to 25% ethyl acetate in hexanes to yield the title compound. MS (ES) 399.9 (M+Na).

Step C. Preparation methyl 2-((3,4-dihydroisoquinolin-2(1H)-yl)methyl)-5-((1,3-dioxoisoindolin-2-yl)methyl)furan-3-carboxylate To a stirred solution of methyl 2-(bromomethyl)-5-((1,3-dioxoisoindolin-2-yl)methyl)furan-3-carboxylate (0.20 mmol) in DCM (0.2 M) and TEA (0.60 mmol) was added 1,2,3,4-tetrahydroisoquinoline (0.25 mmol) at rt. After 1 h, the reaction adsorbed onto silica gel. The material was isolated via silica gel chromatography using a gradient up to 5% methanol in DCM to yield the title compound. MS (ES) 431.1 (M+H).

Step D. Preparation of methyl 5-(aminomethyl)-2-((3,4-dihydroisoquinolin-2(1H)-yl)methyl)furan-3-carboxylate To a stirred solution of methyl 2-((3,4-dihydroisoquinolin-2(1H)-yl)methyl)-5-((1,3-dioxoisoindolin-2-yl)methyl)furan-3-carboxylate (0.070 mmol) in methanol (0.05 M) was added hydrazine hydrate (0.077 mmol) at room temperature. After 2 h, the volatiles were removed in vacuo, the residue was slurried in 1 mL of 1:1 mix of acetonitrile and methanol. The slurry was filtered and the filtrate was purified by the reverse phase preparatory HPLC ($H_2O/CH_3CN$ gradient to 25% $CH_3CN$ 0.1% TFA) to yield the title compound as a white solid. MS (ES) 301.2 (M+H).

Step E. Preparation of methyl 5-((3-(3-(4-chloro-3,5-dimethylphenoxy)propyl)-7-(1,3,5-trimethyl-1H-pyrazol-4-yl)-1H-indole-2-carboxamido)methyl)-2-((3,4-dihydroisoquinolin-2(1H)-yl)methyl)furan-3-carboxylate The title compound was prepared according to the procedure used in Example 266 by substituting methyl 5-(aminomethyl)-2-((3,4-dihydroisoquinolin-2(1H)-yl)methyl)furan-3-carboxylate for ethyl 5-(aminomethyl)furan-2-carboxylate hydrochloride. MS (ES) 748.3 (M+H).

Step E. Example 293

The title compound was prepared according to the procedure used in Example 57 by substituting methyl 5-((3-(3-(4-chloro-3,5-dimethylphenoxy)propyl)-7-(1,3,5-trimethyl-1H-pyrazol-4-yl)-1H-indole-2-carboxamido)methyl)-2-((3,4-dihydroisoquinolin-2(1H)-yl)methyl)furan-3-carboxylate for ethyl 5-((3-(3-(4-chloro-3,5-dimethylphenoxy)propyl)-1H-indole-2-carboxamido)methyl)furan-2-carboxylate. MS (ES) 734.1 (M+H).

Example 294

Preparation of 2-(2-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)ethyl)benzoic acid

I-294

Step A. Preparation of methyl 2-(2-(6-chloro-3-(3-(4-chloro-3,5-dimethylphenoxy)propyl)-7-(1,3,5-trimethyl-1H-pyrazol-4-yl)-1H-indole-2-carboxamido)ethyl)benzoate To a stirred solution of EDC (0.096 mmol), HOBT (0.007 mmol), 6-chloro-3-(3-(4-chloro-3,5-dimethylphenoxy)propyl)-7-(1,3,5-trimethyl-1H-pyrazol-4-yl)-1H-indole-2-carboxylic acid (0.064 mmol) in DCM (0.1M) and TEA (0.255 mmol) was added methyl 2-(2-aminoethyl)benzoate. The reaction mixture was allowed to stir for 15 h. Upon completion the volatiles were removed via rotary evaporation and the residue was then adsorbed onto silica gel. The material was isolated via silica gel chromatography using a gradient up to 10% methanol in DCM to yield the title compound. MS (ES) 661.0 (M+H).

Step B. Preparation of methyl 2-(2-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)ethyl)benzoate To a stirred solution of methyl 2-(2-(6-chloro-3-(3-(4-chloro-3,5-dimethylphenoxy)propyl)-7-(1,3,5-trimethyl-1H-pyrazol-4-yl)-1H-indole-2-carboxamido)ethyl)benzoate (0.038 mmol) in DMF (0.1 M) was added cesium carbonate (0.19 mmol) followed by 1,2-dibromopropane at room temperature. After 15 minutes, the reaction was heated to 60° C. for a period of 15 h. The reaction mixture was filtered and partitioned between ethyl acetate and water. The aqueous phase was extracted with ethyl acetate. The combined organics were diluted with hexanes, washed with water, followed by brine, dried over magnesium sulfate and concentrated via rotary evaporation to give the crude title product, which was taken onto the next step without further purification. MS (ES) 701.1 (M+H).

Step C. Example 294

The title compound was prepared according to the procedure used in Example 57 by substituting methyl 2-(2-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)ethyl)benzoate for ethyl 5-((3-(3-(4-chloro-3,5-dimethylphenoxy)propyl)-1H-indole-2-carboxamido)methyl)furan-2-carboxylate. MS (ES) 687.1 (M+H).

Example 295

Preparation of 2-(4-(8-chloro-11-(3-(4-chloro-3,5-dimethylphenoxy)propyl)-1-oxo-2,3,4,5-tetrahydro-1H-[1,4]diazepino[1,2-a]indol-7-yl)-3,5-dimethyl-1H-pyrazol-1-yl)acetic acid

I-295

Step A. Preparation of ethyl 7-(1-(2-(tert-butoxy)-2-oxoethyl)-3,5-dimethyl-1H-pyrazol-4-yl)-6-chloro-3-(3-(4-chloro-3,5-dimethylphenoxy)propyl)-1H-indole-2-carboxylate To a microwave reaction vial was added tert-butyl 2-(3,5-dimethyl-4-(4,4,5,5-tetramethyl-1,3,2-dioxaborolan-2-yl)-1H-pyrazol-1-yl)acetate (0.446 mmol), ethyl 7-bromo-6-chloro-3-(3-(4-chloro-3,5-dimethylphenoxy)propyl)-1H-indole-2-carboxylate (0.491 mmol), dioxane (0.6 M) and an aqueous solution of 2N potassium carbonate (0.3 M), and a stir bar. Immediately before placing the vessel in the microwave, tetrakis(triphenylphosphine)palladium (0.026 mmol) was added and the vial crimped for heating at 115° C. for a period of 60 min. The reaction was then neutralized to a pH of 7 for extraction with ethyl acetate. The combined organics were then washed with brine, dried over magnesium sulfate, filtered and volatiles were removed in vacuo. The material was then adsorbed onto silica gel for isolation via silica gel chromatography using a gradient up to 50% ethyl acetate in hexanes to yield the title compound as a white foam. $^1$H NMR (d6-DMSO 400 MHz, 25° C.): 10.67 (s, 1H), 7.69 (d, J=8.0 Hz, 1H), 7.2 (d, J=8.0 Hz, 1H), 6.76 (s, 2H), 4.29 (m, 2H), 3.99 (m, 2H), 3.18 (m, 2H), 2.28 (s, 6H), 2.04 (m, 2H), 1.93 (s, 3H), 1.91 (s, 3H), 1.45 (s, 9H), 1.30 (t, J=6.0 Hz, 3H), 1.08 (s, 6H); MS (ES) 628.0 (M+H).

Step B. Preparation of ethyl 7-(1-(2-(tert-butoxy)-2-oxoethyl)-3,5-dimethyl-1H-pyrazol-4-yl)-1-(3-((tert-butoxycarbonyl)amino)propyl)-6-chloro-3-(3-(4-chloro-3,5-dimethylphenoxy)propyl)-1H-indole-2-carboxylate To a stirred solution of ethyl 7-(1-(2-(tert-butoxy)-2-oxoethyl)-3,5-dimethyl-1H-pyrazol-4-yl)-6-chloro-3-(3-(4-chloro-3,5-dimethylphenoxy)propyl)-1H-indole-2-carboxylate (0.13 mmol) and tert-butyl 1,2,3-oxathiazinane-3-carboxylate 2,2-dioxide (0.19 mmol) in DMF (0.1 M) was added NaH as a 60% dispersion in mineral oil (0.377 mmol) at rt. The reaction was allowed to stir for 15 h before quenching with a 10% citric acid solution. After 1 h, ethyl acetate was added and the layers separated. The aqueous phase was extracted twice with ethyl acetate. The combined organics were diluted with hexanes until slightly cloudy and then washed with water twice, then brine. The organics were then dried over magnesium sulfate, filtered and the volatiles were removed in vacuo. The isolated crude title compound was used in the next step without further purification. MS (ES) 785.1 (M+H).

Step C. Preparation of 2-(4-(1-(3-aminopropyl)-6-chloro-3-(3-(4-chloro-3,5-dimethylphenoxy)propyl)-2-(ethoxycarbonyl)-1H-indol-7-yl)-3,5-dimethyl-1H-pyrazol-1-yl)acetic acid To a stirred solution of ethyl 7-(1-(2-(tert-butoxy)-2-oxoethyl)-3,5-dimethyl-1H-pyrazol-4-yl)-1-(3-((tert-butoxycarbonyl)amino)propyl)-6-chloro-3-(3-(4-chloro-3,5-dimethylphenoxy)propyl)-1H-indole-2-carboxylate (0.13 mmol) in THF (0.1 M) was added a solution of 4M HCl in dioxane (0.8 mmol) and the reaction allowed to stir for 15 h before removing the volatiles via rotary evaporation. The residue was then partitioned in a mixture of DCM and saturated sodium bicarbonate (aq), the aqueous phase was extracted with DCM twice. The combined organics were washed with brine, dried over magnesium sulfate, filtered and evaporated to dryness. The crude title compound was used in the next step without further purification. MS (ES) 685.1 (M+H).

Step D. Example 295

To a stirred solution of 2-(4-(1-(3-aminopropyl)-6-chloro-3-(3-(4-chloro-3,5-dimethylphenoxy)propyl)-2-(ethoxycarbonyl)-1H-indol-7-yl)-3,5-dimethyl-1H-pyrazol-1-yl)acetic acid (0.073 mmol) in methanol (0.05 M) was added potassium carbonate (0.182 mmol). The reaction was then heated to 60° C. as a sealed system for a period of 14 hours. The solvent was removed via rotary evaporation and the crude material was partitioned between DCM and water. The aqueous phase was neutralized to a pH of 7 with an aqueous solution of 1M HCL. The layers were separated, the water layer was extracted with DCM three times, the combined organics were washed with brine, dried over magnesium sulfate, filtered and evaporated to dryness. The crude material was then slurried in 1 mL of 1:1 mix of acetonitrile and methanol. The slurry was filtered and the filtrate was purified by reverse phase preparatory HPLC ($H_2O/CH_3CN$ gradient from 40% to 95% $CH_3CN$ 0.1% TFA) to yield the title compound. MS (ES) 583.0 (M+H).

Example 296

Preparation of 3-bromo-5-((11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid

I-296

To a stirred solution of 11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (0.065 mmol) in DMF (0.1 M) was added sodium hydride as a 60% dispersion in mineral oil (0.196 mmol) at room temperature and the reaction allowed to stir for 30 minutes. After the allotted time, methyl 3-bromo-5-(bromomethyl)benzoate was added at room temperature and the reaction allowed to stir for 15 hours. The reaction was then quenched with an aqueous solution of 3M HCL followed by the addition of ethyl acetate. The layers were separated, the water layer was extracted with ethyl acetate three times, the combined organics were washed with brine, dried over magnesium sulfate, filtered and evaporated to dryness. The crude material was then slurried in 1 mL of 1:1 mix of acetonitrile and methanol. The slurry was filtered and the filtrate was purified by reverse phase preparatory HPLC ($H_2O/CH_3CN$ gradient from 50% to 95% $CH_3CN$ 0.1% TFA) to yield the title compound. MS (ES) 718.9 (M+H).

Example 297

Preparation of 3-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-5-methylbenzoic acid

I-297

Title compound was prepared according to the procedure used in Example 296 by substituting methyl 3-(bromomethyl)-5-methylbenzoate and 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one for methyl 3-bromo-5-(bromomethyl)benzoate and 11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one, respectively. MS (ES) 687.0 (M+H).

Example 298

Preparation of 2-chloro-6-((8-chloro-1-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)isonicotinic acid

I-298

Title compound was prepared according to the procedure used in Example 296 by substituting methyl 2-(bromomethyl)-6-chloroisonicotinate and 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one for methyl 3-bromo-5-(bromomethyl)benzoate and 11-(3-(4-chloro-3,5-dimethylphenoxy)propyl)-7-(1,3,5- trimethyl-1H-pyrazol-4-yl)-2,3,4,5-tetrahydro-1H-[1,4]diazepino[1,2-a]indol-1-one, respectively. MS (ES) 708.2 (M+H).

Example 299

Preparation of 3-bromo-5-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid

I-299

Title compound was prepared according to the procedure used in Example 296 by substituting 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one for 11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one, respectively. MS (ES) 752.9 (M+H).

Example 300

Preparation of 3-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-5-(isopentyloxy)benzoic acid

I-300

Title compound was prepared according to the procedure used in Example 296 by substituting methyl 3-(bromomethyl)-5-(isopentyloxy)benzoate and 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one for methyl 3-bromo-5-(bromomethyl)benzoate and 11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one, respectively. MS (ES) 759.1 (M+H).

Example 301

Preparation of 3-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-5-((4-methylpentyl)oxy)benzoic acid

I-301

Title compound was prepared according to the procedure used in Example 296 by substituting methyl 3-(bromomethyl)-5-((4-methylpentyl)oxy)benzoate and 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one for methyl 3-bromo-5-(bromomethyl)benzoate and 11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one, respectively. MS (ES) 773.1 (M+H).

Example 302

Preparation of 2-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-(isopentyloxy)isonicotinic acid

I-302

Title compound was prepared according to the procedure used in Example 296 by substituting methyl 2-(bromomethyl)-6-(isopentyloxy)isonicotinate and 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one for methyl 3-bromo-5-(bromomethyl)benzoate and 11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one, respectively. MS (ES) 760.1 (M+H).

Example 303

Preparation of 2-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-6-((4-methylpentyl)oxy)isonicotinic acid

I-303

Title compound was prepared according to the procedure used in Example 296 by substituting methyl 2-(bromomethyl)-6-((4-methylpentyl)oxy)isonicotinate and 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one for methyl 3-bromo-5-(bromomethyl)benzoate and 11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one, respectively. MS (ES) 774.1 (M+H).

Example 304

Preparation of 2-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)acetic acid

I-304

Title compound was prepared according to the procedure used in Example 296 by substituting tert-butyl 2-bromoacetate and 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one for methyl 3-bromo-5-(bromomethyl)benzoate and 11-(3-(4-chloro-3,5-dimethylphenoxy)propyl)-7-(1,3,5-trimethyl-1H-pyrazol- 4-yl)-2,3,4,5-tetrahydro-1H-[1,4]diazepino[1,2-a]indol-1-one, respectively. MS (ES) 597.1 (M+H).

Example 305

Preparation of (2-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)acetyl)-L-phenylalanine

I-305

To a stirred solution of EDC (0.018 mmol), HOBT (0.001 mmol), 2-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)acetic acid (0.012 mmol) in DCM (0.1M) and TEA (0.047 mmol) was added methyl L-phenylalaninate hydrochloride (0.013 mmol). The reaction mixture was allowed to stir for 20 hours. Upon completion the volatiles were removed via rotary evaporation and the material was dissolved in THF (0.5 mL) and treated with aqueous 2M LiOH (0.2 mL). The reaction was then quenched with an aqueous solution of 3M HCL followed by the addition of ethyl acetate. The layers were separated, the water layer was extracted with ethyl acetate three times, the combined organics were washed with brine, dried over magnesium sulfate, filtered and evaporated to dryness. The crude material was then slurried in 0.5 mL of 1:1 mix of acetonitrile and methanol. The slurry was filtered and the filtrate was purified by reverse phase preparatory HPLC ($H_2O/CH_3CN$ gradient from 50% to 95% $CH_3CN$ 0.1% TFA) to yield the title compound. MS (ES) 744.0 (M+H).

Example 306

Preparation of 5-((8-chloro-1-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-4'-hydroxy-[1,1'-biphenyl]-3-carboxylic acid

I-306

To a microwave reaction vial was added 3-bromo-5-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid (0.041 mmol), (4-hydroxyphenyl)boronic acid (0.049 mmol), dioxane (0.1M) and an aqueous solution of 2N potassium carbonate (0.1 M), and a stir bar. Immediately before placing the vessel in the microwave, tetrakis(triphenylphosphine)palladium (0.026 mmol) was added and the vial crimped for heating at 125° C. for a period of 60 minutes. The reaction was then acidified to a pH of 7 with 1M HCl (aq) for extraction with ethyl acetate. The aqueous phase was extracted three times, the combined organics were then washed with brine, dried over magnesium sulfate, filtered and volatiles were removed in vacuo. The crude material was then slurried in 0.5 mL of 1:1 mix of acetonitrile and methanol. The slurry was filtered and the filtrate was purified by reverse phase preparatory HPLC ($H_2O/CH_3CN$ gradient from 50% to 95% $CH_3CN$ 0.1% TFA) to yield the title compound. MS (ES) 765.0 (M+H).

Example 307

Preparation of 3-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-5-(2-(3-methylbutanamido)ethyl)benzoic acid

I-307

Step A. Preparation of 3-(2-((tert-butoxycarbonyl)amino)ethyl)-5-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid Title compound was prepared according to the procedure used in Example 306 by substituting potassium (2-((tert-butoxycarbonyl)amino)ethyl)trifluoroborate for (4-hydroxyphenyl)boronic acid. MS (ES) 816.0 (M+H).

Step B. Preparation of 3-(2-aminoethyl)-5-((8-chloro-1-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid To a stirred solution of 3-(2-((tert-butoxycarbonyl)amino)ethyl)-5-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid (0.055 mmol) in THF (0.1 M) was added a solution of 4M HCl in dioxane (0.5 mmol) and the reaction allowed to stir for 12 hours before removing the volatiles via rotary evaporation. The residue was then slurried in 0.5 mL of 1:1 mix of acetonitrile and methanol. The slurry was filtered and the filtrate was purified by reverse phase preparatory HPLC ($H_2O/CH_3CN$ gradient from 5 to 95% $CH_3CN$ 0.1% TFA) to yield the title compound. MS (ES) 716.1 (M+H).

Step C. Example 307

To a stirred solution of 3-(2-aminoethyl)-5-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid (0.006 mmol) in DCM (0.05M) and TEA (0.015 mmol) was added isovaleryl chloride (0.017 mmol). The reaction mixture was allowed to stir for 15 hours at room temperature. Upon completion the volatiles were removed via rotary evaporation and the residue was then slurried in 0.5 mL of 1:1 mix of acetonitrile and methanol. The slurry was filtered and the filtrate was purified by reverse phase preparatory HPLC ($H_2O/CH_3CN$ gradient from 5 to 95% $CH_3CN$ 0.1% TFA) to yield the title compound. MS (ES) 800.1 (M+H).

Example 308

Preparation of 5-((8-chloro-1-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-4'-((2-(trifluoromethyl)benzyl)oxy)-[1,1'-biphenyl]-3-carboxylic acid

I-308

To a stirred solution of 5-((8-chloro-11-(3-(4-chloro-3,5-dimethylphenoxy)propyl)-1-oxo-7-(1,3,5-trimethyl-1H- pyrazol-4-yl)-4,5-dihydro-1H-[1,4]diazepino[1,2-a]indol-2 (3H)-yl)methyl)-4'-hydroxy-[1,1'-biphenyl]-3-carboxylic acid (0.033 mmol) in DCM (0.1 M) and 0.25 mL 50% NaOH (aq) was added 1-(bromomethyl)-2-(trifluoromethyl)benzene (0.198 mmol) at room temperature. The reaction stirred for 3 days before acidifying to a pH of 2 with 3M HCl (aq) for extraction with ethyl acetate. The aqueous phase was extracted three times, the combined organics were then washed with brine, dried over magnesium sulfate, filtered and volatiles were removed in vacuo. The crude material was then slurried in 0.5 mL of 1:1 mix of acetonitrile and methanol. The slurry was filtered and the filtrate was purified by reverse phase preparatory HPLC (H$_2$O/CH$_3$CN gradient from 50% to 95% CH$_3$CN 0.1% TFA) to yield the title compound. MS (ES) 923.0 (M+H).

Example 309

Preparation of N-((4-(benzyloxy)phenyl)sulfonyl)-4-((8-chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl) methyl)benzamide

I-309

To a stirred solution of EDC (0.148 mmol), DMAP (0.223 mmol), 4-((8-chloro-11-(3-(4-chloro-3,5-dimethylphenoxy) propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid (0.074 mmol) in DCM (0.1M) and TEA (0.223 mmol) was added 4-(benzyloxy)benzenesulfonamide (0.089 mmol). The reaction mixture was allowed to stir for 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H$_2$O/CH$_3$CN gradient to from 50-95% CH$_3$CN 0.1% TFA) to yield the title compound as a white solid. MS (ES) 918.0 (M+H).

Example 310

Preparation of 4-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1, 2-a]indol-2(3H)-yl)methyl)-N-((4-(pyridin-3-ylmethoxy)phenyl)sulfonyl)benzamide

I-310

The title compound was prepared according to the procedure used in Example 309 by substituting 4-(pyridin-3-ylmethoxy)benzenesulfonamide for 4-(benzyloxy)benzenesulfonamide. MS (ES) 919.0 (M+H).

Example 311

Preparation of 3-bromo-5-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4] diazepino[1,2-a]indol-2(3H)-yl)methyl)benzoic acid

I-311

Title compound was prepared according to the procedure used in Example 296 by substituting 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one for 11-(3-(4-chloro-3,5-dimethylphenoxy) propyl)-7-(1,3,5-trimethyl-1H-pyrazol-4-yl)-2,3,4,5-tetrahydro-1H-[1,4]diazepino[1,2-a]indol-1-one, respectively. MS (ES) 751.1 (M+H).

Example 312

Preparation of 3-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1, 2-a]indol-2(3H)-yl)methyl)-5-((2-(trifluoromethyl) phenoxy)methyl)benzoic acid

I-312

Title compound was prepared according to the procedure used in Example 296 by substituting 3-(bromomethyl)-5-((2-(trifluoromethyl)phenoxy)methyl)benzoic acid and 8-chloro-11-(3-(4-chloro-3,5-dimethylphenoxy)propyl)-7-(1,3,5-trimethyl-1H-pyrazol-4-yl)-2,3,4,5-tetrahydro-1H-[1, 4]diazepino[1,2-a]indol-1-one for methyl 3-bromo-5-(bromomethyl)benzoate and 11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one, respectively. MS (ES) 847.2 (M+H).

Example 313

Preparation of 3-(3-(4-chloro-3,5-dimethylphenoxy) propyl)-N-(1H-pyrazol-3-yl)-7-(1,3,5-trimethyl-1H-pyrazol-4-yl)-1H-indole-2-carboxamide

I-313

To a solution of 3-(3-(4-chloro-3,5-dimethylphenoxy)propyl)-7-(1,3,5-trimethyl-1H-pyrazol-4-yl)-1H-indole-2-carboxylic acid (20 mg, 0.043 mmol) in CH$_2$Cl$_2$ (1 mL) were added 1H-pyrazol-3-amine (4 µL, 0.086 mmol), EDCI (17 mg, 0.086 mmol, 2 eqv.), DMAP (11 mg, 0.086 mmol, 2 eqv.) and the mixture was stirred at room temperature for 16 h at which time LC analysis indicated complete consumption of the starting material. The reaction mixture was extracted in CH$_2$Cl$_2$ (3×15 mL), dried (anhyd. Na$_2$SO$_4$), evaporated and finally purified by the reverse phase HPLC (Phenomenex Gemini C18, H$_2$O/CH$_3$CN gradient from 30-90% CH$_3$CN, 0.1% TFA) to give the title compound (19 mg, 83%) as a colorless solid; MS (ES) 531.1 (M+H); $^1$H NMR (400 MHz, DMSO-d$^6$) δ 8.26 (d, J=3.1 Hz, 1H), 7.79-7.60 (m, 1H), 7.19-7.14 (m, 2H), 6.75 (s, 2H), 6.03 (d, J=3.1 Hz, 1H), 4.00 (t, J=6.20 Hz, 2H), 3.80 (s, 3H), 2.27 (s, 6H), 2.20 (s, 3H), 2.13 (s, 3H), 2.12-1.97 (m, 4H).

Example 314

Preparation of (1R,2S)-2-(3-(3-(4-chloro-3,5-dimethylphenoxy)propyl)-7-(1,3,5-trimethyl-1H-pyrazol-4-yl)-1H-indole-2-carboxamido)cyclopentane-1-carboxylic acid

I-314

To a solution of 3-(3-(4-chloro-3,5-dimethylphenoxy)propyl)-7-(1,3,5-trimethyl-1H-pyrazol-4-yl)-1H-indole-2-carboxylic acid (20 mg, 0.043 mmol) in DMF (1 mL) were added ethyl (1R,2S)-2-aminocyclopentane-1-carboxylate (43 mg, 0.086 mmol), HBTU (60 mg, 0.158 mmol), triethylamine (48 µL, 0.344 mmol), and the mixture was stirred at room temperature for 24 h at which time LC analysis indicated complete consumption of the starting material. Aqueous lithium hydroxide solution (2 M, 1 mL) was added to the mixture and stirring was continued for additional 24 h. The volatiles were evaporated from the mixture in a rotary evaporator followed by acidification with 4M HCl to pH 7. The reaction mixture was extracted in ethyl acetate (3×15 mL), dried (anhyd. Na$_2$SO$_4$), evaporated and finally purified by the reverse phase HPLC (Phenomenex Gemini C18, H$_2$O/CH$_3$CN gradient from 30-75% CH$_3$CN, 0.1% TFA) to give the title compound (23 mg, 91%) as a colorless solid; MS (ES) 577.0 (M+H).

Example 315

Preparation of (1s,4s)-4-(3-(3-(4-chloro-3,5-dimethylphenoxy)propyl)-7-(1,3,5-trimethyl-1H-pyrazol-4-yl)-1H-indole-2-carboxamido)cyclohexane-1-carboxylic acid

I-315

The title compound was prepared (67.4 mg, 0.114 mmol, 82%) according to procedures described in Example 314 using 3-(3-(4-chloro-3,5-dimethylphenoxy)propyl)-7-(1,3,5-trimethyl-1H-pyrazol-4-yl)-1H-indole-2-carboxylic acid (64 mg, 0.139 mmol), ethyl (1s,4s)-4-aminocyclohexane-1-carboxylate (39 mg, 0.279 mmol), HBTU (60 mg, 0.158 mmol), triethylamine (48 µL, 0.344 mmol), and DMF (1 mL); MS (ES) 599.10 (M+H); $^1$H NMR (400 MHz, DMSO-d$^6$) δ 10.54 (s, 1H), 8.04 (d, J=7.5 Hz, 1H), 7.56 (d, J=7.9 Hz, 1H), 7.07 (t, J=7.5 Hz, 1H), 6.93 (d, J=6.9 Hz, 1H), 6.74 (s, 2H), 3.96 (t, J=6.4 Hz, 2H), 3.77 (s, 3H), 3.23 (t, J=0.3 Hz, 2H), 2.55-2.47 (m, 6H), 2.27 (s, 6H), 2.10 (s, 3H), 2.03 (s, 3H), 1.76-1.63 (m, 2H), 1.62-1.41 (m, 4H).

Example 316

Preparation of (1R,2S)-2-(3-(3-(4-chloro-3,5-dimethylphenoxy)propyl)-7-(1,3,5-trimethyl-1H-pyrazol-4-yl)-1H-indole-2-carboxamido)cyclohexane-1-carboxylic acid

I-316

The title compound was prepared (20 mg, 0.034 mmol, 79%) according to procedures described in Example 314 using 3-(3-(4-chloro-3,5-dimethylphenoxy)propyl)-7-(1,3,5-trimethyl-1H-pyrazol-4-yl)-1H-indole-2-carboxylic acid (20 mg, 0.043 mmol), ethyl (1R,2S)-2-aminocyclohexane-1-carboxylate (39 mg, 0.279 mmol), HBTU (60 mg, 0.158 mmol), triethylamine (48 µL, 0.344 mmol), and DMF (1 mL); MS (ES) 599.1 (M+H); $^1$H NMR (400 MHz, DMSO-d$^6$) δ 10.73 (s, 1H), 8.03 (d, J=7.2 Hz, 1H), 7.57 (d, J=7.6 Hz, 1H), 7.07 (t, J=7.6 Hz, 1H), 6.99 (d, J=7.2 Hz, 1H), 6.76 (s, 2H), 4.31-4.15 (m, 1H), 3.98 (t, J=6.4 Hz, 2H), 3.77 (s, 3H), 3.30-3.12 (m, 2H), 2.87-2.78 (m, 1H), 2.27 (s, 6H), 2.12 (s, 3H), 2.05 (s, 3H), 2.04-1.93 (m, 3H), 1.92-1.83 (m, 1H), 1.72-1.53 (m, 3H), 1.51-1.31 (m, 3H).

Example 317

Preparation of (1R,3R)-3-(3-(3-(4-chloro-3,5-dimethylphenoxy)propyl)-7-(1,3,5-trimethyl-1H-pyrazol-4-yl)-1H-indole-2-carboxamido)cyclohexane-1-carboxylic acid

I-317

The title compound was prepared (22 mg, 0.037 mmol, 86%) according to procedures described in Example 314 using 3-(3-(4-chloro-3,5-dimethylphenoxy)propyl)-7-(1,3,5-trimethyl-1H-pyrazol-4-yl)-1H-indole-2-carboxylic acid (20 mg, 0.043 mmol), ethyl (1R,3R)-3-aminocyclohexane-1-carboxylate (38 mg, 0.221 mmol), HBTU (60 mg, 0.158 mmol), triethylamine (48 µL, 0.344 mmol), and DMF (1 mL); MS (ES) 599.1 (M+H).

Example 318

Preparation of 3-(4-(3-(3-(4-chloro-3,5-dimethylphenoxy)propyl)-7-(1,3,5-trimethyl-1H-pyrazol-4-yl)-1H-indole-2-carboxamido)piperidin-1-yl)-3-oxopropanoic acid

I-318

Step A. Synthesis of 3-(3-(4-chloro-3,5-dimethylphenoxy)propyl)-N-(piperidin-4-yl)-7-(1,3,5-trimethyl-1H-pyrazol-4-yl)-1H-indole-2-carboxamide To a solution of 3-(3-(4-chloro-3,5-dimethylphenoxy)propyl)-7-(1,3,5-trimethyl-1H-pyrazol-4-yl)-1H-indole-2-carboxylic acid (20 mg, 0.043 mmol) in DMF (1 mL) were added benzyl 4-aminopiperidine-1-carboxylate (12 mg, 0.047 mmol), HBTU (60 mg, 0.158 mmol), triethylamine (48 µL, 0.344 mmol), and the mixture was stirred at room temperature for 12 h at which time LC analysis indicated complete consumption of the starting material. The reaction mixture was extracted in CH$_2$Cl$_2$ (3×15 mL), dried (anhyd. Na$_2$SO$_4$), evaporated. The crude was taken in MeOH (1 mL) and was added Pd/C (5 mg, 0.05 mmol, 10 mol %) and the mixture was hydrogenated with H$_2$ balloon for 12 h. The reaction mixture was filtered through celite, extracted in CH$_2$Cl$_2$ (3×15 mL), dried (anhyd. Na$_2$SO$_4$), evaporated and was purified by the reverse phase HPLC (Phenomenex Gemini C18, H$_2$O/CH$_3$CN gradient from 30-75% CH$_3$CN, 0.1% TFA) to the title compound (22 mg, 92%) as a colorless solid: MS (ES) 548.1 (M+H).

Step B. 3-(4-(3-(3-(4-chloro-3,5-dimethylphenoxy)propyl)-7-(1,3,5-trimethyl-1H-pyrazol-4-yl)-1H-indole-2-carboxamido)piperidin-1-yl)-3-oxopropanoic acid The title compound was prepared (13.5 mg, 0.021 mmol, 53%) according to procedures described in Example 314 using 3-(3-(4-chloro-3,5-dimethylphenoxy)propyl)-N-(piperidin-4-yl)-7-(1,3,5-trimethyl-1H-pyrazol-4-yl)-1H-indole-2-carboxamide (22 mg, 0.04 mmol), ethyl hydrogen malonate (12 µL, 0.086 mmol), HBTU (60 mg, 0.158 mmol), triethylamine (48 µL, 0.344 mmol), and DMF (1 mL); MS (ES) 634.1 (M+H).

Example 319

Preparation of 2-(4-(3-(3-(4-chloro-3,5-dimethylphenoxy)propyl)-7-(1,3,5-trimethyl-1H-pyrazol-4-yl)-1H-indole-2-carboxamido)piperidin-1-yl)-2-oxoacetic acid

I-319

To a solution of 3-(3-(4-chloro-3,5-dimethylphenoxy)propyl)-N-(piperidin-4-yl)-7-(1,3,5-trimethyl-1H-pyrazol-4-yl)-1H-indole-2-carboxamide (24 mg, 0.043 mmol) in $CH_2Cl_2$ (1 mL) at 0° C. were added triethylamine (24 µL, 0.172 mmol) and the mixture was stirred at that temperature for 10 min. Ethyl chlorooxoacetate (6 µL, 0.0473 mmol, 1.1 eqv.) was then added to the mixture and the mixture was stirred at room temperature for 12 h at which time LC analysis indicated complete consumption of the starting material. The reaction mixture was extracted in $CH_2Cl_2$ (3×15 mL), dried (anhyd. $Na_2SO_4$), evaporated. The crude was taken in THF (1 mL) and was added with aqueous lithium hydroxide solution (2M, 1 mL). The mixture was stirred at room temperature for 6 h. The volatiles were evaporated from the mixture in a rotary evaporator followed by acidification with 4M HCl to pH 7. The reaction mixture was extracted in ethyl acetate (3×15 mL), dried (anhyd. $Na_2SO_4$), evaporated and finally purified by the reverse phase HPLC (Phenomenex Gemini C18, $H_2O/CH_3CN$ gradient from 30-70% $CH_3CN$, 0.1% TFA) to the title compound (24 mg, 89%) as a white solid; MS (ES) 620.1 (M+H); $^1H$ NMR (400 MHz, DMSO-$d^6$) δ 10.44 (s, 1H), 8.17 (d, J=7.2 Hz, 1H), 7.58 (d, J=7.8 Hz, 1H), 7.08 (dd, J=7.8 & 7.2 Hz, 1H), 6.98 (d, J=6.8 Hz, 1H), 6.75 (s, 2H), 5.75 (s, 1H), 3.96 (t, J=6.4 Hz, 2H), 3.76 (s, 3H), 3.30-3.18 (m, 4H), 2.88 (dt, J=10.5 & 1.5 Hz, 1H), 2.27 (s, 6H), 2.09 (s, 3H), 2.06-2.03 (m, 2H), 2.02 (s, 3H), 1.99-1.89 (m, 2H), 1.28-1.17 (m, 4H).

Example 320

Preparation of (1R,4R)-4-((3-(3-(4-chloro-3,5-dimethylphenoxy)propyl)-7-(1,3,5-trimethyl-1H-pyrazol-4-yl)-1H-indole-2-carboxamido)methyl)cyclohexane-1-carboxylic acid

I-320

The title compound was prepared (17 mg, 0.028 mmol, 66%) according to procedures described in Example 314 using 3-(3-(4-chloro-3,5-dimethylphenoxy)propyl)-7-(1,3,5-trimethyl-1H-pyrazol-4-yl)-1H-indole-2-carboxylic acid (20 mg, 0.043 mmol), ethyl (1R,4R)-4-(aminomethyl)cyclohexane-1-carboxylate (46 mg, 0.248 mmol), HBTU (60 mg, 0.158 mmol), triethylamine (48 µL, 0.344 mmol), and DMF (1 mL); MS (ES) 605.2 (M+H).

Example 321

Preparation of 2-(4-(6-chloro-3-(3-(4-chloro-3,5-dimethylphenoxy)propyl)-7-(1,3,5-trimethyl-1H-pyrazol-4-yl)-1H-indole-2-carboxamido)piperidin-1-yl)-2-oxoacetic acid

I-321

The title compound was prepared (9 mg, 0.013 mmol, 31%) according to procedures described in Example 318 using 6-chloro-3-(3-(4-chloro-3,5-dimethylphenoxy)propyl)-7-(1,3,5-trimethyl-1H-pyrazol-4-yl)-1H-indole-2-carboxylic acid (22 mg, 0.043 mmol), benzyl 4-aminopiperidine-1-carboxylate (12 mg, 0.047 mmol, 1.1 eqv.); MS (ES) 654.0 (M+H).

Example 322

Preparation of (1R,3R)-3-(6-chloro-3-(3-(4-chloro-3,5-dimethylphenoxy)propyl)-7-(1,3,5-trimethyl-1H-pyrazol-4-yl)-1H-indole-2-carboxamido)cyclohexane-1-carboxylic acid

I-322

The title compound was prepared (8.4 mg, 0.013 mmol, 58%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (12 mg, 0.023 mmol), ethyl (1S,3S)-3-aminocyclohexane-1-carboxylate (14 mg, 0.079 mmol), HBTU (60 mg, 0.158 mmol), triethylamine (48 µL, 0.344 mmol), and DMF (1 mL); MS (ES) 625.0 (M+H).

Example 323

Preparation of 2-((1-(6-chloro-3-(3-(4-chloro-3,5-dimethylphenoxy)propyl)-7-(1,3,5-trimethyl-1H-pyrazol-4-yl)-1H-indole-2-carbonyl)azetidin-3-yl)amino)-2-oxoacetic acid

I-323

To a solution of 6-chloro-3-(3-(4-chloro-3,5-dimethylphenoxy)propyl)-7-(1,3,5-trimethyl-1H-pyrazol-4-yl)-1H-indole-2-carboxylic acid (20 mg, 0.04 mmol) in DMF (1 mL) were added tert-butyl azetidin-3-ylcarbamate (9 mg, 0.04 mmol), HBTU (60 mg, 0.158 mmol), triethylamine (48 µL, 0.344 mmol), and the mixture was stirred at room temperature for 12 h at which time LC analysis indicated complete consumption of the starting material. The reaction mixture was extracted in $CH_2Cl_2$ (3×15 mL), dried (anhyd. $Na_2SO_4$), evaporated. The crude was taken in dioxane (1 mL) and was added 6N HCl (1 mL) and the mixture was heated to 50° C. with for 2 h. Aqueous $NaHCO_3$ solution (3 mL) was added and the reaction mixture was extracted in $CH_2Cl_2$ (3×15 mL), dried (anhyd. $Na_2SO_4$), evaporated. The crude was taken in $CH_2Cl_2$ (1 mL) and triethylamine (24 µL, 0.172 mmol) was added to the mixture at 0° C. The mixture was stirred at that temperature for 10 mins. Ethyl chlorooxoacetate (6 µL, 0.0473 mmol, 1.1 eqv.) was then added to the mixture and the mixture was stirred at room temperature for 12 h at which time LC analysis indicated complete consumption of the starting material. The reaction mixture was extracted in $CH_2Cl_2$ (3×15 mL), dried (anhyd. $Na_2SO_4$), evaporated. The crude was taken in THF (1 mL) and was added with aqueous lithium hydroxide solution (2M, 1 mL). The mixture was stirred at room temperature for 6 h. The volatiles were evaporated from the mixture in a rotary evaporator followed by acidification with 4M HCl to pH 7. The reaction mixture was extracted in ethyl acetate (3×15 mL), dried (anhyd. $Na_2SO_4$), evaporated and finally purified by the reverse phase HPLC (Phenomenex Gemini C18, $H_2O/CH_3CN$ gradient from 30-70% $CH_3CN$, 0.1% TFA) to the title compound (3 mg, 11%) as a colorless solid; MS (ES) 626.0 (M+H).

Example 324

Preparation of (1r,4r)-4-((6-chloro-3-(3-(4-chloro-3,5-dimethylphenoxy)propyl)-7-(1,3,5-trimethyl-1H-pyrazol-4-yl)-1H-indole-2-carboxamido)methyl)cyclohexane-1-carboxylic acid

I-324

The title compound was prepared (8 mg, 0.013 mmol, 69%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (9 mg, 0.018 mmol), ethyl (1r,4r)-4-(aminomethyl)cyclohexane-1-carboxylate (11 mg, 0.057 mmol), HBTU (25 mg, 0.066 mmol), triethylamine (20 μL, 0.144 mmol), and DMF (1 mL); MS (ES) 639.1 (M+H).

Example 325

Preparation of (S)-2-(3-(6-chloro-3-(3-(4-chloro-3,5-dimethylphenoxy)propyl)-7-(1,3,5-trimethyl-1H-pyrazol-4-yl)-1H-indole-2-carboxamido)pyrrolidin-1-yl)-2-oxoacetic acid

I-325

The title compound was prepared (21 mg, 0.033 mmol, 56%) according to procedures described in Example 318 using 6-chloro-3-(3-(4-chloro-3,5-dimethylphenoxy)propyl)-7-(1,3,5-trimethyl-1H-pyrazol-4-yl)-1H-indole-2-carboxylic acid (30 mg, 0.06 mmol), (S)-1-benzylpyrrolidin-3-amine (22 μL, 0.125 mmol); MS (ES) 640.0 (M+H).

Example 326

Preparation of (R)-2-(3-(6-chloro-3-(3-(4-chloro-3,5-dimethylphenoxy)propyl)-7-(1,3,5-trimethyl-1H-pyrazol-4-yl)-1H-indole-2-carboxamido)pyrrolidin-1-yl)-2-oxoacetic acid

I-326

The title compound was prepared (24 mg, 0.037 mmol, 64%) according to procedures described in Example 318 using 6-chloro-3-(3-(4-chloro-3,5-dimethylphenoxy)propyl)-7-(1,3,5-trimethyl-1H-pyrazol-4-yl)-1H-indole-2-carboxylic acid (30 mg, 0.06 mmol), (R)-1-benzylpyrrolidin-3-amine (22 μL, 0.125 mmol); MS (ES) 640.0 (M+H).

Example 327

Preparation of (R)-2-(3-(6-chloro-3-(3-(4-chloro-3,5-dimethylphenoxy)propyl)-7-(1,3,5-trimethyl-1H-pyrazol-4-yl)-1H-indole-2-carboxamido)piperidin-1-yl)-2-oxoacetic acid

I-327

The title compound was prepared (20 mg, 0.031 mmol, 51%) according to procedures described in Example 318 using 6-chloro-3-(3-(4-chloro-3,5-dimethylphenoxy)propyl)-7-(1,3,5-trimethyl-1H-pyrazol-4-yl)-1H-indole-2-carboxylic acid (30 mg, 0.06 mmol), (R)-1-benzylpiperidin-3-amine (23 μL, 0.125 mmol); MS (ES) 654.0 (M+H).

Example 328

Preparation of 3-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-5-(isopentylamino)benzoic acid

I-328

Step A. Synthesis of 3-amino-5-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid To a solution of 3-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-5-nitrobenzoic acid (42 mg, 0.058 mmol) in MeOH (2 mL) was added Pd/C (5.8 mg, 0.058 mmol) and the mixture was hydrogenated with H₂ balloon for 12 h. The reaction mixture was filtered through celite, extracted in CH₂Cl₂ (3×15 mL), dried (anhyd. Na₂SO₄), evaporated and was purified by the reverse phase HPLC (Phenomenex Gemini C18, H₂O/CH₃CN gradient from 30-70% CH₃CN, 0.1% TFA) to give the title compound (36 mg, 91%) as a white solid: MS (ES) 688.1 (M+H).

Step B. Example 328

To a methanolic solution of 3-amino-5-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid (10 mg, 0.015 mmol) in MeOH (0.5 mL) was added isovaleraldehyde (10 μL, 0.086 mmol) and the reaction mixture was stirred at room temperature for 30 mins. Sodium borohydride (2 mg, 0.043, 1.5 eqv.) was added to the mixture and stirring was continued for additional 4 h. The reaction mixture was filtered through celite, extracted in CH₂Cl₂ (3×5 mL), dried (anhyd. Na₂SO₄), evaporated and was purified by the reverse phase HPLC (Phenomenex Gemini C18, H₂O/CH₃CN gradient from 30-70% CH₃CN, 0.1% TFA) to give the title compound (8 mg, 70%) as a white solid: MS (ES) 758.1 (M+H).

Example 329

Preparation of 3-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-5-(3-methyl-N-(3-methylbutanoyl)butanamido)benzoic acid

I-329

To a solution of 3-amino-5-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)benzoic acid (10 mg, 0.015 mmol) in CH₂Cl₂ (1 mL) were added DMAP (7 mg, 0.06 mmol) and isovaleryl chloride (20 μL, 0.136 mmol), and the mixture was stirred at room temperature for 3 h at which time LC analysis indicated complete consumption of the starting material. The reaction mixture was extracted in CH₂Cl₂ (3×15 mL), dried (anhyd. Na₂SO₄), evaporated and finally purified by the reverse phase HPLC (Phenomenex Gemini

Example 330

Preparation of (1R,3S)-3-(6-chloro-3-(3-(4-chloro-3,5-dimethylphenoxy)propyl)-7-(1,3,5-trimethyl-1H-pyrazol-4-yl)-1H-indole-2-carboxamido)cyclopentane-1-carboxylic acid

I-330

The title compound was prepared (18.5 mg, 0.03 mmol, 44%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (35 mg, 0.018 mmol), ethyl (1R,3S)-3-aminocyclopentane-1-carboxylate (11 mg, 0.069 mmol), HBTU (25 mg, 0.067 mmol), triethylamine (20 µL, 0.144 mmol), and DMF (1 mL); MS (ES) 611.1 (M+H).

Example 331

Preparation of (1R,3S)-3-(6-chloro-3-(3-(4-chloro-3,5-dimethylphenoxy)propyl)-7-(1,3,5-trimethyl-1H-pyrazol-4-yl)-1H-indole-2-carboxamido)cyclohexane-1-carboxylic acid

I-331

The title compound was prepared (42.5 mg, 0.068 mmol, 68%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (50 mg, 0.1 mmol), ethyl (1R,3S)-3-aminocyclohexane-1-carboxylate (19 mg, 0.1 mmol), HBTU (140 mg, 0.37 mmol), triethylamine (112 µL, 0.8 mmol), and DMF (1 mL); MS (ES) 625.0 (M+H).

Example 332

Preparation of (1s,4s)-4-(6-chloro-3-(3-(4-chloro-3,5-dimethylphenoxy)propyl)-7-(1,3,5-trimethyl-1H-pyrazol-4-yl)-1H-indole-2-carboxamido)cyclohexane-1-carboxylic acid

I-332

The title compound was prepared (11 mg, 0.017 mmol, 44%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (20 mg, 0.04 mmol), ethyl (1s,4s)-4-aminocyclohexane-1-carboxylate (11 mg, 0.06 mmol), HBTU (56 mg, 0.148 mmol), triethylamine (45 µL, 0.32 mmol), and DMF (1 mL); MS (ES) 625.0 (M+H).

Example 333

Preparation of (1R,2S)-2-(6-chloro-3-(3-(4-chloro-3,5-dimethylphenoxy)propyl)-7-(1,3,5-trimethyl-1H-pyrazol-4-yl)-1H-indole-2-carboxamido)cyclohexane-1-carboxylic acid

I-333

The title compound was prepared (13 mg, 0.021 mmol, 52%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (20 mg, 0.04 mmol), ethyl (1R,2S)-2-aminocyclohexane-1-carboxylate (11 mg, 0.06 mmol), HBTU (56 mg, 0.148 mmol), triethylamine (45 µL, 0.32 mmol), and DMF (1 mL); MS (ES) 625.0 (M+H).

Example 334

Preparation of (1R,2S)-2-(6-chloro-3-(3-(4-chloro-3,5-dimethylphenoxy)propyl)-7-(1,3,5-trimethyl-1H-pyrazol-4-yl)-1H-indole-2-carboxamido)cyclopentane-1-carboxylic acid

I-334

The title compound was prepared (14.3 mg, 0.023 mmol, 59%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (20 mg, 0.04 mmol), ethyl (1R,2S)-2-aminocyclopentane-1-carboxylate (8 mg, 0.06 mmol), HBTU (56 mg, 0.148 mmol), triethylamine (45 µL, 0.32 mmol), and DMF (1 mL); MS (ES) 611.1 (M+H).

Example 335

Preparation of 4-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoic acid

I-335

The title compound was prepared (156 mg, 0.226 mmol, 76%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (150 mg, 0.299 mmol), ethyl 4-(piperazin-1-yl)benzoate (71 mg, 0.299 mmol), HBTU (420 mg, 1.106 mmol), triethylamine (334 µL, 2.392 mmol), and DMF (20 mL); MS (ES) 688.0 (M+H); $^1$H NMR (400 MHz, DMSO-d$^6$) δ 10.93 (s, 1H), 7.78 (d, J=8.9 Hz, 2H), 7.59 (d, J=8.4 Hz, 1H), 7.19 (d, J=8.4 Hz, 1H), 6.93 (d, J=8.9 Hz, 2H), 6.71 (s, 2H), 3.95 (t, J=6.7 Hz, 2H), 3.75 (s, 3H), 3.35-3.24 (m, 4H), 2.86 (t, J=7.3 Hz, 2H), 2.29-2.25 (m, 2H), 2.21 (s, 6H), 2.05-2.02 (m, 2H), 2.02 (s, 3H), 1.98-1.97 (m, 1H), 1.96 (s, 3H), 1.95-1.93 (m, 1H).

Example 336

Preparation of 1-(6-chloro-3-(3-(4-chloro-3,5-dimethylphenoxy)propyl)-7-(1,3,5-trimethyl-1H-pyrazol-4-yl)-1H-indole-2-carbonyl)pyrrolidine-3-carboxylic acid

I-336

The title compound was prepared (26 mg, 0.043 mmol, 55%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (40 mg, 0.079 mmol), methyl pyrrolidine-3-carboxylate (10.2 mg, 0.079 mmol), HBTU (111 mg, 0.292 mmol), triethylamine (88 µL, 0.632 mmol), and DMF (1 mL); MS (ES) 597.0 (M+H).

Example 337

Preparation of (6-chloro-3-(3-(4-chloro-3,5-dimethylphenoxy)propyl)-7-(1,3,5-trimethyl-1H-pyrazol-4-yl)-1H-indole-2-carbonyl)-L-proline

I-337

The title compound was prepared (18 mg, 0.03 mmol, 38%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (40 mg, 0.079 mmol), methyl L-prolinate (13 mg, 0.079 mmol), HBTU (111 mg, 0.292 mmol), triethylamine (88 μL, 0.632 mmol), and DMF (1 mL); MS (ES) 597.0 (M+H).

Example 338

Preparation of 4-(4-(6-chloro-3-(3-(4-chloro-3,5-dimethylphenoxy)propyl)-1-(pyridin-3-ylmethyl)-7-(1,3,5-trimethyl-1H-pyrazol-4-yl)-1H-indole-2-carbonyl)piperazin-1-yl)benzoic acid

I-338

To a solution of 6-chloro-3-(3-(4-chloro-3,5-dimethylphenoxy)propyl)-7-(1,3,5-trimethyl-1H-pyrazol-4-yl)-1H-indole-2-carboxylic acid (25 mg, 0.05 mmol) in DMF (1 mL) at rt were added methyl 4-(piperazin-1-yl)benzoate (11 mg, 0.05 mmol), HBTU (70 mg, 0.185 mmol), triethylamine (56 μL, 0.4 mmol) and the mixture was stirred at rt for 10 h at which time LC showed complete disappearance of starting carboxylic acid. Water (5 mL) was added to the mixture and it was extracted in $CH_2Cl_2$ (3×5 mL). The organic layer was dried (anhyd. $Na_2SO_4$) and was evaporated. The crude was taken in DMF (1 mL) and NaH (6 mg, 0.15 mmol) at room temperature and the mixture was stirred for 30 min at ambient temperature. A solution of 3-(bromomethyl)pyridine hydrobromide (15 mg, 0.06 mmol) in DMF (1 mL) was added drop wise to the reaction mixture at room temperature and stirring was continued for additional 2 h. The mixture was diluted with water (4 mL) and extracted in $CH_2Cl_2$ (3×5 mL). The organic layer was dried (anhyd. $Na_2SO_4$) and was evaporated. To a solution of crude ester in THF (2 mL) at room temperature was added 2M LiOH (1 mL) the mixture was stirred at the ambient temperature for 10 h. The reaction mixture was evaporated, acidified to pH 7 with 4M HCl, extracted in EtOAc. The organic layer was dried, evaporated and finally purified by the reverse phase HPLC (Phenomenex Gemini C18, $H_2O/CH_3CN$ gradient from 30-70% $CH_3CN$, 0.1% TFA) to give the title compound (37 mg, 95%) as a white solid; MS (ES) 779.1 (M+H).

Example 339

Preparation of 4-(4-(6-chloro-3-(3-(4-chloro-3,5-dimethylphenoxy)propyl)-1-methyl-7-(1,3,5-trimethyl-1H-pyrazol-4-yl)-1H-indole-2-carbonyl)piperazin-1-yl)benzoic acid

I-339

The title compound was prepared (17 mg, 0.024 mmol, 83%) according to procedures described in Example 338 using methyl 4-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoate (20 mg, 0.029 mmol), methyl iodide (8 μL, 0.116 mmol), NaH (4.6 mg, 0.116 mmol) and DMF (1 mL); MS (ES) 702.1 (M+H).

Example 340

Preparation of 4-(4-(6-chloro-3-(3-(4-chloro-3,5-dimethylphenoxy)propyl)-1-(pyridin-4-ylmethyl)-7-(1,3,5-trimethyl-1H-pyrazol-4-yl)-1H-indole-2-carbonyl)piperazin-1-yl)benzoic acid

I-340

The title compound was prepared (37 mg, 0.048 mmol, 95%) according to procedures described in Example 338 using methyl 4-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoate (20 mg, 0.029 mmol), 4-(bromomethyl)pyridine hydrobromide (15 mg, 0.06 mmol), NaH (4.6 mg, 0.116 mmol) and DMF (1 mL); MS (ES) 779.1 (M+H).

Example 341

Preparation of 4-(4-(6-chloro-3-(3-(4-chloro-3,5-dimethylphenoxy)propyl)-1-(pyridin-2-ylmethyl)-7-(1,3,5-trimethyl-1H-pyrazol-4-yl)-1H-indole-2-carbonyl)piperazin-1-yl)benzoic acid

I-341

The title compound was prepared (35 mg, 0.046 mmol, 91%) according to procedures described in Example 338 using methyl 4-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoate (20 mg, 0.029 mmol), 2-(bromomethyl)pyridine hydrobromide (15 mg, 0.06 mmol), NaH (4.6 mg, 0.116 mmol) and DMF (1 mL); MS (ES) 779.1 (M+H).

Example 342

Preparation of 4-(4-(1-benzyl-6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoic acid

I-342

The title compound was prepared (35 mg, 0.045 mmol, 90%) according to procedures described in Example 338 using methyl 4-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoate (20 mg, 0.029 mmol), benzyl bromide (8 μL, 0.06 mmol), NaH (4.6 mg, 0.116 mmol) and DMF (1 mL); MS (ES) 778.0 (M+H).

Example 343

Preparation of 4-(4-(6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carbonyl)piperazin-1-yl)benzoic acid

I-343

The title compound was prepared (29 mg, 0.036 mmol, 72%) according to procedures described in Example 338 using methyl 4-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl)benzoate (20 mg, 0.029 mmol), 4-(2-bromoethyl)morpholine (12 mg, 0.06 mmol), NaH (4.6 mg, 0.116 mmol) and DMF (1 mL); MS (ES) 802.0 (M+H).

Example 344

Preparation of 6-(4-(6-chloro-3-(3-(4-chloro-3,5-dimethylphenoxy)propyl)-7-(1,3,5-trimethyl-1H-pyrazol-4-yl)-1H-indole-2-carbonyl)piperazin-1-yl) nicotinic acid

I-344

Step A. Synthesis of methyl 6-(piperazin-1-yl)nicotinate

To a solution of methyl 6-chloronicotinate (343 mg, 2 mmol) in MeOH (6 mL) at room temperature was added piperazine (860 mg, 10 mmol) and the mixture was heated to 60° C. for 6 h. The mixture was evaporated and the crude was purified by the reverse phase HPLC (Phenomenex Gemini C18, H$_2$O/CH$_3$CN gradient from 30-70% CH$_3$CN, 0.1% TFA) to give the title compound (422 mg, 95%) as a colorless solid; MS (ES) 222.20 (M+H).

Step B. Example 344

The title compound was prepared (31 mg, 0.036 mmol, 90%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (25 mg, 0.05 mmol), methyl 6-(piperazin-1-yl)nicotinate (13 mg, 0.079 mmol), HBTU (70 mg, 0.185 mmol), triethylamine (56 µL, 0.4 mmol), and DMF (1 mL); MS (ES) 689.1 (M+H); $^1$H NMR (400 MHz, DMSO-d$^6$) δ 10.92 (s, 1H), 8.63 (d, J=2.3 Hz, 1H), 7.96 (dd, J=9.0 & 2.3 Hz, 1H), 7.58 (d, J=8.6 Hz, 1H), 7.18 (d, J=8.6 Hz, 1H), 6.84 (d, J=9.1 Hz, 1H), 6.71 (s, 2H), 3.95 (t, J=6.1 Hz, 2H), 3.73 (s, 3H), 3.68-3.56 (m, 6H), 2.86 (t, J=7.3 Hz, 2H), 2.62-2.51 (m, 2H), 2.20 (s, 6H), 2.06-2.03 (m, 1H), 2.01 (s, 3H), 2.00-1.98 (m, 1H), 1.95 (s, 3H).

Example 345

Preparation of 7-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indole-3-carboxylic acid

I-345

Step A. Synthesis of 8-chloro-1-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one To a solution of ethyl 6-chloro-3-(3-(4-chloro-3,5-dimethylphenoxy)propyl)-7-(1,3,5-trimethyl-1H-pyrazol-4-yl)-1H-indole-2-carboxylate (102 mg, 0.193 mmol) in DMF (1 mL) at room temperature was added tert-butyl 1,2,3-oxathiazinane-3-carboxylate 2,2-dioxide (55 mg, 0.23 mmol) and the mixture was stirred at room temperature for 10 min. NaH (6 mg, 0.249 mmol, 1.3 eqiv.) was added to the mixture and stirring was continued to additional 2 h. The mixture was diluted with NH$_4$Cl (4 mL) and extracted in DCM (3×5 mL). The organic layer was dried (anhyd. Na$_2$SO$_4$) and was evaporated. To a solution of crude in dioxane (2 mL) was added 4M HCl and the mixture was stirred at 50° C. for overnight. Saturated aqueous NaHCO$_3$ (4 mL) solution was added to the mixture and it was extracted in DCM (3×5 mL). The organic layer was evaporated and the crude was taken in MeOH (2 mL) followed by potassium carbonate (111 mg, 0.806 mmol) and the mixture was heated at 50° C. for overnight. The mixture was acidified to pH 7 with 4M HCl, extracted in DCM (3×5 mL). The organic layer was dried, evaporated and finally purified in Gilson (30-70% acetonitrile in water) to the title compound (96 mg, 93%) as a colorless solid; MS (ES) 539.1 (M+H).

Step B Preparation of methyl 7-bromo-1-methyl-1H-indole-3-carboxylate

To a solution of methyl 7-bromo-1H-indole-3-carboxylate (330 mg, 1.29 mmol) in DMF (2 mL) was added dimethyl carbonate (1.086 mL, 12.9 mmol) followed by DABCO (15 mg, 0.13 mmol, 10 mol %) and the mixture was heated at 100° C. for 10 h. The mixture was diluted with NH$_4$Cl (4 mL) and extracted in DCM (3×5 mL). The organic layer was dried (anhyd. Na$_2$SO$_4$), evaporated and finally purified by the reverse phase HPLC (Phenomenex Gemini C18, H$_2$O/CH$_3$CN gradient from 30-70% CH$_3$CN, 0.1% TFA) to give the title compound (259 mg, 75%) as a white solid; MS (ES) 268.0 (M+2).

Step C. Example 345

To a solution of 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (54 mg, 0.1 mmol) in dioxane (2 mL) was added methyl 7-bromo-1-methyl-1H-indole-3-carboxylate (32 mg, 0.12 mmol), Xantphos (3.5 mg, 0.006 mmol, 6 mol %), Pd$_2$(dba)$_3$ (2 mg, 0.002 mmol, 2 mol %), cesium carbonate (49 mg, 0.15 mmol) and the mixture was purged with Ar for 30 min. The mixture was heated at 110° C. for 16 h. The mixture was diluted with NH$_4$Cl (4 mL) and extracted in DCM (3×5 mL). The organic layer was dried (anhyd. Na$_2$SO$_4$), evaporated. To a solution of crude ester in THF (2 mL) at room temperature was added 2M LiOH (1 mL) the mixture was stirred at the ambient temperature for 10 h. The reaction mixture was evaporated, acidified to pH 7 with 4M HCl, extracted in EtOAc. The organic layer was dried, evaporated and purified by the reverse phase HPLC (Phenomenex Gemini C18, H$_2$O/CH$_3$CN gradient from 30-70% CH$_3$CN, 0.1% TFA) to give the title compound (58 mg, 81%) as a white solid; MS (ES) 712.0 (M+H); $^1$H NMR (400 MHz, DMSO-d$_6$) δ 8.08 (d, J=7.9 Hz, 1H), 8.04 (s, 1H), 7.73 (d, J=8.5 Hz, 1H), 7.27 (t, J=8.5 Hz, 1H), 7.22 (t, J=7.7 Hz, 1H), 7.13 (dd, J=7.9 & 7.7 Hz, 1H), 6.74 (s, 2H), 4.25-3.90 (m, 7H), 3.82 (s, 3H), 3.79 (s, 3H), 3.21-3.08 (m, 1H), 3.07-2.90 (m, 1H), 2.26 (s, 6H), 2.18-2.08 (m, 1H), 2.06 (s, 3H), 2.00 (s, 3H), 1.97-1.94 (m, 1H), 1.93-1.86 (m, 1H).

Example 346

Preparation of 5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-2-oxothiazolidine-4-carboxylic acid

I-346

The title compound was prepared (52 mg, 0.076 mmol, 76%) according to procedures described in Example 345

Step C using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (54 mg, 0.1 mmol), ethyl 5-bromothiazole-4-carboxylate (28 mg, 0.12 mmol), Xantphos (3.5 mg, 0.006 mmol, 6 mol %), Pd$_2$(dba)$_3$ (2 mg, 0.002 mmol, 2 mol %), cesium carbonate (49 mg, 0.15 mmol) and dioxane (2 mL); MS (ES) 684.1 (M+H).

Example 347

Preparation of 5-((8-chloro-1-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)-2-methylfuran-3-carboxylic acid

I-347

To a solution of 6-chloro-3-(3-(4-chloro-3,5-dimethylphenoxy)propyl)-7-(1,3,5-trimethyl-1H-pyrazol-4-yl)-1H-indole-2-carboxylic acid (100 mg, 0.2 mmol) in DMF (2 mL) were added methyl 5-(aminomethyl)-2-methylfuran-3-carboxylate (41 mg, 0.2 mmol), HBTU (76 mg, 0.2 mmol), triethylamine (84 µL, 0.3 mmol), and the mixture was stirred at room temperature for 10 h at which time LC analysis indicated complete consumption of the starting material. Water (5 mL) was added to the mixture and it was extracted in CH$_2$Cl$_2$ (3×5 mL). The organic layer was dried (anhyd. Na$_2$SO$_4$) and was evaporated. To the solution crude in DMF (3 mL) were added 1,3-dibromopropane (31 µL, 0.3 mmol), Cs$_2$CO$_3$ (130 mg, 0.4 mmol) and the mixture was stirred at 40° C. for 6 h. The mixture was filtered, diluted with water (5 mL) and was extracted in CH$_2$Cl$_2$ (3×5 mL). The organic layer was dried (anhyd. Na$_2$SO$_4$) and was evaporated. To a solution of crude ester in THF (2 mL) at room temperature was added 2M LiOH (1 mL) the mixture was stirred at the ambient temperature for 10 h. The reaction mixture was evaporated, acidified to PH 7 with 4M HCl, extracted in EtOAc. The organic layer was dried, evaporated and finally purified by the reverse phase HPLC (Phenomenex Gemini C18, H$_2$O/CH$_3$CN gradient from 30-70% CH$_3$CN, 0.1% TFA) to give the title compound (116 mg, 86%) as a colorless solid; MS (ES) 677.2 (M+H); $^1$H NMR (400 MHz, DMSO-d$^6$) δ 7.66 (d, J=8.5 Hz, 1H), 7.22 (d, J=8.5 Hz, 1H), 6.71 (s, 2H), 6.53 (s, 1H), 4.65-4.49 (m, 2H), 3.92 (t, J=6.2 Hz, 2H), 3.75 (s, 3H), 3.73-3.65 (m, 2H), 3.21 (t, J=5.9 Hz, 2H), 3.02 (t, J=7.1 Hz, 2H), 2.46 (s, 3H), 2.26 (s, 6H), 2.05 (q, J=6.8 Hz, 2H), 1.99 (s, 1H), 1.95 (s, 3H), 1.91 (s, 1H), 1.86 (s, 3H).

Example 348

Preparation of 2-(4-(8-chloro-11-(3-(4-chloro-3,5-dimethylphenoxy)propyl)-7-(1,3,5-trimethyl-1H-pyrazol-4-yl)-4,5-dihydro-1H-[1,4]diazepino[1,2-a]indol-2(3H)-yl)-1H-indol-1-yl)acetic acid

I-348

Step A. Preparation of tert-butyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1H-indole-1-carboxylate The title compound was prepared (71 mg, 0.094 mmol, 94%) according to procedures described in Example 345 Step C using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (54 mg, 0.1 mmol), tert-butyl 4-bromo-1H-indole-1-carboxylate (36 mg, 0.12 mmol), Xantphos (3.5 mg, 0.006 mmol, 6 mol %), Pd$_2$(dba)$_3$ (2 mg, 0.002 mmol, 2 mol %), cesium carbonate (49 mg, 0.15 mmol) and dioxane (2 mL); MS (ES) 754.3 (M+H).

Step B. Synthesis of 2-(4-(8-chloro-11-(3-(4-chloro-3,5-dimethylphenoxy)propyl)-1-oxo-7-(1,3,5-trimethyl-1H-pyrazol-4-yl)-4,5-dihydro-H-[1,4]diazepino[1,2-a]indol-2(3H)-yl)-1H-indol-1-yl)acetic acid To a solution of tert-butyl 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1H-indole-1-carboxylate (71 mg, 0.094 mmol) in DCM (2 mL) TFA (2 mL) was added and the mixture was stirred at room temperature for 6 h. Saturated aqueous NaHCO$_3$ (8 mL) was added to the mixture and it was extracted in DCM (3×5 mL). The organic layer was dried (anhyd. Na$_2$SO$_4$), evaporated. To a solution of crude in DMF (1 mL) was added NaH (5 mg, 0.12 mmol, 1.2 eqv.) and the mixture was stirred at room temperature for 10 mins. Ethyl bromoacetate (14 µL, 0.12 mmol, 1.2 eqv.) was added to the mixture and it was stirred at ambient temperature for 2 h. The mixture was diluted with water (5 mL) and was extracted in CH$_2$Cl$_2$ (3×5 mL). The organic layer was dried (anhyd. Na$_2$SO$_4$) and was evaporated. To a solution of crude ester in THF (2 mL) at room temperature was added 2M LiOH (1 mL) the mixture was stirred at the ambient temperature for 10 h. The reaction mixture was evaporated, acidified to pH 7 with 4M HCl, extracted in ETOAc. The organic layer was dried, evaporated and finally purified in Gilson (30-70% acetonitrile in water) to the title compound (48 mg, 72%) as a brown solid; MS (ES) 712.2 (M+H); $^1$H NMR (400 MHz, DMSO-d$^6$) δ 7.72 (d, J=8.6 Hz, 1H), 7.37 (d, J=8.3 Hz, 1H), 7.34 (d, J=3.2 Hz, 1H), 7.27 (d, J=8.6 Hz, 1H), 7.14 (d, J=7.8 Hz, 1H), 6.90 (d, J=7.8 Hz, 1H), 6.73 (s, 2H), 6.29 (d, J=3.2 Hz, 1H), 4.11 (t, J=6.5 Hz, 2H), 3.97 (t, J=6.5 Hz, 2H), 3.78 (s, 3H), 3.72-3.61 (m, 4H), 3.05 (t, J=7.4 Hz, 2H), 2.25 (s, 6H), 2.14-2.05 (m, 2H), 2.03 (s, 3H), 1.93 (s, 3H), 1.81-1.67 (m, 2H).

Example 349

Preparation of 2-chloro-6-((8-chloro-1-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)isonicotinic acid

I-349

To a solution of 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (54 mg, 0.1 mmol) in DMF (2 mL) was added NaH (5 mg, 0.12 mmol) and the mixture was stirred at room temperature for 10 min. Methyl 2-(bromomethyl)-6-chloroisonicotinate (32 mg, 0.12 mmol) was added to the mixture followed by TBAI (37 mg, 0.1 mmol) and stirring was continued for additional 2 h. The mixture was diluted with water (5 mL) and was extracted in CH$_2$Cl$_2$ (3×5 mL). The organic layer was dried (anhyd. Na$_2$SO$_4$) and was evaporated. To a solution of crude ester in THF (1 mL) at room temperature was added 2M LiOH (1 mL) the mixture was stirred at the ambient temperature for 5 h. The reaction mixture was evaporated, acidified to pH 7 with 4M HCl, extracted in EtOAc. The organic layer was dried, evaporated and finally purified in Gilson (30-70% acetonitrile in water) to the title compound (62 mg, 87%) as a white solid; MS (ES) 708.1 (M+H).

Example 350

Preparation of 5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)thiazole-4-carboxylic acid

I-350

The title compound was prepared (55 mg, 0.082 mmol, 83%) according to procedures described in Example 345 Step C using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (54 mg, 0.1 mmol), ethyl 5-bromothiazole-4-carboxylate (28 mg, 0.12 mmol), Xantphos (3.5 mg, 0.006 mmol, 6 mol %), $Pd_2(dba)_3$ (2 mg, 0.002 mmol, 2 mol %), cesium carbonate (49 mg, 0.15 mmol) and dioxane (2 mL); MS (ES) 666.1 (M+H).

Example 351

Preparation of 5-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-naphthoic acid

I-351

The title compound was prepared (62 mg, 0.087 mmol, 87%) according to procedures described in Example 345 Step C using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (54 mg, 0.1 mmol), methyl 5-bromo-1-naphthoate (32 mg, 0.12 mmol), Xantphos (3.5 mg, 0.006 mmol, 6 mol %), $Pd_2(dba)_3$ (2 mg, 0.002 mmol, 2 mol %), cesium carbonate (49 mg, 0.15 mmol) and dioxane (2 mL); MS (ES) 709.2 (M+H); $^1$H NMR (400 MHz, DMSO-$d^6$) δ 8.86 (d, J=8.5 Hz, 1H), 8.17 (d, J=7.1 Hz, 1H), 8.00 (d, J=8.5 Hz, 1H), 7.74 (d, J=8.6 Hz, 1H), 7.68 (dd, J=7.7 & 7.5 Hz, 1H), 7.62-7.51 (m, 2H), 7.28 (d, J=8.6 Hz, 1H), 6.73 (s, 2H), 3.99 (t, J=6.3 Hz, 2H), 3.81-3.76 (m, 4H), 3.74 (s, 3H), 3.59-3.45 (m, 1H), 3.14-2.94 (m, 2H), 2.23 (s, 6H), 2.13-2.07 (m, 2H), 2.05 (s, 3H), 1.93 (s, 3H), 1.83-1.63 (m, 1H).

Example 352

Preparation of 6-chloro-3-(3-(4-chloro-3,5-dimethylphenoxy)propyl)-N-(3-cyanophenyl)-7-(1,3,5-trimethyl-1H-pyrazol-4-yl)-1H-indole-2-carboxamide

I-352

In a 20-mL scintillation vial equipped with a stir bar, 6-chloro-3-(3-(4-chloro-3,5-dimethylphenoxy) propyl)-7-(1,3,5-trimethyl-1H-pyrazol-4-yl)-1H-indole-2-carboxylic acid (45 mg, 0.090 mmol), EDC (35 mg, 0.29 mmol), and DMAP (25 mg, 0.16 mmol) were charged and dissolved in DCM (3 mL). The reaction was allowed to stir for 10 min at ambient temperature, followed by addition of 3-aminobenzonitrile (20 mg, 0.157 mmol) in 1 mL of DCM. The reaction was allowed to stir for 6 h at ambient temperature, after which time the reaction was determined to be complete by LCMS. The reaction mixture was diluted into DCM/$H_2O$ (1:1, 20 mL). The organic layer was separated, and the aqueous layer was extracted with DCM (2×10 mL). The combined organic extracts were dried with a phase separator and concentrated in vacuo. The crude material was purified by silica gel flash column chromatography (ISCO Hexanes/ EtOAc 0-100% gradient) to afford 24 mg (0.040 mmol) of the title compound. MS (ES) 600.0 (M+H).

Example 353

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzonitrile

I-353

In a 20-mL scintillation vial equipped with a stir bar, 6-chloro-3-(3-(4-chloro-3,5-dimethylphenoxy)propyl)-N-(3-cyanophenyl)-7-(1,3,5-trimethyl-1H-pyrazol-4-yl)-1H-indole-2-carboxamide (24 mg, 0.40 mmol) was charged and dissolved in DMF (2 mL). Cesium carbonate (50 mg, 0.154 mmol) was added, followed by addition of 1,3-dibromopropane (30 mg, 0.149 mmol). The reaction mixture was stirred for 4 h at 60° C., after which time the reaction was determined to be complete by LCMS. The reaction mixture was cooled to ambient temperature and diluted into DCM/ $H_2O$ (1:1, 20 mL). The organic layer was separated, and the aqueous layer was extracted with DCM (2×10 mL). The combined organic extracts were dried over a phase separator, and concentrated in vacuo. The crude material was dissolved in DMSO (1 mL) and purified by the reverse phase HPLC (Phenomenex Gemini C18, $H_2O/CH_3CN$ 30-95% 0.1% TFA) to give the title compound (16 mg, 0.025 mmol) as a colorless oil. MS (ES) 640.0 (M+H).

Example 354

Preparation of 2-(3-(2H-tetrazol-5-yl)phenyl)-8-chloro-1-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one

I-354

In a 2-dram vial equipped with a stir bar, 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino [1,2-a]indol-2(3H)-yl)benzonitrile (25 mg, 0.039 mmol) was charged and dissolved in DMF (3 mL). Sodium azide (15 mg, 0.231 mmol) and ammonium chloride (15 mg, 0.28 mmol) were added, and the reaction was allowed to stir at 120° C. for 36 h after which time LCMS confirmed presence of desired product and unreacted starting material. The reaction was allowed to cool to ambient temperature, diluted into DCM/$H_2O$ (1:1, 20 mL), and the organic layer was separated. The aqueous layer was extracted with DCM (2×10 mL), and the combined organic layers were dried with a phase separator and concentrated in vacuo. The crude product was dissolved in DMSO (1 mL) and purified by the reverse phase HPLC (Phenomenex Gemini C18, $H_2O/ CH_3CN$ 30-95% 0.1% TFA) to afford 7 mg (0.010 mmol) of the title compound as a white solid. MS (ES) 683.1 (M+H);

¹H NMR (500 MHz in CDCl₃): δ 8.00 (s, 1H), 7.67 (d, J=8.5 Hz, 1H), 7.63 (s, 1H), 7.30 (d, J=8.0 Hz, 1H), 7.21-7.18 (m, 2H), 6.52 (s, 2H), 4.20-4.14 (m, 2H), 3.95-3.90 (m, 3H), 3.73-3.67 (m, 2H), 3.50 (s, 3H), 3.23 (t, J=6.0 Hz, 2H), 2.24-2.21 (m, 2H), 2.19 (s, 6H), 2.12 (s, 3H), 2.10 (3H), 1.94-1.86 (m, 2H).

Example 355

Preparation of 6-chloro-3-(3-(4-chloro-3,5-dimethylphenoxy)propyl)-N-(4-cyanophenyl)-7-(1,3,5-trimethyl-1H-pyrazol-4-yl)-1H-indole-2-carboxamide

I-355

The title compound was prepared according to procedures described in Examples 352 using 6-chloro-3-(3-(4-chloro-3,5-dimethylphenoxy) propyl)-7-(1,3,5-trimethyl-1H-pyrazol-4-yl)-1H-indole-2-carboxylic acid and substituting 3-aminobenzonitrile with 4-aminobenzonitrile. MS (ES) 683.1 (M+H). MS (ES) 600.0 (M+H).

Example 356

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzonitrile

I-356

I The title compound was prepared according to procedures described in Examples 353 substituting 6-chloro-3-(3-(4-chloro-3,5-dimethylphenoxy)propyl)-N-(3-cyanophenyl)-7-(1,3,5-trimethyl-1H-pyrazol-4-yl)-1H-indole-2-carboxamide with 6-chloro-3-(3-(4-chloro-3,5-dimethylphenoxy)propyl)-N-(4-cyanophenyl)-7-(1,3,5-trimethyl-1H-pyrazol-4-yl)-1H-indole-2-carboxamide. MS (ES) 640.0 (M+H).

Example 357

Preparation of 2-(4-(2H-tetrazol-5-yl)phenyl)-8-chloro-1-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one

I-357

The title compound was prepared (8 mg, 0.012 mmol) as a white solid according to procedures described in Examples 354 substituting 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzonitrile with 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzonitrile (20 mg, 0.157 mmol). MS (ES) 683.1 (M+H).

Example 358

Preparation of 2-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)thiazole-5-carboxylic acid

I-358

In a 2-dram vial equipped with a stir bar, 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol), methyl 2-bromothiazole-5-carboxylate (25 mg, 0.113 mmol), Pd₂(dba)₃ (5 mg, 0.005 mmol), Xantphos (7 mg, 0.012 mmol), and cesium carbonate (40 mg, 0.123 mmol) were massed. The vial was purged with argon, and then 1,4-dioxane (1 mL) was added. The reaction was heated to 110° C. for 16 h, after which time the reaction was determined to be complete by LCMS. The reaction mixture was cooled to ambient temperature and diluted into DCM/H₂O (1:1, 20 mL). The organic layer was separated, and the aqueous layer was extracted with DCM (2×10 mL). The combined organic extracts were dried with a phase separator and then concentrated in vacuo. The crude ester was dissolved in DMSO (1 mL) and purified by the reverse phase HPLC (Phenomenex Gemini C18, H₂O/CH₃CN 30-95% 0.1% TFA). The fractions containing product were concentrated, and resultant residue was dissolved in THF/MeOH/H2O (2:1:1, 3 mL). Lithium hydroxide (10 mg, 0.417 mmol) was added, and the reaction was heated to 40° C. for 3 h, after which time the reaction was determined to be complete by LCMS. The reaction was cooled to ambient temperature and concentrated in vacuo. The crude residue was dissolved in DMSO (1 mL) and purified by reverse phase HPLC (Phenomenex Gemini C18, H₂O/CH₃CN 30-95% 0.1% TFA) to afford 1.3 mg (0.0019 mmol) of the title compound as a colorless oil. MS (ES) 666.0 (M+H).

Example 359

Preparation of 2-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)thiazole-4-carboxylic acid

I-359

The title compound was prepared (2.3 mg, 0.0035 mmol) according to procedures described in Example 358 using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol, 1.00 eq) and substituting methyl 2-bromothiazole-5-carboxylate with methyl 2-bromothiazole-4-carboxylate (25 mg, 0.113 mmol). MS (ES) 666.1 (M+H).

Example 360

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)thiazole-2-carboxylic acid

I-360

The title compound was prepared (11.5 mg, 0.017 mmol) according to procedures described in Example 358 using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol) and substituting methyl 2-bromothiazole-5-carboxylate with methyl 4-bromothiazole-2-carboxylate (25 mg, 0.113 mmol). MS (ES) 666.1 (M+H); ¹H NMR: (500 MHz in DMSO-d6) δ 8.02 (s, 1H), 7.76 (d, J=8.5 Hz, 1H), 7.29 (d, J=8.5 Hz, 1H), 6.57 (s, 2H), 4.10-3.95 (m, 2H), 3.80-3.76

(m, 7H), 3.17 (J=6.5 Hz, 2H), 2.12 (s, 6H), 2.08 (t, J=6.5 Hz, 2H), 1.98 (s, 3H), 1.89 (s, 3H), 1.85-1.78 (m, 2H).

Example 361

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-H-[1,4]diazepino[1,2-a]indol-2(3H)-yl)-N-(cyclopropylsulfonyl)benzamide

I-361

Step A. Preparation of 4-bromo-N-(cyclopropylsulfonyl)benzamide

In a scintillation vial, 4-bromobenzoic acid (75 mg, 0.373 mmol) was dissolved in DCM (3 mL). EDC hydrochloride (100 mg, 0.523 mmol), and DMAP (30 mg, 0.245 mmol) were added and the reaction was allowed to stir for 5 min. Cyclopropanesulfonamide (100 mg, 0.826 mmol) was added, and the reaction was allowed to stir at rt for 16 h, after which time the reaction was determined to be complete by LCMS. The reaction was diluted into DCM/H2O (30 mL, 1:1). The organic layer was separated, and the aqueous layer was extracted with DCM (2×20 mL). The combined organic extracts were dried over MgSO$_4$, filtered, and then concentrated in vacuo. The crude material was purified by flash column chromatography (ISCO, Hex/EtOAc 0-100% gradient) to afford the title compound in 96 mg (0.316 mmol, 85% yield) as a white solid. MS (ES) 338.2 (M+H).

Step B. Example 361

The title compound was prepared (6 mg, 0.0079 mmol) according to procedures described in Example 358 using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (35 mg, 0.065 mmol) and substituting methyl 2-bromothiazole-5-carboxylate with 4-bromo-N-(cyclopropylsulfonyl)benzamide (30 mg, 0.099 mmol). MS (ES) 762.2 (M+H).

Example 362

Preparation of 7-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-benzo[d][1,2,3]triazole-5-carboxylic acid

I-362

The title compound was prepared (6.3 mg, 0.0088 mmol) according to procedures described in Example 358 using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (35 mg, 0.065 mmol) and substituting methyl 2-bromothiazole-5-carboxylate with methyl 7-bromo-1-methyl-1H-benzo[d][1,2,3]triazole-5-carboxylate (25 mg, 0.094 mmol). MS (ES) 714.3 (M+H).

Example 363

Preparation of 7-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzo[d][1,3]dioxole-5-carboxylic acid

I-363

The title compound was prepared (4.1 mg, 0.00058 mmol) according to procedures described in Example 358 using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (35 mg, 0.065 mmol) and substituting methyl 2-bromothiazole-5-carboxylate with methyl 7-bromobenzo[d][1,3]dioxole-5-carboxylate (25 mg, 0.097 mmol). MS (ES) 703.2 (M+H).

Example 364

Preparation of 8-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-2,3-dihydrobenzo[b][1,4]dioxine-6-carboxylic acid

I-364

The title compound was prepared (2 mg, 0.0028 mmol) according to procedures described in Example 358 using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (30 mg, 0.056 mmol) and substituting methyl 2-bromothiazole-5-carboxylate with methyl 8-bromo-2,3-dihydrobenzo[b][1,4]dioxine-6-carboxylate (20 mg, 0.073 mmol). MS (ES) 717.3 (M+H); $^1$H NMR (500 MHz in DMSO-d6) δ 7.70 (d, J=8.5 Hz, 1H), 7.40 (dd, J=15, 2.0 Hz, 2H), 7.25 (d, J=8.5 Hz, 1H), 6.74 (s, 2H), 4.30 (q, J=3.6 Hz, 4H), 4.08-4.04 (m, 2H), 3.97 (t, J=6.0 Hz, 2H) 3.78 (s, 3H), 3.52 (t, J=5.8, 2H), 3.02 (t, J=7.2 Hz, 2H), 2.26 (s, 6H), 2.10-2.04 (m, 4H), 2.01 (s, 3H), 1.90 (s, 3H), 1.73-1.71 (m, 2H).

Example 365

Preparation of 4-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-benzo[d]imidazole-6-carboxylic acid

I-365

The title compound was prepared (2 mg, 0.0028 mmol) according to procedures described in Example 358 using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol) and substituting methyl 2-bromothiazole-5-carboxylate with methyl 4-bromo-1-methyl-1H-benzo[d]imidazole-6-carboxylate (20 mg, 0.075 mmol). MS (ES) 713 (M+H).

Example 366

Preparation of 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-2-methyl-2H-benzo[d]imidazole-4-carboxylic acid

I-366

Step A. Preparation of methyl 6-bromo-1-methyl-1H-indazole-4-carboxylate and methyl 6-bromo-2-methyl-2H-indazole-4-carboxylate In a 20-mL scintillation vial equipped with a stir bar, methyl 6-bromo-1H-indazole-4-carboxylate (100 mg, 0.392 mmol) was dissolved in DMF (5 mL). Sodium hydride (30 mg, 0.75 mmol) was added, and the reaction was allowed to stir at ambient temperature for 1 h. Methyl iodide (100 mg, 0.704 mmol) was added, and the reaction was allowed to stir for 2 h, after which time the reaction as determined to be complete by LCMS. The reaction was cooled to 0° C. and quenched with MeOH (0.1 mL). The reaction was then diluted into DCM/H2O (1:1, 20 mL), and the organic layer was separated. The aqueous layer was extracted with DCM (2×20 mL), and the combined organic layers were dried over a phase separator and concentrated in vacuo. The crude residue was dissolved in DMSO (2 mL) and purified by reverse phase HPLC (Phenomenex Gemini C18, $H_2O$/$CH_3CN$ 30-95% 0.1% TFA) to give methyl 6-bromo-1-methyl-1H-indazole-4-carboxylate (A, 32 mg, 0.12 mmol, LCMS: RT=1.418 min, MS (ES) 269.1 (M+H), structure determined by 2D NMR) and methyl 6-bromo-2-methyl-2H-indazole-4-carboxylate (B, 15 mg, 0.056 mmol), LCMS: RT=1.341, MS (ES) 269.1 (M+H), structure determined by 2D NMR).

Step B. Example 366

The title compound was prepared (3 mg, 0.0042 mmol) according to procedures described in Example 358 using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol) and substituting methyl 2-bromothiazole-5-carboxylate with methyl 6-bromo-2-methyl-2H-indazole-4-carboxylate (15 mg, 0.056 mmol). MS (ES) 713.2 (M+H); $^1$H NMR (500 MHz in DMSO-d6) δ 8.60 (s, 1H), 7.80 (s, 1H), 7.74 (s, 1H), 7.70 (d, J=8.5 Hz, 1H), 7.25 (d, J=8.5 Hz, 1H), 6.72 (s, 2H), 4.22 (s, 3H), 4.06-4.02 (m, 2H), 3.95 (t, J=6.0 Hz, 2H), 3.77 (s, 3H), 3.63-3.61 (m, 2H), 3.05 (t, J=7.5 Hz, 2H), 2.21 (s, 6H), 2.08 (t, J=6.5 Hz, 2H), 2.01 (s, 3H), 1.90 (s, 3H), 1.79-1.74 (m, 2H).

Example 367

Preparation of 6-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indazole-4-carboxylic acid

I-367

The title compound was prepared (4.2 mg, 0.0059 mmol) according to procedures described in Example 358 using 8-chloro-11-(3-(4-chloro-3,5-dimethylphenoxy)propyl)-7-(1,3,5-trimethyl-1H-pyrazol-4-yl)-2,3,4,5-tetrahydro-1H-[1,4]diazepino[1,2-a]indol-1-one (25 mg, 0.046 mmol) and substituting methyl 2-bromothiazole-5-carboxylate with methyl 6-bromo-1-methyl-1H-indazole-4-carboxylate (15 mg, 0.056 mmol). MS (ES) 713.2 (M+H); $^1$H NMR (500 MHz in DMSO-d6) δ 8.32 (s, 1H), 7.97 (s, 1H), 7.79 (s, 1H), 7.71 (d, J=8.5 Hz, 1H), 7.26 (d, J=8.5 Hz, 1H), 6.72 (s, 2H), 4.07-4.05 (m, 5H), 3.96 (t, J=6.5, 2H), 3.77 (s, 3H), 3.68 (t, J=4.0 Hz, 2H), 3.05 (t, J=6.5 Hz, 2H), 2.21 (s, 6H), 2.08 (t, J=8.0 Hz, 2H), 2.01 (s, 3H), 1.91 (s, 3H), 1.83-1.78 (m, 2H).

Example 368

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-H-[1,4]diazepino[1,2-a]indol-2(3H)-yl)-N-(methylsulfonyl)benzamide

I-368

In a scintillation vial, 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoic acid (15 mg, 0.023 mmol), EDC hydrochloride (10 mg, 0.052 mmol), and DMAP (3 mg, 0.025 mmol) were massed and dissolved in DCM (2 mL). After 5 min, methanesulfonamide (10 mg, 0.11 mmol, 4.6 eq) was added, and the reaction was allowed to stir for 48 h, after which time it was determined to be complete by LCMS analysis. The reaction was diluted into DCM/$H_2O$ (20 mL, 1:1). The organic layer was separated, and the aqueous layer was extracted with DCM (2×5 mL). The combined organic extracts were dried with a phase separator and concentrated in vacuo. The crude product was dissolved in DMSO (1 mL) and purified by the reverse phase HPLC (Phenomenex Gemini C18, $H_2O$/$CH_3CN$ 30-95% 0.1% TFA) to afford 2.0 mg (0.0019 mmol) of the title compound as a colorless oil. MS (ES) 736.2 (M+H).

Example 369

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-H-[1,4]diazepino[1,2-a]indol-2(3H)-yl)-N-(cyclopropylsulfonyl)benzamide

I-369

The title compound was prepared (1.8 mg, 0.0023 mmol) according to procedures described in Example 367 using 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)benzoic acid (15 mg, 0.023 mmol, 1.0 eq) and substituting methanesulfonamide with cyclopropanesulfonamide (10 mg, 0.083 mmol, 2.3 eq). MS (ES) 762.2 (M+H).

Example 370

Preparation of 3-bromo-5-((6-chloro-3-(3-(4-chloro-3,5-dimethylphenoxy)propyl)-7-(1,3,5-trimethyl-1H-pyrazol-4-yl)-1H-indole-2-carboxamido)methyl)benzoic acid

I-370

The title compound was prepared (8.1 mg, 0.011 mmol, 83%) according to procedures described in Example 314 using 6-chloro-3-(3-(4-chloro-3,5-dimethylphenoxy)propyl)-7-(1,3,5-trimethyl-1H-pyrazol-4-yl)-1H-indole-2-carboxylic acid (6.8 mg, 0.013 mmol), ethyl 3-(aminomethyl)-5-bromobenzoate hydrochloride (5 mg, 0.017 mmol), HBTU (18 mg, 0.048 mmol), triethylamine (15 µL, 0.104 mmol), and DMF (1 mL); MS (ES) 711.1 (M+1).

Example 371

Preparation of (1r,4r)-4-((8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)methyl)cyclohexane-1-carboxylic acid

I-371

To a solution of ethyl (1r,4r)-4-((6-chloro-3-(3-(4-chloro-3,5-dimethylphenoxy)propyl)-7-(1,3,5-trimethyl-1H-pyrazol-4-yl)-1H-indole-2-carboxamido) methyl)cyclohexane-1-carboxylate (16.5 mg, 0.025 mmol) in DMF (0.5 mL) were added 1,3-dibromopropane (25 µL, 0.125 mmol), $Cs_2CO_3$ (81.5 mg, 0.25 mmol) and the mixture was stirred at 80° C. for 3 h. The mixture was filtered, diluted with water (5 mL) and was extracted in $CH_2Cl_2$ (3×5 mL). The organic layer was dried (anhyd. $Na_2SO_4$) and was evaporated. To a solution of crude ester in THF (1 mL) at room temperature was added 2M LiOH (1 mL) the mixture was stirred at the ambient temperature for 5 h. The reaction mixture was evaporated, acidified to pH 7 with 4M HCl, extracted in EtOAc. The organic layer was dried, evaporated and finally purified the reverse phase HPLC (Phenomenex Gemini C18, $H_2O/CH_3CN$ 30-70% 0.1% TFA) to afford the title compound (3.2 mg, 9%) as a white solid; MS (ES) 679.1 (M+H).

Example 372

Preparation of 3-((6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxamido)methyl)benzoic acid

I-372

The title compound was prepared according to the procedures described in Example 373 using 6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxylic acid (12 mg, 0.020 mmol) and substituting methyl 4-(aminomethyl)benzoate with methyl 3-(aminomethyl)benzoate (10 mg, 0.061 mmol) in Step C. MS (ES) 746.3 (M+H).

Example 373

Preparation of 4-((6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxamido)methyl)benzoic acid

I-373

Step A. Preparation of ethyl 6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxylate In a 20-mL scintillation vial equipped with a stir bar, ethyl 6-chloro-3-(3-(4-chloro-3,5-dimethylphenoxy)propyl)-7-(1,3,5-trimethyl-1H-pyrazol-4-yl)-1H-indole-2-carboxylate (30 mg, 0.057 mmol) was dissolved in DMF (3 mL), followed by addition of sodium hydride (5 mg, 0.125 mmol). The reaction was allowed to stir for 30 min at ambient temperature, followed by addition of 4-(2-bromoethyl)morpholine hydrobromide (30 mg, 0.11 mmol). The reaction was allowed to stir at ambient temperature for 3 h, after which time the reaction was determined to be complete by LCMS. The reaction mixture was diluted into $DCM/H_2O$ (1:1, 20 mL). The organic layer was separated, and the aqueous layer was extracted with DCM (2×10 mL). The combined organic extracts were dried with a phase separator, and concentrated in vacuo. The crude material was carried forward to next step without further purification. MS (ES) 641.2 (M+H).

Step B. Preparation of 6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxylic acid In a 20-mL scintillation vial equipped with a stir bar, ethyl 6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxylate (36 mg, 0.057 mmol) was dissolved in $THF/H_2O/MeOH$ (4:1:1, 6 mL), followed by addition of lithium hydroxide (10 mg, 0.42 mmol). The reaction was heated to 50° C. for 2 h, after which time the reaction was determined to be complete by LCMS. The reaction mixture was concentrated in vacuo, then diluted with $DCM/H_2O$ (1:1, 40 mL). The aqueous layer was acidified with 1M HCl, and the layers were separated. The aqueous layer was extracted with DCM (2×20 mL), and the combined organic extracts were dried over $MgSO_4$, filtered, and concentrated in vacuo to afford the title compound (32 mg, 0.52 mmol). MS (ES) 613.2 (M+H).

Step C. Preparation of methyl 4-((6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxamido)methyl)benzoate In a 2-dram vial equipped with a stir bar, 6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxylic acid (12 mg, 0.020 mmol), HATU (10 mg, 0.026 mmol), and DIPEA (10 mg, 0.078 mmol) were massed and dissolved in DMF (2 mL). The reaction was allowed to stir for 10 min, followed by addition of methyl 4-(aminomethyl)benzoate (10 mg, 0.061 mmol). The reaction was allowed to stir for 48 h, after which time the reaction was determined to be complete by LCMS. The reaction was diluted into $DCM/H_2O$ (20 mL, 1:1), and the organic layer was separated. The aqueous layer was extracted with DCM (2×10 mL), and the combined organic layers were dried with a phase separator and then concentrated in vacuo. The crude material was dissolved in DMSO (1 mL) and purified by reverse phase HPLC (Phenomenex Gemini C18, $H_2O/CH_3CN$ 30-95% 0.1% TFA) to give the title compound (10 mg, 0.013 mmol). MS (ES) 760.3 (M+H).

Step D. Example 373

In a 2-dram vial equipped with a stir bar, methyl 4-((6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxamido)methyl)benzoate (3 mg, 0.0039 mmol) was dissolved in THF/H₂O/MeOH (4:1:1, 3 mL). Lithium hydroxide was added (2 mg, 0.083 mmol), and the reaction was heated to 50° C. for 4 h, after which time the reaction was determined to be complete by LCMS. The reaction was concentrated in vacuo, and then diluted into DCM/H2O (1:1, 10 mL). The aqueous layer was acidified with 1M HCl, and the organic layer was separated. The aqueous layer was extracted with DCM (2×10 mL), and the combined organic extracts were dried with a phase separator, and concentrated in vacuo to afford the title compound (2 mg, 0.0027 mmol) as a colorless oil. MS (ES) 746.2 (M+H).

Example 374

Preparation of 4-((6-chloro-3-(3-(4-chloro-3,5-dimethylphenoxy)propyl)-N-methyl-1-(2-morpholinoethyl)-7-(1,3,5-trimethyl-1H-pyrazol-4-yl)-1H-indole-2-carboxamido)methyl)benzoic acid

I-374

Step A. Preparation of methyl 4-((6-chloro-3-(3-(4-chloro-3,5-dimethylphenoxy)propyl)-N-methyl-1-(2-morpholinoethyl)-7-(1,3,5-trimethyl-1H-pyrazol-4-yl)-1H-indole-2-carboxamido)methyl)benzoate In a 2-dram vial equipped with a stir bar, methyl 4-((6-chloro-3-(3-(4-chloro-3,5-dimethylphenoxy)propyl)-1-(2-morpholinoethyl)-7-(1,3,5-trimethyl-1H-pyrazol-4-yl)-1H-indole-2-carboxamido)methyl)benzoate (7 mg, 0.0092 mmol) was dissolved in DMF (2 mL). Sodium hydride (3 mg, 0.075 mmol) was added, and the reaction was allowed to stir for 1 h at ambient temperature. Methyl iodide (5 mg, 0.035 mmol) was added, and the reaction was allowed to stir for 1 h at ambient temperature. The reaction was determined to be complete by LCMS, and then cooled to 0° C. and quenched with MeOH (0.1 mL). The reaction was then diluted into DCM/H₂O (1:1, 20 mL), the organic layer was separated, and the aqueous layer was extracted with DCM (2×10 mL). The combined organic extracts were dried with a phase separator and concentrated in vacuo. The crude material was carried forward without further purification. MS (ES) 774.3 (M+H).

Step B. Example 374

In a 2-dram vial equipped with a stir bar, methyl 4-((6-chloro-3-(3-(4-chloro-3,5-dimethylphenoxy)propyl)-N-methyl-1-(2-morpholinoethyl)-7-(1,3,5-trimethyl-1H-pyrazol-4-yl)-1H-indole-2-carboxamido)methyl)benzoate (7 mg, 0.0092 mmol) was dissolved in THF/H₂O/MeOH (4:1:1, 3 mL). Lithium hydroxide (2 mg, 0.083 mmol) was added, and the reaction was heated to 50° C. for 2 h, after which time the reaction was determined to be complete by LCMS. The reaction was concentrated, and the crude residue dissolved in DMSO (1 mL) and purified by reverse phase HPLC (Phenomenex Gemini C18, H₂O/CH₃CN 30-95% 0.1% TFA) to give the title compound (2 mg, 0.0026 mmol) as a colorless oil. MS (ES) 760.3 (M+H).

Example 375

Preparation of 3-(8-chloro-11-(3-(4-chloro-3,5-dimethylphenoxy)propyl)-1-oxo-7-(1,3,5-trimethyl-1H-pyrazol-4-yl)-4,5-dihydro-1H-[1,4]diazepino[1,2-a]indol-2(3H)-yl)-1-methyl-1H-indazole-6-carboxylic acid

I-375

This compound was synthesized according to the procedures described in Example 104 Step A and B using VU0659697 using methyl 3-bromo-1-methyl-3a,7a-dihydro-1H-indazole-7-carboxylate; ¹H NMR (MeOD, 400 MHz) δ (ppm) 8.28 (s, 1H), 7.81-7.75 (m, 3H), 7.29 (d, J=8.4 Hz, 1H), 6.34 (s, 2H), 4.15 (t, J=6.4 Hz, 2H), 4.12 (s, 3H), 3.97 (t, J=6.4 Hz, 2H), 3.90 (t, J=6.4 Hz, 2H), 3.87 (s, 3H), 3.26 (t, J=7.2 Hz, 2H), 2.24 (s, 6H), 2.23-2.20 (m, 2H), 2.12 (s, 3H), 2.05 (s, 3H), 1.93-1.88 (m, 2H); LCMS (ES) tR: 0.909 min (>99%, ELSD), m/z: 713.0 [M+1]

Example 377

Assays for Bcl-2 Family Proteins Activity

The in vitro modulation of Bcl-2 family proteins was determined as follows.
Bak Peptide Binding Assay
General Provided compounds of the present invention can be demonstrated to compete for binding with fluorescently labeled peptides derived from relevant BH3 domains. In some embodiments, a provided compound exhibit selectivity for Mcl-1 over Bcl-xL and Bcl-2.
Assay Compound affinity was measured using a fluorescence polarization anisotropy competition assay. Anisotropy measurements were carried out in 384-well, black, flat-bottom plates (Greiner Bio-one, Monroe, N.C., USA). The assay was run using either a fluorescein isothiocyanate-labeled BH3 peptide derived from Bak (FITC-AHx-GQVGRQLAI-IGDDINR-NH₂) or a fluorescein isothiocyanate-labeled BH3 peptide derived from Bim (FITC-AHx-EARIAQELR-RIGDEFNETYTR-NH₂) that were purchased from GenScript (Piscataway, N.J.) at >95% purity and used without further purification. 10 nM FITC-Bak peptide and 15 nM recombinant Mcl-1 (residues 172-327) were added to assay buffer (3 mM dithiothreitol, 50 mM NaCl, 20 mM Tris, pH 7.5). The Bim based assay was run with 1 nM FITC-Bim peptide and 1.5 nM recombinant Mcl-1 (residues 172-327) added to assay buffer (20 mM TRIS pH 7.5, 50 mM NaCl, 3 mM DTT, 0.01% CHAPS). For selectivity assays, 40 nM Bcl-2 (residues 1-207$^{A96T,G110R}$, Δ35-91, replaced with Bcl-xL$_{35-50}$) or 4 nM Bcl-xL (residues 1-209, loop 45-86 deleted) were incubated with 10 nM FITC-Bak in assay buffer.

Compounds are diluted in DMSO in a 10-point, 3-fold serial dilution scheme. For the FITC-BAK assay 2.5 uL compound is added to 47.5 μL of assay buffer containing FITC-Bak and protein, for a final DMSO concentration of 5% and a top concentration of 20 μM. A FITC-Bak peptide alone (100% inhibition) and peptide plus protein (0% inhibition) control is included on each assay plate. For the FITC-Bim assay, compound is added to 40 uL of assay buffer containing protein, 15 minutes prior to addition of 10 μL of the FITC-Bim peptide, for a final DMSO concentration of 0.165% and a top concentration of 200 nM. A FITC-Bim peptide alone (100% inhibition) and peptide plus protein (0% inhibition) control is included on each assay plate. The plate was mixed and incubated for 90 minutes at room temperature. Anisotropy is measured at excitation wavelength 480 nm and emission wavelength 535 nm using an EnVision Multi-label plate reader (PerkinElmer, Wellesley, Mass., USA) or a BioTek Cytation 3 (BioTek, Winooski, Vt., USA). Fluorescence anisotropy is plotted against compound concentration to generate an IC₅₀ (inhibitor concentration at which 50% of bound peptide is displaced) by fitting the data to a 4-parameter logistic model using XLFit software (Guildford, Surrey, UK). IC₅₀ is converted to a binding dissociation constant ($K_i$ value) according to the formula of Wang Z. FEBS Lett (1996) 3, 245.

$$K_i=[I]_{50}/([L]_{50}/K_d+[P]_0/K_d+1)$$

where $[I]_{50}$ is the concentration of the free inhibitor at 50% inhibition, $[L]_{50}$ is the concentration of the free labeled ligand at 50% inhibition, $[P]_0$ is the concentration of the free protein at 0% inhibition, $K_d$ represents the dissociation constant of the FITC peptide probe. The results for representative compounds are shown in Table 2 and 3.

TABLE 2

$K_i$ for Examplified Compounds for Inhibition of Mcl-1

| Examples | $K_i$ |
|---|---|
| I-10, I-41, I-42, I-45, I-47, I-50, I-61, I-64, I-66, I-266, I-276, I-289, | 10 μM-50 μM |
| I-1, I-2, I-40, I-43, I-44, I-46, I-48, I-51, I-56, I-259, I-260, I-261, I-264, I-265, I-272, I-275, I-278, I-288, | 1 μM-9.99 μM |
| I-3, I-9, I-11, I-12, I-52, I-54, I-67, I-262, I-313, | 501 nM-999 nM |
| I-6, I-13, I-18, I-25, I-28, I-53, I-55, I-65, I-73, I-101, I-263, I-268, I-279, | 301 nM-500 nM |
| I-4, I-5, I-7, I-8, I-15, I-16, I-17, I-19, I-20, I-21, I-22, I-24, I-49, I-58, I-59, I-60, I-63, I-69, I-78, I-84, I-119, I-203, I-244, I-245, I-246, I-269, I-274, I-281, I-287 | 101 nM-299 nM |
| I-14, I-33, I-57, I-68, I-70, I-75, I-76, I-77, I-79, I-81, I-110, I-112, I-164, I-194, I-202, I-204, I-296, I-297, I-308, I-312, I-314, I-340, I-342, I-352, I-353, I-355, I-356, | 51 nM-100 nM |
| I-23, I-25a, I-26, I-27, I-29, I-30, I-31, I-32, I-34, I-35, I-36, I-37, I-38, I-39, I-62, I-66, I-71, I-72, I-74, I-80, I-82, I-83, I-85, I-86, I-87, I-88, I-89, I-90, I-91, I-92, I-93, I-94, I-95, I-96, I-97, I-98, I-99, I-100, I-102, I-103, I-104, I-105, I-106, I-107, I-108, I-109, I-111, I-113, I-114, I-115, I-116, I-117, I-118, I-120, I-121, I-122, I-123, I-124, I-125, I-126, I-127, I-128, I-129, I-130, I-131, I-132, I-133, I-134, I-135, I-136, I-137, I-138, I-139, I-140, I-141, I-142, I-143, I-144, I-145, I-146, I-147, I-148, I-149, I-150, I-151, I-152, I-153, I-154, I-155, I-156, I-157, I-158, I-159, I-160, I-161, I-162, I-163, I-165, I-166, I-167, I-168, I-169, I-170, I-171, I-172, I-173, I-174, I-175, I-176, I-177, I-178, I-179, I-180, I-181, I-182, I-183, I-184, I-185, I-186, I-187, I-188, I-189, I-190, I-191, I-192, I-193, I-195, I-196, I-197, I-198, I-199, I-200, I-201, I-205, I-206, I-207, I-208, I-209, I-210, I-211, I-212, I-213, I-214, I-215, I-216, I-217, I-218, I-219, I-220, I-221, I-222, I-223, I-224, I-225, I-226, I-227, I-228, I-229, I-230, I-231, I-232, I-233, I-234, I-235, I-236, I-237, I-238, I-239, I-240, I-241, I-242, I-243, I-247, I-248, I-249, I-250, I-251, I-252, I-253, I-254, I-255, I-256, I257, I-258, I-267, I-270, I-271, I-273, I-277, I-280, I-282, I-283, I-284, I-285, I-286, I-290, I-291, I-292, I-293, I-294, I-295, I-298, I-299, I-300, I-301, I-302, I-303, I-304, I-305, I-306, I-307, I-309, I-310, I-311, I-315, I-316, I-317, I-318, I-319, I-320, I-321, I-322, I-323, I-324, I-325, I-326, I-327, I-328, I-329, I-330, I-331, I-332, I-333, I-334, I-335, I-336, I-337, I-338, I-339, I-341, I-343, I-344, I-345, I-346, I-347, I-348, I-349, I-350, I-351, I-354, I-357, I-358, I-359, I-360, I-361, I-362, I-363, I-364, I-365, I-366, I-367, I-368, I-369, I-370, I-371, I-372, I-373, I-374, I-375 | <50 nM |

TABLE 3

Mcl-1 Selectivity over Bcl-xL and Bcl-2 for Representative Compounds.

| Example | Mcl-1 $K_i$ (nM) | Bcl-xL $K_i$ (nM) | Bcl-2 $K_i$ (nM) |
|---|---|---|---|
| I-31 | <7 | 6443 | 2200 |
| I-32 | <7 | 13430 | 3820 |
| I-39 | 7.2 | 4590 | 1540 |
| I-71 | 10 | 13850 | 5950 |
| I-74 | 24 | >100000 | 3540 |
| I-80 | <7 | 6750 | 2340 |

TABLE 3-continued

Mcl-1 Selectivity over Bcl-xL and Bcl-2 for Representative Compounds.

| Example | Mcl-1 $K_i$ (nM) | Bcl-xL $K_i$ (nM) | Bcl-2 $K_i$ (nM) |
|---|---|---|---|
| I-177 | <7 | 8890 | 1900 |
| I-181 | <7 | 61500 | 3200 |
| I-183 | <7 | 14400 | 2900 |
| I-188 | <7 | 15600 | 5300 |
| I-189 | <7 | 4630 | 1370 |
| I-190 | <7 | 45600 | 1640 |
| I-280 | <7 | 27000 | 7900 |

Among other things, these data demonstrate the utility of representative compounds as selective inhibitors of the activity of Mcl-1 protein to bind peptides from relevant BH3 domains.

Cellular Viability of Human Tumor Cell Lines

Human cancer cell lines ALMC-1, ALMC-2, K562, H929, and OPM-2 were cultured in media supplemented with 10% fetal bovine serum (FBS). To evaluate compound effect on cellular proliferation, cells were plated at 1,000 cells/well in 96-well tissue culture plates in a total volume of 90 μL medium supplemented with 10% FBS (Sigma, Saint Louis, Mo.). 24 hours later, 10 μL of compound (in a 2-fold serial dilution) is added to the cells for a top concentration of 50 μM and a final DMSO concentration <1%. After 72 hours, 50 μL of Cell TiterGlo (Promega, Madison, Wis., USA) reagent is added to each well and plates are incubated at room temperature, in the dark, for 30 minutes. Luminescence is measured on a BioTek Cytation 3. Luminescence values are imported into a template in XLFit (Guildford, Surrey, UK) that uses a four-parameter fit to generate an $IC_{50}$ value for each compound dilution series on the plate.

TABLE 4

$IC_{50}$ (in μM) for representative compounds on cellular proliferation of human cancer cell lines

| Compound | ALMC-1 | ALMC-2 | H929 | OPM-2 | K562 |
|---|---|---|---|---|---|
| I-29 | 12.1 | 16.6 | 14 | 40 | 28.6 |
| I-31 | 13.1 | 33.9 | 15 | 16.3 | 40 |
| I-32 | 14.2 | 29.7 | 11.6 | 17.5 | 40 |
| I-38 | 4.2 | 7.6 | 3.2 | 4.9 | 8.7 |
| I-177 | 12.0 | 20.8 | 6.3 | | 23.2 |
| I-178 | 6.1 | 8.7 | 8.7 | 11.7 | 11.8 |
| I-220 | | | 4.9 | | 14.8 |
| I-236 | 6.9 | 12.2 | 7.3 | 7.2 | 25.0 |
| I-239 | 1.5 | 3.2 | 1.8 | 1.5 | 11.1 |
| I-240 | 1.7 | 3.4 | 2.2 | 1.7 | 12.3 |

Apoptosis Assay Protocol (Caspase 3/7 Glo)

Induction of apoptosis was measured by quantifying caspase 3/7 activity using the commercially available Caspase-Glo reagent (Promega, Madison, Wis., USA). This assay relies on the cleavage of a proluminescent substrate by activated caspases, which is then detected on the BioTek Cytation 3. 5000 cells in 90 μL of media (+5% FBS) are plated in each well of a white 96-well plate and incubated overnight at 37° C. in a tissue culture incubator. The following day, compound is diluted in a 10-pt, 2-fold serial dilution scheme for a final top concentration of 50 μM. 10 μL of compound is added directly to the cell assay plate for a final volume of 100 μL. Columns 11 and 12 are reserved for treatment with DMSO to serve as control wells. Plates are incubated for 3 hours. 100 μL of Caspase-Glo reagent is added to each well and plates are incubated at room temperature, in the dark, for 30 minutes. Luminescence is measured on the Cytation 3. Luminescence values are imported into a template in XLFit (Guildford, Surrey, UK) that uses a four-parameter fit to generate an $IC_{50}$ value for each compound dilution series on the plate.

TABLE 5

$EC_{50}$ (in µM) for representative compounds on cellular caspase 3/7 activation of Mcl-1 sensitive human cancer cell lines.

| Compound | H929 |
|---|---|
| I-80 | 3.1 |
| I-175 | 2.3 |
| I-177 | 2.3 |
| I-178 | 3.1 |
| I-184 | 10.0 |
| I-201 | 1.6 |
| I-239 | 0.75 |
| I-240 | 0.76 |
| I-320 | 2.3 |

Among other things, these data demonstrate the utility of representative compounds as inhibitors of cellular proliferation of human cancer cell lines and initiators of apoptosis via caspase 3 and 7 activation in a Mcl-1 sensitive human cancer cell line.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:
1. A compound of formula VI:

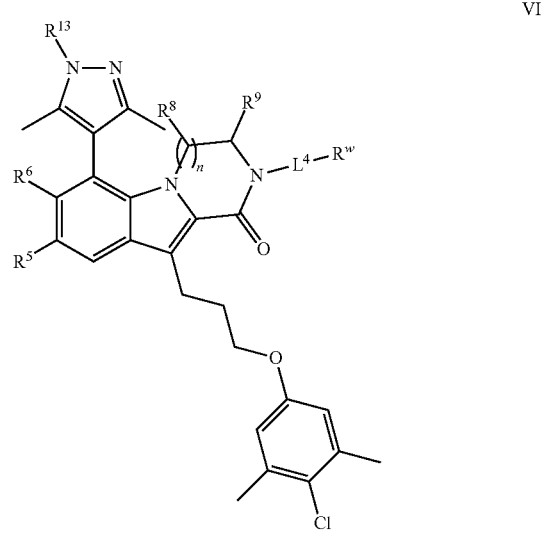

or a pharmaceutically acceptable salt thereof, wherein:
$L^4$ is independently selected from a covalent bond or an optionally substituted bivalent straight or branched $C_{1-8}$ hydrocarbon chain wherein one or more methylene units are optionally and independently replaced with -Cy'-, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;
-Cy'- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, 3-8 membered saturated or partially unsaturated heterocyclylene having 1-4 heteroatoms independently selected from nitrogen, oxygen, or sulfur, an 8-10 membered bicyclic arylene or heteroarylene having 1-4 heteroatoms independently selected from nitrogen, oxygen, or sulfur, or an 8-10 membered saturated or partially unsaturated heterocyclylene having 1-4 heteroatoms independently selected from nitrogen, oxygen, or sulfur;
$R^w$ is selected from hydrogen, R, —SR, —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)OR, —C(O)R$^x$, —S(O)$_2$OH, or —S(O)$_2$R$^y$, or is selected from:

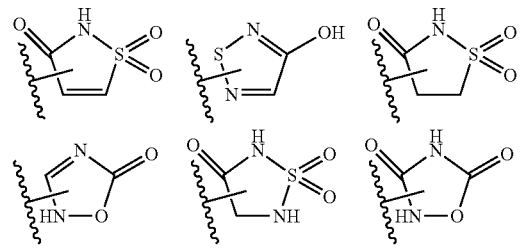

-continued

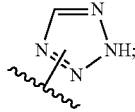

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R;

$R^y$ is selected from —N(R)C(O)CF$_3$, —N(R)C(O)R, or —N(R)C(P)N(R)$_2$;

each R is independently selected from hydrogen or an optionally substituted group selected from C$_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur;

each of $R^5$, $R^6$, $R^8$, $R^9$, and $R^{13}$ is independently selected from R, halogen, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';

each R' is independently selected from hydrogen or optionally substituted C$_{1-4}$ alkyl;

n is selected from 1 or 2; and optionally $R^5$ and $R^6$ are taken together with their intervening atoms to form an optionally substituted ring selected from a 3-8 membered saturated or partially unsaturated carbocyclic ring, phenyl, a 3-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

2. The compound of claim 1, or a pharmaceutically acceptable salt thereof, wherein $R^5$ and $R^6$ are each independently selected from hydrogen or chlorine.

3. The compound of claim 1, or a pharmaceutically acceptable salt thereof, wherein $L^4$ is a covalent bond.

4. The compound of claim 1, or a pharmaceutically acceptable salt thereof, wherein $L^4$ is an optionally substituted bivalent straight or branched C$_{1-8}$ hydrocarbon chain wherein one or more methylene units are optionally and independently replaced with -Cy'-, —S—, —N(R)—, —N(R)C(O)—, —N(R)S(O)$_2$—, —C(O)—, —C(O)N(R)—, —S(O)—, —S(O)$_2$—, or —S(O)$_2$N(R)—.

5. The compound of claim 4, or a pharmaceutically acceptable salt thereof, wherein $L^4$ is an optionally substituted bivalent straight or branched C$_{1-8}$ hydrocarbon chain wherein one or more methylene units are optionally and independently replaced with -Cy'-; and -Cy'- is an optionally substituted bivalent phenylene ring.

6. The compound of claim 4, or a pharmaceutically acceptable salt thereof, wherein $L^4$ is an optionally substituted bivalent straight or branched C$_{1-8}$ hydrocarbon chain wherein one or more methylene units are optionally and independently replaced with -Cy'-; and -Cy'- is an optionally substituted bivalent 3-8 membered saturated or partially unsaturated carbocyclylene ring.

7. The compound of claim 4, or a pharmaceutically acceptable salt thereof, wherein $L^4$ is an optionally substituted bivalent straight or branched C$_{1-8}$ hydrocarbon chain wherein one or more methylene units are optionally and independently replaced with -Cy'-; and -Cy'- is an optionally substituted bivalent 5-6 membered heteroarylene ring having 1-4 heteroatoms independently selected from nitrogen, oxygen, or sulfur.

8. The compound of claim 4, or a pharmaceutically acceptable salt thereof, wherein $L^4$ is an optionally substituted bivalent straight or branched C$_{1-8}$ hydrocarbon chain wherein one or more methylene units are optionally and independently replaced with -Cy'-; and -Cy'- is an optionally substituted bivalent 3-8 membered saturated or partially unsaturated heterocyclylene ring having 1-4 heteroatoms independently selected from nitrogen, oxygen, or sulfur.

9. The compound of claim 4, or a pharmaceutically acceptable salt thereof, wherein $L^4$ is an optionally substituted bivalent straight or branched C$_{1-8}$ hydrocarbon chain wherein one or more methylene units are optionally and independently replaced with -Cy'-; and -Cy'- is an optionally substituted bivalent 8-10 membered bicyclic arylene or heteroarylene ring having 1-4 heteroatoms independently selected from nitrogen, oxygen, or sulfur.

10. The compound of claim 4, or a pharmaceutically acceptable salt thereof, wherein $L^4$ is an optionally substituted bivalent straight or branched C$_{1-8}$ hydrocarbon chain wherein one or more methylene units are optionally and independently replaced with -Cy'-; and -Cy'- is an optionally substituted bivalent 8-10 membered saturated or partially unsaturated heterocyclylene ring having 1-4 heteroatoms independently selected from nitrogen, oxygen, or sulfur.

11. The compound of claim 4, or a pharmaceutically acceptable salt thereof, wherein $L^4$ is an optionally substituted bivalent straight or branched C$_{1-8}$ hydrocarbon chain wherein one or more methylene units are optionally and independently replaced with -Cy'-; and -Cy'- is an optionally substituted bivalent ring selected from the following:

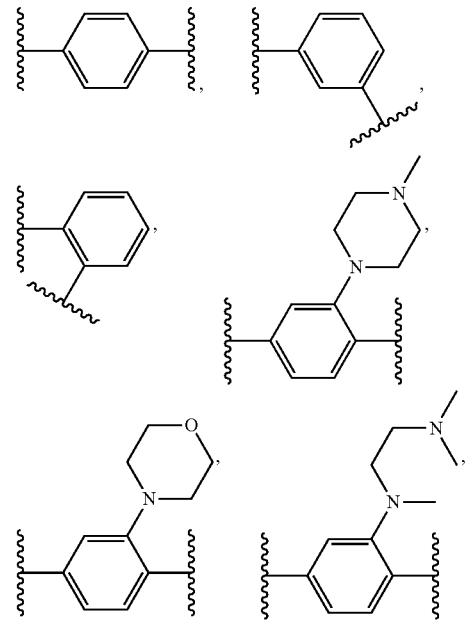

549
-continued
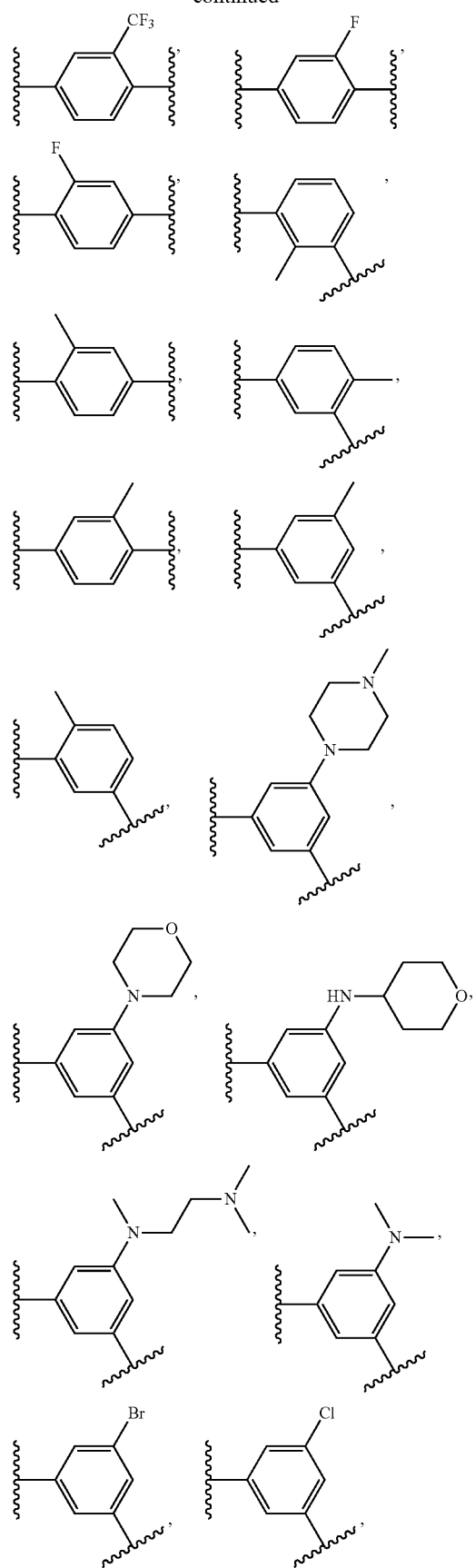
550
-continued
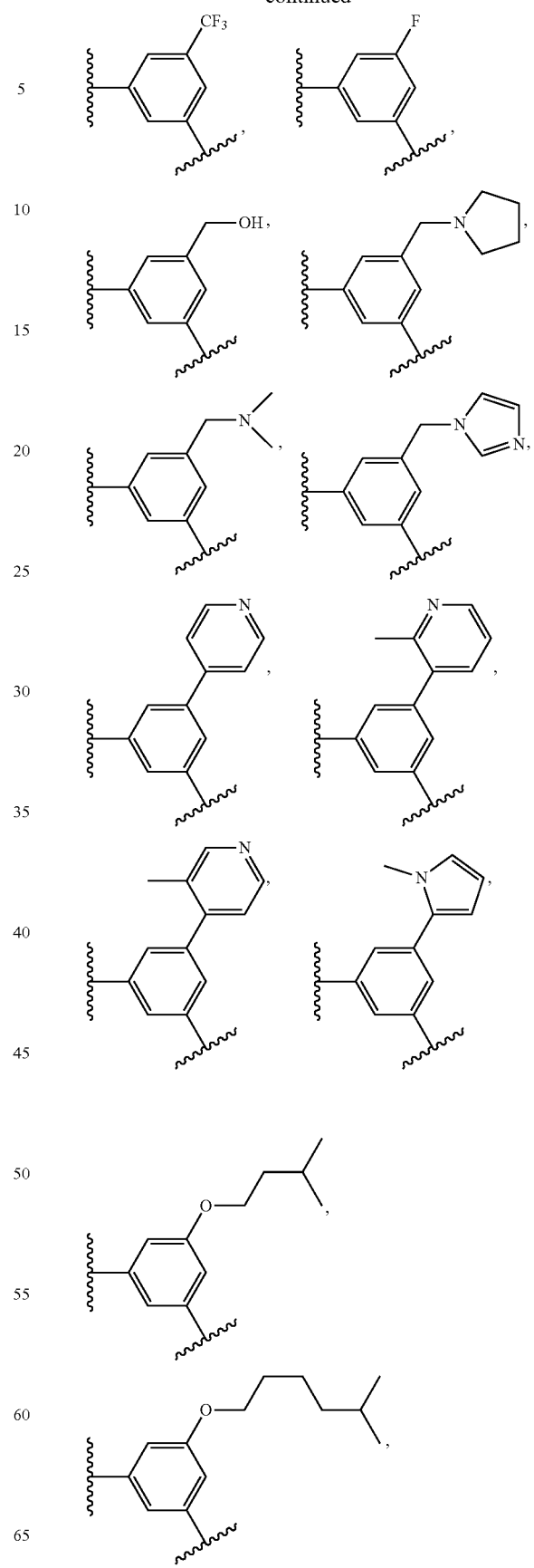

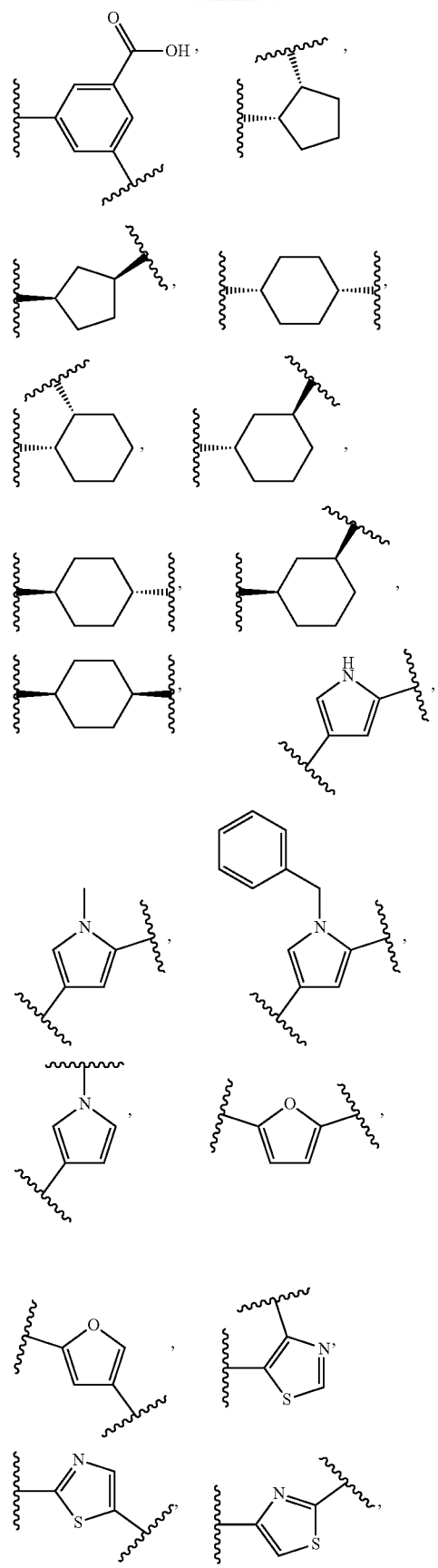
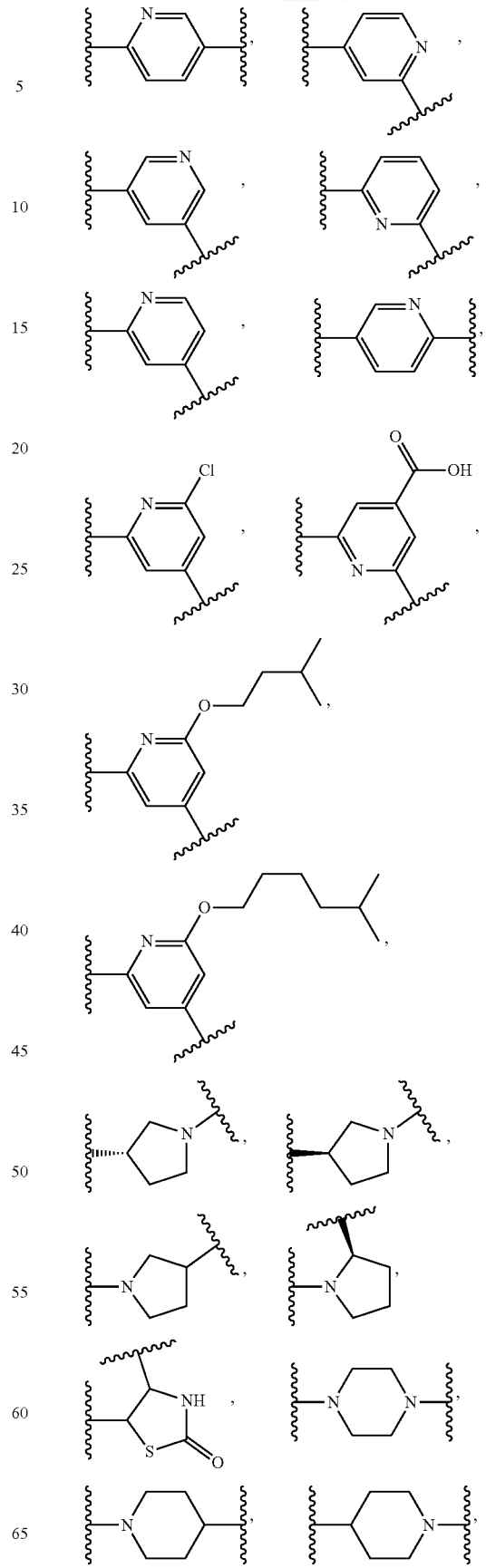

553
-continued
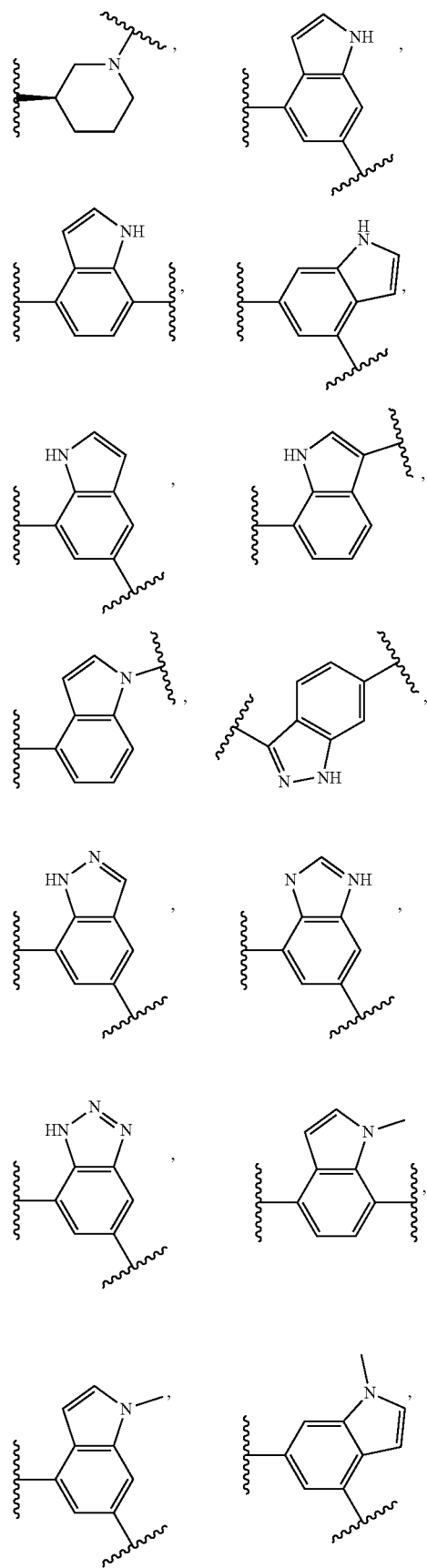
554
-continued
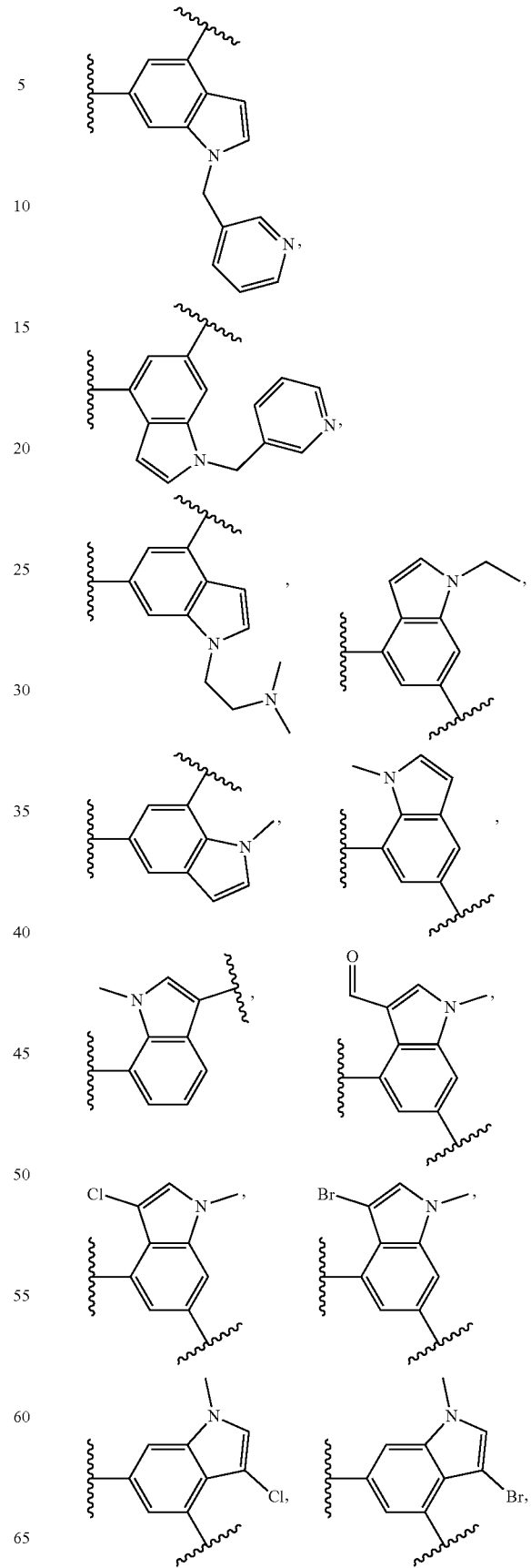

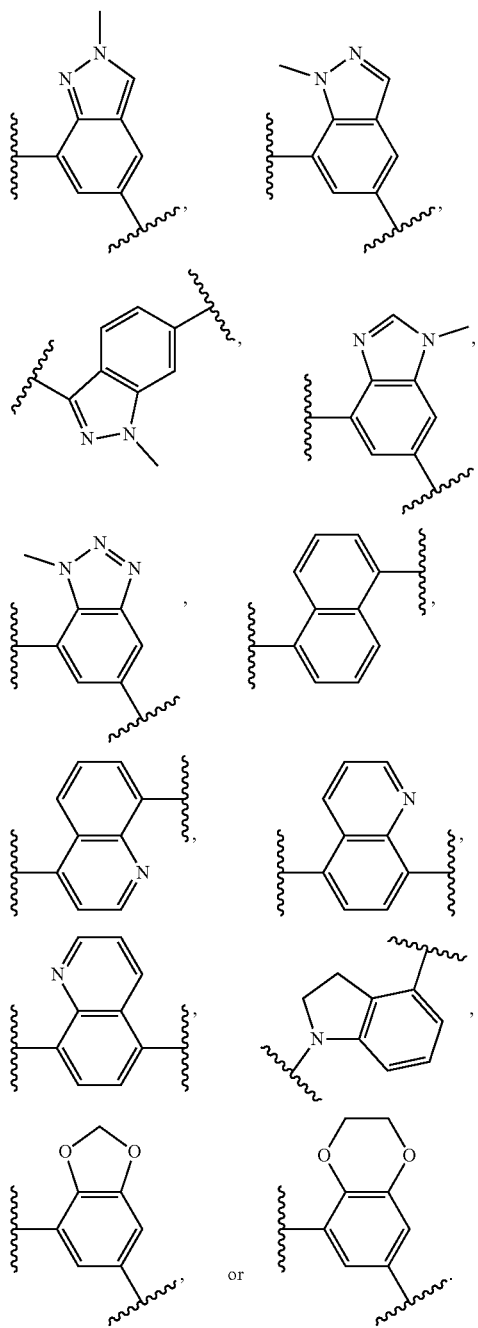
12. The compound of claim 1, or a pharmaceutically acceptable salt thereof, wherein R$^w$ is selected from hydrogen, —R, —C(O)OH, —C(O)OR, or
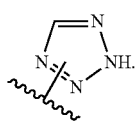
13. The compound of claim 1, or a pharmaceutically acceptable salt thereof, wherein R$^{13}$ is selected from the following:
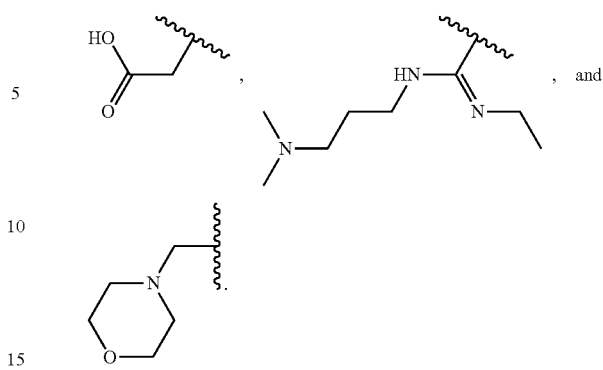
14. A compound selected from the group consisting of
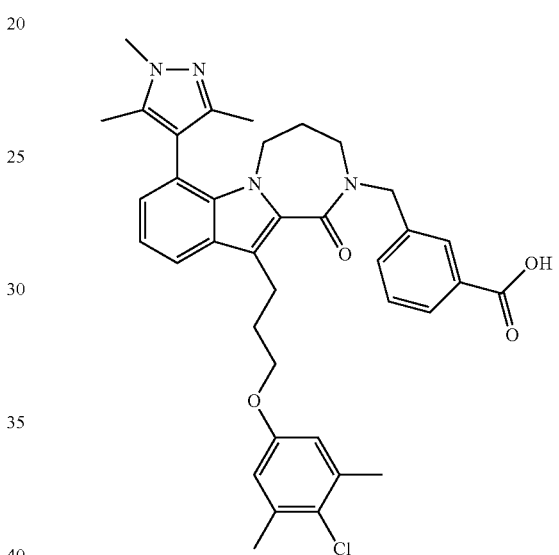
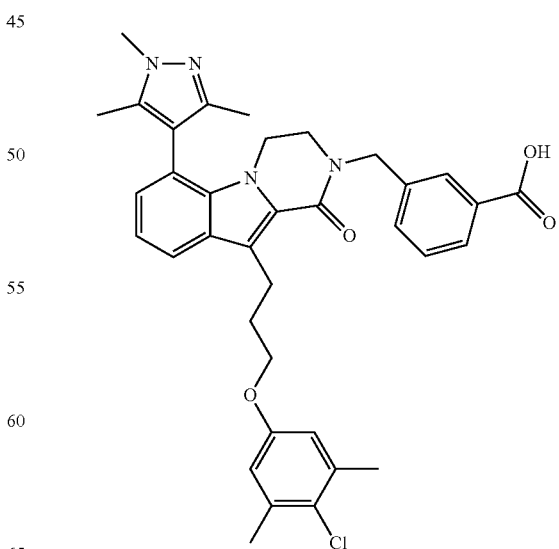

557
-continued
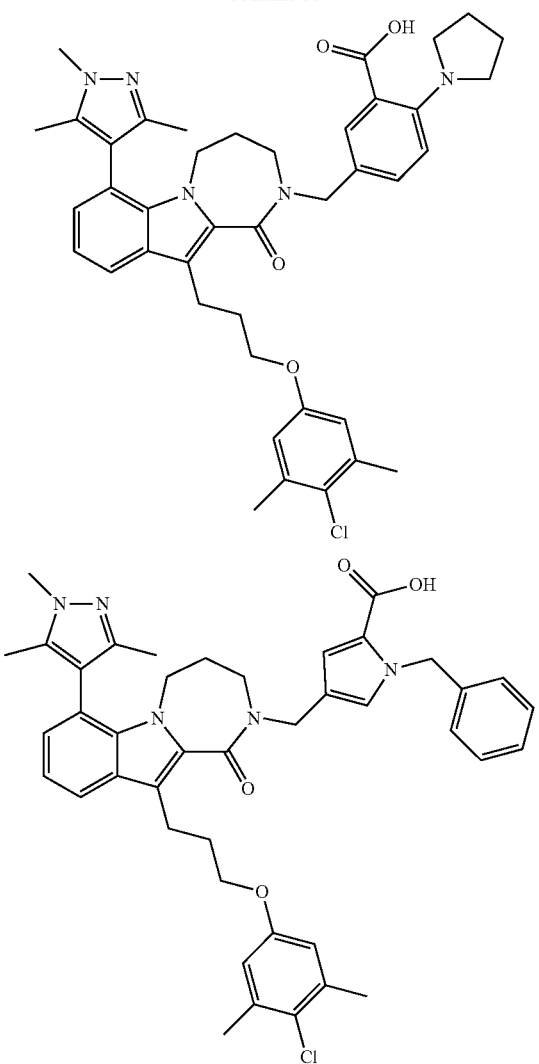
558
-continued
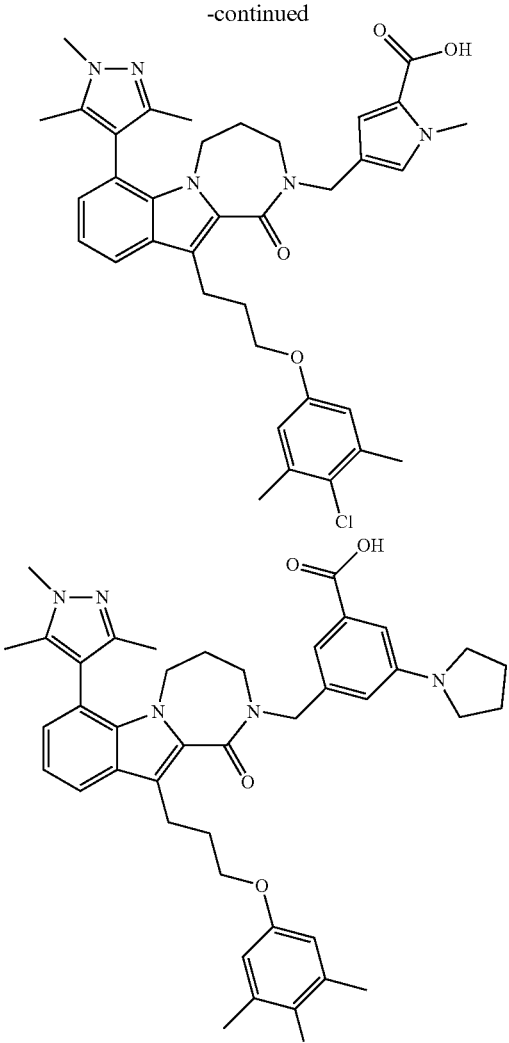

559
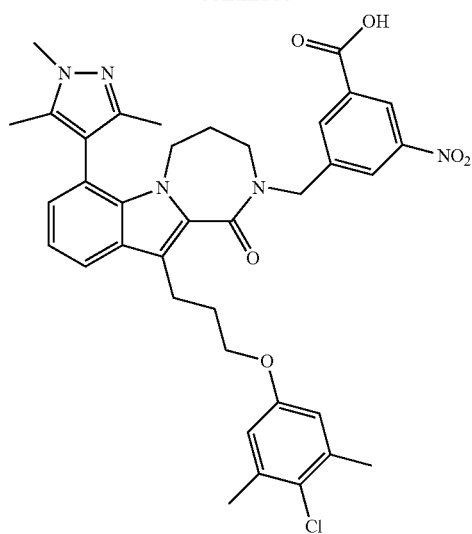
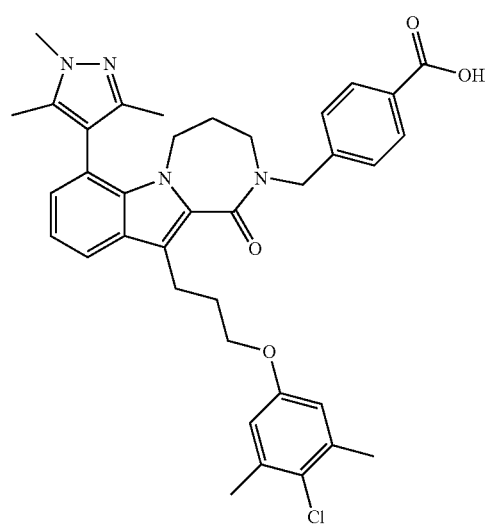
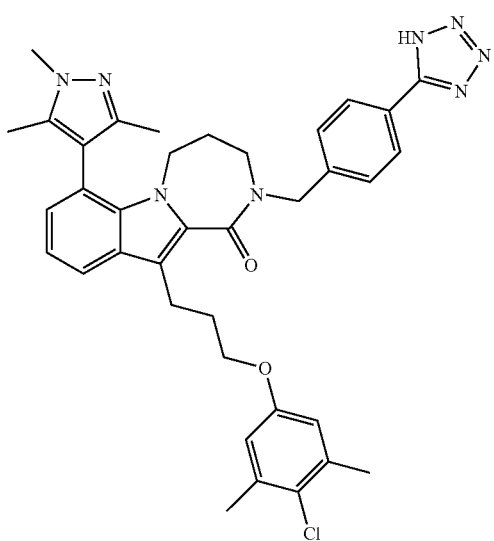
560
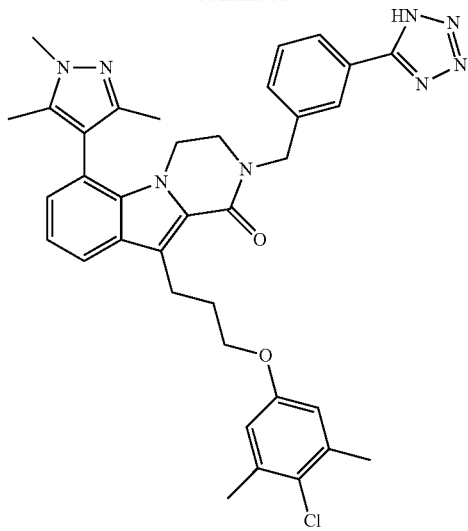
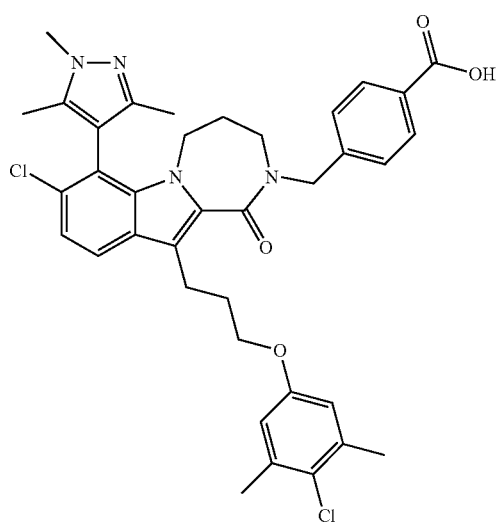

561
-continued
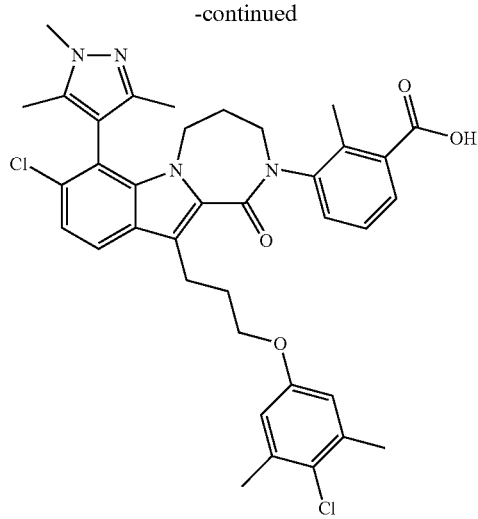
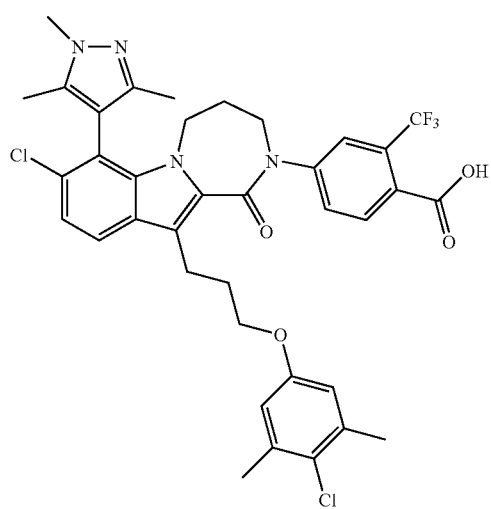
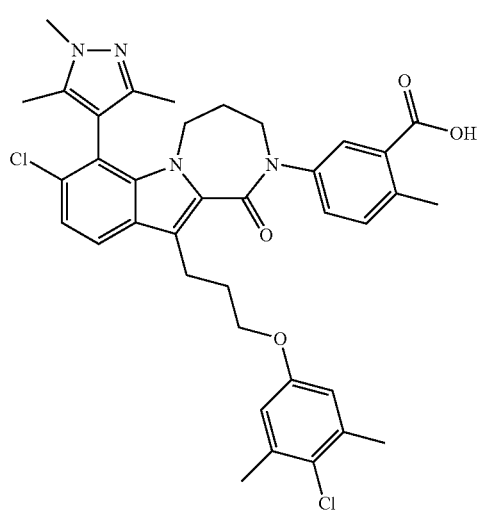
562
-continued
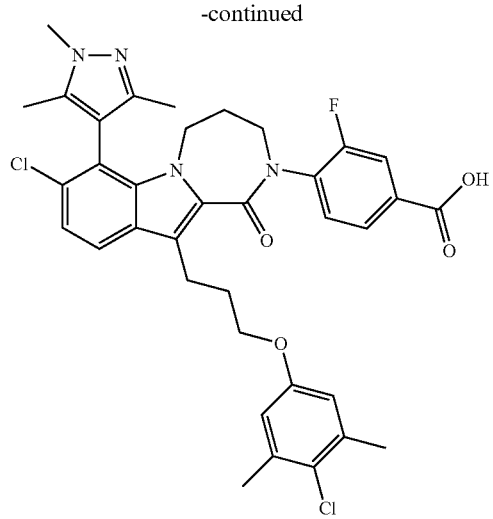
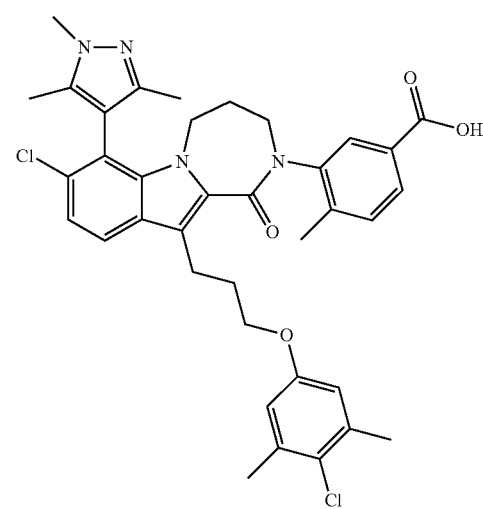
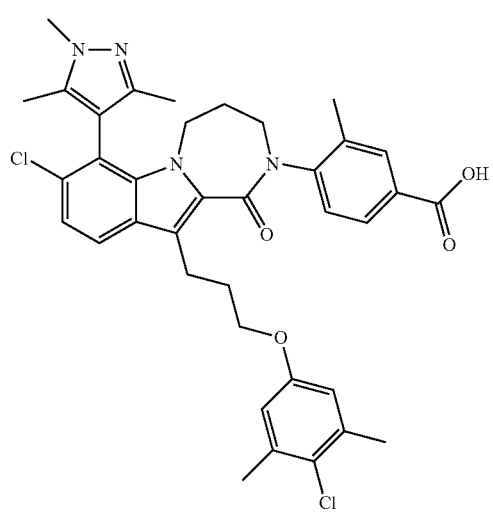

563
-continued
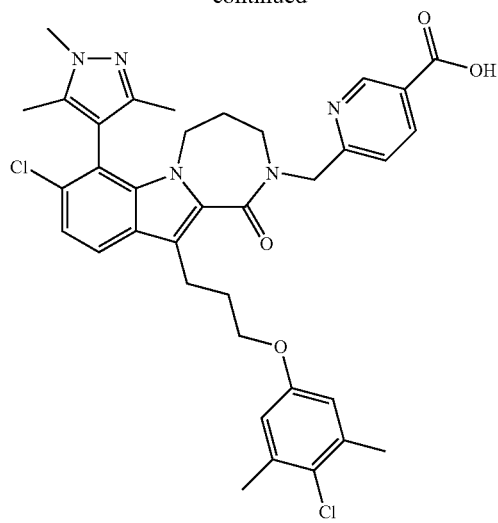
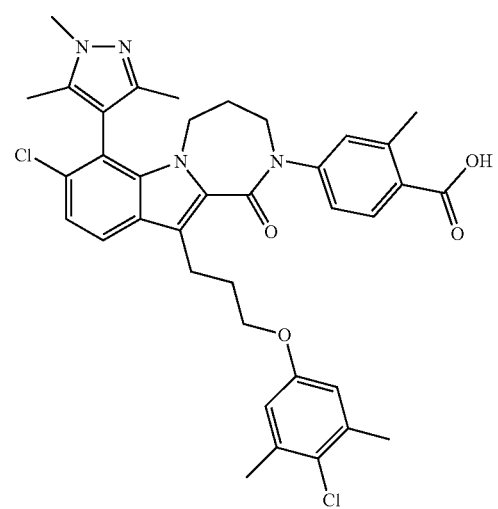 [SMILES: Cc1cc(N2CCCn3c(c(CCCOc4cc(C)c(Cl)c(C)c4)c4ccc(Cl)c(-c5c(C)nn(C)c5C)c43)C2=O)ccc1C(=O)O]
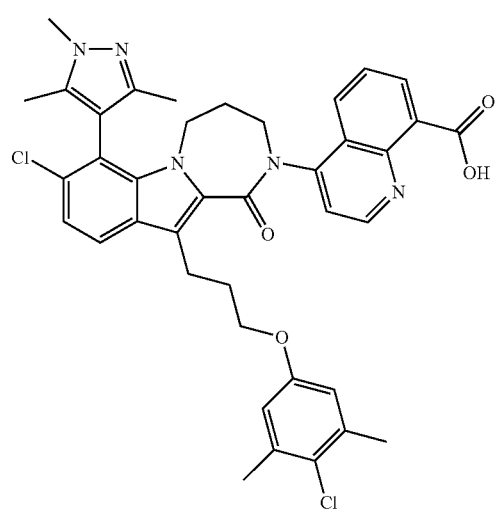
564
-continued
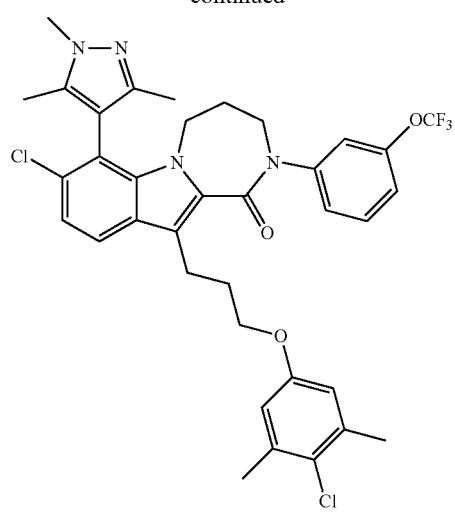
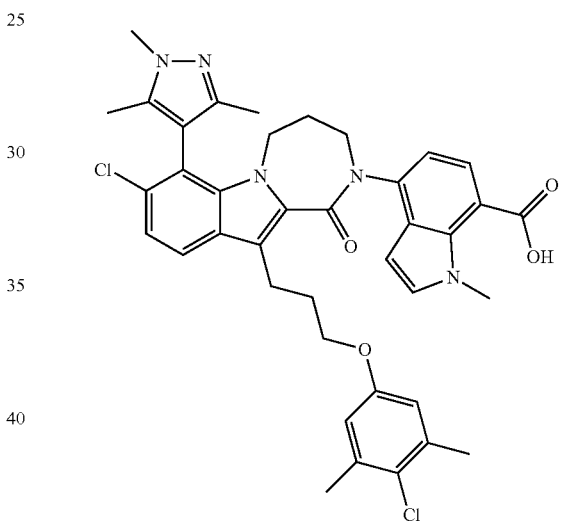
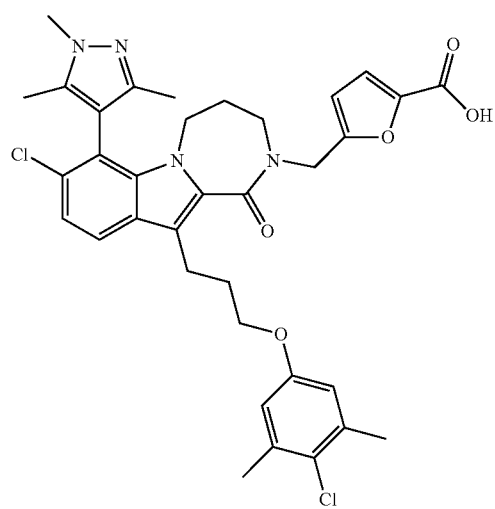

565
-continued
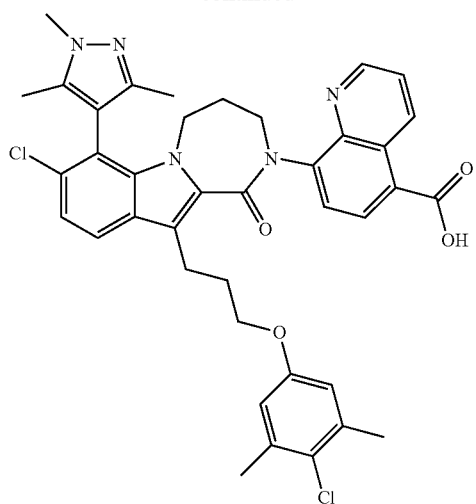
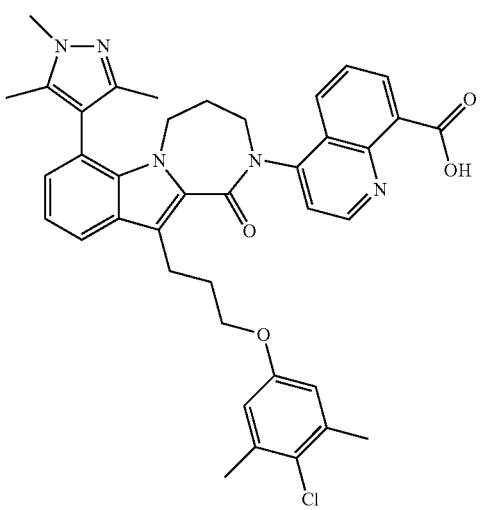
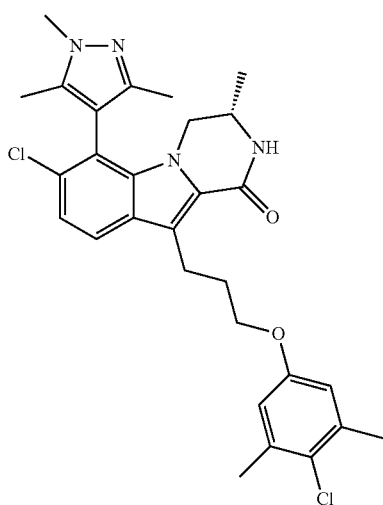
566
-continued
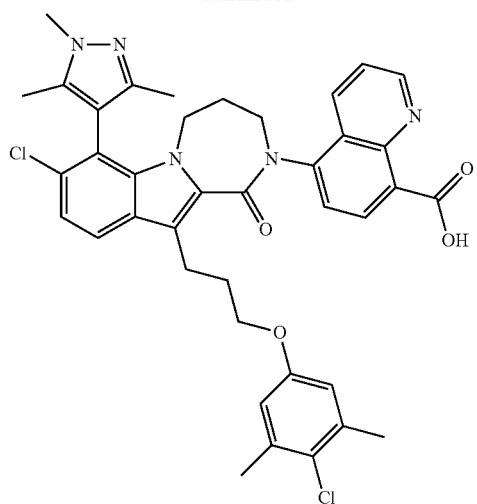
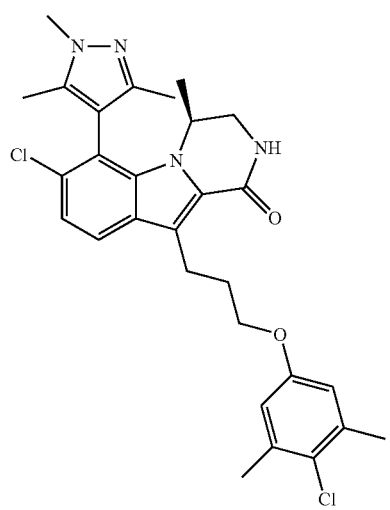
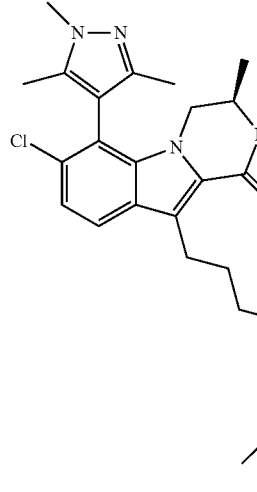

567
-continued
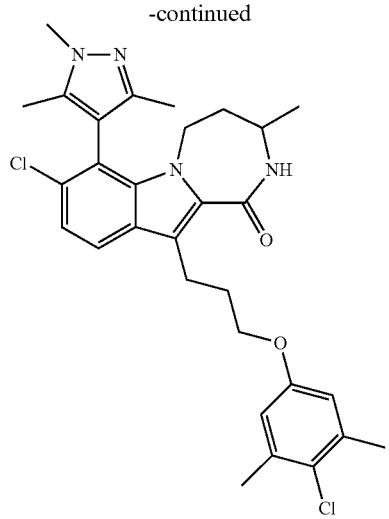
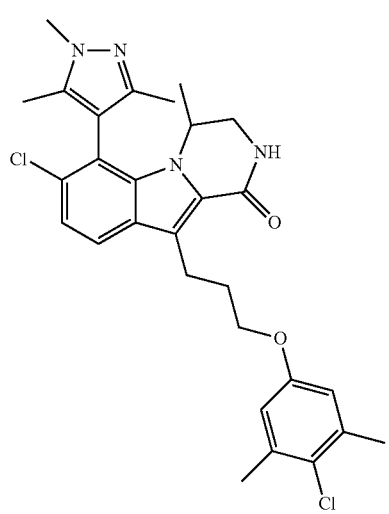
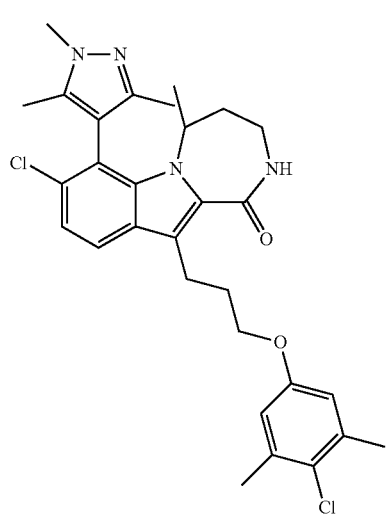
568
-continued
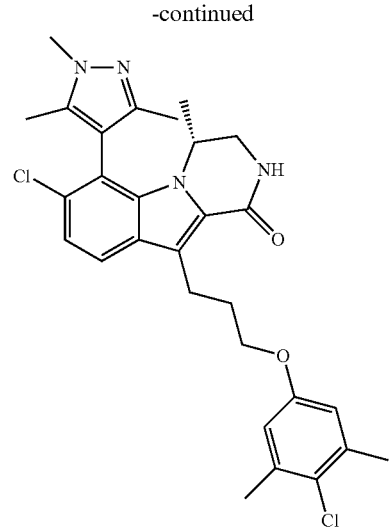
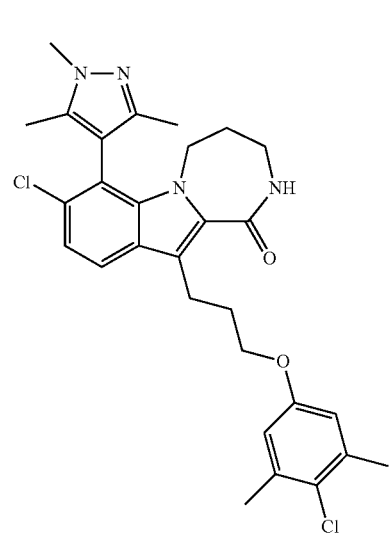
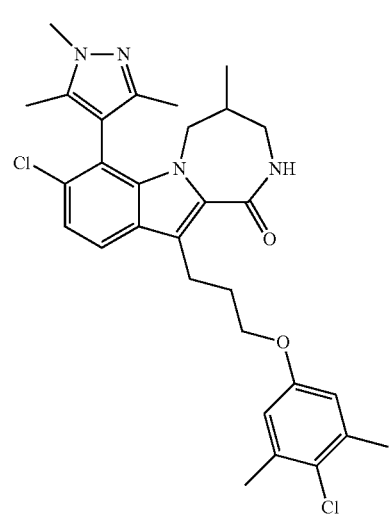

569
-continued
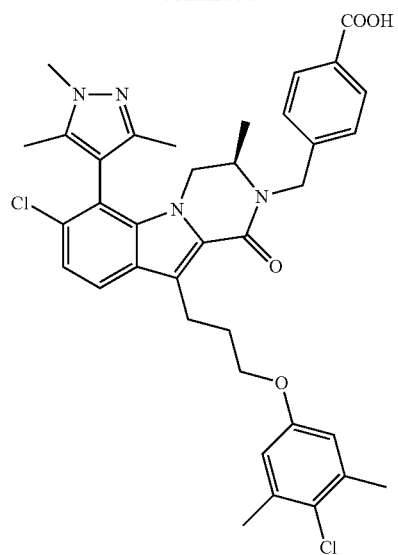
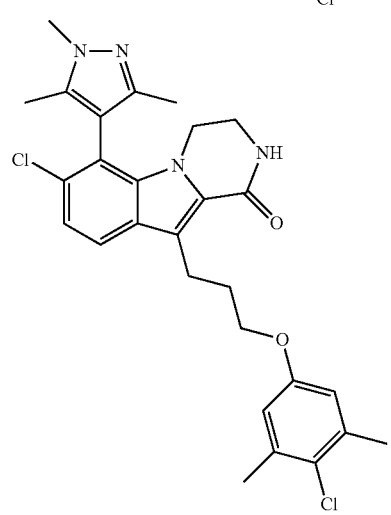
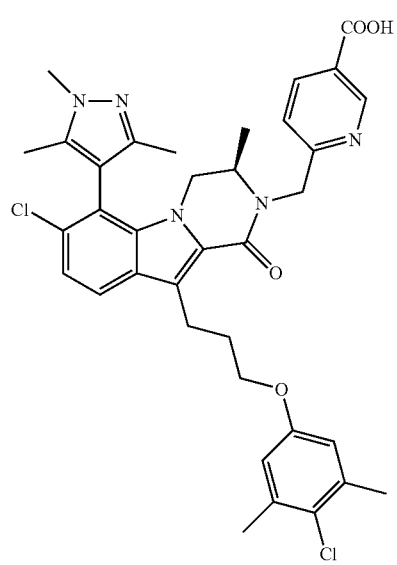
570
-continued
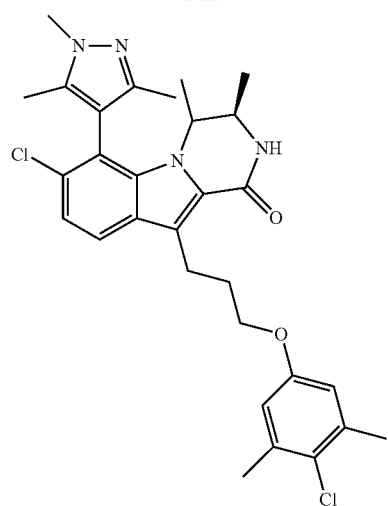
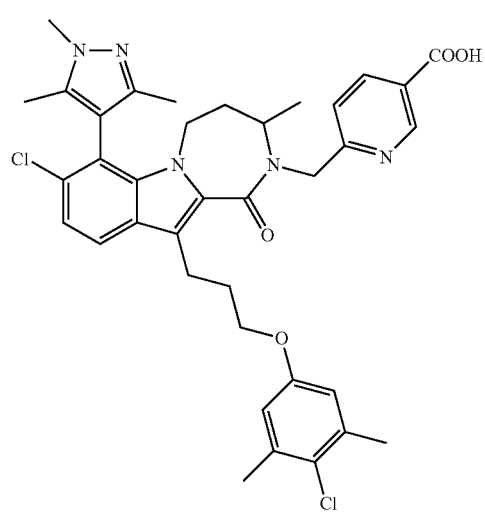

571
-continued
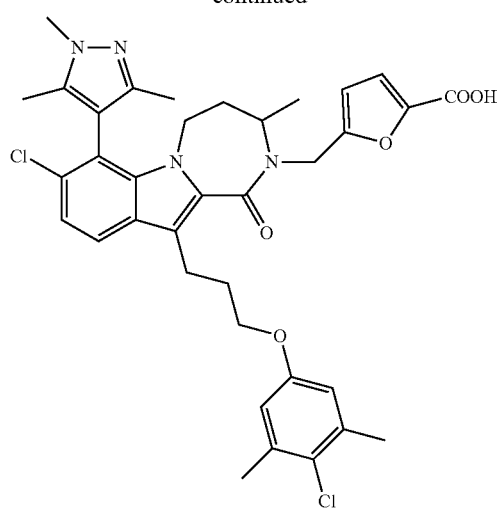
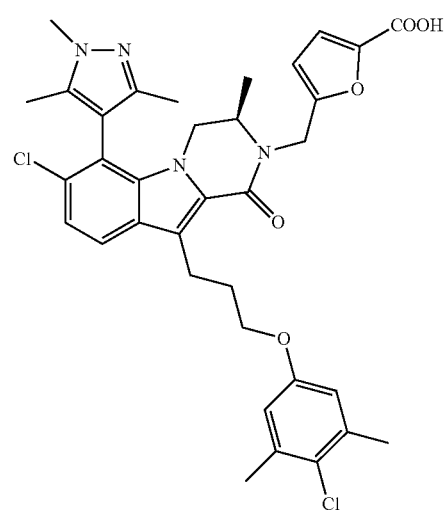
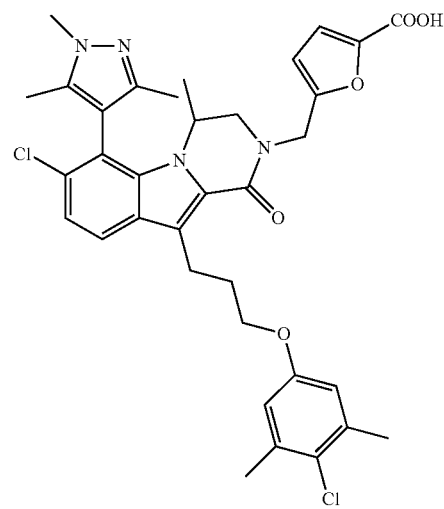
572
-continued
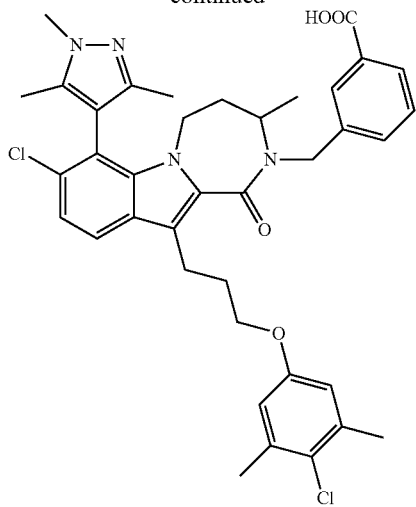
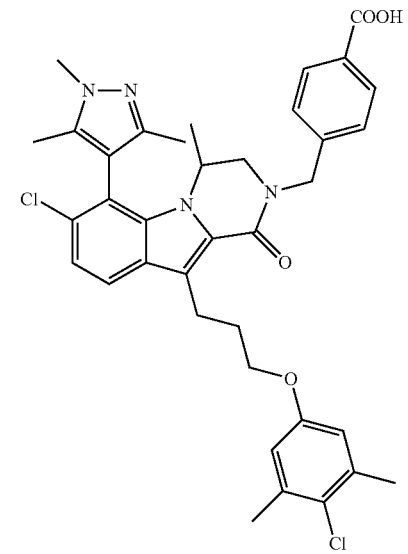
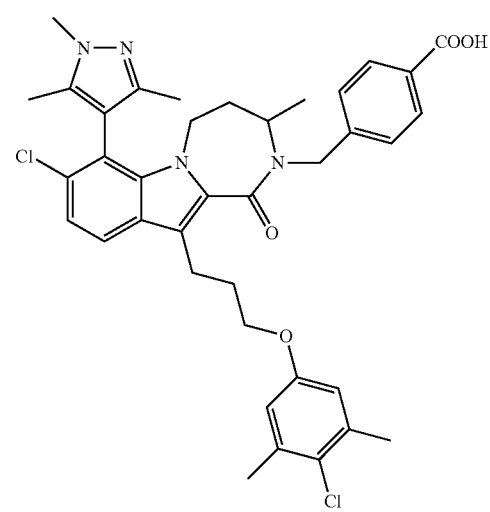

573
-continued
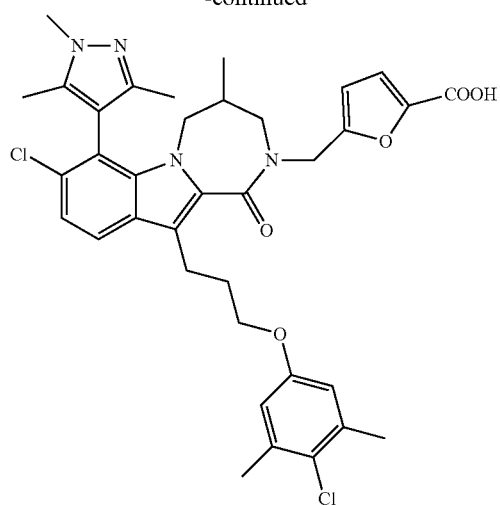
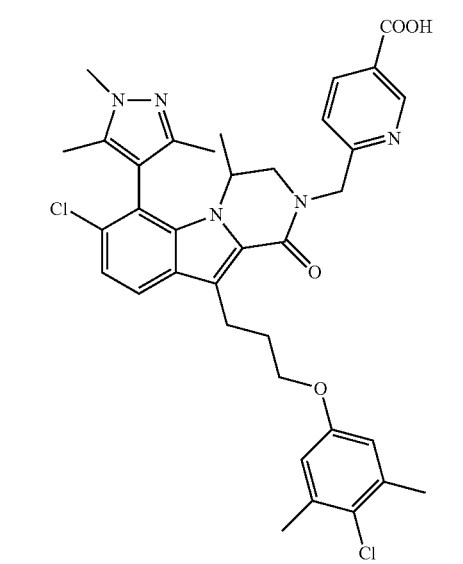
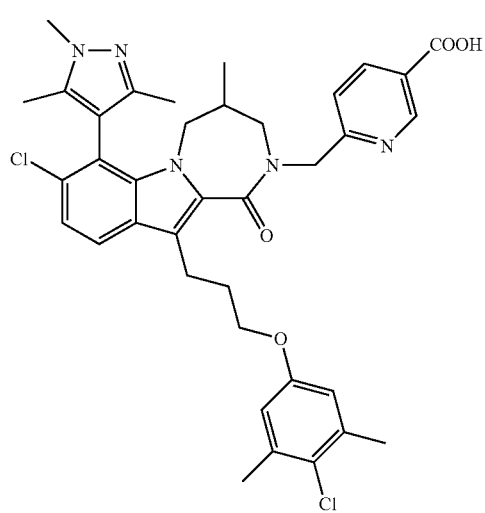
574
-continued
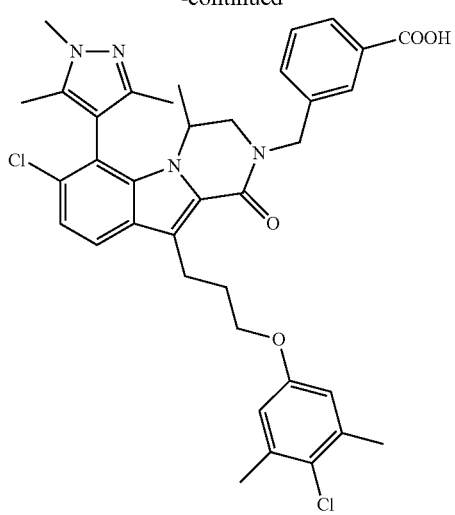
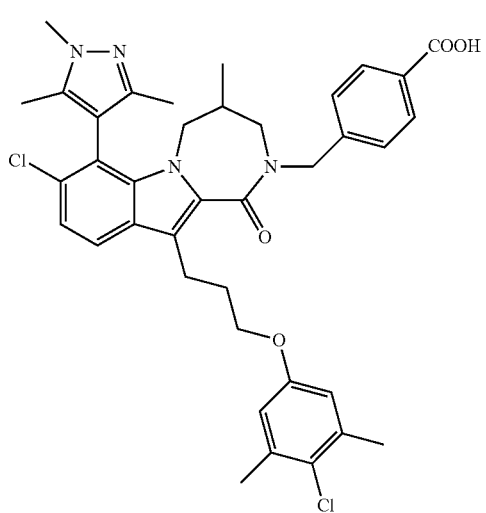

575
-continued
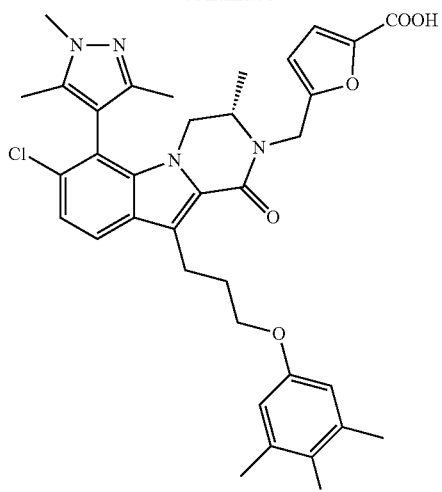
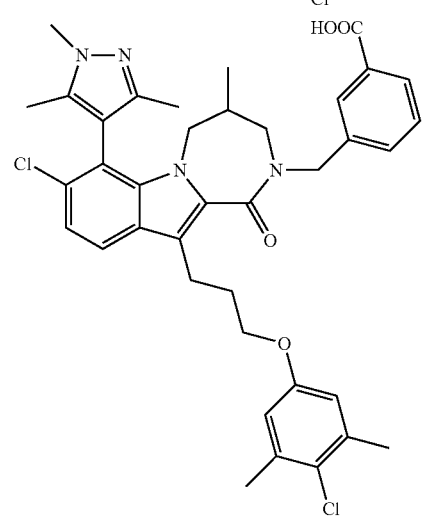
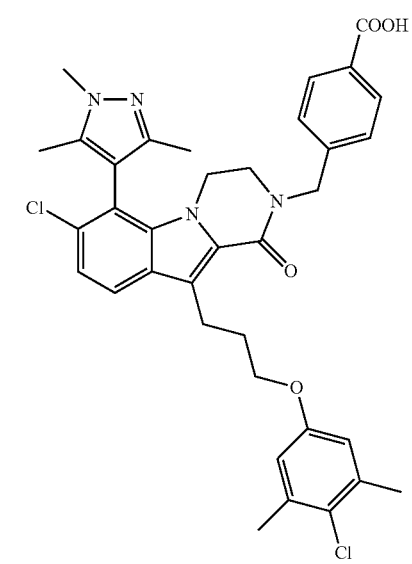
576
-continued
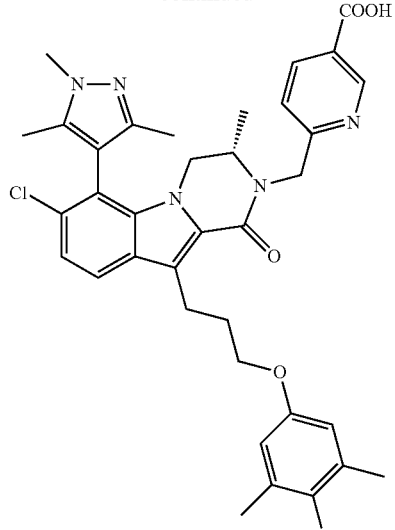
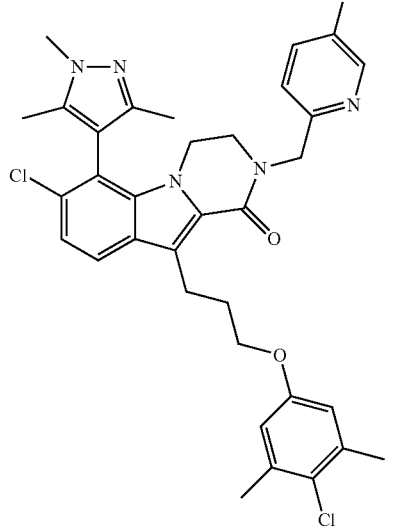
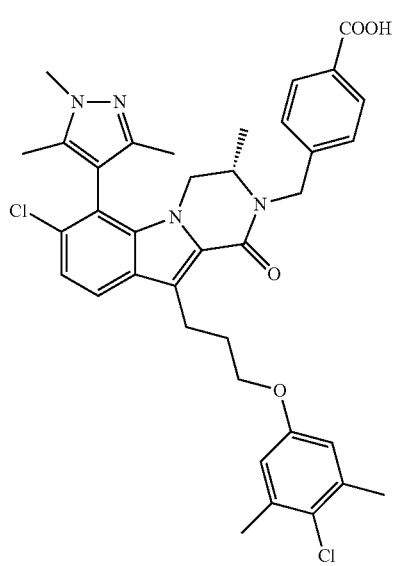

577
-continued
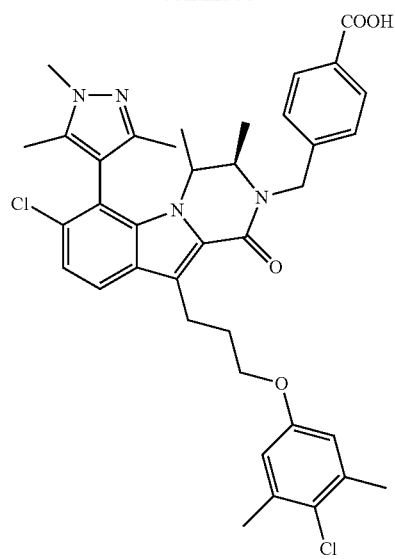
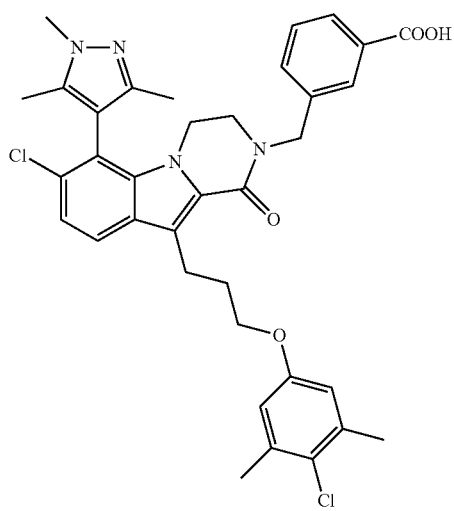
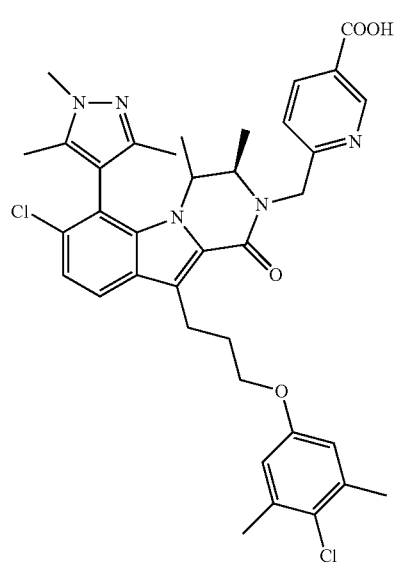
578
-continued
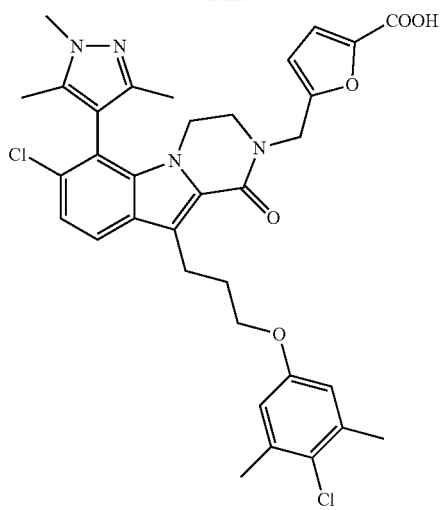

579
-continued
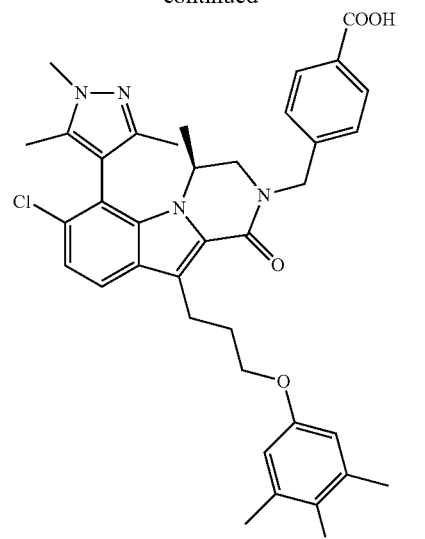
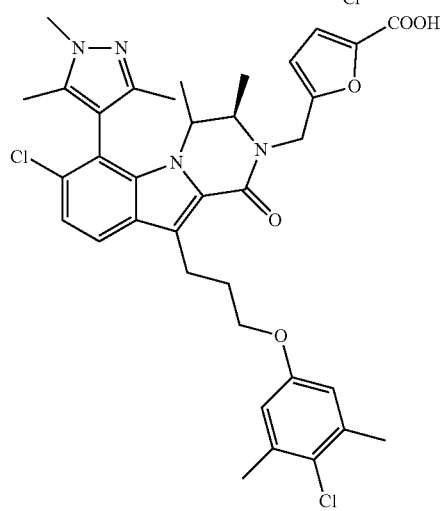
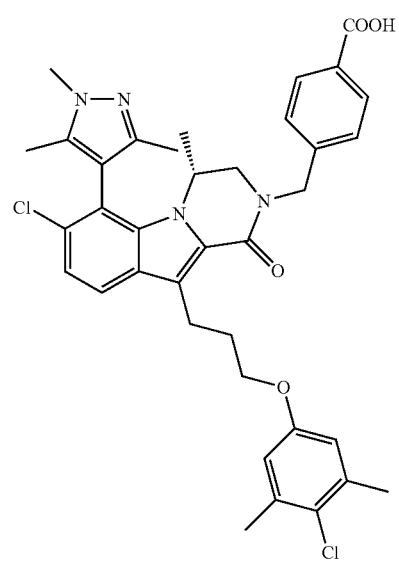
580
-continued
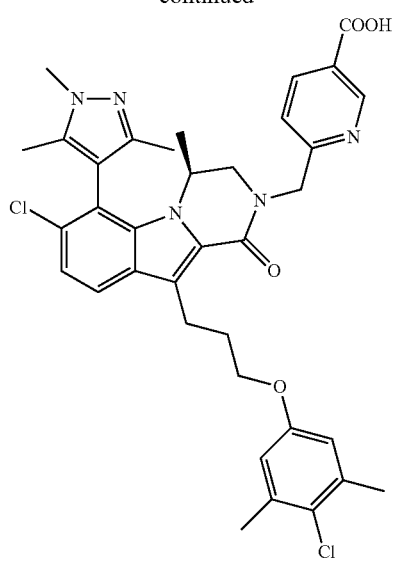
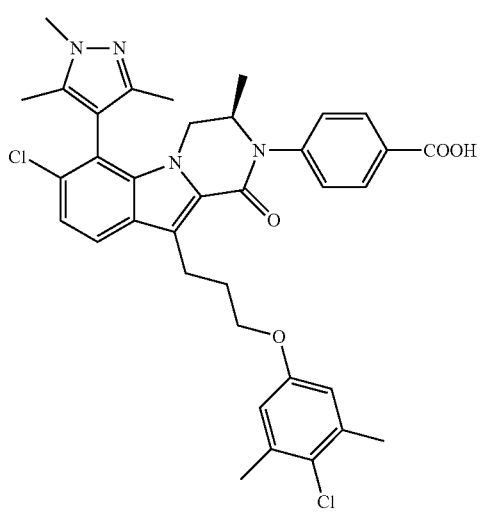
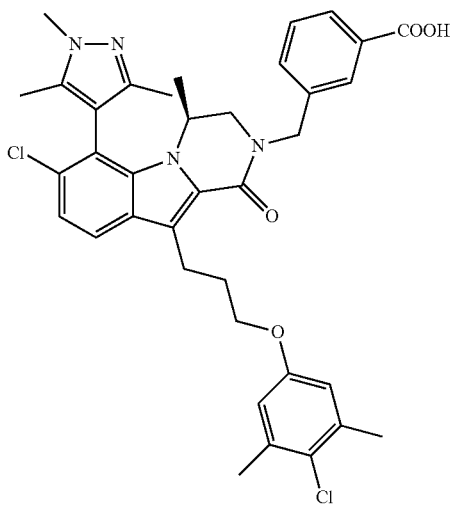

581
-continued
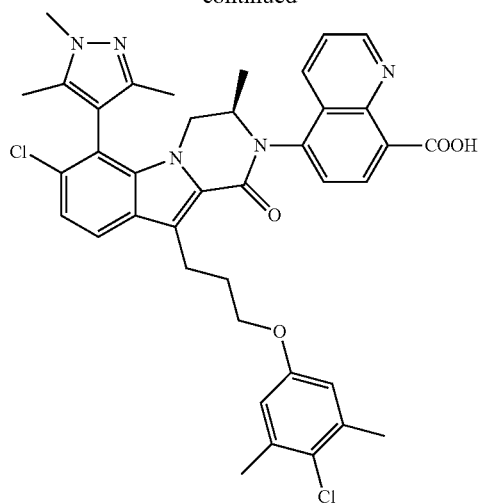
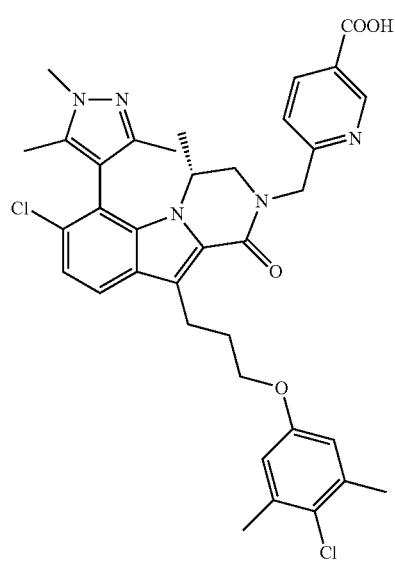
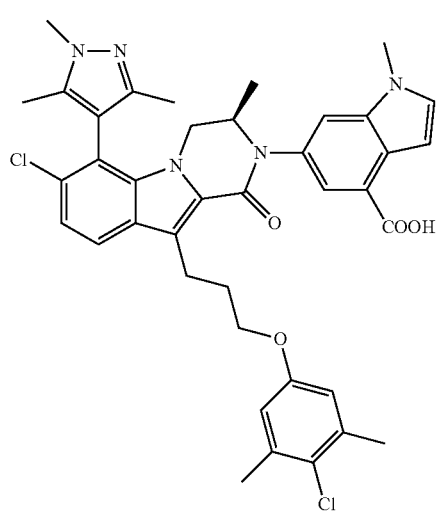
582
-continued
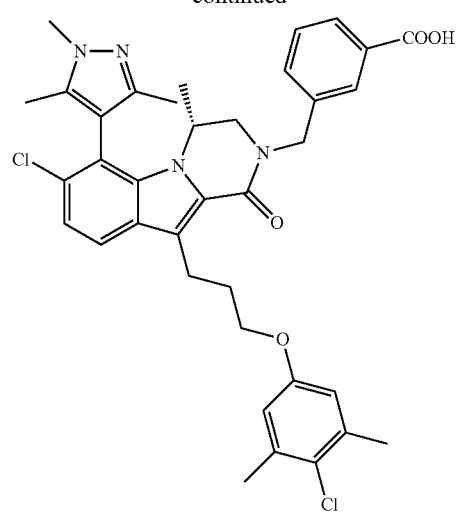
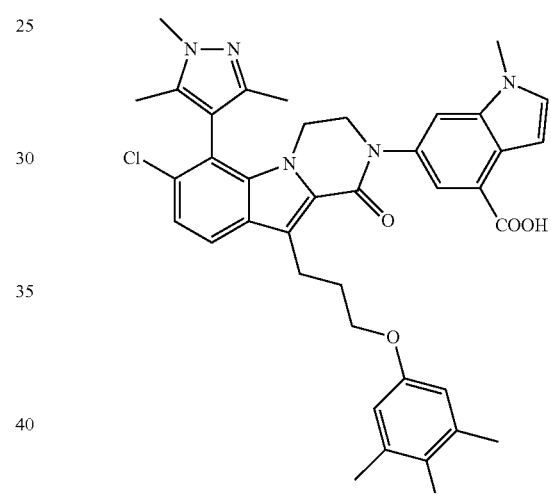
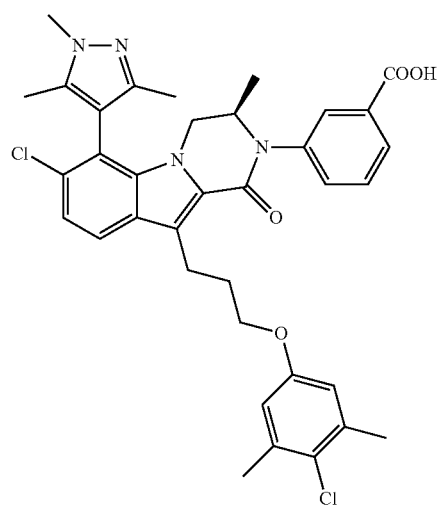

583
-continued
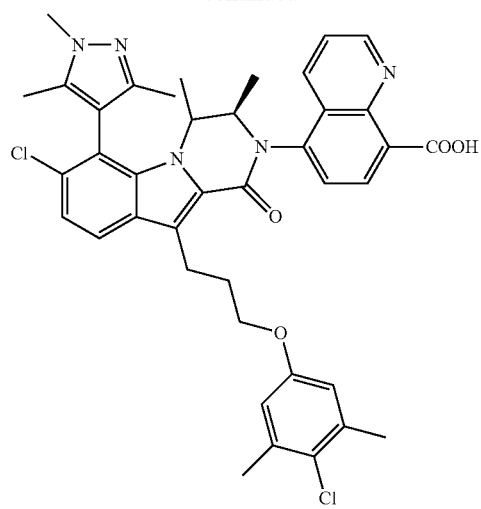
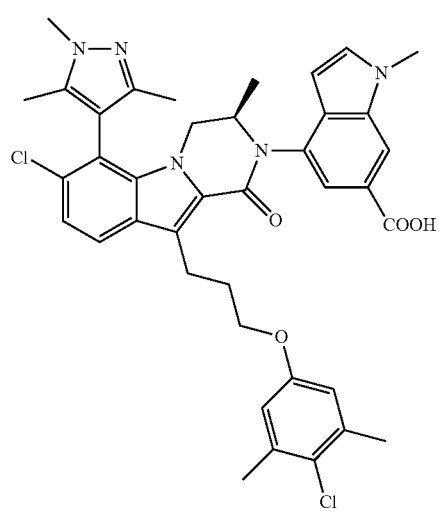
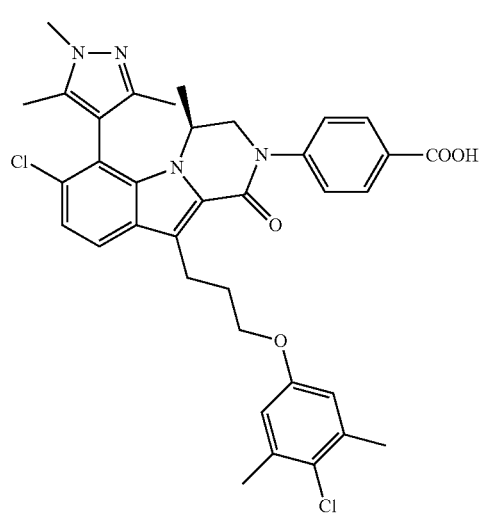
584
-continued
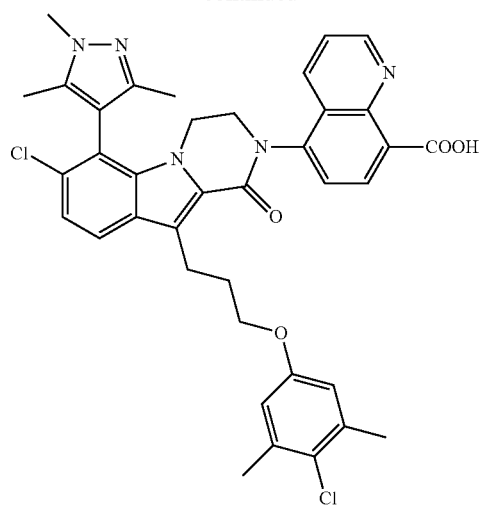
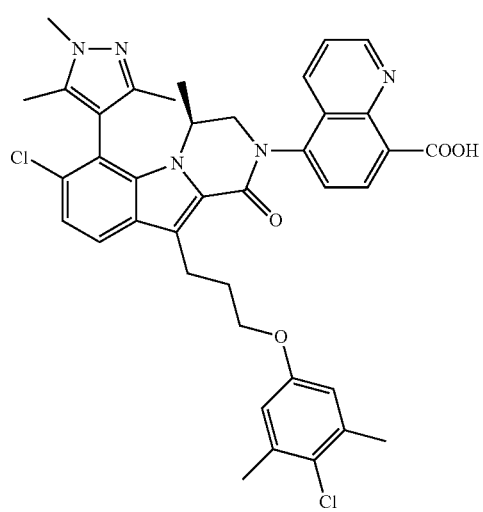
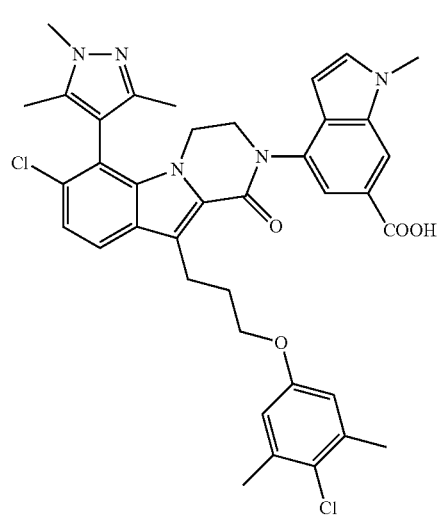

585
-continued
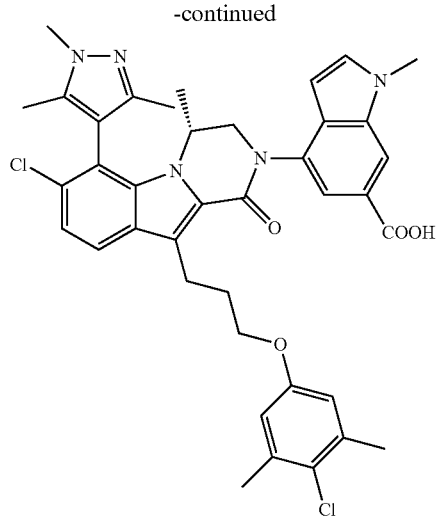
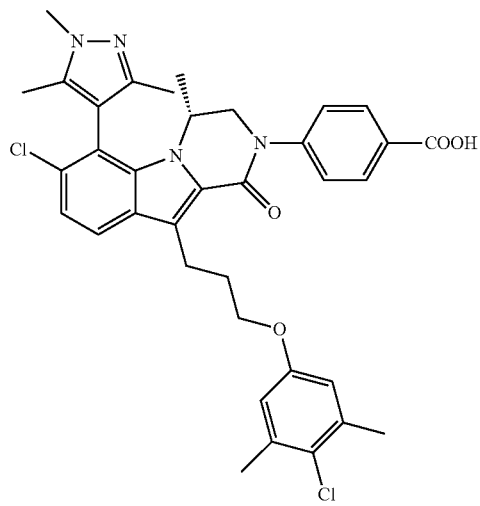
586
-continued
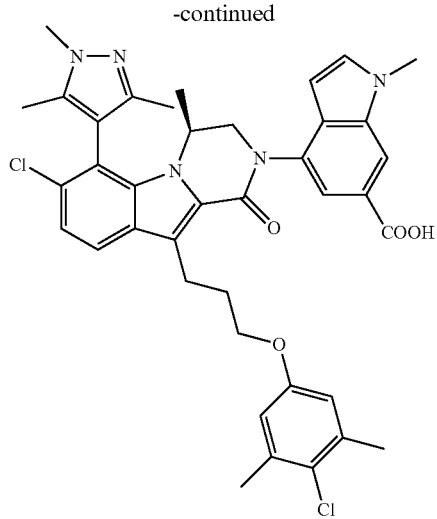
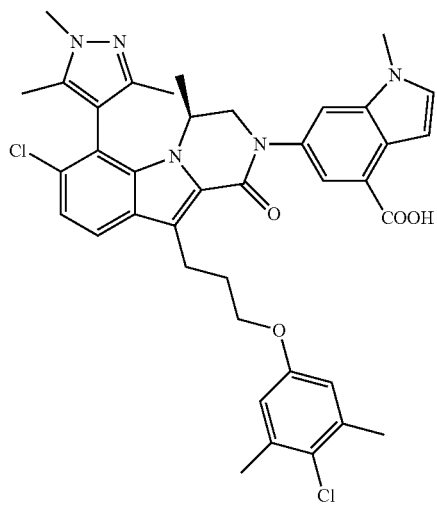

587
-continued
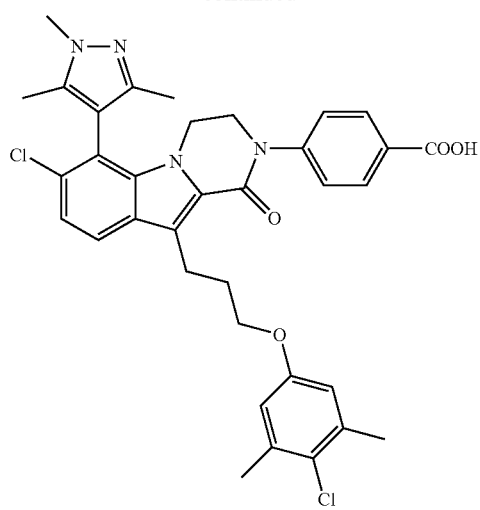
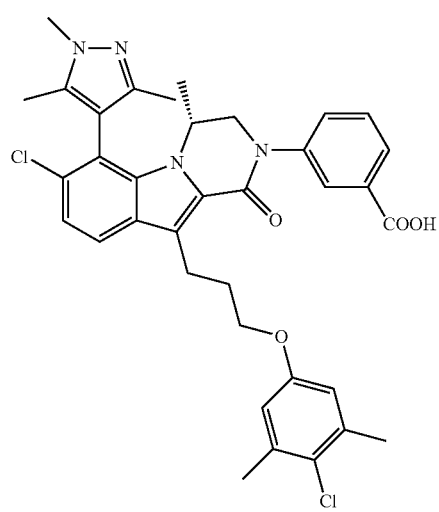
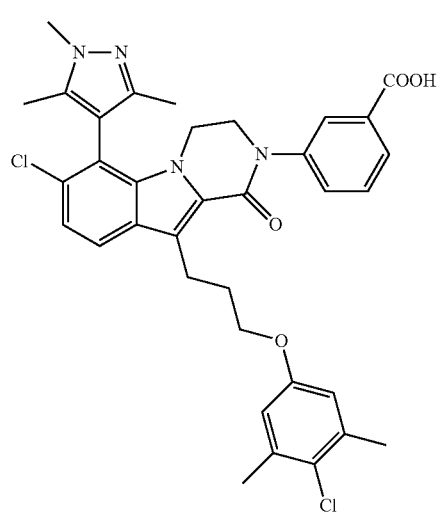
588
-continued
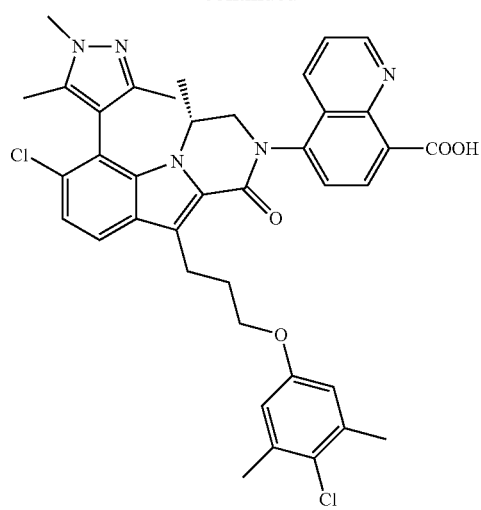
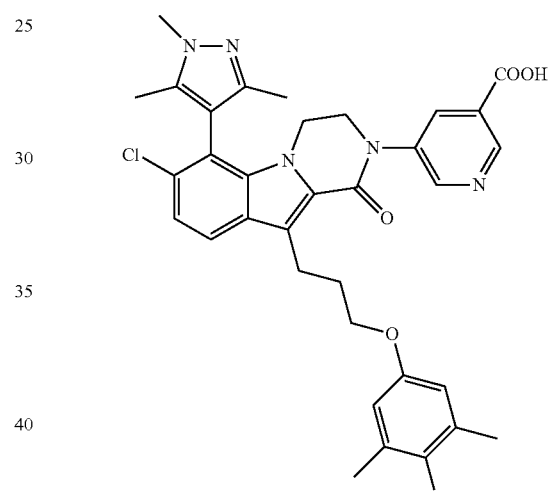
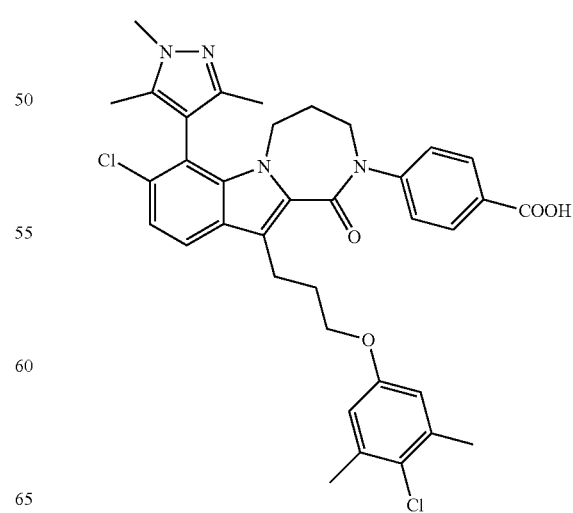

589
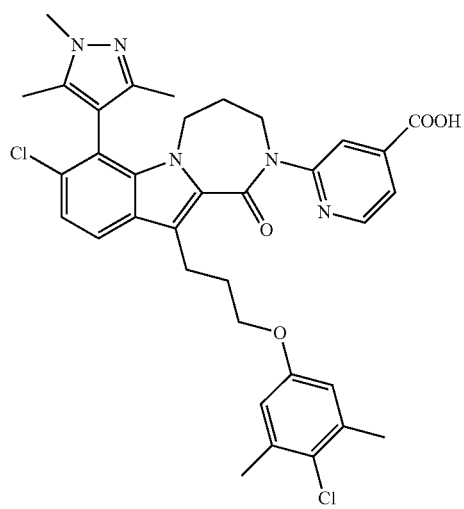
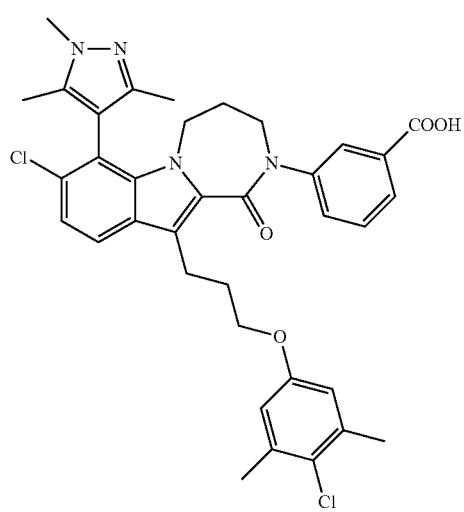
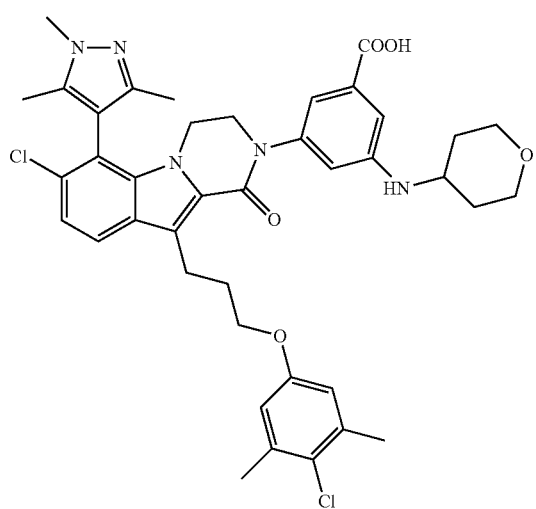
590
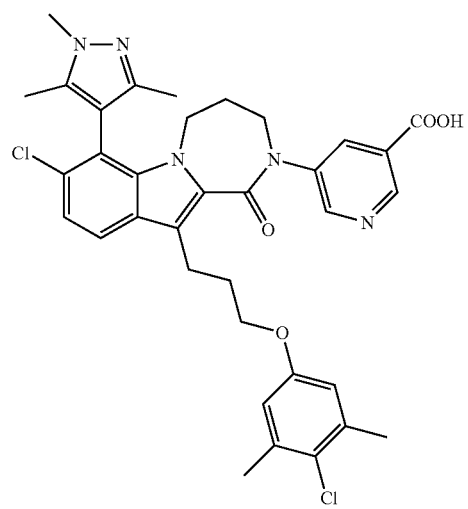
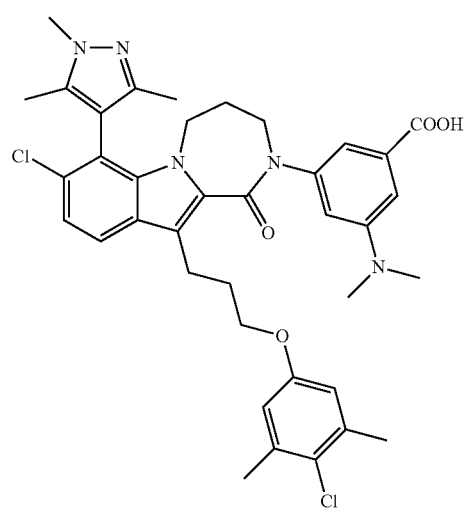
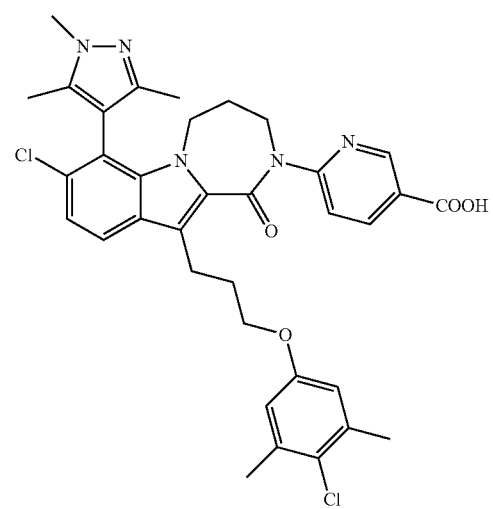

591
-continued
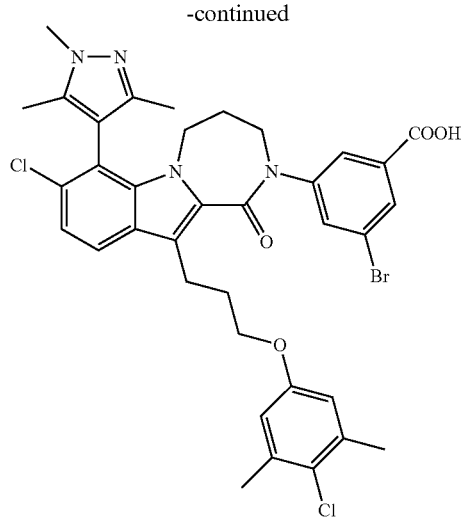
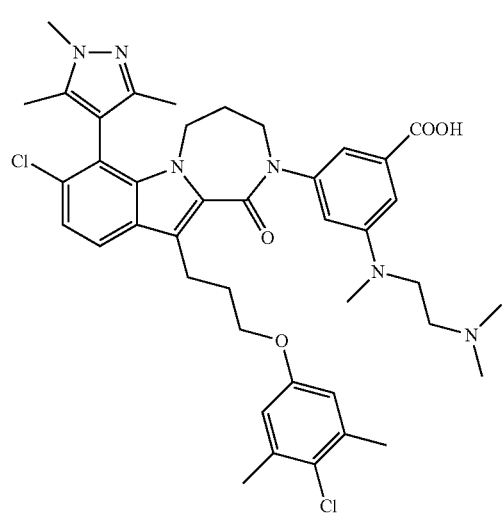
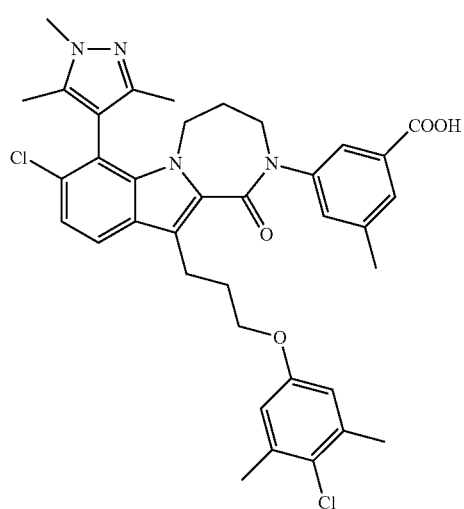
592
-continued
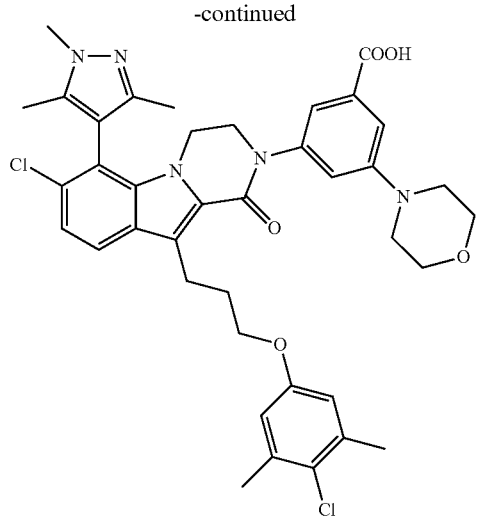
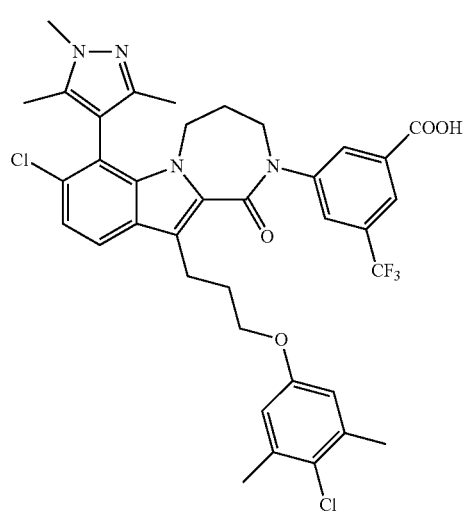
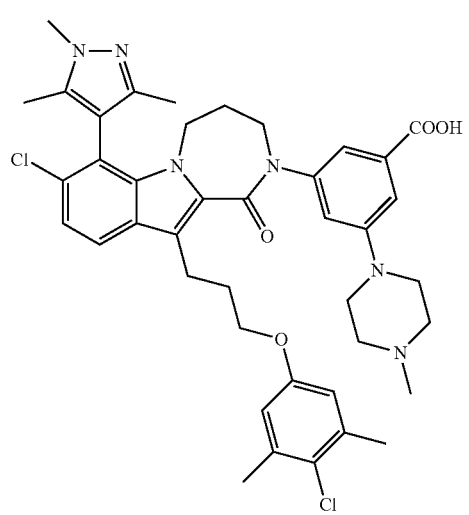

593
-continued
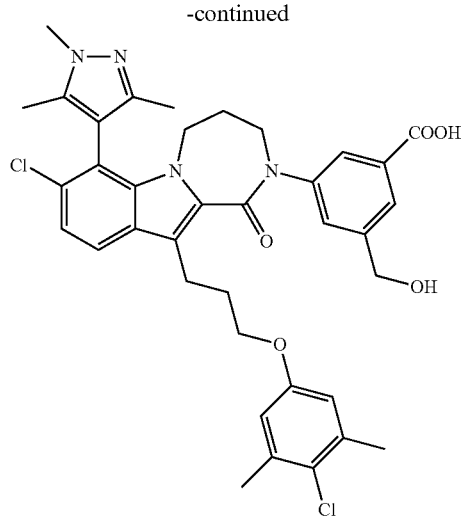
594
-continued
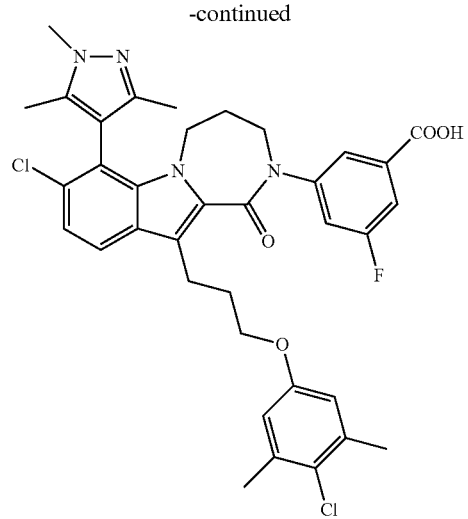
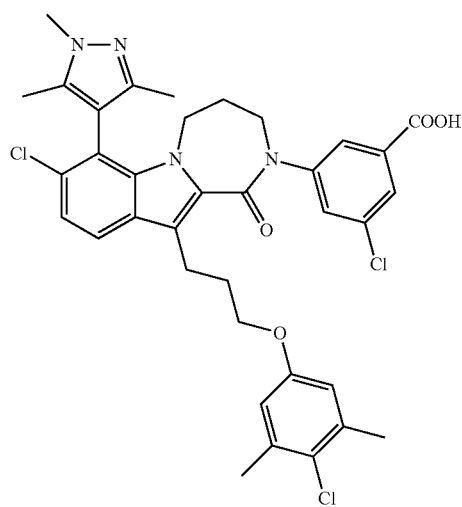
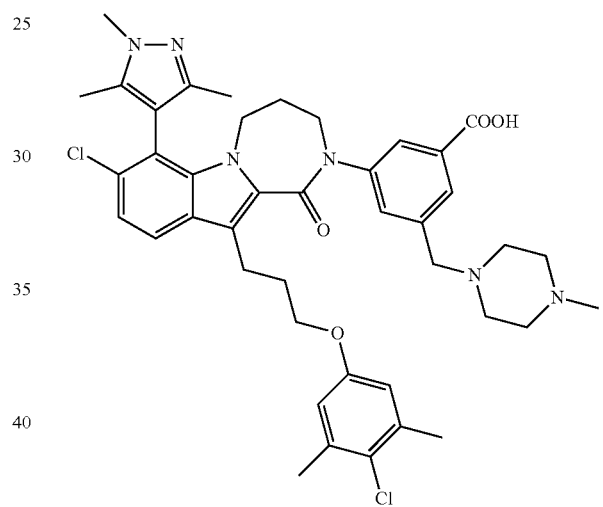
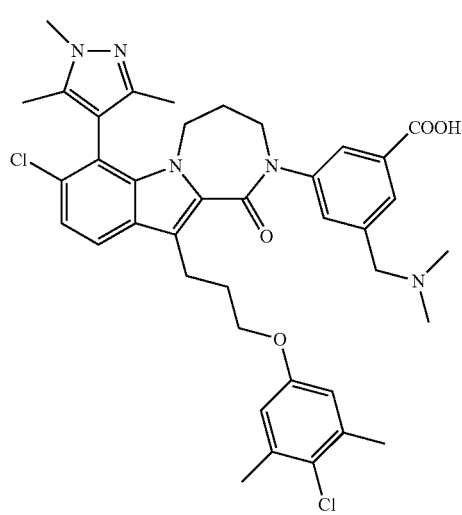
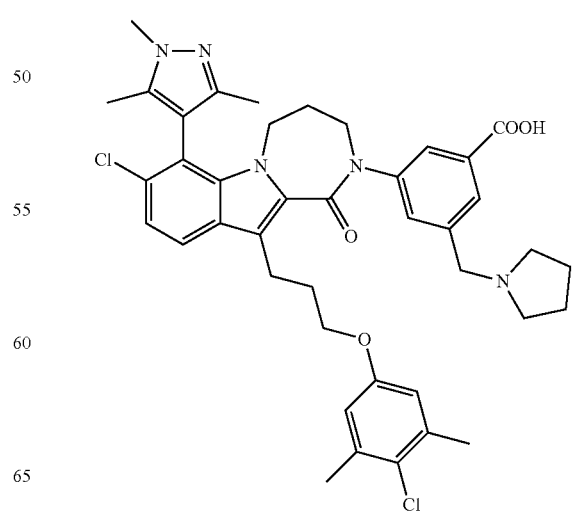

595
-continued
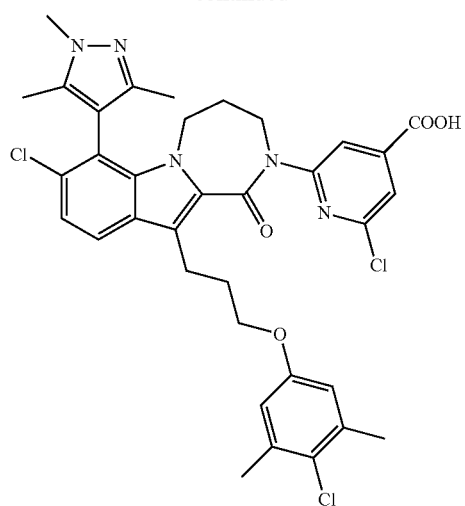
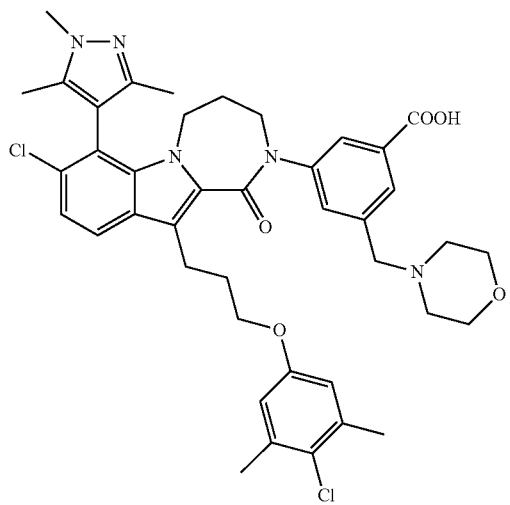
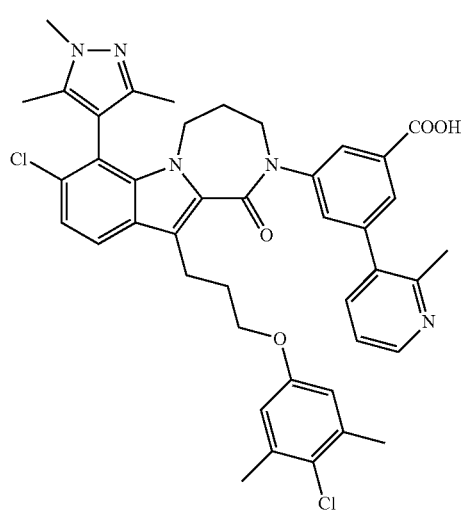
596
-continued
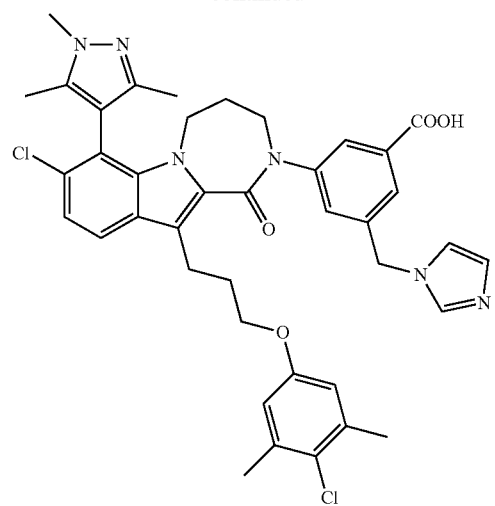
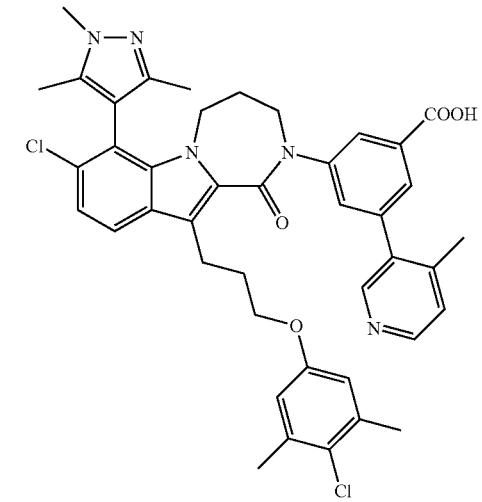
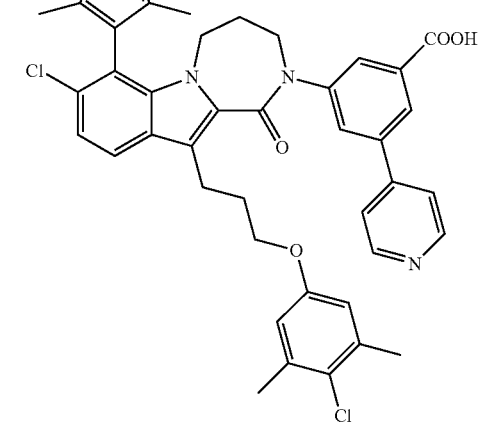

597
-continued
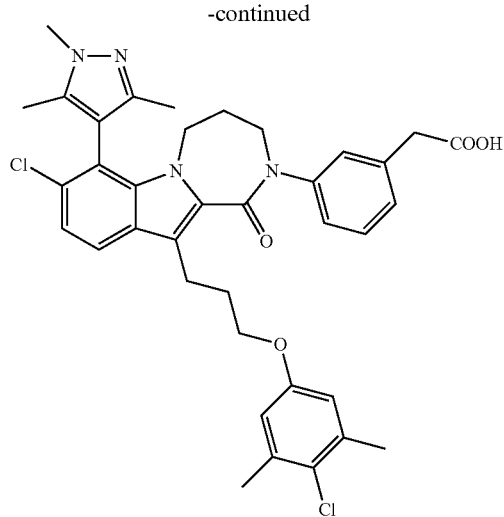
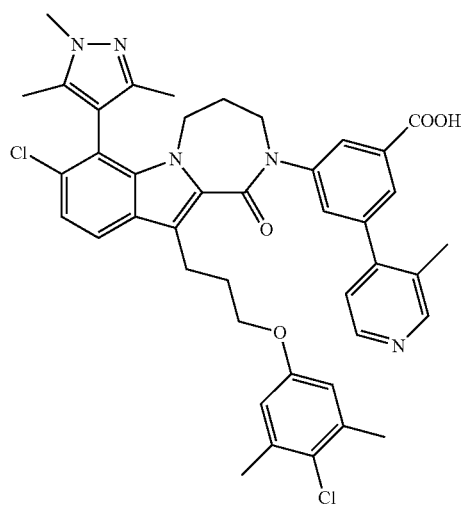
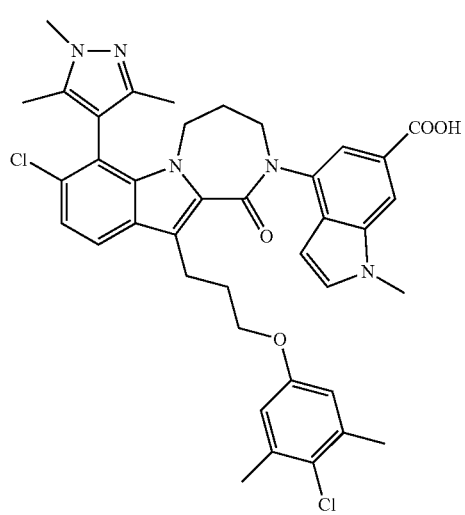
598
-continued
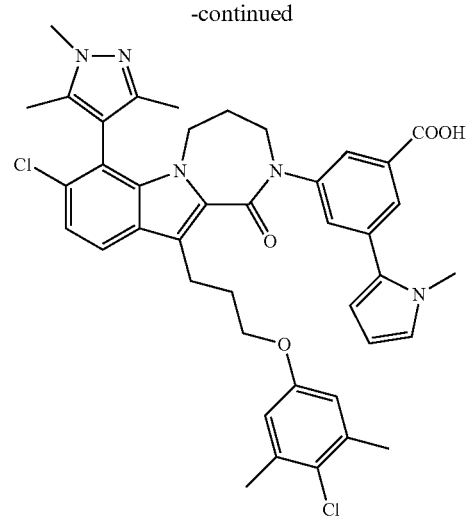
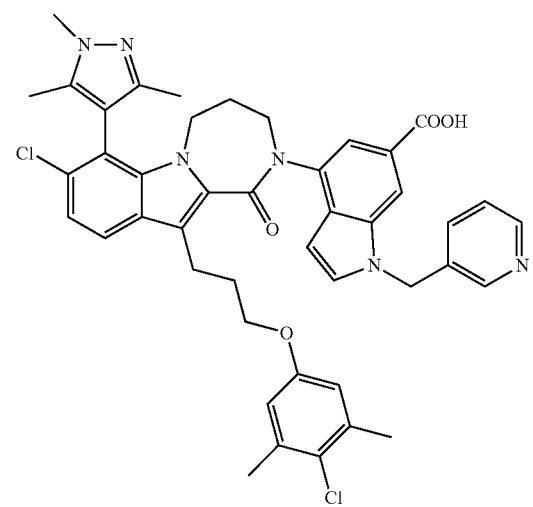
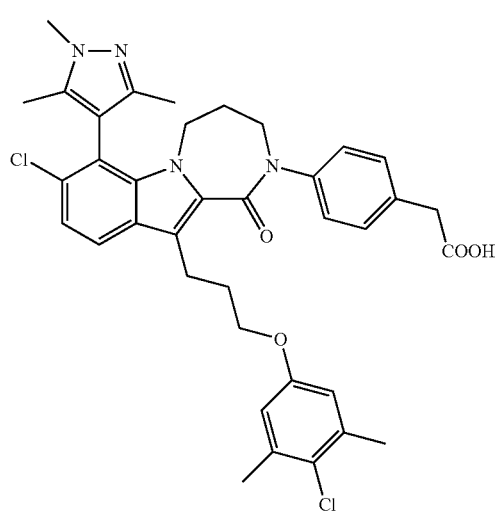

599
-continued
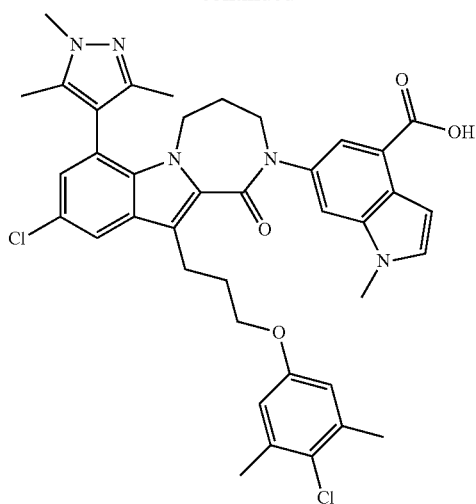
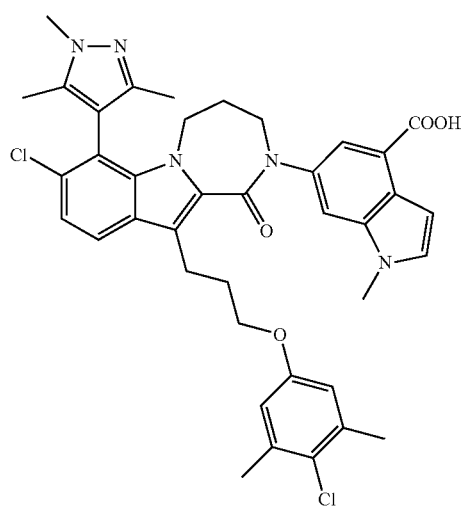
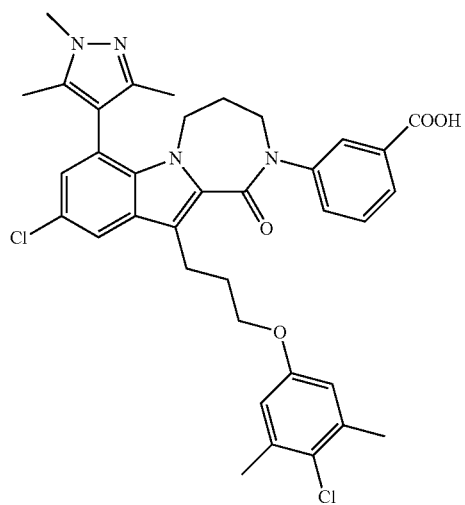
600
-continued
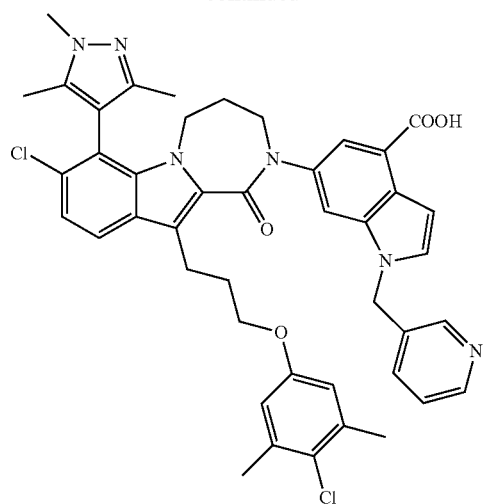
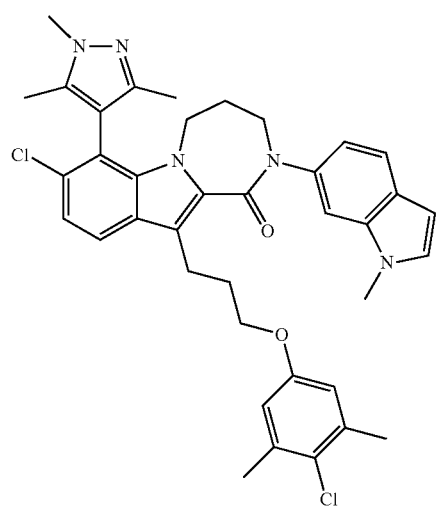
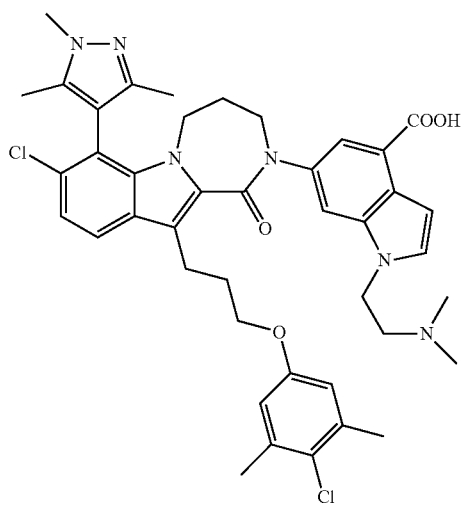

| 601 | 602 |
|---|---|
| -continued | -continued |
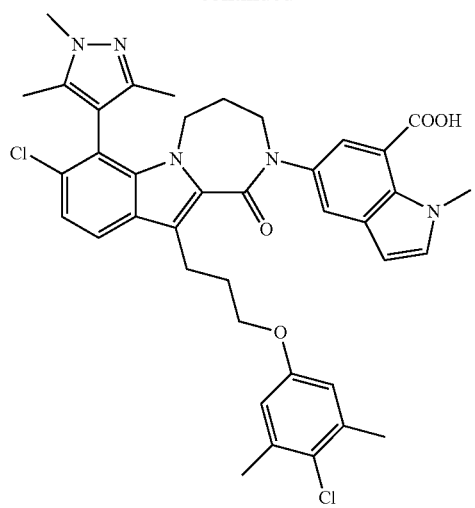
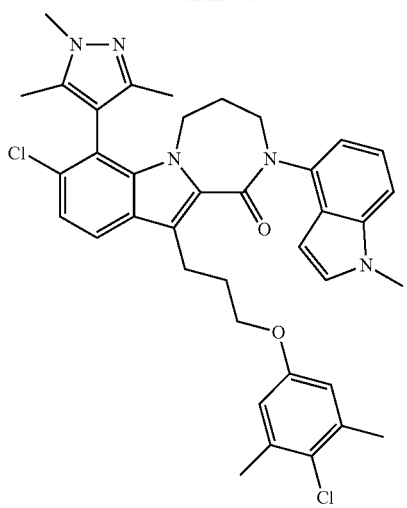

603
-continued
604
-continued
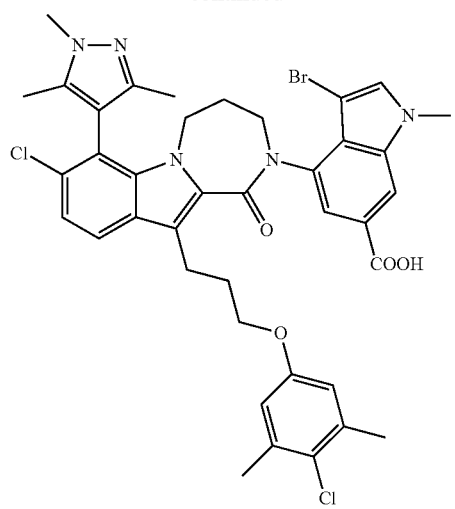
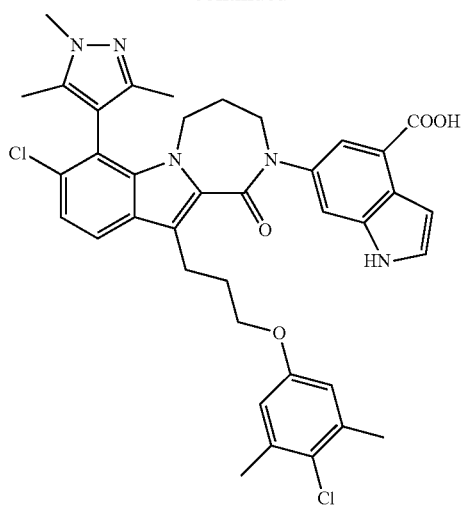

605
-continued
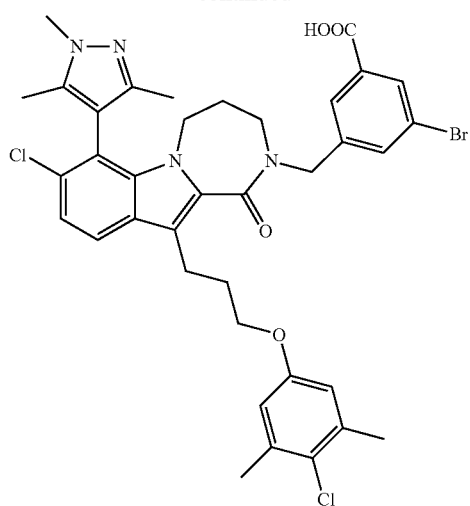
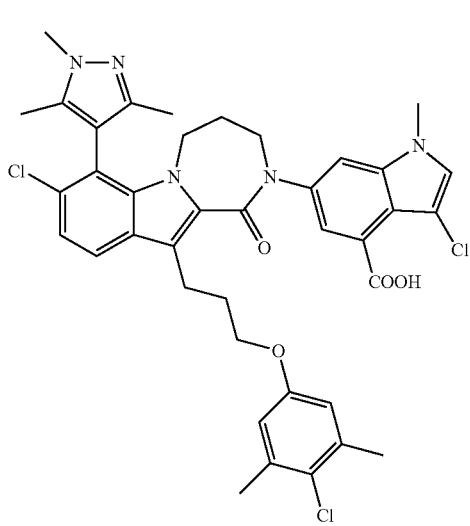
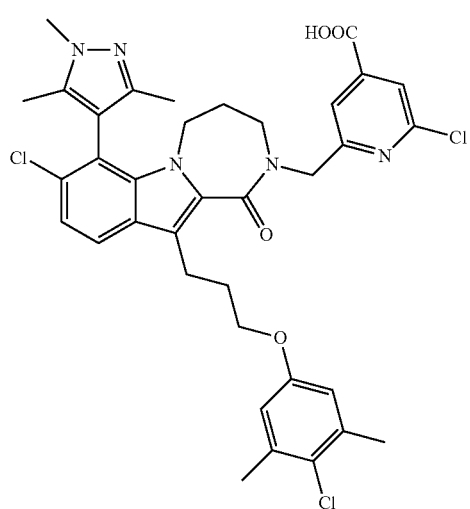
606
-continued
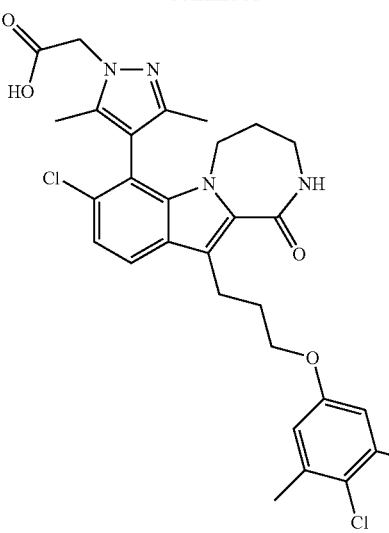
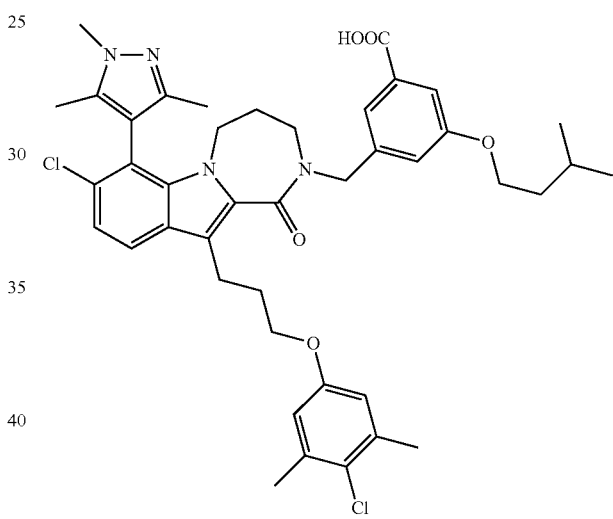
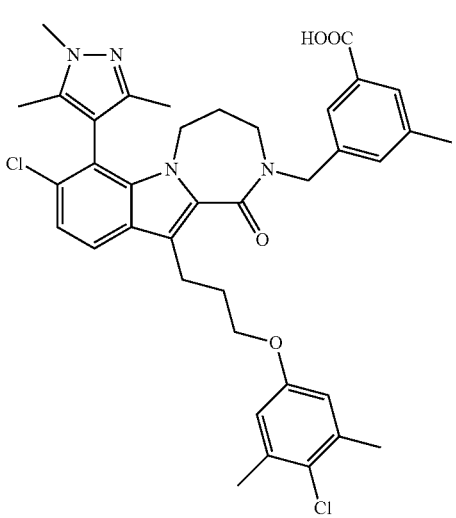

607
-continued
608
-continued
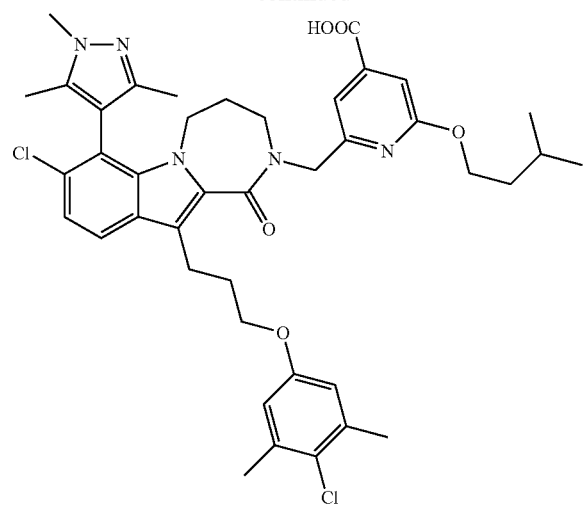
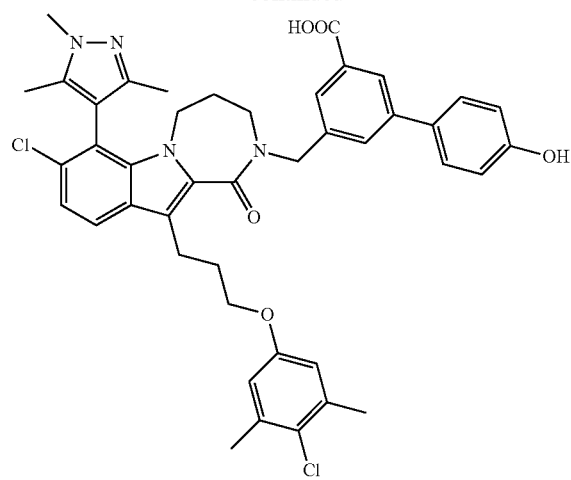
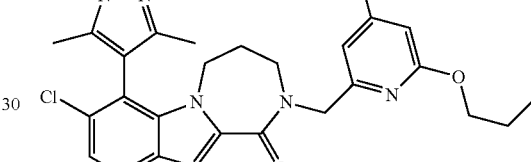

609
-continued
610
-continued
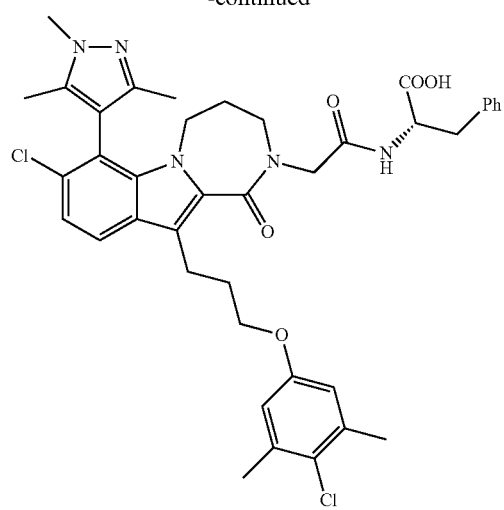
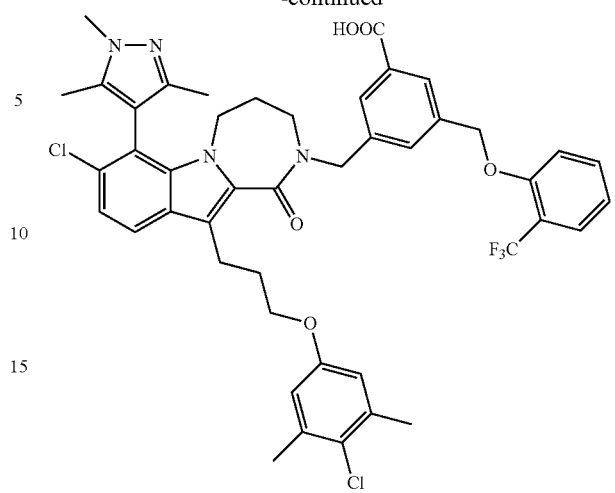
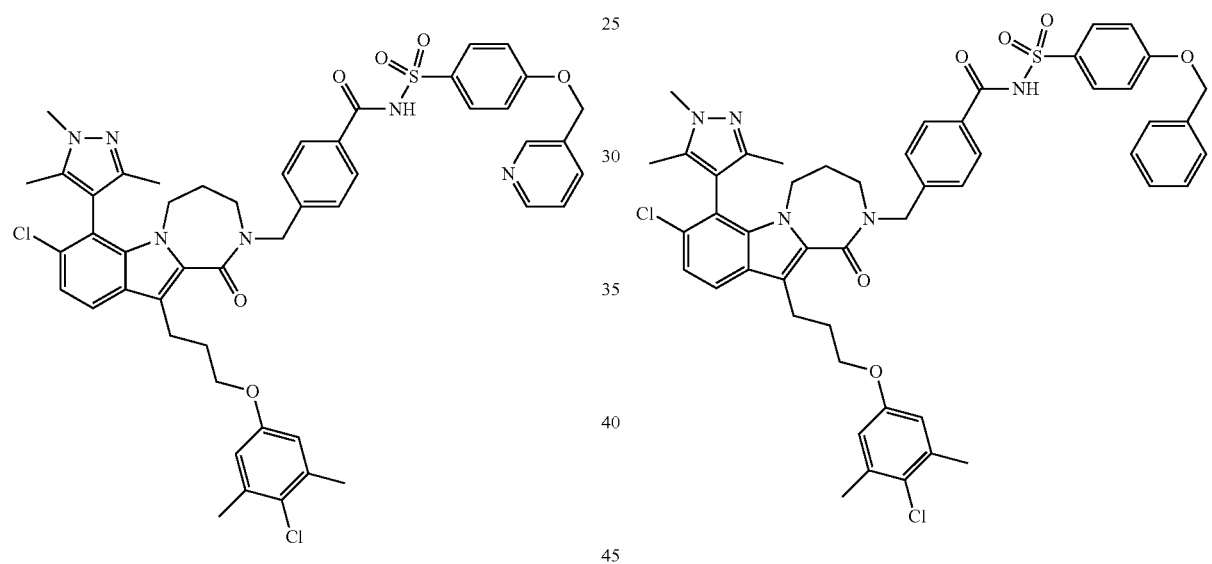
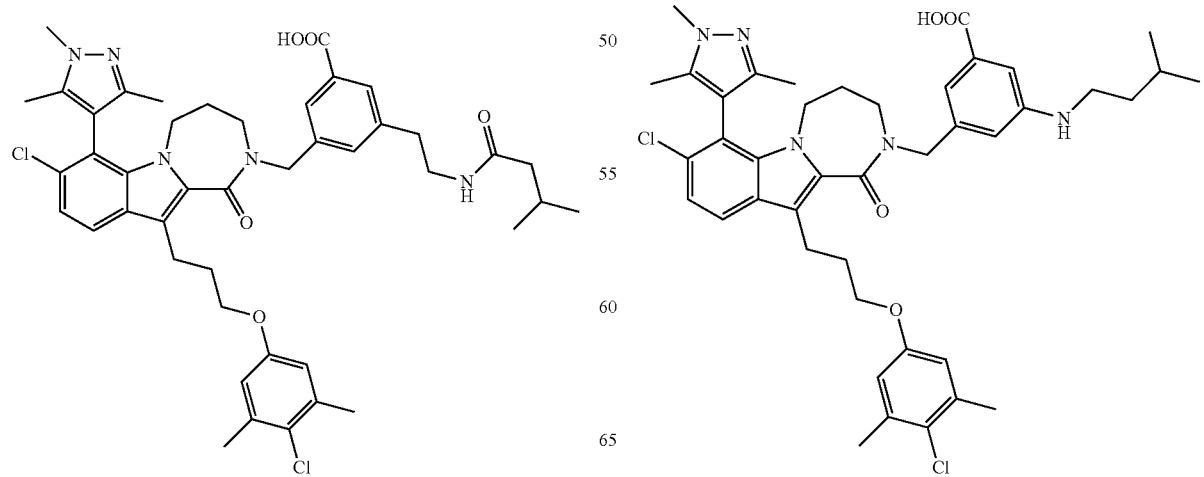

611
-continued
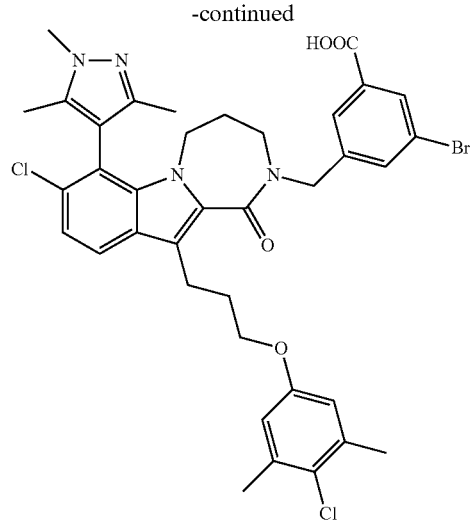
612
-continued
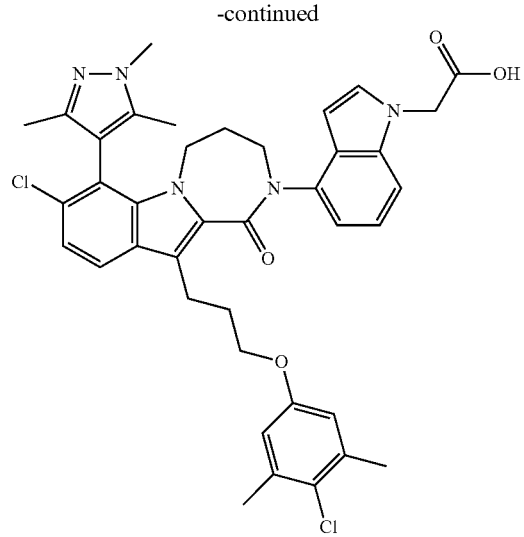
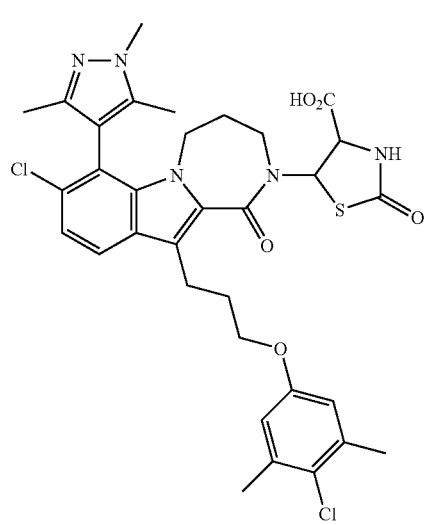
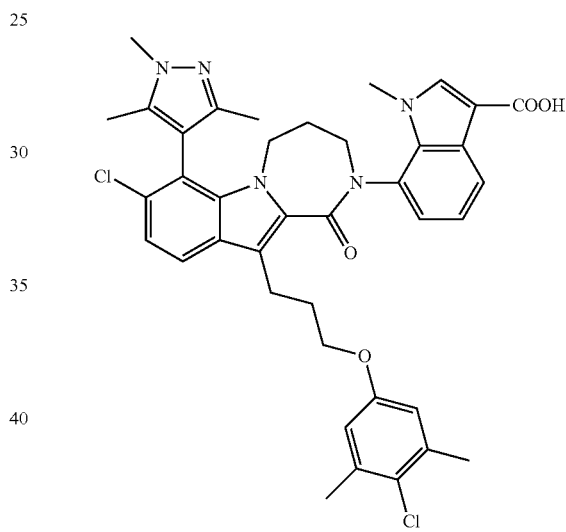
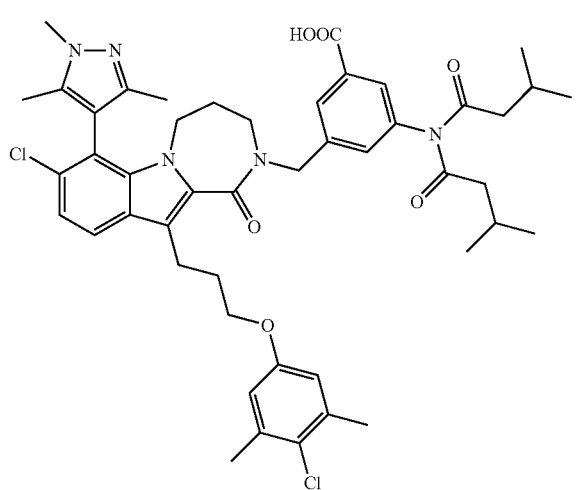
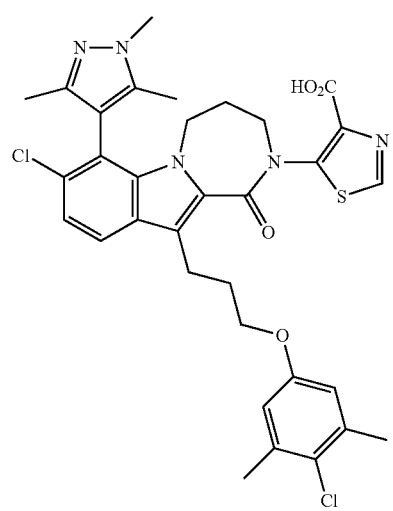

613
-continued
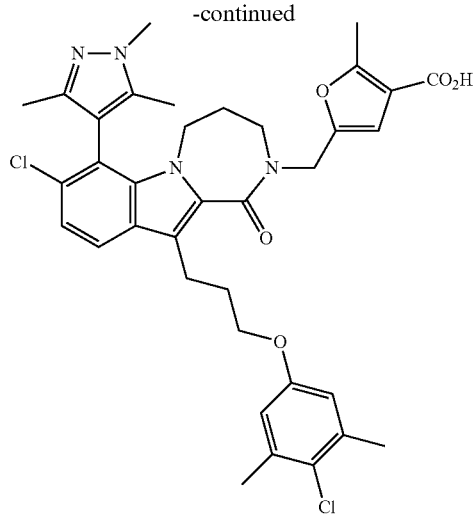
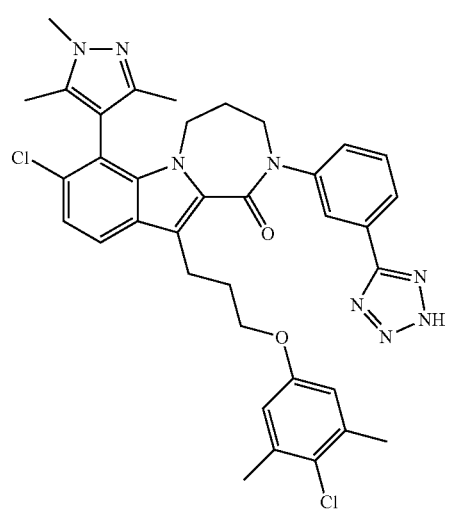
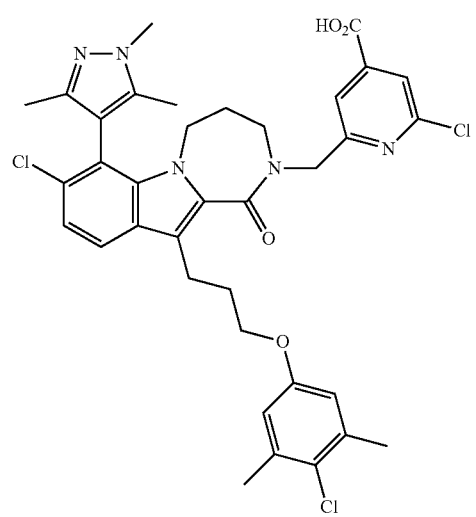
614
-continued
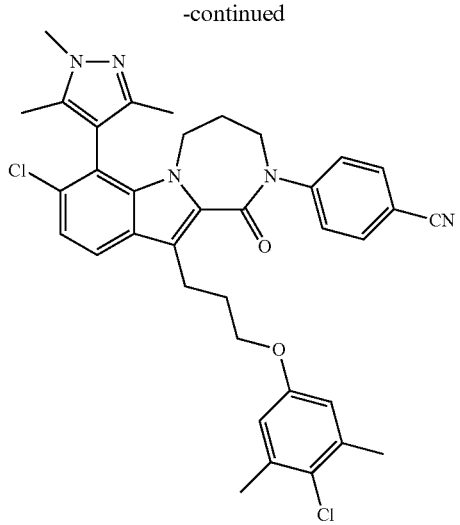
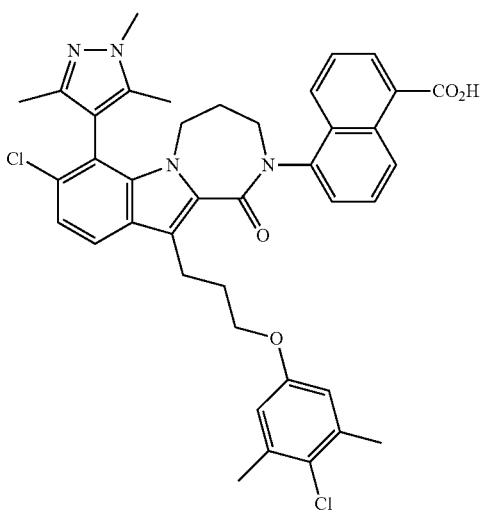
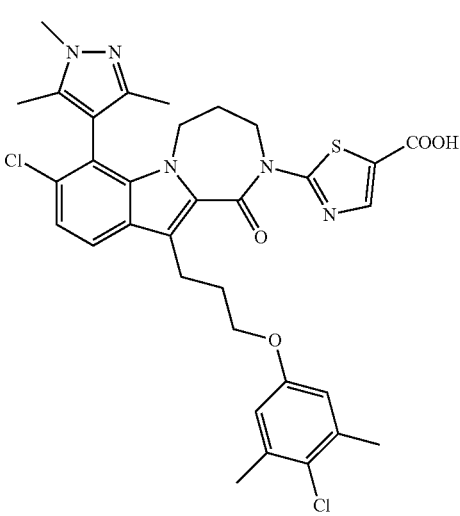

615
-continued
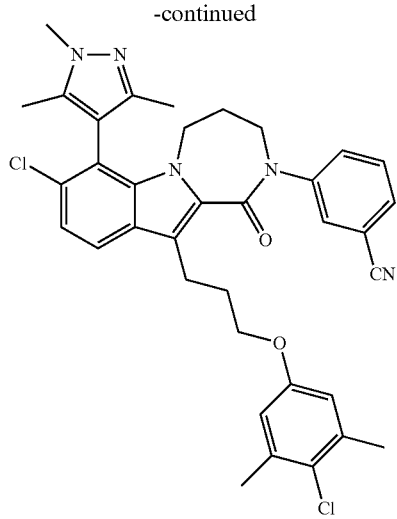
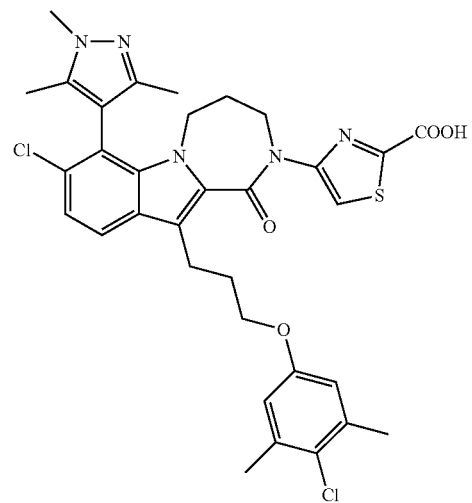
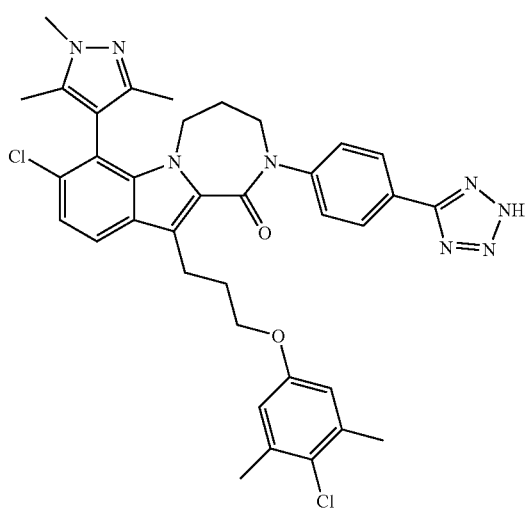
616
-continued
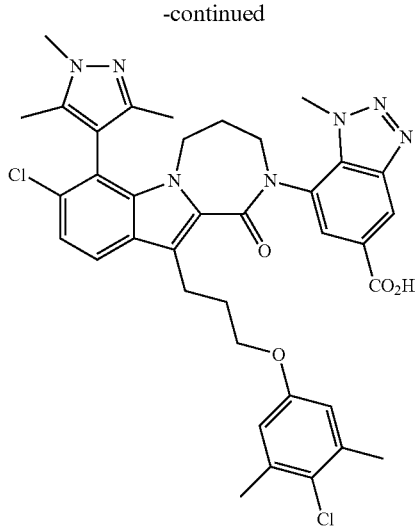
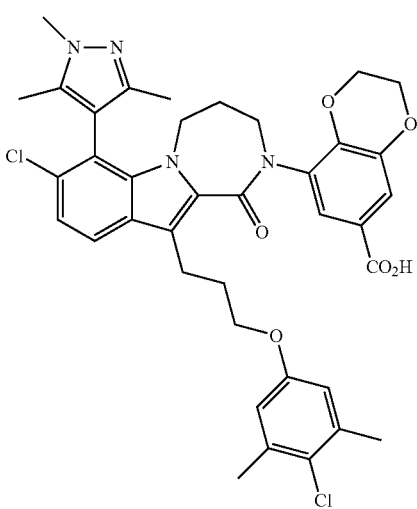
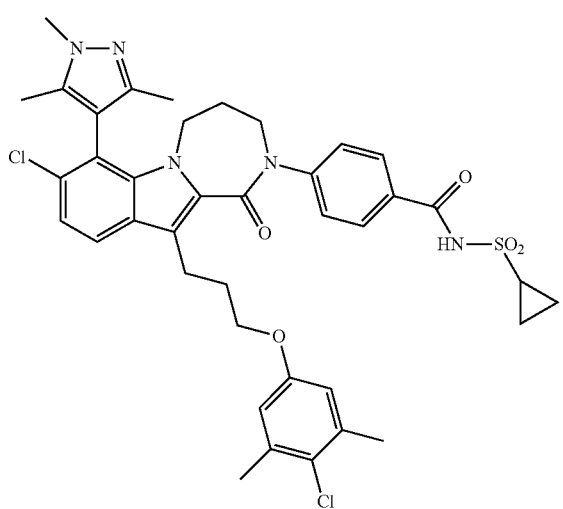

617
-continued
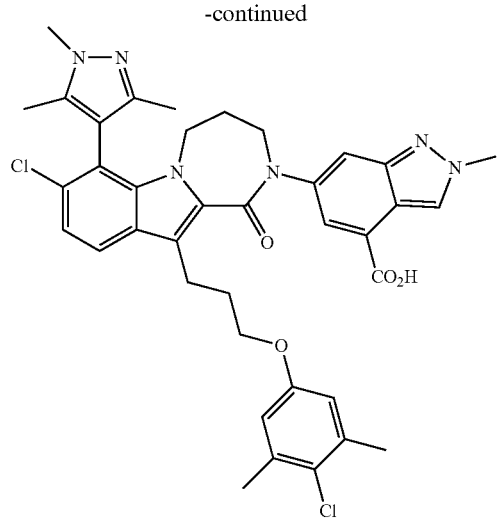
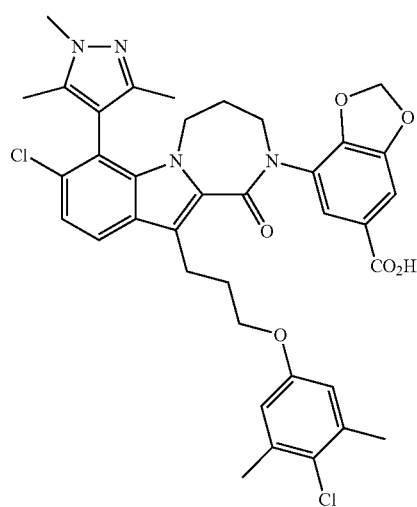
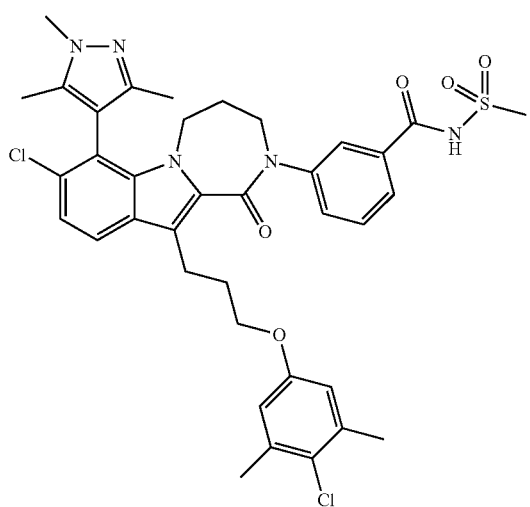
618
-continued
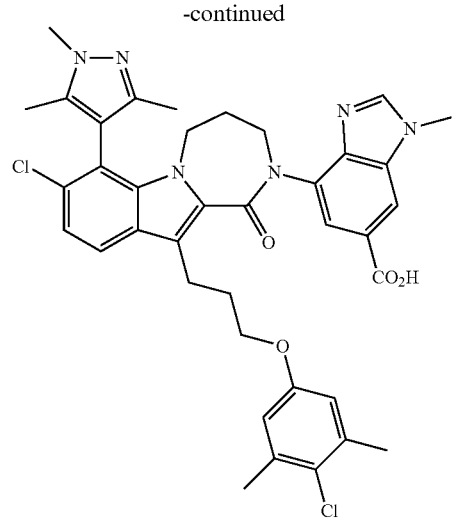
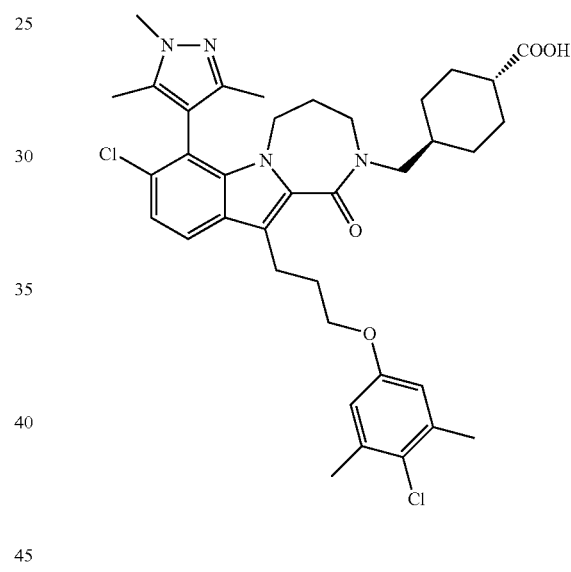
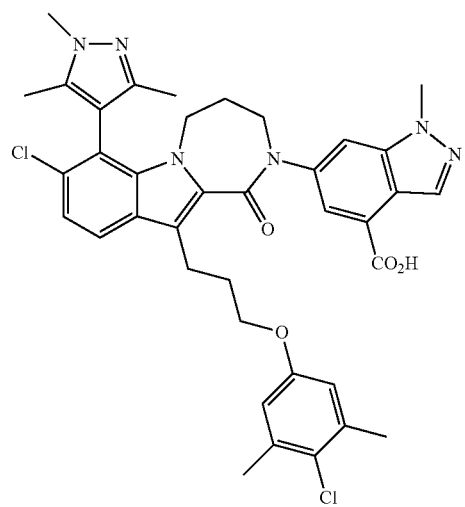

619
-continued
620
-continued
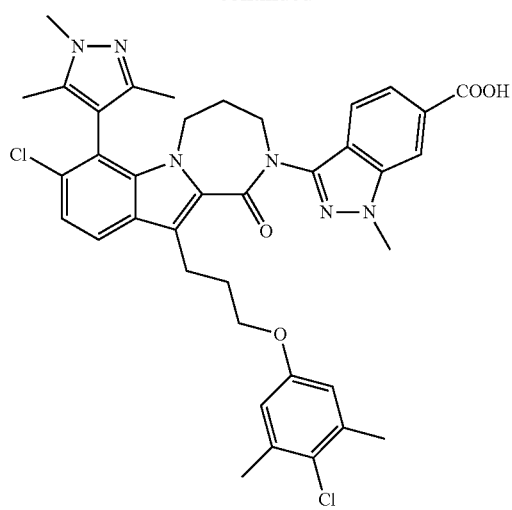
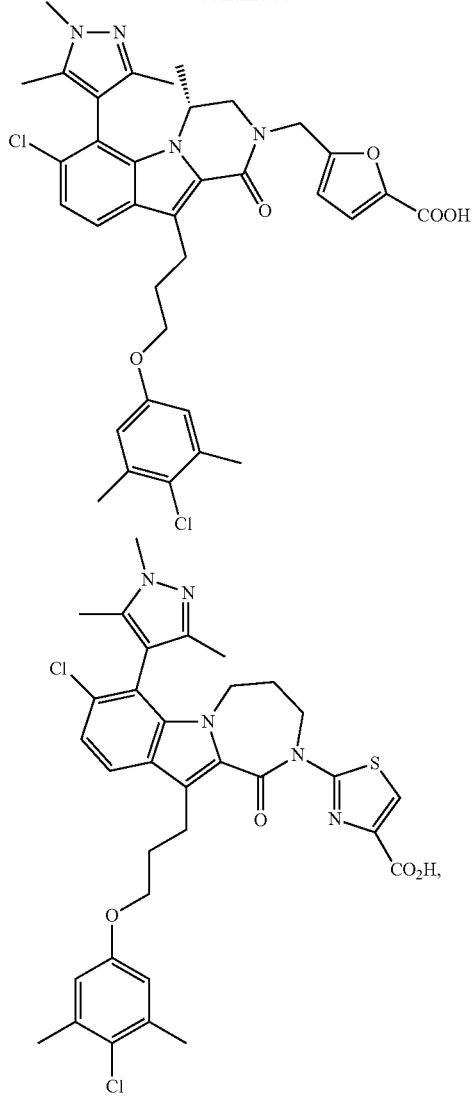
or a pharmaceutically acceptable salt thereof.
15. A pharmaceutical composition comprised of a therapeutically effective amount of a compound of claim 1, or a pharmaceutically acceptable salt thereof, and a pharmaceutically acceptable carrier.
* * * * *